(12) United States Patent
McSwiggen et al.

(10) Patent No.: US 7,176,304 B2
(45) Date of Patent: Feb. 13, 2007

(54) RNA INTERFERENCE MEDIATED INHIBITION OF VASCULAR ENDOTHELIAL GROWTH FACTOR AND VASCULAR ENDOTHELIAL GROWTH FACTOR RECEPTOR GENE EXPRESSION USING SHORT INTERFERING NUCLEIC ACID (SINA)

(76) Inventors: James McSwiggen, 4866 Franklin Dr., Boulder, CO (US) 80301; Leonid Beigelman, 5530 Colt Dr., Longmont, CO (US) 80503; Pamela Pavco, 705 Barberry Cir., Lafayette, CO (US) 80026

( * ) Notice: Subject to any disclaimer, the term of this patent is extended or adjusted under 35 U.S.C. 154(b) by 63 days.

(21) Appl. No.: 10/844,076

(22) Filed: May 11, 2004

(65) Prior Publication Data

US 2005/0171039 A1   Aug. 4, 2005

Related U.S. Application Data

(63) Continuation-in-part of application No. 10/831,620, filed on Apr. 23, 2004, which is a continuation-in-part of application No. 10/764,957, filed on Jan. 26, 2004, which is a continuation-in-part of application No. 10/670,011, filed on Sep. 23, 2003, which is a continuation-in-part of application No. 10/665,255, filed on Sep. 16, 2003, now abandoned, which is a continuation-in-part of application No. PCT/US03/05022, filed on Feb. 20, 2003, application No. 10/844,076, which is a continuation-in-part of application No. 10/758,155, filed on Jan. 12, 2004, which is a continuation-in-part of application No. 10/665,951, filed on Sep. 18, 2003, which is a continuation-in-part of application No. 10/665,255, which is a continuation-in-part of application No. PCT/US03/05022, application No. 10/844,076, which is a continuation-in-part of application No. 10/664,668, filed on Sep. 18, 2003, which is a continuation-in-part of application No. 10/665,255, which is a continuation-in-part of application No. PCT/US03/05022, application No. 10/844,076, which is a continuation-in-part of application No. 10/757,803, filed on Jan. 14, 2004, which is a continuation-in-part of application No. 10/720,448, filed on Nov. 24, 2003, now abandoned, which is a continuation-in-part of application No. 10/693,059, filed on Oct. 23, 2003, now abandoned, which is a continuation-in-part of application No. 10/444,853, filed on May 23, 2003, which is a continuation-in-part of application No. PCT/US03/05346, filed on Feb. 20, 2003, and a continuation-in-part of application No. PCT/US03/05028, filed on Feb. 20, 2003, and application No. PCT/US03/05028, said application No. 10/844,076 is a continuation-in-part of application No. 10/427,160, filed on Apr. 30, 2003, which is a continuation-in-part of application No. PCT/US02/15876, filed on May 17, 2002, said application No. 10/844,076 is a continuation-in-part of application No. 10/712,633, filed on Nov. 3, 2003, now abandoned, which is a continuation-in-part of application No. PCT/US02/17674, filed on May 29, 2002, said application No. PCT/US03/05346 and application No. PCT/US03/05028.

(60) Provisional application No. 60/440,129, filed on Jan. 15, 2003, provisional application No. 60/409,293, filed on Sep. 9, 2002, provisional application No. 60/408,378, filed on Sep. 5, 2002, provisional application No. 60/406,784, filed on Aug. 29, 2002, provisional application No. 60/399,348, filed on Jul. 29, 2002, provisional application No. 60/393,796, filed on Jul. 3, 2002, provisional application No. 60/386,782, filed on Jun. 6, 2002, provisional application No. 60/363,124, filed on Mar. 11, 2002, provisional application No. 60/358,580, filed on Feb. 20, 2002.

(51) Int. Cl.
*C07H 21/04* (2006.01)
*C07H 21/02* (2006.01)
*A61K 48/00* (2006.01)
*C12Q 1/68* (2006.01)

(52) U.S. Cl. .................. 536/24.5; 435/6; 435/325; 435/375; 514/44; 536/23.1; 536/24.3

(58) Field of Classification Search .................. 435/6; 514/44; 536/23.1, 24.3, 24.31, 24.33, 24.5
See application file for complete search history.

(56) References Cited

U.S. PATENT DOCUMENTS 4,501,729 A   2/1985   Boucher et al.

(Continued)

FOREIGN PATENT DOCUMENTS

AU   4037501   8/2000

(Continued)

OTHER PUBLICATIONS

Hammond et al., Post-Transcriptional Gene Silencing by Double-Stranded RNA, 2001, Nature, vol. 2, pp. 110-119.*

(Continued)

*Primary Examiner*—James Schultz
*Assistant Examiner*—Amy H. Bowman
(74) *Attorney, Agent, or Firm*—McDonnell Boehnen Hulbert & Berghoff LLP

(57) ABSTRACT

The present invention concerns methods and reagents useful in modulating vascular endothelial growth factor (VEGF, VEGF-A, VEGF-B, VEGF-C, VEGF-D) and/or vascular endothelial growth factor receptor (e.g., VEGFR1, VEGFR2 and/or VEGFr3) gene expression in a variety of applications, including use in therapeutic, diagnostic, target validation, and genomic discovery applications. Specifically, the invention relates to small nucleic acid molecules, such as short interfering nucleic acid (siNA), short interfering RNA (siRNA), double-stranded RNA (dsRNA), micro-RNA (miRNA), and short hairpin RNA (shRNA) molecules capable of mediating RNA interference (RNAi) against VEGF and/or VEGFr gene expression and/or activity. The small nucleic acid molecules are useful in the diagnosis and treatment of cancer, proliferative diseases, and any other disease or condition that responds to modulation of VEGF and/or VEGFr expression or activity.

2 Claims, 44 Drawing Sheets

U.S. PATENT DOCUMENTS

| | | | |
|---|---|---|---|
| 5,138,045 A | 8/1992 | Cook et al. | |
| 5,214,136 A | 5/1993 | Lin et al. | |
| 5,334,711 A | 8/1994 | Sproat et al. | |
| 5,587,471 A * | 12/1996 | Cook et al. | 536/25.3 |
| 5,624,803 A | 4/1997 | Noonberg et al. | |
| 5,627,053 A | 5/1997 | Usman et al. | |
| 5,631,360 A | 5/1997 | Usman et al. | |
| 5,670,633 A | 9/1997 | Cook et al. | |
| 5,672,695 A | 9/1997 | Eckstein et al. | |
| 5,716,824 A | 2/1998 | Beigelman et al. | |
| 5,792,847 A | 8/1998 | Buhr et al. | |
| 5,804,683 A | 9/1998 | Usman et al. | |
| 5,814,620 A | 9/1998 | Robinson et al. | |
| 5,831,071 A | 11/1998 | Usman et al. | |
| 5,854,038 A | 12/1998 | Sullenger et al. | |
| 5,889,136 A | 3/1999 | Scaringe et al. | |
| 5,898,031 A | 4/1999 | Crooke | |
| 5,902,880 A | 5/1999 | Thompson | |
| 5,916,763 A * | 6/1999 | Williams et al. | 435/69.1 |
| 5,998,203 A | 12/1999 | Adamic et al. | |
| 6,001,311 A | 12/1999 | Brennen | |
| 6,005,087 A | 12/1999 | Cook et al. | |
| 6,008,400 A | 12/1999 | Scaringe et al. | |
| 6,054,576 A | 4/2000 | Bellon et al. | |
| 6,107,094 A | 8/2000 | Crooke | |
| 6,111,086 A | 8/2000 | Scaringe et al. | |
| 6,117,657 A | 9/2000 | Usman et al. | |
| 6,146,886 A | 11/2000 | Thompson et al. | |
| 6,153,737 A | 11/2000 | Manoharan et al. | |
| 6,162,909 A | 12/2000 | Bellon et al. | |
| 6,180,613 B1 | 1/2001 | Kaplitt et al. | |
| 6,362,323 B1 | 3/2001 | Usman et al. | |
| 6,235,310 B1 | 5/2001 | Wang et al. | |
| 6,248,878 B1 | 6/2001 | Matulic-Adamic et al. | |
| 6,300,074 B1 | 10/2001 | Gold et al. | |
| 6,303,773 B1 | 10/2001 | Bellon et al. | |
| 6,335,434 B1 | 1/2002 | Guzaev et al. | |
| 6,346,398 B1 * | 2/2002 | Pavco et al. | 435/91.31 |
| 6,353,098 B1 | 3/2002 | Usman et al. | |
| 6,395,713 B1 | 5/2002 | Beigelman et al. | |
| 6,437,117 B1 | 8/2002 | Usman et al. | |
| 6,447,796 B1 | 9/2002 | Vook et al. | |
| 6,469,158 B1 | 10/2002 | Usman et al. | |
| 6,476,205 B1 | 11/2002 | Buhr et al. | |
| 6,506,559 B1 | 1/2003 | Fire et al. | |
| 6,528,631 B1 | 3/2003 | Cook et al. | |
| 6,565,885 B1 | 5/2003 | Tarara et al. | |
| 6,582,728 B1 | 6/2003 | Platz et al. | |
| 6,586,524 B2 | 7/2003 | Sagara | |
| 6,592,904 B2 | 7/2003 | Platz et al. | |
| 2001/0007666 A1 | 7/2001 | Hoffman et al. | |
| 2002/0130430 A1 | 9/2002 | Castor | |
| 2003/0190635 A1 | 10/2003 | McSwiggen et al. | |
| 2003/0206887 A1 | 11/2003 | Morrissey et al. | |
| 2004/0037780 A1 | 2/2004 | Parsons et al. | |

FOREIGN PATENT DOCUMENTS

| | | | |
|---|---|---|---|
| CA | 2359180 | 8/2000 | |
| EP | 1144623 | 8/2000 | |
| EP | 1325955 | 7/2003 | |
| JP | 08208687 | 8/1996 | |
| WO | 89/02439 | 3/1989 | |
| WO | 90/14090 | 11/1990 | |
| WO | 91/03162 | 3/1991 | |
| WO | 92/07065 | 4/1992 | |
| WO | 93/15187 | 8/1993 | |
| WO | 93/23569 | 11/1993 | |
| WO | 94/01550 | 1/1994 | |
| WO | 94/02595 | 2/1994 | |
| WO | 94/11499 | 5/1994 | |
| WO | 94/21791 | 9/1994 | |
| WO | 95/04142 | 2/1995 | |
| WO | 95/06731 | 3/1995 | |
| WO | 95/11910 | 5/1995 | |
| WO | 95/13380 | 5/1995 | |
| WO | 96/10390 | 4/1996 | |
| WO | 96/10391 | 4/1996 | |
| WO | 96/10392 | 4/1996 | |
| WO | 96/18736 | 6/1996 | |
| WO | 97/00957 | 1/1997 | |
| WO | 97/21808 | 6/1997 | |
| WO | 97/26270 | 7/1997 | |
| WO | 98/13526 | 4/1998 | |
| WO | 99/04819 | 2/1999 | |
| WO | 99/07409 | 2/1999 | |
| WO | 99/14226 | 3/1999 | |
| WO | 99/31262 | 6/1999 | |
| WO | 99/32619 | 7/1999 | |
| WO | 99/49029 | 9/1999 | |
| WO | 99/53050 | 10/1999 | |
| WO | 99/54459 | 10/1999 | |
| WO | 99/55857 | 11/1999 | |
| WO | 99/61631 | 12/1999 | |
| WO | 00/01846 | 1/2000 | |
| WO | 00/44895 | 8/2000 | |
| WO | 00/44914 | 8/2000 | |
| WO | 00/49035 | 8/2000 | |
| WO | 00/53722 | 9/2000 | |
| WO | 00/63364 | 10/2000 | |
| WO | 00/66604 | 11/2000 | |
| WO | 01/04313 | 1/2001 | |
| WO | 01/29058 | 4/2001 | |
| WO | 01/36646 | 5/2001 | |
| WO | 01/38551 | 5/2001 | |
| WO | 01/42443 | 6/2001 | |
| WO | 01/49844 | 7/2001 | |
| WO | 01/53475 | 7/2001 | |
| WO | 01/68836 | 9/2001 | |
| WO | 01/70944 | 9/2001 | |
| WO | 01/70949 | 9/2001 | |
| WO | 01/72774 | 10/2001 | |
| WO | 01/75164 | 10/2001 | |
| WO | 01/92513 | 12/2001 | |
| WO | 01/96584 | 12/2001 | |
| WO | 01/097850 | 12/2001 | |
| WO | 02/07747 | 1/2002 | |
| WO | 02/10378 | 2/2002 | |
| WO | 02/22636 | 3/2002 | |
| WO | 02/38805 | 5/2002 | |
| WO | PCT/US02/15876 | 5/2002 | |
| WO | PCT/US02/17674 | 5/2002 | |
| WO | 02/44321 | 6/2002 | |
| WO | 02/055692 | 7/2002 | |
| WO | 02/055693 | 7/2002 | |
| WO | 02/096927 | 12/2002 | |
| WO | WO 02/096927 A2 * | 12/2002 | 514/44 |
| WO | PCT/US03/05022 | 2/2003 | |
| WO | PCT/US03/05028 | 2/2003 | |
| WO | PCT/US03/05346 | 2/2003 | |
| WO | WO 03/064625 | 2/2003 | |
| WO | WO 03/064626 | 2/2003 | |
| WO | 03/24420 | 3/2003 | |
| WO | WO 03/030989 | 4/2003 | |
| WO | WO 03/043689 | 5/2003 | |
| WO | WO 04/013280 | 5/2003 | |
| WO | 03/46185 | 6/2003 | |
| WO | 03/47518 | 6/2003 | |
| WO | 03/068797 | 8/2003 | |
| WO | 03/070887 | 8/2003 | |
| WO | 03/070896 | 8/2003 | |
| WO | 03/070910 | 8/2003 | |
| WO | 03/074654 | 9/2003 | |
| WO | 03/080638 | 10/2003 | |

| | | |
|---|---|---|
| WO | 04/009769 | 1/2004 |
| WO | 04/043977 | 5/2004 |
| WO | 04/072261 | 8/2004 |

OTHER PUBLICATIONS

Elbashir et al., Functional anatomy of siRNAs for mediating efficienct RNAi in Drosophila melanogaster embryo lysate, 2001, The EMBO Journal, vol. 20, No. 23, pp. 6877-6888.*
Parrish et al., Functional Anatomy of a dsRNA Trigger: Differential Requirement for the Two Trigger Strands in RNA Interference, 2000, Molecular Cell, vol. 6, pp. 1077-1087.*
Schmidt et al., Base and sugar requirements for RNA cleavage of essential nucleoside residues in internal loop of B of the hairpin ribozyme: implications for secondary structure, 1996, Nucleic Acids Research, vol. 24, No. 4, pp. 573-581.*
U.S. Appl. No. 09/226,044, filed Jul. 12, 2001, Hoffman et al.
U.S. Appl. No. 10/151,116, filed May 17, 2002, Matulic-Adamic et al.
U.S. Appl. No. 10/201,394, filed Aug. 13, 2001, Vargeese et al.
U.S. Appl. No. 10/287,949, filed Nov. 4, 2002, Pavco.
U.S. Appl. No. 10/306,747, filed Nov. 27, 2002, Pavco.
U.S. Appl. No. 10/427,160, filed Apr. 30, 2003, Vargeese et al.
U.S. Appl. No. 10/438,493, filed May 15, 2003, Pavco et al.
U.S. Appl. No. 10/444,853, filed May 23, 2003, McSwiggen et al.
U.S. Appl. No. 10/664,668, filed Sep. 18, 2003, McSwiggen et al.
U.S. Appl. No. 10/664,767, filed Sep. 16, 2003, McSwiggen et al.
U.S. Appl. No. 10/665,255, filed Sep. 16, 2003, McSwiggen et al.
U.S. Appl. No. 10/665,951, filed Sep. 18, 2003, McSwiggen et al.
U.S. Appl. No. 10/670,011, filed Sep. 23, 2003, McSwiggen et al.
U.S. Appl. No. 10/693,059, filed Oct. 23, 2003, McSwiggen et al.
U.S. Appl. No. 10/712,633, filed Nov. 13, 2003, McSwiggen et al.
U.S. Appl. No. 10/720,448, filed Nov. 24, 2003, McSwiggen et al.
U.S. Appl. No. 10/727,780, filed Dec. 3, 2003, Vaish et al.
U.S. Appl. No. 10/757,803, filed Jan. 14, 2004, McSwiggen et al.
U.S. Appl. No. 10/758,155, filed Jan. 12, 2004, McSwiggen et al.
U.S. Appl. No. 10/764,957, filed Jan. 26, 2004, McSwiggen et al.
U.S. Appl. No. 10/831,620, filed Apr. 23, 2004, McSwiggen et al.
U.S. Appl. No. 60/082,404, filed Apr. 20, 1998, Thomspon et al.
U.S. Appl. No. 60/334,461, filed Nov. 30, 2001, Pavco.
U.S. Appl. No. 60/358,580, filed Feb. 20, 2002, Beigelman et al.
U.S. Appl. No. 60/363,124, filed Mar. 11, 2002, Beigelman et al.
U.S. Appl. No. 60/386,782, filed Jun. 6, 2002, Beigelman et al.
U.S. Appl. No. 60/393,796, filed Jul. 3, 2002, McSwiggen et al.
U.S. Appl. No. 60/399,348, filed Jul. 29, 2002, McSwiggen et al.
U.S. Appl. No. 60/402,996, filed Aug. 13, 2002, Usman et al.
U.S. Appl. No. 60/406,784, filed Aug. 29, 2002, Beigelman et al.
U.S. Appl. No. 60/408,378, filed Sep. 5, 2002, Beigelman et al.
U.S. Appl. No. 60/409,293, filed Sep. 9, 2002, Beigelman et al.
U.S. Appl. No. 60/440,129, filed Jan. 15, 2003, Beigelman et al.
U.S. Appl. No. 60/543,480, filed Feb. 10, 2004, Jadhav et al.
Adah et al., "Chemistry and Biochemistry of 2',5'-Oligoadenylate-Based Antisense Strategy," Current Medicinal Chemistry, 8, 1189-1212 (2001).
Aiello et al., "Vascular Endothelial Growth Factor in Ocular Fluid of Patients with Diabetic Retinopathy and Other Retinal Disorders," The New England Journal of Medicine 331(22):1480-1487 (1994).
Akhtar and Juliano, "Cellular Uptake and Intracellular Fate of AntiSense Oligonucleotides," Trends Cell Biol. 2:139-144 (1992.
Aldrian-Herrada et al., "A peptide nucleic acid (PNA) is more rapidly internalized in cultured neurons when coupled to a retro-inverso delivery peptide. The antisense activitiy depresses the target mRNA and protein in magnocellular oxytocin neurons," Nucleic Acids Research 26:4910-4916 (1998).
Allshire, "RNAi and Heterochromatin—A Hushed-up Affair," Science 297:1818-1819 (2002).
Andrews and Faller, "A rapid micropreparation technique for extraction of DNA-binding proteins from limiting numbers of mammalian cells," Nucleic Acids Research 19:2499 (1991).
Autiero et al., "Role of PlGF in the intra- and intermolecular cross talk between the VEGF receptors Flt1 and Flk1," Nature Medicine, 9:936-943 (2003).

Baenziger and Fiete, "Galactose and N-Acetylgalactosamine-Specific Endocytosis of Glycopeptides by Isolated Rat Hepatocytes," Cell 22:611-620 (1980).
Bahramian et al., "Transcriptional and Posttranscriptional Silencing of Rodent α1(I) Collagen by a Homologous Transcriptionally Self-Silenced Transgene," Molecular and Cellular Biology, 274-283 (1999).
Bannai et al., "Effect of Injection of Antisense of Oligodeoxynucleotides of GAD Isozymes into Rat Ventromedial Hypothalamus on Food Intake and Locomotor Activity," Brain Research 784:305-315 (1998).
Bannai et al., "Water-absorbent Polymer as a Carrier for a Discrete Deposit of Antisense Oligodeoxynucleotides in the Central Nervous System," Brain Research Protocols 3:83-87 (1998).
Bass, "The short answer," Nature 411:428-429 (2001).
Bass, "Double-Stranded RNA as a Template for Gene Silencing," Cell, 101, 235-238 (2000).
Beaucage and Iyer, "The Functionalization of Oligonucleotides Via Phosphoramidite Derivatives," Tetrahedron 49:1925-1963 (1993).
Beigelman et al., "Chemical Modification of Hammerhead Ribozymes," The Journal of Biological Chemistry 270:25702-25708 (1995).
Bellon et al., "Amino-Linked Ribozymes: Post-Synthetic Conjugation of Half-Ribozymes," Nucleosides & Nucleotides 16:951-954 (1997).
Bellon et al., "Post-synthetically Ligated Ribozymes: An Alternative Approach to Iterative Solid Phase Synthesis," Bioconjugate Chem. 8:204-212 (1997).
Berkman et al., "Expression of the Vascular Permeability Factor/Vascular Endothelial Growth Factor Gene in Central Nervous System Neoplasms," The Journal of Clinical Investigation, Inc. 91:153-159 (1993).
Bernstein et al., "Role for a Bidentate Ribonuclease in the Initiation Step of RNA Interference," Nature 409:363-366 (2001).
Bettinger et al., "Size Reduction of Galactosylated PEI/DNA Complexes Improves Lectin-Mediated Gene Transfer into Hepatocytes," Bioconjugate Chem., 10, 558-561 (1999).
Boado et al., "Drug Delivery of Antisense Molecules to the Brain for Treatment of Alzheimer's Disease and Cerebral AIDS," Journal of Pharmaceutical Sciences 87:1308-1315 (1998).
Boado, "Antisense drug delivery through the blood-brain barrier," Advanced Drug Delivery Reviews 15:73-107 (1995).
Brennan et al., "Two-Dimensional Parallel Array Technology as a New Approach to Automated Combinatorial Solid-Phase Organic Synthesis," Biotechnology and Bioengineering (Combinatorial Chemistry) 61:33-45 (1998).
Broaddus et al., "Distribution and stability of antisense phosphorothioate oligonucleotides in rodent brain following direct intraparenchymal controlled-rate infusion," J Neurosurg 88:734-742 (1998).
Brody and Gold, "Aptamers as therapeutic and diagnostic agents," Reviews in Molecular Biotechnology 74:5-13 (2000).
Burger et al., "Experimental Corneal Neovascularization: Biomicroscopic, Angiographic, and Morphologic Correlation," Cornea 4:35-41 (1985/1986).
Burgin et al., "Chemically Modified Hammerhead Ribozymes with Improved Catalytic Rates," Biochemistry 35:14090-14097 (1996) (vol. no. mistakenly listed as 6).
Burlina et al., "Chemical Engineering of RNase Resistant and Catalytically Active Hammerhead Ribozymes," Bioorganic & Medicinal Chemistry 5:1999-2010 (1997).
Caruthers et al., "Chemical Synthesis of Deoxyoligonucleotides and Deoxyoligonucleotide Analogs," Methods in Enzymology 211:3-19 (1992).
Chen et al., "Multitarget-Ribozyme Directed to Cleave at up to Nine Highly Conserved HIV-1 env RNA Regions Inhibits HIV-1 Replication-Potential Effectiveness Against Most Presently Sequenced HIV-1 Isolates," Nucleic Acids Research 20:4581-4589 (1992).
Chiu et al., "siRNA function in RNAi: A chemical modification analysis," RNA, 9:1034-1048 (2003).
Choi et al., "Effect of Poly(ethylene glycol) Grafting on Polyethylenimine as a Gene Transfer Vector in vitro," Bull. Korean Chem. Soc., 22, 46-52 (2001).

Chowrira et al., "In Vitro and in Vivo Comparison of Hammerhead, Hairpin, and Hepatitis Delta Virus Self-Processing Ribozyme Cassettes," J. Biol. Chem. 269:25856-25864 (1994).

Clark and Yoria, "Ophthalmic Drug Discovery," Nature, 2, 448-459 (2003).

Clemens et al., "The Double-Stranded RNA-Dependent Protein Kinase PKR:Structure and Function," J. Interferon & Cytokine Res., 17, 503-524 (1997).

Cload and Schepartz, "Polyether Tethered Oligonucleotide Probes," J. Am. Chem. Soc. 113:6324-6326 (1991).

Connolly et al., "Binding and Endocytosis of Cluster Glycosides by Rabbit Hepatocytes," The Journ. of Biol. Chem. 257:939-945 (1982).

Conry et al., "Phase I Trial of a Recombinant Vaccinia Virus Encoding Carcinoembryonic Antigen in Metastatic Adenocarcinoma: Comparison of Intradermal versus Subcutaneous Administration," Clinical Cancer Research 5:2330-2337 (1999).

Couture and Stinchcomb, "Anti-gene therapy: the use of ribozymes to inhibit gene function," Trends In Genetics 12:510-515 (1996).

Detmar et al., "Overexpression of Vascular Permeability Factor/Vascular Endothelial Growth Factor and its Receptors in Psoriasis," J. Exp. Med. 180:1141-1146 (1994).

Diebold et al., "Mannose Polyethylenimine Conjugates for Targeted DNA Delivery into Dendritic Cells*," The Journal of Biological Chemistry, 274, 19087-19094 (1999).

Dropulic et al., "Functional Characterization of a U5 Ribozyme: Intracellular Suppression of Human Immunodeficiency Virus Type 1 Expression," Journal of Virology 66:1432-1441 (1992).

Durand et al., "Circular Dichroism Studies of an Oligodeoxyribonucleotide Containing a Hairpin Loop Made of a Hexaethylene Glycol Chain: Conformation and Stability," Nucleic Acids Research 18:6353-6359 (1990) [sometimes referred to as Seela and Kaiser].

Earnshaw et al., "Modified Oligoribonucleotides as Site-Specific Probes of RNA Structure and Function," Biopolymers 48:39-55 (1998).

Economides et al., Cytokine traps: multi-componetnt, high-affinity blockers of cytokine action, Nature Medicine, 9, 1, 47-52 (2003).

Elbashir et al., "Duplexes of 21-nucleotide RNAs mediate RNA interference in cultured mammlian cells," Nature 411:494-498 (2001).

Elbashir et al., "Functional Anatomy of siRNAs for Mediating Efficient RNAi in Drosophila Melanogaster Embryo Lysate," The EMBO Journal 20:6877-6888 (2001).

Elbashir et al., "RNA Interference is Mediated by 21- and 22-Nucleotide RNAs," Genes and Development 15:188-200 (2001).

Elkins and Rossi, "Ch. 2—Cellular Delivery of Ribozymes," in Delivery Strategies for Antisense Oligonucleotide Therapeutics, edited by Akhtar, CRC Press, pp. 17-220 (1995).

Elroy-Stein and Moss, "Cytoplasmic Expression System Based on Constitutive Synthesis of Bacteriophage T7 RNA Polymerase in Mammalian Cells," Proc. Natl. Acad. Sci. USA 87:6743-6747 (1990).

Emerich et al., "Biocompatability of Poly (DL-Lactide-co-Glycolide) Microshperes Implanted Into the Brain," Cell Transplantation 8:47-58 (1999).

Epa et al., "Downregulation of the p75 Neurotrophin Receptor in Tissue Culture and In Vivo, Using β-Cyclodextrin-Adamantane-Oligonucleotide Conjugates," Anitsense Nuc. Acid Drug Dev., 10:469-478 (2000).

Erbacher et al., Transfection and physical properties of various sacccharide, poly(ethylene glycol), and antibody-derivatized polyethylenimines (PEI), The Journal of Gene Medicine, 1, 210-222 (1999) [sometimes incorrectly cited as pp. 1-18].

Fava et al., "Vascular Permeability Factor/Endothelial Growth Factor (VPF/VEGF): Accumulation and Expression in Human Synovial Fluids and Rheumatoid Synovial Tissue," J. Exp. Med. 180:341-346 (1994).

Ferentz and Verdine, "Disulfied Cross-Linked Oligonucleotides," J. Am. Chem. Soc. 113:4000-4002 (1991).

Filleur et al., "SiRNA-mediated Inhibition of Vascular Endothelial Growth Factor Severely Limits Tumor Resistance to Antiangiogenic Thrombospondin-1 and Slows Tumor Vascularization and Growth," Cancer Research, 63, 3919-3922 (2003).

Fire et al., "Potent and Specific Genetic Interference by Double-Stranded RNA in Caenorhabditis Elegans," Nature 391:806-811 (1998).

Fire, "RNA-triggered Gene Silencing," TIG 15:358-363(1999).

Folkman et al., "Long-term Culture of Capillary Endothelial Cells," Proc. Natl. Acad. Sci. USA 76:5217-5221 (1979).

Folkman, Judah, "Tumor Angiogenesis," Advances in Cancer Research 43:175-203 (1985).

Freier et al., "Improved free-energy parameters for predictions of RNA duplex stability," Proc. Natl. Acad. Sci. USA 83:9373-9377 (1986) [sometimes referred to as Frier].

Furgeson et al., "Modified Linear Polyethylenimine—Cholesterol Conjugates for DNA Complexation," Bioconjugate Chem., 14, 840-847 (2003).

Futami et al., "Induction fo apoptosis in HeLa cells with siRNA expression vector targeted against blc-2," Nucleic Acids Research Supplement, 251-252 (2002).

Gao and Huang, "Cytoplasmic Expression of a Reporter Gene by Co-Delievery of T7 RNA Polymerase and T7 Promoter Sequence with Cationic Liposomes," Nucleic Acids Research 21:2867-2872 (1993).

Genbank Accession No. AF020393.
Genbank Accession No. AF022375.
Genbank Accession No. AF024710.
Genbank Accession No. AF035121.
Genbank Accession No. AF063657.
Genbank Accession No. AF063658.
Genbank Accession No. AF092125.
Genbank Accession No. AF092126.
Genbank Accession No. AF092127.
Genbank Accession No. AF095785.
Genbank Accession No. AF098331.
Genbank Accession No. AF437895.
Genbank Accession No. AF468110.
Genbank Accession No. AF486837.
Genbank Accession No. AH006909.
Genbank Accession No. AJ000185.
Genbank Accession No. AJ010438.
Genbank Accession No. AY047581.
Genbank Accession No. D89630.
Genbank Accession No. E13256.
Genbank Accession No. E13332.
Genbank Accession No. E14000.
Genbank Accession No. E14233.
Genbank Accession No. E15156.
Genbank Accession No. E15157.
Genbank Accession No. NM_022019.
Genbank Accession No. NM_002020.
Genbank Accession No. NM_002253.
Genbank Accession No. NM_003376.
Genbank Accession No. NM_003377.
Genbank Accession No. NM_004469.
Genbank Accession No. NM_005429.
Genbank Accession No. U01134.
Genbank Accession No. X62568.
Genbank Accession No. X94216.
Genbank Accession No. Y08736.

Godbey et al., "Poly(ethylenimine) and its role in gene delivery," Journal of Controlled Release, 60, 149-160 (1999).

Godbey et al., "Tracking the intracellular path of poly(ethylenimine)/DNA complexes for gene delivery," Proc. Natl. Acad. Sci. USA, 96, 5177-5181 (1999).

Gold et al., "Diversity of Oligonucleotide Functions," Annu. Rev. Biochem. 64:763-797 (1995).

Gonzalez et al., "New Class of Polymers for the Delivery of Macromolecular Therapeutics," Bioconjugate Chem. 10:1068-1074 (1999).

Good et al., "Expression of small, therapuetic RNAs in human nuclei," Gene Therapy 4:45-54 (1997).

Grant et al., "Insulin-like growth factor 1 acts as an angiogenic agent in rabbit cornea and retina: comparative studies with basic fibroblast growth factor," Diabetologia 36:282-291 (1993).

Hall et al., "Establishment and Maintenance of a Heterochromatin Domain," Science 297:2232-2237 (2002).

Hamilton, et al., "A Species of Small Antisense RNA in Post-transcriptional Gene Silencing in Plants," Science, 286, 950-952 (1999).

Hammond et al., "An RNA-Directed Nuclease Mediates Post-Transcriptional Gene Silencing in Drosophila Cells," Nature 404:293-296 (2000).

Harborth et al., "Sequence, Chemical, and Structural Variation of Small Interfering RNAs and Short Hairpin RNAs and the Effect of Mammalian Gene Silencing," Antisense and Nucleic Acid Drug Development, 13:83-105 (2003).

Hermann and Patel, "Adaptive Recognition by Nucleic Acid Aptamers," Science 287:820-825 (2000).

Hofland and Huang, "Formulation and Delivery of Nucleic Acids," Handbook of Exp. Pharmacol. 137:165-192 (1999).

Hunziker et al., "Nucleic Acid Analogues: Synthesis and Properties, in Modern Synthetic Methods," VCH, 331-417 (1995).

Hutvagner and Zamore, "A MicroRNA in a Multiple-Turnover RNAi Enzyme Complex," Science 297:2056-2060 (2002).

Hutvagner et al., "A Cellular Function for the RNA-Interference Enzyme Dicer in the Maturation of the let-7 Small Temporal RNA," Science 293:834-838 (2001).

International Search Report for PCT/US03/05028 mailed Oct. 17, 2003.

International Search Report for PCT/US03/05346 mailed Oct. 1, 2003.

Ishiwata et al., "Physical-Chemistry Characteristics and Biodistribution of Poly(ethylene glycol)-Coated Liposomes Using Poly(oxyethylene) Cholesteryl Ether," Chem. Pharm. Bull. 43:1005-1011 (1995) (mistakenly referred to as Ishiwataet).

Izant and Weintraub, "Constitutive and Conditional Suppression of Exogenous and Endogeneous Genes by Anti-Sense RNA," Science 229:345-352 (1985).

Jaschke et al., "Automated Incorporation of Polyethylene Glycol into Synthetic Oligonucleotides," Tetrahedron Letters 34:301-304 (1993) (sometimes mistakenly referred to as Jschke).

Jayasena, "Aptamers: An Emerging Class of Molecules that Rival Antibodies in Diagnostics," Clinical Chemistry 45:1628-1650 (1999).

Jenuwein, "An RNA-Guided Pathway for the Epigenome," Science 297:2215-2218 (2002).

Jolliet-Riant and Tillement, "Drug transfer across the blood-brain barrier and improvement of brain delivery," Fundam. Clin. Pharmacol. 13:16-26 (1999).

Karle et al., "Differential Changes in Induced Seizures After Hippocampal Treatment of Rats with an Antisense Oligodeoxynucleotide to the $GABA_A$ Receptor γ2 Subunit," Euro. Jour. of Pharmacology 340:153-160 (1997).

Karpeisky et al, "Highly Efficient Synthesis of 2'-O-Amino Nucleosides And Their Incorporation in Hammerhead Ribozymes," Tetrahedron Letters 39:1131-1134 (1998).

Kashani-Sabet et al., "Reversal of the Malignant Phenotype by an Anti-ras Ribozyme," Antisense Research & Development 2:3-15 (1992).

Kaspareit-Rittinghausen et al., "Animal Model of Human Disease: Hereditary Polycystic Kidney Disease," Amer. Journ. of Pathology 139:693-696 (1991).

Kim et al., "Inhibition of vascular endothelial growth factor-induced angiogenesis suppresses tumour growth in vivo," Nature 362:841-844 (1993).

Koch et al., "Vascular Endothelial Growth Factor," Journal of Immunology 152:4149-4156 (1994).

Kusser, "Chemically modified nucleic acid aptamers for in vitro selections: evolving evolution," Reviews in Molecular Biotechnology 74:27-38 (2000).

Kwak et al., "VEGF Is Major Stimulator in Model of Choroidal Neovascularization," Investigative Ophthalmology & Visual Science, 41(10), 3158-3164 (2000).

Lasic and Needham "The 'Stealth' Liposome: A Prototypical Biomaterial," Chemical Reviews 95:2601-2627 (1995).

Lasic and Papahajopoulos, "Liposomes Revisited," Science 267:1275-1276 (1995).

Lee and Larson, "Modified Liposome Formulations for Cytosolic Delivery of Macromolecules," ACS Symposium Series 752:184-192 (2000).

Lee and Lee, "Preparation of Cluster Glycosides of N-Acetylgalactosamine That Have Subnanomolar Binding Constants Towards the Mammalian Hepatic Gal/GalNAc-specific Receptor," Glycoconjugates J. 4:317-328 (1987).

Lee et al., " Expression of Small Interfering RNA's Targeted Against HIV-1 rev Transcripts in Human Cells," Nature Biotechnology 19:500-505 (2002).

Leirdal et al., "Gene silencing in mammalian cells by preformed small RNA duplexes," Biochemical and Biophysical Research Communications, 295, 744-748 (2002).

Lepri et al., "Effect of Low Molecular Weight Heparan Sulphate on Angiogenesis in the Rat Cornea after Chemical Cauterization," Journal of Ocular Pharmacology 10:273-281 (1994).

L'Huillier et al., "Cytoplasmic Delivery of Ribozymes Leads to Efficient Reduction in α-Lactalbumin mRNA Levels in C1271 Mouse," EMBO J. 11:4411-4418 (1992).

Lieber et al., "Stable High-Level Gene Expression in Mammalian Cells by T7 Phage RNA Polymerase," Methods Enzymol. 217:47-66 (1993).

Limbach et al., "Summary: the modified nucleosides of RNA," Nucleic Acids Research 22(12):2183-2196 (1994).

Lin and Matteucci, "A Cytosine Analogue Capable of Clamp-Like Binding to a Guanine in Helical Nucleic Acid," J. Am. Chem. Soc. 120:8531-8532 (1998).

Lin et al., "A Novel mRNA-cRNA Interference Phenomenon for Silencing bcl-2 Expression in Human LNCaP Cells," Biochemical and Biophysical Research Communications, 281, 639-644 (2001).

Lin et al., "Policing Rogue Genes", Nature 402:128-129 (1999).

Lisziewicz et al., "Inhibition of Human Immunodeficiency Virus Type 1 Replication by Regulated Expression of a Polymeric Tat Activation Response RNA Decoy as a Strategy for Gene Therapy in AIDS," Proc. Natl. Acad. Sci. U.S.A. 90:8000-8004 (1993).

Liu et al., "Cationic Liposome-mediated Intravenous Gene Delivery," J. Biol. Chem. 270(42):24864-24870 (1995).

Loakes, "The Applications of Universal DNA Base Analogues," Nucleic Acids Research 29:2437-2447 (2001).

Ma et al., "Design and Synthesis of RNA Miniduplexes via a Synthetic Linker Approach. 2. Generation of Covalently Closed, Double-Stranded Cyclic HIV-1 TAR RNA Analogs with High Tat-Binding Affinity," Nucleic Acids Research 21:2585-2589 (1993).

Ma et al., "Design and Synthesis of RNA Miniduplexes via a Synthetic Linker Approach," Biochemistry 32:1751-1758 (1993).

Martinez et al., "Single-Stranded Antisense siRNAs Guide Target RNA Cleavage in RNAi," Cell 110:563-574 (2002).

Maurer et al., "Lipid-based systems for the intracellular delivery of genetic drugs," Molecular Membrane Biology 16:129-140 (1999).

McCurdy et al., "Deoxyoligonucleotides with Inverted Polarity: Synthesis and Use in Triple-Helix Formation" Nucleosides & Nucleotides 10:287-290 (1991).

McGarry and Lindquist, "Inhibition of heat shock protein synthesis by heat-inducible antisense RNA," Proc. Natl. Acad. Sci. USA 83:399-403 (1986).

McLaren et al., "Vascular Endothlial Growth Factor (VEGF) Concentrations are Elevated in Peritoneal Fluid of Women with Endometriosis," Human Reproduction 11:220-223 (1996).

McLaren et al., "Vascular Endothlial Growth Factor is Produced by Peritoneal Fluid Macrophages in Endometriosis and Is Regulated by Ovarian Steriods," J. Clin. Invest. 98:482-489 (1996).

McManus et al., "Gene Silencing Using Micro-RNA Designed Hairpins," RNA 8:842-850 (2002).

Mesmaeker et al, "Novel Backbone Replacements for Oligonucleotides," American Chemical Society, pp. 24-39 (1994).

Millauer et al., "Glioblastoma growth inhibited in vivo by a dominant-negative Flk-1 mutant," Letters to Nature 367:576-579 (1994).

Miller et al., "Vascular Endothelial Growth Factor/Vascular Permeability Factor is Temporally and Spatially Correlated with Ocular Angiogenesis in a Primate Model," American Journal of Pathology 145:574-584 (1994).

Miyagishi and Taira, "U6 Promoter-driven siRNAs with Four Uridine 3' Overhangs Efficiently Suppress Targeted Gene Expression in Mammalian Cells," Nature Biotechnology 19:497-500 (2002).

Moore and Sharp, "Site-Specific Modification of Pre-mRNA: The 2'-Hydroxyl Groups at the Splice Sites," Science 256:992-996 (1992).

Mori et al., "Inhibition of Chorodial Neovascularization by Intravenous Injection of Adenoviral Vectors Expressing Secretable Endostatin," American Journal of Pathology, 159(1), 313-320 (2001).

Mori et al., "Pigment epithelium-derived factor inhibits retinal and choroidal neovacularization," Journal of Cellular Physiology, 118(2) 253-263 (2001).

Noonberg et al., In vivo generation of highly abundant sequence-specific oligonucleotides for antisense and triplex gene regulation, Nucleic Acids Research 22(14):2830-2836 (1994).

Norrby, "Angiogenesis: new aspects relating to its initiation and control," APMIA 105:417-437 (1997).

Novina et al., "siRNA-Directed Inhibition of HIV-1 Infection," Nature Medicine 1-6 (2002).

Nykanen et al., "ATP Requirements and Small Interfering RNA Structure in the RNA Interference Pathway," Cell 107:309-321 (2001).

Ohkawa et al., "Activities of HIV-RNA Targeted Ribozymes Transcribed From a 'Shot-Gun' Type Ribozyme-trimming Plasmid," Nucleic Acids Symp. Ser. 27:15-16 (1992).

Ohno-Matsui, et al., "Inducible Expression of Vascular Endothelial Growth Factor in Adult Mice Causes Severe Proliferative Retinopathy and Retinal Detachment," *Animal Models* from the Departments of Ophthalmology and Neuroscience and Molecular Biology and Genetics, *Am. J. Pathology*, 160, 711-719 (2002).

Ojwang et al., "Inhibition of Human Immunodeficiency Virus Type 1 Expression by a Hairpin Ribozyme," Proc. Natl. Acad. Sci. USA 89:10802-10806 (1992).

Oku et al., "Real-time analysis of liposomal trafficking in tumor-bearing mice by use of positron emission tomography," Biochimica et Biophysica Acta 1238:86-90 (1995).

Ono et al., "DNA Triplex Formation of Oligonucleotide Analogues Consisting of Linker Groups and Octamer Segments That Have Opposite Sugar-Phosphate Backbone Polarities," Biochemistry 30:9914-9921 (1991).

O'Reilly et al., "Angiostatin: A Novel Angiogenesis Inhibitor That Mediates the Suppression of Metastases by a Lewis Lung Carcinoma," Cell 79:315-328 (1994).

Orgis et al., "DNA/polyethylenimine transfection particles: Influence of ligands, polymer size, and PEGylation on internalization and gene expression," *AAPS PharmSci.*, 3 (3) article 21 (http://www.pharmsci.org) p. 1-11 (2001).

Ormerod et al., "Effects of Altering the Eicosanoid Precursor Pool on Neovascularization and Inflammation in Alkali-burned Rabbit Cornea," American Journal of Pathology 137:1243-1252 (1990).

Pal-Bhadra et al., "Heterochromatic Silencing and HP1 Localization in *Drosophila* Are Dependent on the RNAi Machinery," *Science*, 303, 669-672 (2004).

Pandey et al., "Role ov B61, the Ligand for the Eck Receptor Tyrosine Kinase, in TNF-α-Induced Angiogensis," Science 268:567-569 (1995).

Pardridge et al., "Vector-mediated delivery of a polyamide ("peptide") nucleic acid analogue through the blood-brain barrier in vivo," Proc. Natl. Acad. Sci. USA 92:5592-5596 (1995).

Parrish, "Functional Anatomy of a dsRNA Trigger: Differential Requirement for the Two Trigger Strands in RNA Interference," Molecular Cell 6:1077-1087 (2000).

Passaniti et al., "A Simple, Quantitative Method for Assessing Angiogenesis and Antiangiogenic Agents Using Reconstituted Basement Membrane, Heparin, and Fibroblast Growth Factor," Laboratory Investigation 67:519-528 (1992).

Paul et al., "Effective Expression of Small Interfering RNA in Human Cells," Nature Biotechnology 20:505-508 (2002).

Perreault et al., "Mixed Deoxyribo- and Ribo-Oligonucleotides with Catalytic Activity," Nature 344:565-567 (1990) (often mistakenly listed as Perrault).

Petersen et al., Polyethylenimine-*graft*-Poly(ethylene glycol) Copolymers: Influence of Copolymer Block Structure on DNA Complexation and Biological Activities as Gene Delivery System, *Bioconjugate Chem.*, 13, 845-854 (2002).

Pieken et al., "Kinetic Characterization of Ribonuclease-Resistant 2'-Modified Hammerhead Ribozymes," Science 253:314-317 (1991).

Pierce et al., "Vascular endothelial growth factor/vascular permeability factor expression in a mouse model of retinal neovascularization," Proc. Natl. Acad. Sci. USA 92:905-909 (1995).

Plate, "Vascular endothelial growth factor is potential tumor angiogenesis factor in human gilomas in vivo," Nature 359:845-848 (1992).

Ponpipom et al., "Cell-Specific Ligands for Selective Drug Delivery to Tissues and Organs," J. Med. Chem. 24:1338-1395 (1981).

Rajakumar et al., "Effects of Intrastriatal Infusion of $D_2$ Receptor Antisense Oligonucleotide on Apomorphine-Induced Behaviors in the Rat," *Synapse* 26:199-208 (1997).

Reich et al., "Small Interfering RNA (siRNA) targeting *VEGF* effectively inhibits ocular neovascularization in a mouse model," *Molecular Vision*, 9, 210-216 (2003).

Reinhart and Bartel, "Small RNAs Correspon to Centromer Heterochromatic Repeats," Science 297:1831 (2002).

Reinhart et al., "MicroRNAs in Plants," Genes & Development 16:1616-1626 (2002).

Reynolds et al., "Rational siRNA designe for RNA intereference," *Nature Biotechnology*, 22, 3, 326-330 (2004).

Richardson and Schepartz, "Tethered Oligonucleotide Probes. A Strategy for the Recognition of Structure RNA," J. Am. Chem. Soc. 113:5109-5111 (1991).

Saenger (ed), "Modified Nucleosides and Nucleotides; Nucleoside Di- and Triphosphates; Coenzymes and Antibiotics, (ch.7)" Principles of Nucleic Acid Structure 158-200 (1984).

Sarver et al., "Ribozymes as Potential Anti-HIV-1 Therapeutic Agents" Science 247:1222-1225 (1990).

Scanlon et al., "Ribozyme-Mediated Cleavage of c-fos mRNA Reduces Gene Expression of DNA Synthesis Enzymes and Metallothionein," Proc. Natl. Acad. Sci. USA 88:10591-10595 (1991).

Scaringe et al., "Chemical synthesis of biologically active oligoribonucleotides using βcyanoethyl protected ribonucleoside phosphoramidites," Nucl Acids Res. 18:5433-5441 (1990).

Schroeder et al., "Diffusion Enhancement of Drugs by Loaded Nanoparticles in Vitro," Prog. Neuro-Psychopharmacol. & Biol. Psychiat. 23:941-949 (1999) sometimes cited by RPI as Prog Neuropsychopharmacol Biol Psychiatry 23:941-949, 1999.

Schwarz et al., "Evidence that siRNAs Function as Guides, Not Primers, in the Drosophila and Human RNAi Pathways," Molecular Cell 10:537-548 (2002).

Schwarz et al., "Asymmetry in the Assembly of the RNAi Enzyme Complex," Cell, 1115, 199-208 (2003).

Seela and Kaiser, "Oligodeoxyribonucleotides containing 1,3-propanediol as nucleoside substitute," Nucleic Acids Research 15:3113-3129 (1987).

Senger et al., "Vascular permeability factor (VPF, VEGF) in tumor biology," Cancer and Matastasis Reviews 12:303-324 (1993).

Shabarova et al., "Chemical ligation of DNA: The first non-enyzmatic assembly of a biologically active gene," Nucleic Acids Research 19:4247-4251 (1991).

Sharp, Philip A., "RNAi and Double-strand RNA", *Genes and Development* 13:139-141 (1999).

Sheehan et al., "Biochemical properties of phosphonoacetate and thiophosphonoacetate oligodeoxyribonucleotides," *Nucleic Acids Research*, 31 (14), 4109-4118 (2003).

Shifren et al., "Ovarian Steroid Regulation of Vascular Endothelial Growth Factor in the Human Endometrium: Implications for Angiogenesis during the Menstrual Cycle and in the Pathogenesis of Endometriosis," The Journal of Clinical Endocrinology & Metabolism 81:3112-3118 (1996).

Shweiki et al., "Patterns of Expression of Vascular Endothelial Growth Factor (VEGF) and VEGF Receptors in Mice Suggest a Role in Hormonally Regulated Angiogenesis," J. Clin. Invest. 91:2235-2243 (1993).

Simantov et al., "Dopamine-Induced Apoptosis in Human Neuronal Cells: Inhibition by Nucleic Acids Antisense to the Dopamine Transporter," Neuroscience 74(1):39-50 (1996).

Sommer at al., "The Spread and Uptake Pattern of Intracerebrally Administered Oligonucleotides in Nerve and Glial Cell Populations of the Rat Brain," Antisense & Nucleic Acid Drug Development 8:75-85 (1998).

Strauss, Evelyn, "Molecular Biology: Candidate 'Gene Silencers' Found" Molecular Biology, 286: 5441, p. 886 (1999).

Sullenger and Cech, "Tethering Ribozymes to a Retroviral Packaging Signal for Destruction of Viral RNA," Science 262:1566-1569 (1993).

Sun, "Technology evaluation: SELEX, Giliad Sciences Inc," Current Opinion in Molecular Therapeutics 2:100-105 (2000).

Taira et al., "Construction of a novel RNA-transcript-trimming plasmid which can be used both in vitro in place of run-off and (G)-free transcriptions and in vivo as multi-sequences transcription vectors," Nucleic Acids Research 19:5125-5130 (1991).

Takahashi et al., "Markedly Increased Amounts of Messenger RNAs for Vascular Endothelial Growth Factor and Placenta Growth Factor in Renal Cell Carcinoma Associated with Angiogenesis," Cancer Research 54:4233-4237 (1994).

Thomas et al., "Enhancing polyethylenimine's delivery of plasmid DNA into mammalian cells," PNAS, 99, 14640-14645 (2002).

Thompson et al., "Improved accumulation and activity of ribozymes expressed from a tRNA-based RNA polymerase III promoter," Nucleic Acids Research 23:2259-2268 (1995).

Turner et al., "Improved Parameters for Prediction of RNA Structure," Cold Spring Harbor Symposia on Quantitative Biology vol. LII, pp. 123-133 (1987).

Turner et al., "Free Energy Increments for Hydrogen Bonds in Nucleic Acid Base Pairs," J. Am. Chem. Soc. 109:3783-3785 (1987).

Tuschl et al., "Targeted mRNA Degradation by Double-Stranded RNA In Vitro," Genes & Development 13:3191-3197 (1999).

Tuschl et al., "Small Interfering RNAs: A Revolutional Tool for the Analysis of Gene Function and Gene Therapy," Molecular Interventions, 295, 3, 158-167 (2002).

Tuschl, "RNA Interference and Small Interfering RNAs," Chembiochem 2:239-245 (2001).

Tyler et al., "Petide nucleic acids targeted to the neurotensin receptor and administered i.p. cross the blood-brain barrier and specifically reduc gene expression," Proc. Natl. Acad. Sci. USA 96:7053-7058 (1999).

Tyler et al., "Specific gene blockade shows that peptide nucleic acids readily enter neuronal cells in vivo," FEBS Letters 421:280-284 (1998).

Uhlmann et al., "Studies on the Mechanism of Stabilization of Partially Phosphorothioated Oligonucleotides Against Nucleolytic Degradation," Antisense & Nucleic Acid Drug Development 7:345-350 (1997).

Ui-Tei et al., "Guidelines for the selection of highly effective siRNA sequences for mammalial and chick RNA interference," Nucleic Acids Research, 32, 3, 936-948 (2004).

Usman and Cedergren, "Exploiting the chemical synthesis of RNA," TIBS 17:334-339 (1992).

Usman and McSwiggen, "Ch. 30—Catalytic RNA (Ribozymes) as Drugs," Annual Reports in Medicinal Chemistry 30:285-294 (1995).

Usman et al., "Automated Chemical Synthesis of Long Oligoribonucleotides Using 2'-O-Silylated Ribonucleoside 3'-O-Phosphoramidites on a Controlled-Pore Glass Support: Synthesis of a 43-Nucleotide Sequence Similar to the 3'-Half Molecule of an Escherichia coli Formylmethoionine tRNA," J. Am. Chem. Soc. 109:7845-7854 (1987).

Usman et al., "Chemical modification of hammerhead ribozymes: activity and nuclease resistance," Nucleic Acids Symposium Series 31:163-164 (1994).

Ventura et al., "Activation of HIV-Specific Ribozyme Activity by Self-Cleavage," Nucleic Acids Research 21:3249-3255 (1993).

Verdel et al., RNAi-Mediated Targeting ofHeterochromatin by the RITS Complex, Science, 303, 672-676 (2004)

Verma and Eckstein, "Modified Oligonucleotides: Synthesis and Strategy for Users," Annu. Rev. Biochem. 67:99-134 (1998).

Volpe et al., "Regulation of Heterochromatic Silencing and Histone H3 Lysine-9 Methylation by RNAi," Science 297:1833-1937 (2002).

Waterhouse, et al., "Virus Resistance and gene Silencing in Plants Can Be Induced by Simultaneous Expression of Sense and Antisense RNA" Proc. Natl. Acad. Sci. USA 99:13959-13964 (1998).

Weckbecker et al., "Intradermal angiogenesis in nude mice induced by human tumor cells or b-FGF," Angiogenesis Key Principles—Science—Technology—Medicine pp. 296-301 (1992).

Weerasinghe et al., "Resistance to Human Immunodeficiency Virus Type 1 (HIV-1) Infection in Human CD4+ Lymphocyte-Derived Cell Lines Conferred by Using Retroviral Vectors Expressing an HIV-1 RNA-Specific Ribozyme," Journal of Virology 65:5531-5534 (1994).

Wellstein and Czubayko, "Inhibition of Fibroblast Growth Factors," Breast Cancer Research and Treatment 38:109-119 (1996).

Wianny and Zernicka-Goetz et al., "Specific Interference with Gene Function by Double-Stranded RNA in Early Mouse Development," Nature Cell Biology 2:70-75 (2000).

Wincott et al., "Synthesis, deprotection, analysis and purification of RNA and ribozymes," Nucleic Acids Research 23(14):2677-2684 (1995).

Wincott et al., "A Practical Method for the Production of RNA Ribozymes," Methods in Molecular Biology 74:59-69 (1997).

Woo et al., "Taxol Inhibits Progression of Congenital Polycystic Kidney Disease," Nature 368:750-753 (1994).

Wu and Wu, "Receptor-mediated in Vitro Gene Transformation by a Soluble DNA Carrier System," The Journ. of Biol. Chem. 262:4429-4432 (1987).

Wu et al., "Cardiac Defects and Renal Failure in Mice with Targeted Mutations in Pkd2," Nature Genetics 24:75-78 (2000).

Wu-Pong et al., "Nucleic Acid Drug Delivery, Part 2; Delivery to the Brain," _32-38 (1999).

Yamada et al., "Nanoparticles for the delivery of genes and drugs to human hepatocytes," Published online: Jun. 29, 2003, doi:10.1038/nbt843 (Aug. 2003 vol. 21 No. 8 pp. 885-890) (2003).

Yu et al., "A Hairpin Ribozyme Inhibits Expression of Diverse Strains of Human Immunodeficiency Virus Type 1," Proc. Natl. Acad. Sci. USA 90:6340-6344 (1993).

Zamore et al., "RNAi: Double-Stranded RNA Directs the ATP-Dependent Cleavage of mRNA at 21 to 23 Nucleotide Intervals," Cell 101:25-33 (2000).

Zhou et al., "Synthesis of Functional mRNA in Mammalian Cells by Bacteriophage T3 RNA Polymerase," Mol. Cell. Biol. 10:4529-4537 (1990).

Ziche et al., "Angiogenesis Can Be Stimulated or Repressed In Vivo by a Change in GM3:GD3 Ganglioside Ratio," Laboratory Investigation 67:711-715 (1992).

Anderson et al., "Bispecific Short Hairpin siRNA Constructs Targeted to CD4, CXCR4, and CCR5 Confer HIV-1 Resistance," Oligonucleotides, 13:303-312 (2003).

Bayard et al., "Increased stability and antiviral activity of 2'-O-phosphoglyceryl derivatives of (2'-5')oligo(adenylate)," Eur. J. Biochem., 142(29):291-298 (1984).

International Search Report for PCT/US03/05022 mailed Jan. 6, 2005.

International Search Report for PCT/US2004/016390 mailed Mar. 31, 2005.

International Search Report for PCT/US2004/027403 mailed Jul. 12, 2005.

International Search Report for PCT/US2004/030488 mailed Jan. 12, 2005.

Jen et al., "Suppression of gene Expression by Targeted Disruption of Messenger RNA: Available Options and Current Strategies," Stem Cells, 18:307-319 (2000).

Kuwabara et al., "A *C. elegans* patched gene, ptc-1, functions in germ-line cytokinesis," *Genes and Development*, 14(15):1933-1944 (2000).

Lu et al., "Tumor Inhibition By RNAi-Mediated VEGF an VEGFR Down Regulation in Xenograft Models," Cancer Gene Therapy, 10, Suppl. 1, S4-S5 (2003).

Parry et al. 1999. "Bioactivity of anti-angiogenic ribozymes targeting *Flt*-1 and *KDR* mRNA," *Nucleic Acid Res*. 27:2569-77.

Shibuya et al., "Nucleotide sequence and expression of a novel human receptor-type tyrosine kinase gene (*flt*) closely related to the *fms* family," *Oncogene* 5:519-524 (1990).

* cited by examiner

*Figure 1*
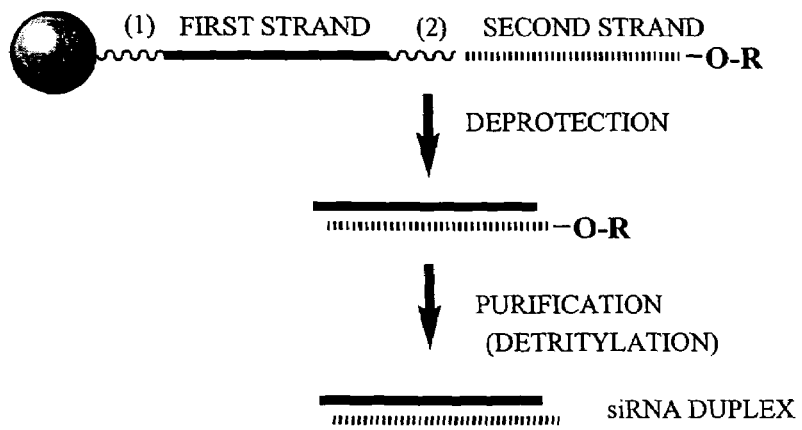
 = SOLID SUPPORT
R = TERMINAL PROTECTING GROUP
FOR EXAMPLE:
DIMETHOXYTRITYL (DMT)
(1) 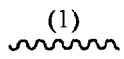 = CLEAVABLE LINKER
(FOR EXAMPLE: NUCLEOTIDE SUCCINATE OR
INVERTED DEOXYABASIC SUCCINATE)
(2) 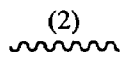 = CLEAVABLE LINKER
(FOR EXAMPLE: NUCLEOTIDE SUCCINATE OR
INVERTED DEOXYABASIC SUCCINATE)
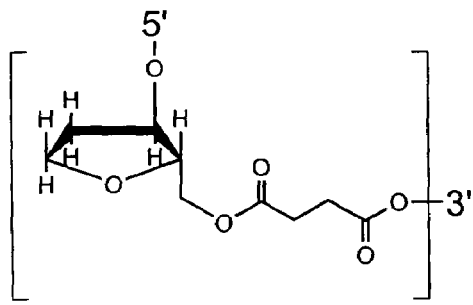
INVERTED DEOXYABASIC SUCCINATE LINKAGE
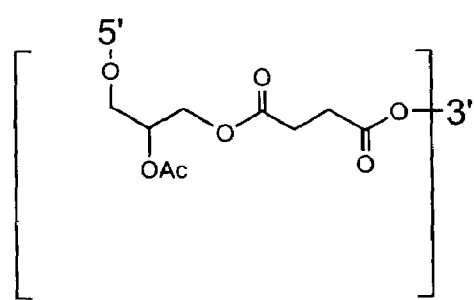
GLYCERYL SUCCINATE LINKAGE POSITIONS (NN) CAN COMPRISE ANY NUCLEOTIDE, SUCH AS DEOXYNUCLEOTIDES (eg. THYMIDINE) OR UNIVERSAL BASES
B = ABASIC, INVERTED ABASIC, INVERTED NUCLEOTIDE OR OTHER TERMINAL CAP THAT IS OPTIONALLY PRESENT
L = GLYCERYL or B THAT IS OPTIONALLY PRESENT
S = PHOSPHOROTHIOATE OR PHOSPHORODITHIOATE that is optionally absent Figure 9: Target site Selection using siRNA R = O, S, N, alkyl, substituted alkyl, O-alkyl, S-alkyl, alkaryl, or aralkyl
B = Independently any nucleotide base, either naturally occurring or chemically modified, or optionally H (abasic).

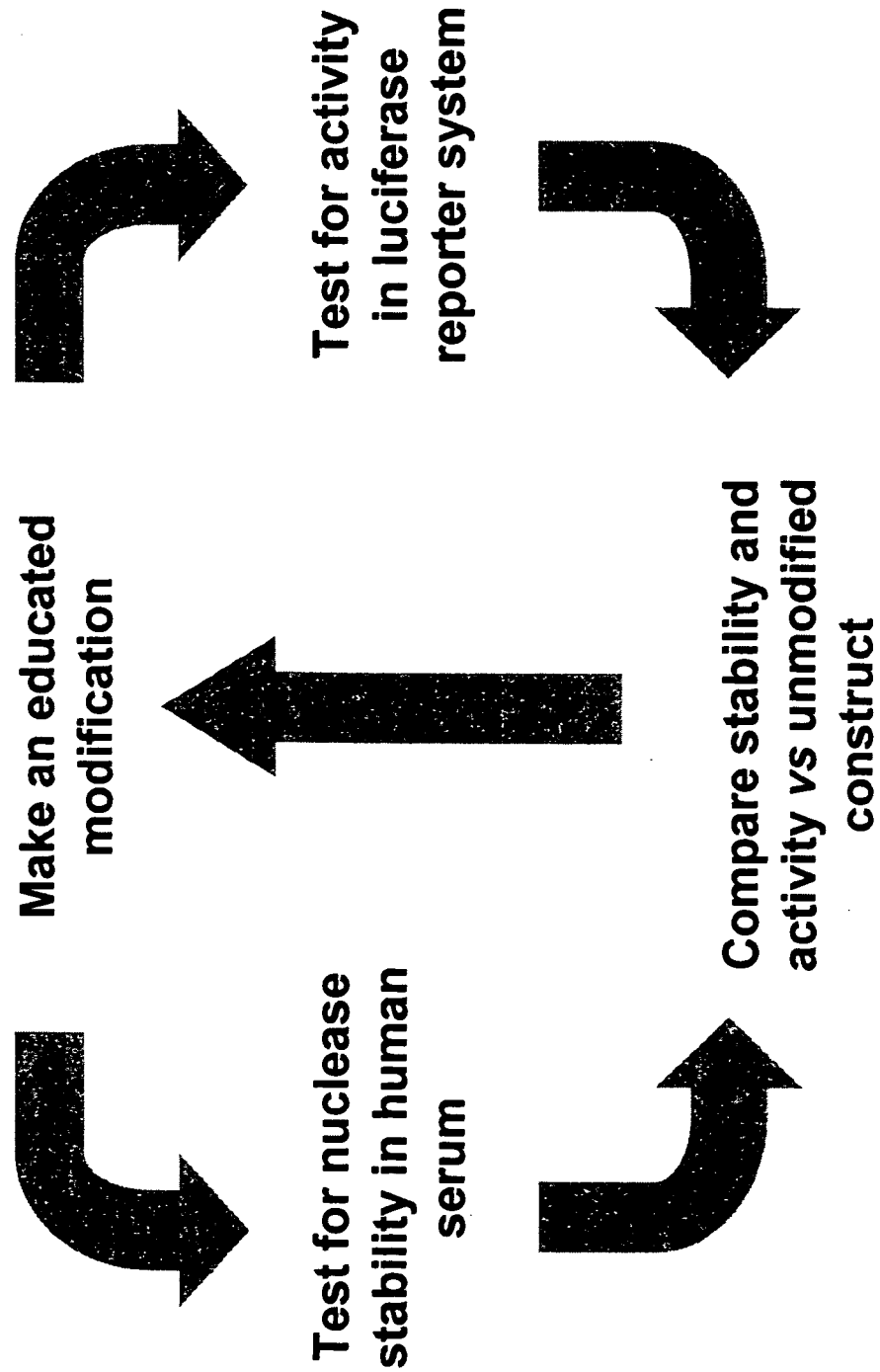
Figure 11: Modification Strategy

*Figure 12: Phosphorylated siNA constructs*
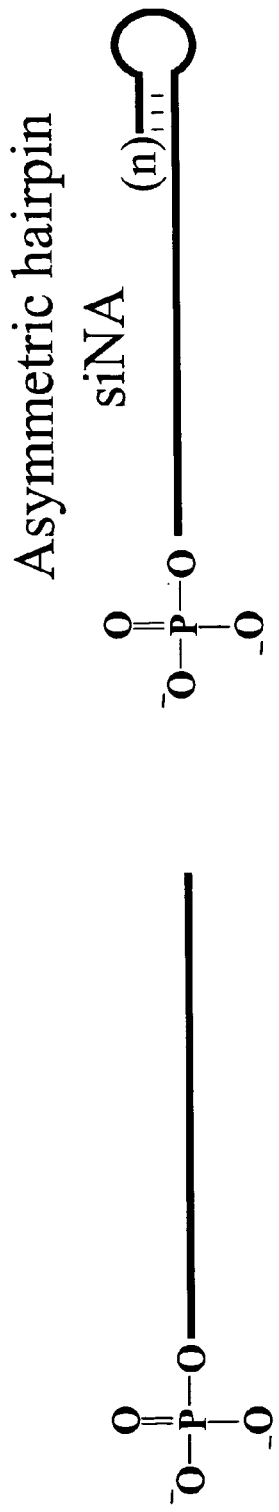
Asymmetric hairpin siNA
Asymmetric duplex siNA
(n) = number of base pairs (e.g. 3-18 bp)
Phosphates can be modified as described herein

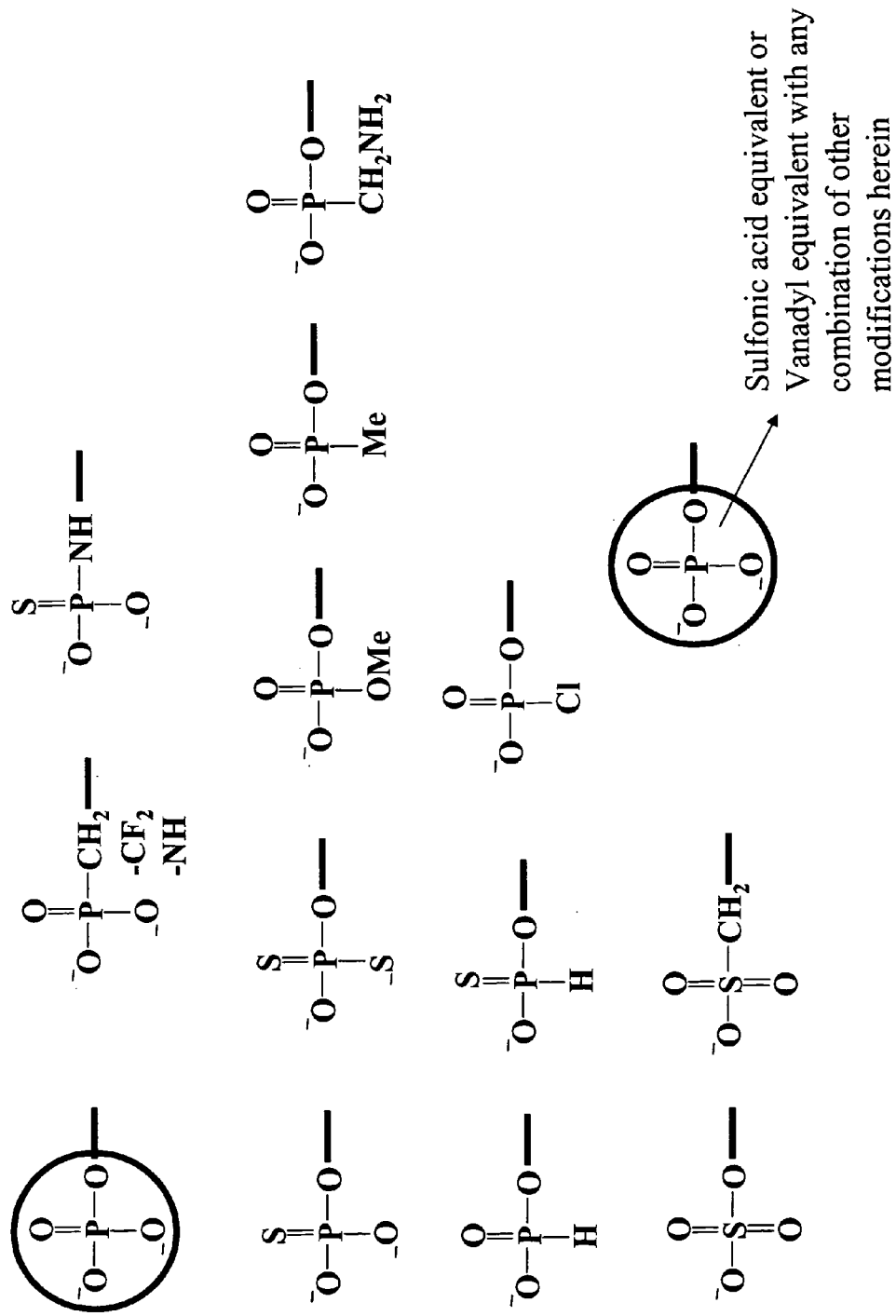
Figure 13: 5'-phosphate modifications

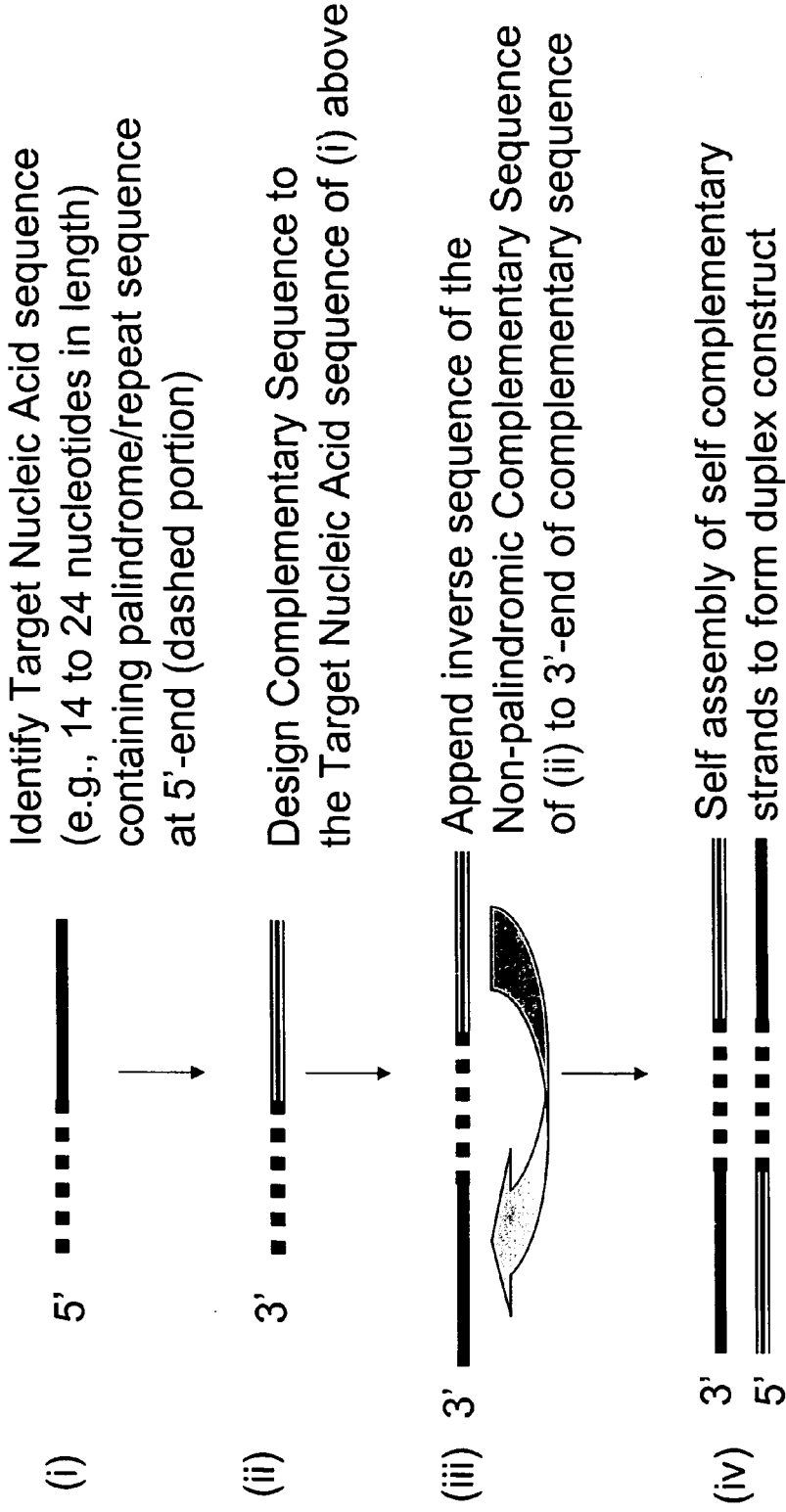
Figure 14A: Duplex forming oligonucleotide constructs that utilize palindrome or repeat sequences

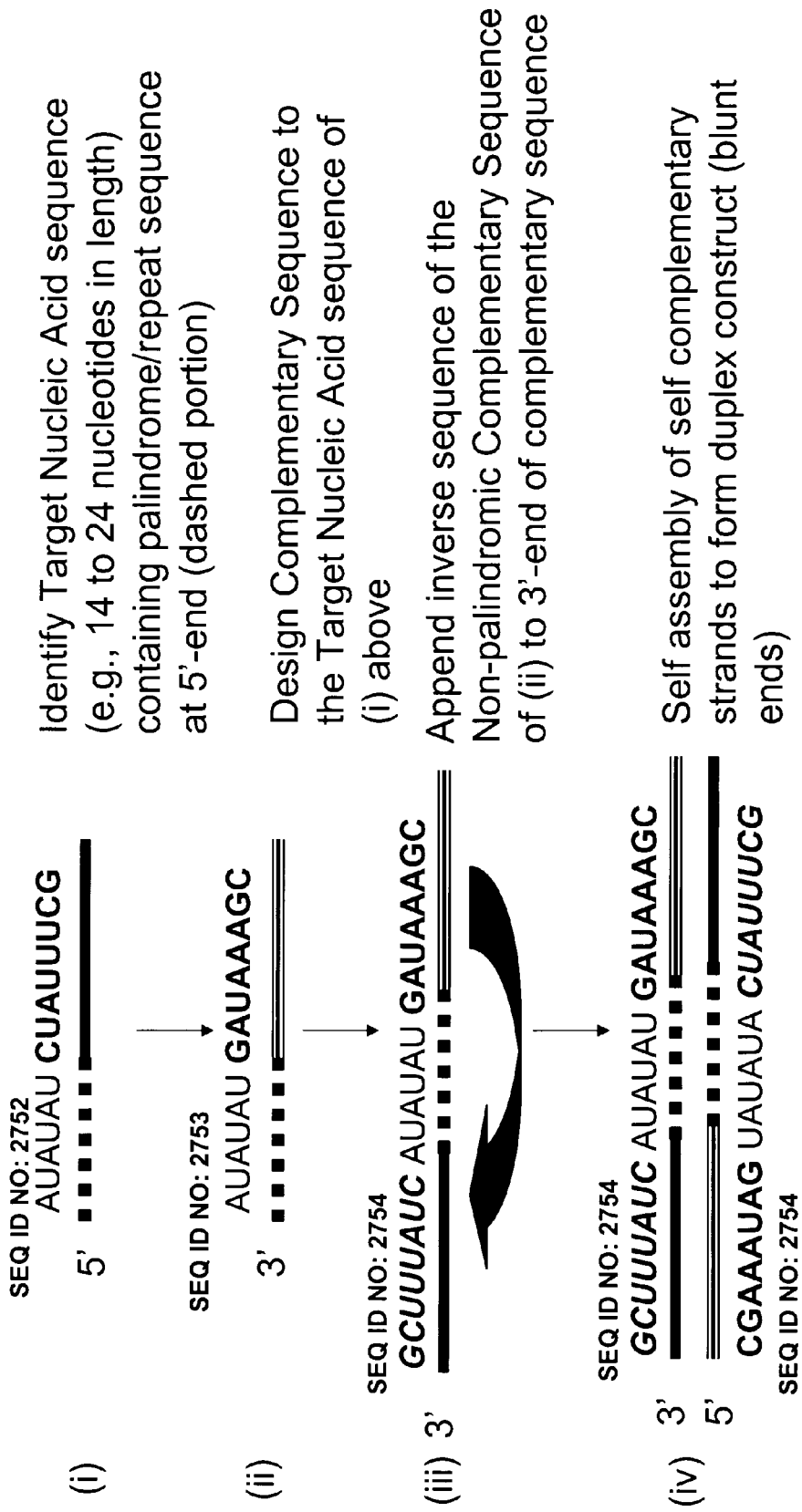
Figure 14B: Example of a duplex forming oligonucleotide sequence that utilizes a palindrome or repeat sequence

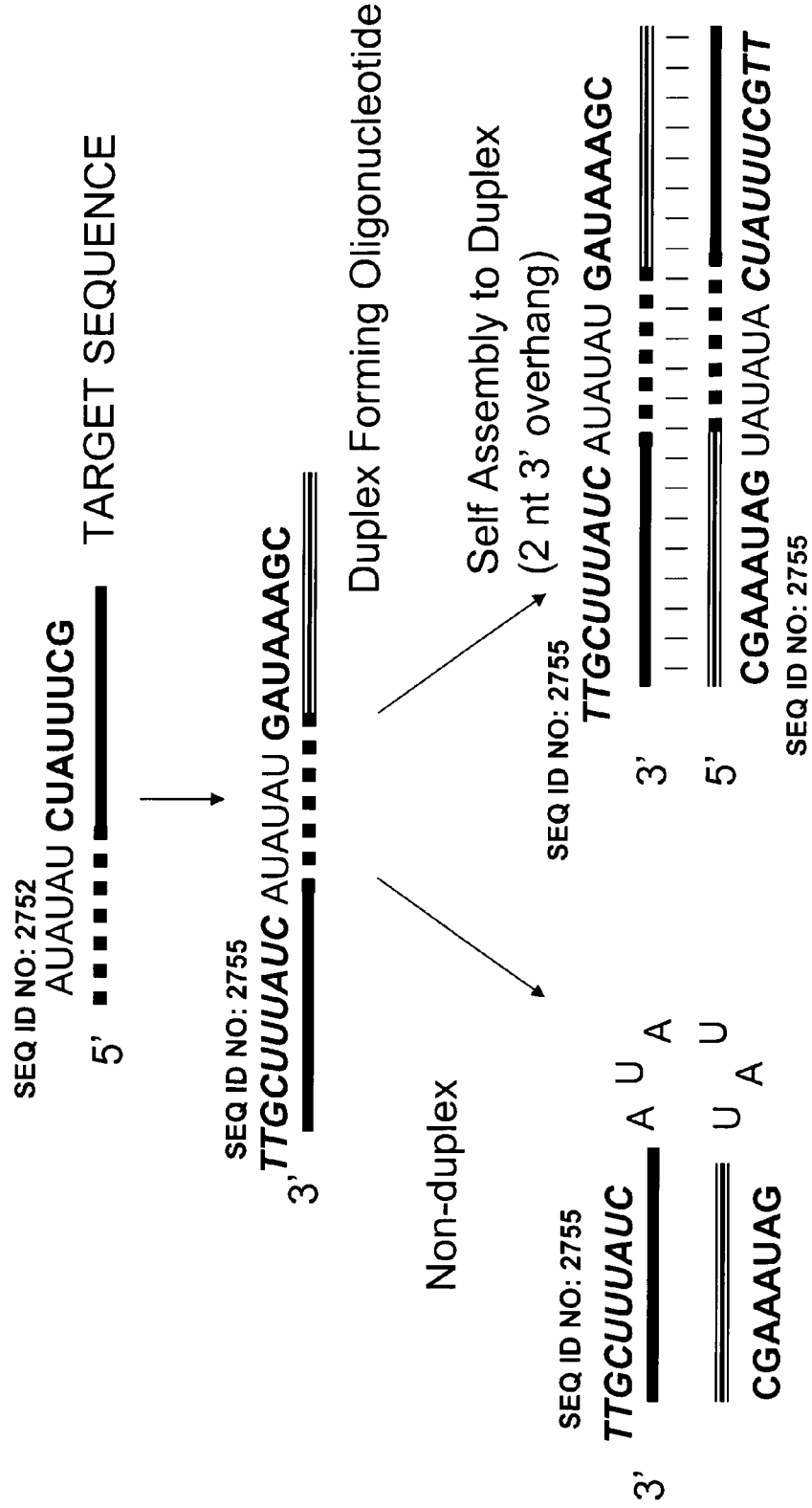
Figure 14C: Example of a duplex forming oligonucleotide sequence that utilizes a palindrome or repeat sequence, self assembly

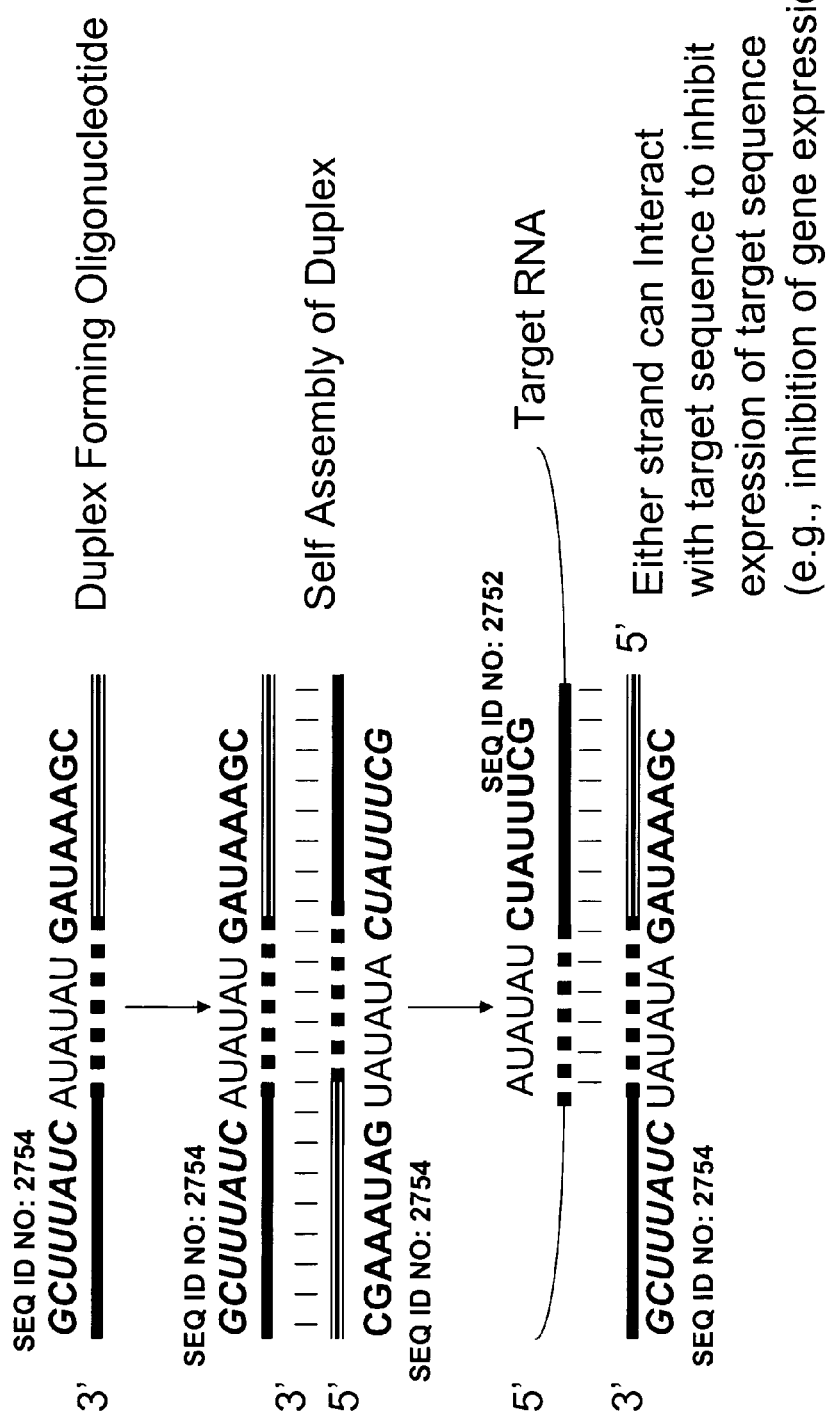
Figure 14D: Example of a duplex forming oligonucleotide sequence that utilizes a palindrome or repeat sequence, self assembly and inhibition of Target Sequence Expression

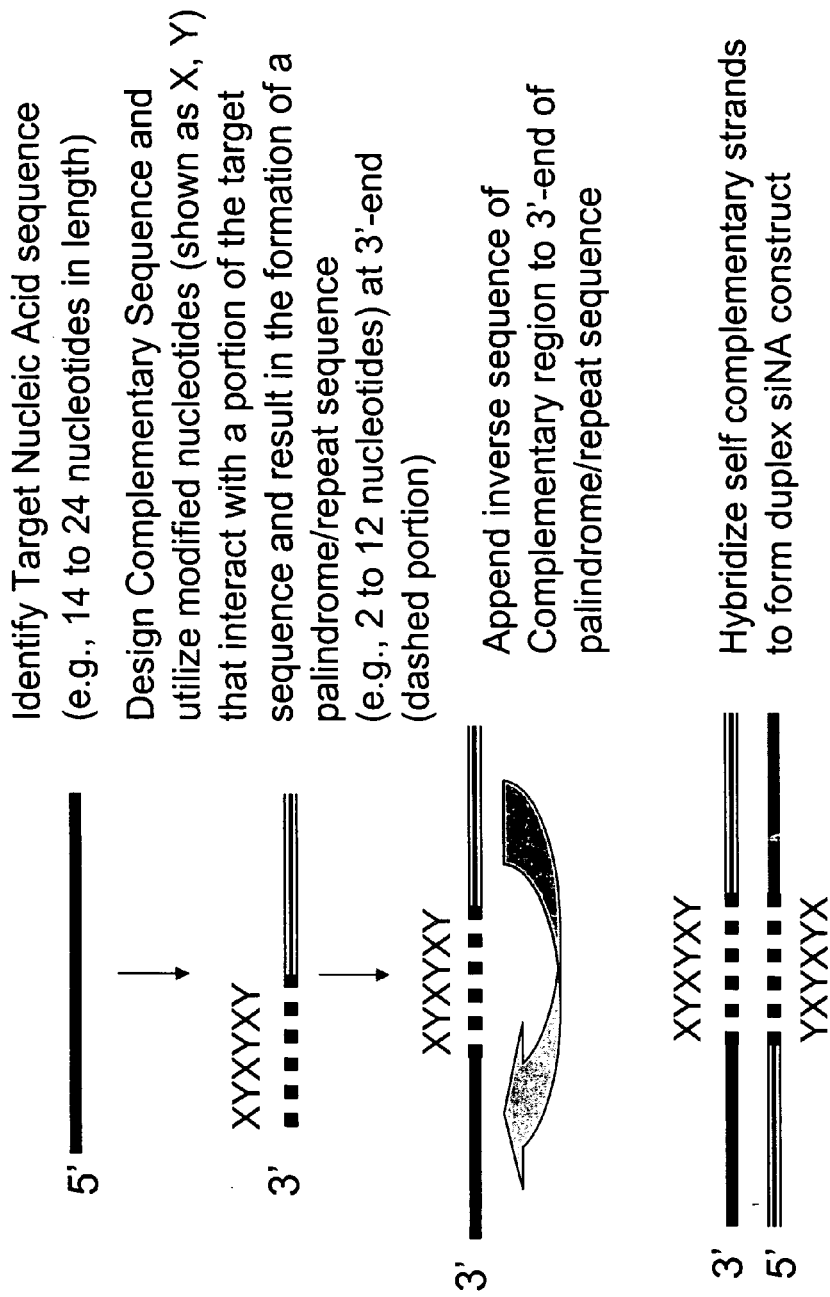
Figure 15: Duplex forming oligonucleotide constructs that utilize artificial palindrome or repeat sequences

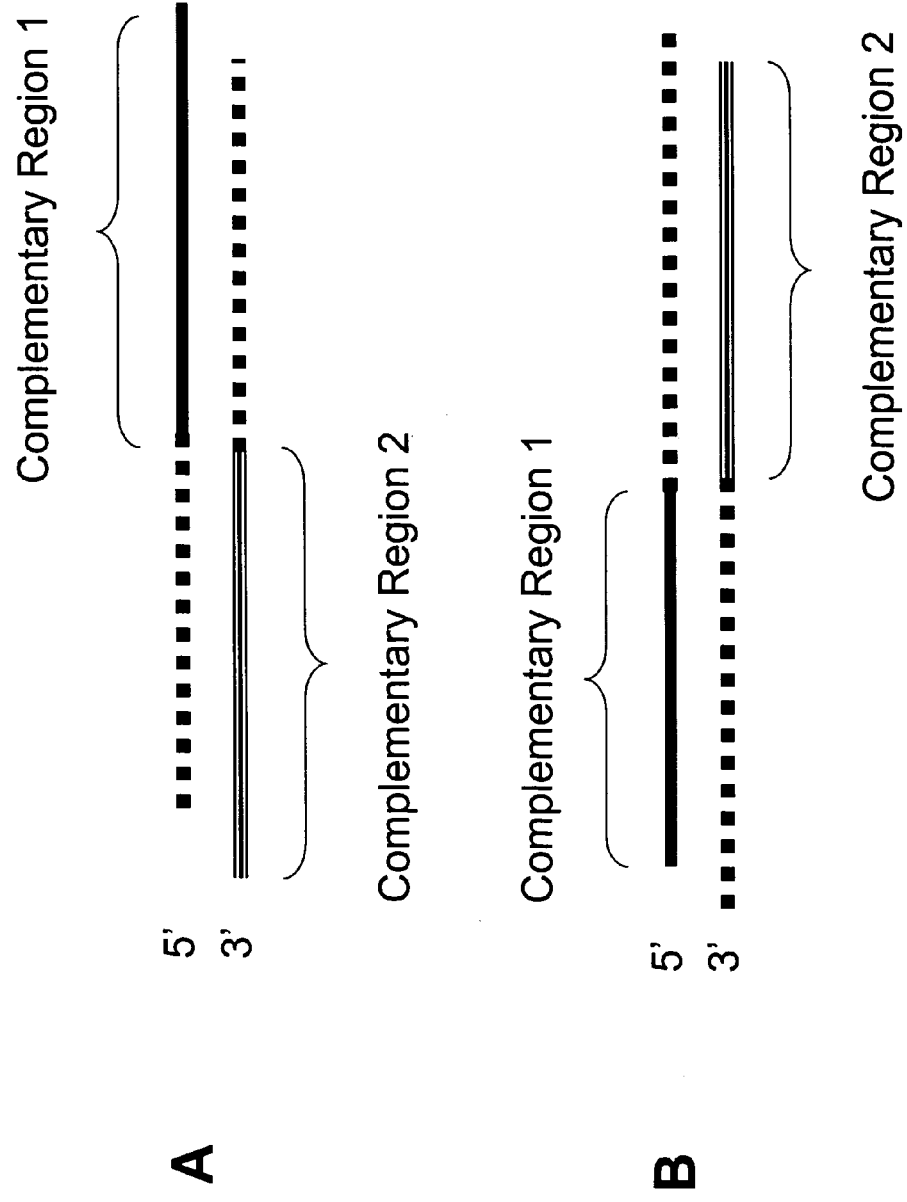
Figure 16: Examples of double stranded multifunctional siNA constructs with distinct complementary regions

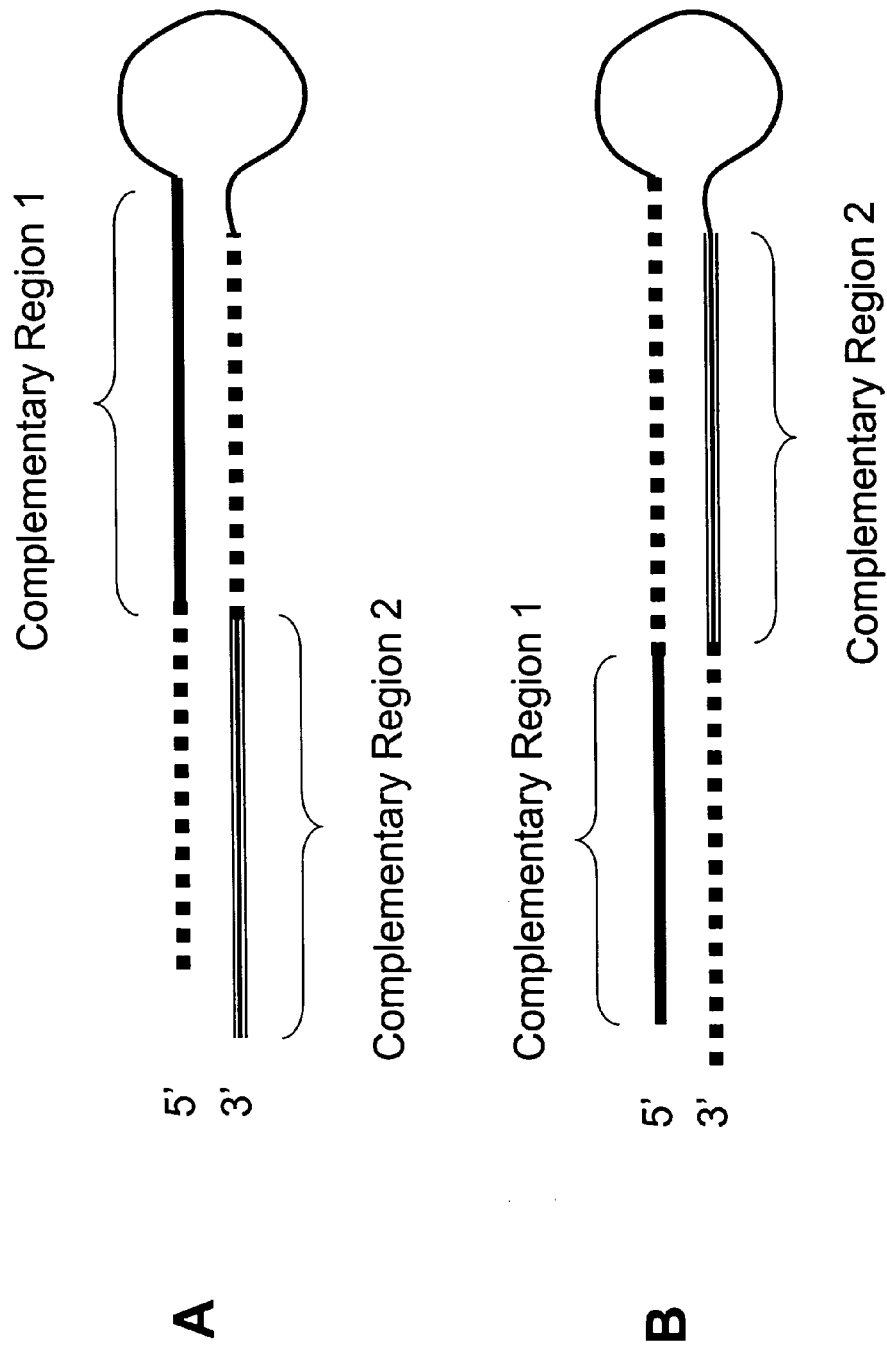
Figure 17: Examples of hairpin multifunctional siNA constructs with distinct complementary regions

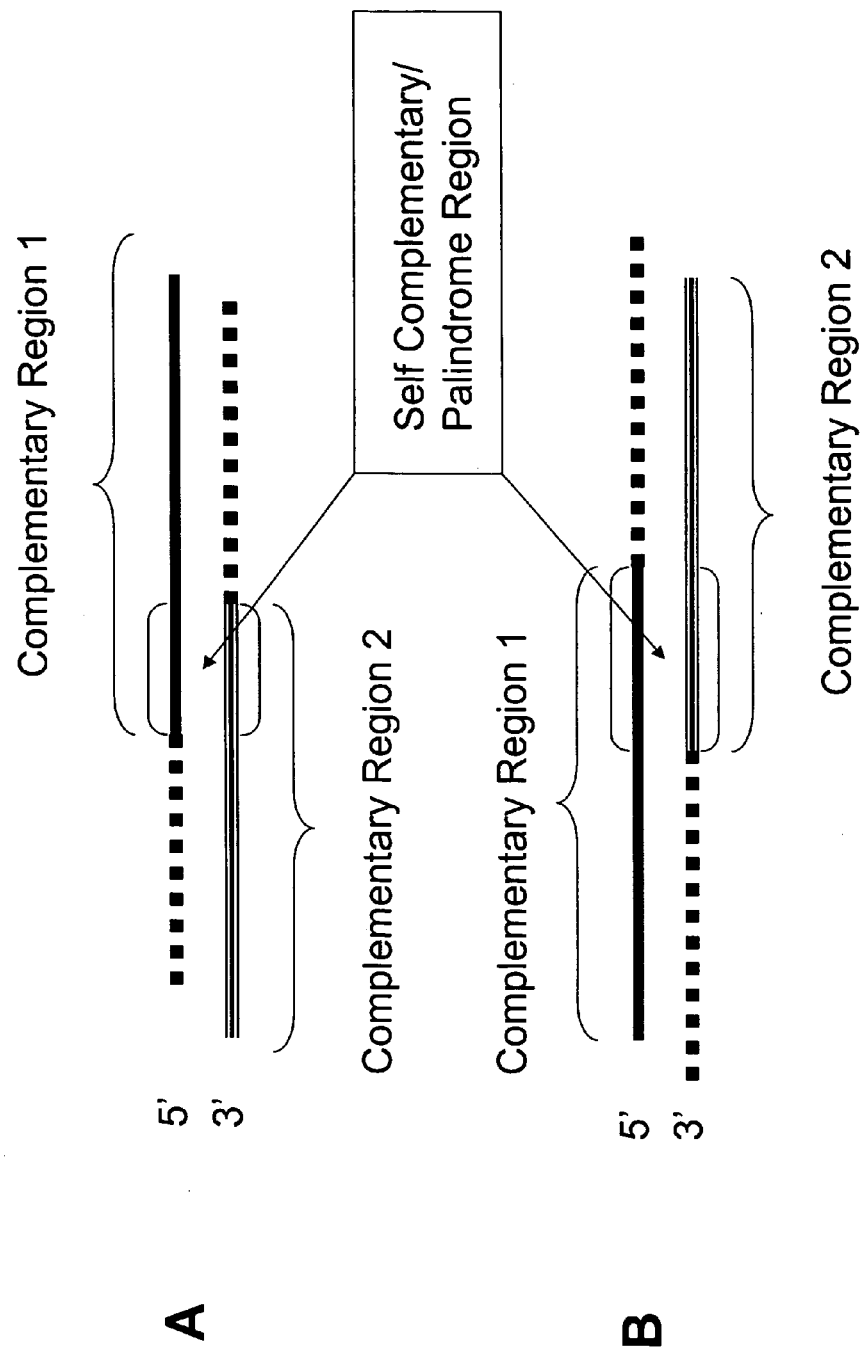
Figure 18: Examples of double stranded multifunctional siNA constructs with distinct complementary regions and a self complementary/palindrome region

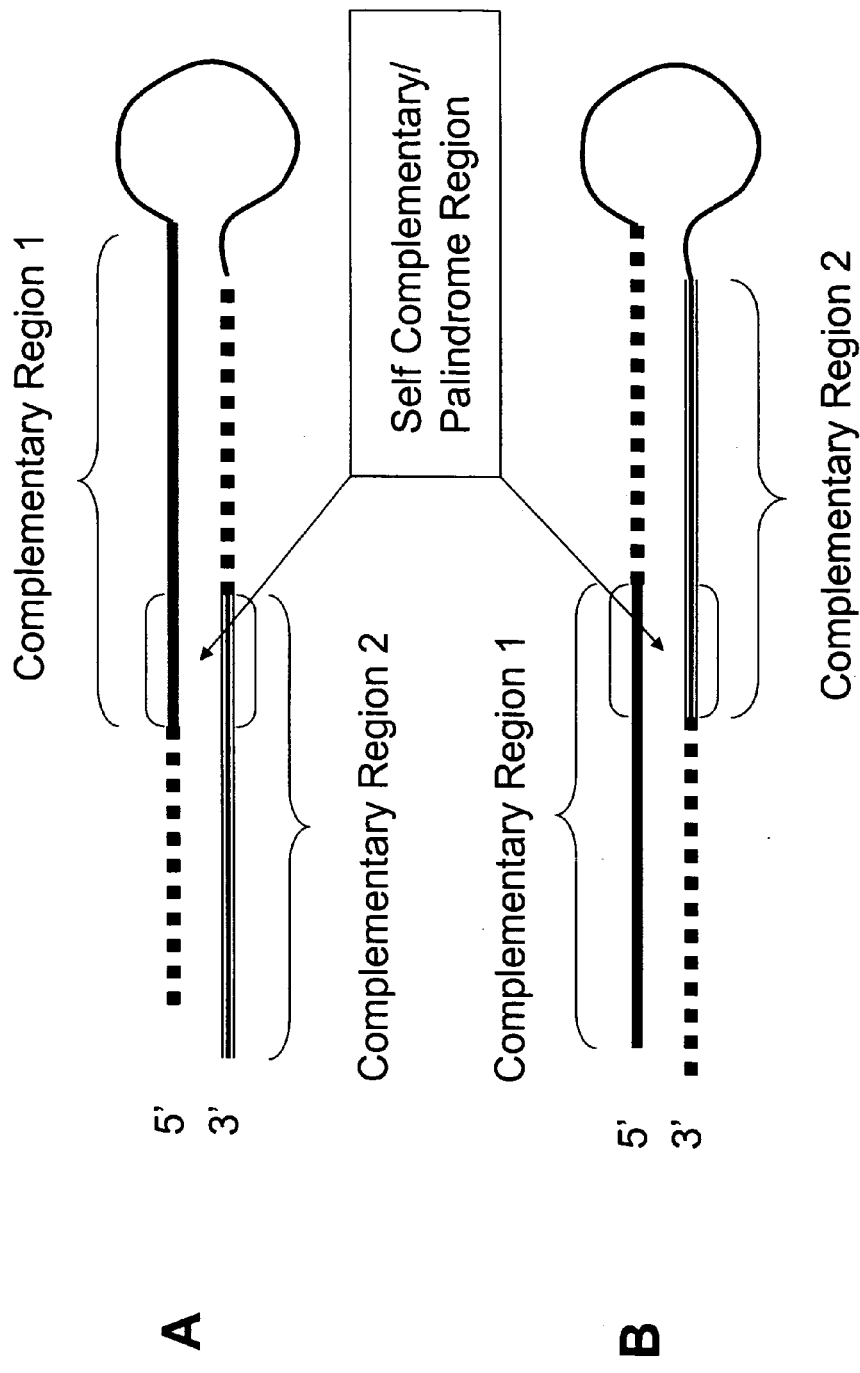
Figure 19: Examples of hairpin multifunctional siNA constructs with distinct complementary regions and a self complementary/palindrome region

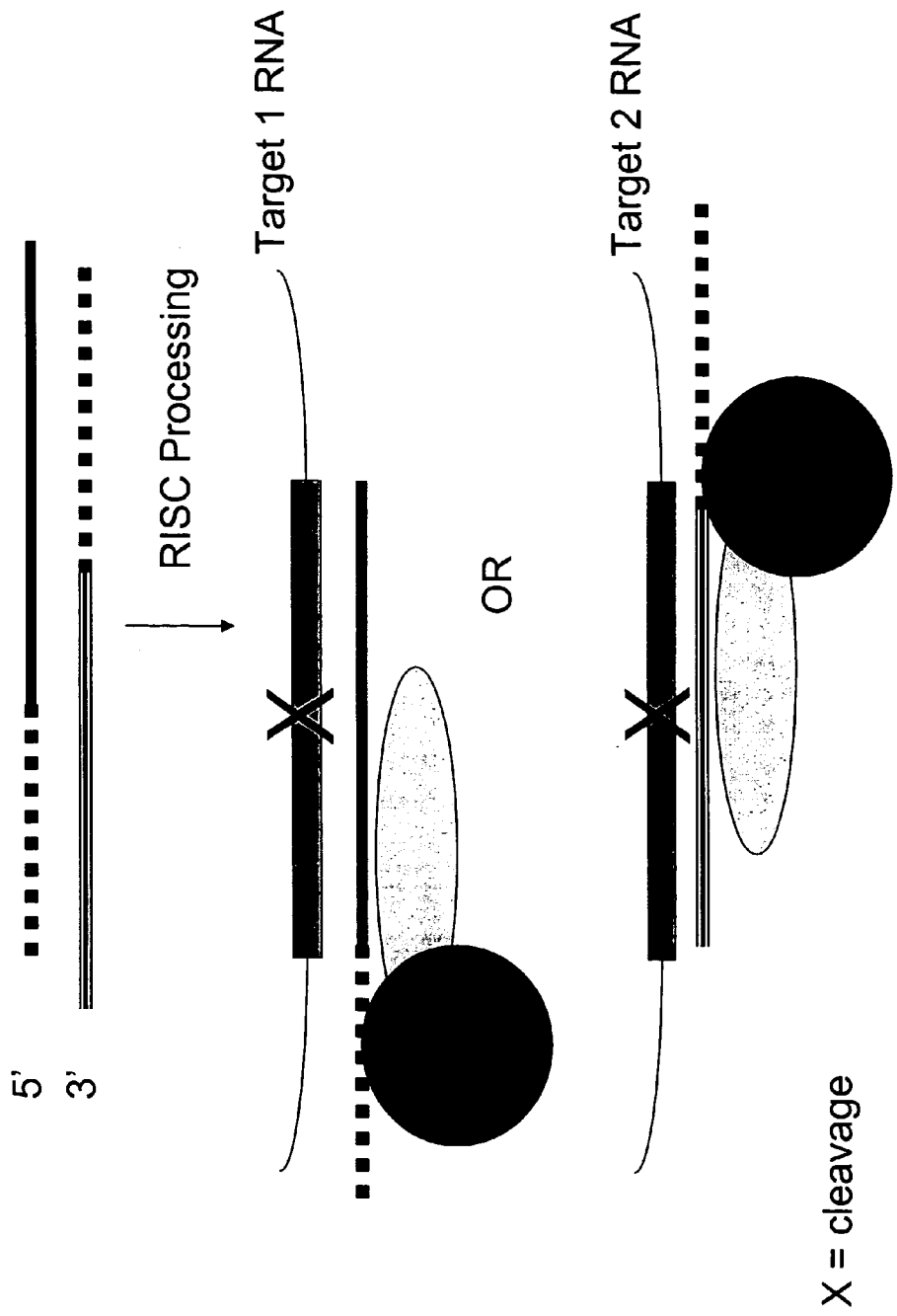
Figure 20: Example of multifunctional siNA targeting two separate Target nucleic acid sequences

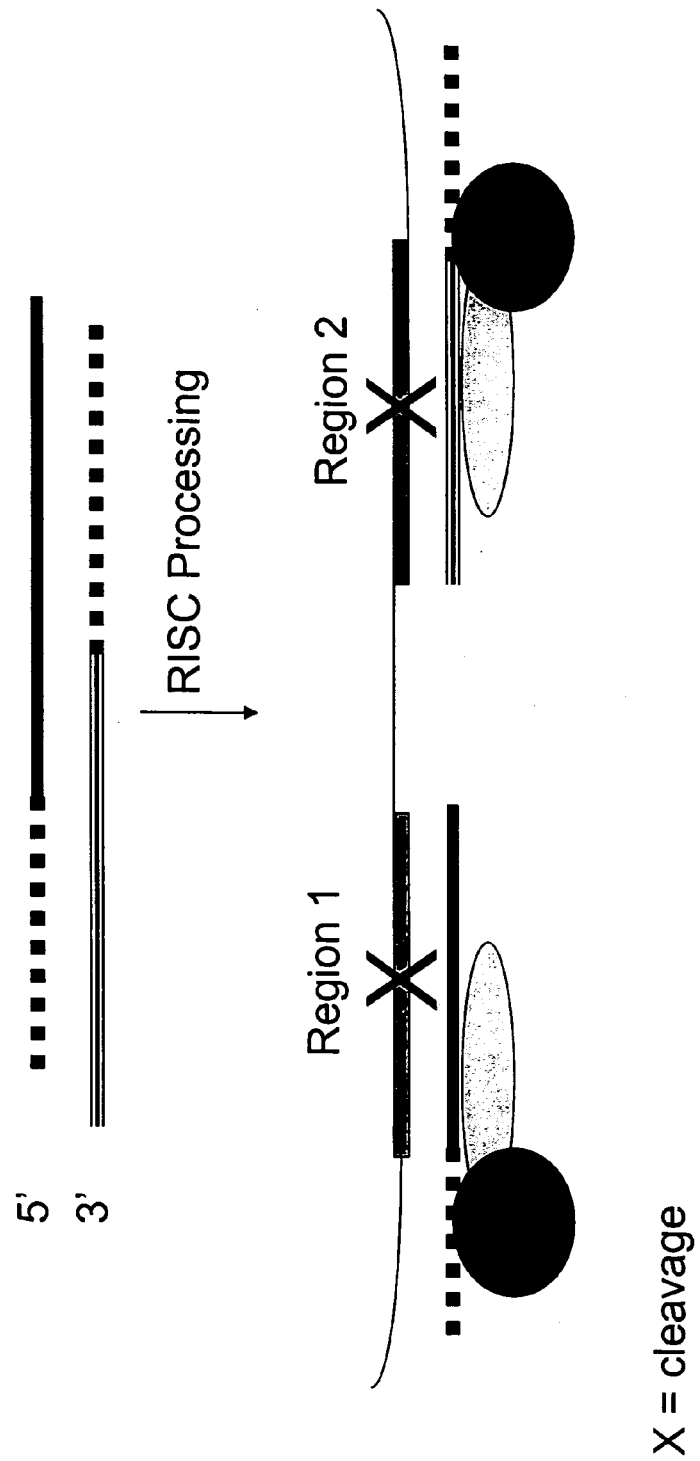
Figure 21: Example of multifunctional siNA targeting two regions within the same target nucleic acid sequence

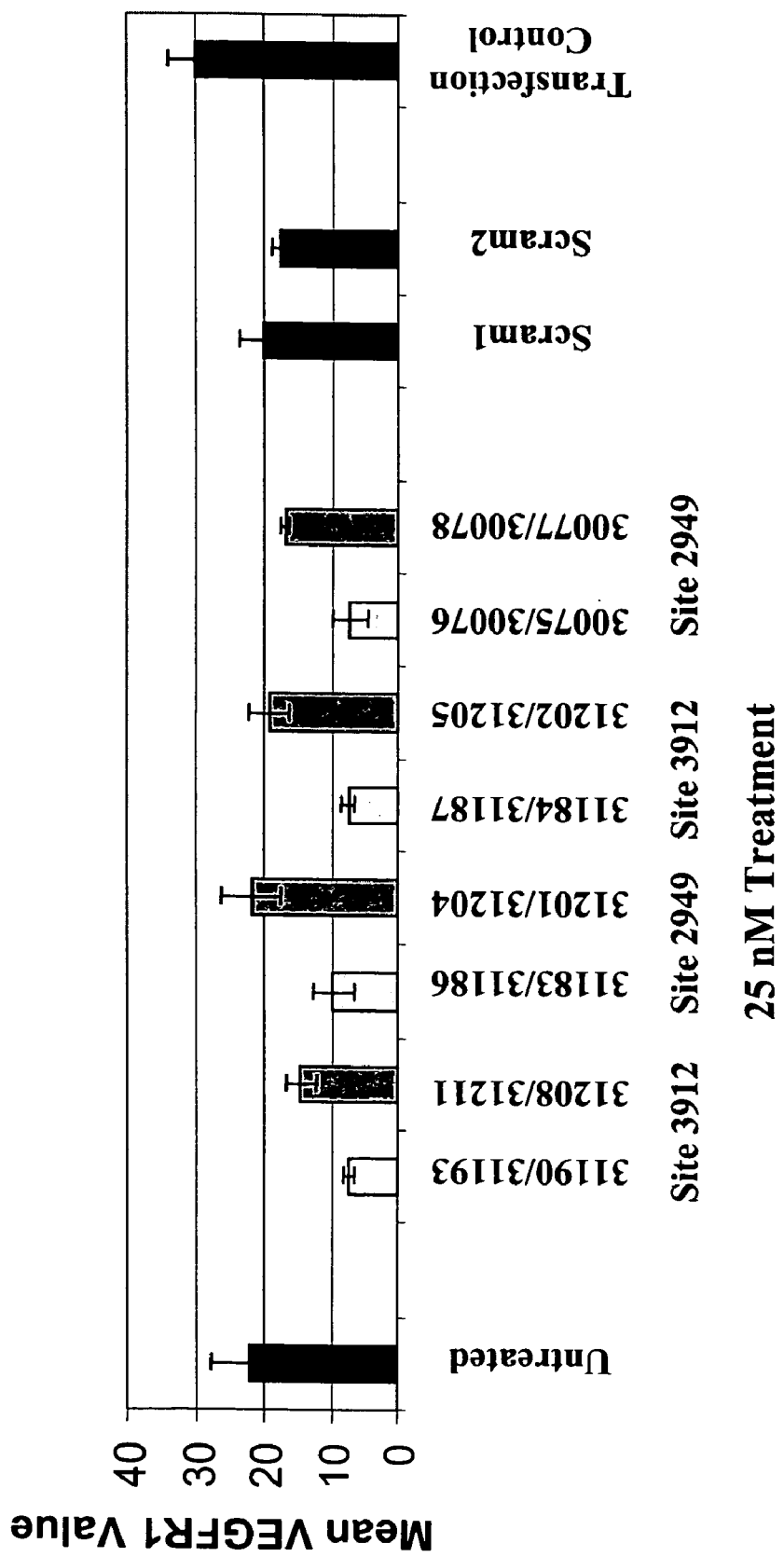
*Figure 22: A375 24h 36B4 VEGFR1 mRNA Expression*

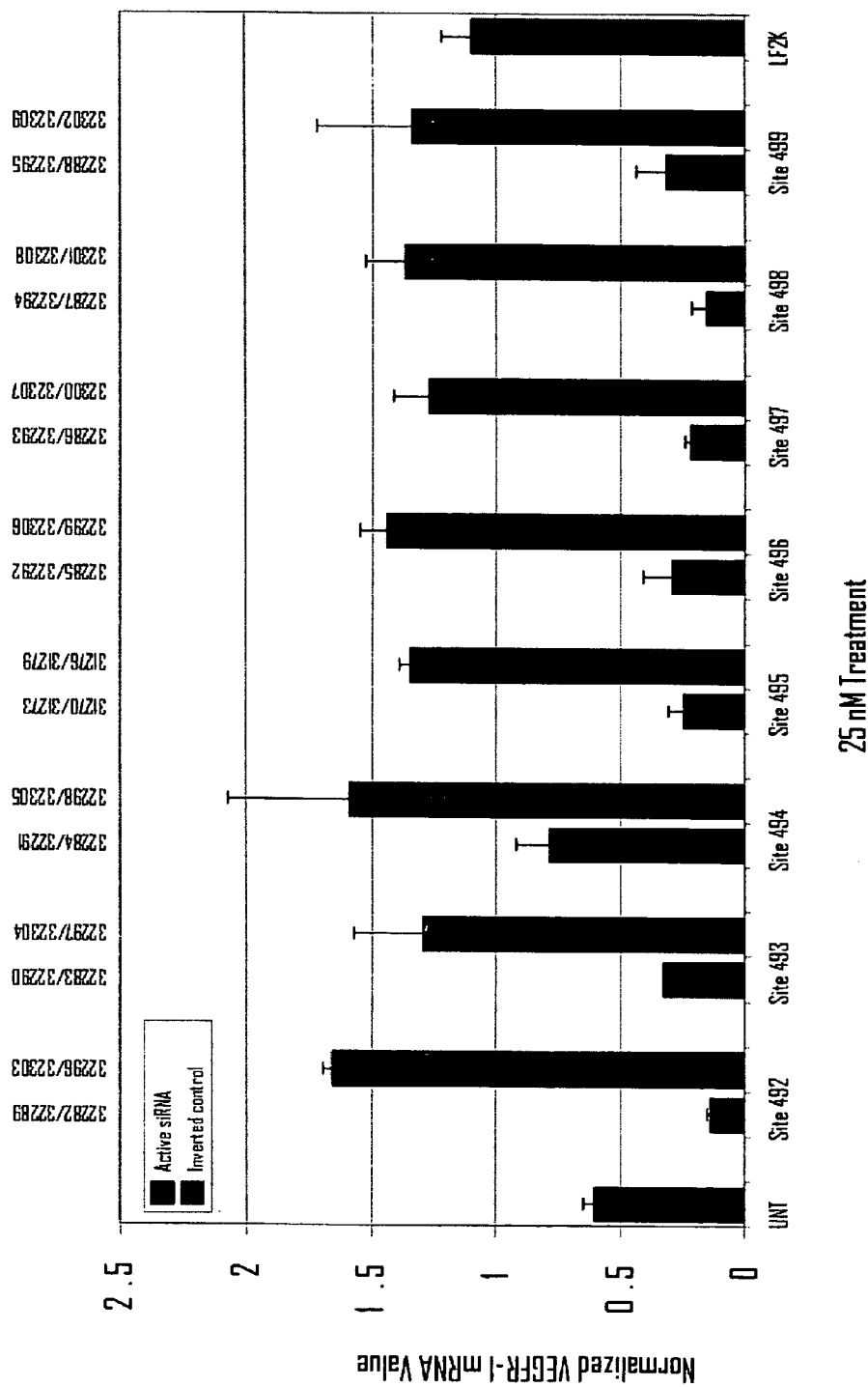

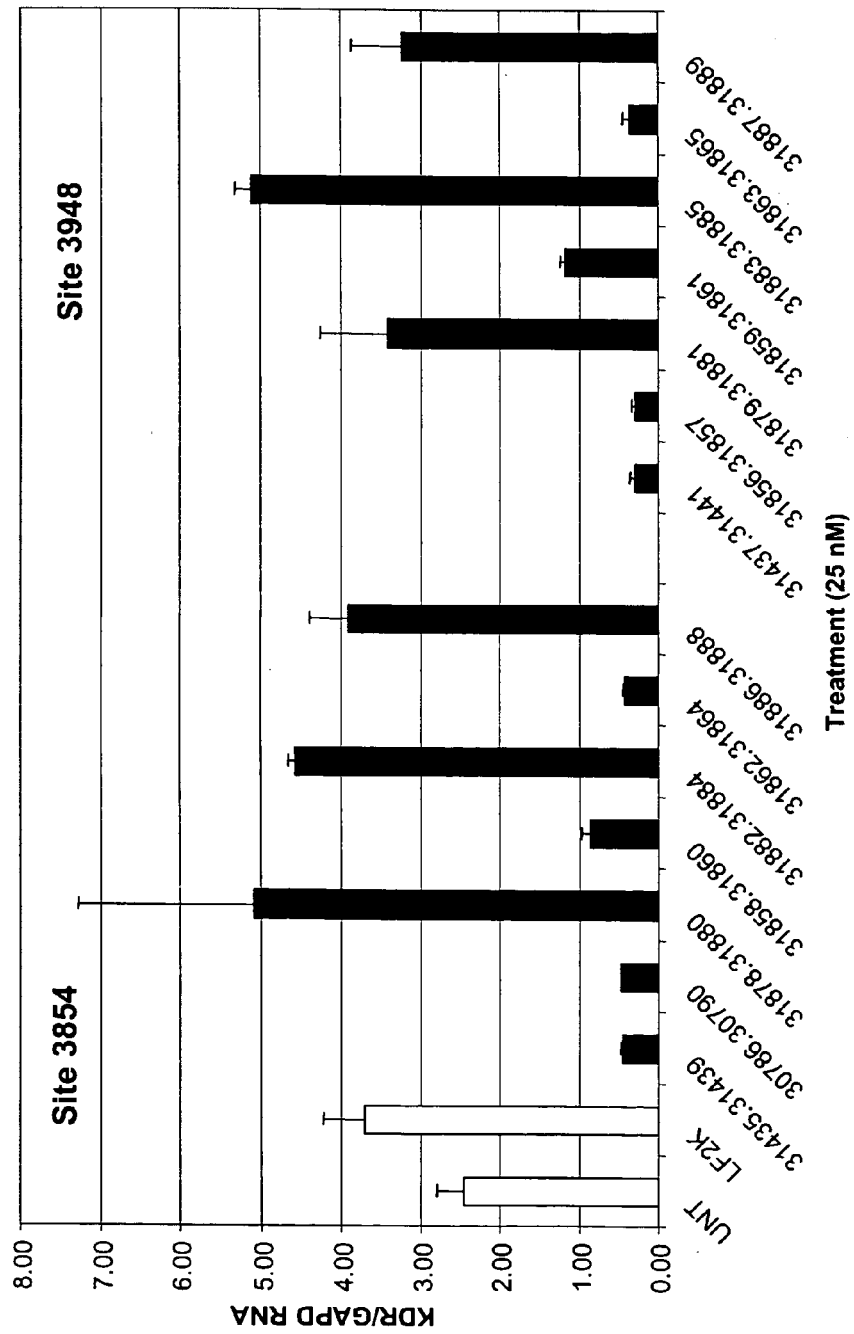

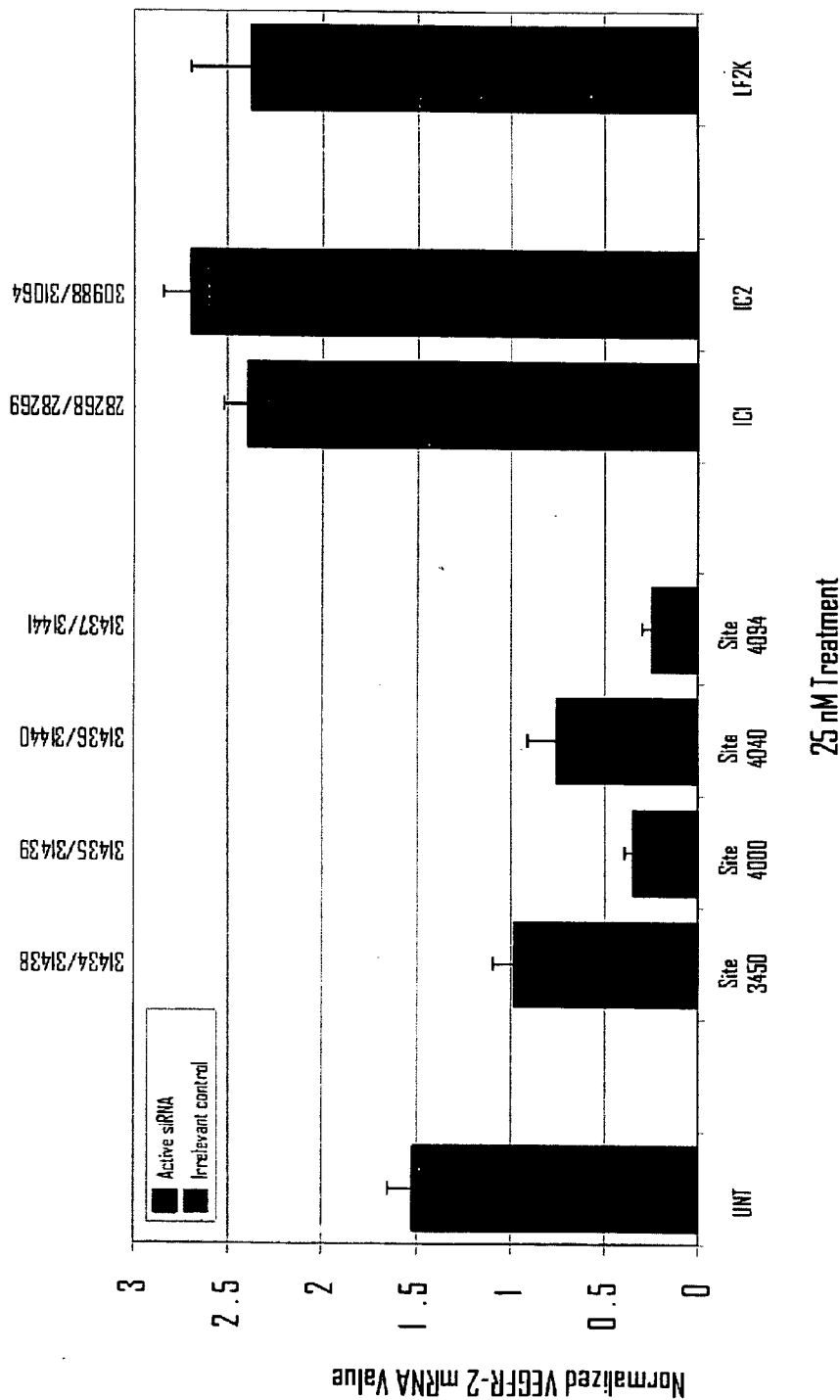
Figure 25: VEGFR2 siNA in HAEC cells

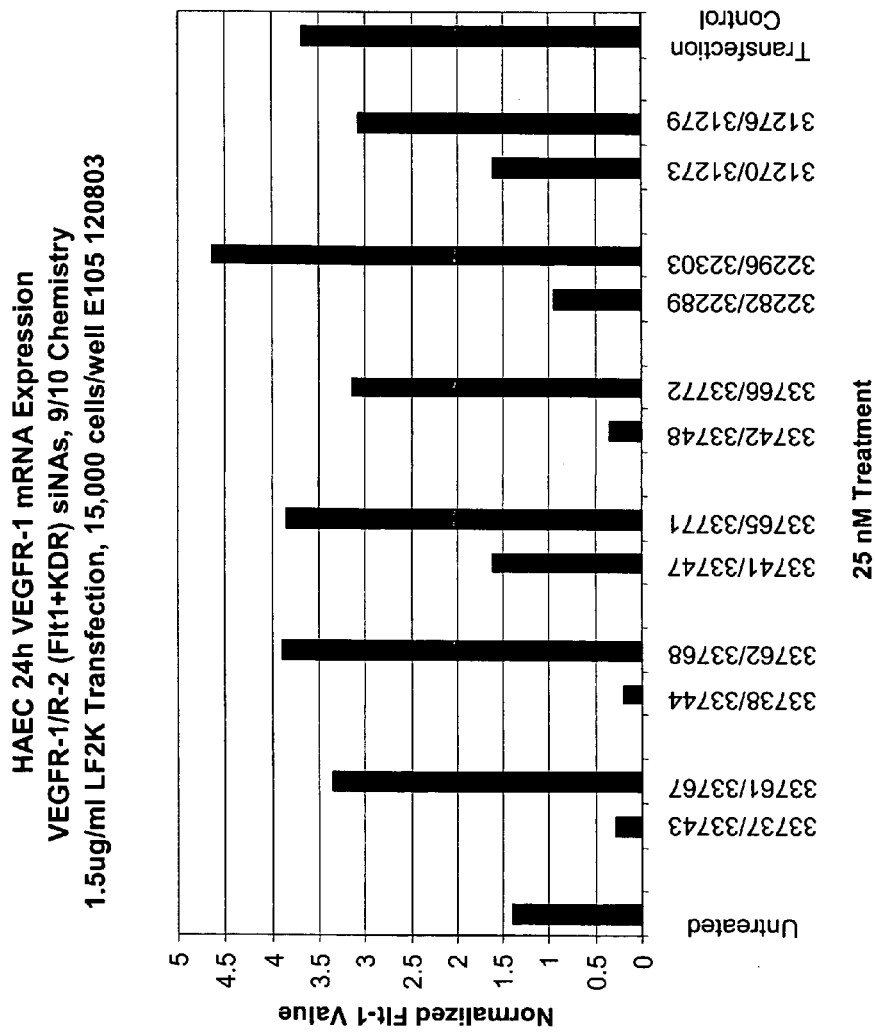
Figure 26A: Inhibition of VEGFR1 RNA expression with siNAs targeting VEGFR1 and VEGFR2 homologous sequences

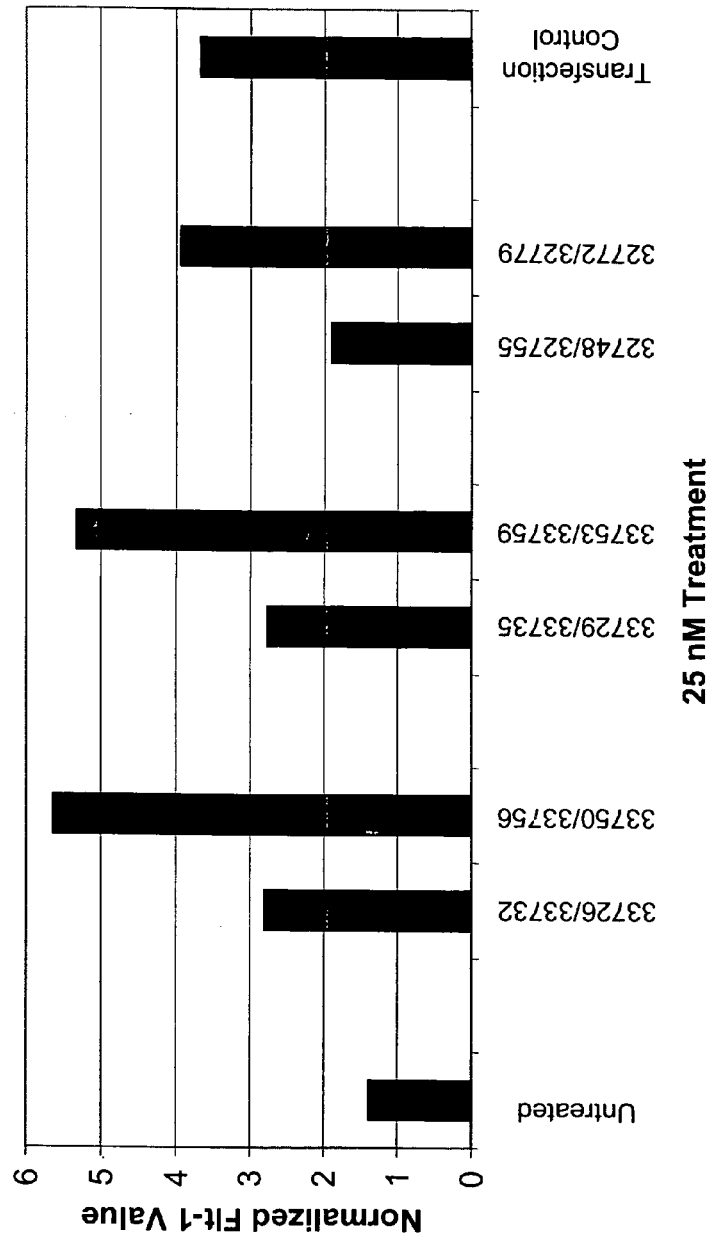
Figure 26B: Inhibition of VEGFR1 RNA expression with siNAs targeting VEGFR1 and VEGFR2 homologous sequences

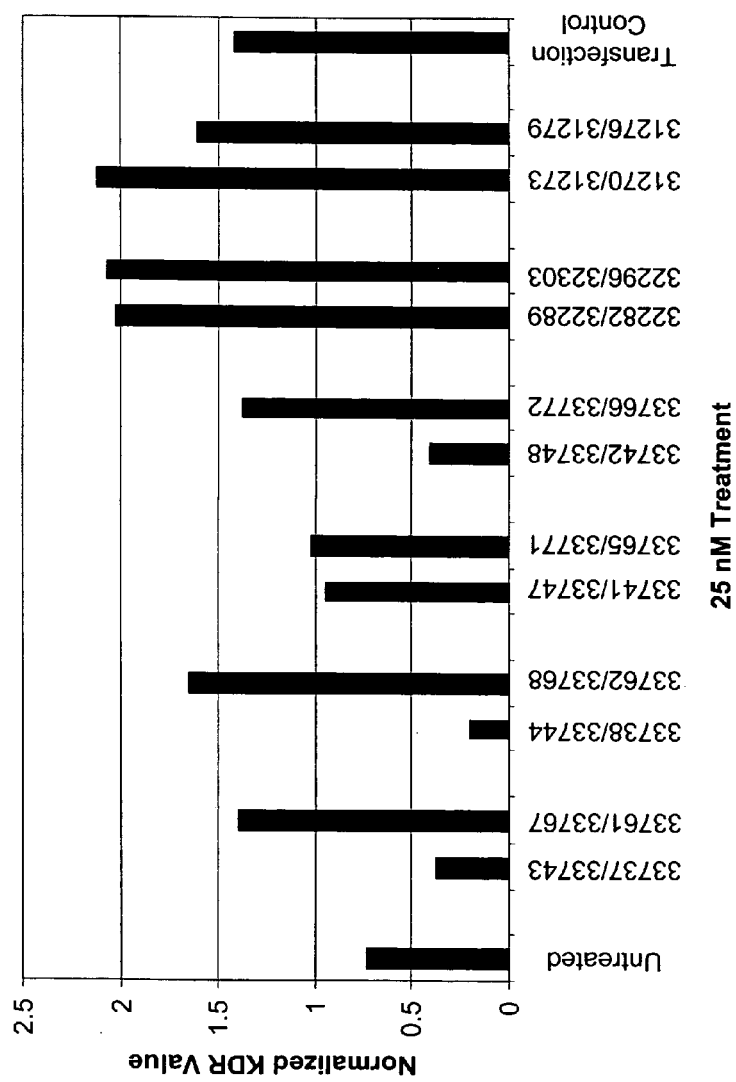
Figure 27A: Inhibition of VEGFR2 RNA expression with siNAs targeting VEGFR1 and VEGFR2 homologous sequences

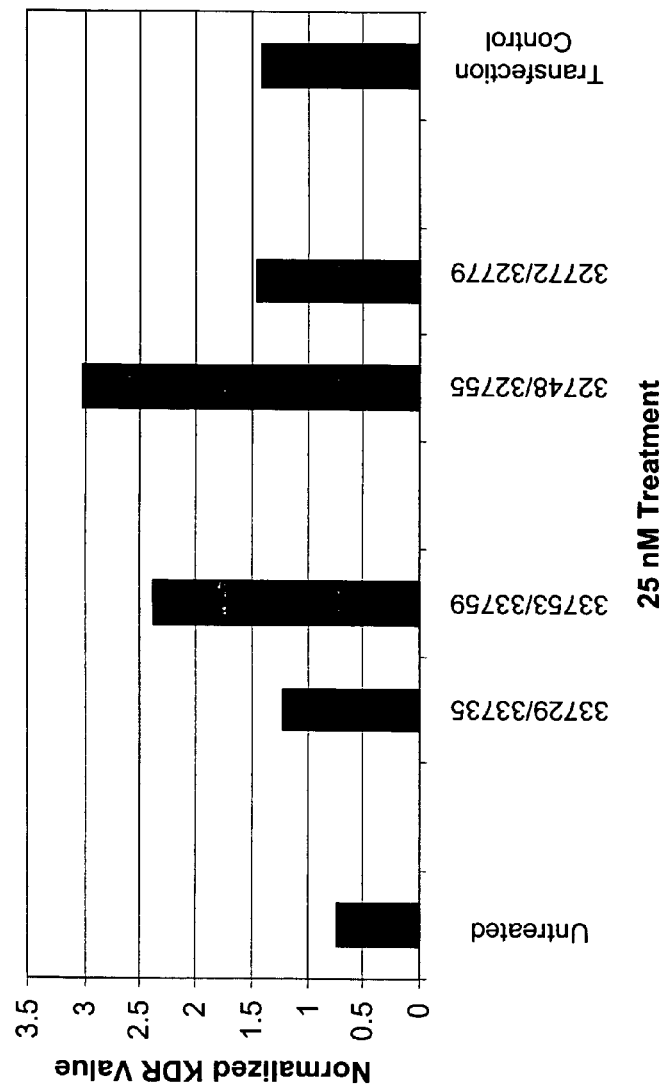
Figure 27B: Inhibition of VEGFR2 RNA expression with siNAs targeting VEGFR1 and VEGFR2 homologous sequences Figure 28: Inhibition of VEGF-Induced Angiogenesis by siNAs

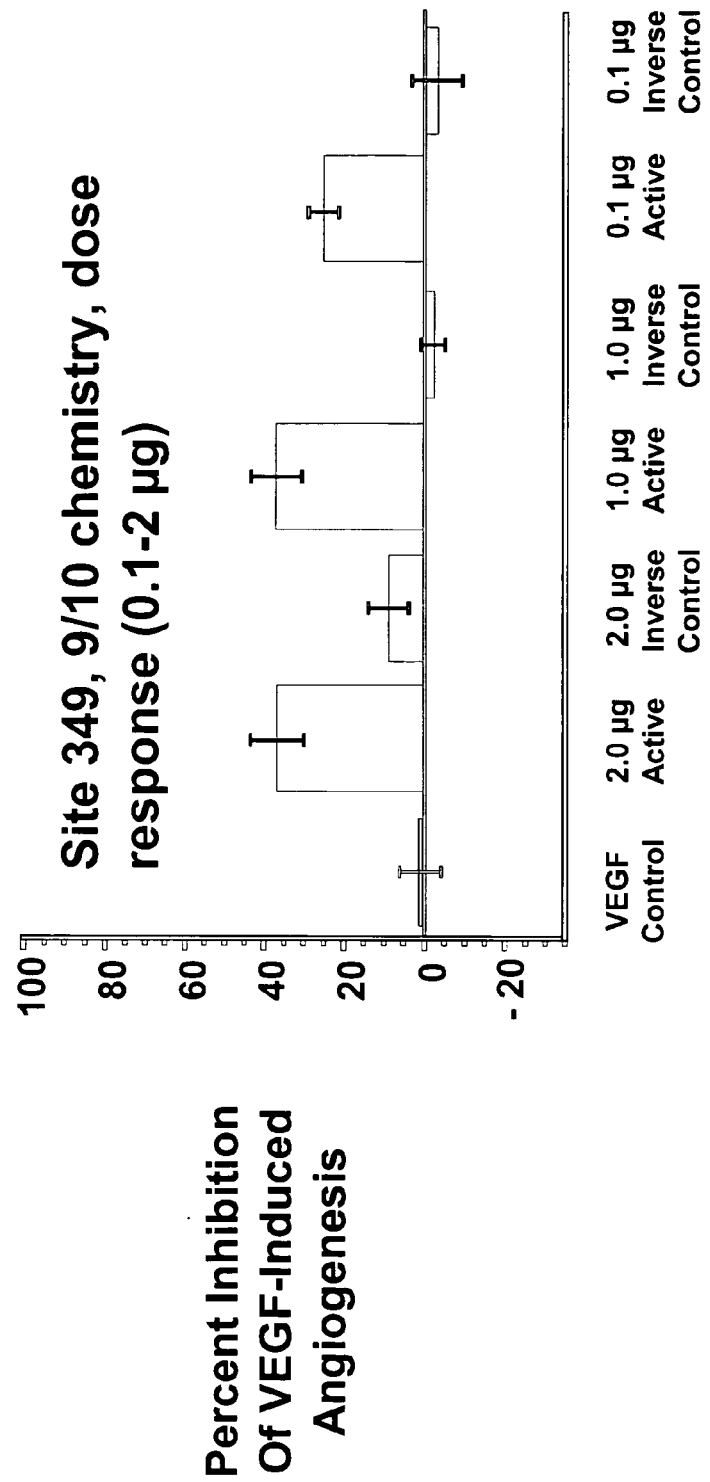
Figure 29: siNA Targeting VEGFR1 Inhibits VEGF-Induced Rat Corneal Angiogenesis

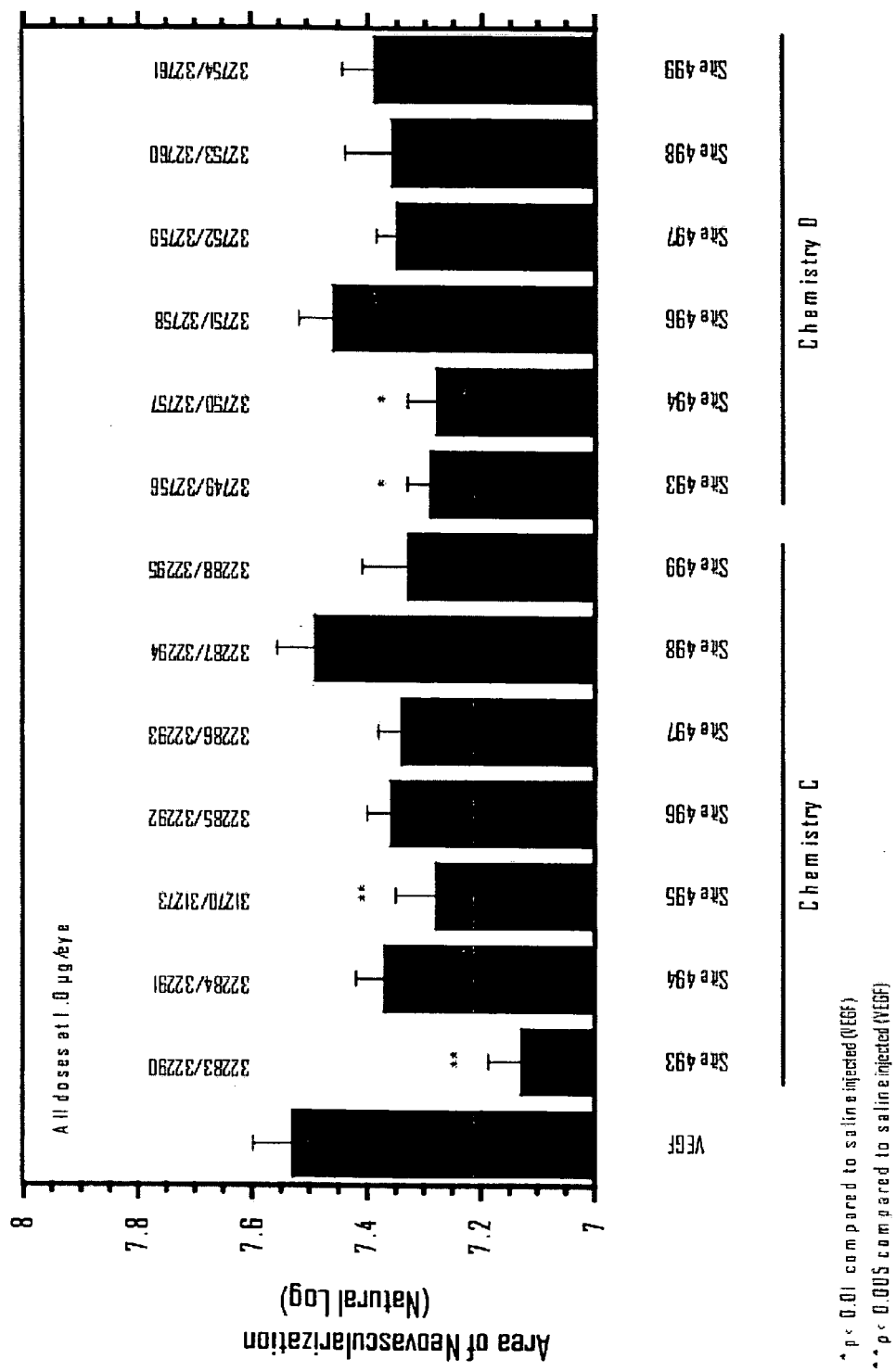

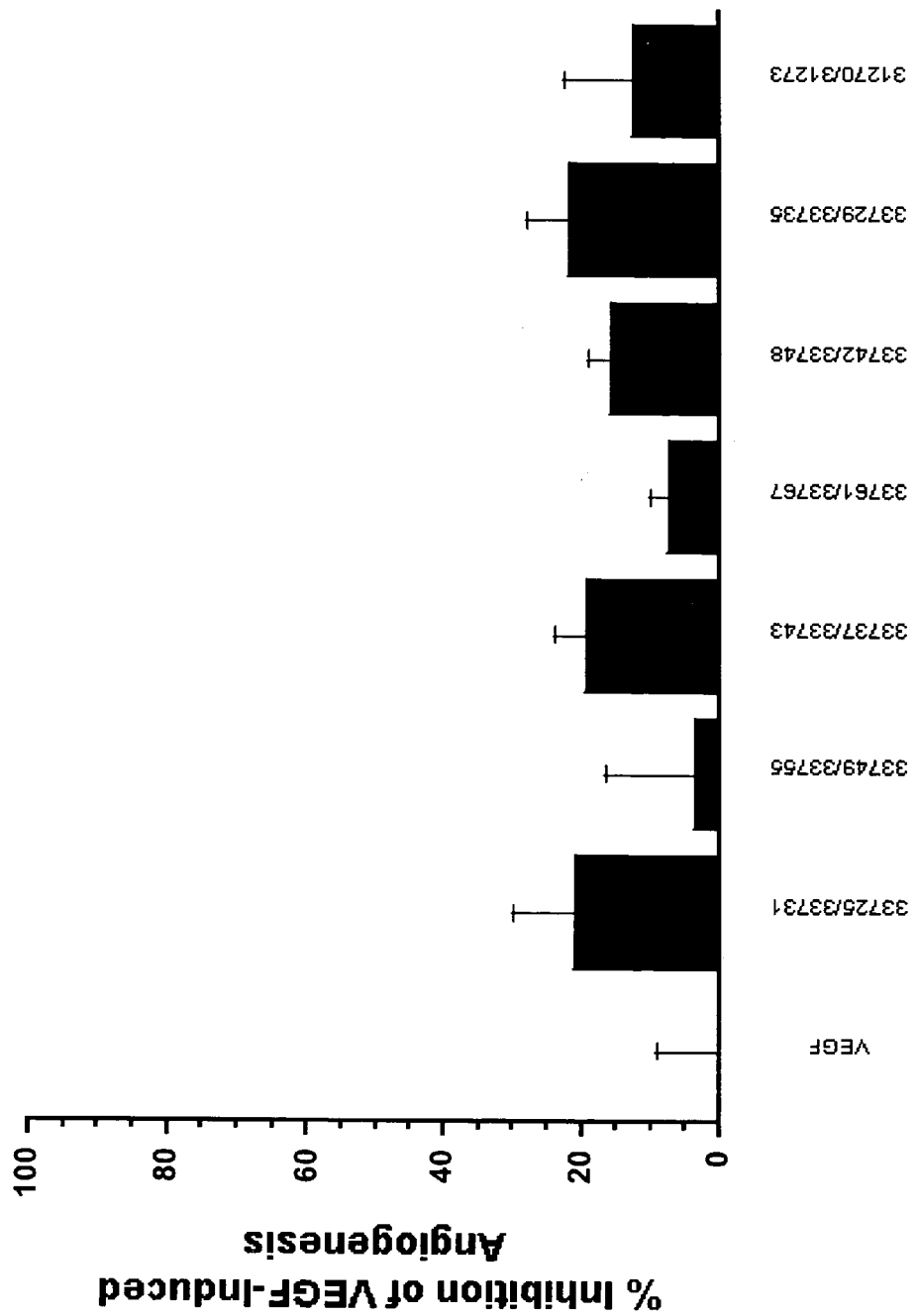
Figure 31: Inhibition of VEGF Induced Ocular Angiogenesis with siNAs targeting VEGFR1 and VEGFR2 homologous sequences

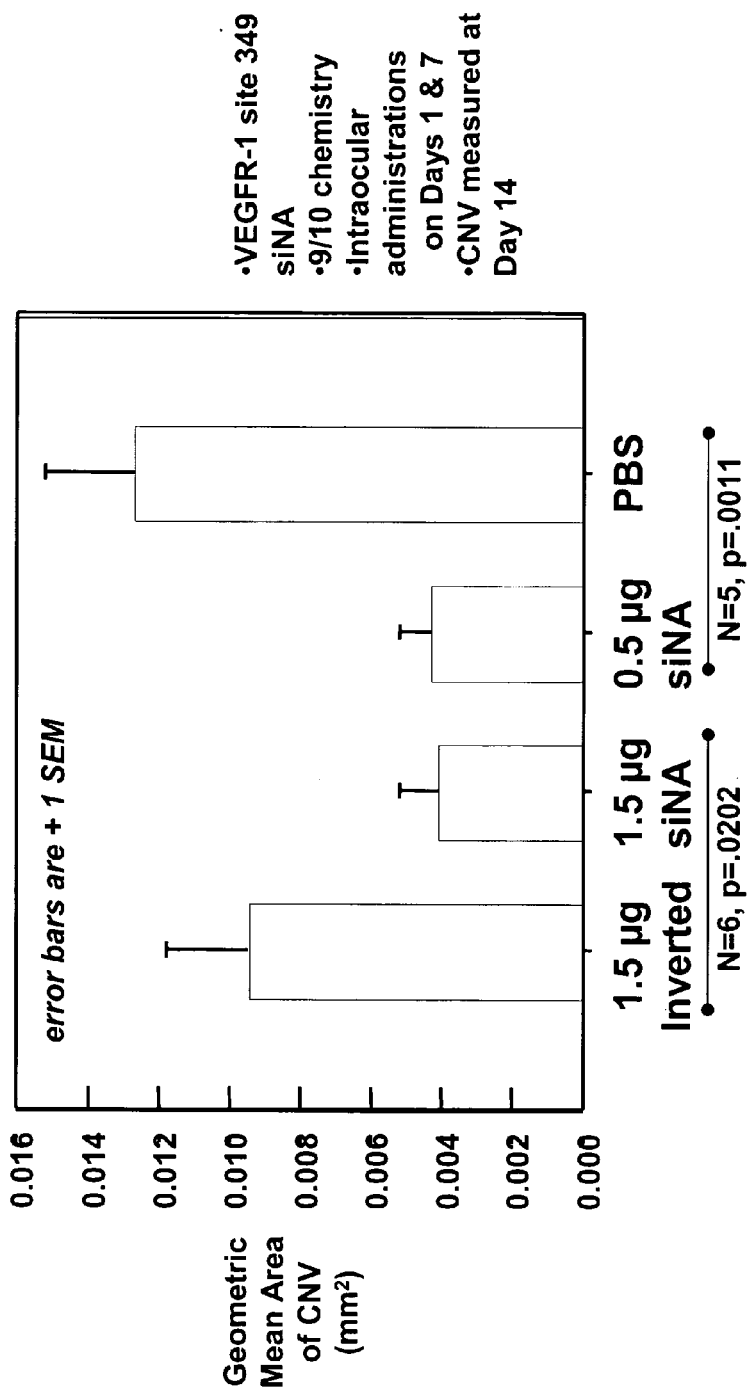
Figure 32: Inhibition of Mouse CNV with anti-VEGFR-1 siNA (intraocular administration)

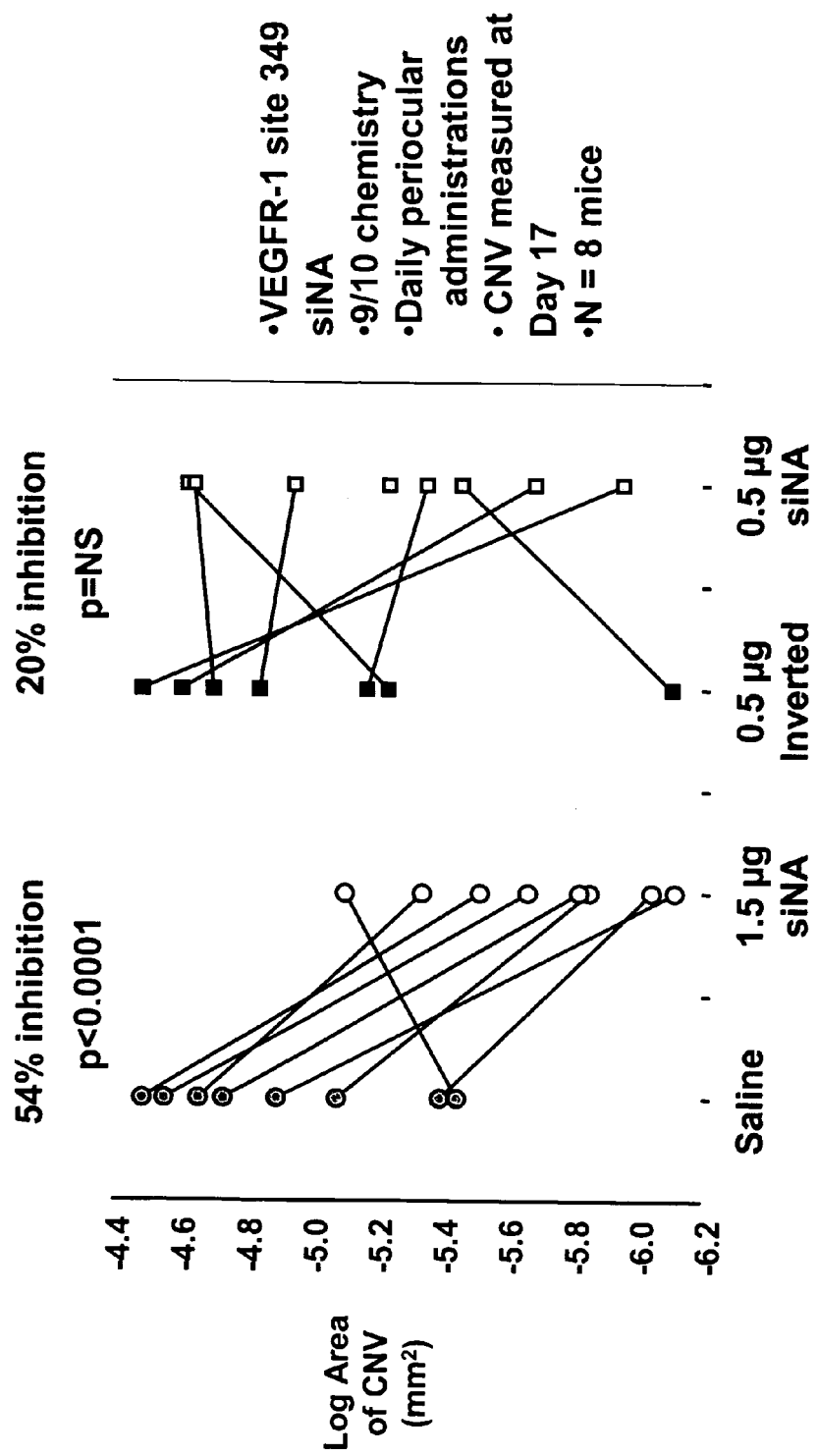
Figure 33: Inhibition of Mouse CNV with anti-VEGFR-1 siNA (periocular administration)

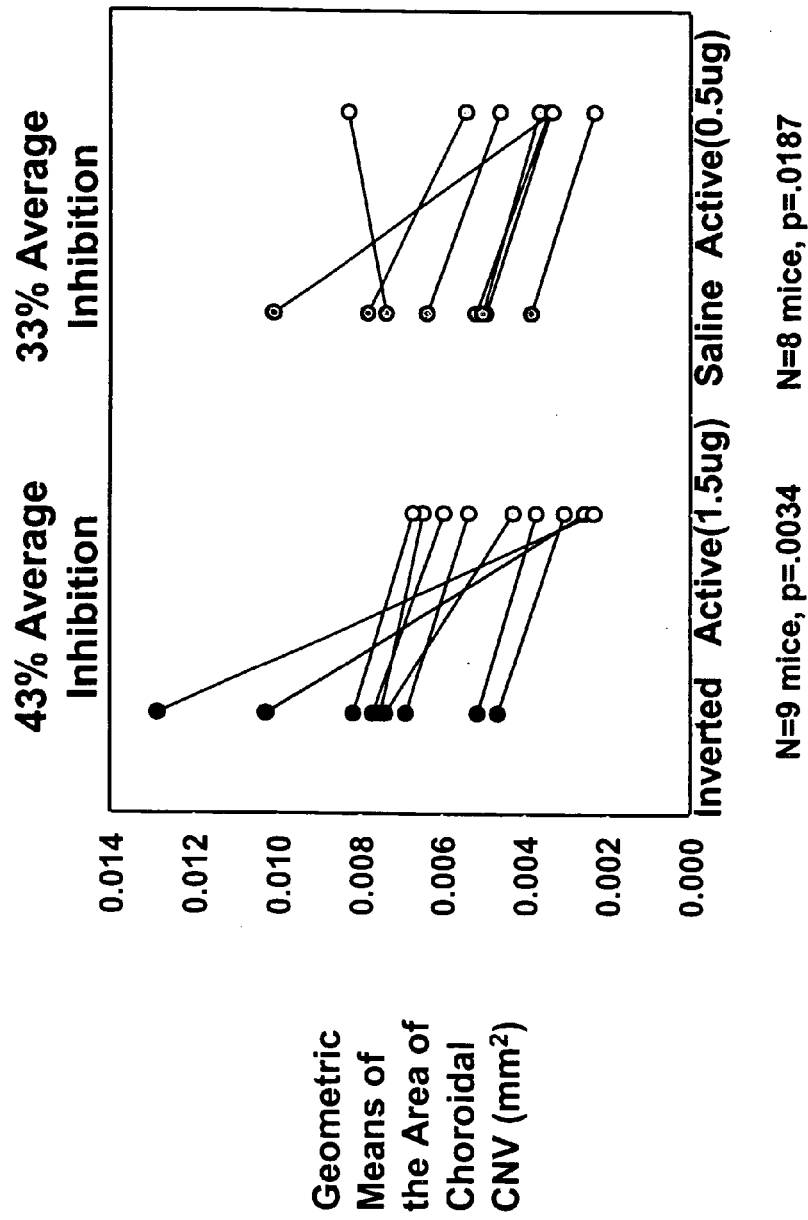
Figure 34: Inhibition of Mouse CNV with anti-VEGFR-1 siNA (periocular administration)

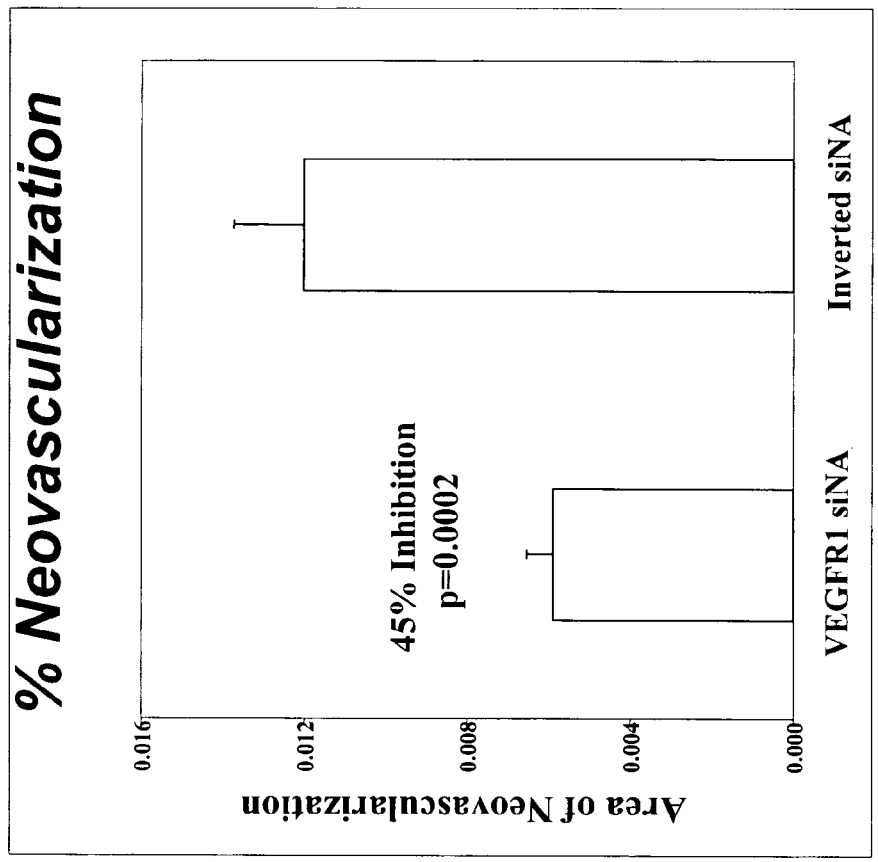
*Figure 35:* siNA Targeting VEGFR-1 CNV Model

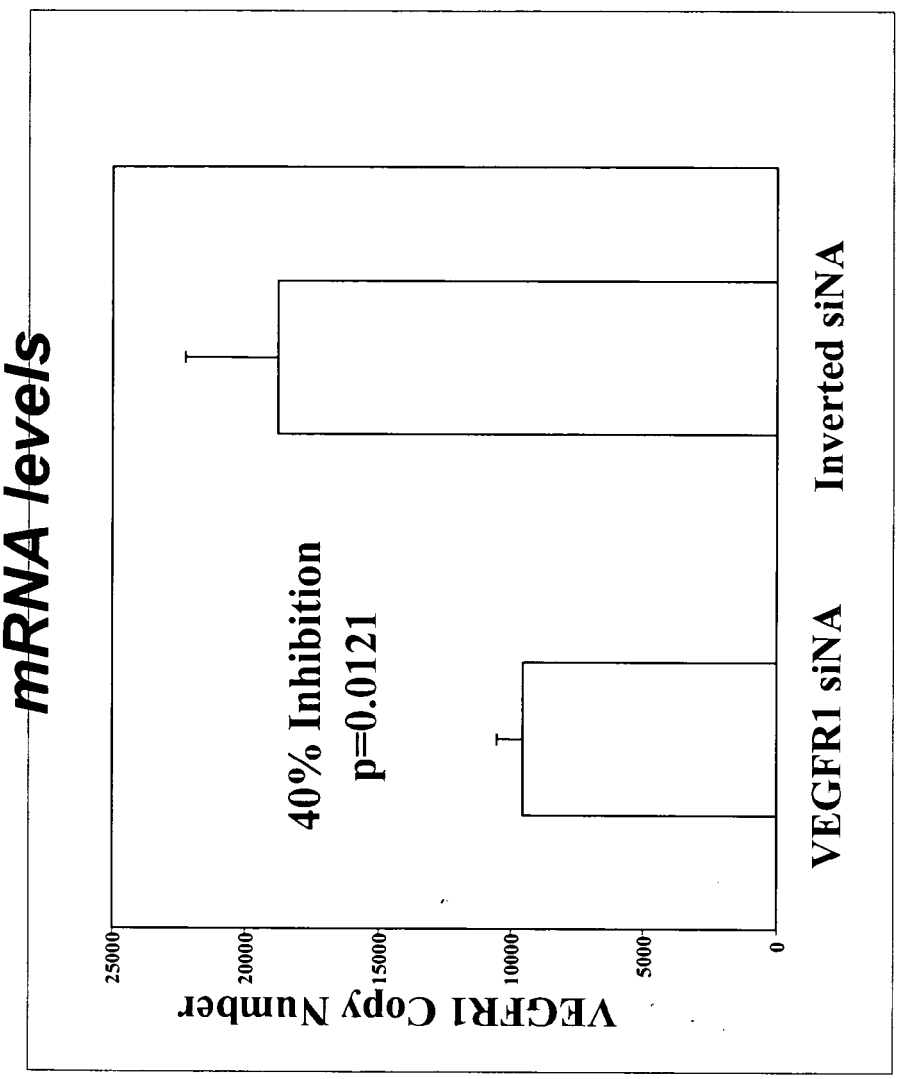
Figure 36: siNA Targeting VEGFR-1 OIR Model mRNA levels

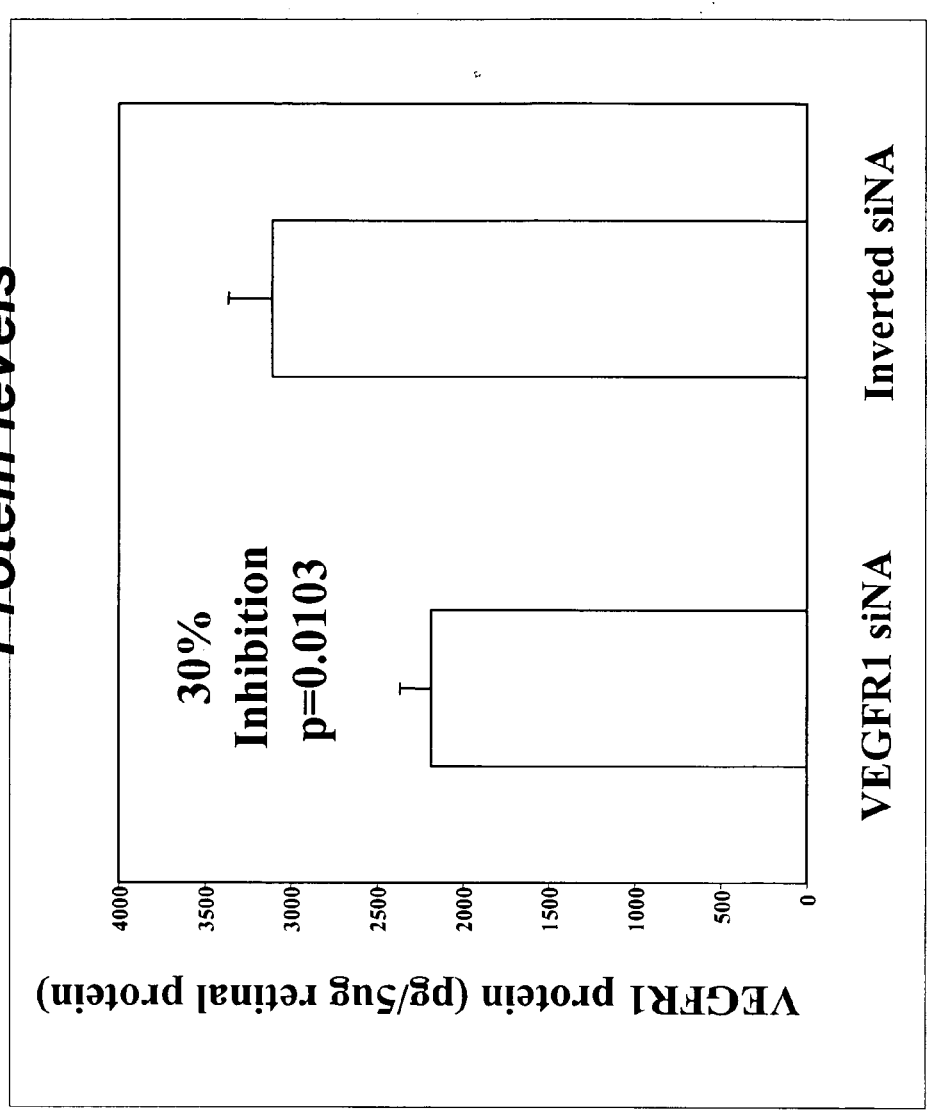
Figure 37: siNA Targeting VEGFR-1 OIR Model Protein levels

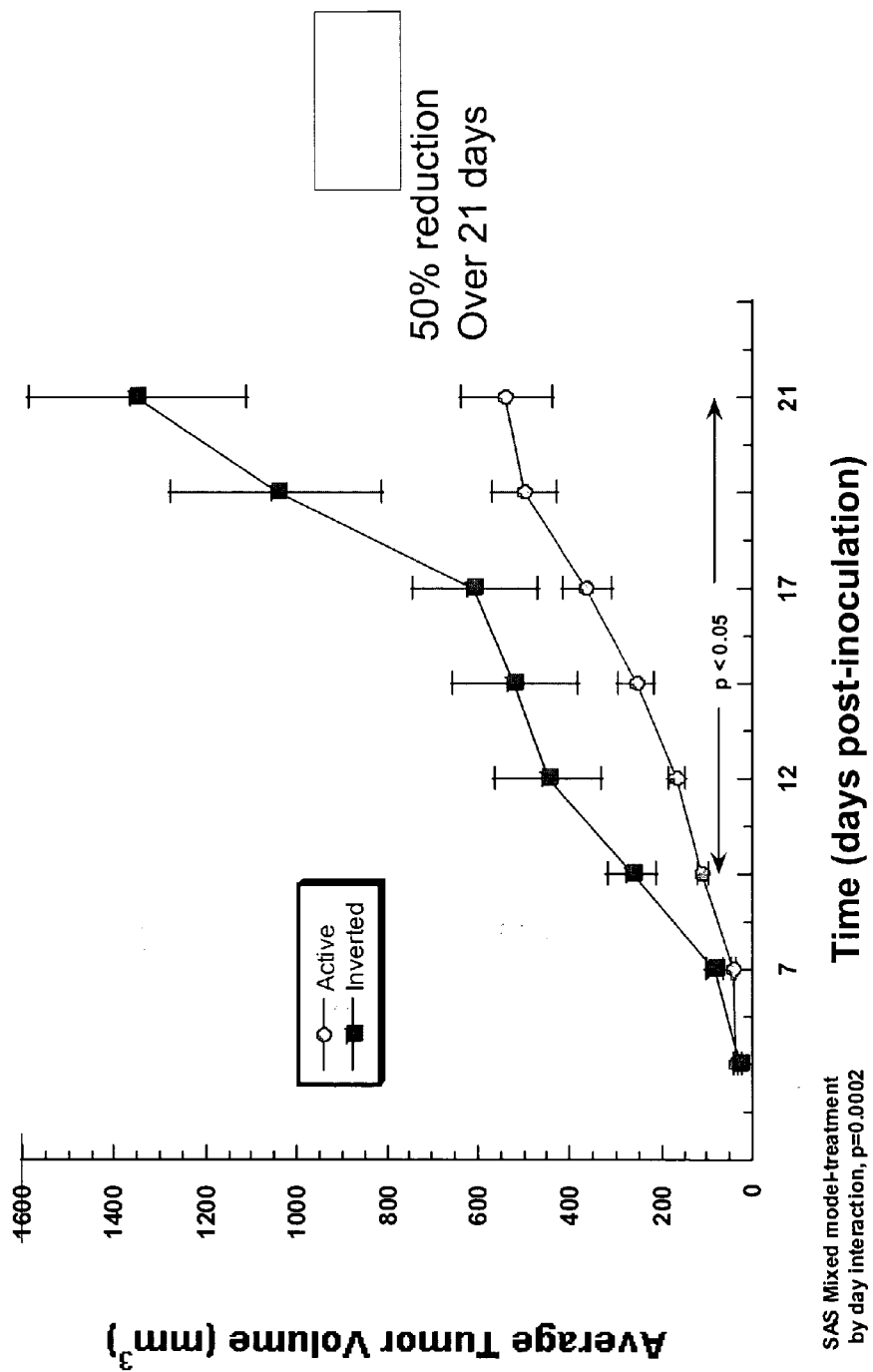
Figure 38: Inhibition of Mouse 4T1 Mammary Tumors with siNA targeting VEGFR1 site 349

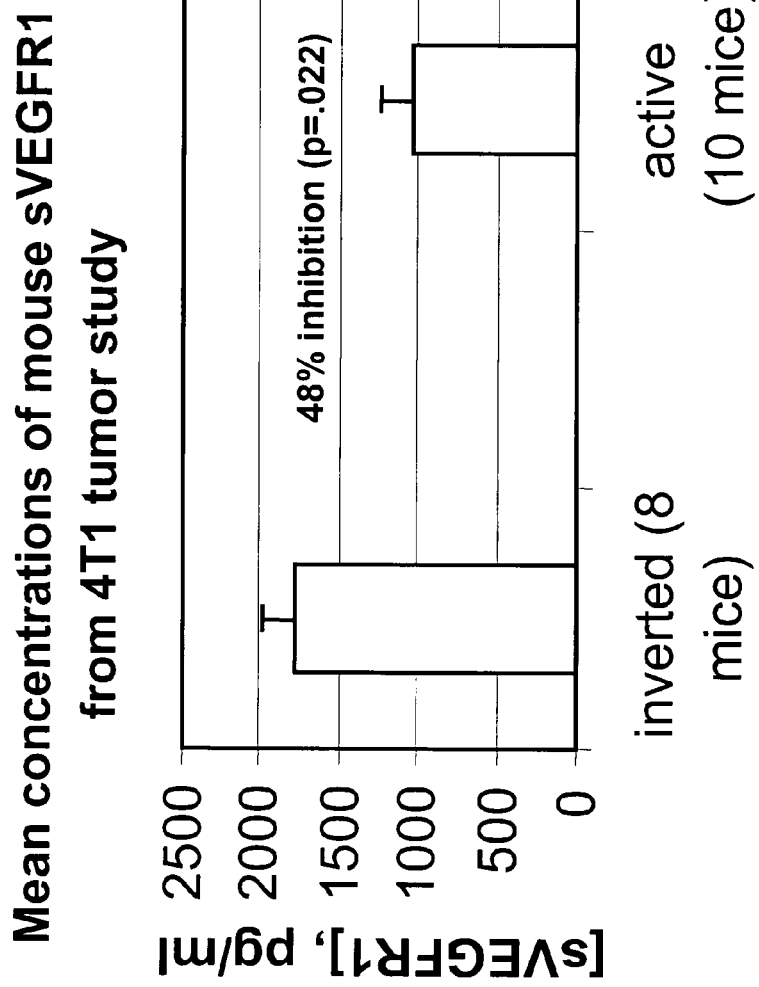
Figure 39: Inhibition of Mouse 4T1 Mammary Tumors with siNA targeting VEGFR1 site 349 Decreased level of Soluble VEGFR1

RNA INTERFERENCE MEDIATED INHIBITION OF VASCULAR ENDOTHELIAL GROWTH FACTOR AND VASCULAR ENDOTHELIAL GROWTH FACTOR RECEPTOR GENE EXPRESSION USING SHORT INTERFERING NUCLEIC ACID (SINA)

This application is a continuation-in-part of U.S. patent application Ser. No. 10/831,620, filed Apr. 23, 2004, which is a continuation-in-part of U.S. patent application Ser. No. 10/764,957, filed Jan. 26, 2004, which is a continuation-in-part of U.S. Ser. No. 10/670,011, filed Sep. 23, 2003, which is a continuation-in-part of U.S. Ser. No. 10/665,255, filed Sep. 16, 2003, now abandoned which is a continuation-in-part of PCT/US03/05022, filed Feb. 20, 2003, which claims the benefit of U.S. Provisional Application No. 60/393,796 filed Jul. 3, 2002 and claims the benefit of U.S. Provisional Application No. 60/399,348 filed Jul. 29, 2002. This application is also a continuation-in-part of U.S. patent application Ser. No. 10/758,155, filed Jan. 12, 2004, which is a continuation-in-part of U.S. Ser. No. 10/665,951, filed Sep. 18, 2003, which is a continuation-in-part of U.S. Ser. No. 10/665,255, filed Sep. 16, 2003, now abandoned which is a continuation-in-part of PCT/US03/05022, filed Feb. 20, 2003 which claims the benefit of U.S. Provisional Application No. 60/393,796 filed Jul. 3, 2002 and claims the benefit of U.S. Provisional Application No. 60/399,348 filed Jul. 29, 2002. This application is also a continuation-in-part of U.S. patent application Ser. No. 10/664,668, filed Sep. 18, 2003, which is a continuation-in-part of U.S. Ser. No. 10/665,255, filed Sep. 16, 2003, now abandoned which is a continuation-in-part of PCT/US03/05022, filed Feb. 20, 2003 which claims the benefit of U.S. Provisional Application No. 60/393,796 filed Jul. 3, 2002 and claims the benefit of U.S. Provisional Application No. 60/399,348 filed Jul. 29, 2002. This application is also a continuation-in-part of U.S. patent application Ser. No. 10/757,803, filed Jan. 14, 2004, which is a continuation-in-part of U.S. patent application Ser. No. 10/720,448, filed Nov. 24, 2003, which is a continuation-in-part of U.S. patent application Ser. No. 10/693,059, filed Oct. 23, 2003, now abandoned which is a continuation-in-part of U.S. patent application Ser. No. 10/444,853, filed May 23, 2003, which is a continuation-in-part of International Patent Application No. PCT/US03/05346, filed Feb. 20, 2003, and a continuation-in-part of International Patent Application No. PCT/US03/05028, filed Feb. 20, 2003, both of which International Patent Applications claim the benefit of U.S. Provisional Application No. 60/358,580 filed Feb. 20, 2002, U.S. Provisional Application No. 60/363,124 filed Mar. 11, 2002, U.S. Provisional Application No. 60/386,782 filed Jun. 6, 2002, U.S. Provisional Application No. 60/406,784 filed Aug. 29, 2002, U.S. Provisional Application No. 60/408,378 filed Sep. 5, 2002, U.S. Provisional Application No. 60/409,293 filed Sep. 9, 2002, and U.S. Provisional Application No. 60/440,129 filed Jan. 15, 2003. This application is also a continuation-in-part of U.S. patent application Ser. No. 10/427,160, filed Apr. 30, 2003 which is a continuation-in-part of International Patent Application No. PCT/US02/15876 filed May 17, 2002. This application is also a continuation-in-part of U.S. patent application Ser. No. 10/712,633, filed Nov. 13, 2003 now abandoned which is a continuation of International Patent Application No. PCT/US02/17674 filed May 29, 2002. The instant application claims the benefit of all the listed applications, which are hereby incorporated by reference herein in their entireties, including the drawings.

The sequence listing submitted on compact disc, in compliance with 37 C.F.R. 1.52(e)(5), is incorporated by reference. Two separate compact discs are submitted, each containing the file "400.159 Sequence Listing" (857,119 bytes in size), each created on CD on Oct. 18, 2004.

FIELD OF THE INVENTION

The present invention relates to compounds, compositions, and methods for the study, diagnosis, and treatment of conditions and diseases that respond to the modulation of vascular endothelial growth factor (VEGF) and/or vascular endothelial growth factor receptor (e.g., VEGFR1, VEGFR2 and/or VEGFr3) gene expression and/or activity. The present invention is also directed to compounds, compositions, and methods relating to conditions and diseases that respond to the modulation of expression and/or activity of genes involved in VEGF and VEGF receptor pathways. Specifically, the invention relates to small nucleic acid molecules, such as short interfering nucleic acid (siNA), short interfering RNA (siRNA), double-stranded RNA (dsRNA), micro-RNA (miRNA), and short hairpin RNA (shRNA) molecules capable of mediating RNA interference (RNAi) against VEGF and VEGF receptor gene expression.

BACKGROUND OF THE INVENTION

The following is a discussion of relevant art pertaining to RNAi. The discussion is provided only for understanding of the invention that follows. The summary is not an admission that any of the work described below is prior art to the claimed invention.

RNA interference refers to the process of sequence-specific post-transcriptional gene silencing in animals mediated by short interfering RNAs (siRNAs) (Zamore et al., 2000, Cell, 101, 25–33; Fire et al., 1998, Nature, 391, 806; Hamilton et al., 1999, Science, 286, 950–951; Lin et al., 1999, Nature, 402, 128–129; Sharp, 1999, Genes & Dev., 13:139–141; and Strauss, 1999, Science, 286, 886). The corresponding process in plants (Heifetz et al., International PCT Publication No. WO 99/61631) is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., 1999, Trends Genet., 15, 358). Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA. The presence of dsRNA in cells triggers the RNAi response through a mechanism that has yet to be fully characterized. This mechanism appears to be different from other known mechanisms involving double stranded RNA-specific ribonucleases, such as the interferon response that results from dsRNA-mediated activation of protein kinase PKR and 2',5'-oligoadenylate synthetase resulting in non-specific cleavage of MRNA by ribonuclease L (see for example U.S. Pat. Nos. 6,107,094; 5,898,031; Clemens et al., 1997, J. Interferon & Cytokine Res., 17, 503–524; Adah et al., 2001, Curr. Med. Chem., 8, 1189).

The presence of long dsRNAs in cells stimulates the activity of a ribonuclease III enzyme referred to as dicer (Bass, 2000, Cell, 101, 235; Zamore et al., 2000, Cell, 101, 25–33; Hammond et al., 2000, Nature, 404, 293). Dicer is involved in the processing of the dsRNA into short pieces of dsRNA known as short interfering RNAs (siRNAs) (Zamore et al., 2000, Cell, 101, 25–33; Bass, 2000, Cell, 101, 235; Berstein et al., 2001, *Nature*, 409, 363). Short interfering RNAs derived from dicer activity are typically about 21 to about 23 nucleotides in length and comprise about 19 base pair duplexes (Zamore et al., 2000, Cell, 101, 25–33; Elbashir et al., 2001, *Genes Dev.*, 15, 188). Dicer has also been implicated in the excision of 21- and 22-nucleotide small temporal RNAs (stRNAs) from precursor RNA of conserved structure that are implicated in translational control (Hutvagner et al., 2001, *Science*, 293, 834). The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex (Elbashir et al., 2001, *Genes Dev.*, 15, 188).

RNAi has been studied in a variety of systems. Fire et al., 1998, *Nature*, 391, 806, were the first to observe RNAi in *C. elegans*. Bahramian and Zarbl, 1999, *Molecular and Cellular Biology*, 19, 274–283 and Wianny and Goetz, 1999, *Nature Cell Biol.*, 2, 70, describe RNAi mediated by dsRNA in mammalian systems. Hammond et al., 2000, *Nature*, 404, 293, describe RNAi in *Drosophila* cells transfected with dsRNA. Elbashir et al., 2001, *Nature*, 411, 494 and Tuschl et al., International PCT Publication No. WO 01/75164, describe RNAi induced by introduction of duplexes of synthetic 21-nucleotide RNAs in cultured mammalian cells including human embryonic kidney and HeLa cells. Recent work in *Drosophila* embryonic lysates (Elbashir et al., 2001, *EMBO J.*, 20, 6877 and Tuschl et al., International PCT Publication No. WO 01/75164) has revealed certain requirements for siRNA length, structure, chemical composition, and sequence that are essential to mediate efficient RNAi activity. These studies have shown that 21-nucleotide siRNA duplexes are most active when containing 3'-terminal dinucleotide overhangs. Furthermore, complete substitution of one or both siRNA strands with 2'-deoxy (2'-H) or 2'-O-methyl nucleotides abolishes RNAi activity, whereas substitution of the 3'-terminal siRNA overhang nucleotides with 2'-deoxy nucleotides (2'-H) was shown to be tolerated. Single mismatch sequences in the center of the siRNA duplex were also shown to abolish RNAi activity. In addition, these studies also indicate that the position of the cleavage site in the target RNA is defined by the 5'-end of the siRNA guide sequence rather than the 3'-end of the guide sequence (Elbashir et al., 2001, *EMBO J.*, 20, 6877). Other studies have indicated that a 5'-phosphate on the target-complementary strand of a siRNA duplex is required for siRNA activity and that ATP is utilized to maintain the 5'-phosphate moiety on the siRNA (Nykanen et al., 2001, *Cell*, 107, 309).

Studies have shown that replacing the 3'-terminal nucleotide overhanging segments of a 21-mer siRNA duplex having two-nucleotide 3'-overhangs with deoxyribonucleotides does not have an adverse effect on RNAi activity. Replacing up to four nucleotides on each end of the siRNA with deoxyribonucleotides has been reported to be well tolerated, whereas complete substitution with deoxyribonucleotides results in no RNAi activity (Elbashir et al., 2001, *EMBO J.*, 20, 6877 and Tuschl et al., International PCT Publication No. WO 01/75164). In addition, Elbashir et al., supra, also report that substitution of siRNA with 2'-O-methyl nucleotides completely abolishes RNAi activity. Li et al., International PCT Publication No. WO 00/44914, and Beach et al., International PCT Publication No. WO 01/68836 preliminarily suggest that siRNA may include modifications to either the phosphate-sugar backbone or the nucleoside to include at least one of a nitrogen or sulfur heteroatom, however, neither application postulates to what extent such modifications would be tolerated in siRNA molecules, nor provides any further guidance or examples of such modified siRNA. Kreutzer et al., Canadian Patent Application No. 2,359,180, also describe certain chemical modifications for use in dsRNA constructs in order to counteract activation of double-stranded RNA-dependent protein kinase PKR, specifically 2'-amino or 2'-O-methyl nucleotides, and nucleotides containing a 2'-O or 4'-C methylene bridge. However, Kreutzer et al. similarly fails to provide examples or guidance as to what extent these modifications would be tolerated in dsRNA molecules.

Parrish et al., 2000, *Molecular Cell*, 6, 1077–1087, tested certain chemical modifications targeting the unc-22 gene in *C. elegans* using long (>25 nt) siRNA transcripts. The authors describe the introduction of thiophosphate residues into these siRNA transcripts by incorporating thiophosphate nucleotide analogs with T7 and T3 RNA polymerase and observed that RNAs with two phosphorothioate modified bases also had substantial decreases in effectiveness as RNAi. Further, Parrish et al. reported that phosphorothioate modification of more than two residues greatly destabilized the RNAs in vitro such that interference activities could not be assayed. Id. at 1081. The authors also tested certain modifications at the 2'-position of the nucleotide sugar in the long siRNA transcripts and found that substituting deoxynucleotides for ribonucleotides produced a substantial decrease in interference activity, especially in the case of Uridine to Thymidine and/or Cytidine to deoxy-Cytidine substitutions. Id. In addition, the authors tested certain base modifications, including substituting, in sense and antisense strands of the siRNA, 4-thiouracil, 5-bromouracil, 5-iodouracil, and 3-(aminoallyl)uracil for uracil, and inosine for guanosine. Whereas 4-thiouracil and 5-bromouracil substitution appeared to be tolerated, Parrish reported that inosine produced a substantial decrease in interference activity when incorporated in either strand. Parrish also reported that incorporation of 5-iodouracil and 3-(aminoallyl)uracil in the antisense strand resulted in a substantial decrease in RNAi activity as well.

The use of longer dsRNA has been described. For example, Beach et al., International PCT Publication No. WO 01/68836, describes specific methods for attenuating gene expression using endogenously-derived dsRNA. Tuschl et al., International PCT Publication No. WO 01/75164, describe a *Drosophila* in vitro RNAi system and the use of specific siRNA molecules for certain functional genomic and certain therapeutic applications; although Tuschl, 2001, *Chem. Biochem.*, 2, 239–245, doubts that RNAi can be used to cure genetic diseases or viral infection due to the danger of activating interferon response. Li et al., International PCT Publication No. WO 00/44914, describe the use of specific long (141 bp–488 bp) enzymatically synthesized or vector expressed dsRNAs for attenuating the expression of certain target genes. Zernicka-Goetz et al., International PCT Publication No. WO 01/36646, describes certain methods for inhibiting the expression of particular genes in mammalian cells using certain long (550 bp–714 bp), enzymatically synthesized or vector expressed dsRNA molecules. Fire et al., International PCT Publication No. WO 99/32619, describe particular methods for introducing certain long dsRNA molecules into cells for use in inhibiting gene expression in nematodes. Plaetinck et al., International PCT Publication No. WO 00/01846, describe certain methods for identifying specific genes responsible for conferring a particular phenotype in a cell using specific long dsRNA molecules. Mello et al., International PCT Publication No. WO 01/29058, describe the identification of specific genes involved in dsRNA-mediated RNAi. Pachuck et al., International PCT Publication No. WO 00/63364, describe certain long (at least 200 nucleotide) dsRNA constructs. Deschamps Depaillette et al., International PCT Publication No. WO 99/07409, describe specific compositions consisting of particular dsRNA molecules combined with certain antiviral agents. Waterhouse et al., International PCT Publication No. 99/53050 and 1998, *PNAS*, 95, 13959–13964, describe certain methods for decreasing the phenotypic expression of a nucleic acid in plant cells using certain dsRNAs. Driscoll et al., International PCT Publication No. WO 01/49844, describe specific DNA expression constructs for use in facilitating gene silencing in targeted organisms.

Others have reported on various RNAi and gene-silencing systems. For example, Parrish et al., 2000, *Molecular Cell*, 6, 1077–1087, describe specific chemically-modified dsRNA constructs targeting the unc-22 gene of *C. elegans*. Grossniklaus, International PCT Publication No. WO 01/38551, describes certain methods for regulating polycomb gene expression in plants using certain dsRNAs. Churikov et al., International PCT Publication No. WO 01/42443, describe certain methods for modifying genetic characteristics of an organism using certain dsRNAs. Cogoni et al, International PCT Publication No. WO 01/53475, describe certain methods for isolating a Neurospora silencing gene and uses thereof. Reed et al., International PCT Publication No. WO 01/68836, describe certain methods for gene silencing in plants. Honer et al., International PCT Publication No. WO 01/70944, describe certain methods of drug screening using transgenic nematodes as Parkinson's Disease models using certain dsRNAs. Deak et al., International PCT Publication No. WO 01/72774, describe certain *Drosophila*-derived gene products that may be related to RNAi in *Drosophila*. Arndt et al., International PCT Publication No. WO 01/92513 describes certain methods for mediating gene suppression by using factors that enhance RNAi. Tuschl et al., International PCT Publication No. WO 02/44321, describe certain synthetic siRNA constructs. Pachuk et al., International PCT Publication No. WO 00/63364, and Satishchandran et al., International PCT Publication No. WO 01/04313, describe certain methods and compositions for inhibiting the function of certain polynucleotide sequences using certain long (over 250 bp), vector expressed dsRNAs. Echeverri et al., International PCT Publication No. WO 02/38805, describe certain *C. elegans* genes identified via RNAi. Kreutzer et al., International PCT Publications Nos. WO 02/055692, WO 02/055693, and EP 1144623 B1 describe certain methods for inhibiting gene expression using dsRNA. Graham et al., International PCT Publications Nos. WO 99/49029 and WO 01/70949, and AU 4037501 describe certain vector expressed siRNA molecules. Fire et al., U.S. Pat. No. 6,506,559, describe certain methods for inhibiting gene expression in vitro using certain long dsRNA (299 bp–1033 bp) constructs that mediate RNAi. Martinez et al., 2002, *Cell*, 110, 563–574, describe certain single stranded siRNA constructs, including certain 5'-phosphorylated single stranded siRNAs that mediate RNA interference in Hela cells. Harborth et al., 2003, Antisense & Nucleic Acid Drug Development, 13, 83–105, describe certain chemically and structurally modified siRNA molecules. Chiu and Rana, 2003, RNA, 9, 1034–1048, describe certain chemically and structurally modified siRNA molecules. Woolf et al., International PCT Publication Nos. WO 03/064626 and WO 03/064625 describe certain chemically modified dsRNA constructs.

SUMMARY OF THE INVENTION

This invention relates to compounds, compositions, and methods useful for modulating the expression of genes, such as those genes associated with angiogenesis and proliferation, using short interfering nucleic acid (siNA) molecules. This invention further relates to compounds, compositions, and methods useful for modulating the expression and activity of vascular endothelial growth factor (VEGF) and/or vascular endothelial growth factor receptor (e.g., VEGFR1, VEGFR2, VEGFr3) genes, or genes involved in VEGF and/or VEGFr pathways of gene expression and/or VEGF activity by RNA interference (RNAi) using small nucleic acid molecules. In particular, the instant invention features small nucleic acid molecules, such as short interfering nucleic acid (siNA), short interfering RNA (siRNA), double-stranded RNA (dsRNA), micro-RNA (miRNA), and short hairpin RNA (shRNA) molecules and methods used to modulate the expression of VEGF and/or VEGFr genes. A siNA of the invention can be unmodified or chemically-modified. A siNA of the instant invention can be chemically synthesized, expressed from a vector or enzymatically synthesized. The instant invention also features various chemically-modified synthetic short interfering nucleic acid (siNA) molecules capable of modulating VEGF and/or VEGFr gene expression or activity in cells by RNA interference (RNAi). The use of chemically-modified siNA improves various properties of native siNA molecules through increased resistance to nuclease degradation in vivo and/or through improved cellular uptake. Further, contrary to earlier published studies, siNA having multiple chemical modifications retains its RNAi activity. The siNA molecules of the instant invention provide useful reagents and methods for a variety of therapeutic, diagnostic, target validation, genomic discovery, genetic engineering, and pharmacogenomic applications.

In one embodiment, the invention features one or more siNA molecules and methods that independently or in combination modulate the expression of gene(s) encoding proteins, such as vascular endothelial growth factor (VEGF) and/or vascular endothelial growth factor receptors (e.g., VEGFR1, VEGFR2, VEGFr3), associated with the maintenance and/or development of cancer and other proliferative diseases, such as genes encoding sequences comprising those sequences referred to by GenBank Accession Nos. shown in Table I, referred to herein generally as VEGF and/or VEGFr. The description below of the various aspects and embodiments of the invention is provided with reference to the exemplary VEGF and VEGFr (e.g., VEGFR1, VEGFR2, VEGFr3) genes referred to herein as VEGF and VEGFr respectively. However, the various aspects and embodiments are also directed to other VEGF and/or VEGFr genes, such as mutant VEGF and/or VEGFr genes, splice variants of VEGF and/or VEGFr genes, other VEGF and/or VEGFr ligands and receptors. The various aspects and embodiments are also directed to other genes that are involved in VEGF and/or VEGFr mediated pathways of signal transduction or gene expression that are involved in the progression, development, and/or maintenance of disease (e.g., cancer). These additional genes can be analyzed for target sites using the methods described for VEGF and/or VEGFr genes herein. Thus, the modulation of other genes and the effects of such modulation of the other genes can be performed, determined, and measured as described herein.

In one embodiment, the invention features a double-stranded short interfering nucleic acid (siNA) molecule that down-regulates expression of a vascular endothelial growth factor (e.g., VEGF, VEGF-A, VEGF-B, VEGF-C, VEGF-D) gene, wherein said siNA molecule comprises about 19 to about 21 base pairs.

In one embodiment, the invention features a double-stranded short interfering nucleic acid (siNA) molecule that down-regulates expression of a vascular endothelial growth factor receptor (e.g., VEGFR1, VEGFR2, and/or VEGFr3) gene, wherein said siNA molecule comprises about 19 to about 21 base pairs.

In one embodiment, the invention features a siNA molecule that down-regulates expression of a VEGF gene, for example, a VEGF gene comprising VEGF encoding sequence.

In one embodiment, the invention features a siNA molecule that down-regulates expression of a VEGFr gene, for example, a VEGFr gene comprising VEGFr encoding sequence.

In one embodiment, the invention features a siNA molecule having RNAi activity against VEGF and/or VEGFr RNA, wherein the siNA molecule comprises a sequence complementary to any RNA having VEGF and/or VEGFr or other VEGF and/or VEGFr encoding sequence, such as those sequences having GenBank Accession Nos. shown in Table I. In another embodiment, the invention features a siNA molecule having RNAi activity against VEGF and/or VEGFr RNA, wherein the siNA molecule comprises a sequence complementary to an RNA having variant VEGF and/or VEGFr encoding sequence, for example mutant VEGF and/or VEGFr genes, splice variants of VEGF and/or VEGFr genes, variants of VEGF and/or VEGFr genes with conservative substitutions, and homologous VEGF and/or VEGFr ligands and receptors. Chemical modifications as shown in Tables III and IV or otherwise described herein can be applied to any siNA construct of the invention.

In one embodiment, the invention features a siNA molecule having RNAi activity against VEGF and/or VEGFr RNA, wherein the siNA molecule comprises a sequence complementary to any RNA having VEGF and/or VEGFr encoding sequence, such as those sequences having VEGF and/or VEGFr GenBank Accession Nos. shown in Table I. In another embodiment, the invention features a siNA molecule having RNAi activity against VEGF and/or VEGFr RNA, wherein the siNA molecule comprises a sequence complementary to an RNA having other VEGF and/or VEGFr encoding sequence, for example, mutant VEGF and/or VEGFr genes, splice variants of VEGF and/or VEGFr genes, VEGF and/or VEGFr variants with conservative substitutions, and homologous VEGF and/or VEGFr ligands and receptors. Chemical modifications as shown in Tables III and IV or otherwise described herein can be applied to any siNA construct of the invention.

In another embodiment, the invention features a siNA molecule having RNAi activity against a VEGF and/or VEGFr gene, wherein the siNA molecule comprises nucleotide sequence complementary to nucleotide sequence of a VEGF and/or VEGFr gene, such as those VEGF and/or VEGFr sequences having GenBank Accession Nos. shown in Table I or other VEGF and/or VEGFr encoding sequence, such as mutant VEGF and/or VEGFr genes, splice variants of VEGF and/or VEGFr genes, variants with conservative substitutions, and homologous VEGF and/or VEGFr ligands and receptors. In another embodiment, a siNA molecule of the invention includes nucleotide sequence that can interact with nucleotide sequence of a VEGF and/or VEGFr gene and thereby mediate silencing of VEGF and/or VEGFr gene expression, for example, wherein the siNA mediates regulation of VEGF and/or VEGFr gene expression by cellular processes that modulate the chromatin structure of the VEGF and/or VEGFr gene and prevent transcription of the VEGF and/or VEGFr gene.

In one embodiment, siNA molecules of the invention are used to down regulate or inhibit the expression of soluble VEGF receptors (e.g. sVEGFR1 or sVEGFR2). Analysis of soluble VEGF receptor levels can be used to identify subjects with certain cancer types. These cancers can be amenable to treatment, for example, treatment with siNA molecules of the invention and any other chemotherapeutic composition. As such, analysis of soluble VEGF receptor levels can be used to determine treatment type and the course of therapy in treating a subject. Monitoring of soluble VEGF receptor levels can be used to predict treatment outcome and to determine the efficacy of compounds and compositions that modulate the level and/or activity of VEGF receptors (see for example Pavco U.S. Ser. No. 10/438,493, incorporated by reference herein in its entirety including the drawings).

In another embodiment, the invention features a siNA molecule comprising nucleotide sequence, for example, nucleotide sequence in the antisense region of the siNA molecule that is complementary to a nucleotide sequence or portion of sequence of a VEGF and/or VEGFr gene. In another embodiment, the invention features a siNA molecule comprising a region, for example, the antisense region of the siNA construct, complementary to a sequence comprising a VEGF and/or VEGFr gene sequence or a portion thereof.

In one embodiment, the antisense region of VEGFR1 siNA constructs comprises a sequence complementary to sequence having any of SEQ ID NOs. 1–427, 1997–2000, 2009–2012, or 2244–2255. In one embodiment, the antisense region can also comprise sequence having any of SEQ ID NOs. 428–854, 2024–2027, 2032–2035, 2040–2043, 2188–2190, 2197–2200, 2203, 2217, 2278–2280, 2292–2298, 2313–2318, 2326–2332, 2347–2364, 2444–2448, 2451–2452, 2455–2456, 2564, 2566, 2568, or 2571. In another embodiment, the sense region of VEGFR1 constructs can comprise sequence having any of SEQ ID NOs. 1–427, 1997–2000, 2009–2012, 2020–2023, 2028–2031, 2036–2039, 2185–2187, 2201–2202, 2218, 2220, 2222, 2224, 2244–2255, 2275–2277, 2281–2291, 2299–2305, 2319–2325, 2333–2339, 2347–2364, 2438–2439, 2449–2450, 2563, 2565, 2567, 2569, or 2570. The sense region can comprise a sequence of SEQ ID NO. 2554 and the antisense region can comprise a sequence of SEQ ID NO. 2555. The sense region can comprise a sequence of SEQ ID NO. 2556 and the antisense region can comprise a sequence of SEQ ID NO. 2557. The sense region can comprise a sequence of SEQ ID NO. 2558 and the antisense region can comprise a sequence of SEQ ID NO. 2559. The sense region can comprise a sequence of SEQ ID NO. 2560 and the antisense region can comprise a sequence of SEQ ID NO. 2557. The sense region can comprise a sequence of SEQ ID NO. 2561 and the antisense region can comprise a sequence of SEQ ID NO. 2557. The sense region can comprise a sequence of SEQ ID NO. 2560 and the antisense region can comprise a sequence of SEQ ID NO. 2562.

In one embodiment, the antisense region of VEGFR2 siNA constructs can comprise a sequence complementary to sequence having any of SEQ ID NOs. 855–1178, 2001–2004, or 2017–2019 or 2256–2271. In one embodiment, the antisense region can also comprise sequence having any of SEQ ID NOs. 1179–1502, 2048–2051, 2056–2059, 2064–2067, 2208–2210, 2214–2216, 2226–2227, 2230–2231, 2377–2388, 2391–2392, 2401–2405, 2420–2423, 2498–2501, or 2506–2509. In another embodiment, the sense region of VEGFR2 constructs can comprise sequence having any of SEQ ID NOs. 855–1178, 2001–2004, 2017–2019, 2256–2271, 2044–2047, 2052–2055, 2060–2063, 2205–2207, 2211–2213, 2228–2229, 2365–2376, 2389–2390, 2393–2394, 2397–2400, 2406–2410, 2416–2419, 2424–2427, 2494–2497, or 2502–2505. The sense region can comprise a sequence of SEQ ID NO. 2438 and the antisense region can comprise a sequence of SEQ ID NO. 2439. The sense region can comprise a sequence of SEQ ID NO. 2554 and the antisense region can comprise a sequence of SEQ ID NO. 2555. The sense region can comprise a sequence of SEQ ID NO. 2556 and the antisense region can comprise a sequence of SEQ ID NO. 2557. The sense region can comprise a sequence of SEQ ID NO. 2558 and the antisense region can comprise a sequence of SEQ ID NO. 2559. The sense region can comprise a sequence of SEQ ID NO. 2560 and the antisense region can comprise a sequence of SEQ ID NO. 2557. The sense region can comprise a sequence of SEQ ID NO. 2561 and the antisense region can comprise a sequence of SEQ ID NO. 2557. The sense region can comprise a sequence of SEQ ID NO. 2560 and the antisense region can comprise a sequence of SEQ ID NO. 2562.

In one embodiment, the antisense region of VEGFr3 siNA constructs can comprise a sequence complementary to sequence having any of SEQ ID NOs. 1503–1749, 2005–2008, or 2272–2274. In one embodiment, the antisense region can also comprise sequence having any of SEQ ID NOs. 1750–1996, 2072–2075, 2080–2083, 2088–2091, 2435–2437, or 2534–2548. In another embodiment, the sense region of VEGFr3 constructs can comprise sequence having any of SEQ ID NOs. 1503–1749, 2005–2008, 2068–2071, 2076–2079, or 2084–2087, 2272–2274, 2432–2434, 2440–2443, or 2526–2533. The sense region can comprise a sequence of SEQ ID NO. 2554 and the antisense region can comprise a sequence of SEQ ID NO. 2555. The sense region can comprise a sequence of SEQ ID NO. 2556 and the antisense region can comprise a sequence of SEQ ID NO. 2557. The sense region can comprise a sequence of SEQ ID NO. 2558 and the antisense region can comprise a sequence of SEQ ID NO. 2559. The sense region can comprise a sequence of SEQ ID NO. 2560 and the antisense region can comprise a sequence of SEQ ID NO. 2557. The sense region can comprise a sequence of SEQ ID NO. 2561 and the antisense region can comprise a sequence of SEQ ID NO. 2557. The sense region can comprise a sequence of SEQ ID NO. 2560 and the antisense region can comprise a sequence of SEQ ID NO. 2562.

In one embodiment, a siNA molecule of the invention comprises any of SEQ ID NOs. 1–2562. The sequences shown in SEQ ID NOs: 1–2562 are not limiting. A siNA molecule of the invention can comprise any contiguous VEGF and/or VEGFr sequence (e.g., about 19 to about 25, or about 19, 20, 21, 22, 23, 24 or 25 contiguous VEGF and/or VEGFr nucleotides).

In yet another embodiment, the invention features a siNA molecule comprising a sequence, for example, the antisense sequence of the siNA construct, complementary to a sequence or portion of sequence comprising sequence represented by GenBank Accession Nos. shown in Table I. Chemical modifications in Tables III and IV and described herein can be applied to any siNA construct of the invention.

In one embodiment of the invention a siNA molecule comprises an antisense strand having about 19 to about 29 (e.g., about 19, 20, 21, 22, 23, 24, 25, 26, 27, 28, or 29) nucleotides, wherein the antisense strand is complementary to a RNA sequence encoding a VEGF and/or VEGFr protein, and wherein said siNA further comprises a sense strand having about 19 to about 29 (e.g., about 19, 20, 21, 22, 23, 24, 25, 26, 27, 28, or 29) nucleotides, and wherein said sense strand and said antisense strand are distinct nucleotide sequences with at least about 19 complementary nucleotides.

In another embodiment of the invention a siNA molecule of the invention comprises an antisense region having about 19 to about 29 (e.g., about 19, 20, 21, 22, 23, 24, 25, 26, 27, 28, or 29) nucleotides, wherein the antisense region is complementary to a RNA sequence encoding a VEGF and/or VEGFr protein, and wherein said siNA further comprises a sense region having about 19 to about 29 (e.g., about 19, 20, 21, 22, 23, 24, 25, 26, 27, 28, or 29) nucleotides, wherein said sense region and said antisense region comprise a linear molecule with at least about 19 complementary nucleotides.

In one embodiment, a siNA molecule of the invention has RNAi activity that modulates expression of RNA encoded by a VEGF and/or VEGFr gene. Because VEGF and/or VEGFr genes can share some degree of sequence homology with each other, siNA molecules can be designed to target a class of VEGF and/or VEGFr genes or alternately specific VEGF and/or VEGFr genes (e.g., polymorphic variants) by selecting sequences that are either shared amongst different VEGF and/or VEGFr targets or alternatively that are unique for a specific VEGF and/or VEGFr target. Therefore, in one embodiment, the siNA molecule can be designed to target conserved regions of VEGF and/or VEGFr RNA sequence having homology between several VEGF and/or VEGFr gene variants so as to target a class of VEGF and/or VEGFr genes with one siNA molecule. Accordingly, in one embodiment, the siNA molecule of the invention modulates the expression of one or both VEGF and/or VEGFr alleles in a subject. In another embodiment, the siNA molecule can be designed to target a sequence that is unique to a specific VEGF and/or VEGFr RNA sequence (e.g., a single VEGF and/or VEGFr allele or VEGF and/or VEGFr single nucleotide polymorphism (SNP)) due to the high degree of specificity that the siNA molecule requires to mediate RNAi activity.

In one embodiment, a siNA molecule of the invention has RNAi activity that modulates expression of RNA encoded by a VEGFr gene. Because VEGFr genes can share some degree of sequence homology with each other, siNA molecules can be designed to target a class of VEGFr genes (and associated receptor or ligand genes) or alternately specific VEGFr genes by selecting sequences that are either shared amongst different VEGFr targets or alternatively that are unique for a specific VEGFr target. Therefore, in one embodiment, the siNA molecule can be designed to target conserved regions of VEGFr RNA sequence having homology between several VEGFr genes so as to target several VEGFr genes (e.g., VEGFR1, VEGFR2 and/or VEGFr3, different VEGFr isoforms, splice variants, mutant genes etc.) with one siNA molecule. In one embodiment, the siNA molecule can be designed to target conserved regions of VEGFR1 and VEGFR2 RNA sequence having shared sequence homology (see for example Table III). Accordingly, in one embodiment, the siNA molecule of the invention modulates the expression of more than one VEGFr gene, i.e., VEGFR1, VEGFR2, and VEGFr3, or any combination thereof. In another embodiment, the siNA molecule can be designed to target a sequence that is unique to a specific VEGFr RNA sequence due to the high degree of specificity that the siNA molecule requires to mediate RNAi activity In one embodiment, a siNA molecule of the invention has RNAi activity that modulates expression of RNA encoded by a VEGF gene. Because VEGF genes can share some degree of sequence homology with each other, siNA molecules can be designed to target a class of VEGF genes (and associated receptor or ligand genes) or alternately specific VEGF genes by selecting sequences that are either shared amongst different VEGF targets or alternatively that are unique for a specific VEGF target. Therefore, in one embodiment, the siNA molecule can be designed to target conserved regions of VEGF RNA sequence having homology between several VEGF genes so as to target several VEGF genes (e.g., VEGF-A, VEGF-B, VEGF-C and/or VEGF-D, different VEGF isoforms, splice variants, mutant genes etc.) with one siNA molecule. Accordingly, in one embodiment, the siNA molecule of the invention modulates the expression of more than one VEGF gene, i.e., VEGF-A, VEGF-B, VRGF-C, and VEGF-D or any combination thereof. In another embodiment, the siNA molecule can be designed to target a sequence that is unique to a specific VEGF RNA sequence due to the high degree of specificity that the siNA molecule requires to mediate RNAi activity.

In one embodiment, a siNA molecule of the invention targeting one or more VEGF receptor genes (e.g., VEGFR1, VEGFR2, and/or VEGFr3) is used in combination with a siNA molecule of the invention targeting a VEGF gene (e.g., VEGF-A, VEGF-B, VEGF-C and/or VEGF-D) according to a use described herein, such as treating a subject with an angiogenesis or neovascularization related disease, such as tumor angiogenesis and cancer, including but not limited to breast cancer, lung cancer (including non-small cell lung carcinoma), prostate cancer, colorectal cancer, brain cancer, esophageal cancer, bladder cancer, pancreatic cancer, cervical cancer, head and neck cancer, skin cancers, nasopharyngeal carcinoma, liposarcoma, epithelial carcinoma, renal cell carcinoma, gallbladder adeno carcinoma, parotid adenocarcinoma, ovarian cancer, melanoma, lymphoma, glioma, endometrial sarcoma, multidrug resistant cancers, diabetic retinopathy, macular degeneration, neovascular glaucoma, myopic degeneration, arthritis, psoriasis, endometriosis, female reproduction, verruca vulgaris, angiofibroma of tuberous sclerosis, pot-wine stains, Sturge Weber syndrome, Kippel-Trenaunay-Weber syndrome, Osler-Weber-Rendu syndrome, renal disease such as Autosomal dominant polycystic kidney disease (ADPKD), and any other diseases or conditions that are related to or will respond to the levels of VEGF, VEGFR1, and VEGFR2 in a cell or tissue, alone or in combination with other therapies.

In another embodiment, a siNA molecule of the invention that targets homologous VEGFR1 and VEGFR2 sequence is used in combination with a siNA molecule that targets VEGF-A according to a use described herein, such as treating a subject with an angiogenesis or neovascularization related disease such as tumor angiogenesis and cancer, including but not limited to breast cancer, lung cancer (including non-small cell lung carcinoma), prostate cancer, colorectal cancer, brain cancer, esophageal cancer, bladder cancer, pancreatic cancer, cervical cancer, head and neck cancer, skin cancers, nasopharyngeal carcinoma, liposarcoma, epithelial carcinoma, renal cell carcinoma, gallbladder adeno carcinoma, parotid adenocarcinoma, ovarian cancer, melanoma, lymphoma, glioma, endometrial sarcoma, multidrug resistant cancers, diabetic retinopathy, macular degeneration, neovascular glaucoma, myopic degeneration, arthritis, psoriasis, endometriosis, female reproduction, verruca vulgaris, angiofibroma of tuberous sclerosis, pot-wine stains, Sturge Weber syndrome, Kippel-Trenaunay-Weber syndrome, Osler-Weber-Rendu syndrome, renal disease such as Autosomal dominant polycystic kidney disease (ADPKD), and any other diseases or conditions that are related to or will respond to the levels of VEGF, VEGFR1, and VEGFR2 in a cell or tissue, alone or in combination with other therapies.

In one embodiment, a siNA of the invention is used to inhibit the expression of VEGFR1, VEGFR2, and/or VEGFr3 genes, wherein the VEGFR1, VEGFR2, and/or VEGFr3 sequences share sequence homology. Such homologous sequences can be identified as is known in the art, for example using sequence alignments. siNA molecules can be designed to target such homologous sequences, for example using perfectly complementary sequences or by incorporating non-canonical base pairs, for example mismatches and/or wobble base pairs, that can provide additional target sequences. Non limiting examples of sequence alignments between VEGFR1 and VEGFR2 are shown in Table m. In instances where mismatches are shown, non-canonical base pairs, for example mismatches and/or wobble bases, can be used to generate siNA molecules that target both VEGFR1 and VEGFR2 RNA sequences. In a non-limiting example, non-canonical base pairs such as UU and CC base pairs are used to generate siNA molecules that are capable of targeting differing VEGF and/or VEGFR sequences (e.g. VEGFR1 and VEGFR2). As such, one advantage of using siNAs of the invention is that a single siNA can be designed to include nucleic acid sequence that is complementary to the nucleotide sequence that is conserved between the VEGF receptors (i.e., VEGFR1, VEGFR2, and/or VEGFR3) such that the siNA can interact with RNAs of the receptors and mediate RNAi to achieve inhibition of expression of the VEGF receptors. In this approach, a single siNA can be used to inhibit expression of more than one VEGF receptor instead of using more than one siNA molecule to target the different receptors.

In one embodiment, the invention features a method of designing a single siNA to inhibit the expression of both VEGFR1 and VEGFR2 genes comprising designing an siNA having nucleotide sequence that is complementary to nucleotide sequence encoded by or present in both VEGFR1 and VEGFR2 genes or a portion thereof, wherein the siNA mediates RNAi to inhibit the expression of both VEGFR1 and VEGFR2 genes. For example, a single siNA can inhibit the expression of two genes by binding to conserved or homologous sequence present in RNA encoded by VEGFR1 and VEGFR2 genes or a portion thereof.

In one embodiment, the invention features a method of designing a single siNA to inhibit the expression of both VEGFR1 and VEGFr3 genes comprising designing an siNA having nucleotide sequence that is complementary to nucleotide sequence encoded by or present in both VEGFR1 and VEGFr3 genes or a portion thereof, wherein the siNA mediates RNAi to inhibit the expression of both VEGFR1 and VEGFr3 genes. For example, a single siNA can inhibit the expression of two genes by binding to conserved or homologous sequence present in RNA encoded by VEGFR1 and VEGFr3 genes or a portion thereof.

In one embodiment, the invention features a method of designing a single siNA to inhibit the expression of both VEGFR2 and VEGFr3 genes comprising designing an siNA having nucleotide sequence that is complementary to nucleotide sequence encoded by or present in both VEGFR2 and VEGFr3 genes or a portion thereof, wherein the siNA mediates RNAi to inhibit the expression of both VEGFR2 and VEGFr3 genes. For example, a single siNA can inhibit the expression of two genes by binding to conserved or homologous sequence present in RNA encoded by VEGFR2 and VEGFr3 genes or a portion thereof.

In one embodiment, the invention features a method of designing a single siNA to inhibit the expression of VEGFR1, VEGFR2 and VEGFr3 genes comprising designing an siNA having nucleotide sequence that is complementary to nucleotide sequence encoded by or present in VEGFR1, VEGFR2 and VEGFr3 genes or a portion thereof, wherein the siNA mediates RNAi to inhibit the expression of VEGFR1, VEGFR2 and VEGFr3 genes. For example, a single siNA can inhibit the expression of two genes by binding to conserved or homologous sequence present in RNA encoded by VEGFR1, VEGFR2 and VEGFr3 genes or a portion thereof.

In one embodiment, nucleic acid molecules of the invention that act as mediators of the RNA interference gene silencing response are double-stranded nucleic acid molecules. In another embodiment, the siNA molecules of the invention consist of duplex nucleic acid molecules containing about 19 base pairs between oligonucleotides comprising about 19 to about 25 (e.g., about 19, 20, 21, 22, 23, 24, or 25) nucleotides. In yet another embodiment, siNA molecules of the invention comprise duplex nucleic acid molecules with overhanging ends of about 1 to about 3 (e.g., about 1, 2, or 3) nucleotides, for example, about 21-nucleotide duplexes with about 19 base pairs and 3'-terminal mononucleotide, dinucleotide, or trinucleotide overhangs.

In one embodiment, the invention features one or more chemically-modified siNA constructs having specificity for VEGF and/or VEGFr expressing nucleic acid molecules, such as RNA encoding a VEGF and/or VEGFr protein. Non-limiting examples of such chemical modifications include without limitation phosphorothioate internucleotide linkages, 2'-deoxyribonucleotides, 2'-O-methyl ribonucleotides, 2'-deoxy-2'-fluoro ribonucleotides, "universal base" nucleotides, "acyclic" nucleotides, 5-C-methyl nucleotides, and terminal glyceryl and/or inverted deoxy abasic residue incorporation. These chemical modifications, when used in various siNA constructs, are shown to preserve RNAi activity in cells while at the same time, dramatically increasing the serum stability of these compounds. Furthermore, contrary to the data published by Parrish et al., supra, applicant demonstrates that multiple (greater than one) phosphorothioate substitutions are well-tolerated and confer substantial increases in serum stability for modified siNA constructs.

In one embodiment, a siNA molecule of the invention comprises modified nucleotides while maintaining the ability to mediate RNAi. The modified nucleotides can be used to improve in vitro or in vivo characteristics such as stability, activity, and/or bioavailability. For example, a siNA molecule of the invention can comprise modified nucleotides as a percentage of the total number of nucleotides present in the siNA molecule. As such, a siNA molecule of the invention can generally comprise about 5% to about 100% modified nucleotides (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given siNA molecule will depend on the total number of nucleotides present in the siNA. If the siNA molecule is single stranded, the percent modification can be based upon the total number of nucleotides present in the single stranded siNA molecules. Likewise, if the siNA molecule is double stranded, the percent modification can be based upon the total number of nucleotides present in the sense strand, antisense strand, or both the sense and antisense strands.

One aspect of the invention features a double-stranded short interfering nucleic acid (siNA) molecule that down-regulates expression of a VEGF and/or VEGFr gene. In one embodiment, the double stranded siNA molecule comprises one or more chemical modifications and each strand of the double-stranded siNA is about 21 nucleotides long. In one embodiment, the double-stranded siNA molecule does not contain any ribonucleotides. In another embodiment, the double-stranded siNA molecule comprises one or more ribonucleotides. In one embodiment, each strand of the double-stranded siNA molecule comprises about 19 to about 29 (e.g., about 19, 20, 21, 22, 23, 24, 25, 26, 27, 28, or 29) nucleotides, wherein each strand comprises about 19 nucleotides that are complementary to the nucleotides of the other strand. In one embodiment, one of the strands of the double-stranded siNA molecule comprises a nucleotide sequence that is complementary to a nucleotide sequence, or a portion thereof, of the VEGF and/or VEGFr gene, and the second strand of the double-stranded siNA molecule comprises a nucleotide sequence substantially similar to the nucleotide sequence of the VEGF and/or VEGFr gene, or a portion thereof.

In another embodiment, the invention features a double-stranded short interfering nucleic acid (siNA) molecule that down-regulates expression of a VEGF and/or VEGFr gene comprising an antisense region, wherein the antisense region comprises a nucleotide sequence that is complementary to a nucleotide sequence of the VEGF and/or VEGFr gene or a portion thereof, and a sense region, wherein the sense region comprises a nucleotide sequence substantially similar to the nucleotide sequence of the VEGF and/or VEGFr gene or a portion thereof. In one embodiment, the antisense region and the sense region each comprise about 19 to about 23 (e.g. about 19, 20, 21, 22, or 23) nucleotides, wherein the antisense region comprises about 19 nucleotides that are complementary to nucleotides of the sense region.

In another embodiment, the invention features a double-stranded short interfering nucleic acid (siNA) molecule that down-regulates expression of a VEGF and/or VEGFr gene comprising a sense region and an antisense region, wherein the antisense region comprises a nucleotide sequence that is complementary to a nucleotide sequence of RNA encoded by the VEGF and/or VEGFr gene or a portion thereof and the sense region comprises a nucleotide sequence that is complementary to the antisense region.

In one embodiment, a siNA molecule of the invention comprises blunt ends, i.e., ends that do not include any overhanging nucleotides. For example, a siNA molecule comprising modifications described herein (e.g., comprising nucleotides having Formulae I–VII or siNA constructs comprising Stab00–Stab24 or any combination thereof (see Table IV)) and/or any length described herein can comprise blunt ends or ends with no overhanging nucleotides.

In one embodiment, any siNA molecule of the invention can comprise one or more blunt ends, i.e. where a blunt end does not have any overhanging nucleotides. In one embodiment, the blunt ended siNA molecule has a number of base pairs equal to the number of nucleotides present in each strand of the siNA molecule. In another embodiment, the siNA molecule comprises one blunt end, for example, wherein the 5'-end of the antisense strand and the 3'-end of the sense strand do not have any overhanging nucleotides. In another example, the siNA molecule comprises one blunt end, for example, wherein the 3'-end of the antisense strand and the 5'-end of the sense strand do not have any overhanging nucleotides. In another example, a siNA molecule comprises two blunt ends, for example wherein the 3'-end of the antisense strand and the 5'-end of the sense strand as well as the 5'-end of the antisense strand and 3'-end of the sense strand do not have any overhanging nucleotides. A blunt ended siNA molecule can comprise, for example, from about 18 to about 30 nucleotides (e.g., about 18, 19, 20, 21, 22, 23, 24, 25, 26, 27, 28, 29, or 30 nucleotides). Other nucleotides present in a blunt ended siNA molecule can comprise mismatches, bulges, loops, or wobble base pairs, for example, to modulate the activity of the siNA molecule to mediate RNA interference.

By "blunt ends" is meant symmetric termini or termini of a double stranded siNA molecule having no overhanging nucleotides. The two strands of a double stranded siNA molecule align with each other without over-hanging nucleotides at the termini. For example, a blunt ended siNA construct comprises terminal nucleotides that are complementary between the sense and antisense regions of the siNA molecule.

In one embodiment, the invention features a double-stranded short interfering nucleic acid (siNA) molecule that down-regulates expression of a VEGF and/or VEGFr gene, wherein the siNA molecule is assembled from two separate oligonucleotide fragments wherein one fragment comprises the sense region and the second fragment comprises the antisense region of the siNA molecule. The sense region can be connected to the antisense region via a linker molecule, such as a polynucleotide linker or a non-nucleotide linker.

In one embodiment, the invention features a double-stranded short interfering nucleic acid (siNA) molecule that down-regulates expression of a VEGF and/or VEGFr gene, wherein the siNA molecule comprises about 19 to about 21 base pairs, and wherein each strand of the siNA molecule comprises one or more chemical modifications. In another embodiment, one of the strands of the double-stranded siNA molecule comprises a nucleotide sequence that is complementary to a nucleotide sequence of a VEGF and/or VEGFr gene or portion thereof, and the second strand of the double-stranded siNA molecule comprises a nucleotide sequence substantially similar to the nucleotide sequence or a portion thereof of the VEGF and/or VEGFr gene. In another embodiment, one of the strands of the double-stranded siNA molecule comprises a nucleotide sequence that is complementary to a nucleotide sequence of a VEGF and/or VEGFr gene or portion thereof, and the second strand of the double-stranded siNA molecule comprises a nucleotide sequence substantially similar to the nucleotide sequence or a portion thereof of the VEGF and/or VEGFr gene. In another embodiment, each strand of the siNA molecule comprises about 19 to about 23 nucleotides, and each strand comprises at least about 19 nucleotides that are complementary to the nucleotides of the other strand. The VEGF and/or VEGFr gene can comprise, for example, sequences referred to in Table I.

In one embodiment, a siNA molecule of the invention comprises no ribonucleotides. In another embodiment, a siNA molecule of the invention comprises ribonucleotides.

In one embodiment, a siNA molecule of the invention comprises an antisense region comprising a nucleotide sequence that is complementary to a nucleotide sequence of a VEGF and/or VEGFr gene or a portion thereof, and the siNA further comprises a sense region comprising a nucleotide sequence substantially similar to the nucleotide sequence of the VEGF and/or VEGFr gene or a portion thereof. In another embodiment, the antisense region and the sense region each comprise about 19 to about 23 nucleotides and the antisense region comprises at least about 19 nucleotides that are complementary to nucleotides of the sense region. The VEGF and/or VEGFr gene can comprise, for example, sequences referred to in Table I.

In one embodiment, a siNA molecule of the invention comprises a sense region and an antisense region, wherein the antisense region comprises a nucleotide sequence that is complementary to a nucleotide sequence of RNA encoded by a VEGF and/or VEGFr gene, or a portion thereof, and the sense region comprises a nucleotide sequence that is complementary to the antisense region. In one embodiment, the siNA molecule is assembled from two separate oligonucleotide fragments, wherein one fragment comprises the sense region and the second fragment comprises the antisense region of the siNA molecule. In another embodiment, the sense region is connected to the antisense region via a linker molecule. In another embodiment, the sense region is connected to the antisense region via a linker molecule, such as a nucleotide or non-nucleotide linker. The VEGF and/or VEGFr gene can comprise, for example, sequences referred in to Table I.

In one embodiment, the invention features a double-stranded short interfering nucleic acid (siNA) molecule that down-regulates expression of a VEGF and/or VEGFr gene comprising a sense region and an antisense region, wherein the antisense region comprises a nucleotide sequence that is complementary to a nucleotide sequence of RNA encoded by the VEGF and/or VEGFr gene or a portion thereof and the sense region comprises a nucleotide sequence that is complementary to the antisense region, and wherein the siNA molecule has one or more modified pyrimidine and/or purine nucleotides. In one embodiment, the pyrimidine nucleotides in the sense region are 2'-O-methyl pyrimidine nucleotides or 2'-deoxy-2'-fluoro pyrimidine nucleotides and the purine nucleotides present in the sense region are 2'-deoxy purine nucleotides. In another embodiment, the pyrimidine nucleotides in the sense region are 2'-deoxy-2'-fluoro pyrimidine nucleotides and the purine nucleotides present in the sense region are 2'-O-methyl purine nucleotides. In another embodiment, the pyrimidine nucleotides in the sense region are 2'-deoxy-2'-fluoro pyrimidine nucleotides and the purine nucleotides present in the sense region are 2'-deoxy purine nucleotides. In one embodiment, the pyrimidine nucleotides in the antisense region are 2'-deoxy-2'-fluoro pyrimidine nucleotides and the purine nucleotides present in the antisense region are 2'-O-methyl or 2'-deoxy purine nucleotides. In another embodiment of any of the above-described siNA molecules, any nucleotides present in a non-complementary region of the sense strand (e.g. overhang region) are 2'-deoxy nucleotides.

In one embodiment, the invention features a double-stranded short interfering nucleic acid (siNA) molecule that down-regulates expression of a VEGF and/or VEGFr gene, wherein the siNA molecule is assembled from two separate oligonucleotide fragments wherein one fragment comprises the sense region and the second fragment comprises the antisense region of the siNA molecule, and wherein the fragment comprising the sense region includes a terminal cap moiety at the 5'-end, the 3'-end, or both of the 5' and 3' ends of the fragment. In one embodiment, the terminal cap moiety is an inverted deoxy abasic moiety or glyceryl moiety. In one embodiment, each of the two fragments of the siNA molecule comprise about 21 nucleotides.

In one embodiment, the invention features a siNA molecule comprising at least one modified nucleotide, wherein the modified nucleotide is a 2'-deoxy-2'-fluoro nucleotide. The siNA can be, for example, of length between about 12 and about 36 nucleotides. In one embodiment, all pyrimidine nucleotides present in the siNA are 2'-deoxy-2'-fluoro pyrimidine nucleotides. In one embodiment, the modified nucleotides in the siNA include at least one 2'-deoxy-2'-fluoro cytidine or 2'-deoxy-2'-fluoro uridine nucleotide. In one embodiment, the modified nucleotides in the siNA include at least one 2'-fluoro cytidine and at least one 2'-deoxy-2'-fluoro uridine nucleotides. In one embodiment, all uridine nucleotides present in the siNA are 2'-deoxy-2'-fluoro uridine nucleotides. In one embodiment, all cytidine nucleotides present in the siNA are 2'-deoxy-2'-fluoro cytidine nucleotides. In one embodiment, all adenosine nucleotides present in the siNA are 2'-deoxy-2'-fluoro adenosine nucleotides. In one embodiment, all guanosine nucleotides present in the siNA are 2'-deoxy-2'-fluoro guanosine nucleotides. The siNA can further comprise at least one modified internucleotidic linkage, such as phosphorothioate linkage. In another embodiment, the 2'-deoxy-2'-fluoronucleotides are present at specifically selected locations in the siNA that are sensitive to cleavage by ribonucleases, such as locations having pyrimidine nucleotides.

In one embodiment, the invention features a method of increasing the stability of a siNA molecule against cleavage by ribonucleases comprising introducing at least one modified nucleotide into the siNA molecule, wherein the modified nucleotide is a 2'-deoxy-2'-fluoro nucleotide. In one embodiment, all pyrimidine nucleotides present in the siNA are 2'-deoxy-2'-fluoro pyrimidine nucleotides. In one embodiment, the modified nucleotides in the siNA include at least one 2'-deoxy-2'-fluoro cytidine or 2'-deoxy-2'-fluoro uridine nucleotide. In one embodiment, the modified nucleotides in the siNA include at least one 2'-fluoro cytidine and at least one 2'-deoxy-2'-fluoro uridine nucleotides. In one embodiment, all uridine nucleotides present in the siNA are 2'-deoxy-2'-fluoro uridine nucleotides. In one embodiment, all cytidine nucleotides present in the siNA are 2'-deoxy-2'-fluoro cytidine nucleotides. In one embodiment, all adenosine nucleotides present in the siNA are 2'-deoxy-2'-fluoro adenosine nucleotides. In one embodiment, all guanosine nucleotides present in the siNA are 2'-deoxy-2'-fluoro guanosine nucleotides. The siNA can further comprise at least one modified internucleotidic linkage, such as phosphorothioate linkage. In one embodiment, the 2'-deoxy-2'-fluoronucleotides are present at specifically selected locations in the siNA that are sensitive to cleavage by ribonucleases, such as locations having pyrimidine nucleotides.

In one embodiment, the invention features a double-stranded short interfering nucleic acid (siNA) molecule that down-regulates expression of a VEGF and/or VEGFr gene comprising a sense region and an antisense region, wherein the antisense region comprises a nucleotide sequence that is complementary to a nucleotide sequence of RNA encoded by the VEGF and/or VEGFr gene or a portion thereof and the sense region comprises a nucleotide sequence that is complementary to the antisense region, and wherein the purine nucleotides present in the antisense region comprise 2'-deoxy-purine nucleotides. In an alternative embodiment, the purine nucleotides present in the antisense region comprise 2'-O-methyl purine nucleotides. In either of the above embodiments, the antisense region can comprise a phosphorothioate internucleotide linkage at the 3' end of the antisense region. Alternatively, in either of the above embodiments, the antisense region can comprise a glyceryl modification at the 3' end of the antisense region. In another embodiment of any of the above-described siNA molecules, any nucleotides present in a non-complementary region of the antisense strand (e.g. overhang region) are 2'-deoxy nucleotides.

In one embodiment, the antisense region of a siNA molecule of the invention comprises sequence complementary to a portion of a VEGF and/or VEGFr transcript having sequence unique to a particular VEGF and/or VEGFr disease related allele, such as sequence comprising a single nucleotidepolymorphism (SNP) associated with the disease specific allele. As such, the antisense region of a siNA molecule of the invention can comprise sequence complementary to sequences that are unique to a particular allele to provide specificity in mediating selective RNAi against the disease related allele.

In one embodiment, the invention features a double-stranded short interfering nucleic acid (siNA) molecule that down-regulates expression of a VEGF and/or VEGFr gene, wherein the siNA molecule is assembled from two separate oligonucleotide fragments wherein one fragment comprises the sense region and the second fragment comprises the antisense region of the siNA molecule. In another embodiment about 19 nucleotides of each fragment of the siNA molecule are base-paired to the complementary nucleotides of the other fragment of the siNA molecule and wherein at least two 3' terminal nucleotides of each fragment of the siNA molecule are not base-paired to the nucleotides of the other fragment of the siNA molecule. In one embodiment, each of the two 3' terminal nucleotides of each fragment of the siNA molecule is a 2'-deoxy-pyrimidine nucleotide, such as a 2'-deoxy-thymidine. In another embodiment, all 21 nucleotides of each fragment of the siNA molecule are base-paired to the complementary nucleotides of the other fragment of the siNA molecule. In another embodiment, about 19 nucleotides of the antisense region are base-paired to the nucleotide sequence or a portion thereof of the RNA encoded by the VEGF and/or VEGFr gene. In another embodiment, about 21 nucleotides of the antisense region are base-paired to the nucleotide sequence or a portion thereof of the RNA encoded by the VEGF and/or VEGFr gene. In any of the above embodiments, the 5'-end of the fragment comprising said antisense region can optionally includes a phosphate group.

In one embodiment, the invention features a double-stranded short interfering nucleic acid (siNA) molecule that inhibits the expression of a VEGF and/or VEGFr RNA sequence (e.g., wherein said target RNA sequence is encoded by a VEGF and/or VEGFr gene involved in the VEGF and/or VEGFr pathway), wherein the siNA molecule does not contain any ribonucleotides and wherein each strand of the double-stranded siNA molecule is about 21 nucleotides long. Examples of non-ribonucleotide containing siNA constructs are combinations of stabilization chemistries shown in Table IV in any combination of Sense/Antisense chemistries, such as Stab 7/8, Stab 7/11, Stab 8/8, Stab 18/8, Stab 18/11, Stab 12/13, Stab 7/13, Stab 18/13, Stab 7/19, Stab 8/19, Stab 18/19, Stab 7/20, Stab 8/20, or Stab 18/20.

In one embodiment, the invention features a chemically synthesized double stranded RNA molecule that directs cleavage of a VEGF and/or VEGFr RNA via RNA interference, wherein each strand of said RNA molecule is about 21 to about 23 nucleotides in length; one strand of the RNA molecule comprises nucleotide sequence having sufficient complementarity to the VEGF and/or VEGFr RNA for the RNA molecule to direct cleavage of the VEGF and/or VEGFr RNA via RNA interference; and wherein at least one strand of the RNA molecule comprises one or more chemically modified nucleotides described herein, such as deoxy-nucleotides, 2'-O-methyl nucleotides, 2'-deoxy-2'-fluoro nucloetides, 2'-O-methoxyethyl nucleotides etc.

In one embodiment, the invention features a medicament comprising a siNA molecule of the invention.

In one embodiment, the invention features an active ingredient comprising a siNA molecule of the invention.

In one embodiment, the invention features the use of a double-stranded short interfering nucleic acid (siNA) molecule to down-regulate expression of a VEGF and/or VEGFr gene, wherein the siNA molecule comprises one or more chemical modifications and each strand of the double-stranded siNA is about 18 to about 28 or more (e.g., about 18, 19, 20, 21, 22, 23, 24, 25, 26, 27,28 or more) nucleotides long.

In one embodiment, the invention features the use of a double-stranded short interfering nucleic acid (siNA) molecule to down-regulate expression of a VEGF and/or VEGFr gene, wherein the siNA molecule comprises one or more chemical modifications and each strand of the double-stranded siNA is about 21 nucleotides long.

In one embodiment, a VEGFr gene contemplated by the invention is a VEGFR1, VEGFR2, or VEGFr3 gene.

In one embodiment, the invention features the use of a double-stranded short interfering nucleic acid (siNA) molecule that inhibits expression of a VEGF and/or VEGFr gene, wherein one of the strands of the double-stranded siNA molecule is an antisense strand which comprises nucleotide sequence that is complementary to nucleotide sequence of VEGF and/or VEGFr RNA or a portion thereof, the other strand is a sense strand which comprises nucleotide sequence that is complementary to a nucleotide sequence of the antisense strand and wherein a majority of the pyrimidine nucleotides present in the double-stranded siNA molecule comprises a sugar modification. In one embodiment, the VEGFr gene is VEGFR2. In one embodiment, the VEGFr gene is VEGFR1.

In one embodiment, the invention features a double-stranded short interfering nucleic acid (siNA) molecule that inhibits expression of a VEGF and/or VEGFr gene, wherein one of the strands of the double-stranded siNA molecule is an antisense strand which comprises nucleotide sequence that is complementary to nucleotide sequence of VEGF and/or VEGFr RNA or a portion thereof, wherein the other strand is a sense strand which comprises nucleotide sequence that is complementary to a nucleotide sequence of the antisense strand and wherein a majority of the pyrimidine nucleotides present in the double-stranded siNA molecule comprises a sugar modification. In one embodiment, the VEGFr gene is VEGFR2. In one embodiment, the VEGFr gene is VEGFR1.

In one embodiment, the invention features a double-stranded short interfering nucleic acid (siNA) molecule that inhibits expression of a VEGF and/or VEGFr gene, wherein one of the strands of the double-stranded siNA molecule is an antisense strand which comprises nucleotide sequence that is complementary to nucleotide sequence of VEGF and/or VEGFr RNA or a portion thereof, the other strand is a sense strand which comprises nucleotide sequence that is complementary to a nucleotide sequence of the antisense strand and wherein a majority of the pyrimidine nucleotides present in the double-stranded siNA molecule comprises a sugar modification. In one embodiment, each strand of the siNA molecule comprises about 18 to about 29 or more (e.g., about 18, 19, 20, 21, 22, 23, 24, 25, 26, 27, 28, 29 or more) nucleotides, wherein each strand comprises at least about 18 nucleotides that are complementary to the nucleotides of the other strand. In another embodiment, the siNA molecule is assembled from two oligonucleotide fragments, wherein one fragment comprises the nucleotide sequence of the antisense strand of the siNA molecule and a second fragment comprises nucleotide sequence of the sense region of the siNA molecule. In one embodiment, the sense strand is connected to the antisense strand via a linker molecule, such as a polynucleotide linker or a non-nucleotide linker. In a further embodiment, the pyrimidine nucleotides present in the sense strand are 2'-deoxy-2'-fluoro pyrimidine nucleotides and the purine nucleotides present in the sense region are 2'-deoxy purine nucleotides. In another embodiment, the pyrimidine nucleotides present in the sense strand are 2'-deoxy-2'-fluoro pyrimidine nucleotides and the purine nucleotides present in the sense region are 2'-O-methyl purine nucleotides. In still another embodiment, the pyrimidine nucleotides present in the antisense strand are 2'-deoxy-2'-fluoro pyrimidine nucleotides and any purine nucleotides present in the antisense strand are 2'-deoxy purine nucleotides. In one embodiment, the antisense strand comprises one or more 2'-deoxy-2'-fluoro pyrimidine nucleotides and one or more 2'-O-methyl purine nucleotides. In another embodiment, the pyrimidine nucleotides present in the antisense strand are 2'-deoxy-2'-fluoro pyrimidine nucleotides and any purine nucleotides present in the antisense strand are 2'-O-methyl purine nucleotides. In a further embodiment the sense strand comprises a 3'-end and a 5'-end, wherein a terminal cap moiety (e.g., an inverted deoxy abasic moiety or inverted deoxy nucleotide moiety such as inverted thymidine) is present at the 5'-end, the 3'-end, or both of the 5' and 3' ends of the sense strand. In another embodiment, the antisense strand comprises a phosphorothioate internucleotide linkage at the 3' end of the antisense strand. In another embodiment, the antisense strand comprises a glyceryl modification at the 3' end. In another embodiment, the 5'-end of the antisense strand optionally includes a phosphate group.

In any of the above-described embodiments of a double-stranded short interfering nucleic acid (siNA) molecule that inhibits expression of a VEGF and/or VEGFr gene, wherein a majority of the pyrimidine nucleotides present in the double-stranded siNA molecule comprises a sugar modification, each of the two strands of the siNA molecule can comprise about 21 nucleotides. In one embodiment, about 21 nucleotides of each strand of the siNA molecule are base-paired to the complementary nucleotides of the other strand of the siNA molecule. In another embodiment, about 19 nucleotides of each strand of the siNA molecule are base-paired to the complementary nucleotides of the other strand of the siNA molecule, wherein at least two 3' terminal nucleotides of each strand of the siNA molecule are not base-paired to the nucleotides of the other strand of the siNA molecule. In one embodiment, each of the two 3' terminal nucleotides of each fragment of the siNA molecule is a 2'-deoxy-pyrimidine, such as 2'-deoxy-thymidine. In one embodiment, each strand of the siNA molecule is base-paired to the complementary nucleotides of the other strand of the siNA molecule. In one embodiment, about 19 nucleotides of the antisense strand are base-paired to the nucleotide sequence of the VEGF and/or VEGFr RNA or a portion thereof. In another embodiment, about 21 nucleotides of the antisense strand are base-paired to the nucleotide sequence of the VEGF and/or VEGFr RNA or a portion thereof.

In one embodiment, the invention features a double-stranded short interfering nucleic acid (siNA) molecule that inhibits expression of a VEGF and/or VEGFr gene, wherein one of the strands of the double-stranded siNA molecule is an antisense strand which comprises nucleotide sequence that is complementary to nucleotide sequence of VEGF and/or VEGFr RNA or a portion thereof, the other strand is a sense strand which comprises nucleotide sequence that is complementary to a nucleotide sequence of the antisense strand and wherein a majority of the pyrimidine nucleotides present in the double-stranded siNA molecule comprises a sugar modification, and wherein the 5'-end of the antisense strand optionally includes a phosphate group.

In one embodiment, the invention features a double-stranded short interfering nucleic acid (siNA) molecule that inhibits expression of a VEGF and/or VEGFr gene, wherein one of the strands of the double-stranded siNA molecule is an antisense strand which comprises nucleotide sequence that is complementary to nucleotide sequence of VEGF and/or VEGFr RNA or a portion thereof, the other strand is a sense strand which comprises nucleotide sequence that is complementary to a nucleotide sequence of the antisense strand and wherein a majority of the pyrimidine nucleotides present in the double-stranded siNA molecule comprises a sugar modification, and wherein the nucleotide sequence or a portion thereof of the antisense strand is complementary to a nucleotide sequence of the untranslated region or a portion thereof of the VEGF and/or VEGFr RNA.

In one embodiment, the invention features a double-stranded short interfering nucleic acid (siNA) molecule that inhibits expression of a VEGF and/or VEGFr gene, wherein one of the strands of the double-stranded siNA molecule is an antisense strand which comprises nucleotide sequence that is complementary to nucleotide sequence of VEGF and/or VEGFr RNA or a portion thereof, wherein the other strand is a sense strand which comprises nucleotide sequence that is complementary to a nucleotide sequence of the antisense strand, wherein a majority of the pyrimidine nucleotides present in the double-stranded siNA molecule comprises a sugar modification, and wherein the nucleotide sequence of the antisense strand is complementary to a nucleotide sequence of the VEGF and/or VEGFr RNA or a portion thereof that is present in the VEGF and/or VEGFr RNA.

In one embodiment, the invention features a composition comprising a siNA molecule of the invention in a pharmaceutically acceptable carrier or diluent.

In a non-limiting example, the introduction of chemically-modified nucleotides into nucleic acid molecules provides a powerful tool in overcoming potential limitations of in vivo stability and bioavailability inherent to native RNA molecules that are delivered exogenously. For example, the use of chemically-modified nucleic acid molecules can enable a lower dose of a particular nucleic acid molecule for a given therapeutic effect since chemically-modified nucleic acid molecules tend to have a longer half-life in serum. Furthermore, certain chemical modifications can improve the bioavailability of nucleic acid molecules by targeting particular cells or tissues and/or improving cellular uptake of the nucleic acid molecule. Therefore, even if the activity of a chemically-modified nucleic acid molecule is reduced as compared to a native nucleic acid molecule, for example, when compared to an all-RNA nucleic acid molecule, the overall activity of the modified nucleic acid molecule can be greater than that of the native molecule due to improved stability and/or delivery of the molecule. Unlike native unmodified siNA, chemically-modified siNA can also minimize the possibility of activating interferon activity in humans.

In any of the embodiments of siNA molecules described herein, the antisense region of a siNA molecule of the invention can comprise a phosphorothioate internucleotide linkage at the 3'-end of said antisense region. In any of the embodiments of siNA molecules described herein, the antisense region can comprise about one to about five phosphorothioate internucleotide linkages at the 5'-end of said antisense region. In any of the embodiments of siNA molecules described herein, the 3'-terminal nucleotide overhangs of a siNA molecule of the invention can comprise ribonucleotides or deoxyribonucleotides that are chemically-modified at a nucleic acid sugar, base, or backbone. In any of the embodiments of siNA molecules described herein, the 3'-terminal nucleotide overhangs can comprise one or more universal base ribonucleotides. In any of the embodiments of siNA molecules described herein, the 3'-terminal nucleotide overhangs can comprise one or more acyclic nucleotides.

One embodiment of the invention provides an expression vector comprising a nucleic acid sequence encoding at least one siNA molecule of the invention in a manner that allows expression of the nucleic acid molecule. Another embodiment of the invention provides a mammalian cell comprising such an expression vector. The mammalian cell can be a human cell. The siNA molecule of the expression vector can comprise a sense region and an antisense region. The antisense region can comprise sequence complementary to a RNA or DNA sequence encoding VEGF and/or VEGFr and the sense region can comprise sequence complementary to the antisense region. The siNA molecule can comprise two distinct strands having complementary sense and anfisense regions. The siNA molecule can comprise a single strand having complementary sense and antisense regions.

In one embodiment, the invention features a chemically-modified short interfering nucleic acid (siNA) molecule capable of mediating RNA interference (RNAi) against VEGF and/or VEGFr inside a cell or reconstituted in vitro system, wherein the chemical modification comprises one or more (e.g., about 1, 2, 3, 4, 5, 6, 7, 8, 9, 10, or more) nucleotides comprising a backbone modified internucleotide linkage having Formula I:

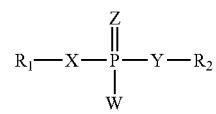

wherein each R1 and R2 is independently any nucleotide, non-nucleotide, or polynucleotide which can be naturally-occurring or chemically-modified, each X and Y is independently O, S, N, alkyl, or substituted alkyl, each Z and W is independently O, S, N, alkyl, substituted alkyl, O-alkyl, S-alkyl, alkaryl, aralkyl, or acetyl and wherein W, X, Y, and Z are optionally not all O. In another embodiment, a backbone modification of the invention comprises a phosphonoacetate and/or thiophosphonoacetate internucleotide linkage (see for example Sheehan et al., 2003, Nucleic Acids Research, 31, 41094118).

The chemically-modified internucleotide linkages having Formula I, for example, wherein any Z, W, X, and/or Y independently comprises a sulphur atom, can be present in one or both oligonucleotide strands of the siNA duplex, for example, in the sense strand, the antisense strand, or both strands. The siNA molecules of the invention can comprise one or more (e.g., about 1, 2, 3, 4, 5, 6, 7, 8, 9, 10, or more) chemically-modified internucleotide linkages having Formula I at the 3'-end, the 5'-end, or both of the 3' and 5'-ends of the sense strand, the anti sense strand, or both strands. For example, an exemplary siNA molecule of the invention can comprise about 1 to about 5 or more (e.g., about 1, 2, 3, 4, 5, or more) chemically-modified internucleotide linkages having Formula I at the 5'-end of the sense strand, the antisense strand, or both strands. In another non-limiting example, an exemplary siNA molecule of the invention can comprise one or more (e.g., about 1, 2, 3, 4, 5, 6, 7, 8, 9, 10, or more) pyrimidine nucleotides with chemically-modified internucleotide linkages having Formula I in the sense strand, the antisense strand, or both strands. In yet another non-limiting example, an exemplary siNA molecule of the invention can comprise one or more (e.g., about 1, 2, 3, 4, 5, 6, 7, 8, 9, 10, or more) purine nucleotides with chemically-modified internucleotide linkages having Formula I in the sense strand, the antisense strand, or both strands. In another embodiment, a siNA molecule of the invention having internucleotide linkage(s) of Formula I also comprises a chemically-modified nucleotide or non-nucleotide having any of Formulae I–VII.

In one embodiment, the invention features a chemically-modified short interfering nucleic acid (siNA) molecule capable of mediating RNA interference (RNAi) against VEGF and/or VEGFr inside a cell or reconstituted in vitro system, wherein the chemical modification comprises one or more (e.g., about 1, 2, 3, 4, 5, 6, 7, 8, 9, 10, or more) nucleotides or non-nucleotides having Formula II:

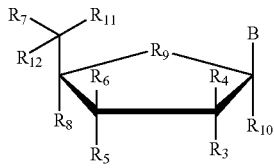

wherein each R3, R4, R5, R6, R7, R8, R10, R 11 and R12 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-S-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalklylamino, substituted silyl, or group having Formula I or II; R9 is O, S, CH2, S=O, CHF, or CF2, and B is a nucleosidic base such as adenine, guanine, uracil, cytosine, thymine, 2-aminoadenosine, 5-methylcytosine, 2,6-diaminopurine, or any other non-naturally occurring base that can be complementary or non-complementary to target RNA or a non-nucleosidic base such as phenyl, naphthyl, 3-nitropyrrole, 5-nitroindole, nebularine, pyridone, pyridinone, or any other non-naturally occurring universal base that can be complementary or non-complementary to target RNA.

The chemically-modified nucleotide or non-nucleotide of Formula II can be present in one or both oligonucleotide strands of the siNA duplex, for example in the sense strand, the antisense strand, or both strands. The siNA molecules of the invention can comprise one or more chemically-modified nucleotide or non-nucleotide of Formula II at the 3'-end, the 5'-end, or both of the 3' and 5'-ends of the sense strand, the antisense strand, or both strands. For example, an exemplary siNA molecule of the invention can comprise about 1 to about 5 or more (e.g., about 1, 2, 3, 4, 5, or more) chemically-modified nucleotides or non-nucleotides of Formula II at the 5'-end of the sense strand, the antisense strand, or both strands. In anther non-limiting example, an exemplary siNA molecule of the invention can comprise about 1 to about 5 or more (e.g., about 1, 2, 3, 4, 5, or more) chemically-modified nucleotides or non-nucleotides of Formula II at the 3'-end of the sense strand, the antisense strand, or both strands.

In one embodiment, the invention features a chemically-modified short interfering nucleic acid (siNA) molecule capable of mediating RNA interference (RNAi) against VEGF and/or VEGFr inside a cell or reconstituted in vitro system, wherein the chemical modification comprises one or more (e.g., about 1, 2, 3, 4, 5, 6, 7, 8, 9, 10, or more) nucleotides or non-nucleotides having Formula III:

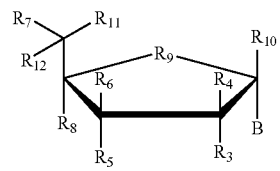

wherein each R3, R4, R5, R6, R7, R8, R10, R11 and R12 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-S-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalklylamino, substituted silyl, or group having Formula I or II; R9 is O, S, CH2, S=O, CHF, or CF2, and B is a nucleosidic base such as adenine, guanine, uracil, cytosine, thymine, 2-aminoadenosine, 5-methylcytosine, 2,6-diaminopurine, or any other non-naturally occurring base that can be employed to be complementary or non-complementary to target RNA or a non-nucleosidic base such as phenyl, naphthyl, 3-nitropyrrole, 5-nitroindole, nebularine, pyridone, pyridinone, or any other non-naturally occurring universal base that can be complementary or non-complementary to target RNA.

The chemically-modified nucleotide or non-nucleotide of Formula III can be present in one or both oligonucleotide strands of the siNA duplex, for example, in the sense strand, the antisense strand, or both strands. The siNA molecules of the invention can comprise one or more chemically-modified nucleotide or non-nucleotide of Formula III at the 3'-end, the 5'-end, or both of the 3' and 5'-ends of the sense strand, the antisense strand, or both strands. For example, an exemplary siNA molecule of the invention can comprise about 1 to about 5 or more (e.g., about 1, 2, 3, 4, 5, or more) chemically-modified nucleotide(s) or non-nucleotide(s) of Formula III at the 5'-end of the sense strand, the antisense strand, or both strands. In anther non-limiting example, an exemplary siNA molecule of the invention can comprise about 1 to about 5 or more (e.g., about 1, 2, 3, 4, 5, or more)

chemically-modified nucleotide or non-nucleotide of Formula III at the 3'-end of the sense strand, the antisense strand, or both strands.

In another embodiment, a siNA molecule of the invention comprises a nucleotide having Formula II or III, wherein the nucleotide having Formula II or III is in an inverted configuration. For example, the nucleotide having Formula II or III is connected to the siNA construct in a 3'-3', 3'-2', 2'-3', or 5'-5' configuration, such as at the 3'-end, the 5'- or both of the 3' and 5'-ends of one or both siNA strands.

In one embodiment, the invention features a chemically-modified short interfering nucleic acid (siNA) molecule capable of mediating RNA interference (RNAi) against VEGF and/or VEGFr inside a cell or reconstituted in vitro system, wherein the chemical modification comprises a 5'-terminal phosphate group having Formula IV:

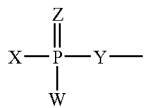

wherein each X and Y is independently O, S, N, alkyl, substituted alkyl, or alkylhalo; wherein each Z and W is independently O, S, N, alkyl, substituted alkyl, O-alkyl, S-alkyl, alkaryl, aralkyl, alkylhalo, or acetyl; and wherein W, X, Y and Z are not all O.

In one embodiment, the invention features a siNA molecule having a 5'-terminal phosphate group having Formula IV on the target-complementary strand, for example, a strand complementary to a target RNA, wherein the siNA molecule comprises an all RNA siNA molecule. In another embodiment, the invention features a siNA molecule having a 5'-terminal phosphate group having Formula IV on the target-complementary strand wherein the siNA molecule also comprises about 1 to about 3 (e.g., about 1, 2, or 3) nucleotide 3'-terminal nucleotide overhangs having about 1 to about 4 (e.g., about 1, 2, 3, or 4) deoxyribonucleotides on the 3'-end of one or both strands. In another embodiment, a 5'-terminal phosphate group having Formula IV is present on the target-complementary strand of a siNA molecule of the invention, for example a siNA molecule having chemical modifications having any of Formulae I–VII.

In one embodiment, the invention features a chemically-modified short interfering nucleic acid (siNA) molecule capable of mediating RNA interference (RNAi) against VEGF and/or VEGFr inside a cell or reconstituted in vitro system, wherein the chemical modification comprises one or more phosphorothioate internucleotide linkages. For example, in a non-limiting example, the invention features a chemically-modified short interfering nucleic acid (siNA) having about 1, 2, 3, 4, 5, 6, 7, 8 or more phosphorothioate internucleotide linkages in one siNA strand. In yet another embodiment, the invention features a chemically-modified short interfering nucleic acid (siNA) individually having about 1, 2, 3, 4, 5, 6, 7, 8 or more phosphorothioate internucleotide linkages in both siNA strands. The phosphorothioate internucleotide linkages can be present in one or both oligonucleotide strands of the siNA duplex, for example in the sense strand, the antisense strand, or both strands. The siNA molecules of the invention can comprise one or more phosphorothioate internucleotide linkages at the 3'-end, the 5'-end, or both of the 3'- and 5'-ends of the sense strand, the antisense strand, or both strands. For example, an exemplary siNA molecule of the invention can comprise about 1 to about 5 or more (e.g., about 1, 2, 3, 4, 5, or more) consecutive phosphorothioate internucleotide linkages at the 5'-end of the sense strand, the antisense strand, or both strands. In another non-limiting example, an exemplary siNA molecule of the invention can comprise one or more (e.g., about 1, 2, 3, 4, 5, 6, 7, 8, 9, 10, or more) pyrimidine phosphorothioate internucleotide linkages in the sense strand, the antisense strand, or both strands. In yet another non-limiting example, an exemplary siNA molecule of the invention can comprise one or more (e.g., about 1, 2, 3, 4, 5, 6, 7, 8, 9, 10, or more) purine phosphorothioate internucleotide linkages in the sense strand, the antisense strand, or both strands.

In one embodiment, the invention features a siNA molecule, wherein the sense strand comprises one or more, for example, about 1, 2, 3, 4, 5, 6, 7, 8, 9, 10, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or about one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and wherein the antisense strand comprises about 1 to about 10 or more, specifically about 1, 2, 3, 4, 5, 6, 7, 8, 9, 10, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In another embodiment, one or more, for example about 1, 2, 3, 4, 5, 6, 7, 8, 9, 10, or more, pyrimidine nucleotides of the sense and/or antisense siNA strand are chemically-modified with 2'-deoxy, 2'-O-methyl and/or 2'-deoxy-2'-fluoro nucleotides, with or without one or more, for example about 1, 2, 3, 4, 5, 6, 7, 8, 9, 10, or more, phosphorothioate internucleotide linkages and/or a terminal cap molecule at the 3'-end, the 5'-end, or both of the 3'- and 5'-ends, being present in the same or different strand.

In another embodiment, the invention features a siNA molecule, wherein the sense strand comprises about 1 to about 5, specifically about 1, 2, 3, 4, or 5 phosphorothioate internucleotide linkages, and/or one or more (e.g., about 1, 2, 3, 4, 5, or more) 2'-deoxy, 2'-O-methyl, 2'-deoxy-2'-fluoro, and/or one or more (e.g., about 1, 2, 3, 4, 5, or more) universal base modified nucleotides, and optionally a terminal cap molecule at the 3-end, the 5'-end, or both of the 3'- and 5'-ends of the sense strand; and wherein the antisense strand comprises about 1 to about 5 or more, specifically about 1, 2, 3, 4, 5, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In another embodiment, one or more, for example about 1, 2, 3, 4, 5, 6, 7, 8, 9, 10, or more, pyrimidine nucleotides of the sense and/or antisense siNA strand are chemically-modified with 2'-deoxy, 2'-O-methyl and/or 2'-deoxy-2'-fluoro nucleotides, with or without about 1 to about 5 or more, for example about 1, 2, 3, 4, 5, or more phosphorothioate internucleotide linkages and/or a terminal cap molecule at the 3'-end, the 5'-end, or both of the 3'- and 5'-ends, being present in the same or different strand.

In one embodiment, the invention features a siNA molecule, wherein the antisense strand comprises one or more, for example, about 1, 2, 3, 4, 5, 6, 7, 8, 9, 10, or more phosphorothioate internucleotide linkages, and/or about one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and wherein the antisense strand comprises about 1 to about 10 or more, specifically about 1, 2, 3, 4, 5, 6, 7, 8, 9, 10 or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In another embodiment, one or more, for example about 1, 2, 3, 4, 5, 6, 7, 8, 9, 10 or more pyrimidine nucleotides of the sense and/or antisense siNA strand are chemically-modified with 2'-deoxy, 2'-O-methyl and/or 2'-deoxy-2'-fluoro nucleotides, with or without one or more, for example, about 1, 2, 3, 4, 5, 6, 7, 8, 9, 10 or more phosphorothioate internucleotide linkages and/or a terminal cap molecule at the 3'-end, the 5'-end, or both of the 3' and 5'-ends, being present in the same or different strand.

In another embodiment, the invention features a siNA molecule, wherein the antisense strand comprises about 1 to about 5 or more, specifically about 1, 2, 3, 4, 5 or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and wherein the antisense strand comprises about 1 to about 5 or more, specifically about 1, 2, 3, 4, 5 or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In another embodiment, one or more, for example about 1, 2, 3, 4, 5, 6, 7, 8, 9, 10 or more pyrimidine nucleotides of the sense and/or antisense siNA strand are chemically-modified with 2'-deoxy, 2'-O-methyl and/or 2'-deoxy-2'-fluoro nucleotides, with or without about 1 to about 5, for example about 1, 2, 3, 4, 5 or more phosphorothioate internucleotide linkages and/or a terminal cap molecule at the 3'-end, the 5'-end, or both of the 3'- and 5'-ends, being present in the same or different strand.

In one embodiment, the invention features a chemically-modified short interfering nucleic acid (siNA) molecule having about 1 to about 5, specifically about 1, 2, 3, 4, 5 or more phosphorothioate internucleotide linkages in each strand of the siNA molecule.

In another embodiment, the invention features a siNA molecule comprising 2'-5' internucleotide linkages. The 2'-5' internucleotide linkage(s) can be at the 3'-end, the 5'-end, or both of the 3'- and 5'-ends of one or both siNA sequence strands. In addition, the 2'-5' internucleotide linkage(s) can be present at various other positions within one or both siNA sequence strands, for example, about 1, 2, 3, 4, 5, 6, 7, 8, 9, 10, or more including every internucleotide linkage of a pyrimidine nucleotide in one or both strands of the siNA molecule can comprise a 2'-5' internucleotide linkage, or about 1, 2, 3, 4, 5, 6, 7, 8, 9, 10, or more including every internucleotide linkage of a purine nucleotide in one or both strands of the siNA molecule can comprise a 2'-5' internucleotide linkage.

In another embodiment, a chemically-modified siNA molecule of the invention comprises a duplex having two strands, one or both of which can be chemically-modified, wherein each strand is about 18 to about 27 (e.g., about 18, 19, 20, 21, 22, 23, 24, 25, 26, or 27) nucleotides in length, wherein the duplex has about 18 to about 23 (e.g., about 18, 19, 20, 21, 22, or 23) base pairs, and wherein the chemical modification comprises a structure having any of Formulae I–VII. For example, an exemplary chemically-modified siNA molecule of the invention comprises a duplex having two strands, one or both of which can be chemically-modified with a chemical modification having any of Formulae I–VII or any combination thereof, wherein each strand consists of about 21 nucleotides, each having a 2-nucleotide 3'-terminal nucleotide overhang, and wherein the duplex has about 19 base pairs. In another embodiment, a siNA molecule of the invention comprises a single stranded hairpin structure, wherein the siNA is about 36 to about 70 (e.g., about 36, 40, 45, 50, 55, 60, 65, or 70) nucleotides in length having about 18 to about 23 (e.g., about 18, 19, 20, 21, 22, or 23) base pairs, and wherein the siNA can include a chemical modification comprising a structure having any of Formulae I–VII or any combination thereof. For example, an exemplary chemically-modified siNA molecule of the invention comprises a linear oligonucleotide having about 42 to about 50 (e.g., about 42, 43, 44, 45, 46, 47, 48, 49, or 50) nucleotides that is chemically-modified with a chemical modification having any of Formulae I–VII or any combination thereof, wherein the linear oligonucleotide forms a hairpin structure having about 19 base pairs and a 2-nucleotide 3'-terminal nucleotide overhang. In another embodiment, a linear hairpin siNA molecule of the invention contains a stem loop motif, wherein the loop portion of the siNA molecule is biodegradable. For example, a linear hairpin siNA molecule of the invention is designed such that degradation of the loop portion of the siNA molecule in vivo can generate a double-stranded siNA molecule with 3'-terminal overhangs, such as 3'-terminal nucleotide overhangs comprising about 2 nucleotides.

In another embodiment, a siNA molecule of the invention comprises a hairpin structure, wherein the siNA is about 25 to about 50 (e.g., about 25, 26, 27, 28, 29, 30, 31, 32, 33, 34, 35, 36, 37, 38, 39, 40, 41, 42, 43, 44, 45, 46, 47, 48, 49, or 50) nucleotides in length having about 3 to about 25 (e.g., about 3, 4, 5, 6, 7, 8, 9, 10, 11, 12, 13, 14, 15, 16, 17, 18, 19, 20, 21, 22, 23, 24, or 25) base pairs, and wherein the siNA can include one or more chemical modifications comprising a structure having any of Formulae I–VII or any combination thereof. For example, an exemplary chemically-modified siNA molecule of the invention comprises a linear oligonucleotide having about 25 to about 35 (e.g., about 25, 26, 27, 28, 29, 30, 31, 32, 33, 34, or 35) nucleotides that is chemically-modified with one or more chemical modifications having any of Formulae I–VII or any combination thereof, wherein the linear oligonucleotide forms a hairpin structure having about 3 to about 23 (e.g., about 3, 4,5, 6, 7, 8, 9, 10, 11, 12, 13, 14, 15, 16, 17, 18, 19, 20, 21,22, or 23) base pairs and a 5'-terminal phosphate group that can be chemically modified as described herein (for example a 5'-terminal phosphate group having Formula IV). In one embodiment, a linear hairpin siNA molecule of the invention contains a stem loop motif, wherein the loop portion of the siNA molecule is biodegradable. In another embodiment, a linear hairpin siNA molecule of the invention comprises a loop portion comprising a non-nucleotide linker.

In another embodiment, a siNA molecule of the invention comprises an asymmetric hairpin structure, wherein the siNA is about 25 to about 50 (e.g., about 25, 26, 27, 28, 29, 30, 31, 32, 33, 34, 35, 36, 37, 38, 39, 40, 41, 42, 43, 44, 45, 46, 47, 48, 49, or 50) nucleotides in length having about 3 to about 20 (e.g., about 3, 4, 5, 6, 7, 8, 9, 10, 11, 12, 13, 14, 15, 16, 17, 18, 19, or 20) base pairs, and wherein the siNA can include one or more chemical modifications comprising a structure having any of Formulae I–VII or any combination thereof. For example, an exemplary chemically-modified siNA molecule of the invention comprises a linear oligonucleotide having about 25 to about 35 (e.g., about 25, 26, 27, 28, 29, 30, 31, 32, 33, 34, or 35) nucleotides that is chemically-modified with one or more chemical modifications having any of Formulae I–VII or any combination thereof, wherein the linear oligonucleotide forms an asymmetric hairpin structure having about 3 to about 18 (e.g., about 3, 4, 5, 6, 7, 8, 9, 10, 11, 12, 13, 14, 15, 16, 17, or 18) base pairs and a 5'-terminal phosphate group that can be chemically modified as described herein (for example a 5'-terminal phosphate group having Formula IV). In one embodiment, an asymmetric hairpin siNA molecule of the invention contains a stem loop motif, wherein the loop portion of the siNA molecule is biodegradable. In another embodiment, an asymmetric hairpin siNA molecule of the invention comprises a loop portion comprising a non-nucleotide linker.

In another embodiment, a siNA molecule of the invention comprises an asymmetric double stranded structure having separate polynucleotide strands comprising sense and antisense regions, wherein the antisense region is about 16 to about 25 (e.g., about 16, 17, 18, 19, 20, 21, 22, 23, 24, or 25) nucleotides in length, wherein the sense region is about 3 to about 18 (e.g., about 3, 4, 5, 6, 7, 8, 9, 10, 11, 12, 13, 14, 15, 16, 17, or 18) nucleotides in length, wherein the sense region and the antisense region have at least 3 complementary nucleotides, and wherein the siNA can include one or more chemical modifications comprising a structure having any of Formulae I–VII or any combination thereof. For example, an exemplary chemically-modified siNA molecule of the invention comprises an asymmetric double stranded structure having separate polynucleotide strands comprising sense and antisense regions, wherein the antisense region is about 18 to about 22 (e.g., about 18, 19, 20, 21, or 22) nucleotides in length and wherein the sense region is about 3 to about 15 (e.g., about 3, 4, 5, 6, 7, 8, 9, 10, 11, 12, 13, 14, or 15) nucleotides in length, wherein the sense region the antisense region have at least 3 complementary nucleotides, and wherein the siNA can include one or more chemical modifications comprising a structure having any of Formulae I–VII or any combination thereof. In another embodiment, the asymmetic double stranded siNA molecule can also have a 5'-terminal phosphate group that can be chemically modified as described herein (for example a 5'-terminal phosphate group having Formula IV).

In another embodiment, a siNA molecule of the invention comprises a circular nucleic acid molecule, wherein the siNA is about 38 to about 70 (e.g., about 38, 40, 45, 50, 55, 60, 65, or 70) nucleotides in length having about 18 to about 23 (e.g., about 18, 19, 20, 21, 22, or 23) base pairs, and wherein the siNA can include a chemical modification, which comprises a structure having any of Formulae I–VII or any combination thereof. For example, an exemplary chemically-modified siNA molecule of the invention comprises a circular oligonucleotide having about 42 to about 50 (e.g., about 42, 43, 44, 45, 46, 47, 48, 49, or 50) nucleotides that is chemically-modified with a chemical modification having any of Formulae I–VII or any combination thereof, wherein the circular oligonucleotide forms a dumbbell shaped structure having about 19 base pairs and 2 loops.

In another embodiment, a circular siNA molecule of the invention contains two loop motifs, wherein one or both loop portions of the siNA molecule is biodegradable. For example, a circular siNA molecule of the invention is designed such that degradation of the loop portions of the siNA molecule in vivo can generate a double-stranded siNA molecule with 3'-terminal overhangs, such as 3'-terminal nucleotide overhangs comprising about 2 nucleotides.

In one embodiment, a siNA molecule of the invention comprises at least one (e.g., about 1, 2, 3, 4, 5, 6, 7, 8, 9, 10, or more) abasic moiety, for example a compound having Formula V:

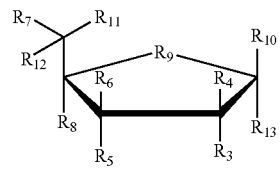

wherein each R3, R4, R5, R6, R7, R8, R10, R11, R12, and R13 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-S-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalklylamino, substituted silyl, or group having Formula I or II; R9 is O, S, CH2, S=O, CHF, or CF2.

In one embodiment, a siNA molecule of the invention comprises at least one (e.g., about 1, 2, 3, 4, 5, 6, 7, 8, 9, 10, or more) inverted abasic moiety, for example a compound having Formula VI:

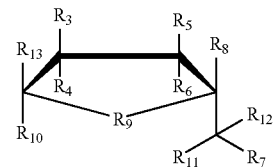

wherein each R3, R4, R5, R6, R7, R8, R10, R11, R12, and R13 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-S-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalklylamino, substituted silyl, or group having Formula I or II; R9 is O, S, CH2, S=O, CHF, or CF2, and either R2, R3, R8 or R13 serve as points of attachment to the siNA molecule of the invention.

In another embodiment, a siNA molecule of the invention comprises at least one (e.g., about 1, 2, 3, 4, 5, 6, 7, 8, 9, 10, or more) substituted polyalkyl moieties, for example a compound having Formula VII:

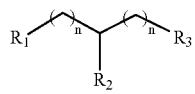

wherein each n is independently an integer from 1 to 12, each R1, R2 and R3 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-S-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalklylamino, substituted silyl, or a group having Formula I, and R1, R2 or R3 serves as points of attachment to the siNA molecule of the invention.

In another embodiment, the invention features a compound having Formula VII, wherein R1 and R2 are hydroxyl (OH) groups, n=1, and R3 comprises O and is the point of attachment to the 3'-end, the 5'-end, or both of the 3' and 5'-ends of one or both strands of a double-stranded siNA molecule of the invention or to a single-stranded siNA molecule of the invention. This modification is referred to herein as "glyceryl" (for example modification 6 in FIG. 10).

In another embodiment, a moiety having any of Formula V, VI or VII of the invention is at the 3'-end, the 5'-end, or both of the 3' and 5'-ends of a siNA molecule of the invention. For example, a moiety having Formula V, VI or VII can be present at the 3'-end, the 5'-end, or both of the 3' and 5'-ends of the antisense strand, the sense strand, or both antisense and sense strands of the siNA molecule. In addition, a moiety having Formula VII can be present at the 3'-end or the 5'-end of a hairpin siNA molecule as described herein.

In another embodiment, a siNA molecule of the invention comprises an abasic residue having Formula V or VI, wherein the abasic residue having Formula VI or VI is connected to the siNA construct in a 3'-3', 3'-2', 2'-3', or 5'-5' configuration, such as at the 3'-end, the 5'-end, or both of the 3' and 5'-ends of one or both siNA strands.

In one embodiment, a siNA molecule of the invention comprises one or more (e.g., about 1, 2, 3, 4, 5, 6, 7, 8, 9, 10, or more) locked nucleic acid (LNA) nucleotides, for example at the 5'-end, the 3'-end, both of the 5' and 3'-ends, or any combination thereof, of the siNA molecule.

In another embodiment, a siNA molecule of the invention comprises one or more (e.g., about 1, 2, 3, 4, 5, 6, 7, 8, 9, 10, or more) acyclic nucleotides, for example at the 5'-end, the 3'-end, both of the 5' and 3'-ends, or any combination thereof, of the siNA molecule.

In one embodiment, the invention features a chemically-modified short interfering nucleic acid (siNA) molecule of the invention comprising a sense region, wherein any (e.g., one or more or all) pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any (e.g., one or more or all) purine nucleotides present in the sense region are 2'-deoxy purine nucleotides (e.g., wherein all purine nucleotides are 2'-deoxy purine nucleotides or alternately a plurality of purine nucleotides are 2'-deoxy purine nucleotides).

In one embodiment, the invention features a chemically-modified short interfering nucleic acid (siNA) molecule of the invention comprising a sense region, wherein any (e.g., one or more or all) pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any (e.g., one or more or all) purine nucleotides present in the sense region are 2'-deoxy purine nucleotides (e.g., wherein all purine nucleotides are 2'-deoxy purine nucleotides or alternately a plurality of purine nucleotides are 2'-deoxy purine nucleotides), wherein any nucleotides comprising a 3'-terminal nucleotide overhang that are present in said sense region are 2'-deoxy nucleotides.

In one embodiment, the invention features a chemically-modified short interfering nucleic acid (siNA) molecule of the invention comprising a sense region, wherein any (e.g., one or more or all) pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any (e.g., one or more or all) purine nucleotides present in the sense region are 2'-O-methyl purine nucleotides (e.g., wherein all purine nucleotides are 2'-O-methyl purine nucleotides or alternately a plurality of purine nucleotides are 2'-O-methyl purine nucleotides).

In one embodiment, the invention features a chemically-modified short interfering nucleic acid (siNA) molecule of the invention comprising a sense region, wherein any (e.g., one or more or all) pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), wherein any (e.g., one or more or all) purine nucleotides present in the sense region are 2'-O-methyl purine nucleotides (e.g., wherein all purine nucleotides are 2'-O-methyl purine nucleotides or alternately a plurality of purine nucleotides are 2'-O-methyl purine nucleotides), and wherein any nucleotides comprising a 3'-terminal nucleotide overhang that are present in said sense region are 2'-deoxy nucleotides.

In one embodiment, the invention features a chemically-modified short interfering nucleic acid (siNA) molecule of the invention comprising an antisense region, wherein any (e.g., one or more or all) pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any (e.g., one or more or all) purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides).

In one embodiment, the invention features a chemically-modified short interfering nucleic acid (siNA) molecule of the invention comprising an antisense region, wherein any (e.g., one or more or all) pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), wherein any (e.g., one or more or all) purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides), and wherein any nucleotides comprising a 3'-terminal nucleotide overhang that are present in said antisense region are 2'-deoxy nucleotides.

In one embodiment, the invention features a chemically-modified short interfering nucleic acid (siNA) molecule of the invention comprising an antisense region, wherein any (e.g., one or more or all) pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any (e.g., one or more or all) purine nucleotides present in the antisense region are 2'-deoxy purine nucleotides (e.g., wherein all purine nucleotides are 2'-deoxy purine nucleotides or alternately a plurality of purine nucleotides are 2'-deoxy purine nucleotides).

In one embodiment, the invention features a chemically-modified short interfering nucleic acid (siNA) molecule of the invention comprising an antisense region, wherein any (e.g., one or more or all) pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any (e.g., one or more or all) purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides).

In one embodiment, the invention features a chemically-modified short interfering nucleic acid (siNA) molecule of the invention capable of mediating RNA interference (RNAi) against VEGF and/or VEGFr inside a cell or reconstituted in vitro system comprising a sense region, wherein one or more pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and one or more purine nucleotides present in the sense region are 2'-deoxy purine nucleotides (e.g., wherein all purine nucleotides are 2'-deoxy purine nucleotides or alternately a plurality of purine nucleotides are 2'-deoxy purine nucleotides), and an antisense region, wherein one or more pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and one or more purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides). The sense region and/or the antisense region can have a terminal cap modification, such as any modification described herein or shown in FIG. 10, that is optionally present at the 3'-end, the 5'-end, or both of the 3' and 5'-ends of the sense and/or antisense sequence. The sense and/or antisense region can optionally further comprise a 3'-terminal nucleotide overhang having about 1 to about 4 (e.g., about 1, 2, 3, or 4) 2'-deoxynucleotides. The overhang nucleotides can further comprise one or more (e.g., about 1, 2, 3, 4 or more) phosphorothioate, phosphonoacetate, and/or thiophosphonoacetate internucleotide linkages. Non-limiting examples of these chemically-modified siNAs are shown in FIGS. 4 and 5 and Tables III and IV herein. In any of these described embodiments, the purine nucleotides present in the sense region are alternatively 2'-O-methyl purine nucleotides (e.g., wherein all purine nucleotides are 2'-O-methyl purine nucleotides or alternately a plurality of purine nucleotides are 2'-O-methyl purine nucleotides) and one or more purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides). Also, in any of these embodiments, one or more purine nucleotides present in the sense region are alternatively purine ribonucleotides (e.g., wherein all purine nucleotides are purine ribonucleotides or alternately a plurality of purine nucleotides are purine ribonucleotides) and any purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides). Additionally, in any of these embodiments, one or more purine nucleotides present in the sense region and/or present in the antisense region are alternatively selected from the group consisting of 2'-deoxy nucleotides, locked nucleic acid (LNA) nucleotides, 2'-methoxyethyl nucleotides, 4'-thionucleotides, and 2'-O-methyl nucleotides (e.g., wherein all purine nucleotides are selected from the group consisting of 2'-deoxy nucleotides, locked nucleic acid (LNA) nucleotides, 2'-methoxyethyl nucleotides, 4'-thionucleotides, and 2'-O-methyl nucleotides or alternately a plurality of purine nucleotides are selected from the group consisting of 2'-deoxy nucleotides, locked nucleic acid (LNA) nucleotides, 2'-methoxyethyl nucleotides, 4'-thionucleotides, and 2'-O-methyl nucleotides).

In another embodiment, any modified nucleotides present in the siNA molecules of the invention, preferably in the antisense strand of the siNA molecules of the invention, but also optionally in the sense and/or both antisense and sense strands, comprise modified nucleotides having properties or characteristics similar to naturally occurring ribonucleotides. For example, the invention features siNA molecules including modified nucleotides having a Northern conformation (e.g., Northern pseudorotation cycle, see for example Saenger, *Principles of Nucleic Acid Structure*, Springer-Verlag ed., 1984). As such, chemically modified nucleotides present in the siNA molecules of the invention, preferably in the antisense strand of the siNA molecules of the invention, but also optionally in the sense and/or both antisense and sense strands, are resistant to nuclease degradation while at the same time maintaining the capacity to mediate RNAi. Non-limiting examples of nucleotides having a northern configuration include locked nucleic acid (LNA) nucleotides (e.g., 2'-O, 4'-C-methylene-(D-ribofuranosyl)nucleotides); 2'-methoxyethoxy (MOE) nucleotides; 2'-methyl-thio-ethyl, 2'-deoxy-2'-fluoro nucleotides, 2'-deoxy-2'-chloro nucleotides, 2'-azido nucleotides, and 2'-O-methyl nucleotides.

In one embodiment, the sense strand of a double stranded siNA molecule of the invention comprises a terminal cap moiety, (see for example FIG. 10) such as an inverted deoxyabaisc moiety, at the 3'-end, 5'-end, or both 3' and 5'-ends of the sense strand.

In one embodiment, the invention features a chemically-modified short interfering nucleic acid molecule (siNA) capable of mediating RNA interference (RNAi) against VEGF and/or VEGFr inside a cell or reconstituted in vitro system, wherein the chemical modification comprises a conjugate covalently attached to the chemically-modified siNA molecule. Non-limiting examples of conjugates contemplated by the invention include conjugates and ligands described in Vargeese et al., U.S. Ser. No. 10/427,160, filed Apr. 30, 2003, incorporated by reference herein in its entirety, including the drawings. In another embodiment, the conjugate is covalently attached to the chemically-modified siNA molecule via a biodegradable linker. In one embodiment, the conjugate molecule is attached at the 3'-end of either the sense strand, the antisense strand, or both strands of the chemically-modified siNA molecule. In another embodiment, the conjugate molecule is attached at the 5'-end of either the sense strand, the antisense strand, or both strands of the chemically-modified siNA molecule. In yet another embodiment, the conjugate molecule is attached both the 3'-end and 5'-end of either the sense strand, the antisense strand, or both strands of the chemically-modified siNA molecule, or any combination thereof. In one embodiment, a conjugate molecule of the invention comprises a molecule that facilitates delivery of a chemically-modified siNA molecule into a biological system, such as a cell. In another embodiment, the conjugate molecule attached to the chemically-modified siNA molecule is a polyethylene glycol, human serum albumin, or a ligand for a cellular receptor that can mediate cellular uptake. Examples of specific conjugate molecules contemplated by the instant invention that can be attached to chemically-modified siNA molecules are described in Vargeese et al., U.S. Ser. No. 10/201,394, filed Jul. 22, 2002 incorporated by reference herein. The type of conjugates used and the extent of conjugation of siNA molecules of the invention can be evaluated for improved pharmacokinetic profiles, bioavailability, and/or stability of siNA constructs while at the same time maintaining the ability of the siNA to mediate RNAi activity. As such, one skilled in the art can screen siNA constructs that are modified with various conjugates to determine whether the siNA conjugate complex possesses improved properties while maintaining the ability to mediate RNAi, for example in animal models as are generally known in the art.

In one embodiment, the invention features a short interfering nucleic acid (siNA) molecule of the invention, wherein the siNA further comprises a nucleotide, non-nucleotide, or mixed nucleotide/non-nucleotide linker that joins the sense region of the siNA to the antisense region of the siNA. In one embodiment, a nucleotide linker of the invention can be a linker of ≧2 nucleotides in length, for example about 3, 4, 5, 6, 7, 8, 9, or 10 nucleotides in length. In another embodiment, the nucleotide linker can be a nucleic acid aptamer. By "aptamer" or "nucleic acid aptamer" as used herein is meant a nucleic acid molecule that binds specifically to a target molecule wherein the nucleic acid molecule has sequence that comprises a sequence recognized by the target molecule in its natural setting. Alternately, an aptamer can be a nucleic acid molecule that binds to a target molecule where the target molecule does not naturally bind to a nucleic acid. The target molecule can be any molecule of interest. For example, the aptamer can be used to bind to a ligand-binding domain of a protein, thereby preventing interaction of the naturally occurring ligand with the protein. This is a non-limiting example and those in the art will recognize that other embodiments can be readily generated using techniques generally known in the art. (See, for example, Gold et al., 1995, *Annu. Rev. Biochem.*, 64, 763; Brody and Gold, 2000, *J. Biotechnol.*, 74, 5; Sun, 2000, *Curr. Opin. Mol. Ther.*, 2, 100; Kusser, 2000, *J. Biotechnol.*, 74, 27; Hermann and Patel, 2000, *Science*, 287, 820; and Jayasena, 1999, *Clinical Chemistry*, 45, 1628.)

In yet another embodiment, a non-nucleotide linker of the invention comprises abasic nucleotide, polyether, polyamine, polyamide, peptide, carbohydrate, lipid, polyhydrocarbon, or other polymeric compounds (e.g. polyethylene glycols such as those having between 2 and 100 ethylene glycol units). Specific examples include those described by Seela and Kaiser, *Nucleic Acids Res.* 1990, 18:6353 and *Nucleic Acids Res.* 1987, 15:3113; Cload and Schepartz, *J. Am. Chem. Soc.* 1991, 113:6324; Richardson and Schepartz, *J. Am. Chem. Soc.* 1991, 113:5109; Ma et al., *Nucleic Acids Res.* 1993, 21:2585 and *Biochemistry* 1993, 32:1751; Durand et al., *Nucleic Acids Res.* 1990, 18:6353; McCurdy et al., *Nucleosides & Nucleotides* 1991, 10:287; Jschke et al., *Tetrahedron Lett.* 1993, 34:301; Ono et al., *Biochemistry* 1991, 30:9914; Arnold et al., International Publication No. WO 89/02439; Usman et al., International Publication No. WO 95/06731; Dudycz et al., International Publication No. WO 95/11910 and Ferentz and Verdine, *J. Am. Chem. Soc.* 1991, 113:4000, all hereby incorporated by reference herein. A "non-nucleotide" further means any group or compound that can be incorporated into a nucleic acid chain in the place of one or more nucleotide units, including either sugar and/or phosphate substitutions, and allows the remaining bases to exhibit their enzymatic activity. The group or compound can be abasic in that it does not contain a commonly recognized nucleotide base, such as adenosine, guanine, cytosine, uracil or thymine, for example at the C1 position of the sugar.

In one embodiment, the invention features a short interfering nucleic acid (siNA) molecule capable of mediating RNA interference (RNAi) inside a cell or reconstituted in vitro system, wherein one or both strands of the siNA molecule that are assembled from two separate oligonucleotides do not comprise any ribonucleotides. For example, a siNA molecule can be assembled from a single oligonculeotide where the sense and antisense regions of the siNA comprise separate oligonucleotides that do not have any ribonucleotides (e.g., nucleotides having a 2'-OH group) present in the oligonucleotides. In another example, a siNA molecule can be assembled from a single oligonculeotide where the sense and antisense regions of the siNA are linked or circularized by a nucleotide or non-nucleotide linker as described herein, wherein the oligonucleotide does not have any ribonucleotides (e.g., nucleotides having a 2'-OH group) present in the oligonucleotide. Applicant has surprisingly found that the presense of ribonucleotides (e.g., nucleotides having a 2'-hydroxyl group) within the siNA molecule is not required or essential to support RNAi activity. As such, in one embodiment, all positions within the siNA can include chemically modified nucleotides and/or non-nucleotides such as nucleotides and or non-nucleotides having Formula I, II, III, IV, V, VI, or VII or any combination thereof to the extent that the ability of the siNA molecule to support RNAi activity in a cell is maintained.

In one embodiment, a siNA molecule of the invention is a single stranded siNA molecule that mediates RNAi activity in a cell or reconstituted in vitro system comprising a single stranded polynucleotide having complementarity to a target nucleic acid sequence. In another embodiment, the single stranded siNA molecule of the invention comprises a 5'-terminal phosphate group. In another embodiment, the single stranded siNA molecule of the invention comprises a 5'-terminal phosphate group and a 3'-terminal phosphate group (e.g., a 2',3'-cyclic phosphate). In another embodiment, the single stranded siNA molecule of the invention comprises about 19 to about 29 (e.g., about 19, 20, 21, 22, 23, 24, 25, 26, 27, 28, or 29) nucleotides. In yet another embodiment, the single stranded siNA molecule of the invention comprises one or more chemically modified nucleotides or non-nucleotides described herein. For example, all the positions within the siNA molecule can include chemically-modified nucleotides such as nucleotides having any of Formulae I–VII, or any combination thereof to the extent that the ability of the siNA molecule to support RNAi activity in a cell is maintained.

In one embodiment, a siNA molecule of the invention is a single stranded siNA molecule that mediates RNAi activity in a cell or reconstituted in vitro system comprising a single stranded polynucleotide having complementarity to a target nucleic acid sequence, wherein one or more pyrimidine nucleotides present in the siNA are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides), and a terminal cap modification, such as any modification described herein or shown in FIG. 10, that is optionally present at the 3'-end, the 5'-end, or both of the 3' and 5'-ends of the antisense sequence. The siNA optionally further comprises about 1 to about 4 or more (e.g., about 1, 2, 3, 4 or more) terminal 2'-deoxynucleotides at the 3'-end of the siNA molecule, wherein the terminal nucleotides can further comprise one or more (e.g., 1, 2, 3, 4 or more) phosphorothioate, phosphonoacetate, and/or thiophosphonoacetate internucleotide linkages, and wherein the siNA optionally further comprises a terminal phosphate group, such as a 5'-terminal phosphate group. In any of these embodiments, any purine nucleotides present in the antisense region are alternatively 2'-deoxy purine nucleotides (e.g., wherein all purine nucleotides are 2'-deoxy purine nucleotides or alternately a plurality of purine nucleotides are 2'-deoxy purine nucleotides). Also, in any of these embodiments, any purine nucleotides present in the siNA (i.e., purine nucleotides present in the sense and/or antisense region) can alternatively be locked nucleic acid (LNA) nucleotides (e.g., wherein all purine nucleotides are LNA nucleotides or alternately a plurality of purine nucleotides are LNA nucleotides). Also, in any of these embodiments, any purine nucleotides present in the siNA are alternatively 2'-methoxyethyl purine nucleotides (e.g., wherein all purine nucleotides are 2'-methoxyethyl purine nucleotides or alternately a plurality of purine nucleotides are 2'-methoxyethyl purine nucleotides). In another embodiment, any modified nucleotides present in the single stranded siNA molecules of the invention comprise modified nucleotides having properties or characteristics similar to naturally occurring ribonucleotides. For example, the invention features siNA molecules including modified nucleotides having a Northern conformation (e.g., Northern pseudorotation cycle, see for example Saenger, *Principles of Nucleic Acid Structure*, Springer-Verlag ed., 1984). As such, chemically modified nucleotides present in the single stranded siNA molecules of the invention are preferably resistant to nuclease degradation while at the same time maintaining the capacity to mediate RNAi.

In one embodiment, the invention features a method for modulating the expression of a VEGF and/or VEGFr gene within a cell comprising: (a) synthesizing a siNA molecule of the invention, which can be chemically-modified, wherein one of the siNA strands comprises a sequence complementary to RNA of the VEGF and/or VEGFr gene; and (b) introducing the siNA molecule into a cell under conditions suitable to modulate the expression of the VEGF and/or VEGFr gene in the cell.

In one embodiment, the invention features a method for modulating the expression of a VEGF and/or VEGFr gene within a cell comprising: (a) synthesizing a siNA molecule of the invention, which can be chemically-modified, wherein one of the siNA strands comprises a sequence complementary to RNA of the VEGF and/or VEGFr gene and wherein the serise strand sequence of the siNA comprises a sequence identical or substantially similar to the sequence of the target RNA; and (b) introducing the siNA molecule into a cell under conditions suitable to modulate the expression of the VEGF and/or VEGFr gene in the cell.

In another embodiment, the invention features a method for modulating the expression of more than one VEGF and/or VEGFr gene within a cell comprising: (a) synthesizing siNA molecules of the invention, which can be chemically-modified, wherein one of the siNA strands comprises a sequence complementary to RNA of the VEGF and/or VEGFr genes; and (b) introducing the siNA molecules into a cell under conditions suitable to modulate the expression of the VEGF and/or VEGFr genes in the cell.

In another embodiment, the invention features a method for modulating the expression of two or more VEGF and/or VEGFr genes within a cell comprising: (a) synthesizing one or more siNA molecules of the invention, which can be chemically-modified, wherein the siNA strands comprise sequences complementary to RNA of the VEGF and/or VEGFr genes and wherein the sense strand sequences of the siNAs comprise sequences identical or substantially similar to the sequences of the target RNAs; and (b) introducing the siNA molecules into a cell under conditions suitable to modulate the expression of the VEGF and/or VEGFr genes in the cell.

In another embodiment, the invention features a method for modulating the expression of more than one VEGF and/or VEGFr gene within a cell comprising: (a) synthesizing a siNA molecule of the invention, which can be chemically-modified, wherein one of the siNA strands comprises a sequence complementary to RNA of the VEGF and/or VEGFr gene and wherein the sense strand sequence of the siNA comprises a sequence identical or substantially similar to the sequences of the target RNAs; and (b) introducing the siNA molecule into a cell under conditions suitable to modulate the expression of the VEGF and/or VEGFr genes in the cell.

In one embodiment, siNA molecules of the invention are used as reagents in ex vivo applications. For example, siNA reagents are introduced into tissue or cells that are transplanted into a subject for therapeutic effect. The cells and/or tissue can be derived from an organism or subject that later receives the explant, or can be derived from another organism or subject prior to transplantation. The siNA molecules can be used to modulate the expression of one or more genes in the cells or tissue, such that the cells or tissue obtain a desired phenotype or are able to perform a function when transplanted in vivo. In one embodiment, certain target cells from a patient are extracted. These extracted cells are contacted with siNAs targeting a specific nucleotide sequence within the cells under conditions suitable for uptake of the siNAs by these cells (e.g. using delivery reagents such as cationic lipids, liposomes and the like or using techniques such as electroporation to facilitate the delivery of siNAs into cells). The cells are then reintroduced back into the same patient or other patients. In one embodiment, the invention features a method of modulating the expression of a VEGF and/or VEGFr gene in a tissue explant comprising: (a) synthesizing a siNA molecule of the invention, which can be chemically-modified, wherein one of the siNA strands comprises a sequence complementary to RNA of the VEGF and/or VEGFr gene; and (b) introducing the siNA molecule into a cell of the tissue explant derived from a particular organism under conditions suitable to modulate the expression of the VEGF and/or VEGFr gene in the tissue explant. In another embodiment, the method further comprises introducing the tissue explant back into the organism the tissue was derived from or into another organism under conditions suitable to modulate the expression of the VEGF and/or VEGFr gene in that organism.

In one embodiment, the invention features a method of modulating the expression of a VEGF and/or VEGFr gene in a tissue explant comprising: (a) synthesizing a siNA molecule of the invention, which can be chemically-modified, wherein one of the siNA strands comprises a sequence complementary to RNA of the VEGF and/or VEGFr gene and wherein the sense strand sequence of the siNA comprises a sequence identical or substantially similar to the sequence of the target RNA; and (b) introducing the siNA molecule into a cell of the tissue explant derived from a particular organism under conditions suitable to modulate the expression of the VEGF and/or VEGFr gene in the tissue explant. In another embodiment, the method further comprises introducing the tissue explant back into the organism the tissue was derived from or into another organism under conditions suitable to modulate the expression of the VEGF and/or VEGFr gene in that organism.

In another embodiment, the invention features a method of modulating the expression of more than one VEGF and/or VEGFr gene in a tissue explant comprising: (a) synthesizing siNA molecules of the invention, which can be chemically-modified, wherein one of the siNA strands comprises a sequence complementary to RNA of the VEGF and/or VEGFr genes; and (b) introducing the siNA molecules into a cell of the tissue explant derived from a particular organism under conditions suitable to modulate the expression of the VEGF and/or VEGFr genes in the tissue explant. In another embodiment, the method further comprises introducing the tissue explant back into the organism the tissue was derived from or into another organism under conditions suitable to modulate the expression of the VEGF and/or VEGFr genes in that organism.

In one embodiment, the invention features a method of modulating the expression of a VEGF and/or VEGFr gene in an organism comprising: (a) synthesizing a siNA molecule of the invention, which can be chemically-modified, wherein one of the siNA strands comprises a sequence complementary to RNA of the VEGF and/or VEGFr gene; and (b) introducing the siNA molecule into the organism under conditions suitable to modulate the expression of the VEGF and/or VEGFr gene in the organism. The level of VEGF or VEGFr can be determined as is known in the art or as described in Pavco U.S. Ser. No. 10/438,493, incorporated by reference herein in its entirety including the drawings.

In another embodiment, the invention features a method of modulating the expression of more than one VEGF and/or VEGFr gene in an organism comprising: (a) synthesizing siNA molecules of the invention, which can be chemically-modified, wherein one of the siNA strands comprises a sequence complementary to RNA of the VEGF and/or VEGFr genes; and (b) introducing the siNA molecules into the organism under conditions suitable to modulate the expression of the VEGF and/or VEGFr genes in the organism. The level of VEGF or VEGFr can be determined as is known in the art or as described in Pavco U.S. Ser. No. 10/438,493, incorporated by reference herein in its entirety including the drawings.

In one embodiment, the invention features a method for modulating the expression of a VEGF and/or VEGFr gene within a cell comprising: (a) synthesizing a siNA molecule of the invention, which can be chemically-modified, wherein the siNA comprises a single stranded sequence having complementarity to RNA of the VEGF and/or VEGFr gene; and (b) introducing the siNA molecule into a cell under conditions suitable to modulate the expression of the VEGF and/or VEGFr gene in the cell.

In another embodiment, the invention features a method for modulating the expression of more than one VEGF and/or VEGFr gene within a cell comprising: (a) synthesizing siNA molecules of the invention, which can be chemically-modified, wherein the siNA comprises a single stranded sequence having complementarity to RNA of the VEGF and/or VEGFr gene; and (b) contacting the cell in vitro or in vivo with the siNA molecule under conditions suitable to modulate the expression of the VEGF and/or VEGFr genes in the cell.

In one embodiment, the invention features a method of modulating the expression of a VEGF and/or VEGFr gene in a tissue explant comprising: (a) synthesizing a siNA molecule of the invention, which can be chemically-modified, wherein the siNA comprises a single stranded sequence having complementarity to RNA of the VEGF and/or VEGFr gene; and (b) contacting the cell of the tissue explant derived from a particular organism with the siNA molecule under conditions suitable to modulate the expression of the VEGF and/or VEGFr gene in the tissue explant. In another embodiment, the method further comprises introducing the tissue explant back into the organism the tissue was derived from or into another organism under conditions suitable to modulate the expression of the VEGF and/or VEGFr gene in that organism.

In another embodiment, the invention features a method of modulating the expression of more than one VEGF and/or VEGFr gene in a tissue explant comprising: (a) synthesizing siNA molecules of the invention, which can be chemically-modified, wherein the siNA comprises a single stranded sequence having complementarity to RNA of the VEGF and/or VEGFr gene; and (b) introducing the siNA molecules into a cell of the tissue explant derived from a particular organism under conditions suitable to modulate the expression of the VEGF and/or VEGFr genes in the tissue explant. In another embodiment, the method further comprises introducing the tissue explant back into the organism the tissue was derived from or into another organism under conditions suitable to modulate the expression of the VEGF and/or VEGFr genes in that organism.

In one embodiment, the invention features a method of modulating the expression of a VEGF and/or VEGFr gene in an organism comprising: (a) synthesizing a siNA molecule of the invention, which can be chemically-modified, wherein the siNA comprises a single stranded sequence having complementarity to RNA of the VEGF and/or VEGFr gene; and (b) introducing the siNA molecule into the organism under conditions suitable to modulate the expression of the VEGF and/or VEGFr gene in the organism.

In another embodiment, the invention features a method of modulating the expression of more than one VEGF and/or VEGFr gene in an organism comprising: (a) synthesizing siNA molecules of the invention, which can be chemically-modified, wherein the siNA comprises a single stranded sequence having complementarity to RNA of the VEGF and/or VEGFr gene; and (b) introducing the siNA molecules into the organism under conditions suitable to modulate the expression of the VEGF and/or VEGFr genes in the organism.

In one embodiment, the invention features a method of modulating the expression of a VEGF and/or VEGFr gene in an organism comprising contacting the organism with a siNA molecule of the invention under conditions suitable to modulate the expression of the VEGF and/or VEGFr gene in the organism.

In another embodiment, the invention features a method of modulating the expression of more than one VEGF and/or VEGFr gene in an organism comprising contacting the organism with one or more siNA molecules of the invention under conditions suitable to modulate the expression of the VEGF and/or VEGFr genes in the organism.

The siNA molecules of the invention can be designed to down regulate or inhibit target (e.g., VEGF and/or VEGFr) gene expression through RNAi targeting of a variety of RNA molecules. In one embodiment, the siNA molecules of the invention are used to target various RNAs corresponding to a target gene. Non-limiting examples of such RNAs include messenger RNA (mRNA), alternate RNA splice variants of target gene(s), post-transcriptionally modified RNA of target gene(s), pre-mRNA of target gene(s), and/or RNA templates. If alternate splicing produces a family of transcripts that are distinguished by usage of appropriate exons, the instant invention can be used to inhibit gene expression through the appropriate exons to specifically inhibit or to distinguish among the functions of gene family members. For example, a protein that contains an alternatively spliced transmembrane domain can be expressed in both membrane bound and secreted forms. Use of the invention to target the exon containing the transmembrane domain can be used to determine the functional consequences of pharmaceutical targeting of membrane bound as opposed to the secreted form of the protein. Non-limiting examples of applications of the invention relating to targeting these RNA molecules include therapeutic pharmaceutical applications, pharmaceutical discovery applications, molecular diagnostic and gene function applications, and gene mapping, for example using single nucleotide polymorphism mapping with siNA molecules of the invention. Such applications can be implemented using known gene sequences or from partial sequences available from an expressed sequence tag (EST).

In another embodiment, the siNA molecules of the invention are used to target conserved sequences corresponding to a gene family or gene families such as VEGF and/or VEGFr family genes. As such, siNA molecules targeting multiple VEGF and/or VEGFr targets can provide increased therapeutic effect. In addition, siNA can be used to characterize pathways of gene function in a variety of applications. For example, the present invention can be used to inhibit the activity of target gene(s) in a pathway to determine the function of uncharacterized gene(s) in gene function analysis, mRNA function analysis, or translational analysis. The invention can be used to determine potential target gene pathways involved in various diseases and conditions toward pharmaceutical development. The invention can be used to understand pathways of gene expression involved in, for example, the progression and/or maintenance of cancer.

In one embodiment, siNA molecule(s) and/or methods of the invention are used to down regulate the expression of gene(s) that encode RNA referred to by Genbank Accession, for example VEGF and/or VEGFr genes encoding RNA sequence(s) referred to herein by Genbank Accession number, for example, Genbank Accession Nos. shown in Table I.

In one embodiment, the invention features a method comprising: (a) generating a library of siNA constructs having a predetermined complexity; and (b) assaying the siNA constructs of (a) above, under conditions suitable to determine RNAi target sites within the target RNA sequence. In one embodiment, the siNA molecules of (a) have strands of a fixed length, for example, about 23 nucleotides in length. In another embodiment, the siNA molecules of (a) are of differing length, for example having strands of about 19 to about 25 (e.g., about 19, 20, 21, 22, 23, 24, or 25) nucleotides in length. In one embodiment, the assay can comprise a reconstituted in vitro siNA assay as described herein. In another embodiment, the assay can comprise a cell culture system in which target RNA is expressed. In another embodiment, fragments of target RNA are analyzed for detectable levels of cleavage, for example by gel electrophoresis, northern blot analysis, or RNAse protection assays, to determine the most suitable target site(s) within the target RNA sequence. The target RNA sequence can be obtained as is known in the art, for example, by cloning and/or transcription for in vitro systems, and by cellular expression in in vivo systems.

In one embodiment, the invention features a method comprising: (a) generating a randomized library of siNA constructs having a predetermined complexity, such as of $4^N$, where N represents the number of base paired nucleotides in each of the siNA construct strands (eg. for a siNA construct having 21 nucleotide sense and antisense strands with 19 base pairs, the complexity would be $4^{19}$); and (b) assaying the siNA constructs of (a) above, under conditions suitable to determine RNAi target sites within the target VEGF and/or VEGFr RNA sequence. In another embodiment, the siNA molecules of (a) have strands of a fixed length, for example about 23 nucleotides in length. In yet another embodiment, the siNA molecules of (a) are of differing length, for example having strands of about 19 to about 25 (e.g., about 19, 20, 21, 22, 23, 24, or 25) nucleotides in length. In one embodiment, the assay can comprise a reconstituted in vitro siNA assay as described in Example 7 herein. In another embodiment, the assay can comprise a cell culture system in which target RNA is expressed. In another embodiment, fragments of VEGF and/or VEGFr RNA are analyzed for detectable levels of cleavage, for example by gel electrophoresis, northern blot analysis, or RNAse protection assays, to determine the most suitable target site(s) within the target VEGF and/or VEGFr RNA sequence. The target VEGF and/or VEGFr RNA sequence can be obtained as is known in the art, for example, by cloning and/or transcription for in vitro systems, and by cellular expression in in vivo systems.

In another embodiment, the invention features a method comprising: (a) analyzing the sequence of a RNA target encoded by a target gene; (b) synthesizing one or more sets of siNA molecules having sequence complementary to one or more regions of the RNA of (a); and (c) assaying the siNA molecules of (b) under conditions suitable to determine RNAi targets within the target RNA sequence. In one embodiment, the siNA molecules of (b) have strands of a fixed length, for example about 23 nucleotides in length. In another embodiment, the siNA molecules of (b) are of differing length, for example having strands of about 19 to about 25 (e.g., about 19, 20, 21, 22, 23, 24, or 25) nucleotides in length. In one embodiment, the assay can comprise a reconstituted in vitro siNA assay as described herein. In another embodiment, the assay can comprise a cell culture system in which target RNA is expressed. Fragments of target RNA are analyzed for detectable levels of cleavage, for example by gel electrophoresis, northern blot analysis, or RNAse protection assays, to determine the most suitable target site(s) within the target RNA sequence. The target RNA sequence can be obtained as is known in the art, for example, by cloning and/or transcription for in vitro systems, and by expression in in vivo systems.

By "target site" is meant a sequence within a target RNA that is "targeted" for cleavage mediated by a siNA construct which contains sequences within its antisense region that are complementary to the target sequence.

By "detectable level of cleavage" is meant cleavage of target RNA (and formation of cleaved product RNAs) to an extent sufficient to discern cleavage products above the background of RNAs produced by random degradation of the target RNA. Production of cleavage products from 1–5% of the target RNA is sufficient to detect above the background for most methods of detection.

In one embodiment, the invention features a composition comprising a siNA molecule of the invention, which can be chemically-modified, in a pharmaceutically acceptable carrier or diluent. In another embodiment, the invention features a pharmaceutical composition comprising siNA molecules of the invention, which can be chemically-modified, targeting one or more genes in a pharmaceutically acceptable carrier or diluent. In another embodiment, the invention features a method for diagnosing a disease or condition in a subject comprising administering to the subject a composition of the invention under conditions suitable for the diagnosis of the disease or condition in the subject. In another embodiment, the invention features a method for treating or preventing a disease or condition in a subject, comprising administering to the subject a composition of the invention under conditions suitable for the treatment or prevention of the disease or condition in the subject, alone or in conjunction with one or more other therapeutic compounds. In yet another embodiment, the invention features a method for reducing or preventing tissue rejection in a subject comprising administering to the subject a composition of the invention under conditions suitable for the reduction or prevention of tissue rejection in the subject.

In another embodiment, the invention features a method for validating a VEGF and/or VEGFr gene target, comprising: (a) synthesizing a siNA molecule of the invention, which can be chemically-modified, wherein one of the siNA strands includes a sequence complementary to RNA of a VEGF and/or VEGFr target gene; (b) introducing the siNA molecule into a cell, tissue, or organism under conditions suitable for modulating expression of the VEGF and/or VEGFr target gene in the cell, tissue, or organism; and (c) determining the function of the gene by assaying for any phenotypic change in the cell, tissue, or organism.

In another embodiment, the invention features a method for validating a VEGF and/or VEGFr target comprising: (a) synthesizing a siNA molecule of the invention, which can be chemically-modified, wherein one of the siNA strands includes a sequence complementary to RNA of a VEGF and/or VEGFr target gene; (b) introducing the siNA molecule into a biological system under conditions suitable for modulating expression of the VEGF and/or VEGFr target gene in the biological system; and (c) determining the function of the gene by assaying for any phenotypic change in the biological system.

By "biological system" is meant, material, in a purified or unpurified form, from biological sources, including but not limited to human or animal, wherein the system comprises the components required for RNAi activity. The term "biological system" includes, for example, a cell, tissue, or organism, or extract thereof. The term biological system also includes reconstituted RNAi systems that can be used in an in vitro setting.

By "phenotypic change" is meant any detectable change to a cell that occurs in response to contact or treatment with a nucleic acid molecule of the invention (e.g., siNA). Such detectable changes include, but are not limited to, changes in shape, size, proliferation, motility, protein expression or RNA expression or other physical or chemical changes as can be assayed by methods known in the art. The detectable change can also include expression of reporter genes/molecules such as Green Florescent Protein (GFP) or various tags that are used to identify an expressed protein or any other cellular component that can be assayed.

In one embodiment, the invention features a kit containing a siNA molecule of the invention, which can be chemically-modified, that can be used to modulate the expression of a VEGF and/or VEGFr target gene in a biological system, including, for example, in a cell, tissue, or organism. In another embodiment, the invention features a kit containing more than one siNA molecule of the invention, which can be chemically-modified, that can be used to modulate the expression of more than one VEGF and/or VEGFr target gene in a biological system, including, for example, in a cell, tissue, or organism.

In one embodiment, the invention features a cell containing one or more siNA molecules of the invention, which can be chemically-modified. In another embodiment, the cell containing a siNA molecule of the invention is a mammalian cell. In yet another embodiment, the cell containing a siNA molecule of the invention is a human cell.

In one embodiment, the synthesis of a siNA molecule of the invention, which can be chemically-modified, comprises: (a) synthesis of two complementary strands of the siNA molecule; (b) annealing the two complementary strands together under conditions suitable to obtain a double-stranded siNA molecule. In another embodiment, synthesis of the two complementary strands of the siNA molecule is by solid phase oligonucleotide synthesis. In yet another embodiment, synthesis of the two complementary strands of the siNA molecule is by solid phase tandem oligonucleotide synthesis.

In one embodiment, the invention features a method for synthesizing a siNA duplex molecule comprising: (a) synthesizing a first oligonucleotide sequence strand of the siNA molecule, wherein the first oligonucleotide sequence strand comprises a cleavable linker molecule that can be used as a scaffold for the synthesis of the second oligonucleotide sequence strand of the siNA; (b) synthesizing the second oligonucleotide sequence strand of siNA on the scaffold of the first oligonucleotide sequence strand, wherein the second oligonucleotide sequence strand further comprises a chemical moiety than can be used to purify the siNA duplex; (c) cleaving the linker molecule of (a) under conditions suitable for the two siNA oligonucleotide strands to hybridize and form a stable duplex; and (d) purifying the siNA duplex utilizing the chemical moiety of the second oligonucleotide sequence strand. In one embodiment, cleavage of the linker molecule in (c) above takes place during deprotection of the oligonucleotide, for example under hydrolysis conditions using an alkylamine base such as methylamine. In one embodiment, the method of synthesis comprises solid phase synthesis on a solid support such as controlled pore glass (CPG) or polystyrene, wherein the first sequence of (a) is synthesized on a cleavable linker, such as a succinyl linker, using the solid support as a scaffold. The cleavable linker in (a) used as a scaffold for synthesizing the second strand can comprise similar reactivity as the solid support derivatized linker, such that cleavage of the solid support derivatized linker and the cleavable linker of (a) takes place concomitantly. In another embodiment, the chemical moiety of (b) that can be used to isolate the attached oligonucleotide sequence comprises a trityl group, for example a dimethoxytrityl group, which can be employed in a trityl-on synthesis strategy as described herein. In yet another embodiment, the chemical moiety, such as a dimethoxytrityl group, is removed during purification, for example, using acidic conditions.

In a further embodiment, the method for siNA synthesis is a solution phase synthesis or hybrid phase synthesis wherein both strands of the siNA duplex are synthesized in tandem using a cleavable linker attached to the first sequence which acts a scaffold for synthesis of the second sequence. Cleavage of the linker under conditions suitable for hybridization of the separate siNA sequence strands results in formation of the double-stranded siNA molecule.

In another embodiment, the invention features a method for synthesizing a siNA duplex molecule comprising: (a) synthesizing one oligonucleotide sequence strand of the siNA molecule, wherein the sequence comprises a cleavable linker molecule that can be used as a scaffold for the synthesis of another oligonucleotide sequence; (b) synthesizing a second oligonucleotide sequence having complementarity to the first sequence strand on the scaffold of (a), wherein the second sequence comprises the other strand of the double-stranded siNA molecule and wherein the second sequence further comprises a chemical moiety than can be used to isolate the attached oligonucleotide sequence; (c) purifying the product of (b) utilizing the chemical moiety of the second oligonucleotide sequence strand under conditions suitable for isolating the full-length sequence comprising both siNA oligonucleotide strands connected by the cleavable linker and under conditions suitable for the two siNA oligonucleotide strands to hybridize and form a stable duplex. In one embodiment, cleavage of the linker molecule in (c) above takes place during deprotection of the oligonucleotide, for example under hydrolysis conditions. In another embodiment, cleavage of the linker molecule in (c) above takes place after deprotection of the oligonucleotide. In another embodiment, the method of synthesis comprises solid phase synthesis on a solid support such as controlled pore glass (CPG) or polystyrene, wherein the first sequence of (a) is synthesized on a cleavable linker, such as a succinyl linker, using the solid support as a scaffold. The cleavable linker in (a) used as a scaffold for synthesizing the second strand can comprise similar reactivity or differing reactivity as the solid support derivatized linker, such that cleavage of the solid support derivatized linker and the cleavable linker of (a) takes place either concomitantly or sequentially. In one embodiment, the chemical moiety of (b) that can be used to isolate the attached oligonucleotide sequence comprises a trityl group, for example a dimethoxytrityl group.

In another embodiment, the invention features a method for making a double-stranded siNA molecule in a single synthetic process comprising: (a) synthesizing an oligonucleotide having a first and a second sequence, wherein the first sequence is complementary to the second sequence, and the first oligonucleotide sequence is linked to the second sequence via a cleavable linker, and wherein a terminal 5'-protecting group, for example, a 5'-O-dimethoxytrityl group (5'-O-DMT) remains on the oligonucleotide having the second sequence; (b) deprotecting the oligonucleotide whereby the deprotection results in the cleavage of the linker joining the two oligonucleotide sequences; and (c) purifying the product of (b) under conditions suitable for isolating the double-stranded siNA molecule, for example using a trityl-on synthesis strategy as described herein.

In another embodiment, the method of synthesis of siNA molecules of the invention comprises the teachings of Scaringe et al., U.S. Pat. Nos. 5,889,136; 6,008,400; and 6,111,086, incorporated by reference herein in their entirety.

In one embodiment, the invention features siNA constructs that mediate RNAi against VEGF and/or VEGFr, wherein the siNA construct comprises one or more chemical modifications, for example, one or more chemical modifications having any of Formulae I–VII or any combination thereof that increases the nuclease resistance of the siNA construct.

In another embodiment, the invention features a method for generating siNA molecules with increased nuclease resistance comprising (a) introducing nucleotides having any of Formula I–VII or any combination thereof into a siNA molecule, and (b) assaying the siNA molecule of step (a) under conditions suitable for isolating siNA molecules having increased nuclease resistance.

In one embodiment, the invention features siNA constructs that mediate RNAi against VEGF and/or VEGFr, wherein the siNA construct comprises one or more chemical modifications described herein that modulates the binding affinity between the sense and antisense strands of the siNA construct.

In another embodiment, the invention features a method for generating siNA molecules with increased binding affinity between the sense and antisense strands of the siNA molecule comprising (a) introducing nucleotides having any of Formula I–VII or any combination thereof into a siNA molecule, and (b) assaying the siNA molecule of step (a) under conditions suitable for isolating siNA molecules having increased binding affinity between the sense and antisense strands of the siNA molecule.

In one embodiment, the invention features siNA constructs that mediate RNAi against VEGF and/or VEGFr, wherein the siNA construct comprises one or more chemical modifications described herein that modulates the binding affinity between the antisense strand of the siNA construct and a complementary target RNA sequence within a cell.

In one embodiment, the invention features siNA constructs that mediate RNAi against VEGF and/or VEGFr, wherein the siNA construct comprises one or more chemical modifications described herein that modulates the binding affinity between the antisense strand of the siNA construct and a complementary target DNA sequence within a cell.

In another embodiment, the invention features a method for generating siNA molecules with increased binding affinity between the antisense strand of the siNA molecule and a complementary target RNA sequence comprising (a) introducing nucleotides having any of Formula I–VII or any combination thereof into a siNA molecule, and (b) assaying the siNA molecule of step (a) under conditions suitable for isolating siNA molecules having increased binding affinity between the antisense strand of the siNA molecule and a complementary target RNA sequence.

In another embodiment, the invention features a method for generating siNA molecules with increased binding affinity between the antisense strand of the siNA molecule and a complementary target DNA sequence comprising (a) introducing nucleotides having any of Formula I–VII or any combination thereof into a siNA molecule, and (b) assaying the siNA molecule of step (a) under conditions suitable for isolating siNA molecules having increased binding affinity between the antisense strand of the siNA molecule and a complementary target DNA sequence.

In one embodiment, the invention features siNA constructs that mediate RNAi against VEGF and/or VEGFr, wherein the siNA construct comprises one or more chemical modifications described herein that modulate the polymerase activity of a cellular polymerase capable of generating additional endogenous siNA molecules having sequence homology to the chemically-modified siNA construct.

In another embodiment, the invention features a method for generating siNA molecules capable of mediating increased polymerase activity of a cellular polymerase capable of generating additional endogenous siNA molecules having sequence homology to a chemically-modified siNA molecule comprising (a) introducing nucleotides having any of Formula I–VII or any combination thereof into a siNA molecule, and (b) assaying the siNA molecule of step (a) under conditions suitable for isolating siNA molecules capable of mediating increased polymerase activity of a cellular polymerase capable of generating additional endogenous siNA molecules having sequence homology to the chemically-modified siNA molecule.

In one embodiment, the invention features chemically-modified siNA constructs that mediate RNAi against VEGF and/or VEGFr in a cell, wherein the chemical modifications do not significantly effect the interaction of siNA with a target RNA molecule, DNA molecule and/or proteins or other factors that are essential for RNAi in a manner that would decrease the efficacy of RNAi mediated by such siNA constructs.

In another embodiment, the invention features a method for generating siNA molecules with improved RNAi activity against VEGF and/or VEGFr comprising (a) introducing nucleotides having any of Formula I–VII or any combination thereof into a siNA molecule, and (b) assaying the siNA molecule of step (a) under conditions suitable for isolating siNA molecules having improved RNAi activity.

In yet another embodiment, the invention features a method for generating siNA molecules with improved RNAi activity against VEGF and/or VEGFr target RNA comprising (a) introducing nucleotides having any of Formula I–VII or any combination thereof into a siNA molecule, and (b) assaying the siNA molecule of step (a) under conditions suitable for isolating siNA molecules having improved RNAi activity against the target RNA.

In yet another embodiment, the invention features a method for generating siNA molecules with improved RNAi activity against VEGF and/or VEGFr target DNA comprising (a) introducing nucleotides having any of Formula I–VII or any combination thereof into a siNA molecule, and (b) assaying the siNA molecule of step (a) under conditions suitable for isolating siNA molecules having improved RNAi activity against the target DNA.

In one embodiment, the invention features siNA constructs that mediate RNAi against VEGF and/or VEGFr, wherein the siNA construct comprises one or more chemical modifications described herein that modulates the cellular uptake of the siNA construct.

In another embodiment, the invention features a method for generating siNA molecules against VEGF and/or VEGFr with improved cellular uptake comprising (a) introducing nucleotides having any of Formula I–VII or any combination thereof into a siNA molecule, and (b) assaying the siNA molecule of step (a) under conditions suitable for isolating siNA molecules having improved cellular uptake.

In one embodiment, the invention features siNA constructs that mediate RNAi against VEGF and/or VEGFr, wherein the siNA construct comprises one or more chemical modifications described herein that increases the bioavailability of the siNA construct, for example, by attaching polymeric conjugates such as polyethyleneglycol or equivalent conjugates that improve the pharmacokinetics of the siNA construct, or by attaching conjugates that target specific tissue types or cell types in vivo. Non-limiting examples of such conjugates are described in Vargeese et al., U.S. Ser. No. 10/201,394 incorporated by reference herein.

In one embodiment, the invention features a method for generating siNA molecules of the invention with improved bioavailability, comprising (a) introducing a conjugate into the structure of a siNA molecule, and (b) assaying the siNA molecule of step (a) under conditions suitable for isolating siNA molecules having improved bioavailability. Such conjugates can include ligands for cellular receptors, such as peptides derived from naturally occurring protein ligands; protein localization sequences, including cellular ZIP code sequences; antibodies; nucleic acid aptamers; vitamins and other co-factors, such as folate and N-acetylgalactosamine; polymers, such as polyethyleneglycol (PEG); phospholipids; cholesterol; polyamines, such as spermine or spermidine; and others.

In one embodiment, the invention features a double stranded short interfering nucleic acid (siNA) molecule that comprises a first nucleotide sequence complementary to a target RNA sequence or a portion thereof, and a second sequence having complementarity to said first sequence, wherein said second sequence is chemically modified in a manner that it can no longer act as a guide sequence for efficiently mediating RNA interference and/or be recognized by cellular proteins that facilitate RNAi.

In one embodiment, the invention features a double stranded short interfering nucleic acid (siNA) molecule that comprises a first nucleotide sequence complementary to a target RNA sequence or a portion thereof, and a second sequence having complementarity to said first sequence, wherein the second sequence is designed or modified in a manner that prevents its entry into the RNAi pathway as a guide sequence or as a sequence that is complementary to a target nucleic acid (e.g., RNA) sequence. Such design or modifications are expected to enhance the activity of siNA and/or improve the specificity of siNA molecules of the invention. These modifications are also expected to minimize any off-target effects and/or associated toxicity.

In one embodiment, the invention features a double stranded short interfering nucleic acid (siNA) molecule that comprises a first nucleotide sequence complementary to a target RNA sequence or a portion thereof, and a second sequence having complementarity to said first sequence, wherein said second sequence is incapable of acting as a guide sequence for mediating RNA interference.

In one embodiment, the invention features a double stranded short interfering nucleic acid (siNA) molecule that comprises a first nucleotide sequence complementary to a target RNA sequence or a portion thereof, and a second sequence having complementarity to said first sequence, wherein said second sequence does not have a terminal 5'-hydroxyl (5'-OH) or 5'-phosphate group.

In one embodiment, the invention features a double stranded short interfering nucleic acid (siNA) molecule that comprises a first nucleotide sequence complementary to a target RNA sequence or a portion thereof, and a second sequence having complementarity to said first sequence, wherein said second sequence comprises a terminal cap moiety at the 5'-end of said second sequence. In one embodiment, the terminal cap moiety comprises an inverted abasic, inverted deoxy abasic, inverted nucleotide moiety, a group shown in FIG. 10, an alkyl or cycloalkyl group, a heterocycle, or any other group that prevents RNAi activity in which the second sequence serves as a guide sequence or template for RNAi.

In one embodiment, the invention features a double stranded short interfering nucleic acid (siNA) molecule that comprises a first nucleotide sequence complementary to a target RNA sequence or a portion thereof, and a second sequence having complementarity to said first sequence, wherein said second sequence comprises a terminal cap moiety at the 5'-end and 3'-end of said second sequence. In one embodiment, each terminal cap moiety individually comprises an inverted abasic, inverted deoxy abasic, inverted nucleotide moiety, a group shown in FIG. 10, an alkyl or cycloalkyl group, a heterocycle, or any other group that prevents RNAi activity in which the second sequence serves as a guide sequence or template for RNAi.

In one embodiment, the invention features a method for generating siNA molecules of the invention with improved specificity for down regulating or inhibiting the expression of a target nucleic acid (e.g., a DNA or RNA such as a gene or its corresponding RNA), comprising (a) introducing one or more chemical modifications into the structure of a siNA molecule, and (b) assaying the siNA molecule of step (a) under conditions suitable for isolating siNA molecules having improved specificity. In another embodiment, the chemical modification used to improve specificity comprises terminal cap modifications at the 5'-end, 3'-end, or both 5' and 3'-ends of the siNA molecule. The terminal cap modifications can comprise, for example, structures shown in FIG. 10 (e.g. inverted deoxyabasic moieties) or any other chemical modification that renders a portion of the siNA molecule (e.g. the sense strand) incapable of mediating RNA interference against an off target nucleic acid sequence. In a non-limiting example, a siNA molecule is designed such that only the antisense sequence of the siNA molecule can serve as a guide sequence for RISC mediated degradation of a corresponding target RNA sequence. This can be accomplished by rendering the sense sequence of the siNA inactive by introducing chemical modifications to the sense strand that preclude recognition of the sense strand as a guide sequence by RNAi machinery. In one embodiment, such chemical modifications comprise any chemical group at the 5'-end of the sense strand of the siNA, or any other group that serves to render the sense strand inactive as a guide sequence for mediating RNA interference. These modifications, for example, can result in a molecule where the 5'-end of the sense strand no longer has a free 5'-hydroxyl (5'-OH) or a free 5'-phosphate group (e.g., phosphate, diphosphate, triphosphate, cyclic phosphate etc.). Non-limiting examples of such siNA constructs are described herein, such as "Stab 9/10", "Stab 7/8", "Stab 7/19", "Stab 16/8", "Stab 18/8", "Stab 17/22", and "Stab 23/24" chemistries and variants thereof (see Table IV) wherein the 5'-end and 3'-end of the sense strand of the siNA do not comprise a hydroxyl group or phosphate group.

In one embodiment, the invention features a method for generating siNA molecules of the invention with improved specificity for down regulating or inhibiting the expression of a target nucleic acid (e.g., a DNA or RNA such as a gene or its corresponding RNA), comprising introducing one or more chemical modifications into the structure of a siNA molecule that prevent a strand or portion of the siNA molecule from acting as a template or guide sequence for RNAi activity. In one embodiment, the inactive strand or sense region of the siNA molecule is the sense strand or sense region of the siNA molecule, i.e. the strand or region of the siNA that does not have complementarity to the target nucleic acid sequence. In one embodiment, such chemical modifications comprise any chemical group at the 5'-end of the sense strand or region of the siNA that does not comprise a 5'-hydroxyl (5'-OH) or 5'-phosphate group, or any other group that serves to render the sense strand or sense region inactive as a guide sequence for mediating RNA interference. Non-limiting examples of such siNA constructs are described herein, such as "Stab 9/10", "Stab 7/8", "Stab 7/19", "Stab 16/8", "Stab 18/8", "Stab 17/22", and "Stab 23/24" chemistries and variants thereof (see Table IV) wherein the 5'-end and 3'-end of the sense strand of the siNA do not comprise a hydroxyl group or phosphate group.

In one embodiment, the invention features a method for screening siNA molecules that are active in mediating RNA interference against a target nucleic acid sequence comprising (a) generating a plurality of unmodified siNA molecules, (b) screening the siNA molecules of step (a) under conditions suitable for isolating siNA molecules that are active in mediating RNA interference against the target nucleic acid sequence, and (c) introducing chemical modifications (e.g. chemical modifications as described herein or as otherwise known in the art) into the active siNA molecules of (b). In one embodiment, the method further comprises re-screening the chemically modified siNA molecules of step (c) under conditions suitable for isolating chemically modified siNA molecules that are active in mediating RNA interference against the target nucleic acid sequence.

In one embodiment, the invention features a method for screening chemically modified siNA molecules that are active in mediating RNA interference against a target nucleic acid sequence comprising (a) generating a plurality of chemically modified siNA molecules (e.g. siNA molecules as described herein or as otherwise known in the art), and (b) screening the siNA molecules of step (a) under conditions suitable for isolating chemically modified siNA molecules that are active in mediating RNA interference against the target nucleic acid sequence.

The term "ligand" refers to any compound or molecule, such as a drug, peptide, hormone, or neurotransmitter, that is capable of interacting with another compound, such as a receptor, either directly or indirectly. The receptor that interacts with a ligand can be present on the surface of a cell or can alternately be an intercullular receptor. Interaction of the ligand with the receptor can result in a biochemical reaction, or can simply be a physical interaction or association.

In another embodiment, the invention features a method for generating siNA molecules of the invention with improved bioavailability comprising (a) introducing an excipient formulation to a siNA molecule, and (b) assaying the siNA molecule of step (a) under conditions suitable for isolating siNA molecules having improved bioavailability.

Such excipients include polymers such as cyclodextrins, lipids, cationic lipids, polyamines, phospholipids, nanoparticles, receptors, ligands, and others.

In another embodiment, the invention features a method for generating siNA molecules of the invention with improved bioavailability comprising (a) introducing nucleotides having any of Formulae I–VII or any combination thereof into a siNA molecule, and (b) assaying the siNA molecule of step (a) under conditions suitable for isolating siNA molecules having improved bioavailability.

In another embodiment, polyethylene glycol (PEG) can be covalently attached to siNA compounds of the present invention. The attached PEG can be any molecular weight, preferably from about 2,000 to about 50,000 daltons (Da).

The present invention can be used alone or as a component of a kit having at least one of the reagents necessary to carry out the in vitro or in vivo introduction of RNA to test samples and/or subjects. For example, preferred components of the kit include a siNA molecule of the invention and a vehicle that promotes introduction of the siNA into cells of interest as described herein (e.g., using lipids and other methods of transfection known in the art, see for example Beigelman et al, U.S. Pat. No. 6,395,713). The kit can be used for target validation, such as in determining gene function and/or activity, or in drug optimization, and in drug discovery (see for example Usman et al., U.S. Ser. No. 60/402,996). Such a kit can also include instructions to allow a user of the kit to practice the invention.

The term "short interfering nucleic acid", "siNA", "short interfering RNA", "siRNA", "short interfering nucleic acid molecule", "short interfering oligonucleotide molecule", or "chemically-modified short interfering nucleic acid molecule" as used herein refers to any nucleic acid molecule capable of inhibiting or down regulating gene expression or viral replication, for example by mediating RNA interference "RNAi" or gene silencing in a sequence-specific manner; see for example Zamore et al., 2000, Cell, 101, 25–33; Bass, 2001, Nature, 411, 428–429; Elbashir et al., 2001, Nature, 411, 494–498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, Science, 297, 1818–1819; Volpe et al., 2002, Science, 297, 1833–1837; Jenuwein, 2002, Science, 297, 2215–2218; and Hall et al., 2002, Science, 297, 2232–2237; Hutvagner and Zamore, 2002, Science, 297, 2056–60; McManus et al., 2002, RNA, 8, 842–850; Reinhart et al., 2002, Gene & Dev., 16, 1616–1626; and Reinhart & Bartel, 2002, Science, 297, 1831). Non limiting examples of siNA molecules of the invention are shown in FIGS. 4–6, and Tables II and III herein. For example the siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The siNA can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double stranded structure, for example wherein the double stranded region is about 19 base pairs); the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof. Alternatively, the siNA is assembled from a single oligonucleotide, where the self-complementary sense and antisense regions of the siNA are linked by means of a nucleic acid based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (for example, where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., 2002, Cell., 110, 563–574 and Schwarz et al., 2002, Molecular Cell, 10, 537–568), or 5',3'-diphosphate. In certain embodiments, the siNA molecule of the invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic intercations, and/or stacking interactions. In certain embodiments, the siNA molecules of the invention comprise nucleotide sequence that is complementary to nucleotide sequence of a target gene. In another embodiment, the siNA molecule of the invention interacts with nucleotide sequence of a target gene in a manner that causes inhibition of expression of the target gene. As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. Applicant describes in certain embodiments short interfering nucleic acids that do not require the presence of nucleotides having a 2'-hydroxy group for mediating RNAi and as such, short interfering nucleic acid molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON." As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, siNA molecules of the invention can be used to epigenetically silence genes at both the post-transcriptional level or the pre-transcriptional level. In a non-limiting example, epigenetic regulation of gene expression by siNA molecules of the invention can result from siNA mediated modification of chromatin structure to alter gene expression (see, for example, Verdel et al., 2004, Science, 303, 672–676; Pal-Bhadra et al., 2004, Science, 303, 669–672; Allshire, 2002, Science, 297, 1818–1819; Volpe et al., 2002, Science, 297, 1833–1837; Jenuwein, 2002, Science, 297, 2215–2218; and Hall et al., 2002, Science, 297, 2232–2237).

In one embodiment, a siNA molecule of the invention is a duplex forming oligonucleotide "DFO", (see for example FIGS. 14–15 and Vaish et al., U.S. Ser. No. 10/727,780 filed Dec. 3, 2003).

In one embodiment, a siNA molecule of the invention is a multifunctional siNA, (see for example FIGS. 16–22 and Jadhav et al., U.S. Ser. No. 60/543,480 filed Feb. 10, 2004). The multifunctional siNA of the invention can comprise sequence targeting, for example, two regions of VEGF and/or VEGFr RNA (see for example target sequences in Tables II and III).

By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop. For example, an asymmetric hairpin siNA molecule of the invention can comprise an antisense region having length sufficient to mediate RNAi in a cell or in vitro system (e.g. about 19 to about 22, or about 19, 20, 21, or 22) nucleotides) and a loop region comprising about 4 to about 8 (e.g., about 4, 5, 6, 7, or 8) nucleotides, and a sense region having about 3 to about 18 (e.g., about 3, 4, 5, 6, 7, 8, 9, 10, 11, 12, 13, 14, 15, 16, 17, or 18) nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

By "asymmetric duplex" as used herein is meant a siNA molecule having two separate strands comprising a sense region and an antisense region, wherein the sense region comprises fewer nucleotides than the antisense region to the extent that the sense region has enough complementary nucleotides to base pair with the antisense region and form a duplex. For example, an asymmetric duplex siNA molecule of the invention can comprise an antisense region having length sufficient to mediate RNAi in a cell or in vitro system e.g. about 19 to about 22 (e.g. about 19, 20, 21, or 22) nucleotides and a sense region having about 3 to about 18 (e.g., about 3, 4, 5, 6, 7, 8, 9, 10, 11, 12, 13, 14, 15, 16, 17, or 18) nucleotides that are complementary to the antisense region.

By "modulate" is meant that the expression of the gene, or level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. For example, the term "modulate" can mean "inhibit," but the use of the word "modulate" is not limited to this definition.

By "inhibit", "down-regulate", or "reduce", it is meant that the expression of the gene, or level of RNA molecules or equivalent RNA molecules encoding one or more proteins or protein subunits, or activity of one or more proteins or protein subunits, is reduced below that observed in the absence of the nucleic acid molecules (e.g., siNA) of the invention. In one embodiment, inhibition, down-regulation or reduction with an siNA molecule is below that level observed in the presence of an inactive or attenuated molecule. In another embodiment, inhibition, down-regulation, or reduction with siNA molecules is below that level observed in the presence of, for example, an siNA molecule with scrambled sequence or with mismatches. In another embodiment, inhibition, down-regulation, or reduction of gene expression with a nucleic acid molecule of the instant invention is greater in the presence of the nucleic acid molecule than in its absence.

By "gene", or "target gene", is meant, a nucleic acid that encodes an RNA, for example, nucleic acid sequences including, but not limited to, structural genes encoding a polypeptide. A gene or target gene can also encode a functional RNA (fRNA) or non-coding RNA (ncRNA), such as small temporal RNA (stRNA), micro RNA (miRNA), small nuclear RNA (snRNA), short interfering RNA (siRNA), small nucleolar RNA (snRNA), ribosomal RNA (rRNA), transfer RNA (tRNA) and precursor RNAs thereof. Such non-coding RNAs can serve as target nucleic acid molecules for siNA mediated RNA interference in modulating the activity of fRNA or ncRNA involved in functional or regulatory cellular processes. Abberant fRNA or ncRNA activity leading to disease can therefore be modulated by siNA molecules of the invention. siNA molecules targeting fRNA and ncRNA can also be used to manipulate or alter the genotype or phenotype of an organism or cell, by intervening in cellular processes such as genetic imprinting, transcription, translation, or nucleic acid processing (e.g., transamination, methylation etc.). The target gene can be a gene derived from a cell, an endogenous gene, a transgene, or exogenous genes such as genes of a pathogen, for example a virus, which is present in the cell after infection thereof. The cell containing the target gene can be derived from or contained in any organism, for example a plant, animal, protozoan, virus, bacterium, or fungus. Non-limiting examples of plants include monocots, dicots, or gymnosperms. Non-limiting examples of animals include vertebrates or invertebrates. Non-limiting examples of fungi include molds or yeasts.

By "VEGF" as used herein is meant, any vascular endothelial growth factor (e.g., VEGF, VEGF-A, VEGF-B, VEGF-C, VEGF-D) protein, peptide, or polypeptide having vascular endothelial growth factor activity, such as encoded by VEGF Genbank Accession Nos. shown in Table I. The term VFGF also refers to nucleic acid sequences encloding any vascular endothelial growth factor protein, peptide, or polypeptide having vascular endothelial growth factor activity.

By "VEGF-B" is meant, protein, peptide, or polypeptide receptor or a derivative thereof, such as encoded by Genbank Accession No. NM_003377, having vascular endothelial growth factor type B activity. The term VEGF-B also refers to nucleic acid sequences encloding any VEGF-B protein, peptide, or polypeptide having VEGF-B activity.

By "VEGF-C" is meant, protein, peptide, or polypeptide receptor or a derivative thereof, such as encoded by Genbank Accession No. NM_005429, having vascular endothelial growth factor type C activity. The term VEGF-C also refers to nucleic acid sequences encloding any VEGF-C protein, peptide, or polypeptide having VEGF-C activity.

By "VEGF-D" is meant, protein, peptide, or polypeptide receptor or a derivative thereof, such as encoded by Genbank Accession No. NM_004469, having vascular endothelial growth factor type D activity. The term VEGF-D also refers to nucleic acid sequences encloding any VEGF-D protein, peptide, or polypeptide having VEGF-D activity.

By "VEGFR" as used herein is meant, any vascular endothelial growth factor receptor protein, peptide, or polypeptide (e.g., VEGFR1, VEGFR2, or VEGFr3, including both membrane bound and/or soluble forms thereof) having vascular endothelial growth factor receptor activity, such as encoded by VEGFr Genbank Accession Nos. shown in Table I. The term VEGFr also refers to nucleic acid sequences encloding any vascular endothelial growth factor receptor protein, peptide, or polypeptide having vascular endothelial growth factor receptor activity.

By "VEGFR1" is meant, protein, peptide, or polypeptide receptor or a derivative thereof, such as encoded by Genbank Accession No. NM_002019, having vascular endothelial growth factor receptor type 1 (flt) activity, for example, having the ability to bind a vascular endothelial growth factor. The term VEGF1 also refers to nucleic acid sequences encloding any VEGFR1 protein, peptide, or polypeptide having VEGFR1 activity.

By "VEGFR2" is meant, protein, peptide, or polypeptide receptor or a derivative thereof, such as encoded by Genbank Accession No. NM_002253, having vascular endothelial growth factor receptor type 2 (kdr) activity, for example, having the ability to bind a vascular endothelial growth factor. The term VEGF2 also refers to nucleic acid sequences encloding any VEGFR2 protein, peptide, or polypeptide having VEGFR2 activity.

By "VEGFr3" is meant, protein, peptide, or polypeptide receptor or a derivative thereof, such as encoded by Genbank Accession No. NM_002020 having vascular endothelial growth factor receptor type 3 (kdr) activity, for example, having the ability to bind a vascular endothelial growth factor. The term VEGF3 also refers to nucleic acid sequences encloding any VEGFr3 protein, peptide, or polypeptide having VEGFr3 activity.

By "proliferative disease" or "cancer" as used herein is meant, any disease or condition characterized by unregulated cell growth or replication as is known in the art; including breast cancer, cancers of the head and neck including various lymphomas such as mantle cell lymphoma, non-Hodgkins lymphoma, adenoma, squamous cell carcinoma, laryngeal carcinoma, cancers of the retina, cancers of the esophagus, multiple myeloma, ovarian cancer, uterine cancer, melanoma, colorectal cancer, lung cancer, bladder cancer, prostate cancer, glioblastoma, lung cancer (including non-small cell lung carcinoma), pancreatic cancer, cervical cancer, head and neck cancer, skin cancers, nasopharyngeal carcinoma, liposarcoma, epithelial carcinoma, renal cell carcinoma, gallbladder adeno carcinoma, parotid adenocarcinoma, endometrial sarcoma, multidrug resistant cancers; and proliferative diseases and conditions, such as neovascularization associated with tumor angiogenesis, macular degeneration (e.g., wet/dry AMD), corneal neovascularization, diabetic retinopathy, neovascular glaucoma, myopic degeneration and other proliferative diseases and conditions such as restenosis and polycystic kidney disease, and any other cancer or proliferative disease or condition that can respond to the level of VEGF and/or VEGFr in a cell or tissue, alone or in combination with other therapies.

By "ocular disease" as used herein is meant, any disease or condition of the eye and related structures, such as Cystoid Macular Edema, Asteroid Hyalosis, Pathological Myopia and Posterior Staphyloma, Toxocariasis (Ocular Larva Migrans), Retinal Vein Occlusion, Posterior Vitreous Detachment, Tractional Retinal Tears, Epiretinal Membrane, Diabetic Retinopathy, Lattice Degeneration, Retinal Vein Occlusion, Retinal Artery Occlusion, Macular Degeneration (e.g., age related macular degeneration such as wet AMD or dry AMD), Toxoplasmosis, Choroidal Melanoma, Acquired Retinoschisis, Hollenhorst Plaque, Idiopathic Central Serous Chorioretinopathy, Macular Hole, Presumed Ocular Histoplasmosis Syndrome, Retinal Macroaneursym, Retinitis Pigmentosa, Retinal Detachment, Hypertensive Retinopathy, Retinal Pigment Epithelium (RPE) Detachment, Papillophlebitis, Ocular Ischemic Syndrome, Coats' Disease, Leber's Miliary Aneurysm, Conjunctival Neoplasms, Allergic Conjunctivitis, Vernal Conjunctivitis, Acute Bacterial Conjunctivitis, Allergic Conjunctivitis & Vernal Keratoconjunctivitis, Viral Conjunctivitis, Bacterial Conjunctivitis, Chlamydial & Gonococcal Conjunctivitis, Conjunctival Laceration, Episcleritis, Scleritis, Pingueculitis, Pterygium, Superior Limbic Keratoconjunctivitis (SLK of Theodore), Toxic Conjunctivitis, Conjunctivitis with Pseudomembrane, Giant Papillary Conjunctivitis, Terrien's Marginal Degeneration, Acanthamoeba Keratitis, Fungal Keratitis, Filamentary Keratitis, Bacterial Keratitis, Keratitis Sicca/Dry Eye Syndrome, Bacterial Keratitis, Herpes Simplex Keratitis, Sterile Corneal Infiltrates, Phlyctenulosis, Corneal Abrasion & Recurrent Corneal Erosion, Corneal Foreign Body, Chemical Burs, Epithelial Basement Membrane Dystrophy (EBMD), Thygeson's Superficial Punctate Keratopathy, Corneal Laceration, Salzmann's Nodular Degeneration, Fuchs' Endothelial Dystrophy, Crystalline Lens Subluxation, Ciliary-Block Glaucoma, Primary Open-Angle Glaucoma, Pigment Dispersion Syndrome and Pigmentary Glaucoma, Pseudoexfoliation Syndrom and Pseudoexfoliative Glaucoma, Anterior Uveitis, Primary Open Angle Glaucoma, Uveitic Glaucoma & Glaucomatocyclitic Crisis, Pigment Dispersion Syndrome & Pigmentary Glaucoma, Acute Angle Closure Glaucoma, Anterior Uveitis, Hyphema, Angle Recession Glaucoma, Lens Induced Glaucoma, Pseudoexfoliation Syndrome and Pseudoexfoliative Glaucoma, Axenfeld-Rieger Syndrome, Neovascular Glaucoma, Pars Planitis, Choroidal Rupture, Duane's Retraction Syndrome, Toxic/Nutritional Optic Neuropathy, Aberrant Regeneration of Cranial Nerve III, Intracranial Mass Lesions, Carotid-Cavemous Sinus Fistula, Anterior Ischemic Optic Neuropathy, Optic Disc Edema & Papilledema, Cranial Nerve III Palsy, Cranial Nerve IV Palsy, Cranial Nerve VI Palsy, Cranial Nerve VII (Facial Nerve) Palsy, Horner's Syndrome, Internuclear Ophthalmoplegia, Optic Nerve Head Hypoplasia, Optic Pit, Tonic Pupil, Optic Nerve Head Drusen, Demyelinating Optic Neuropathy (Optic Neuritis, Retrobulbar Optic Neuritis), Amaurosis Fugax and Transient Ischemic Attack, Pseudotumor Cerebri, Pituitary Adenoma, Molluscum Contagiosum, Canaliculitis, Verruca and Papilloma, Pediculosis and Pthiriasis, Blepharitis, Hordeolum, Preseptal Cellulitis, Chalazion, Basal Cell Carcinoma, Herpes Zoster Ophthalmicus, Pediculosis & Phthiriasis, Blowout Fracture, Chronic Epiphora, Dacryocystitis, Herpes Simplex Blepharitis, Orbital Cellulitis, Senile Entropion, and Squamous Cell Carcinoma. See for example (Clark and Yorio, 2003, Nature, 2, 448–459).

By "non-canonical base pair" is meant any non-Watson Crick base pair, such as mismatches and/or wobble base pairs, inlcuding flipped mismatches, single hydrogen bond mismatches, trans-type mismatches, triple base interactions, and quadruple base interactions. Non-limiting examples of such non-canonical base pairs include, but are not limited to, AC reverse Hoogsteen, AC wobble, AU reverse Hoogsteen, GU wobble, AA N7 amino, CC 2-carbonyl-amino(H1)-N3-amino(H2), GA sheared, UC 4-carbonyl-amino, UU iminocarbonyl, AC reverse wobble, AU Hoogsteen, AU reverse Watson Crick, CG reverse Watson Crick, GC N3-amino-amino N3, AA Ni-amino symmetric, AA N7-amino symmetric, GA N7-N1 amino-carbonyl, GA+ carbonyl-amino N7-N1, GG N1-carbonyl symmetric, GG N3-amino symmetric, CC carbonyl-amino symmetric, CC N3-amino symmetric, UU 2-carbonyl-imino symmetric, UU 4-carbonyl-imino symmetric, AA amino-N3, AA Ni-amino, AC amino 2-carbonyl, AC N3-amino, AC N7-amino, AU amino-4-carbonyl, AU N1-imino, AU N3-imino, AU N7-imino, CC carbonyl-amino, GA amino-N1, GA amino-N7, GA carbonyl-amino, GA N3-amino, GC amino-N3, GC carbonyl-amino, GC N3-amino, GC N7-amino, GG amino-N7, GG carbonyl-imino, GG N7-amino, GU amino-2-carbonyl, GU carbonyl-imino, GU imino-2-carbonyl, GU N7-imino, psiU imino-2-carbonyl, UC 4-carbonyl-amino, UC imino-carbonyl, UU imino-4-carbonyl, AC C2-H-N3, GA carbonyl-C2-H, UU imino-4-carbonyl 2 carbonyl-C5-H, AC amino(A) N3(C)-carbonyl, GC imino amino-carbonyl, Gpsi imino-2-carbonyl amino-2-carbonyl, and GU imino amino-2-carbonyl base pairs.

By "homologous sequence" is meant, a nucleotide sequence that is shared by one or more polynucleotide sequences, such as genes, gene transcripts and/or non-coding polynucleotides. For example, a homologous sequence can be a nucleotide sequence that is shared by two or more genes encoding related but different proteins, such as different members of a gene family, different protein epitopes, different protein isoforms or completely divergent genes, such as a cytokine and its corresponding receptors. A homologous sequence can be a nucleotide sequence that is shared by two or more non-coding polynucleotides, such as noncoding DNA or RNA, regulatory sequences, introns, and sites of transcriptional control or regulation. Homologous sequences can also include conserved sequence regions shared by more than one polynucleotide sequence. Homology does not need to be perfect homology (e.g., 100%), as partially homologous sequences are also contemplated by the instant invention (e.g., about 99%, 98%, 97%, 96%, 95%, 94%, 93%, 92%, 91%, 90%, 89%, 88%, 87%, 86%, 85%, 84%, 83%, 82%, 81%, 80% etc.).

By "conserved sequence region" is meant, a nucleotide sequence of one or more regions in a polynucleotide does not vary significantly between generations or from one biological system or organism to another biological system or organism. The polynucleotide can include both coding and non-coding DNA and RNA.

By "sense region" is meant a nucleotide sequence of a siNA molecule having complementarity to an antisense region of the siNA molecule. In addition, the sense region of a siNA molecule can comprise a nucleic acid sequence having homology with a target nucleic acid sequence.

By "antisense region" is meant a nucleotide sequence of a siNA molecule having complementarity to a target nucleic acid sequence. In addition, the antisense region of a siNA molecule can optionally comprise a nucleic acid sequence having complementarity to a sense region of the siNA molecule.

By "target nucleic acid" is meant any nucleic acid sequence whose expression or activity is to be modulated. The target nucleic acid can be DNA or RNA.

By "complementarity" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al., 1987, *CSH Symp. Quant. Biol.* LII pp.123–133; Frier et al., 1986, *Proc. Nat. Acad. Sci. USA* 83:9373–9377; Turner et al., 1987, *J. Am. Chem. Soc.* 109:3783–3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonuelcotide being based paired to a second nucleic acid sequence having 10 nucleotides represents 50%, 60%, 70%, 80%, 90%, and 100% complementary respectively). "Perfectly complementary" means that all the contiguous residues of a nucleic acid sequence will hydrogen bond with the same number of contiguous residues in a second nucleic acid sequence.

The siNA molecules of the invention represent a novel therapeutic approach to treat a variety of disease and conditions such as proliferative diseases and conditions and/or cancer including breast cancer, cancers of the head and neck including various lymphomas such as mantle cell lymphoma, non-Hodgkins lymphoma, adenoma, squamous cell carcinoma, laryngeal carcinoma, cancers of the retina, cancers of the esophagus, multiple myeloma, ovarian cancer, uterine cancer, melanoma, colorectal cancer, lung cancer, bladder cancer, prostate cancer, glioblastoma, lung cancer (including non-small cell lung carcinoma), pancreatic cancer, cervical cancer, head and neck cancer, skin cancers, nasopharyngeal carcinoma, liposarcoma, epithelial carcinoma, renal cell carcinoma, gallbladder adeno carcinoma, parotid adenocarcinoma, endometrial sarcoma, multidrug resistant cancers; and proliferative diseases and conditions, such as neovascularization associated with tumor angiogenesis, macular degeneration (e.g., wet/dry AMD), corneal neovascularization, diabetic retinopathy, neovascular glaucoma, myopic degeneration and other proliferative diseases and conditions such as arthritis, psoriasis, endometriosis, female reproduction, verruca vulgaris, angiofibroma of tuberous sclerosis, pot-wine stains, Sturge Weber syndrome, Kippel-Trenaunay-Weber syndrome, Osler-Weber-Rendu syndrome, restenosis and polycystic kidney disease; and any other diseases or conditions that are related to or will respond to the levels of VEGF and/or VEGFr in a cell or tissue, alone or in combination with other therapies. The reduction of VEGF and/or VEGFr expression and thus reduction in the level of the respective protein relieves, to some extent, the symptoms of the disease or condition.

In one embodiment of the present invention, each sequence of a siNA molecule of the invention is independently about 18 to about 24 nucleotides in length, in specific embodiments about 18, 19, 20, 21, 22, 23, or 24 nucleotides in length. In another embodiment, the siNA duplexes of the invention independently comprise about 17 to about 23 base pairs (e.g., about 17, 18, 19, 20, 21, 22, or 23). In yet another embodiment, siNA molecules of the invention comprising hairpin or circular structures are about 35 to about 55 (e.g., about 35, 40, 45, 50 or 55) nucleotides in length, or about 38 to about 44 (e.g., about 38, 39, 40, 41, 42, 43, or 44) nucleotides in length and comprising about 16 to about 22 (e.g., about 16, 17, 18, 19, 20, 21 or 22) base pairs. Exemplary siNA molecules of the invention are shown in Table II. Exemplary synthetic siNA molecules of the invention are shown in Table III and/or FIGS. 4–5.

As used herein "cell" is used in its usual biological sense, and does not refer to an entire multicellular organism, e.g., specifically does not refer to a human. The cell can be present in an organism, e.g., birds, plants and mammals such as humans, cows, sheep, apes, monkeys, swine, dogs, and cats. The cell can be prokaryotic (e.g., bacterial cell) or eukaryotic (e.g., mammalian or plant cell). The cell can be of somatic or germ line origin, totipotent or pluripotent, dividing or non-dividing. The cell can also be derived from or can comprise a gamete or embryo, a stem cell, or a fully differentiated cell.

The siNA molecules of the invention are added directly, or can be complexed with cationic lipids, packaged within liposomes, or otherwise delivered to target cells or tissues. The nucleic acid or nucleic acid complexes can be locally administered to relevant tissues ex vivo, or in vivo through injection, infusion pump or stent, with or without their incorporation in biopolymers. In particular embodiments, the nucleic acid molecules of the invention comprise sequences shown in Tables II–III and/or FIGS. 4–5. Examples of such nucleic acid molecules consist essentially of sequences defined in these tables and figures. Furthermore, the chemically modified constructs described in Table IV can be applied to any siNA sequence of the invention.

In another aspect, the invention provides mammalian cells containing one or more siNA molecules of this invention. The one or more siNA molecules can independently be targeted to the same or different sites.

By "RNA" is meant a molecule comprising at least one ribonucleotide residue. By "ribonucleotide" is meant a nucleotide with a hydroxyl group at the 2' position of a β-D-ribofuranose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

By "subject" is meant an organism, which is a donor or recipient of explanted cells or the cells themselves. "Subject" also refers to an organism to which the nucleic acid molecules of the invention can be administered. A subject can be a mammal or mammalian cells, including a human or human cells.

The term "phosphorothioate" as used herein refers to an internucleotide linkage having Formula I, wherein Z and/or W comprise a sulfur atom. Hence, the term phosphorothioate refers to both phosphorothioate and phosphorodithioate internucleotide linkages.

The term "phosphonoacetate" as used herein refers to an internucleotide linkage having Formula I, wherein Z and/or W comprise an acetyl or protected acetyl group.

The term "thiophosphonoacetate" as used herein refers to an internucleotide linkage having Formula I, wherein Z comprises an acetyl or protected acetyl group and W comprises a sulfur atom or alternately W comprises an acetyl or protected acetyl group and Z comprises a sulfur atom.

The term "universal base" as used herein refers to nucleotide base analogs that form base pairs with each of the natural DNA/RNA bases with little discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see for example Loakes, 2001, *Nucleic Acids Research*, 29, 2437–2447).

The term "acyclic nucleotide" as used herein refers to any nucleotide having an acyclic ribose sugar, for example where any of the ribose carbons (C1, C2, C3, C4, or C5), are independently or in combination absent from the nucleotide.

The nucleic acid molecules of the instant invention, individually, or in combination or in conjunction with other drugs, can be used to treat diseases or conditions discussed herein (e.g., cancers and other proliferative conditions, inflammatory diseases and conditions, and/or autoimmune diseases and conditions). For example, to treat a particular disease or condition, the siNA molecules can be administered to a subject or can be administered to other appropriate cells evident to those skilled in the art, individually or in combination with one or more drugs under conditions suitable for the treatment.

In a further embodiment, the siNA molecules can be used in combination with other known treatments to treat conditions or diseases discussed above. For example, the described molecules could be used in combination with one or more known therapeutic agents to treat a disease or condition. Non-limiting examples of other therapeutic agents that can be readily combined with a siNA molecule of the invention are enzymatic nucleic acid molecules, allosteric nucleic acid molecules, antisense, decoy, or aptamer nucleic acid molecules, antibodies such as monoclonal antibodies, small molecules, and other organic and/or inorganic compounds including metals, salts and ions.

In one embodiment, the invention features an expression vector comprising a nucleic acid sequence encoding at least one siNA molecule of the invention, in a manner which allows expression of the siNA molecule. For example, the vector can contain sequence(s) encoding both strands of a siNA molecule comprising a duplex. The vector can also contain sequence(s) encoding a single nucleic acid molecule that is self-complementary and thus forms a siNA molecule. Non-limiting examples of such expression vectors are described in Paul et al., 2002, *Nature Biotechnology*, 19, 505; Miyagishi and Taira, 2002, *Nature Biotechnology*, 19, 497; Lee et al., 2002, *Nature Biotechnology*, 19, 500; and Novina et al., 2002, *Nature Medicine*, advance online publication doi: 10.1038/nm725.

In another embodiment, the invention features a mammalian cell, for example, a human cell, including an expression vector of the invention.

In yet another embodiment, the expression vector of the invention comprises a sequence for a siNA molecule having complementarity to a RNA molecule referred to by a Genbank Accession numbers, for example Genbank Accession Nos. shown in Table I.

In one embodiment, an expression vector of the invention comprises a nucleic acid sequence encoding two or more siNA molecules, which can be the same or different.

In another aspect of the invention, siNA molecules that interact with target RNA molecules and down-regulate gene encoding target RNA molecules (for example target RNA molecules referred to by Genbank Accession numbers herein) are expressed from transcription units inserted into DNA or RNA vectors. The recombinant vectors can be DNA plasmids or viral vectors. siNA expressing viral vectors can be constructed based on, but not limited to, adeno-associated virus, retrovirus, adenovirus, or alphavirus. The recombinant vectors capable of expressing the siNA molecules can be delivered as described herein, and persist in target cells. Alternatively, viral vectors can be used that provide for transient expression of siNA molecules. Such vectors can be repeatedly administered as necessary. Once expressed, the siNA molecules bind and down-regulate gene function or expression via RNA interference (RNAi). Delivery of siNA expressing vectors can be systemic, such as by intravenous or intramuscular administration, by administration to target cells ex-planted from a subject followed by reintroduction into the subject, or by any other means that would allow for introduction into the desired target cell.

By "vectors" is meant any nucleic acid- and/or viral-based technique used to deliver a desired nucleic acid.

Other features and advantages of the invention will be apparent from the following description of the preferred embodiments thereof, and from the claims.

BRIEF DESCRIPTION OF THE DRAWINGS

FIG. 1 shows a non-limiting example of a scheme for the synthesis of siNA molecules. The complementary siNA sequence strands, strand 1 and strand 2, are synthesized in tandem and are connected by a cleavable linkage, such as a nucleotide succinate or abasic succinate, which can be the same or different from the cleavable linker used for solid phase synthesis on a solid support. The synthesis can be either solid phase or solution phase, in the example shown, the synthesis is a solid phase synthesis. The synthesis is performed such that a protecting group, such as a dimethoxytrityl group, remains intact on the terminal nucleotide of the tandem oligonucleotide. Upon cleavage and deprotection of the oligonucleotide, the two siNA strands spontaneously hybridize to form a siNA duplex, which allows the purification of the duplex by utilizing the properties of the terminal protecting group, for example by applying a trityl on purification method wherein only duplexes/oligonucleotides with the terminal protecting group are isolated.

FIG. 4A: The sense strand comprises 21 nucleotides wherein the two terminal 3'-nucleotides are optionally base paired and wherein all nucleotides present are ribonucleotides except for (N N) nucleotides, which can comprise ribonucleotides, deoxynucleotides, universal bases, or other chemical modifications described herein. The antisense strand comprises 21 nucleotides, optionally having a 3'-terminal glyceryl moiety wherein the two terminal 3'-nucleotides are optionally complementary to the target RNA sequence, and wherein all nucleotides present are ribonucleotides except for (N N) nucleotides, which can comprise ribonucleotides, deoxynucleotides, universal bases, or other chemical modifications described herein. A modified internucleotide linkage, such as a phosphorothioate, phosphorodithioate or other modified internucleotide linkage as described herein, shown as "s", optionally connects the (N N) nucleotides in the antisense strand.

FIG. 4B: The sense strand comprises 21 nucleotides wherein the two terminal 3'-nucleotides are optionally base paired and wherein all pyrimidine nucleotides that may be present are 2'-deoxy-2'-fluoro modified nucleotides and all purine nucleotides that may be present are 2'-O-methyl modified nucleotides except for (N N) nucleotides, which can comprise ribonucleotides, deoxynucleotides, universal bases, or other chemical modifications described herein. The antisense strand comprises 21 nucleotides, optionally having a 3'-terminal glyceryl moiety and wherein the two terminal 3'-nucleotides are optionally complementary to the target RNA sequence, and wherein all pyrimidine nucleotides that may be present are 2'-deoxy-2'-fluoro modified nucleotides and all purine nucleotides that may be present are 2'-O-methyl modified nucleotides except for (N N) nucleotides, which can comprise ribonucleotides, deoxynucleotides, universal bases, or other chemical modifications described herein. A modified internucleotide linkage, such as a phosphorothioate, phosphorodithioate or other modified internucleotide linkage as described herein, shown as "s", optionally connects the (N N) nucleotides in the sense and antisense strand.

FIG. 4C: The sense strand comprises 21 nucleotides having 5'- and 3'-terminal cap moieties wherein the two terminal 3'-nucleotides are optionally base paired and wherein all pyrimidine nucleotides that may be present are 2'-O-methyl or 2'-deoxy-2'-fluoro modified nucleotides except for (N N) nucleotides, which can comprise ribonucleotides, deoxynucleotides, universal bases, or other chemical modifications described herein. The antisense strand comprises 21 nucleotides, optionally having a 3'-terminal glyceryl moiety and wherein the two terminal 3'-nucleotides are optionally complementary to the target RNA sequence, and wherein all pyrimidine nucleotides that may be present are 2'-deoxy-2'-fluoro modified nucleotides except for (N N) nucleotides, which can comprise ribonucleotides, deoxynucleotides, universal bases, or other chemical modifications described herein. A modified internucleotide linkage, such as a phosphorothioate, phosphorodithioate or other modified internucleotide linkage as described herein, shown as "s", optionally connects the (N N) nucleotides in the antisense strand.

FIG. 4D: The sense strand comprises 21 nucleotides having 5'- and 3'-terminal cap moieties wherein the two terminal 3'-nucleotides are optionally base paired and wherein all pyrimidine nucleotides that may be present are 2'-deoxy-2'-fluoro modified nucleotides except for (N N) nucleotides, which can comprise ribonucleotides, deoxynucleotides, universal bases, or other chemical modifications described herein and wherein and all purine nucleotides that may be present are 2'-deoxy nucleotides. The antisense strand comprises 21 nucleotides, optionally having a 3'-terminal glyceryl moiety and wherein the two terminal 3'-nucleotides are optionally complementary to the target RNA sequence, wherein all pyrimidine nucleotides that may be present are 2'-deoxy-2'-fluoro modified nucleotides and all purine nucleotides that may be present are 2'-O-methyl modified nucleotides except for (N N) nucleotides, which can comprise ribonucleotides, deoxynucleotides, universal bases, or other chemical modifications described herein. A modified internucleotide linkage, such as a phosphorothioate, phosphorodithioate or other modified internucleotide linkage as described herein, shown as "s", optionally connects the (N N) nucleotides in the antisense strand.

FIG. 4E: The sense strand comprises 21 nucleotides having 5'- and 3'-terminal cap moieties wherein the two terminal 3'-nucleotides are optionally base paired and wherein all pyrimidine nucleotides that may be present are 2'-deoxy-2'-fluoro modified nucleotides except for (N N) nucleotides, which can comprise ribonucleotides, deoxynucleotides, universal bases, or other chemical modifications described herein. The antisense strand comprises 21 nucleotides, optionally having a 3'-terminal glyceryl moiety and wherein the two terminal 3'-nucleotides are optionally complementary to the target RNA sequence, and wherein all pyrimidine nucleotides that may be present are 2'-deoxy-2'-fluoro modified nucleotides and all purine nucleotides that may be present are 2'-O-methyl modified nucleotides except for (N N) nucleotides, which can comprise ribonucleotides, deoxynucleotides, universal bases, or other chemical modifications described herein. A modified internucleotide linkage, such as a phosphorothioate, phosphorodithioate or other modified internucleotide linkage as described herein, shown as "s", optionally connects the (N N) nucleotides in the antisense strand.

FIG. 4F: The sense strand comprises 21 nucleotides having 5'- and 3'-terminal cap moieties wherein the two terminal 3'-nucleotides are optionally base paired and wherein all pyrimidine nucleotides that may be present are 2'-deoxy-2'-fluoro modified nucleotides except for (N N) nucleotides, which can comprise ribonucleotides, deoxynucleotides, universal bases, or other chemical modifications described herein and wherein and all purine nucleotides that may be present are 2'-deoxy nucleotides. The antisense strand comprises 21 nucleotides, optionally having a 3'-terminal glyceryl moiety and wherein the two terminal 3'-nucleotides are optionally complementary to the target RNA sequence, and having one 3'-terminal phosphorothioate internucleotide linkage and wherein all pyrimidine nucleotides that may be present are 2'-deoxy-2'-fluoro modified nucleotides and all purine nucleotides that may be present are 2'-deoxy nucleotides except for (N N) nucleotides, which can comprise ribonucleotides, deoxynucleotides, universal bases, or other chemical modifications described herein. A modified internucleotide linkage, such as a phosphorothioate, phosphorodithioate or other modified internucleotide linkage as described herein, shown as "s", optionally connects the (N N) nucleotides in the antisense strand. The antisense strand of constructs A–F comprise sequence complementary to any target nucleic acid sequence of the invention. Furthermore, when a glyceryl moiety (L) is present at the 3'-end of the antisense strand for any construct shown in FIG. 4A–F, the modified internucleotide linkage is optional.

FIG. 7A: A DNA oligomer is synthesized with a 5'-restriction site (R1) sequence followed by a region having sequence identical (sense region of siNA) to a predetermined VEGF and/or VEGFr target sequence, wherein the sense region comprises, for example, about 19, 20, 21, or 22 nucleotides (N) in length, which is followed by a loop sequence of defined sequence (X), comprising, for example, about 3 to about 10 nucleotides.

FIG. 7B: The synthetic construct is then extended by DNA polymerase to generate a hairpin structure having self-complementary sequence that will result in a siNA transcript having specificity for a VEGF and/or VEGFr target sequence and having self-complementary sense and antisense regions.

FIG. 7C: The construct is heated (for example to about 95° C.) to linearize the sequence, thus allowing extension of a complementary second DNA strand using a primer to the 3'-restriction sequence of the first strand. The double-stranded DNA is then inserted into an appropriate vector for expression in cells. The construct can be designed such that a 3'-terminal nucleotide overhang results from the transcription, for example by engineering restriction sites and/or utilizing a poly-U termination region as described in Paul et al., 2002, *Nature Biotechnology*, 29, 505–508.

FIG. 8A: A DNA oligomer is synthesized with a 5'-restriction (R1) site sequence followed by a region having sequence identical (sense region of siNA) to a predetermined VEGF and/or VEGFr target sequence, wherein the sense region comprises, for example, about 19, 20, 21, or 22 nucleotides (N) in length, and which is followed by a 3'-restriction site (R2) which is adjacent to a loop sequence of defined sequence (X).

FIG. 8B: The synthetic construct is then extended by DNA polymerase to generate a hairpin structure having self-complementary sequence.

FIG. 8C: The construct is processed by restriction enzymes specific to R1 and R2 to generate a double-stranded DNA which is then inserted into an appropriate vector for expression in cells. The transcription cassette is designed such that a U6 promoter region flanks each side of the dsDNA which generates the separate sense and antisense strands of the siNA. Poly T termination sequences can be added to the constructs to generate U overhangs in the resulting transcript.

FIG. 9A: A pool of siNA oligonucleotides are synthesized wherein the antisense region of the siNA constructs has complementarity to target sites across the target nucleic acid sequence, and wherein the sense region comprises sequence complementary to the antisense region of the siNA.

FIG. 9B&C: (FIG. 9B) The sequences are pooled and are inserted into vectors such that (FIG. 9C) transfection of a vector into cells results in the expression of the siNA.

FIG. 9D: Cells are sorted based on phenotypic change that is associated with modulation of the target nucleic acid sequence.

FIG. 9E: The siNA is isolated from the sorted cells and is sequenced to identify efficacious target sites within the target nucleic acid sequence.

FIG. 11 shows a non-limiting example of a strategy used to identify chemically modified siNA constructs of the invention that are nuclease resistance while preserving the ability to mediate RNAi activity. Chemical modifications are introduced into the siNA construct based on educated design parameters (e.g. introducing 2'-mofications, base modifications, backbone modifications, terminal cap modifications etc). The modified construct in tested in an appropriate system (e.g. human serum for nuclease resistance, shown, or an animal model for PK/delivery parameters). In parallel, the siNA construct is tested for RNAi activity, for example in a cell culture system such as a luciferase reporter assay). Lead siNA constructs are then identified which possess a particular characteristic while maintaining RNAi activity, and can be further modified and assayed once again. This same approach can be used to identify siNA-conjugate molecules with improved pharmacokinetic profiles, delivery, and RNAi activity.

FIG. 12 shows non-limiting examples of phosphorylated siNA molecules of the invention, including linear and duplex constructs and asymmetric derivatives thereof.

FIG. 13 shows non-limiting examples of chemically modified terminal phosphate groups of the invention.

FIG. 14A shows a non-limiting example of methodology used to design self complementary DFO constructs utilizing palidrome and/or repeat nucleic acid sequences that are identifed in a target nucleic acid sequence. (i) A palindrome or repeat sequence is identified in a nucleic acid target sequence. (ii) A sequence is designed that is complementary to the target nucleic acid sequence and the palindrome sequence. (iii) An inverse repeat sequence of the non-palindrome/repeat portion of the complementary sequence is appended to the 3'-end of the complementary sequence to generate a self complmentary DFO molecule comprising sequence complementary to the nucleic acid target. (iv) The DFO molecule can self-assemble to form a double stranded oligonucleotide. FIG. 14B shows a non-limiting representative example of a duplex forming oligonucleotide sequence. FIG. 14C shows a non-limiting example of the self assembly schematic of a representative duplex forming oligonucleotide sequence. FIG. 14D shows a non-limiting example of the self assembly schematic of a representative duplex forming oligonucleotide sequence followed by interaction with a target nucleic acid sequence resulting in modulation of gene expression.

FIG. 15 shows a non-limiting example of the design of self complementary DFO constructs utilizing palidrome and/or repeat nucleic acid sequences that are incorporated into the DFO constructs that have sequence complementary to any target nucleic acid sequence of interest. Incorporation of these palindrome/repeat sequences allow the design of DFO constructs that form duplexes in which each strand is capable of mediating modulation of target gene expression, for example by RNAi. First, the target sequence is identified. A complementary sequence is then generated in which nucleotide or non-nucleotide modifications (shown as X or Y) are introduced into the complementary sequence that generate an artificial palindrome (shown as XYXYXY in the Figure). An inverse repeat of the non-palindrome/repeat complementary sequence is appended to the 3'-end of the complementary sequence to generate a self complmentary DFO comprising sequence complementary to the nucleic acid target. The DFO can self-assemble to form a double stranded oligonucleotide.

FIG. 16 shows non-limiting examples of multifunctional siNA molecules of the invention comprising two separate polynucleotide sequences that are each capable of mediating RNAi directed cleavage of differing target nucleic acid sequences. FIG. 16A shows a non-limiting example of a multifunctional siNA molecule having a first region that is complementary to a first target nucleic acid sequence (complementary region 1) and a second region that is complementary to a second target nucleic acid sequence (complementary region 2), wherein the first and second complementary regions are situated at the 3'-ends of each polynucleotide sequence in the multifunctional siNA. The dashed portions of each polynucleotide sequence of the multifunctional siNA construct have complementarity with regard to corresponding portions of the siNA duplex, but do not have complementarity to the target nucleic acid sequences. FIG. 16B shows a non-limiting example of a multifunctional siNA molecule having a first region that is complementary to a first target nucleic acid sequence (complementary region 1) and a second region that is complementary to a second target nucleic acid sequence (complementary region 2), wherein the first and second complementary regions are situated at the 5'-ends of each polynucleotide sequence in the multifunctional siNA. The dashed portions of each polynucleotide sequence of the multifunctional siNA construct have complementarity with regard to corresponding portions of the siNA duplex, but do not have complementarity to the target nucleic acid sequences.

FIG. 17 shows non-limiting examples of multifunctional siNA molecules of the invention comprising a single polynucleotide sequence comprising distinct regions that are each capable of mediating RNAi directed cleavage of differing target nucleic acid sequences. FIG. 17A shows a non-limiting example of a multifunctional siNA molecule having a first region that is complementary to a first target nucleic acid sequence (complementary region 1) and a second region that is complementary to a second target nucleic acid sequence (complementary region 2), wherein the second complementary region is situated at the 3'-end of the polynucleotide sequence in the multifunctional siNA. The dashed portions of each polynucleotide sequence of the multifunctional siNA construct have complementarity with regard to corresponding portions of the siNA duplex, but do not have complementarity to the target nucleic acid sequences. FIG. 17B shows a non-limiting example of a multifunctional siNA molecule having a first region that is complementary to a first target nucleic acid sequence (complementary region 1) and a second region that is complementary to a second target nucleic acid sequence (complementary region 2), wherein the first complementary region is situated at the 5'-end of the polynucleotide sequence in the multifunctional siNA. The dashed portions of each polynucleotide sequence of the multifunctional siNA construct have complementarity with regard to corresponding portions of the siNA duplex, but do not have complementarity to the target nucleic acid sequences. In one embodiment, these multifunctional siNA constructs are processed in vivo or in vitro to generate multifunctional siNA constructs as shown in FIG. 16.

FIG. 18 shows non-limiting examples of multifunctional siNA molecules of the invention comprising two separate polynucleotide sequences that are each capable of mediating RNAi directed cleavage of differing target nucleic acid sequences and wherein the multifunctional siNA construct further comprises a self complementary, palindrome, or repeat region, thus enabling shorter bifunctional siNA constructs that can mediate RNA interference against differing target nucleic acid sequences. FIG. 18A shows a non-limiting example of a multifunctional siNA molecule having a first region that is complementary to a frist target nucleic acid sequence (complementary region 1) and a second region that is complementary to a second target nucleic acid sequence (complementary region 2), wherein the first and second complementary regions are situated at the 3'-ends of each polynucleotide sequence in the multifunctional siNA, and wherein the first and second complementary regions further comprise a self complementary, palindrome, or repeat region. The dashed portions of each polynucleotide sequence of the multifunctional siNA construct have complementarity with regard to corresponding portions of the siNA duplex, but do not have complementarity to the target nucleic acid sequences. FIG. 18B shows a non-limiting example of a multifunctional siNA molecule having a first region that is complementary to a frist target nucleic acid sequence (complementary region 1) and a second region that is complementary to a second target nucleic acid sequence (complementary region 2), wherein the first and second complementary regions are situated at the 5'-ends of each polynucleotide sequence in the multifunctional siNA, and wherein the first and second complementary regions further comprise a self complementary, palindrome, or repeat region. The dashed portions of each polynucleotide sequence of the multifunctional siNA construct have complementarity with regard to corresponding portions of the siNA duplex, but do not have complementarity to the target nucleic acid sequences.

FIG. 19 shows non-limiting examples of multifunctional siNA molecules of the invention comprising a single polynucleotide sequence comprising distinct regions that are each capable of mediating RNAi directed cleavage of differing target nucleic acid sequences and wherein the multifunctional siNA construct further comprises a self complementary, palindrome, or repeat region, thus enabling shorter bifuctional siNA constructs that can mediate RNA interference against differing target nucleic acid sequences. FIG. 19A shows a non-limiting example of a multifunctional siNA molecule having a first region that is complementary to a first target nucleic acid sequence (complementary region 1) and a second region that is complementary to a second target nucleic acid sequence (complementary region 2), wherein the second complementary region is situated at the 3'-end of the polynucleotide sequence in the multifunctional siNA, and wherein the first and second complementary regions further comprise a self complementary, palindrome, or repeat region. The dashed portions of each polynucleotide sequence of the multifunctional siNA construct have complementarity with regard to corresponding portions of the siNA duplex, but do not have complementarity to the target nucleic acid sequences. FIG. 19B shows a non-limiting example of a multifunctional siNA molecule having a first region that is complementary to a frist target nucleic acid sequence (complementary region 1) and a second region that is complementary to a second target nucleic acid sequence (complementary region 2), wherein the first complementary region is situated at the 5'-end of the polynucleotide sequence in the multifunctional siNA, and wherein the first and second complementary regions further comprise a self complementary, palindrome, or repeat region. The dashed portions of each polynucleotide sequence of the multifunctional siNA construct have complementarity with regard to corresponding portions of the siNA duplex, but do not have complementarity to the target nucleic acid sequences. In one embodiment, these multifunctional siNA constructs are processed in vivo or in vitro to generate multifunctional siNA constructs as shown in FIG. 18.

FIG. 20 shows a non-limiting example of how multifunctional siNA molecules of the invention can target two separate target nucleic acid molecules, such as separate RNA molecules encoding differing proteins, for example a cytokine and its corresponding receptor, differing viral strains, a virus and a cellular protein involved in viral infection or replication, or differing proteins involved in a common or divergent biologic pathway that is implicated in the maintenance of progression of disease. Each strand of the multifunctional siNA construct comprises a region having complementarity to separate target nucleic acid molecules. The multifunctional siNA molecule is designed such that each strand of the siNA can be utilized by the RISC complex to initiate RNA interferance mediated cleavage of its corresponding target. These design parameters can include destabilization of each end of the siNA construct (see for example Schwarz et al., 2003, *Cell*, 115, 199–208). Such destabilization can be accomplished for example by using guanosine-cytidine base pairs, alternate base pairs (e.g., wobbles), or destabilizing chemically modified nucleotides at terminal nucleotide positions as is known in the art.

FIG. 21 shows a non-limiting example of how multifunctional siNA molecules of the invention can target two separate target nucleic acid seqeunces within the same target nucleic acid molecule, such as alternate coding regions of a RNA, coding and non-coding regions of a RNA, or alternate splice variant regions of a RNA. Each strand of the multifunctional siNA construct comprises a region having complementarity to the separate regions of the target nucleic acid molecule. The multifunctional siNA molecule is designed such that each strand of the siNA can be utilized by the RISC complex to initiate RNA interferance mediated cleavage of its corresponding target region. These design parameters can include destabilization of each end of the siNA construct (see for example Schwarz et al., 2003, *Cell*, 115, 199–208). Such destabilization can be accomplished for example by using guanosine-cytidine base pairs, alternate base pairs (e.g., wobbles), or destabilizing chemically modified nucleotides at terminal nucleotide positions as is known in the art.

FIG. 22 shows a non-limiting example of reduction of VEGFR1 mRNA in A375 cells mediated by chemically-modified siNAs that target VEGFR1 mRNA. A549 cells were transfected with 0.25 ug/well of lipid complexed with 25 nM siNA. A screen of siNA constructs (Stabilization "Stab" chemistries are shown in Table IV, constructs are referred to by RPI number, see Table III) comprising Stab 4/5 chemistry (RPI 31190/31193), Stab 1/2 chemistry (RPI 31183/31186 and RPI 31184/31187), and unmodified RNA (RPI 30075/30076) were compared to untreated cells, matched chemistry inverted control siNA constructs, (RPI 31208/31211, RPI 31201/31204, RPI 31202/31205, and RPI 30077/30078) scrambled siNA control constructs (Scram1 and Scram2), and cells transfected with lipid alone (transfection control). All of the siNA constructs show significant reduction of VEGFR1 RNA expression.

FIG. 23 shows a non-limiting example of reduction of VEGFR1 mRNA levels in HAEC cell culture using Stab 9/10 directed against eight sites in VEGFR1 mRNA compared to matched chemistry inverted controls siNA constructs. Controls UNT and LF2K refer to untreated cells and cells treated with LF2K transfection reagent alone, respectively.

FIG. 24 shows a non-limiting example of reduction of VEGFr2 mRNA in HAEC cells mediated by chemically-modified siNAs that target VEGFr2 mRNA. HAEC cells were transfected with 0.25 ug/well of lipid complexed with 25 nM siNA. A screen of siNA constructs (Stabilization "Stab" chemistries are shown in Table IV, constructs are referred to by Compound No., see Table III) in site 3854 comprising Stab 4/5 chemistry (Compound No. 30786/30790), Stab 7/8 chemistry (Compound No. 31858/31860), and Stab 9/10 chemistry (Compound No. 31862/31864) and in site 3948 comprising Stab 4/5 chemistry (Compound No. 31856/31857), Stab 7/8 chemistry (Compound No. 31859/31861), and Stab 9/10 chemistry (Compound No. 31863/31865) were compared to untreated cells, matched chemistry inverted control siNA constructs in site 3854 (Compound No. 31878/31880, Compound No. 31882/31884, and Compound No. 31886/31888), and in site 3948 (Compound No. 31879/31881, Compound No. 31883/31885, and Compound No. 31887/31889), cells transfected with LF2K (transfection reagent), and an all RNA control (Compound No. 31435/31439 in site 3854 and Compound No. 31437/31441 in site 3948). All of the siNA constructs show significant reduction of VEGFr2 RNA expression.

FIG. 25 shows a non-limiting example of reduction of VEGFR2 mRNA levels in HAEC cell culture using Stab 0/0 directed against four sites in VEGFR2 mRNA compared to irrelevant control siNA constructs (IC1, IC2). Controls UNT and LF2K refer to untreated cells and cells treated with LF2K transfection reagent alone, respectively.

FIG. 26 shows non-limiting examples of reduction of VEGFRl (Flt-1) mRNA levels in HAEC cells (15,000 cells/well) 24 hours after treatment with siNA molecules targeting sequences having VEGFR1 (Flt-1) and VEGFR2 (KDR) homology. HAEC cells were transfected with 1.5 ug/well of lipid complexed with 25 nM siNA. Activity of the siNA moleclues is shown compared to matched chemistry inverted siNA controls, untreated cells, and cells treated with lipid only (transfection control). siNA molecules and controls are referred to by compound numbers (sense/antisense), see Table III for sequences. FIG. 26A shows data for Stab 9/10 siNA constructs. FIG. 26B shows data for Stab 7/8 siNA constructs. The FIG. 26B study includes a construct that targets only VEGFR1 (32748/32755) and a matched chemistry inverted control thereof (32772/32779) as additional controls. As shown in the figures, the siNA constructs that target both VEGFR1 and VEGFR2 sequences demonstrate potent efficacy in inhibiting VEGFR1 expression in cell cuture experiments.

FIG. 27 shows non-limiting examples of reduction of VEGFr2 (KDR) mRNA levels in HAEC cells (15,000 cells/well) 24 hours after treatment with siNA molecules targeting sequences having VEGFr1 and VEGFr2 homology. HAEC cells were transfected with 1.5 ug/well of lipid complexed with 25 nM siNA. Activity of the siNA moleclues is shown compared to matched chemistry inverted siNA controls, untreated cells, and cells treated with lipid only (transfection control). siNA molecules and controls are referred to by compound numbers (sense/antisense), see Table III for sequences. FIG. 27A shows data for Stab 9/10 siNA constructs. FIG. 237 shows data for Stab 7/8 siNA constructs. The FIG. 27B study includes a construct that targets only VEGFr1 (32748/32755) and a matched chemistry inverted control thereof (32772/32779) as additional controls. As shown in the figures, the siNA constructs that target both VEGFr1 and VEGFr2 sequences demonstrate potent efficacy in inhibiting VEGFr2 expression in cell cuture experiments.

FIG. 28 shows a non-limiting example of siNA mediated inhibition of VEGF-induced angiogenesis using the rat corneal model of angiogenesis. siNA targeting site 2340 of VEGFR1 RNA (shown as RPI No. 29695/29699 sense strand/antisense strand) was compared to an inverted control siNA (shown as RPI No. 29983/29984 sense strand/antisense strand) at three different concentrations (1 ug, 3 ug, and 10 ug) and compared to a VEGF control in which no siNA was administered. As shown in the Figure, siNA constructs targeting VEGFR1 RNA can provide significant inhibition of angiogenesis in the rat corneal model.

FIG. 29 shows a non-limiting example of inhibition of VEGF induced neovascularization in the rat corneal model. VEGFR1 site 349 active siNA having "Stab 9/10" chemistry (Compound No. 31270/31273) was tested for inhibition of VEGF-induced angiogenesis at three different concentrations (2.0 ug, 1.0 ug, and 0.1 ug dose response) as compared to a matched chemistry inverted control sNA construct (Compound No. 31276/31279) at each concentration and a VEGF control in which no siNA was administered. As shown in the figure, the active siNA construct having "Stab 9/10" chemistry (Compound No. 31270/31273) is highly effective in inhibiting VEGF-induced angiogenesis in the rat corneal model compared to the matched chemistry inverted control siNA at concentrations from 0.1 ug to 2.0 ug.

FIG. 30 shows a non-limiting example of a study in which sites adjacent to VEGFR1 site 349 were evaluated for efficacy using two different siNA stabilization chemistries. Chemistry C=Stab 9/10 whereas Chemistry D=Stab 7/8.

FIG. 31 shows a non-limiting example of inhibition of VEGF induced ocular angiogenesis using siNA constructs that target homologous sequences shared by VEGFR1 and VEGFR2 via subconjuctival administration of the siNA after VEGF disk implantation. siNA constructs were administered intraocularly on days 1 and 7 following laser induced injury to the choroid, and choroidal neovascularization assessed on day 14.

FIG. 32 shows a non-limiting example of inhibition of VEGF induced neovascularization in a mouse model of coroidal neovascularization via intraocular administration of siNA. VEGFR1 site 349 active siNA having "Stab 9/10" chemistry (Compound No. 31270/31273) was tested for inhibition of neovascularization at two different concentrations (1.5 ug, and 0.5 ug) as compared to a matched chemistry inverted control siNA construct (Compound No. 31276/31279) and phosphate buffered saline (PBS). siNA constructs were administered intraocularly on days 1 and 7 following laser induced injury to the choroid, and choroidal neovascularization assessed on day 14. As shown in the figure, the active siNA construct having "Stab 9/10" chemistry (Compound No. 31270/31273) is highly effective in inhibiting neovascularization via intraocular administration in this model.

FIG. 33 shows a non-limiting example of inhibition of VEGF induced neovascularization in a mouse model of coroidal neovascularization via periocular administration of siNA. VEGFR1 site 349 active siNA having "Stab 9/10" chemistry (Compound No. 31270/31273) was tested for inhibition of neovascularization at two different concentrations (1.5 ug with a saline control, and 0.5 ug with an inverted siNA control, Compound No. 31276/31279). Eight mice were used in each arm of the study with one eye receiving the active siNA and the other eye receiving the saline or inverted control. siNA constructs and controls were administered daily up to 14 days, and neovascularization was assessed at day 17 following laser induced injury to the choroid. As shown in the figure, the active siNA construct having "Stab 9/10" chemistry (Compound No. 31270/31273) is highly effective in inhibiting neovascularization via periocular administration in this model.

FIG. 34 shows another non-limiting example of inhibition of VEGF induced neovascularization in a mouse model of coroidal neovascularization via periocular administration of siNA. VEGFR1 site 349 active siNA having "Stab 9/10" chemistry (Compound No. 31270/31273) was tested for inhibition of neovascularization at two different concentrations (1.5 ug with an inverted siNA control, Compound No. 31276/31279 and 0.5 ug with a saline control). Nine mice were used in the active versus inverted arm of the study with one eye receiving the active siNA and the other eye receiving the inverted control. Eight mice were used in the active versus saline arm of the study with one eye receiving the active siNA and the other eye receiving the saline control. siNA constructs and controls were administered daily up to 14 days, and neovascularization was assessed at day 17 following laser induced injury to the choroid. As shown in the figure, the active siNA construct having "Stab 9/10" chemistry (Compound No. 31270/31273) is highly effective in inhibiting neovascularization via periocular administration in this model.

FIG. 35 shows a non-limiting example of siNA mediated inhibition of choroidal neovascularization (CNV) in mice injected with active siNA (31270/31273) targeting site 349 of VEGFR1 mRNA compared to mice injected with a matched chemistry inverted control siNA construct (31276/31279) in a mouse model of ocular neovascularization. Periocular injections were performed every three days after rupture of Bruch's membrane. Eyes treated with active siNA had significantly smaller areas of CNV than eyes treated with inverted control siNA constructs (n=13, p=0.0002).

FIG. 36 shows a non-limiting example of siNA mediated inhibition of VEGFR1 mRNA levels in mice injected with active siNA (31270/31273) targeting site 349 of VEGFR1 mRNA compared to mice injected with a matched chemistry inverted control siNA construct (31276/31279) in a mouse model of oxygen induced retinopathy (OIR). Periocular injections of VEGFR1 siNA (31270/31273) (5 µl; 1.5 µg/l) on P12, P14, and P16 significantly reduced VEGFR1 mRNA expression compared to injections with a matched chemistry inverted control siNA construct (31276/31279), (40% inhibition; n=9, p=0.0121).

FIG. 37 shows a non-limiting example of siNA mediated inhibition of VEGFR1 protein levels in mice injected with active siNA (31270/31273) targeting site 349 of VEGFR1 mRNA compared to mice injected with a matched chemistry inverted control siNA construct (31276/31279) in a mouse model of oxygen induced retinopathy (OIR). Intraocular injections of VEGFR1 siNA (31270/31273) (5 µg), significantly reduced VEGFR1 protein levels compared to injections with a matched chemistry inverted control siNA construct (31276/31279), (30% inhibition; n=7, p=0.0103).

FIG. 38 shows a non-limiting example of the reduction of primary tumor volume in a mouse 4T1-luciferase mammary carcinoma syngeneic tumor model using active Stab 9/10 siNA targeting site 349 of VEGFR1 RNA (Compound #31270/31273) compared to a matched chemistry inactive inverted control siNA (Compound #31276/31279) and saline. As shown in the figure, the active siNA construct is effective in reducing tumor volume in this model.

FIG. 39 shows a non-limiting example of the reduction of soluble VEGFR1 serum levels in a mouse 4T1-luciferase mammary carcinoma syngeneic tumor model using active Stab 9/10 siNA targeting site 349 of VEGFR1 RNA (Compound #31270/31273) compared to a matched chemistry inactive inverted control siNA (Compound #31276/31279). As shown in the figure, the active siNA construct is effective in reducing soluble VEGFR1 serum levels in this model.

DETAILED DESCRIPTION OF THE INVENTION

Figure 2:
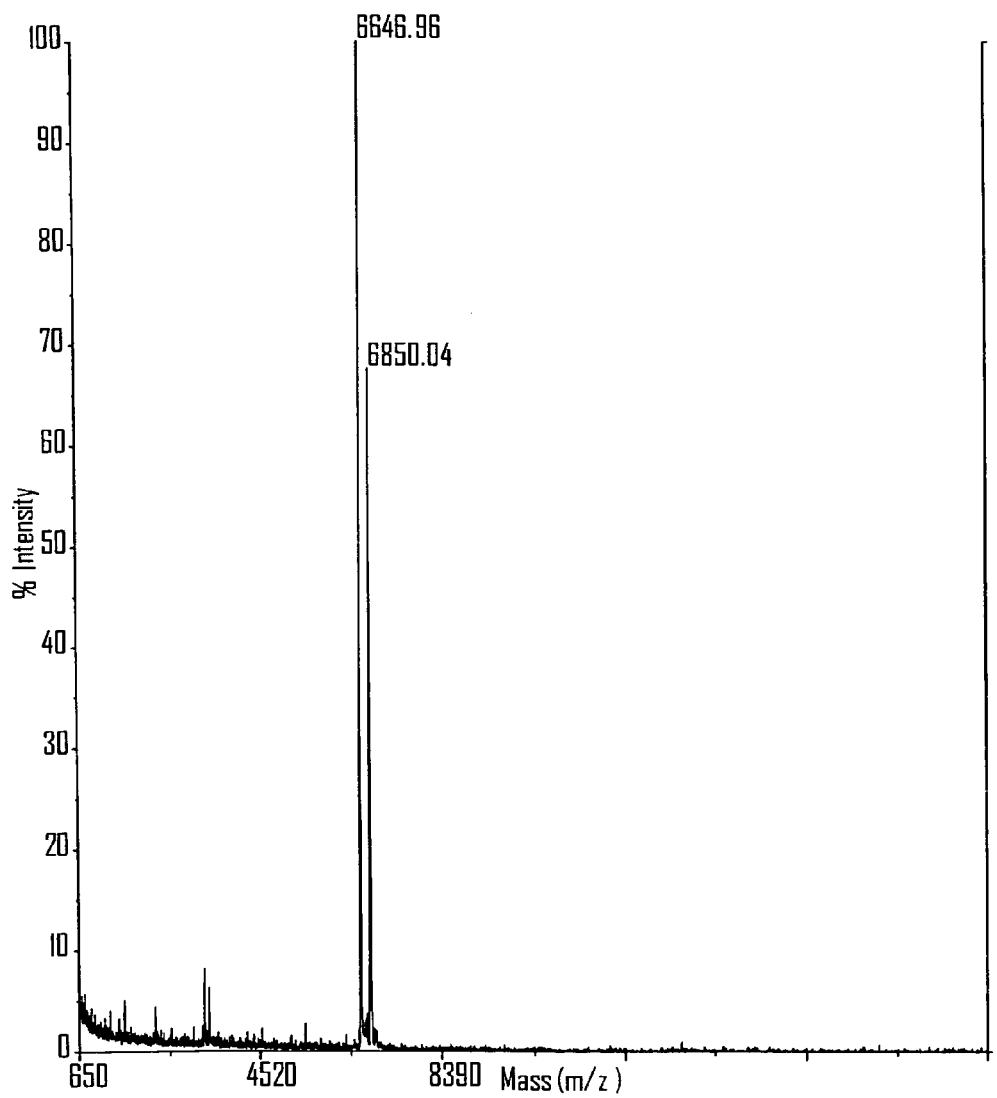
FIG. 2 shows a MALDI-TOF mass spectrum of a purified siNA duplex synthesized by a method of the invention. The two peaks shown correspond to the predicted mass of the separate siNA sequence strands. This result demonstrates that the siNA duplex generated from tandem synthesis can be purified as a single entity using a simple trityl-on purification methodology.
Figure 3:
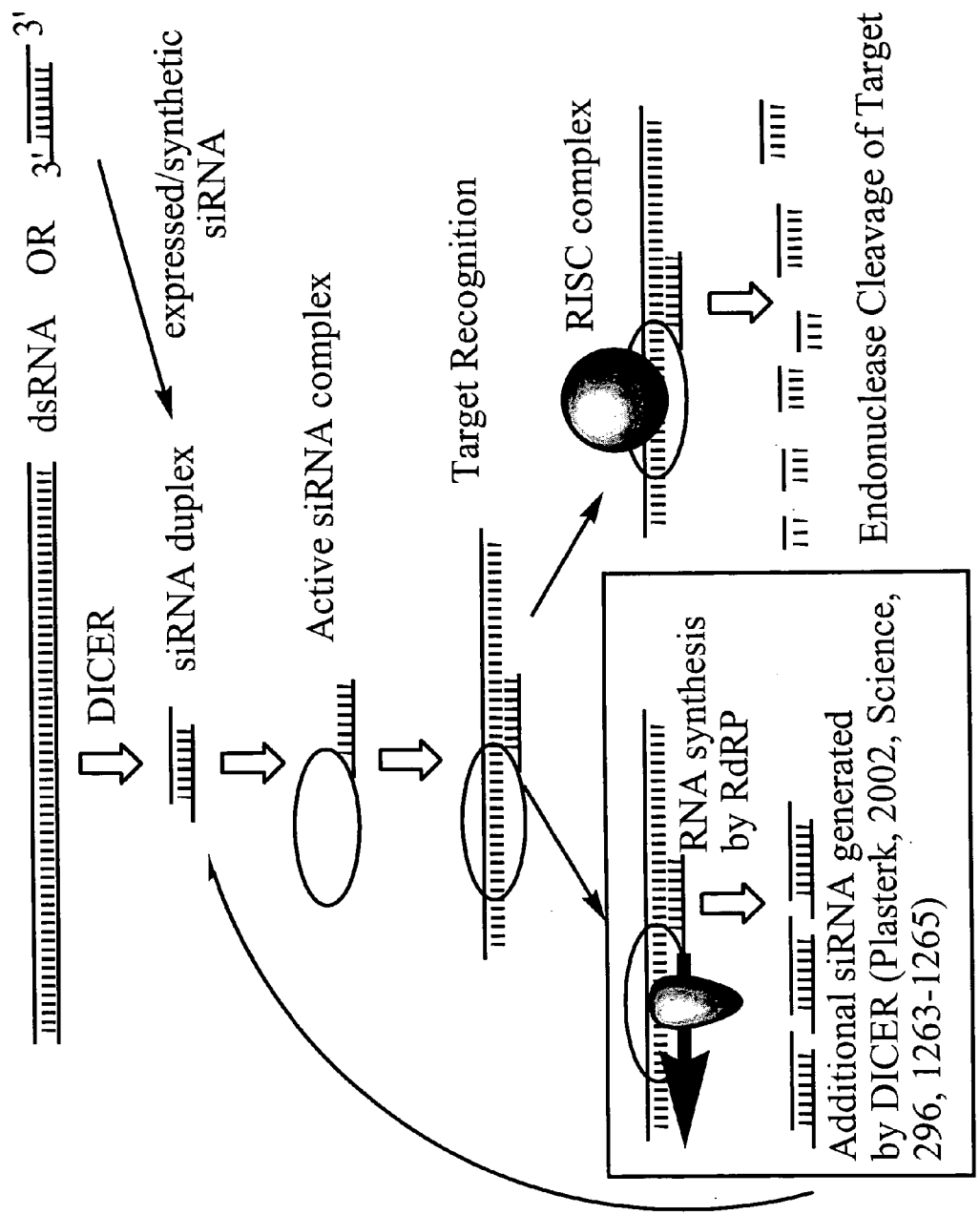
FIG. 3 shows a non-limiting proposed mechanistic representation of target RNA degradation involved in RNAi. Double-stranded RNA (dsRNA), which is generated by RNA-dependent RNA polymerase (RdRP) from foreign single-stranded RNA, for example viral, transposon, or other exogenous RNA, activates the DICER enzyme that in turn generates siNA duplexes. Alternately, synthetic or expressed siNA can be introduced directly into a cell by appropriate means. An active siNA complex forms which recognizes a target RNA, resulting in degradation of the target RNA by the RISC endonuclease complex or in the synthesis of additional RNA by RNA-dependent RNA polymerase (RdRP), which can activate DICER and result in additional siNA molecules, thereby amplifying the RNAi response.
Figure 4:
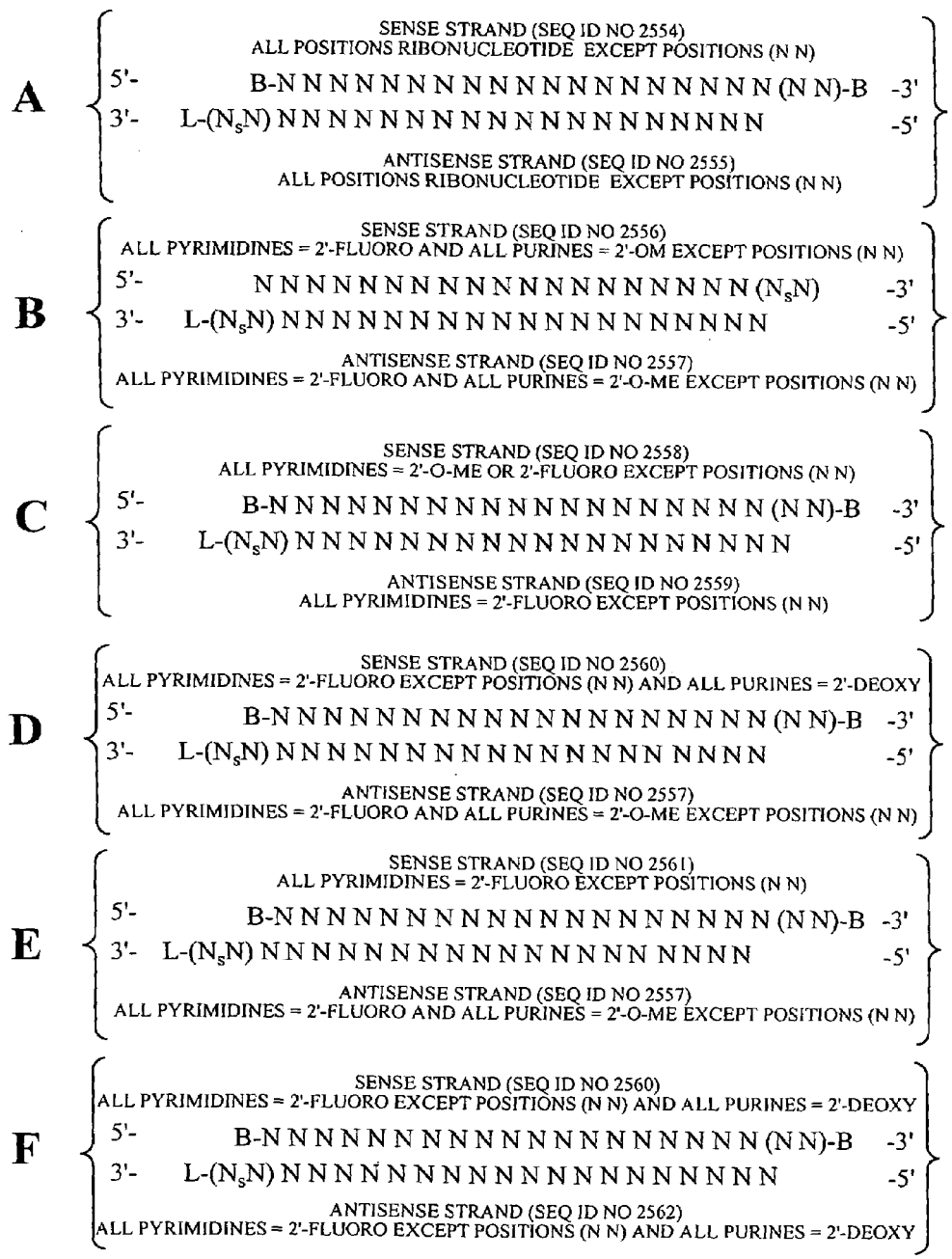
FIG. 4A–F shows non-limiting examples of chemically-modified siNA constructs of the present invention. In the figure, N stands for any nucleotide (adenosine, guanosine, cytosine, uridine, or optionally thymidine, for example thymidine can be substituted in the overhanging regions designated by parenthesis (N N). Various modifications are shown for the sense and antisense strands of the siNA constructs.
Figure 5:
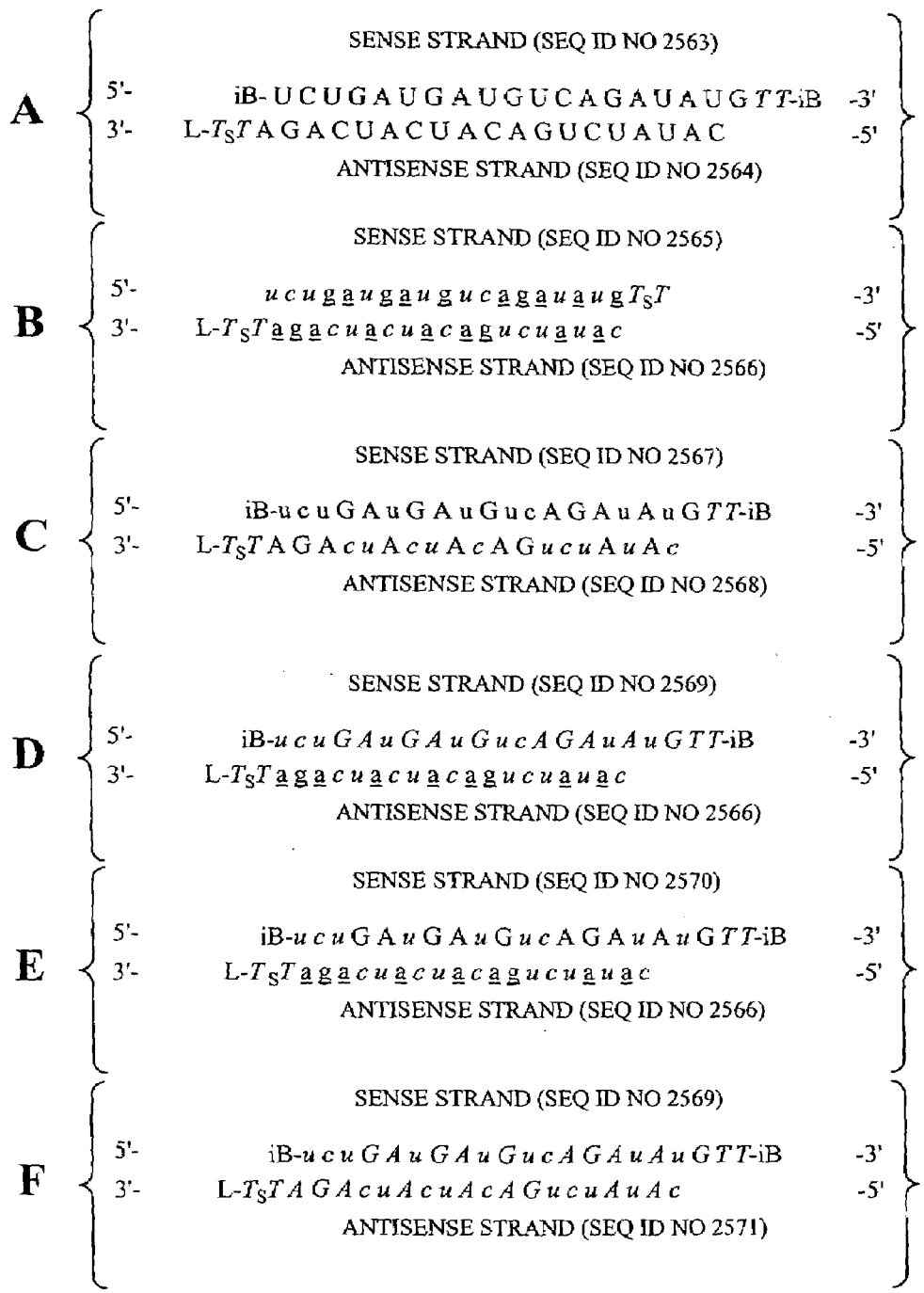
FIG. 5A–F shows non-limiting examples of specific chemically-modified siNA sequences of the invention. A–F applies the chemical modifications described in FIG. 4A–F to a VEGFR1 siNA sequence. Such chemical modifications can be applied to any VEGF and/or VEGFr sequence.
Figure 6:
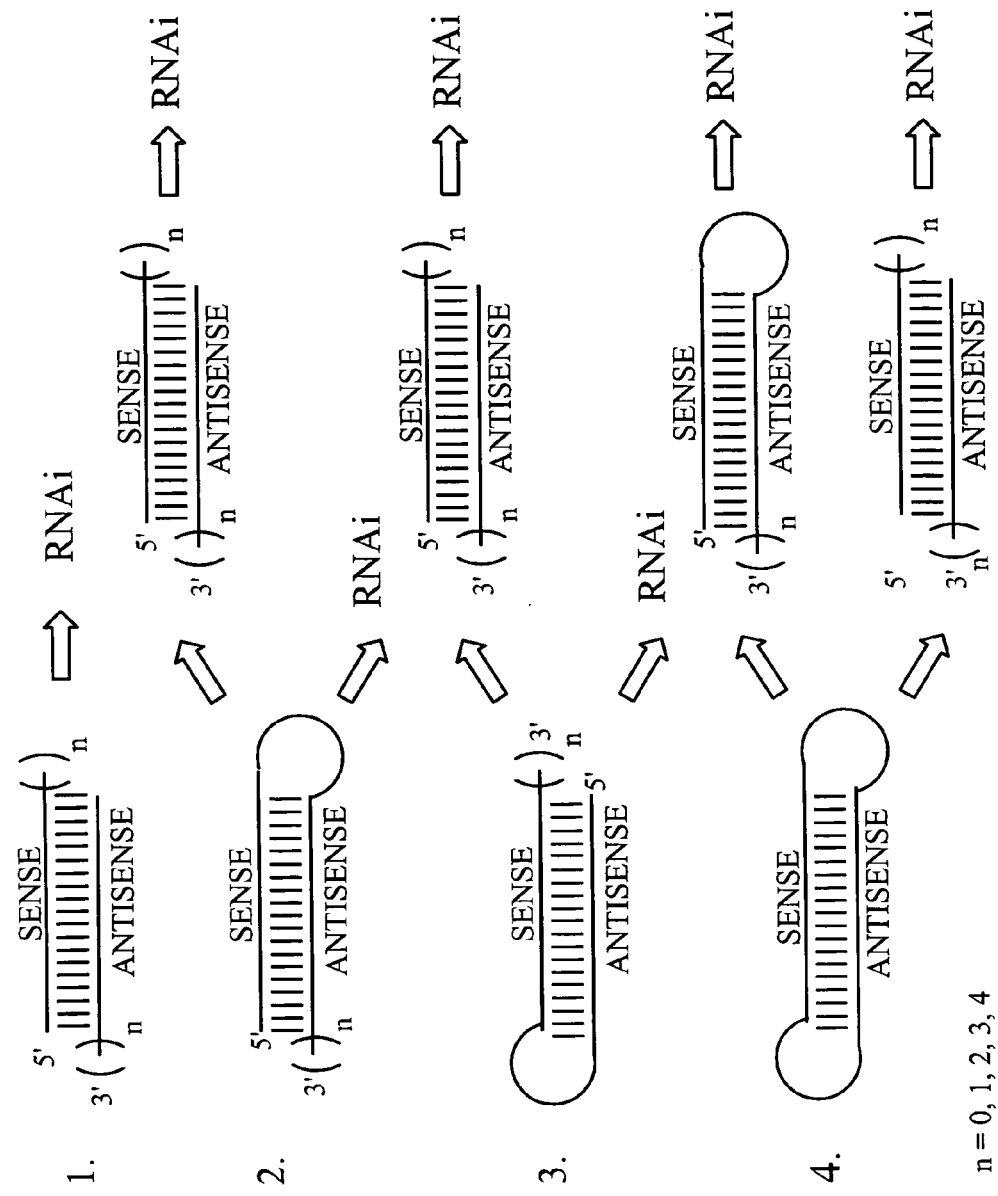
FIG. 6 shows non-limiting examples of different siNA constructs of the invention. The examples shown (constructs 1, 2, and 3) have 19 representative base pairs; however, different embodiments of the invention include any number of base pairs described herein. Bracketed regions represent nucleotide overhangs, for example comprising about 1, 2, 3, or 4 nucleotides in length, preferably about 2 nucleotides. Constructs 1 and 2 can be used independently for RNAi activity. Construct 2 can comprise a polynucleotide or non-nucleotide linker, which can optionally be designed as a biodegradable linker. In one embodiment, the loop structure shown in construct 2 can comprise a biodegradable linker that results in the formation of construct 1 in vivo and/or in vitro. In another example, construct 3 can be used to generate construct 2 under the same principle wherein a linker is used to generate the active siNA construct 2 in vivo and/or in vitro, which can optionally utilize another biodegradable linker to generate the active siNA construct 1 in vivo and/or in vitro. As such, the stability and/or activity of the siNA constructs can be modulated based on the design of the siNA construct for use in vivo or in vitro and/or in vitro.

Mechanism of Action of Nucleic Acid Molecules of the Invention

The discussion that follows discusses the proposed mechanism of RNA interference mediated by short interfering RNA as is presently known, and is not meant to be limiting and is not an admission of prior art. Applicant demonstrates herein that chemically-modified short interfering nucleic acids possess similar or improved capacity to mediate RNAi as do siRNA molecules and are expected to possess improved stability and activity in vivo; therefore, this discussion is not meant to be limiting only to siRNA and can be applied to siNA as a whole. By "improved capacity to mediate RNAi" or "improved RNAi activity" is meant to include RNAi activity measured in vitro and/or in vivo where the RNAi activity is a reflection of both the ability of the siNA to mediate RNAi and the stability of the siNAs of the invention. In this invention, the product of these activities can be increased in vitro and/or in vivo compared to an all RNA siRNA or a siNA containing a plurality of ribonucleotides. In some cases, the activity or stability of the siNA molecule can be decreased (i.e., less than ten-fold), but the overall activity of the siNA molecule is enhanced in vitro and/or in vivo.

RNA interference refers to the process of sequence specific post-transcriptional gene silencing in animals mediated by short interfering RNAs (siRNAs) (Fire et al., 1998, Nature, 391, 806). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes which is commonly shared by diverse flora and phyla (Fire et al., 1999, Trends Genet., 15, 358). Such protection from foreign gene expression may have evolved in response to the production of double-stranded RNAs (dsRNAs) derived from viral infection or the random integration of transposon elements into a host genome via a cellular response that specifically destroys homologous single-stranded RNA or viral genomic RNA. The presence of dsRNA in cells triggers the RNAi response though a mechanism that has yet to be fully characterized. This mechanism appears to be different from the interferon response that results from dsRNA-mediated activation of protein kinase PKR and 2',5'-oligoadenylate synthetase resulting in non-specific cleavage of mRNA by ribonuclease L.

The presence of long dsRNAs in cells stimulates the activity of a ribonuclease III enzyme referred to as Dicer. Dicer is involved in the processing of the dsRNA into short pieces of dsRNA known as short interfering RNAs (siRNAs) (Berstein et al., 2001, Nature, 409, 363). Short interfering RNAs derived from Dicer activity are typically about 21 to about 23 nucleotides in length and comprise about 19 base pair duplexes. Dicer has also been implicated in the excision of 21- and 22-nucleotide small temporal RNAs (stRNAs) from precursor RNA of conserved structure that are implicated in translational control (Hutvagner et al., 2001, Science, 293, 834). The RNAi response also features an endonuclease complex containing a siRNA, commonly referred to as an RNA-induced silencing complex (RISC), which mediates cleavage of single-stranded RNA having sequence homologous to the siRNA. Cleavage of the target RNA takes place in the middle of the region complementary to the guide sequence of the siRNA duplex (Elbashir et al., 2001, Genes Dev., 15, 188). In addition, RNA interference can also involve small RNA (e.g., micro-RNA or miRNA) mediated gene silencing, presumably though cellular mechanisms that regulate chromatin structure and thereby prevent transcription of target gene sequences (see for example Allshire, 2002, Science, 297, 1818–1819; Volpe et al., 2002, Science, 297, 1833–1837; Jenuwein, 2002, Science, 297, 2215–2218; and Hall et al., 2002, Science, 297, 2232–2237). As such, siNA molecules of the invention can be used to mediate gene silencing via interaction with RNA transcripts or alternately by interaction with particular gene sequences, wherein such interaction results in gene silencing either at the transcriptional level or post-transcriptional level.

RNAi has been studied in a variety of systems. Fire et al., 1998, Nature, 391, 806, were the first to observe RNAi in C. elegans. Wianny and Goetz, 1999, Nature Cell Biol., 2, 70, describe RNAi mediated by dsRNA in mouse embryos. Hammond et al., 2000, Nature, 404, 293, describe RNAi in Drosophila cells transfected with dsRNA. Elbashir et al., 2001, Nature, 411, 494, describe RNAi induced by introduction of duplexes of synthetic 21-nucleotide RNAs in cultured mammalian cells including human embryonic kidney and HeLa cells. Recent work in Drosophila embryonic lysates has revealed certain requirements for siRNA length, structure, chemical composition, and sequence that are essential to mediate efficient RNAi activity. These studies have shown that 21 nucleotide siRNA duplexes are most active when containing two 2-nucleotide 3'-terminal nucleotide overhangs. Furthermore, substitution of one or both siRNA strands with 2'-deoxy or 2'-O-methyl nucleotides abolishes RNAi activity, whereas substitution of 3'-terminal siRNA nucleotides with deoxy nucleotides was shown to be tolerated. Mismatch sequences in the center of the siRNA duplex were also shown to abolish RNAi activity. In addition, these studies also indicate that the position of the cleavage site in the target RNA is defined by the 5'-end of the siRNA guide sequence rather than the 3'-end (Elbashir et al., 2001, EMBO J., 20, 6877). Other studies have indicated that a 5'-phosphate on the target-complementary strand of a siRNA duplex is required for siRNA activity and that ATP is utilized to maintain the 5'-phosphate moiety on the siRNA (Nykanen et al., 2001, Cell, 107, 309); however, siRNA molecules lacking a 5'-phosphate are active when introduced exogenously, suggesting that 5'-phosphorylation of siRNA constructs may occur in vivo.

Synthesis of Nucleic acid Molecules

Synthesis of nucleic acids greater than 100 nucleotides in length is difficult using automated methods, and the therapeutic cost of such molecules is prohibitive. In this invention, small nucleic acid motifs ("small" refers to nucleic acid motifs no more than 100 nucleotides in length, preferably no more than 80 nucleotides in length, and most preferably no more than 50 nucleotides in length; e.g., individual siNA oligonucleotide sequences or siNA sequences synthesized in tandem) are preferably used for exogenous delivery. The simple structure of these molecules increases the ability of the nucleic acid to invade targeted regions of protein and/or RNA structure. Exemplary molecules of the instant invention are chemically synthesized, and others can similarly be synthesized.

Oligonucleotides (e.g., certain modified oligonucleotides or portions of oligonucleotides lacking ribonucleotides) are synthesized using protocols known in the art, for example as described in Caruthers et al., 1992, Methods in Enzymology 211, 3–19, Thompson et al., International PCT Publication No. WO 99/54459, Wincott et al., 1995, *Nucleic Acids Res.* 23, 2677–2684, Wincott et al., 1997, *Methods Mol. Bio.*, 74, 59, Brennan et al., 1998, *Biotechnol Bioeng.*, 61, 33–45, and Brennan, U.S. Pat. No. 6,001,311. All of these references are incorporated herein by reference. The synthesis of oligonucleotides makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 μmol scale protocol with a 2.5 min coupling step for 2'-O-methylated nucleotides and a 45 second coupling step for 2'-deoxy nucleotides or 2'-deoxy-2'-fluoro nucleotides. Table V outlines the amounts and the contact times of the reagents used in the synthesis cycle. Alternatively, syntheses at the 0.2 μmol scale can be performed on a 96-well plate synthesizer, such as the instrument produced by Protogene (Palo Alto, Calif.) with minimal modification to the cycle. A 33-fold excess (60 μL of 0.11 M=6.6 μmol) of 2'-O-methyl phosphoramidite and a 105-fold excess of S-ethyl tetrazole (60 μL of 0.25 M=15 μmol) can be used in each coupling cycle of 2'-O-methyl residues relative to polymer-bound 5'-hydroxyl. A 22-fold excess (40 μL of 0.11 M=4.4 μmol) of deoxy phosphoramidite and a 70-fold excess of S-ethyl tetrazole (40 μL of 0.25 M=10 μmol) can be used in each coupling cycle of deoxy residues relative to polymer-bound 5'-hydroxyl. Average coupling yields on the 394 Applied Biosystems, Inc. synthesizer, determined by colorimetric quantitation of the trityl fractions, are typically 97.5–99%. Other oligonucleotide synthesis reagents for the 394 Applied Biosystems, Inc. synthesizer include the following: detritylation solution is 3% TCA in methylene chloride (ABI); capping is performed with 16% N-methyl imidazole in THF (ABI) and 10% acetic anhydride/10% 2,6-lutidine in THF (ABI); and oxidation solution is 16.9 mM 12, 49 mM pyridine, 9% water in THF (PerSeptive Biosystems, Inc.). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide, 0.05 M in acetonitrile) is used.

Deprotection of the DNA-based oligonucleotides is performed as follows: the polymer-bound trityl-on oligoribonucleotide is transferred to a 4 mL glass screw top vial and suspended in a solution of 40% aqueous methylamine (1 mL) at 65° C. for 10 minutes. After cooling to −20° C., the supernatant is removed from the polymer support. The support is washed three times with 1.0 mL of EtOH:MeCN:H2O/3:1:1, vortexed and the supernatant is then added to the first supernatant. The combined supernatants, containing the oligoribonucleotide, are dried to a white powder.

The method of synthesis used for RNA including certain siNA molecules of the invention follows the procedure as described in Usman et al., 1987, *J. Am. Chem. Soc.*, 109, 7845; Scaringe et al., 1990, *Nucleic Acids Res.*, 18, 5433; and Wincott et al., 1995, *Nucleic Acids Res.* 23, 2677–2684 Wincott et al., 1997, *Methods Mol. Bio.*, 74, 59, and makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 μmol scale protocol with a 7.5 min coupling step for alkylsilyl protected nucleotides and a 2.5 min coupling step for 2'-O-methylated nucleotides. Table V outlines the amounts and the contact times of the reagents used in the synthesis cycle. Alternatively, syntheses at the 0.2 μmol scale can be done on a 96-well plate synthesizer, such as the instrument produced by Protogene (Palo Alto, Calif.) with minimal modification to the cycle. A 33-fold excess (60 μL of 0.11 M=6.6 μmol) of 2'-O-methyl phosphoramidite and a 75-fold excess of S-ethyl tetrazole (60 μL of 0.25 M=15 μmol) can be used in each coupling cycle of 2'-O-methyl residues relative to polymer-bound 5'-hydroxyl. A 66-fold excess (120 μL of 0.11 M=13.2 μmol) of alkylsilyl (ribo) protected phosphoramidite and a 150-fold excess of S-ethyl tetrazole (120 μL of 0.25 M=30 μmol) can be used in each coupling cycle of ribo residues relative to polymer-bound 5'-hydroxyl. Average coupling yields on the 394 Applied Biosystems, Inc. synthesizer, determined by colorimetric quantitation of the trityl fractions, are typically 97.5–99%. Other oligonucleotide synthesis reagents for the 394 Applied Biosystems, Inc. synthesizer include the following: detritylation solution is 3% TCA in methylene chloride (ABI); capping is performed with 16% N-methyl imidazole in THF (ABI) and 10% acetic anhydride/10% 2,6-lutidine in THF (ABI); oxidation solution is 16.9 mM 12, 49 mM pyridine, 9% water in THF (PerSeptive Biosystems, Inc.). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide 0.05 M in acetonitrile) is used.

Deprotection of the RNA is performed using either a two-pot or one-pot protocol. For the two-pot protocol, the polymer-bound trityl-on oligoribonucleotide is transferred to a 4 mL glass screw top vial and suspended in a solution of 40% aq. methylamine (1 mL) at 65° C. for 10 min. After cooling to −20° C., the supernatant is removed from the polymer support. The support is washed three times with 1.0 mL of EtOH:MeCN:H2O/3:1:1, vortexed and the supernatant is then added to the first supernatant. The combined supernatants, containing the oligoribonucleotide, are dried to a white powder. The base deprotected oligoribonucleotide is resuspended in anhydrous TEA/HF/NMP solution (300 μL of a solution of 1.5 mL N-methylpyrrolidinone, 750 μL TEA and 1 mL TEA.3HF to provide a 1.4 M HF concentration) and heated to 65° C. After 1.5 h, the oligomer is quenched with 1.5 M NH4HCO3.

Alternatively, for the one-pot protocol, the polymer-bound trityl-on oligoribonucleotide is transferred to a 4 mL glass screw top vial and suspended in a solution of 33% ethanolic methylamine/DMSO: 1/1 (0.8 mL) at 65° C. for 15 minutes. The vial is brought to room temperature TEA.3HF (0.1 mL) is added and the vial is heated at 65° C. for 15 minutes. The sample is cooled at −20° C. and then quenched with 1.5 M NH4HCO3.

For purification of the trityl-on oligomers, the quenched NH4HCO3 solution is loaded onto a C-18 containing cartridge that had been prewashed with acetonitrile followed by 50 mM TEAA. After washing the loaded cartridge with water, the RNA is detritylated with 0.5% TFA for 13 minutes. The cartridge is then washed again with water, salt exchanged with 1 M NaCl and washed with water again. The oligonucleotide is then eluted with 30% acetonitrile.

The average stepwise coupling yields are typically >98% (Wincott et al., 1995 *Nucleic Acids Res.* 23, 2677–2684). Those of ordinary skill in the art will recognize that the scale of synthesis can be adapted to be larger or smaller than the example described above including but not limited to 96-well format.

Alternatively, the nucleic acid molecules of the present invention can be synthesized separately and joined together post-synthetically, for example, by ligation (Moore et al., 1992, *Science* 256, 9923; Draper et al., International PCT publication No. WO 93/23569; Shabarova et al., 1991, *Nucleic Acids Research* 19, 4247; Bellon et al., 1997, *Nucleosides & Nucleotides*, 16, 951; Bellon et al., 1997, *Bioconjugate Chem.* 8, 204), or by hybridization following synthesis and/or deprotection.

The siNA molecules of the invention can also be synthesized via a tandem synthesis methodology as described in Example 1 herein, wherein both siNA strands are synthesized as a single contiguous oligonucleotide fragment or strand separated by a cleavable linker which is subsequently cleaved to provide separate siNA fragments or strands that hybridize and permit purification of the siNA duplex. The linker can be a polynucleotide linker or a non-nucleotide linker. The tandem synthesis of siNA as described herein can be readily adapted to both multiwell/multiplate synthesis platforms such as 96 well or similarly larger multi-well platforms. The tandem synthesis of siNA as described herein can also be readily adapted to large scale synthesis platforms employing batch reactors, synthesis columns and the like.

A siNA molecule can also be assembled from two distinct nucleic acid strands or fragments wherein one fragment includes the sense region and the second fragment includes the antisense region of the RNA molecule.

The nucleic acid molecules of the present invention can be modified extensively to enhance stability by modification with nuclease resistant groups, for example, 2'-amino, 2'-C-allyl, 2'-fluoro, 2'-O-methyl, 2'-H (for a review see Usman and Cedergren, 1992, *TIBS* 17, 34; Usman et al., 1994, *Nucleic Acids Symp. Ser.* 31, 163). siNA constructs can be purified by gel electrophoresis using general methods or can be purified by high pressure liquid chromatography (HPLC; see Wincott et al., supra, the totality of which is hereby incorporated herein by reference) and re-suspended in water.

In another aspect of the invention, siNA molecules of the invention are expressed from transcription units inserted into DNA or RNA vectors. The recombinant vectors can be DNA plasmids or viral vectors. siNA expressing viral vectors can be constructed based on, but not limited to, adeno-associated virus, retrovirus, adenovirus, or alphavirus. The recombinant vectors capable of expressing the siNA molecules can be delivered as described herein, and persist in target cells. Alternatively, viral vectors can be used that provide for transient expression of siNA molecules.

Optimizing Activity of the Nucleic Acid Molecule of the Invention.

Chemically synthesizing nucleic acid molecules with modifications (base, sugar and/or phosphate) can prevent their degradation by serum ribonucleases, which can increase their potency (see e.g., Eckstein et al., International Publication No. WO 92/07065; Perrault et al., 1990 *Nature* 344, 565; Pieken et al., 1991, *Science* 253, 314; Usman and Cedergren, 1992, *Trends in Biochem. Sci.* 17, 334; Usman et al., International Publication No. WO 93/15187; and Rossi et al., International Publication No. WO 91/03162; Sproat, U.S. Pat. No. 5,334,711; Gold et al., U.S. Pat. No. 6,300,074; and Burgin et al., supra; all of which are incorporated by reference herein). All of the above references describe various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications (for a review see Usman and Cedergren, 1992, *TIBS*. 17, 34; Usman et al., 1994, *Nucleic Acids Symp. Ser.* 31, 163; Burgin et al., 1996, *Biochemistry*, 35, 14090). Sugar modification of nucleic acid molecules have been extensively described in the art (see Eckstein et al., International Publication PCT No. WO 92/07065; Perrault et al. *Nature*, 1990, 344, 565–568; Pieken et al. *Science*, 1991, 253, 314–317; Usman and Cedergren, *Trends in Biochem. Sci.*, 1992, 17, 334–339; Usman et al. International Publication PCT No. WO 93/15187; Sproat, U.S. Pat. No. 5,334,711 and Beigelman et al., 1995, *J. Biol. Chem.*, 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, *Tetrahedron Lett.*, 39, 1131; Earnshaw and Gait, 1998, *Biopolymers (Nucleic Acid Sciences)*, 48, 39–55; Verma and Eckstein, 1998, *Annu. Rev. Biochem.*, 67, 99–134; and Burlina et al., 1997, *Bioorg. Med. Chem.*, 5, 1999–2010; all of the references are hereby incorporated in their totality by reference herein). Such publications describe general methods and strategies to determine the location of incorporation of sugar, base and/or phosphate modifications and the like into nucleic acid molecules without modulating catalysis, and are incorporated by reference herein. In view of such teachings, similar modifications can be used as described herein to modify the siNA nucleic acid molecules of the instant invention so long as the ability of siNA to promote RNAi is cells is not significantly inhibited.

While chemical modification of oligonucleotide intemucleotide linkages with phosphorothioate, phosphorodithioate, and/or 5'-methylphosphonate linkages improves stability, excessive modifications can cause some toxicity or decreased activity. Therefore, when designing nucleic acid molecules, the amount of these intemucleotide linkages should be minimized. The reduction in the concentration of these linkages should lower toxicity, resulting in increased efficacy and higher specificity of these molecules.

Short interfering nucleic acid (siNA) molecules having chemical modifications that maintain or enhance activity are provided. Such a nucleic acid is also generally more resistant to nucleases than an unmodified nucleic acid. Accordingly, the in vitro and/or in vivo activity should not be significantly lowered. In cases in which modulation is the goal, therapeutic nucleic acid molecules delivered exogenously should optimally be stable within cells until translation of the target RNA has been modulated long enough to reduce the levels of the undesirable protein. This period of time varies between hours to days depending upon the disease state. Improvements in the chemical synthesis of RNA and DNA (Wincott et al., 1995, *Nucleic Acids Res.* 23, 2677; Caruthers et al., 1992, *Methods in Enzymology* 211, 3–19 (incorporated by reference herein)) have expanded the ability to modify nucleic acid molecules by introducing nucleotide modifications to enhance their nuclease stability, as described above.

In one embodiment, nucleic acid molecules of the invention include one or more (e.g., about 1, 2, 3, 4, 5, 6, 7, 8, 9, 10, or more) G-clamp nucleotides. A G-clamp nucleotide is a modified cytosine analog wherein the modifications confer the ability to hydrogen bond both Watson-Crick and Hoogsteen faces of a complementary guanine within a duplex, see for example Lin and Matteucci, 1998, *J. Am. Chem. Soc.*, 120, 8531–8532. A single G-clamp analog substitution within an oligonucleotide can result in substantially enhanced helical thermal stability and mismatch discrimination when hybridized to complementary oligonucleotides. The inclusion of such nucleotides in nucleic acid molecules of the invention results in both enhanced affinity and specificity to nucleic acid targets, complementary sequences, or template strands. In another embodiment, nucleic acid molecules of the invention include one or more (e.g., about 1, 2, 3, 4, 5, 6, 7, 8, 9, 10, or more) LNA "locked nucleic acid" nucleotides such as a 2',4'-C methylene bicyclo nucleotide (see for example Wengel et al., International PCT Publication No. WO 00/66604 and WO 99/14226).

In another embodiment, the invention features conjugates and/or complexes of siNA molecules of the invention. Such conjugates and/or complexes can be used to facilitate delivery of siNA molecules into a biological system, such as a cell. The conjugates and complexes provided by the instant invention can impart therapeutic activity by transferring therapeutic compounds across cellular membranes, altering the pharmacokinetics, and/or modulating the localization of nucleic acid molecules of the invention. The present invention encompasses the design and synthesis of novel conjugates and complexes for the delivery of molecules, including, but not limited to, small molecules, lipids, cholesterol, phospholipids, nucleosides, nucleotides, nucleic acids, antibodies, toxins, negatively charged polymers and other polymers, for example proteins, peptides, hormones, carbohydrates, polyethylene glycols, or polyamines, across cellular membranes. In general, the transporters described are designed to be used either individually or as part of a multi-component system, with or without degradable linkers. These compounds are expected to improve delivery and/or localization of nucleic acid molecules of the invention into a number of cell types originating from different tissues, in the presence or absence of serum (see Sullenger and Cech, U.S. Pat. No. 5,854,038). Conjugates of the molecules described herein can be attached to biologically active molecules via linkers that are biodegradable, such as biodegradable nucleic acid linker molecules.

The term "biodegradable linker" as used herein, refers to a nucleic acid or non-nucleic acid linker molecule that is designed as a biodegradable linker to connect one molecule to another molecule, for example, a biologically active molecule to a siNA molecule of the invention or the sense and antisense strands of a siNA molecule of the invention. The biodegradable linker is designed such that its stability can be modulated for a particular purpose, such as delivery to a particular tissue or cell type. The stability of a nucleic acid-based biodegradable linker molecule can be modulated by using various chemistries, for example combinations of ribonucleotides, deoxyribonucleotides, and chemically-modified nucleotides, such as 2'-O-methyl, 2'-fluoro, 2'-amino, 2'-O-amino, 2'-C-allyl, 2'-O-allyl, and other 2'-modified or base modified nucleotides. The biodegradable nucleic acid linker molecule can be a dimer, trimer, tetramer or longer nucleic acid molecule, for example, an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus-based linkage, for example, a phosphoramidate or phosphodiester linkage. The biodegradable nucleic acid linker molecule can also comprise nucleic acid backbone, nucleic acid sugar, or nucleic acid base modifications.

The term "biodegradable" as used herein, refers to degradation in a biological system, for example enzymatic degradation or chemical degradation.

The term "biologically active molecule" as used herein, refers to compounds or molecules that are capable of eliciting or modifying a biological response in a system. Non-limiting examples of biologically active siNA molecules either alone or in combination with other molecules contemplated by the instant invention include therapeutically active molecules such as antibodies, cholesterol, hormones, antivirals, peptides, proteins, chemotherapeutics, small molecules, vitamins, co-factors, nucleosides, nucleotides, oligonucleotides, enzymatic nucleic acids, antisense nucleic acids, triplex forming oligonucleotides, 2,5-A chimeras, siNA, dsRNA, allozymes, aptamers, decoys and analogs thereof. Biologically active molecules of the invention also include molecules capable of modulating the pharmacokinetics and/or pharmacodynamics of other biologically active molecules, for example, lipids and polymers such as polyamines, polyamides, polyethylene glycol and other polyethers.

The term "phospholipid" as used herein, refers to a hydrophobic molecule comprising at least one phosphorus group. For example, a phospholipid can comprise a phosphorus-containing group and saturated or unsaturated alkyl group, optionally substituted with OH, COOH, oxo, amine, or substituted or unsubstituted aryl groups.

Therapeutic nucleic acid molecules (e.g., siNA molecules) delivered exogenously optimally are stable within cells until reverse transcription of the RNA has been modulated long enough to reduce the levels of the RNA transcript. The nucleic acid molecules are resistant to nucleases in order to function as effective intracellular therapeutic agents. Improvements in the chemical synthesis of nucleic acid molecules described in the instant invention and in the art have expanded the ability to modify nucleic acid molecules by introducing nucleotide modifications to enhance their nuclease stability as described above.

In yet another embodiment, siNA molecules having chemical modifications that maintain or enhance enzymatic activity of proteins involved in RNAi are provided. Such nucleic acids are also generally more resistant to nucleases than unmodified nucleic acids. Thus, in vitro and/or in vivo the activity should not be significantly lowered.

Use of the nucleic acid-based molecules of the invention will lead to better treatment of the disease progression by affording the possibility of combination therapies (e.g., multiple siNA molecules targeted to different genes; nucleic acid molecules coupled with known small molecule modulators; or intermittent treatment with combinations of molecules, including different motifs and/or other chemical or biological molecules). The treatment of subjects with siNA molecules can also include combinations of different types of nucleic acid molecules, such as enzymatic nucleic acid molecules (ribozymes), allozymes, antisense, 2,5-A oligoadenylate, decoys, and aptamers.

In another aspect a siNA molecule of the invention comprises one or more 5' and/or a 3'-cap structure, for example on only the sense siNA strand, the antisense siNA strand, or both siNA strands.

By "cap structure" is meant chemical modifications, which have been incorporated at either terminus of the oligonucleotide (see, for example, Adamic et al., U.S. Pat.

No. 5,998,203, incorporated by reference herein). These terminal modifications protect the nucleic acid molecule from exonuclease degradation, and may help in delivery and/or localization within a cell. The cap may be present at the 5'-terminus (5'-cap) or at the 3'-terminal (3'-cap) or may be present on both termini. In non-limiting examples, the 5'-cap includes, but is not limited to, glyceryl, inverted deoxy abasic residue (moiety); 4',5'-methylene nucleotide; 1-(beta-D-erythrofuranosyl)nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

Non-limiting examples of the 3'-cap include, but are not limited to, glyceryl, inverted deoxy abasic residue (moiety), 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, 1993, *Tetrahedron* 49, 1925; incorporated by reference herein).

By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine and therefore lacks a base at the 1'-position.

An "alkyl" group refers to a saturated aliphatic hydrocarbon, including straight-chain, branched-chain, and cyclic alkyl groups. Preferably, the alkyl group has 1 to 12 carbons. More preferably, it is a lower alkyl of from 1 to 7 carbons, more preferably 1 to 4 carbons. The alkyl group can be substituted or unsubstituted. When substituted the substituted group(s) is preferably, hydroxyl, cyano, alkoxy, =O, =S, $NO_2$ or $N(CH_3)_2$, amino, or SH. The term also includes alkenyl groups that are unsaturated hydrocarbon groups containing at least one carbon-carbon double bond, including straight-chain, branched-chain, and cyclic groups. Preferably, the alkenyl group has 1 to 12 carbons. More preferably, it is a lower alkyl of from 1 to 7 carbons, more preferably 1 to 4 carbons. The alkenyl group may be substituted or unsubstituted. When substituted the substituted group(s) is preferably, hydroxyl, cyano, alkoxy, =O, =S, $NO_2$, halogen, $N(CH_3)_2$, amino, or SH. The term "alkyl" also includes alkynyl groups that have an unsaturated hydrocarbon group containing at least one carbon-carbon triple bond, including straight-chain, branched-chain, and cyclic groups. Preferably, the alkynyl group has 1 to 12 carbons. More preferably, it is a lower alkynyl of from 1 to 7 carbons, more preferably 1 to 4 carbons. The alkynyl group may be substituted or unsubstituted. When substituted the substituted group(s) is preferably, hydroxyl, cyano, alkoxy, =O, =S, $NO_2$ or $N(CH_3)_2$, amino or SH.

Such alkyl groups can also include aryl, alkylaryl, carbocyclic aryl, heterocyclic aryl, amide and ester groups. An "aryl" group refers to an aromatic group that has at least one ring having a conjugated pi electron system and includes carbocyclic aryl, heterocyclic aryl and biaryl groups, all of which may be optionally substituted. The preferred substituent(s) of aryl groups are halogen, trihalomethyl, hydroxyl, SH, OH, cyano, alkoxy, alkyl, alkenyl, alkynyl, and amino groups. An "alkylaryl" group refers to an alkyl group (as described above) covalently joined to an aryl group (as described above). Carbocyclic aryl groups are groups wherein the ring atoms on the aromatic ring are all carbon atoms. The carbon atoms are optionally substituted. Heterocyclic aryl groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted. An "amide" refers to an —C(O)—NH—R, where R is either alkyl, aryl, alkylaryl or hydrogen. An "ester" refers to an —C(O)—OR', where R is either alkyl, aryl, alkylaryl or hydrogen.

By "nucleotide" as used herein is as recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see, for example, Usman and McSwiggen, supra; Eckstein et al., International PCT Publication No. WO 92/07065; Usman et al., International PCT Publication No. WO 93/15187; Uhlman & Peyman, supra, all are hereby incorporated by reference herein). There are several examples of modified nucleic acid bases known in the art as summarized by Limbach et al., 1994, *Nucleic Acids Res.* 22, 2183. Some of the non-limiting examples of base modifications that can be introduced into nucleic acid molecules include, inosine, purine, pyridin4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others (Burgin et al., 1996, *Biochemistry*, 35, 14090; Uhlman & Peyman, supra). By "modified bases" in this aspect is meant nucleotide bases other than adenine, guanine, cytosine and uracil at 1' position or their equivalents.

In one embodiment, the invention features modified siNA molecules, with phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications, see Hunziker and Leumann, 1995, *Nucleic Acid Analogues. Synthesis and Properties*, in

*Modern Synthetic Methods*, VCH, 331–417, and Mesmaeker et al., 1994, *Novel Backbone Replacements for Oligonucleotides*, in *Carbohydrate Modifications in Antisense Research*, ACS, 24–39.

By "abasic" is meant sugar moieties lacking a base or having other chemical groups in place of a base at the 1' position, see for example Adamic et al., U.S. Pat. No. 5,998,203.

By "unmodified nucleoside" is meant one of the bases adenine, cytosine, guanine, thymine, or uracil joined to the 1' carbon of β-D-ribo-furanose.

By "modified nucleoside" is meant any nucleotide base which contains a modification in the chemical structure of an unmodified nucleotide base, sugar and/or phosphate. Non-limiting examples of modified nucleotides are shown by Formulae I–VII and/or other modifications described herein.

In connection with 2'-modified nucleotides as described for the present invention, by "amino" is meant 2'-$NH_2$ or 2'-O—$NH_2$, which can be modified or unmodified. Such modified groups are described, for example, in Eckstein et al., U.S. Pat. No. 5,672,695 and Matulic-Adamic et al., U.S. Pat. No. 6,248,878, which are both incorporated by reference in their entireties.

Various modifications to nucleic acid siNA structure can be made to enhance the utility of these molecules. Such modifications will enhance shelf-life, half-life in vitro, stability, and ease of introduction of such oligonucleotides to the target site, e.g., to enhance penetration of cellular membranes, and confer the ability to recognize and bind to targeted cells.

Administration of Nucleic Acid Molecules

A siNA molecule of the invention can be adapted for use to treat, for example, variety of disease and conditions described herein, such as proliferative diseases and conditions and/or cancer including breast cancer, cancers of the head and neck including various lymphomas such as mantle cell lymphoma, non-Hodgkins lymphoma, adenoma, squamous cell carcinoma, laryngeal carcinoma, cancers of the retina, cancers of the esophagus, multiple myeloma, ovarian cancer, uterine cancer, melanoma, colorectal cancer, lung cancer, bladder cancer, prostate cancer, glioblastoma, lung cancer (including non-small cell lung carcinoma), pancreatic cancer, cervical cancer, head and neck cancer, skin cancers, nasopharyngeal carcinoma, liposarcoma, epithelial carcinoma, renal cell carcinoma, gallbladder adeno carcinoma, parotid adenocarcinoma, endometrial sarcoma, multidrug resistant cancers; and proliferative diseases and conditions, such as neovascularization associated with tumor angiogenesis, ocular diseases such as macular degeneration (e.g., wet/dry AMD), corneal neovascularization, diabetic retinopathy, neovascular glaucoma, myopic degeneration and other proliferative diseases and conditions such as restenosis and polycystic kidney disease, and any other diseases or conditions that are related to or will respond to the levels of VEGF and/or VEGFr in a cell or tissue, alone or in combination with other therapies. For example, a siNA molecule can comprise a delivery vehicle, including liposomes, for administration to a subject, carriers and diluents and their salts, and/or can be present in pharmaceutically acceptable formulations. Methods for the delivery of nucleic acid molecules are described in Akhtar et al., 1992, *Trends Cell Bio.*, 2, 139; *Delivery Strategies for Antisense Oligonucleotide Therapeutics*, ed. Akhtar, 1995, Maurer et al., 1999, *Mol. Membr. Biol.*, 16, 129–140; Hofland and Huang, 1999, *Handb. Exp. Pharmacol.*, 137, 165–192; and Lee et al., 2000, *ACS Symp. Ser.*, 752, 184–192, all of which are incorporated herein by reference. Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule. Nucleic acid molecules can be administered to cells by a variety of methods known to those of skill in the art, including, but not restricted to, encapsulation in liposomes, by iontophoresis (see for example WO 03/043689 and WO 03/030989), or by incorporation into other vehicles, such as biodegradable polymers, hydrogels, cyclodextrins (see for example Gonzalez et al., 1999, *Bioconjugate Chem.*, 10, 1068–1074; Wang et al., International PCT publication Nos. WO 03/47518 and WO 03/46185), poly(lactic-co-glycolic)acid (PLGA) and PLCA microspheres (see for example U.S. Pat. No. 6,447,796 and U.S. Patent Application Publication No. U.S. 2002130430), biodegradable nanocapsules, and bioadhesive microspheres, or by proteinaceous vectors (O'Hare and Normand, International PCT Publication No. WO 00/53722). In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives. Alternatively, the nucleic acid/vehicle combination is locally delivered by direct injection or by use of an infusion pump.

In one embodiment, a siNA molecule of the invention is designed or formulated to specifically target endothelial cells or tumor cells. For example, various formulations and conjugates can be utilized to specifically target endothelial cells or tumor cells, including PEI-PEG-folate, PEI-PEG-RGD, PEI-PEG-biotin, PEI-PEG-cholesterol, and other conjugates known in the art that enable specific targeting to endothelial cells and/or tumor cells.

In one embodiment, a compound, molecule, or composition for the treatment of ocular conditions (e.g., macular degeneration, diabetic retinopathy etc.) is administered to a subject intraocularly or by intraocular means. In another embodiment, a compound, molecule, or composition for the treatment of ocular conditions (e.g., macular degeneration, diabetic retinopathy etc.) is administered to a subject periocularly or by periocular means (see for example Ahlheim et al., International PCT publication No. WO 03/24420). In one embodiment, a siNA molecule and/or formulation or composition thereof is administered to a subject intraocularly or by intraocular means. In another embodiment, a siNA molecule and/or formualtion or composition thereof is administered to a subject periocularly or by periocular means. Periocular administration generally provides a less invasive approach to administering siNA molecules and formualtion or composition thereof to a subject (see for example Ahlheim et al., International PCT publication No. WO 03/24420). The use of periocular administraction also minimizes the risk of retinal detachment, allows for more frequent dosing or administraction, provides a clinically relevant route of administraction for macular degeneration and other optic conditions, and also provides the possiblilty of using resevoirs (e.g., implants, pumps or other devices) for drug delivery. In one embodiment, siNA compounds and compositions of the invention are administered locally, e.g., via intraocular or periocular means, such as injection, iontophoresis (see, for example, WO 03/043689 and WO 03/030989), or implant, about every 1–50 weeks (e.g., about every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 weeks), alone or in combination with other compounds and/or therapy is herein. In one embodiment, siNA compounds and compositions of the invention are administered systemically (e.g., via intravenous, subcutaneous, intramuscular, infusion, pump, implant etc.) about every 1–50 weeks (e.g., about every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 weeks), alone or in combination with other compounds and/or therapies described herein and/or otherwise known in the art.

In one embodiment, the nucleic acid molecules or the invention are administered to the CNS. Experiments have demonstrated the efficient in vivo uptake of nucleic acids by neurons. As an example of local administration of nucleic acids to nerve cells, Sommer et al., 1998, *Antisense Nuc. Acid Drug Dev.*, 8, 75, describe a study in which a 15 mer phosphorothioate antisense nucleic acid molecule to c-fos is administered to rats via microinjection into the brain. Antisense molecules labeled with tetramethylrhodamine-isothiocyanate (TRITC) or fluorescein isothiocyanate (FITC) were taken up by exclusively by neurons thirty minutes post-injection. A diffuse cytoplasmic staining and nuclear staining was observed in these cells. As an example of systemic administration of nucleic acid to nerve cells, Epa et al., 2000, *Antisense Nuc. Acid Drug Dev.*, 10, 469, describe an in vivo mouse study in which beta-cyclodextrin-adamantane-oligonucleotide conjugates were used to target the p75 neurotrophin receptor in neuronally differentiated PC12 cells. Following a two week course of IP administration, pronounced uptake of p75 neurotrophin receptor antisense was observed in dorsal root ganglion (DRG) cells. In addition, a marked and consistent down-regulation of p75 was observed in DRG neurons. Additional approaches to the targeting of nucleic acid to neurons are described in Broaddus et al., 1998, *J. Neurosurg.*, 88(4), 734; Karle et al., 1997, *Eur. J. Pharmocol.*, 340(2/3), 153; Bannai et al., 1998, *Brain Research*, 784(1,2), 304; Rajakumar et al., 1997, *Synapse*, 26(3), 199; Wu-pong et al., 1999, *BioPharm*, 12(1), 32; Bannai et al., 1998, *Brain Res. Protoc.*, 3(1), 83; Simantov et al., 1996, *Neuroscience*, 74(1), 39. Nucleic acid molecules of the invention are therefore amenable to delivery to and uptake by cells that express VEGF and/or VEGFr for modulation of VEGF and/or VEGFr gene expression. The delivery of nucleic acid molecules of the invention, targeting VEGF and/or VEGFr is provided by a variety of different strategies. Traditional approaches to CNS delivery that can be used include, but are not limited to, intrathecal and intracerebroventricular administration, implantation of catheters and pumps, direct injection or perfusion at the site of injury or lesion, injection into the brain arterial system, or by chemical or osmotic opening of the blood-brain barrier. Other approaches can include the use of various transport and carrier systems, for example though the use of conjugates and biodegradable polymers. Furthermore, gene therapy approaches, for example as described in Kaplitt et al., U.S. Pat. No. 6,180,613 and Davidson, WO 04/013280, can be used to express nucleic acid molecules in the CNS.

In one embodiment, the nucleic acid molecules or the invention are administered via pulmonary delivery, such as by inhalation of an aerosol or spray dried formulation administered by an inhalation device or nebulizer, providing rapid local uptake of the nucleic acid molecules into relevant pulmonary tissues. Solid particulate compositions containing respirable dry particles of micronized nucleic acid compositions can be prepared by grinding dried or lyophilized nucleic acid compositions, and then passing the micronized composition through, for example, a 400 mesh screen to break up or separate out large agglomerates. A solid particulate composition comprising the nucleic acid compositions of the invention can optionally contain a dispersant which serves to facilitate the formation of an aerosol as well as other therapeutic compounds. A suitable dispersant is lactose, which can be blended with the nucleic acid compound in any suitable ratio, such as a 1 to 1 ratio by weight. Aerosols of liquid particles comprising a nucleic acid composition of the invention can be produced by any suitable means, such as with a nebulizer (see for example U.S. Pat. No. 4,501,729). Nebulizers are commercially available devices which transform solutions or suspensions of an active ingredient into a therapeutic aerosol mist either by means of acceleration of a compressed gas, typically air or oxygen, through a narrow venturi orifice or by means of ultrasonic agitation. Suitable formulations for use in nebulizers comprise the active ingredient in a liquid carrier in an amount of up to 40% w/w preferably less than 20% w/w of the formulation. The carrier is typically water or a dilute aqueous alcoholic solution, preferably made isotonic with body fluids by the addition of, for example, sodium chloride or other suitable salts. Optional additives include preservatives if the formulation is not prepared sterile, for example, methyl hydroxybenzoate, anti-oxidants, flavorings, volatile oils, buffering agents and emulsifiers and other formulation surfactants. The aerosols of solid particles comprising the active composition and surfactant can likewise be produced with any solid particulate aerosol generator. Aerosol generators for administering solid particulate therapeutics to a subject produce particles which are respirable, as explained above, and generate a volume of aerosol containing a predetermined metered dose of a therapeutic composition at a rate suitable for human administration. One illustrative type of solid particulate aerosol generator is an insufflator. Suitable formulations for administration by insufflation include finely comminuted powders which can be delivered by means of an insufflator. In the insufflator, the powder, e.g., a metered dose thereof effective to carry out the treatments described herein, is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation. A second type of illustrative aerosol generator comprises a metered dose inhaler. Metered dose inhalers are pressurized aerosol dispensers, typically containing a suspension or solution formulation of the active ingredient in a liquified propellant. During use these devices discharge the formulation through a valve adapted to deliver a metered volume to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation can additionally contain one or more co-solvents, for example, ethanol, emulsifiers and other formulation surfactants, such as oleic acid or sorbitan trioleate, anti-oxidants and suitable flavoring agents. Other methods for pulmonary delivery are described in, for example U.S. Patent Application No. 20040037780, and U.S. Pat. Nos. 6,592,904; 6,582,728; 6,565,885.

In one embodiment, a siNA molecule of the invention is administered iontophoretically, for example to a particular organ or compartment (e.g., the eye, back of the eye, heart, liver, kidney, bladder, prostate, tumor, CNS etc.). Non-limiting examples of iontophoretic delivery are described in, for example, WO 03/043689 and WO 03/030989, which are incorporated by reference in their entireties herein.

In one embodiment, a siNA molecule of the invention is complexed with membrane disruptive agents such as those described in U.S. patent appliaction Publication No. 20010007666, incorporated by reference herein in its entirety including the drawings. In another embodiment, the membrane disruptive agent or agents and the siNA molecule are also complexed with a cationic lipid or helper lipid molecule, such as those lipids described in U.S. Pat. No. 6,235,310, incorporated by reference herein in its entirety including the drawings.

Thus, the invention features a pharmaceutical composition comprising one or more nucleic acid(s) of the invention in an acceptable carrier, such as a stabilizer, buffer, and the like. The polynucleotides of the invention can be administered (e.g., RNA, DNA or protein) and introduced into a subject by any standard means, with or without stabilizers, buffers, and the like, to form a pharmaceutical composition. When it is desired to use a liposome delivery mechanism, standard protocols for formation of liposomes can be followed. The compositions of the present invention can also be formulated and used as tablets, capsules or elixirs for oral administration, suppositories for rectal administration, sterile solutions, suspensions for injectable administration, and the other compositions known in the art.

The present invention also includes pharmaceutically acceptable formulations of the compounds described. These formulations include salts of the above compounds, e.g., acid addition salts, for example, salts of hydrochloric, hydrobromic, acetic acid, and benzene sulfonic acid.

A pharmacological composition or formulation refers to a composition or formulation in a form suitable for administration, e.g., systemic administration, into a cell or subject, including for example a human. Suitable forms, in part, depend upon the use or the route of entry, for example oral, transdermal, or by injection. Such forms should not prevent the composition or formulation from reaching a target cell (i.e., a cell to which the negatively charged nucleic acid is desirable for delivery). For example, pharmacological compositions injected into the blood stream should be soluble. Other factors are known in the art, and include considerations such as toxicity and forms that prevent the composition or formulation from exerting its effect.

By "systemic administration" is meant in vivo systemic absorption or accumulation of drugs in the blood stream followed by distribution throughout the entire body. Administration routes that lead to systemic absorption include, without limitation: intravenous, subcutaneous, intraperitoneal, inhalation, oral, intrapulmonary and intramuscular. Each of these administration routes exposes the siNA molecules of the invention to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation that can facilitate the association of drug with the surface of cells, such as, lymphocytes and macrophages is also useful. This approach can provide enhanced delivery of the drug to target cells by taking advantage of the specificity of macrophage and lymphocyte immune recognition of abnormal cells, such as cells producing excess VEGF and/or VEGFr genes.

By "pharmaceutically acceptable formulation" is meant, a composition or formulation that allows for the effective distribution of the nucleic acid molecules of the instant invention in the physical location most suitable for their desired activity. Non-limiting examples of agents suitable for formulation with the nucleic acid molecules of the instant invention include: P-glycoprotein inhibitors (such as Pluronic P85),; biodegradable polymers, such as poly (DL-lactide-coglycolide) microspheres for sustained release delivery (Emerich, DF et al, 1999, *Cell Transplant*, 8, 47–58); and loaded nanoparticles, such as those made of polybutylcyanoacrylate. Other non-limiting examples of delivery strategies for the nucleic acid molecules of the instant invention include material described in Boado et al., 1998, *J. Pharm. Sci.*, 87, 1308–1315; Tyler et al., 1999, *FEBS Lett.*, 421, 280–284; Pardridge et al., 1995, *PNAS USA.*, 92, 5592–5596; Boado, 1995, *Adv. Drug Delivery Rev.*, 15, 73–107; Aldrian-Herrada et al., 1998, *Nucleic Acids Res.*, 26, 4910–4916; and Tyler et al., 1999, *PNAS USA.*, 96, 7053–7058.

The invention also features the use of the composition comprising surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev.* 1995, 95, 2601–2627; Ishiwata et al., *Chem. Pharm. Bull.* 1995, 43, 1005–1011). Such liposomes have been shown to accumulate selectively in tumors, presumably by extravasation and capture in the neovascularized target tissues (Lasic et al., *Science* 1995, 267, 1275–1276; Oku et al., 1995, *Biochim. Biophys. Acta*, 1238, 86–90). The long-circulating liposomes enhance the pharmacokinetics and pharmacodynamics of DNA and RNA, particularly compared to conventional cationic liposomes which are known to accumulate in tissues of the MPS (Liu et al., *J. Biol. Chem.* 1995, 42, 24864–24870; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

The present invention also includes compositions prepared for storage or administration that include a pharmaceutically effective amount of the desired compounds in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co. (A. R. Gennaro edit. 1985), hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered dependent upon potency of the negatively charged polymer.

The nucleic acid molecules of the invention and formulations thereof can be administered orally, topically, parenterally, by inhalation or spray, or rectally in dosage unit formulations containing conventional non-toxic pharmaceutically acceptable carriers, adjuvants and/or vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule of the invention and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions containing nucleic acid molecules of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono-or diglycerides. In addition, fatty acids such as oleic acid find use in the preparation of injectables.

The nucleic acid molecules of the invention can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per subject per day). The amount of active ingredient that can be combined with the carrier materials to produce a single dosage form varies depending upon the host treated and the particular mode of administration. Dosage unit forms generally contain between from about 1 mg to about 500 mg of an active ingredient.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

In one embodiment, the invention comprises compositions suitable for administering nucleic acid molecules of the invention to specific cell types. For example, the asialoglycoprotein receptor (ASGPr) (Wu and Wu, 1987, *J. Biol. Chem.* 262, 4429–4432) is unique to hepatocytes and binds branched galactose-terminal glycoproteins, such as asialoorosomucoid (ASOR). In another example, the folate receptor is overexpressed in many cancer cells. Binding of such glycoproteins, synthetic glycoconjugates, or folates to the receptor takes place with an affinity that strongly depends on the degree of branching of the oligosaccharide chain, for example, triatennary structures are bound with greater affinity than biatenarry or monoatennary chains (Baenziger and Fiete, 1980, *Cell*, 22, 611–620; Connolly et al., 1982, *J. Biol. Chem.*, 257, 939–945). Lee and Lee, 1987, *Glycoconjugate J.*, 4, 317–328, obtained this high specificity through the use of N-acetyl-D-galactosamine as the carbohydrate moiety, which has higher affinity for the receptor, compared to galactose. This "clustering effect" has also been described for the binding and uptake of mannosyl-terminating glycoproteins or glycoconjugates (Ponpipom et al., 1981, *J. Med. Chem.*, 24, 1388–1395). The use of galactose, galactosamine, or folate based conjugates to transport exogenous compounds across cell membranes can provide a targeted delivery approach to, for example, the treatment of liver disease, cancers of the liver, or other cancers. The use of bioconjugates can also provide a reduction in the required dose of therapeutic compounds required for treatment. Furthermore, therapeutic bioavialability, pharmacodynamics, and pharmacokinetic parameters can be modulated through the use of nucleic acid bioconjugates of the invention. Non-limiting examples of such bioconjugates are described in Vargeese et al., U.S. Ser. No. 10/201,394, filed Aug. 13, 2001; and Matulic-Adamic et al., U.S. Ser. No. 10/151,116, filed May 17, 2002. In one embodiment, nucleic acid molecules of the invention are complexed with or covalently attached to nanoparticles, such as Hepatitis B virus S, M, or L evelope proteins (see for example Yamado et al., 2003, *Nature Biotechnology*, 21, 885). In one embodiment, nucleic acid molecules of the invention are delivered with specificity for human tumor cells, specifically non-apoptotic human tumor cells including for example T-cells, hepatocytes, breast carcinoma cells, ovarian carcinoma cells, melanoma cells, intestinal epithelial cells, prostate cells, testicular cells, non-small cell lung cancers, small cell lung cancers, etc.

Alternatively, certain siNA molecules of the instant invention can be expressed within cells from eukaryotic promoters (e.g., Izant and Weintraub, 1985, *Science*, 229, 345; McGarry and Lindquist, 1986, *Proc. Natl. Acad. Sci., USA* 83, 399; Scanlon et al., 1991, *Proc. Natl. Acad. Sci. USA*, 88, 10591–5; Kashani-Sabet et al., 1992, *Antisense Res. Dev.*, 2, 3–15; Dropulic et al., 1992, *J. Virol.*, 66, 143241; Weerasinghe et al., 1991, *J. Virol.*, 65, 55314; Ojwang et al., 1992, *Proc. Natl. Acad. Sci. USA*, 89, 10802–6; Chen et al., 1992, *Nucleic Acids Res.*, 20, 4581–9; Sarver et al., 1990 *Science*, 247, 1222–1225; Thompson et al., 1995, *Nucleic Acids Res.*, 23, 2259; Good et al., 1997, *Gene Therapy*, 4, 45. Those skilled in the art realize that any nucleic acid can be expressed in eukaryotic cells from the appropriate DNA/RNA vector. The activity of such nucleic acids can be augmented by their release from the primary transcript by a enzymatic nucleic acid (Draper et al., PCT WO 93/23569, and Sullivan et al., PCT WO 94/02595; Ohkawa et al., 1992, *Nucleic Acids Symp. Ser.*, 27, 15–6; Taira et al., 1991, *Nucleic Acids Res.*, 19, 5125–30; Ventura et al., 1993, *Nucleic Acids Res.*, 21, 3249–55; Chowrira et al., 1994, *J. Biol. Chem*, 269, 25856.

In another aspect of the invention, RNA molecules of the present invention can be expressed from transcription units (see for example Couture et al., 1996, *TIG.*, 12, 510) inserted into DNA or RNA vectors. The recombinant vectors can be DNA plasmids or viral vectors. siNA expressing viral vectors can be constructed based on, but not limited to, adeno-associated virus, retrovirus, adenovirus, or alphavirus. In another embodiment, pol III based constructs are used to express nucleic acid molecules of the invention (see for example Thompson, U.S. Pas. Nos. 5,902,880 and 6,146, 886). The recombinant vectors capable of expressing the siNA molecules can be delivered as described above, and persist in target cells. Alternatively, viral vectors can be used that provide for transient expression of nucleic acid molecules. Such vectors can be repeatedly administered as necessary. Once expressed, the siNA molecule interacts with the target mRNA and generates an RNAi response. Delivery of siNA molecule expressing vectors can be systemic, such as by intravenous or intramuscular administration, by administration to target cells ex-planted from a subject followed by reintroduction into the subject, or by any other means that would allow for introduction into the desired target cell (for a review see Couture et al., 1996, *TIG.*, 12, 510).

In one aspect the invention features an expression vector comprising a nucleic acid sequence encoding at least one siNA molecule of the instant invention. The expression vector can encode one or both strands of a siNA duplex, or a single self-complementary strand that self hybridizes into a siNA duplex. The nucleic acid sequences encoding the siNA molecules of the instant invention can be operably linked in a manner that allows expression of the siNA molecule (see for example Paul et al., 2002, *Nature Bio-* technology, 19, 505; Miyagishi and Taira, 2002, *Nature Biotechnology*, 19, 497; Lee et al., 2002, *Nature Biotechnology*, 19, 500; and Novina et al, 2002, *Nature Medicine*, advance online publication doi: 10.103 8/nm725).

In another aspect, the invention features an expression vector comprising: a) a transcription initiation region (e.g., eukaryotic pol I, II or III initiation region); b) a transcription termination region (e.g., eukaryotic pol I, II or III termination region); and c) a nucleic acid sequence encoding at least one of the siNA molecules of the instant invention,wherein said sequence is operably linked to said initiation region and said termination region in a manner that allows expression and/or delivery of the siNA molecule. The vector can optionally include an open reading frame (ORF) for a protein operably linked on the 5' side or the 3'-side of the sequence encoding the siNA of the invention; and/or an intron (intervening sequences).

Transcription of the siNA molecule sequences can be driven from a promoter for eukaryotic RNA polymerase I (pol I), RNA polymerase II (pol II), or RNA polymerase III (pol III). Transcripts from pol II or pol III promoters are expressed at high levels in all cells; the levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990, *Proc. Natl. Acad. Sci. USA*, 87, 6743–7; Gao and Huang 1993, *Nucleic Acids Res.*, 21, 2867–72; Lieber et al, 1993, *Methods Enzymol.*, 217, 47–66; Zhou et al., 1990, *Mol. Cell. Biol.*, 10, 4529–37). Several investigators have demonstrated that nucleic acid molecules expressed from such promoters can function in mammalian cells (e.g. Kashani-Sabet et al., 1992, *Antisense Res. Dev.*, 2, 3–15; Ojwang et al., 1992, *Proc. Natl. Acad. Sci. USA*, 89, 10802–6; Chen et al., 1992, *Nucleic Acids Res.*, 20, 4581–9; Yu et al., 1993, *Proc. Natl. Acad. Sci. USA*, 90, 6340–4; L'Huillier et al., 1992, *EMBO J*, 11, 4411–8; Lisziewicz et al., 1993, *Proc. Natl. Acad. Sci. U.S.A.*, 90, 8000–4; Thompson et al., 1995, *Nucleic Acids Res.*, 23, 2259; Sullenger & Cech, 1993, *Science*, 262, 1566). More specifically, transcription units such as the ones derived from genes encoding U6 small nuclear (snRNA), transfer RNA (tRNA) and adenovirus VA RNA are useful in generating high concentrations of desired RNA molecules such as siNA in cells (Thompson et al., supra; Couture and Stinchcomb, 1996, supra; Noonberg et al, 1994, *Nucleic Acid Res.*, 22, 2830; Noonberg et al., U.S. Pat. No. 5,624,803; Good et al., 1997, *Gene Ther.*, 4, 45; Beigelman et al., International PCT Publication No. WO 96/18736. The above siNA transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (for a review see Couture and Stinchcomb, 1996, supra).

In another aspect the invention features an expression vector comprising a nucleic acid sequence encoding at least one of the siNA molecules of the invention in a manner that allows expression of that siNA molecule. The expression vector comprises in one embodiment; a) a transcription initiation region; b) a transcription termination region; and c) a nucleic acid sequence encoding at least one strand of the siNA molecule, wherein the sequence is operably linked to the initiation region and the termination region in a manner that allows expression and/or delivery of the siNA molecule.

In another embodiment the expression vector comprises: a) a transcription initiation region; b) a transcription termination region; c) an open reading frame; and d) a nucleic acid sequence encoding at least one strand of a siNA molecule, wherein the sequence is operably linked to the 3'-end of the open reading frame and wherein the sequence is operably linked to the initiation region, the open reading frame and the termination region in a manner that allows expression and/or delivery of the siNA molecule. In yet another embodiment, the expression vector comprises: a) a transcription initiation region; b) a transcription termination region; c) an intron; and d) a nucleic acid sequence encoding at least one siNA molecule, wherein the sequence is operably linked to the initiation region, the intron and the termination region in a manner which allows expression and/or delivery of the nucleic acid molecule.

In another embodiment, the expression vector comprises: a) a transcription initiation region; b) a transcription termination region; c) an intron; d) an open reading frame; and e) a nucleic acid sequence encoding at least one strand of a siNA molecule, wherein the sequence is operably linked to the 3'-end of the open reading frame and wherein the sequence is operably linked to the initiation region, the intron, the open reading frame and the termination region in a manner which allows expression and/or delivery of the siNA molecule.

VEGF/VEGFr Biology and Biochemistry

The following discussion is adapted from R&D Systems, Cytokine Mini Reviews, Vascular Endothelial Growth Factor (VEGF), Copyright ©2002 R&D Systems. Angiogenesis is a process of new blood vessel development from preexisting vasculature. It plays an essential role in embryonic development, normal growth of tissues, wound healing, the female reproductive cycle (i.e., ovulation, menstruation and placental development), as well as a major role in many diseases. Particular interest has focused on cancer, since tumors cannot grow beyond a few millimeters in size without developing a new blood supply. Angiogenesis is also necessary for the spread and growth of tumor cell metastases.

One of the most important growth and survival factors for endothelium is vascular endothelial growth factor (VEGF). VEGF induces angiogenesis and endothelial cell proliferation and plays an important role in regulating vasculogenesis. VEGF is a heparin-binding glycoprotein that is secreted as a homodimer of 45 kDa. Most types of cells, but usually not endothelial cells themselves, secrete VEGF. Since the initially discovered VEGF, VEGF-A, increases vascular permeability, it was known as vascular permeability factor. In addition, VEGF causes vasodilatation, partly through stimulation of nitric oxide synthase in endothelial cells. VEGF can also stimulate cell migration and inhibit apoptosis.

There are several splice variants of VEGF-A. The major ones include: 121, 165, 189 and 206 amino acids (aa), each one comprising a specific exon addition. VEGF165 is the most predominant protein, but transcripts of VEGF 121 may be more abundant. VEGF206 is rarely expressed and has been detected only in fetal liver. Recently, other splice variants of 145 and 183 aa have also been described. The 165, 189 and 206 aa splice variants have heparin-binding domains, which help anchor them in extracellular matrix and are involved in binding to heparin sulfate and presentation to VEGF receptors. Such presentation is a key factor for VEGF potency (i.e., the heparin-binding forms are more active).

Several other members of the VEGF family have been cloned including VEGF-B, -C, and -D. Placenta growth factor (PlGF) is also closely related to VEGF-A. VEGF-A, -B, -C, -D, and PlGF are all distantly related to platelet-derived growth factors-A and -B. Less is known about the function and regulation of VEGF-B, -C, and -D, but they do not seem to be regulated by the major pathways that regulate VEGF-A.

VEGF-A transcription is potentiated in response to hypoxia and by activated oncogenes. The transcription factors, hypoxia inducible factor-1a (hif-1a) and -2a, are degraded by proteosomes in normoxia and stabilized in hypoxia. This pathway is dependent on the Von Hippel-Lindau gene product. Hif-1a and hif-2 a heterodimerize with the aryl hydrocarbon nuclear translocator in the nucleus and bind the VEGF promoter/enhancer. This is a key pathway expressed in most types of cells. Hypoxia inducibility, in particular, characterizes VEGF-A versus other members of the VEGF family and other angiogenic factors. VEGF transcription in normoxia is activated by many oncogenes, including H-ras and several transmembrane tyrosine kinases, such as the epidermal growth factor receptor and erbB2. These pathways together account for a marked upregulation of VEGF-A in tumors compared to normal tissues and are often of prognostic importance.

There are three receptors in the VEGF receptor family. They have the common properties of multiple IgG-like extracellular domains and tyrosine kinase activity. The enzyme domains of VEGF receptor 1 (VEGFR1, also known as Flt-1), VEGFR2 (also known as KDR or Flk-1), and VEGFr3 (also known as Flt-4) are divided by an inserted sequence. Endothelial cells also express additional VEGF receptors, Neuropilin-1 and Neuropilin-2. VEGF-A binds to VEGFR1 and VEGFR2 and to Neuropilin-1 and Neuropilin-2. PlGF and VEGF-B bind VEGFR1 and Neuropilin-1. VEGF-C and -D bind VEGFr3 and VEGFR2.

The VEGF-C/VEGFr3 pathway is important for lymphatic proliferation. VEGFr3 is specifically expressed on lymphatic endothelium. A soluble form of Flt-1 can be detected in peripheral blood and is a high affinity ligand for VEGF. Soluble Flt-1 can be used to antagonize VEGF function. VEGFR1 and VEGFR2 are upregulated in tumor and proliferating endothelium, partly by hypoxia and also in response to VEGF-A itself. VEGFR1 and VEGFR2 can interact with multiple downstream signaling pathways via proteins such as PLC-g, Ras, Shc, Nck, PKC and P13-kinase. VEGFR1 is of higher affinity than VEGFR2 and mediates motility and vascular permeability. VEGFR2 is necessary for proliferation.

VEGF can be detected in both plasma and serum samples of patients, with much higher levels in serum. Platelets release VEGF upon aggregation and may be a major source of VEGF delivery to tumors. Several studies have shown that association of high serum levels of VEGF with poor prognosis in cancer patients may be correlated with an elevated platelet count. Many tumors release cytokines that can stimulate the production of megakaryocytes in the marrow and elevate the platelet count. This can result in an indirect increase of VEGF delivery to tumors.

VEGF is implicated in several other pathological conditions associated with enhanced angiogenesis. For example, VEGF plays a role in both psoriasis and rheumatoid arthritis. Diabetic retinopathy is associated with high intraocular levels of VEGF. Inhibition of VEGF function may result in infertility by blockade of corpus luteum function. Direct demonstration of the importance of VEGF in tumor growth has been achieved using dominant negative VEGF receptors to block in vivo proliferation, as well as blocking antibodies to VEGF39 or to VEGFR2.

The use of small interfering nucleic acid molecules targeting VEGF and corresponding receptors and ligands therefore provides a class of novel therapeutic agents that can be used in the diagnosis of and the treatment of cancer, proliferative diseases, or any other disease or condition that responds to modulation of VEGF and/or VEGFr genes.

EXAMPLES

The following are non-limiting examples showing the selection, isolation, synthesis and activity of nucleic acids of the instant invention.

Example 1

Tandem Synthesis of siNA Constructs

Exemplary siNA molecules of the invention are synthesized in tandem using a cleavable linker, for example, a succinyl-based linker. Tandem synthesis as described herein is followed by a one-step purification process that provides RNAi molecules in high yield. This approach is highly amenable to siNA synthesis in support of high throughput RNAi screening, and can be readily adapted to multi-column or multi-well synthesis platforms.

After completing a tandem synthesis of a siNA oligo and its complement in which the 5'-terminal dimethoxytrityl (5'-O-DMT) group remains intact (trityl on synthesis), the oligonucleotides are deprotected as described above. Following deprotection, the siNA sequence strands are allowed to spontaneously hybridize. This hybridization yields a duplex in which one strand has retained the 5'-O-DMT group while the complementary strand comprises a terminal 5'-hydroxyl. The newly formed duplex behaves as a single molecule during routine solid-phase extraction purification (Trityl-On purification) even though only one molecule has a dimethoxytrityl group. Because the strands form a stable duplex, this dimethoxytrityl group (or an equivalent group, such as other trityl groups or other hydrophobic moieties) is all that is required to purify the pair of oligos, for example, by using a C18 cartridge.

Standard phosphoramidite synthesis chemistry is used up to the point of introducing a tandem linker, such as an inverted deoxy abasic succinate or glyceryl succinate linker (see FIG. 1) or an equivalent cleavable linker. A non-limiting example of linker coupling conditions that can be used includes a hindered base such as diisopropylethylamine (DIPA) and/or DMAP in the presence of an activator reagent such as Bromotripyrrolidinophosphoniumhexaflurorophosphate (PyBrOP). After the linker is coupled, standard synthesis chemistry is utilized to complete synthesis of the second sequence leaving the terminal the 5'-O-DMT intact. Following synthesis, the resulting oligonucleotide is deprotected according to the procedures described herein and quenched with a suitable buffer, for example with 50 mM NaOAc or 1.5M $NH_4H_2CO_3$.

Purification of the siNA duplex can be readily accomplished using solid phase extraction, for example using a Waters C18 SepPak 1 g cartridge conditioned with 1 column volume (CV) of acetonitrile, 2 CV $H_2O$, and 2 CV 50 mM NaOAc. The sample is loaded and then washed with 1 CV $H_2O$ or 50 mM NaOAc. Failure sequences are eluted with 1 CV 14% ACN (Aqueous with 50 mM NaOAc and 50 mM NaCl). The column is then washed, for example with 1 CV H2O followed by on-column detritylation, for example by passing 1 CV of 1% aqueous trifluoroacetic acid (TFA) over the column, then adding a second CV of 1% aqueous TFA to the column and allowing to stand for approximately 10 minutes. The remaining TFA solution is removed and the column washed with H2O followed by 1 CV 1M NaCl and additional H2O. The siNA duplex product is then eluted, for example, using 1 CV 20% aqueous CAN.

FIG. 2 provides an example of MALDI-TOF mass spectrometry analysis of a purified siNA construct in which each peak corresponds to the calculated mass of an individual siNA strand of the siNA duplex. The same purified siNA provides three peaks when analyzed by capillary gel electrophoresis (CGE), one peak presumably corresponding to the duplex siNA, and two peaks presumably corresponding to the separate siNA sequence strands. Ion exchange HPLC analysis of the same siNA contract only shows a single peak. Testing of the purified siNA construct using a luciferase reporter assay described below demonstrated the same RNAi activity compared to siNA constructs generated from separately synthesized oligonucleotide sequence strands.

Example 2

Identification of Potential siNA Target Sites in any RNA Sequence

The sequence of an RNA target of interest, such as a viral or human mRNA transcript, is screened for target sites, for example by using a computer folding algorithm. In a non-limiting example, the sequence of a gene or RNA gene transcript derived from a database, such as Genbank, is used to generate siNA targets having complementarity to the target. Such sequences can be obtained from a database, or can be determined experimentally as known in the art. Target sites that are known, for example, those target sites determined to be effective target sites based on studies with other nucleic acid molecules, for example ribozymes or antisense, or those targets known to be associated with a disease or condition such as those sites containing mutations or deletions, can be used to design siNA molecules targeting those sites. Various parameters can be used to determine which sites are the most suitable target sites within the target RNA sequence. These parameters include but are not limited to secondary or tertiary RNA structure, the nucleotide base composition of the target sequence, the degree of homology between various regions of the target sequence, or the relative position of the target sequence within the RNA transcript. Based on these determinations, any number of target sites within the RNA transcript can be chosen to screen siNA molecules for efficacy, for example by using in vitro RNA cleavage assays, cell culture, or animal models. In a non-limiting example, anywhere from 1 to 1000 target sites are chosen within the transcript based on the size of the siNA construct to be used. High throughput screening assays can be developed for screening siNA molecules using methods known in the art, such as with multi-well or multi-plate assays to determine efficient reduction in target gene expression.

Example 3

Selection of siNA Molecule Target Sites in a RNA

The following non-limiting steps can be used to carry out the selection of siNAs targeting a given gene sequence or transcript.

1. The target sequence is parsed in silico into a list of all fragments or subsequences of a particular length, for example 23 nucleotide fragments, contained within the target sequence. This step is typically carried out using a custom Perl script, but commercial sequence analysis programs such as Oligo, MacVector, or the GCG Wisconsin Package can be employed as well.

2. In some instances the siNAs correspond to more than one target sequence; such would be the case for example in targeting different transcripts of the same gene, targeting different transcripts of more than one gene, or for targeting both the human gene and an animal homolog. In this case, a subsequence list of a particular length is generated for each of the targets, and then the lists are compared to find matching sequences in each list. The subsequences are then ranked according to the number of target sequences that contain the given subsequence; the goal is to find subsequences that are present in most or all of the target sequences. Alternately, the ranking can identify subsequences that are unique to a target sequence, such as a mutant target sequence. Such an approach would enable the use of siNA to target specifically the mutant sequence and not effect the expression of the normal sequence.

3. In some instances the siNA subsequences are absent in one or more sequences while present in the desired target sequence; such would be the case if the siNA targets a gene with a paralogous family member that is to remain untargeted. As in case 2 above, a subsequence list of a particular length is generated for each of the targets, and then the lists are compared to find sequences that are present in the target gene but are absent in the untargeted paralog.

4. The ranked siNA subsequences can be further analyzed and ranked according to GC content. A preference can be given to sites containing 30–70% GC, with a further preference to sites containing 40–60% GC.

5. The ranked siNA subsequences can be further analyzed and ranked according to self-folding and internal hairpins. Weaker internal folds are preferred; strong hairpin structures are to be avoided.

6. The ranked siNA subsequences can be further analyzed and ranked according to whether they have runs of GGG or CCC in the sequence. GGG (or even more Gs) in either strand can make oligonucleotide synthesis problematic and can potentially interfere with RNAi activity, so it is avoided whenever better sequences are available. CCC is searched in the target strand because that will place GGG in the antisense strand.

7. The ranked siNA subsequences can be further analyzed and ranked according to whether they have the dinucleotide UU (uridine dinucleotide) on the 3'-end of the sequence, and/or AA on the 5'-end of the sequence (to yield 3' UU on the antisense sequence). These sequences allow one to design siNA molecules with terminal TT thymidine dinucleotides.

8. Four or five target sites are chosen from the ranked list of subsequences as described above. For example, in subsequences having 23 nucleotides, the right 21 nucleotides of each chosen 23-mer subsequence are then designed and synthesized for the upper (sense) strand of the siNA duplex, while the reverse complement of the left 21 nucleotides of each chosen 23-mer subsequence are then designed and synthesized for the lower (antisense) strand of the siNA duplex (see Tables II and III). If terminal TT residues are desired for the sequence (as described in paragraph 7), then the two 3' terminal nucleotides of both the sense and antisense strands are replaced by TT prior to synthesizing the oligos.

9. The siNA molecules are screened in an in vitro, cell culture or animal model system to identify the most active siNA molecule or the most preferred target site within the target RNA sequence.

10. Other design considerations can be used when selecting target nucleic acid sequences, see for example Reynolds et al., 2004, *Nature Biotechnology Advanced Online Publication*, 1 Feb. 2004, doi:10.1038/nbt936 and Ui-Tei et al., 2004, Nucleic Acids Research, 32, doi:10.1093/nar/gkh247.

Figure 7:
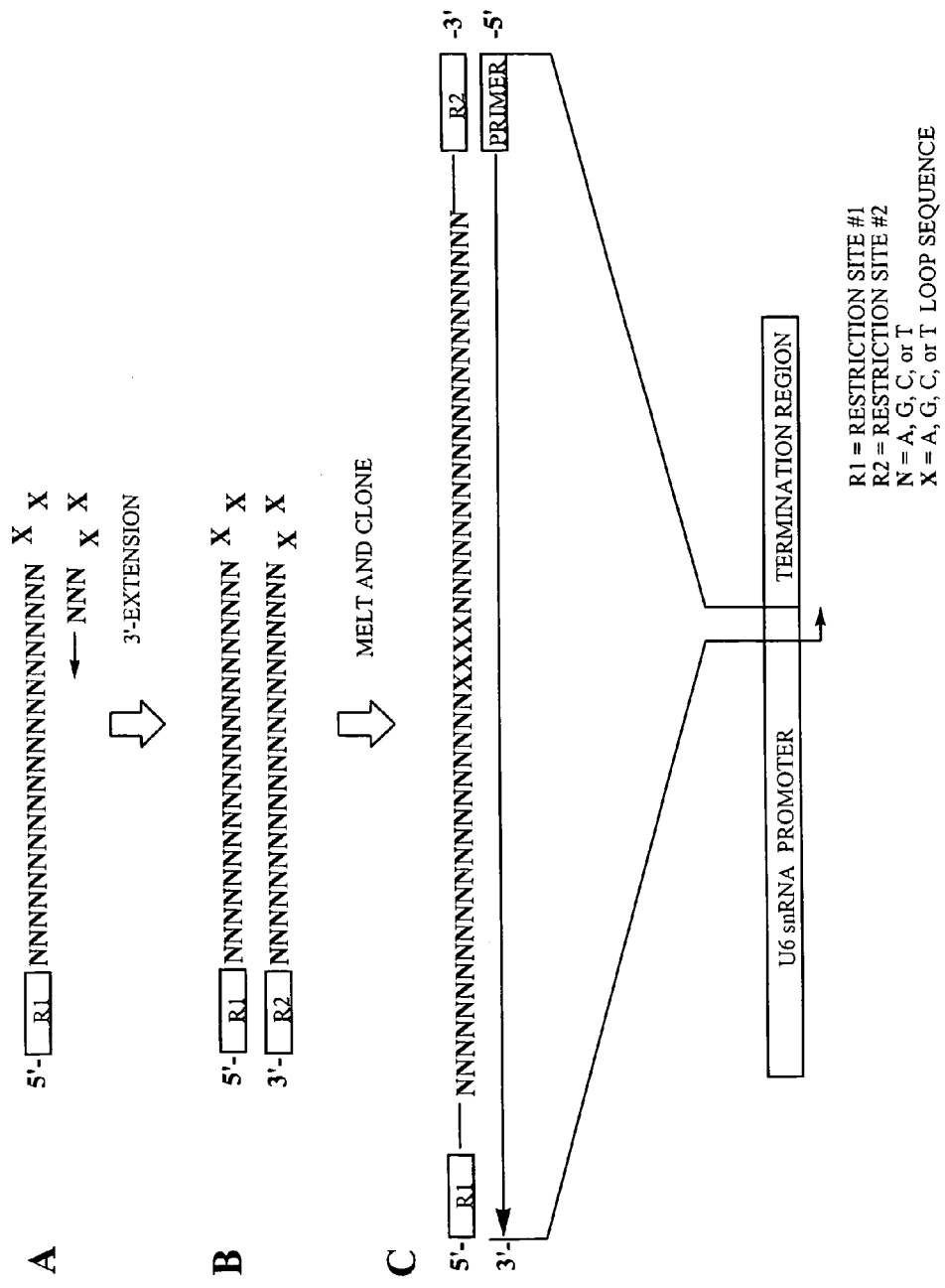
FIG. 7A–C is a diagrammatic representation of a scheme utilized in generating an expression cassette to generate siNA hairpin constructs.
Figure 8:
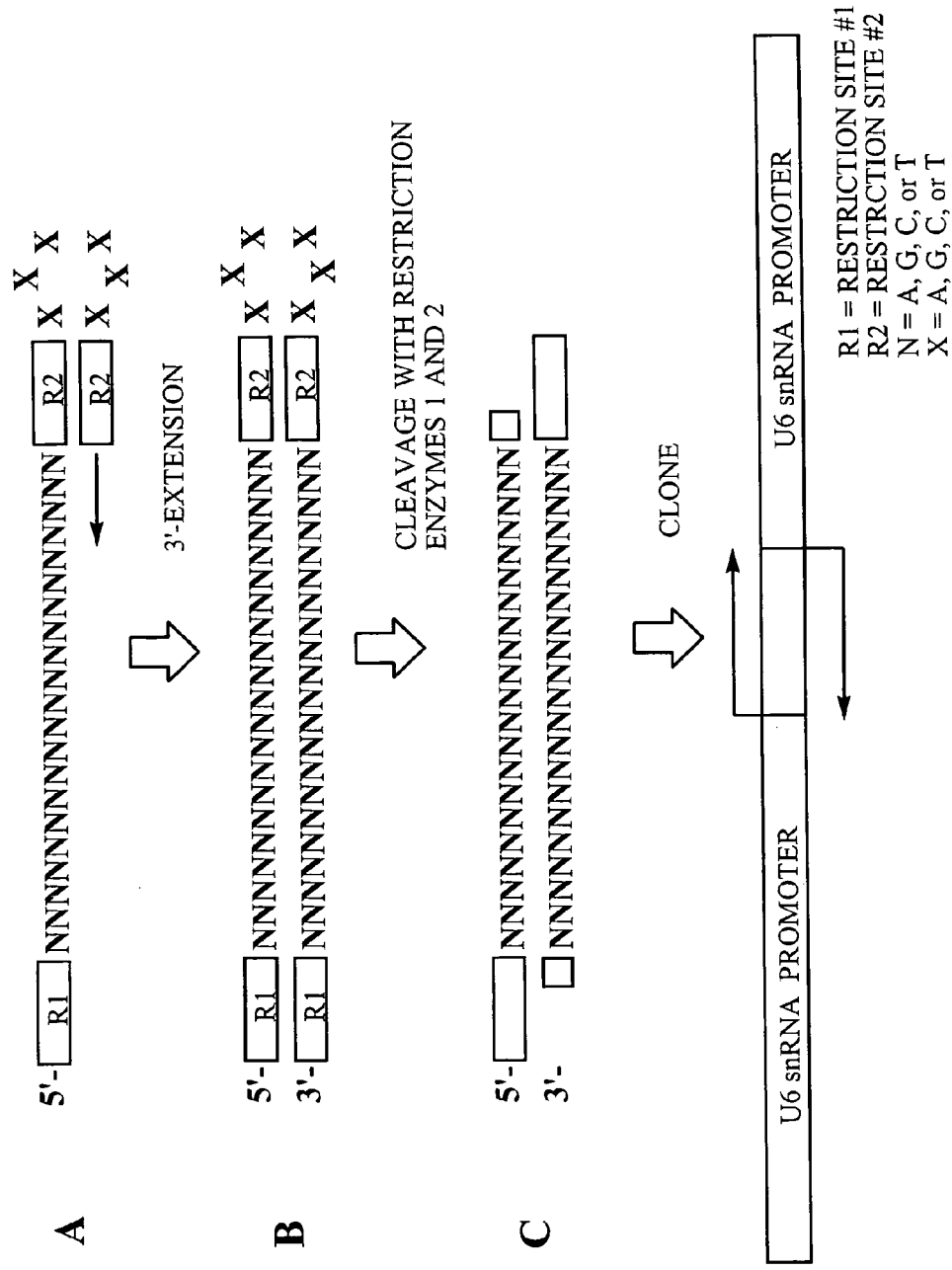
FIG. 8A–C is a diagrammatic representation of a scheme utilized in generating an expression cassette to generate double-stranded siNA constructs.
Figure 9:
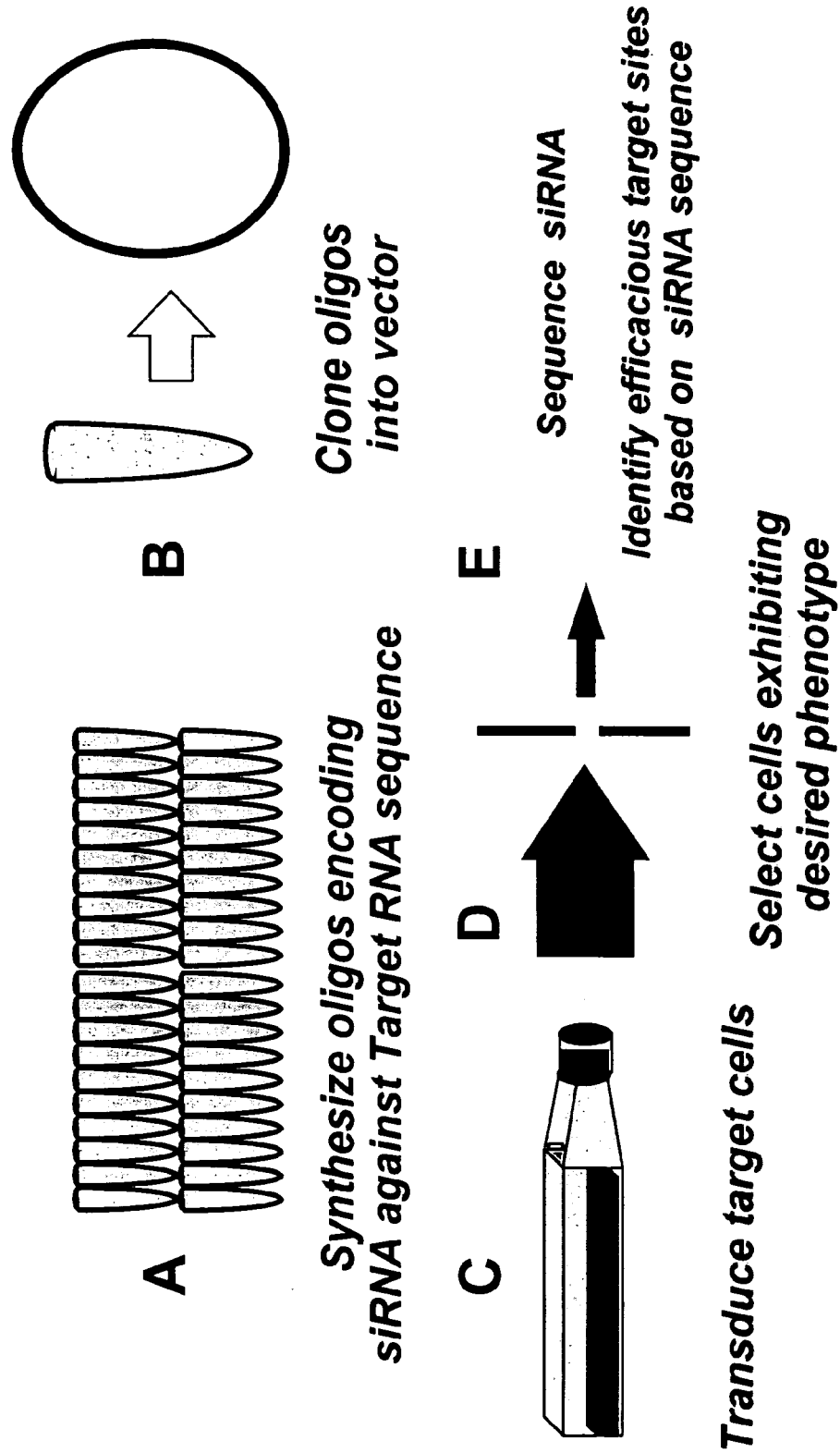
FIG. 9A–E is a diagrammatic representation of a method used to determine target sites for siNA mediated RNAi within a particular target nucleic acid sequence, such as messenger RNA.

In an alternate approach, a pool of siNA constructs specific to a VEGF and/or VEGFr target sequence is used to screen for target sites in cells expressing VEGF and/or VEGFr RNA, such as HUVEC, HMVEC, or A375 cells. The general strategy used in this approach is shown in FIG. 9. A non-limiting example of such is a pool comprising sequences having any of SEQ ID NOS 1–2549. Cells expressing VEGF and/or VEGFr (e.g., HUVEC, HMVEC, or A375 cells) are transfected with the pool of siNA constructs and cells that demonstrate a phenotype associated with VEGF and/or VEGFr inhibition are sorted. The pool of siNA constructs can be expressed from transcription cassettes inserted into appropriate vectors (see for example FIG. 7 and FIG. 8). The siNA from cells demonstrating a positive phenotypic change (e.g., decreased proliferation, decreased VEGF and/or VEGFr mRNA levels or decreased VEGF and/or VEGFr protein expression), are sequenced to determine the most suitable target site(s) within the target VEGF and/or VEGFr RNA sequence.

Example 4

VEGF and/or VEGFr Targeted siNA Design siNA target sites were chosen by analyzing sequences of the VEGF and/or VEGFr RNA target and optionally prioritizing the target sites on the basis of folding (structure of any given sequence analyzed to determine siNA accessibility to the target), by using a library of siNA molecules as described in Example 3, or alternately by using an in vitro siNA system as described in Example 6 herein. siNA molecules were designed that could bind each target and are optionally individually analyzed by computer folding to assess whether the siNA molecule can interact with the target sequence. Varying the length of the siNA molecules can be chosen to optimize activity. Generally, a sufficient number of complementary nucleotide bases are chosen to bind to, or otherwise interact with, the target RNA, but the degree of complementarity can be modulated to accommodate siNA duplexes or varying length or base composition. By using such methodologies, siNA molecules can be designed to target sites within any known RNA sequence, for example those RNA sequences corresponding to the any gene transcript.

Chemically modified siNA constructs are designed to provide nuclease stability for systemic administration in vivo and/or improved pharmacokinetic, localization, and delivery properties while preserving the ability to mediate RNAi activity. Chemical modifications as described herein are introduced synthetically using synthetic methods described herein and those generally known in the art. The synthetic siNA constructs are then assayed for nuclease stability in serum and/or cellular/tissue extracts (e.g. liver extracts). The synthetic siNA constructs are also tested in parallel for RNAi activity using an appropriate assay, such as a luciferase reporter assay as described herein or another suitable assay that can quantity RNAi activity. Synthetic siNA constructs that possess both nuclease stability and RNAi activity can be further modified and re-evaluated in stability and activity assays. The chemical modifications of the stabilized active siNA constructs can then be applied to any siNA sequence targeting any chosen RNA and used, for example, in target screening assays to pick lead siNA compounds for therapeutic development (see for example FIG. 11).

Example 5

Chemical Synthesis and Purification of siNA siNA molecules can be designed to interact with various sites in the RNA message, for example, target sequences within the RNA sequences described herein. The sequence of one strand of the siNA molecule(s) is complementary to the target site sequences described above. The siNA molecules can be chemically synthesized using methods described herein. Inactive siNA molecules that are used as control sequences can be synthesized by scrambling the sequence of the siNA molecules such that it is not complementary to the target sequence. Generally, siNA constructs can by synthesized using solid phase oligonucleotide synthesis methods as described herein (see for example Usman et al., U.S. Pat. Nos. 5,804,683; 5,831,071; 5,998,203; 6,117,657; 6,353,098; 6,362,323; 6,437,117; 6,469,158; Scaringe et al., U.S. Pat. Nos. 6,111,086; 6,008,400; 6,111,086 all incorporated by reference herein in their entirety).

In a non-limiting example, RNA oligonucleotides are synthesized in a stepwise fashion using the phosphoramidite chemistry as is known in the art. Standard phosphoramidite chemistry involves the use of nucleosides comprising any of 5'-O-dimethoxytrityl, 2'-O-tert-butyldimethylsilyl, 3'-O-2-Cyanoethyl N,N-diisopropylphosphoroamidite groups, and exocyclic amine protecting groups (e.g. N6-benzoyl adenosine, N4 acetyl cytidine, and N2-isobutyryl guanosine). Alternately, 2'-O-Silyl Ethers can be used in conjunction with acid-labile 2'-O-orthoester protecting groups in the synthesis of RNA as described by Scaringe supra. Differing 2' chemistries can require different protecting groups, for example 2'-deoxy-2'-amino nucleosides can utilize N-phthaloyl protection as described by Usman et al., U.S. Pat. No. 5,631,360, incorporated by reference herein in its entirety).

During solid phase synthesis, each nucleotide is added sequentially (3'- to 5'-direction) to the solid support-bound oligonucleotide. The first nucleoside at the 3'-end of the chain is covalently attached to a solid support (e.g., controlled pore glass or polystyrene) using various linkers. The nucleotide precursor, a ribonucleoside phosphoramidite, and activator are combined resulting in the coupling of the second nucleoside phosphoramidite onto the 5'-end of the first nucleoside. The support is then washed and any unreacted 5'-hydroxyl groups are capped with a capping reagent such as acetic anhydride to yield inactive 5'-acetyl moieties. The trivalent phosphorus linkage is then oxidized to a more stable phosphate linkage. At the end of the nucleotide addition cycle, the 5'-O-protecting group is cleaved under suitable conditions (e.g., acidic conditions for trityl-based groups and Fluoride for silyl-based groups). The cycle is repeated for each subsequent nucleotide.

Modification of synthesis conditions can be used to optimize coupling efficiency, for example by using differing coupling times, differing reagent/phosphoramidite concentrations, differing contact times, differing solid supports and solid support linker chemistries depending on the particular chemical composition of the siNA to be synthesized. Deprotection and purification of the siNA can be performed as is generally described in Deprotection and purification of the siNA can be performed as is generally described in Usman et al., U.S. Pat. No. 5,831,071, U.S. Pat. No. 6,353,098, U.S. Pat. No. 6,437,117, and Bellon et al., U.S. Pat. No. 6,054,576, U.S. Pat. No. 6,162,909, U.S. Pat. No. 6,303,773, or Scaringe supra, incorporated by reference herein in their entireties. Additionally, deprotection conditions can be modified to provide the best possible yield and purity of siNA constructs. For example, applicant has observed that oligonucleotides comprising 2'-deoxy-2'-fluoro nucleotides can degrade under inappropriate deprotection conditions. Such oligonucleotides are deprotected using aqueous methylamine at about 35° C. for 30 minutes. If the 2'-deoxy-2'-fluoro containing oligonucleotide also comprises ribonucleotides, after deprotection with aqueous methylamine at about 35° C. for 30 minutes, TEA-HF is added and the reaction maintained at about 65° C. for an additional 15 minutes.

Example 6

RNAi In Vitro Assay to Assess siNA Activity

An in vitro assay that recapitulates RNAi in a cell-free system is used to evaluate siNA constructs targeting VEGF and/or VEGFr RNA targets. The assay comprises the system described by Tuschl et al., 1999, *Genes and Development*, 13, 3191–3197 and Zamore et al., 2000, *Cell*, 101, 25–33 adapted for use with VEGF and/or VEGFr target RNA. A *Drosophila* extract derived from syncytial blastoderm is used to reconstitute RNAi activity in vitro. Target RNA is generated via in vitro transcription from an appropriate VEGF and/or VEGFr expressing plasmid using T7 RNA polymerase or via chemical synthesis as described herein. Sense and antisense siNA strands (for example 20 uM each) are annealed by incubation in buffer (such as 100 mM potassium acetate, 30 mM HEPES-KOH, pH 7.4, 2 mM magnesium acetate) for 1 minute at 90° C. followed by 1 hour at 37° C., then diluted in lysis buffer (for example 100 mM potassium acetate, 30 mM HEPES-KOH at pH 7.4, 2 mM magnesium acetate). Annealing can be monitored by gel electrophoresis on an agarose gel in TBE buffer and stained with ethidium bromide. The *Drosophila* lysate is prepared using zero to two-hour-old embryos from Oregon R flies collected on yeasted molasses agar that are dechorionated and lysed. The lysate is centrifuged and the supernatant isolated. The assay comprises a reaction mixture containing 50% lysate [vol/vol], RNA (10–50 pM final concentration), and 10% [vol/vol] lysis buffer containing siNA (10 nM final concentration). The reaction mixture also contains 10 mM creatine phosphate, 10 ug/ml creatine phosphokinase, 100 um GTP, 100 uM UTP, 100 uM CTP, 500 uM ATP, 5 mM DTT, 0.1 U/uL RNasin (Promega), and 100 uM of each amino acid. The final concentration of potassium acetate is adjusted to 100 mM. The reactions are pre-assembled on ice and preincubated at 25° C. for 10 minutes before adding RNA, then incubated at 25° C. for an additional 60 minutes. Reactions are quenched with 4 volumes of 1.25×Passive Lysis Buffer (Promega). Target RNA cleavage is assayed by RT-PCR analysis or other methods known in the art and are compared to control reactions in which siNA is omitted from the reaction.

Alternately, internally-labeled target RNA for the assay is prepared by in vitro transcription in the presence of [alpha-$^{32}$P] CTP, passed over a G 50 Sephadex column by spin chromatography and used as target RNA without further purification. Optionally, target RNA is 5'-$^{32}$P-end labeled using T4 polynucleotide kinase enzyme. Assays are performed as described above and target RNA and the specific RNA cleavage products generated by RNAi are visualized on an autoradiograph of a gel. The percentage of cleavage is determined by PHOSPHOR IMAGER® (autoradiography) quantitation of bands representing intact control RNA or RNA from control reactions without siNA and the cleavage products generated by the assay.

In one embodiment, this assay is used to determine target sites the VEGF and/or VEGFr RNA target for siNA mediated RNAi cleavage, wherein a plurality of siNA constructs are screened for RNAi mediated cleavage of the VEGF and/or VEGFr RNA target, for example, by analyzing the assay reaction by electrophoresis of labeled target RNA, or by northern blotting, as well as by other methodology well known in the art.

Example 7

Nucleic Acid Inhibition of VEGF and/or VEGFr Target RNA In Vivo siNA molecules targeted to the human VEGF and/or VEGFr RNA are designed and synthesized as described above. These nucleic acid molecules can be tested for cleavage activity in vivo, for example, using the following procedure. The target sequences and the nucleotide location within the VEGF and/or VEGFr RNA are given in Table II and III.

Two formats are used to test the efficacy of siNAs targeting VEGF and/or VEGFr. First, the reagents are tested in cell culture using, for example, HUVEC, HMVEC, or A375 cells to determine the extent of RNA and protein inhibition. siNA reagents (e.g.; see Tables II and III) are selected against the VEGF and/or VEGFr target as described herein. RNA inhibition is measured after delivery of these reagents by a suitable transfection agent to, for example, HUVEC, HMVEC, or A375 cells. Relative amounts of target RNA are measured versus actin using real-time PCR monitoring of amplification (eg., ABI 7700 TAQMAN®). A comparison is made to a mixture of oligonucleotide sequences made to unrelated targets or to a randomized siNA control with the same overall length and chemistry, but randomly substituted at each position. Primary and secondary lead reagents are chosen for the target and optimization performed. After an optimal transfection agent concentration is chosen, a RNA time-course of inhibition is performed with the lead siNA molecule. In addition, a cell-plating format can be used to determine RNA inhibition.

Delivery of siNA to Cells

Cells (e.g., HUVEC, HMVEC, or A375 cells) are seeded, for example, at $1\times10^5$ cells per well of a six-well dish in EGM-2 (BioWhittaker) the day before transfection. siNA (final concentration, for example 20 nM) and cationic lipid (e.g., final concentration 2 μg/ml) are complexed in EGM basal media (Biowhittaker) at 37° C. for 30 minutes in polystyrene tubes. Following vortexing, the complexed siNA is added to each well and incubated for the times indicated. For initial optimization experiments, cells are seeded, for example, at $1\times10^3$ in 96 well plates and siNA complex added as described. Efficiency of delivery of siNA to cells is determined using a fluorescent siNA complexed with lipid. Cells in 6-well dishes are incubated with siNA for 24 hours, rinsed with PBS and fixed in 2% paraformaldehyde for 15 minutes at room temperature. Uptake of siNA is visualized using a fluorescent microscope.

TAQMAN® (Real-Time PCR Monitoring of Amplification) and Lightcycler Quantification of mRNA Total RNA is prepared from cells following siNA delivery, for example, using Qiagen RNA purification kits for 6-well or Rneasy extraction kits for 96-well assays. For TAQMAN® analysis (real-time PCR monitoring of amplification), dual-labeled probes are synthesized with the reporter dye, FAM or JOE, covalently linked at the 5'-end and the quencher dye TAMRA conjugated to the 3'-end. One-step RT-PCR amplifications are performed on, for example, an ABI PRISM 7700 Sequence Detector using 50 µl reactions consisting of 10 µl total RNA, 100 nM forward primer, 900 nM reverse primer, 100 nM probe, 1× TaqMan PCR reaction buffer (PE-Applied Biosystems), 5.5 mM $MgCl_2$, 300 µM each dATP, dCTP, dGTP, and dTTP, 10U RNase Inhibitor (Promega), 1.25U AMPLITAQ GOLD® (DNA polymerase) (PE-Applied Biosystems) and 10U M-MLV Reverse Transcriptase (Promega). The thermal cycling conditions can consist of 30 minutes at 48° C., 10 minutes at 95° C., followed by 40 cycles of 15 seconds at 95° C. and 1 minute at 60° C. Quantitation of mRNA levels is determined relative to standards generated from serially diluted total cellular RNA (300, 100, 33, 11 ng/reaction) and normalizing to β-actin or GAPDH mRNA in parallel TAQMAN® reactions (real-time PCR monitoring of amplification). For each gene of interest an upper and lower primer and a fluorescently labeled probe are designed. Real time incorporation of SYBR Green I dye into a specific PCR product can be measured in glass capillary tubes using a lightcyler. A standard curve is generated for each primer pair using control cRNA. Values are represented as relative expression to GAPDH in each sample.

Western Blotting

Nuclear extracts can be prepared using a standard micro preparation technique (see for example Andrews and Faller, 1991, *Nucleic Acids Research*, 19, 2499). Protein extracts from supernatants are prepared, for example using TCA precipitation. An equal volume of 20% TCA is added to the cell supernatant, incubated on ice for 1 hour and pelleted by centrifugation for 5 minutes. Pellets are washed in acetone, dried and resuspended in water. Cellular protein extracts are run on a 10% Bis-Tris NuPage (nuclear extracts) or 4–12% Tris-Glycine (supernatant extracts) polyacrylamide gel and transferred onto nitro-cellulose membranes. Non-specific binding can be blocked by incubation, for example, with 5% non-fat milk for 1 hour followed by primary antibody for 16 hour at 4° C. Following washes, the secondary antibody is applied, for example (1:10,000 dilution) for 1 hour at room temperature and the signal detected with SuperSignal reagent (Pierce).

Example 8

Animal Models Useful to Evaluate the Down-Regulation of VEGF and/or VEGFr Gene Expression There are several animal models in which the anti-angiogenesis effect of nucleic acids of the present invention, such as siRNA, directed against VEGF, VEGFR1, VEGFR2 and/or VEGFr3 mRNAs can be tested. Typically a corneal model has been used to study angiogenesis in rat and rabbit since recruitment of vessels can easily be followed in this normally avascular tissue (Pandey et al., 1995 *Science* 268: 567–569). In these models, a small Teflon or Hydron disk pretreated with an angiogenesis factor (e.g. bFGF or VEGF) is inserted into a pocket surgically created in the cornea. Angiogenesis is monitored 3 to 5 days later. siRNA directed against VEGF, VEGFR1, VEGFR2 and/or VEGFr3 mRNAs are delivered in the disk as well, or dropwise to the eye over the time course of the experiment. In another eye model, hypoxia has been shown to cause both increased expression of VEGF and neovascularization in the retina (Pierce et al., 1995 *Proc. Natl. Acad. Sci. U.S.A.* 92: 905–909; Shweiki et al., 1992 *J. Clin. Invest.* 91: 2235–2243).

In human glioblastomas, it has been shown that VEGF is at least partially responsible for tumor angiogenesis (Plate et al., 1992 *Nature* 359, 845). Animal models have been developed in which glioblastoma cells are implanted subcutaneously into nude mice and the progress of tumor growth and angiogenesism is studied (Kim et al., 1993 supra; Millauer et al., 1994 supra).

Another animal model that addresses neovascularization involves Matrigel, an extract of basement membrane that becomes a solid gel when injected subcutaneously (Passaniti et al., 1992 *Lab. Invest.* 67: 519–528). When the Matrigel is supplemented with angiogenesis factors such as VEGF, vessels grow into the Matrigel over a period of 3 to 5 days and angiogenesis can be assessed. Again, nucleic acids directed against VEGFr mRNAs are delivered in the Matrigel.

Several animal models exist for screening of anti-angiogenic agents. These include corneal vessel formation following corneal injury (Burger et al., 1985 *Cornea* 4: 35–41; Lepri, et al., 1994 *J. Ocular Pharmacol.* 10: 273–280; Ormerod et al., 1990 *Am. J. Pathol.* 137: 1243–1252) or intracorneal growth factor implant (Grant et al., 1993 *Diabetologia* 36: 282–291; Pandey et al. 1995 supra; Zieche et al., 1992 *Lab. Invest.* 67: 711–715), vessel growth into Matrigel matrix containing growth factors (Passaniti et al., 1992 supra), female reproductive organ neovascularization following hormonal manipulation (Shweiki et al., 1993 *Clin. Invest.* 91: 2235–2243), several models involving inhibition of tumor growth in highly vascularized solid tumors (O'Reilly et al., 1994 *Cell* 79: 315–328; Senger et al., 1993 *Cancer and Metas. Rev.* 12: 303–324; Takahasi et al., 1994 *Cancer Res.* 54: 4233–4237; Kim et al., 1993 supra), and transient hypoxia-induced neovascularization in the mouse retina (Pierce et al., 1995 *Proc. Natl. Acad. Sci. U.S.A.* 92: 905–909). Other model systems to study tumor angiogenesis are reviewed by Folkman, 1985 *Adv. Cancer. Res.*, 43, 175.

Ocular Models of Angiogenesis

The cornea model, described in Pandey et al. supra, is the most common and well characterized model for screening anti-angiogenic agent efficacy. This model involves an avascular tissue into which vessels are recruited by a stimulating agent (growth factor, thermal or alkalai burn, endotoxin). The corneal model utilizes the intrastromal corneal implantation of a Teflon pellet soaked in a VEGF-Hydron solution to recruit blood vessels toward the pellet, which can be quantitated using standard microscopic and image analysis techniques. To evaluate their anti-angiogenic efficacy, nucleic acids are applied topically to the eye or bound within Hydron on the Teflon pellet itself. This avascular cornea as well as the Matrigel (see below) provide for low background assays. While the corneal model has been performed extensively in the rabbit, studies in the rat have also been conducted.

The mouse model (Passaniti et al., supra) is a non-tissue model that utilizes Matrigel, an extract of basement membrane (Kleinman et al., 1986) or Millipore® filter disk, which can be impregnated with growth factors and anti-angiogenic agents in a liquid form prior to injection. Upon subcutaneous administration at body temperature, the Matrigel or Millipore® filter disk forms a solid implant. VEGF embedded in the Matrigel or Millipore® filter disk is used to recruit vessels within the matrix of the Matrigel or Millipore® filter disk which can be processed histologically for endothelial cell specific vWF (factor VIII antigen) immunohistochemistry, Trichrome-Masson stain, or hemoglobin content. Like the cornea, the Matrigel or Millipore® filter disk is avascular; however, it is not tissue. In the Matrigel or Millipore® filter disk model, nucleic acids are administered within the matrix of the Matrigel or Millipore® filter disk to test their anti-angiogenic efficacy. Thus, delivery issues in this model, as with delivery of nucleic acids by Hydron-coated Teflon pellets in the rat cornea model, may be less problematic due to the homogeneous presence of the nucleic acid within the respective matrix.

Additionally, siNA molecules of the invention targeting VEGF and/or VEGFr (e.g. VEGFR1, VEGFR2, and/or VEGFR3) can be assesed for activity transgenic mice to determine whether modulation of VEGF and/or VEGFr can inhibit optic neovasculariation. Animal models of choroidal neovascularization are described in, for exmaple, Mori et al., 2001, *Journal of Cellular Physiology*, 188, 253; Mori et al., 2001, *American Journal of Pathology*, 159, 313; Ohno-Matsui et al., 2002, *American Journal of Pathology*, 160, 711; and Kwak et al., 2000, *Investigative Ophthalmology & Visual Science*, 41, 3158. VEGF plays a central role in causing retinal neovascularization. Increased expression of VEGFR2 in retinal photoreceptors of transgenic mice stimulates neovascularization within the retina, and a blockade of VEGFR2 signaling has been shown to inhibit retinal choroidal neovascularization (CNV) (Mori et al.,2001, *J. Cell. Physiol.*, 188, 253).

CNV is laser induced in, for example, adult C57BL/6 mice. The mice are also given an intravitreous, periocular or a subretinal injection of VEGF and/or VEGFr (e.g., VEGFR2) siNA in each eye. Intravitreous injections are made using a Harvard pump microinjection apparatus and pulled glass micropipets. Then a micropipette is passed through the sclera just behind the limbus into the vitreous cavity. The subretinal injections are made using a condensing lens system on a dissecting microscope. The pipet tip is then passed through the sclera posterior to the limbus and positioned above the retina. Five days after the injection of the vector the mice are anesthetized with ketamine hydrochloride (100 mg/kg body weight), 1% tropicamide is also used to dilate the pupil, and a diode laser photocoagulation is used to rupture Bruch's membrane at three locations in each eye. A slit lamp delivery system and a hand-held cover slide are used for laser photocoagulation. Burns are made in the 9, 12, and 3 o'clock positions 2–3 disc diameters from the optic nerve (Mori et al., supra).

The mice typically develop subretinal neovasculariation due to the expression of VEGF in photoreceptors beginning at prenatal day 7. At prenatal day 21, the mice are anesthetized and perfused with 1 ml of phosphate-buffered saline containing 50 mg/ml of fluorescein-labeled dextran. Then the eyes are removed and placed for 1 hour in a 10% phosphate-buffered formalin. The retinas are removed and examined by fluorescence microscopy (Mori et al., supra).

Fourteen days after the laser induced rupture of Bruch's membrane, the eyes that received intravitreous and subretinal injection of siNA are evaluated for smaller appearing areas of CNV, while control eyes are evaluated for large areas of CNV. The eyes that receive intravitreous injections or a subretinal injection of siNA are also evaluated for fewer areas of neovasculariation on the outer surface of the retina and potenial abortive sprouts from deep retinal capillaries that do not reach the retinal surface compared to eyes that did not receive an injection of siNA.

Tumor Models of Angiogenesis

Use of Murine Models

For a typical systemic study involving 10 mice (20 g each) per dose group, 5 doses (1, 3, 10, 30 and 100 mg/kg daily over 14 days continuous administration), approximately 400 mg of siRNA, formulated in saline is used. A similar study in young adult rats (200 g) requires over 4 g. Parallel pharmacokinetic studies involve the use of similar quantities of siRNA further justifying the use of murine models.

Lewis Lung Carcinoma and B-16 Melanoma Murine Models

Identifying a common animal model for systemic efficacy testing of nucleic acids is an efficient way of screening siNA for systemic efficacy.

The Lewis lung carcinoma and B-16 murine melanoma models are well accepted models of primary and metastatic cancer and are used for initial screening of anti-cancer agents. These murine models are not dependent upon the use of immunodeficient mice, are relatively inexpensive, and minimize housing concerns. Both the Lewis lung and B-16 melanoma models involve subcutaneous implantation of approximately $10^6$ tumor cells from metastatically aggressive tumor cell lines (Lewis lung lines 3LL or D122, LLc-LN7; B-16-BL6 melanoma) in C57BL/6J mice. Alternatively, the Lewis lung model can be produced by the surgical implantation of tumor spheres (approximately 0.8 mm in diameter). Metastasis also can be modeled by injecting the tumor cells directly intravenously. In the Lewis lung model, microscopic metastases can be observed approximately 14 days following implantation with quantifiable macroscopic metastatic tumors developing within 21–25 days. The B-16 melanoma exhibits a similar time course with tumor neovascularization beginning 4 days following implantation. Since both primary and metastatic tumors exist in these models after 21–25 days in the same animal, multiple measurements can be taken as indices of efficacy. Primary tumor volume and growth latency as well as the number of micro- and macroscopic metastatic lung foci or number of animals exhibiting metastases can be quantitated. The percent increase in lifespan can also be measured. Thus, these models provide suitable primary efficacy assays for screening systemically administered siRNA nucleic acids and siRNA nucleic acid formulations.

In the Lewis lung and B-16 melanoma models, systemic pharmacotherapy with a wide variety of agents usually begins 1–7 days following tumor implantation/inoculation with either continuous or multiple administration regimens. Concurrent pharmacokinetic studies can be performed to determine whether sufficient tissue levels of siRNA can be achieved for pharmacodynamic effect to be expected. Furthermore, primary tumors and secondary lung metastases can be removed and subjected to a variety of in vitro studies (i.e. target RNA reduction).

In addition, animal models are useful in screening compounds, eg. siNA molecules, for efficacy in treating renal failure, such as a result of autosomal dominant polycystic kidney disease (ADPKD). The Han:SPRD rat model, mice with a targeted mutation in the Pkd2 gene and congenital polycystic kidney (cpk) mice, closely resemble human ADPKD and provide animal models to evaluate the therapeutic effect of siRNA constructs that have the potential to interfere with one or more of the pathogenic elements of ADPKD mediated renal failure, such as angiogenesis. Angiogenesis may be necessary in the progression of ADPKD for growth of cyst cells as well as increased vascular permeability promoting fluid secretion into cysts. Proliferation of cystic epithelium is also a feature of ADPKD because cyst cells in culture produce soluble vascular endothelial growth factor (VEGF). VEGFR1 has also been detected in epithelial cells of cystic tubules but not in endothelial cells in the vasculature of cystic kidneys or normal kidneys. VEGFR2 expression is increased in endothelial cells of cyst vessels and in endothelial cells during renal ischemia-reperfusion. It is proposed that inhibition of VEGF receptors with anti-VEGFR1 and anti-VEGFR2 siRNA molecules would attenuate cyst formation, renal failure and mortality in ADPKD. Anti-VEGFR2 siRNA molecules would therefore be designed to inhibit angiogenesis involved in cyst formation. As VEGFR1 is present in cystic epithelium and not in vascular endothelium of cysts, it is proposed that anti-VEGFR1 siRNA molecules would attenuate cystic epithelial cell proliferation and apoptosis which would in turn lead to less cyst formation. Further, it is proposed that VEGF produced by cystic epithelial cells is one of the stimuli for angiogenesis as well as epithelial cell proliferation and apoptosis. The use of Han:SPRD rats (see for eaxmple Kaspareit-Rittinghausen et al., 1991, *Am. J. Pathol.* 139, 693–696), mice with a targeted mutation in the Pkd2 gene (Pkd2−/− mice, see for example Wu et al., 2000, *Nat. Genet.* 24, 75–78) and cpk mice (see for example Woo et al., 1994, *Nature*, 368, 750–753) all provide animal models to study the efficacy of siRNA molecules of the invention against VEGFR1 and VEGFR2 mediated renal failure.

VEGF, VEGFR1 VGFR2 and/or VEGFr3 protein levels can be measured clinically or experimentally by FACS analysis. VEGF, VEGFR1 VGFR2 and/or VEGFr3 encoded mRNA levels are assessed by Northern analysis, RNase-protection, primer extension analysis and/or quantitative RT-PCR. siRNA nucleic acids that block VEGF, VEGFR1 VGFR2 and/or VEGFr3 protein encoding mRNAs and therefore result in decreased levels of VEGF, VEGFR1 VGFR2 and/or VEGFr3 activity by more than 20% in vitro can be identified.

Example 9

RNAi Mediated Inhibition of VEGFr Expression in Cell Culture

Inhibition of VEGFR1 RNA expression using siNA targeting VEGFR1 RNA siNA constructs (Table III) are tested for efficacy in reducing VEGF and/or VEGFr RNA expression in, for example, HUVEC, HMVEC, or A375 cells. Cells are plated approximately 24 hours before transfection in 96-well plates at 5,000–7,500 cells/well, 100 µl/well, such that at the time of transfection cells are 70–90% confluent. For transfection, annealed siNAs are mixed with the transfection reagent (Lipofectamine 2000, Invitrogen) in a volume of 50 µl/well and incubated for 20 min. at room temperature. The siNA transfection mixtures are added to cells to give a final siNA concentration of 25 nM in a volume of 150 µl. Each siNA transfection mixture is added to 3 wells for triplicate siNA treatments. Cells are incubated at 37° for 24 h in the continued presence of the siNA transfection mixture. At 24 h, RNA is prepared from each well of treated cells. The supernatants with the transfection mixtures are first removed and discarded, then the cells are lysed and RNA prepared from each well. Target gene expression following treatment is evaluated by RT-PCR for the target gene and for a control gene (36B4, an RNA polymerase subunit) for normalization. The triplicate data is averaged and the standard deviations determined for each treatment. Normalized data are graphed and the percent reduction of target mRNA by active siNAs in comparison to their respective inverted control siNAs is determined.

FIG. 22 shows a non-limiting example of reduction of VEGFR1 mRNA in A375 cells mediated by chemically-modified siNAs that target VEGFR1 mRNA. A549 cells were transfected with 0.25 ug/well of lipid complexed with 25 nM siNA. A screen of siNA constructs (Stabilization "Stab" chemistries are shown in Table IV, constructs are referred to by RPI number, see Table III) comprising Stab 4/5 chemistry (Sima/RPI 31190/31193), Stab 1/2 chemistry (Sirna/RPI 31183/31186 and Sirna/RPI 31184/31187), and unmodified RNA (Sirna/RPI 30075/30076) were compared to untreated cells, matched chemistry inverted control siNA constructs (Sirna/RPI 31208/31211, Sirna/RPI 31201/31204, Sirna/RPI 31202/31205, and Sirna/RPI 30077/30078), scrambled siNA control constructs (Scram1 and Scram2), and cells transfected with lipid alone (transfection control). As shown in the figure, all of the siNA constructs significantly reduce VEGFR1 RNA expression. Additional stabilization chemistries as described in Table IV are similarly assayed for activity. These siNA constructs are compared to appropriate matched chemistry inverted controls. In addition, the siNA constructs are also compared to untreated cells, cells transfected with lipid and scrambled siNA constructs, and cells transfected with lipid alone (transfection control).

FIG. 23 shows a non-limiting example of reduction of VEGFR1 mRNA levels in HAEC cell culture using Stab 9/10 directed against eight sites in VEGFR1 mRNA compared to matched chemistry inverted controls siNA constructs. Controls UNT and LF2K refer to untreated cells and cells treated with LF2K transfection reagent alone, respectively.

Inhibition of VEGFR2 RNA Expression Using siNA Targeting VEGFR2 RNA siNA constructs (Table III) are tested for efficacy in reducing VEGF and/or VEGFr RNA expression in, for example, HUVEC, HMVEC, or A375 cells. Cells are plated approximately 24 hours before transfection in 96-well plates at 5,000–7,500 cells/well, 100 µl/well, such that at the time of transfection cells are 70–90% confluent. For transfection, annealed siNAs are mixed with the transfection reagent (Lipofectamine 2000, Invitrogen) in a volume of 50 µl/well and incubated for 20 min. at room temperature. The siNA transfection mixtures are added to cells to give a final siNA concentration of 25 nM in a volume of 150 µl. Each siNA transfection mixture is added to 3 wells for triplicate siNA treatments. Cells are incubated at 37° for 24 h in the continued presence of the siNA transfection mixture. At 24 h, RNA is prepared from each well of treated cells. The supernatants with the transfection mixtures are first removed and discarded, then the cells are lysed and RNA prepared from each well. Target gene expression following treatment is evaluated by RT-PCR for the target gene and for a control gene (36B4, an RNA polymerase subunit) for normalization. The triplicate data is averaged and the standard deviations determined for each treatment. Normalized data are graphed and the percent reduction of target mRNA by active siNAs in comparison to their respective inverted control siNAs is determined.

FIG. 24 shows a non-limiting example of reduction of VEGFR2 mRNA in HAEC cells mediated by chemically-modified siNAs that target VEGFR2 mRNA. HAEC cells were transfected with 0.25 ug/well of lipid complexed with 25 nM siNA. A screen of siNA constructs (Stabilization "Stab" chemistries are shown in Table IV, constructs are referred to by Compound No., see Table III) in site 3854 comprising Stab 4/5 chemistry (Compound No. 30786/30790), Stab 7/8 chemistry (Compound No. 31858/31860), and Stab 9/10 chemistry (Compound No. 31862/31864) and in site 3948 comprising Stab 4/5 chemistry (Compound No. 31856/31857), Stab 7/8 chemistry (Compound No. 31859/31861), and Stab 9/10 chemistry (Compound No. 31863/31865) were compared to untreated cells, matched chemistry inverted control siNA constructs in site 3854 (Compound No. 31878/31880, Compound No. 31882/31884, and Compound No. 31886/31888) and in site 3948 (Compound No. 31879/31881, Compound No. 31883/31885, and Compound No. 31887/31889), and cells transfected with LF2K (transfection reagent), and an all RNA control (Compound No. 31435/31439 in site 3854 and Compound No. 31437/31441 in site 3948). As shown in the figure, all of the siNA constructs significantly reduce VEGFR2 RNA expression. Additional stabilization chemistries as described in Table IV are similarly assayed for activity. These siNA constructs are compared to appropriate matched chemistry inverted controls. In addition, the siNA constructs are also compared to untreated cells, cells transfected with lipid and scrambled siNA constructs, and cells transfected with lipid alone (transfection control).

FIG. 25 shows a non-limiting example of reduction of VEGFR2 mRNA levels in HAEC cell culture using Stab 0/0 directed against four sites in VEGFR2 mRNA compared to irrelevant control siNA constructs (IC1, IC2). Controls UNT and LF2K refer to untreated cells and cells treated with LF2K transfection reagent alone, respectively.

Inhibition of VEGFR1 and VEGFR2 RNA Expression using siNA Targeting VEGFR1 and VEGFR2 Homologous RNA Sequences VEGFR1 and VEGFR2 RNA levels were assessed in HAEC cells 24 hours after treatment with siNA molecules targeting sequences having VEGFR1 and VEGFR2 homology. HAEC cells were transfected with 1.5 ug/well of lipid complexed with 25 nM siNA. Activity of the siNA moleclues is shown compared to matched chemistry inverted siNA controls, untreated cells, and cells treated with lipid only (transfection control). siNA molecules and controls are referred to by compound numbers (sense/antisense), see Table III for sequences. As shown in FIGS. 26A and B, siNA constructs that target both VEGFR1 and VEGFR2 sequences demonstrate potent efficacy in inhibiting VEGFR1 expression in cell cuture experiments. As shown in FIGS. 27A and B, siNA constructs that target both VEGFR1 and VEGFR2 sequences demonstrate potent efficacy in inhibiting VEGFR2 expression in cell cuture experiments.

Example 10 siNA-Mediated Inhibition of Angiogenesis In Vivo

Evaluation of siNA molecules in the rat cornea model of VEGF induced angiogenesis The purpose of this study was to assess the anti-angiogenic activity of siNA targeted against VEGFR1, using the rat cornea model of VEGF induced angiogenesis. The siNA molecules referred to in FIG. 28 have matched inverted controls which are inactive since they are not able to interact with the RNA target. The siNA molecules and VEGF were co-delivered using the filter disk method. Nitrocellulose filter disks (Millipore®) of 0.057 diameter were immersed in appropriate solutions and were surgically implanted in rat cornea as described by Pandey et al., supra.

The stimulus for angiogenesis in this study was the treatment of the filter disk with 30 μM VEGF, which is implanted within the cornea's stroma. This dose yields reproducible neovascularization stemming from the pericorneal vascular plexus growing toward the disk in a dose-response study 5 days following implant. Filter disks treated only with the vehicle for VEGF show no angiogenic response. The siNA were co-adminstered with VEGF on a disk in three different siNA concentrations. One concern with the simultaneous administration is that the siNA would not be able to inhibit angiogenesis since VEGF receptors can be stimulated. However, Applicant has observed that in low VEGF doses, the neovascular response reverts to normal suggesting that the VEGF stimulus is essential for maintaining the angiogenic response. Blocking the production of VEGF receptors using simultaneous administration of anti-VEGF-R mRNA siNA could attenuate the normal neovascularization induced by the filter disk treated with VEGF.

Materials and Methods:

Test Compounds and Controls
R&D Systems VEGF, carrier free at 75 μM in 82 mM Tris-Cl, pH 6.9
Active siNA constructs and inverted controls (Table III)

Animals
Harlan Sprague-Dawley Rats, Approximately 225–250 g 45 males, 5 animals per group.

Husbandry
Animals are housed in groups of two. Feed, water, temperature and humidity are determined according to Pharmacology Testing Facility performance standards (SOP's) which are in accordance with the 1996 Guide for the Care and Use of Laboratory Animals (NRC). Animals are acclimated to the facility for at least 7 days prior to experimentation. During this time, animals are observed for overall health and sentinels are bled for baseline serology.

Experimental Groups
Each solution (VEGF and siNAs) was prepared as a 1× solution for final concentrations shown in the experimental groups described in Table III.

siNA Annealing Conditions
siNA sense and antisense strands are annealed for 1 minute in $H_2O$ at 1.67 mg/mL/strand followed by a 1 hour incubation at 37° C. producing 3.34 mg/mL of duplexed siNA. For the 20 μg/eye treatment, 6 μLs of the 3.34 mg/mL duplex is injected into the eye (see below). The 3.34 mg/mL duplex siNA can then be serially diluted for dose response assays.

Preparation of VEGF Filter Disk

For corneal implantation, 0.57 mm diameter nitrocellulose disks, prepared from 0.45 μm pore diameter nitrocellulose filter membranes (Millipore Corporation), were soaked for 30 min in 1 μL of 75 μM VEGF in 82 mM Tris HCl (pH 6.9) in covered petri dishes on ice. Filter disks soaked only with the vehicle for VEGF (83 mM Tris-Cl pH 6.9) elicit no angiogenic response.

Corneal Surgery

The rat corneal model used in this study was a modified from Koch et al. Supra and Pandey et al., supra. Briefly, corneas were irrigated with 0.5% povidone iodine solution followed by normal saline and two drops of 2% lidocaine. Under a dissecting microscope (Leica MZ-6), a stromal pocket was created and a presoaked filter disk (see above) was inserted into the pocket such that its edge was 1 mm from the corneal limbus.

Intraconjunctival Injection of Test Solutions

Immediately after disk insertion, the tip of a 40–50 μm OD injector (constructed in our laboratory) was inserted within the conjunctival tissue 1 mm away from the edge of the corneal limbus that was directly adjacent to the VEGF-soaked filter disk. Six hundred nanoliters of test solution (siNA, inverted control or sterile water vehicle) were dispensed at a rate of 1.2 μL/min using a syringe pump (Kd Scientific). The injector was then removed, serially rinsed in 70% ethanol and sterile water and immersed in sterile water between each injection. Once the test solution was injected, closure of the eyelid was maintained using microaneurism clips until the animal began to recover gross motor activity. Following treatment, animals were warmed on a heating pad at 37° C.

Quantitation of Angiogenic Response

Five days after disk implantation, animals were euthanized following administration of 0.4 mg/kg atropine and corneas were digitally imaged. The neovascular surface area (NSA, expressed in pixels) was measured postmortem from blood-filled corneal vessels using computerized morphometry (Image Pro Plus, Media Cybernetics, v2.0). The individual mean NSA was determined in triplicate from three regions of identical size in the area of maximal neovascularization between the filter disk and the limbus. The number of pixels corresponding to the blood-filled corneal vessels in these regions was summated to produce an index of NSA. A group mean NSA was then calculated. Data from each treatment group were normalized to VEGF/siNA vehicle-treated control NSA and finally expressed as percent inhibition of VEGF-induced angiogenesis.

Statistics

After determining the normality of treatment group means, group mean percent inhibition of VEGF-induced angiogenesis was subjected to a one-way analysis of variance. This was followed by two post-hoc tests for significance including Dunnett's (comparison to VEGF control) and Tukey-Kramer (all other group mean comparisons) at alpha=0.05. Statistical analyses were performed using JMP v.3.1.6 (SAS Institute).

Results of the study are graphically represented in FIGS. 28 and 29. As shown in FIG. 28, VEGFR1 site 4229 active siNA (Sirna/RPI 29695/29699) at three concentrations was effective at inhibiting angiogenesis compared to the inverted siNA control (Sirna/RPI 29983/29984) and the VEGF control. A chemically modified version of the VEGFR1 site 4229 active siNA comprising a sense strand having 2'-deoxy-2'-fluoro pyrimidines and ribo purines with 5' and 3' terminal inverted deoxyabasic residues and an antisense strand having having 2'-deoxy-2'-fluoro pyrimidines and ribo purines with a terminal 3'-phosphorothioate internucleotide linkage (Sima/RPI 30196/30416), showed similar inhibition. Furthermore, VEGFR1 site 349 active siNA having "Stab 9/10" chemistry (Compound No. 31270/31273) was tested for inhibition of VEGF-induced angiogenesis at three different concentrations (2.0 ug, 1.0 ug, and 0.1 ug dose response) as compared to a matched chemistry inverted control siNA construct (Compound No. 31276/31279) at each concentration and a VEGF control in which no siNA was administered. As shown in FIG. 29, the active siNA construct having "Stab 9/10" chemistry (Compound No. 31270/31273) is highly effective in inhibiting VEGF-induced angiogenesis in the rat corneal model compared to the matched chemistry inverted control siNA at concentrations from 0.1 ug to 2.0 ug. These results demonstrate that siNA molecules having different chemically modified compositions, such as the modifications described herein, are capable of significantly inhibiting angiogenesis in vivo. Results of a follow study in which sites adjacent to VEGFR1 site 349 were evaluated for efficacy using two different siNA stabilization chemistries is shown in FIG. 30.

Evaluation of siNA Molecules Targeting Homologous VEGFR1 and VEGFR2 Sequences in the Rat Cornea Model of VEGF Induced Angiogenesis The above model was utilized to evaluate the efficacy of siNA molecules targeting homologous VEGFR1 and VEGFR2 sequences in inibiting VEGF induced ocular angiogenesis. Test compounds and controls are referred to in Table VII, sequences are shown in Table II. The siNAs or other test articles were administered by subconjunctival injection after VEGF disk implantation. The siNAs were preannealed prior to administration. Subconjuctival injections were performed using polyimide coated fused silica glass catheter tubing (OD=148 μm, ID=74 μm). This tubing was inserted into a borosilicate glass micropipette that was pulled to a fine point of approximately 40–50 microns OD using a Flaming/Brown Micropipette Puller (Model P-87, Sutter Instrument Co.). The micropipette was inserted into the pericorneal conjunctiva in the vicinity of the implanted filter disc and a volume of 1.2 μL was delivered over 15 seconds using a Hamilton Gastight syringe (25 μL) and a syringe pump. The rat eye was prepared by trimming the whiskers around the eye and washing the eye with providone iodine following topical lidocaine anesthesia. The silver nitrate sticks were touched to the surface of the cornea to induce a wound healing response and concurrent neovascularization. On day five, animals were anesthetized using ketamine/xylazine/acepromazine and vessel growth scores obtained. Animals were euthanized by $CO_2$ inhalation and digital images of each eye were obtained for quantitation of vessel growth using Image Pro Plus. Quantitated neovascular surface area was analyzed by ANOVA followed by two post-hoc tests including Dunnet's and Tukey-Kramer tests for significance at the 95% confidence level. Results are shown in FIG. 31 as percent inhibition of VEGF induced angiogenesis compared to VEGF control. As shown in the figure, several siNA constructs that target both VEGFR1 and VEGFR2 via homologous sequences (e.g., compound Nos. 33725/33731, 33737/33743, 33742/33748, and 33729/33735) provide inhibition of VEGF-induced angiogenesis in this model. These compounds appear to provide equal or greater inhibition than a siNA construct (Compound No. 31270/31273) targeting VEGFR1 only.

Evaluation of siNA Molecules in the Mouse Coroidal Model of Neovascularization.

Intraocular Administration of siNA

Female C57BL/6 mice (4–5 weeks old) were anesthetized with a 0.2 ml of a mixture of ketamine/xylazine (8:1), and the pupils were dilated with a single drop of 1% tropicamide. Then a 532 nm diode laser photocoagulation (75 µm spot size, 0.1-second duration, 120 mW) was used to generate three laser spots in each eye surrounding the optic nerve by using a hand-held coverslip as a contact lens. A bubble formed at the laser spot indicating a rupture of the Bruch's membrane. Next, the laser spots were evaluated for the presence of CNV on day 17 after laser treatment.

After laser induction of multiple CNV lesions in mice, the siNA was administered by intraocular injections under a dissecting microscope. Intravitreous injections were performed with a Harvard pump microinjection apparatus and pulled glass micropipets. Each micropipet was calibrated to deliver 1 µL of vehicle containing 0.5 ug or 1.5 ug of siNA, inverted control siNA, or saline. The mice were anesthetized, pupils were dilated, and, the sharpened tip of the micropipet was passed through the sclera, just behind the limbus into the vitreous cavity, and the foot switch was depressed. The injection was repeated at day 7 after laser photocoagulation.

At the time of death, mice were anesthetized (ketamine/xylazine mixture, 8:1) and perfused through the heart with 1 ml PBS containing 50 mg/ml fluorescein-labeled dextran (FITC-Dextran, 2 million average molecular weight, Sigma). The eyes were removed and fixed for overnight in 1% phosphate-buffered 4% Formalin. The cornea and the lens were removed and the neurosensory retina was carefully dissected from the eyecup. Five radial cuts were made from the edge of the eyecup to the equator; the sclera-choroid-retinal pigment epithelium (RPE) complex was flat-mounted, with the sclera facing down, on a glass slide in Aquamount. Flat mounts were examined with a Nikon fluorescence microscope. A laser spot with green vessels was scored CNV-positive, and a laser spot lacking green vessels was scored CNV-negative. Flatmounts were examined by fluorescence microscopy (Axioskop; Carl Zeiss, Thornwood, N.Y.), and images were digitized with a three-color charge-coupled device (CCD) video camera and a frame grabber. Image-analysis software (Image-Pro Plus; Media Cybernetics, Silver Spring, Md.) was used to measure the total area of hyperfluorescence associated with each burn, corresponding to the total fibrovascular scar. The areas within each eye were averaged to give one experimental value per eye for plotting the areas.

Measurement of VEGFR1 expression was also determined using RT-PCR and/or real-time PCR. Retinal RNA was isolated by a Rnaeasy kit, and reverse transcription was performed with approximately 0.5 µg total RNA, reverse transcriptase (SuperScript II), and 5.0 µM oligo-d(T) primer. PCR amplification was performed using primers specific for VEGFR-1 (5'-AAGATGCCAGCCGAAGGAGA-3', SEQ ID NO: 2550) and (5'-GGCTCGGCACCTATAGACA-3', SEQ ID NO: 2551). Titrations were determined to ensure that PCR reactions were performed in the linear range of amplification. Mouse S16 ribosomal protein primers (5'-CACTGCAAACGGGGAAATGG-3', SEQ ID NO: 2552 and 5'-TGAGATGGACTGTCGGATGG-3', SEQ ID NO: 2553) were used to provide an internal control for the amount of template in the PCR reactions.

VEGFR1 site 349 active siNA having "Stab 9/10" chemistry (Compound No. 31270/31273, Table III) was tested for inhibition of VEGF-induced neovascularization at two different concentrations (1.5 ug, and 0.5 ug dose response) as compared to a matched chemistry 1.5 ug inverted control siNA construct (Compound No.31276/31279, Table III) and a saline control. As shown in FIG. 32, the active siNA construct having "Stab 9/10" chemistry is highly effective in inhibiting VEGFR1 induced neovascularization (57% inhibition) in the C57BL/6 mice intraocular delivery model compared to the matched chemistry inverted control siNA. The active siNA construct was also highly effective in inhibiting VEGFR1 induced neovascularization (66% inhibition) compared to the saline control. Additionally, RT-PCR analysis of VEGFR1 site 349 siNA having "Stab 9/10" chemistry (Compound No. 31270/31273, Table III) showed significant reduction in the level of VEGFR1 mRNA compared to the inverted siNA construct (Compound No. 31276/31279, Table III) and saline. Furthermore, ELISA analysis of VEGFR1 protein using the active siNA and inverted control siNA above showed significant reduction in the level of VEGFR1 protein expression using the active siNA compared to the inactive siNA construct. These results demonstrate that siNA molecules having different chemically modified compositions, such as the modifications described herein, are capable of significantly inhibiting neovascularization as shown in this model of intraocular administration.

Periocular Administration of siNA

Female C57BL/6 mice (4–5 weeks old) were anesthetized with a 0.2 ml of a mixture of ketamine/xylazine (8:1), and the pupils were dilated with a single drop of 1% tropicamide. Then a 532 nm diode laser photocoagulation (75 µm spot size, 0.1-s duration, 120 mW) was used to generate three laser spots in each eye surrounding the optic nerve by using a hand-held coverslip as a contact lens. A bubble formed at the laser spot indicating a rupture of the Bruch's membrane. Next, the laser spots were evaluated for the presence of CNV on day 17 after laser treatment.

After laser induction of multiple CNV lesions in mice, the siNA was administered via periocular injections under a dissecting microscope. Periocular injections were performed with a Harvard pump microinjection apparatus and pulled glass micropipets. Each micropipet was calibrated to deliver 5 µL of vehicle containing test siNA at concentrations of 0.5 ug or 1.5 ug of siNA. The mice were anesthetized, pupils were dilated, and, the sharpened tip of the micropipet was passed, and the foot switch was depressed. Periocular injections were given daily starting at day 1 through day 14 after laser photocoagulation. Alternately, periocular injections are given every 3 days after rupture of Bruch's membrane.

At the time of death, mice were anesthetized (ketamine/xylazine mixture, 8:1) and perfused through the heart with 1 mL PBS containing 50 mg/mL fluorescein-labeled dextran (FITC-Dextran, 2 million average molecular weight, Sigma). The eyes were removed and fixed overnight in 1% phosphate-buffered 4% Formalin. The cornea and the lens were removed and the neurosensory retina was carefully dissected from the eyecup. Five radial cuts were made from the edge of the eyecup to the equator; the sclera-choroid-retinal pigment epithelium (RPE) complex was flat-mounted, with the sclera facing down, on a glass slide in Aquamount. Flat mounts were examined with a Nikon fluorescence microscope. A laser spot with green vessels was scored CNV-positive, and a laser spot lacking green vessels was scored CNV-negative. Flatmounts were examined by fluorescence microscopy (Axioskop; Carl Zeiss, Thornwood, N.Y.) and images were digitized with a three-color charge-coupled device (CCD) video camera and a frame grabber. Image-analysis software (Image-Pro Plus; Media Cybernetics, Silver Spring, Md.) was used to measure the total area of hyperfluorescence associated with each burn, corresponding to the total fibrovascular scar. The areas within each eye were averaged to give one experimental value per eye.

VEGFR1 site 349 active siNA having "Stab 9/10" chemistry (Compound No. 31270/31273, Table III) was tested for inhibition of VEGF-induced neovascularization at two different concentrations (1.5 ug, and 0.5 ug dose response) as compared to a matched chemistry saline control and 0.5 ug inverted control siRNA construct (Compound No. 31276/31279, Table III). As shown in FIG. 33, the active siNA construct having "Stab 9/10" chemistry (Compound No. 31270/31273) is effective in inhibiting VEGFR1 induced neovascularization (20% inhibition) in the C57BL/6 mice periocular delivery model compared to the matched chemistry inverted control siNA. The active siNA construct was also highly effective in inhibiting VEGFR1 induced neovascularization (54% inhibition) compared to the saline control. In an additional assay shown in FIG. 34, VEGFR1 site 349 active siNA having "Stab 9/10" chemistry (Compound No. 31270/31273) at two concentrations was effective at inhibiting neovascularization in CNV lesions compared to the inverted siNA control and the saline control. As shown in FIG. 34, the active siNA construct having "Stab 9/10" chemistry (Compound No. 31270/31273) is effective in inhibiting VEGFR1 induced neovascularization (43% inhibition) in the C57BL/6 mice periocular delivery model compared to the matched chemistry inverted control siNA. The active siNA construct was also effective in inhibiting VEGFR1 induced neovascularization (45% inhibition) compared to the saline control with periocular injection treatment given every 3 days after rupture of Bruch's membrane (see FIG. 35). These results demonstrate that siNA molecules having different chemically modified compositions, such as the modifications described herein, are capable of significantly inhibiting neovascularization as shown in this model of periocular administration.

Evaluation of siNA Molecules in the Mouse Retinopathy of Prematurity Model

The following protocol was used to evaluate siNA molecules targeting VEGF receptor mRNA in an oxygen-induced ischemic retinopathy/retinopathy of prematurity model. Pups from female C57BL/6 mice were placed into a 75% oxygen (ROP) environment at P7 (seven days after birth). Mothers were changed quickly at P10. Mice were removed from 75% oxygen chamber at P12. Pups were injected on P12, three hours after being removed from the 75% oxygen environment. siNA was delivered via an intravitreal or periocular injection under a dissecting microscope. A Harvard pump microinjection apparatus and pulled glass micropipette were used for injection. Each micropipette was calibrated to deliver 1 µL of vehicle containing test siRNA. The mice were anesthetized, the pupils were dilated, and the sharpened tip of the micropipette was passed through the limbus and the foot of the microinjection apparatus was depressed. Mice were sacrificed by cervical dislocation for RNA and protein extraction on P15, three days after being removed from the high oxygen environment. The retinas were removed and placed in appropriate lysis buffer (see below for protein and RNA analysis methods).

Protein Analysis: Protein lysis buffer contained 50 µL 1M Tris-HCl (pH 7.4), 50 µL 10% SDS (Sodium Dodecyl Sulfate), 5 µL 100 nM PHSF (Phenylmethaneculfonyl) and 5 mL serilized, de-ionized water. 200 µL of lysis buffer was added to fresh tissue, and homogenized by pipeting. Tissue was sonicated at 4° C. for 25 minutes, and spun at 13K for 5 minutes at 4° C. The pellet was discarded, and supernate transferred to fresh tube. BioRad assay was used to measure protein concentration using BSA as a standard. Samples were stored at −80° C. ELISAs were carried out using VEGFR1 and R2 kits from R&D Systems (Quantikine® Immunoassay). The protocols provided in the manuals were followed exactly.

RNA analysis: RNA was extracted using Quiagen, RNeasy mini kit and following protocol for extraction from animal cells. RNA samples were treated with DNA-free™ by Ambion following company protocol. First Strand cDNA was then synthesized for real time PCR using Invitrogen, Superscript 1st Strand System for RT-PCR, and following protocol. Real-time PCR was then preformed in a Roche Lightcycler using Fast Start DNA Master SYBR Green I. Cyclophilin A was used as a control, and purified PCR products were used as standards.

Analysis of neovascularization: Mice were sacrificed on P17 by cervical dislocation. Eyes were removed and fresh frozen in OCT and stored at −80° C. Eyes were then sectioned and immunohistochemically stained for lectin. 10 µm frozen sections of eyes were histochemically stained with biotinylated Griffonia simplicifolia lectin B4 (GSA; Vector Laboratories, Burlingame, Calif.), which selectively binds to endothelial cells. Slides were dried and fixed with 4% PFA for 20 minutes, then incubated in methanol/H2O2 for 10 minutes at room temperature. After washing with 0.05 M Tris-buffered saline, pH 7.6 (TBS), the slides were blocked with 10% swine serum for 30 minutes. Slides were first stained with biotinylated GSA for 2 hours at room temperature, followed by a thorough wash with 0.05 M TBS. The slides were further stained with avidin coupled to alkaline phosphatase (Vector Laboratories) for 45 minutes at room temperature. Slides were incubated with a red stain (Histomark Red; Kirkegaard and Perry, Gaithersburg, Md.) to give a red reaction product. A computer and image-analysis software (Image-Pro Plus software; Media Cybernetics, Silver Spring, Md.) was used to quantify GSA-stained cells on the surface of the retina, and their area was measured. The mean of the 15 measurements from each eye was used as a single experimental value.

Results of a representative study are shown in FIGS. 36 and 37. As shown in FIG. 36, in mice with oxygen induced retinopathy (OIR), periocular injections of VEGFR1 siNA (31270/31273) (5 µl; 1.5 µg/µl) on P12, P14, and P16 significantly reduced VEGFR1 mRNA expression compared to injections with a matched chemistry inverted control siNA construct (31276/31279), (40% inhibition; n=9, p=0.0121). As shown in FIG. 37, in mice with oxygen induced retinopathy (OIR), intraocular injections of VEGFR1 siNA (31270/31273) (5 µg), significantly reduced VEGFR1 protein levels compared to injections with a matched chemistry inverted control siNA construct (31276/31279), (30% inhibition; n=7, p=0.0103).

Evaluation of siNA Molecules in the Mouse 4T1-Luciferase Mammary Carcinoma Syngeneic Tumor Model The current study was designed to determine if systemically administered siRNA directed against VEGFR-1 inhibits the growth of subcutaneous tumors. Test compounds included active Stab 9/10 siNA targeting site 349 of VEGFR-1 RNA (Compound #31270/31273), a matched chemistry inactive inverted control siNA (Compound #31276/31279) and saline. Animal subjects were female Balb/c mice approximately 20–25 g (5–7 weeks old). The number of subjects tested was 40 mice; treatment groups are described in Table VI. Mice were housed in groups of four. The feed, water, temperature and humidity conditions followed Pharmacology Testing Facility performance standards (SOP's) which are in accordance with the 1996 Guide for the Care and Use of Laboratory Animals (NRC). Animals were acclimated to the facility for at least 3 days prior to experimentation. During this time, animals were observed for overall health and sentinels were bled for baseline serology. 4T1-luc mammary carcinoma tumor cells were maintained in cell culture until injection into animals used in the study. On day 0 of the study, animals were anesthetized with ketamine/xylazine and $1.0\times10^6$ cells in an injection volume of 100 µl were subcutaneously inoculated in the right flank. Primary tumor volume was measured using microcalipers. Length and width measurements were obtained from each tumor 3x/week (M,W,F) beginning 3 days after inoculation up through and including 21 days after inoculation. Tumor volumes were calculated from the length/width measurements according to the equation: Tumor volume=(a) (b)$^2$/2 where a=the long axis of the tumor and b=the shorter axis of the tumor. Tumors were allowed to grow for a period of 3 days prior to dosing. Dosing consisted of a daily intravenous tail vein injection of the test compounds for 18 days. On day 21, animals were euthanized 24 hours following the last dose of test compound, or when the animals began to exhibit signs of moribundity (such as weight loss, lethargia, lack of grooming etc.) using $CO_2$ inhalation and lungs were subsequently removed. Lung metastases were counted under a Leitz dissecting microscope at 25x magnification. Tumors were removed and flash frozen in $LN_2$ for analysis of immunohistochemical endpoints or mRNA levels. Results are shown in FIG. 38. As shown in the Figure, the active siNA construct inhibited tumor growth by 50% compared to the inactive control siNA construct.

In addition, levels of soluble VEGFR1 in plasma were assessed in mice treated with the active and inverted control siNA constucts. FIG. 39 shows the reduction of soluble VEGFR1 serum levels in the mouse 4T1-luciferase mammary carcinoma syngeneic tumor model using active Stab 9/10 siNA targeting site 349 of VEGFR1 RNA (Compound #31270/31273) compared to a matched chemistry inactive inverted control siNA (Compound #31276/31279). As shown in FIG. 39, the active siNA construct is effective in reducing soluble VEGFR1 serum levels in this model.

Example 11

Indications

The present body of knowledge in VEGF and/or VEGFr research indicates the need for methods to assay VEGF and/or VEGFr activity and for compounds that can regulate VEGF and/or VEGFr expression for research, diagnostic, and therapeutic use. As described herein, the nucleic acid molecules of the present invention can be used in assays to diagnose disease state related of VEGF and/or VEGFr levels. In addition, the nucleic acid molecules can be used to treat disease state related to VEGF and/or VEGFr levels.

Particular conditions and disease states that can be associated with VEGF and/or VEGFr expression modulation include, but are not limited to:

1) Tumor angiogenesis: Angiogenesis has been shown to be necessary for tumors to grow into pathological size (Folkman, 1971, *PNAS* 76, 5217–5221; Wellstein & Czubayko, 1996, *Breast Cancer Res and Treatment* 38, 109–119). In addition, it allows tumor cells to travel through the circulatory system during metastasis. Increased levels of gene expression of a number of angiogenic factors such as vascular endothelial growth factor (VEGF) have been reported in vascularized and edema-associated brain tumors (Berkman et al., 1993 *J. Clin. Invest*. 91, 153). A more direct demostration of the role of VEGF in tumor angiogenesis was demonstrated by Jim Kim et al., 1993 *Nature* 362,841 wherein, monoclonal antibodies against VEGF were successfully used to inhibit the growth of rhabdomyosarcoma, glioblastoma multiforme cells in nude mice. Similarly, expression of a dominant negative mutated form of the flt-1 VEGF receptor inhibits vascularization induced by human glioblastoma cells in nude mice (Millauer et al., 1994, *Nature* 367, 576). Specific tumor/cancer types that can be targeted using the nucleic acid molecules of the invention include but are not limited to the tumor/cancer types described herein.

2) Ocular diseases: Neovascularization has been shown to cause or exacerbate ocular diseases including, but not limited to, macular degeneration, including age related macular degeneration (AMD), dry AMD, wet AMD, predominantly classic AMD (PD AMD), minimally classic AMD (MC AMD), and occult AMD; neovascular glaucoma, diabetic retinopathy, including diabetic macular edema (DME) and proliferative diabetic retinopathy; myopic degeneration, uveitis, and trachoma (Norrby, 1997, *APMIS* 105, 417–437). Aiello et al., 1994 *New Engl. J. Med*. 331, 1480, showed that the ocular fluid of a majority of patients suffering from diabetic retinopathy and other retinal disorders contains a high concentration of VEGF. Miller et al., 1994 *Am. J. Pathol*. 145, 574, reported elevated levels of VEGF mRNA in patients suffering from retinal ischemia. These observations support a direct role for VEGF in ocular diseases. Other factors, including those that stimulate VEGF synthesis, may also contribute to these indications.

3) Dermatological Disorders: Many indications have been identified which may beangiogenesis dependent, including but not limited to, psoriasis, verruca vulgaris, angiofibroma of tuberous sclerosis, pot-wine stains, Sturge Weber syndrome, Kippel-Trenaunay-Weber syndrome, and Osler-Weber-Rendu syndrome (Norrby, supra). Intradermal injection of the angiogenic factor b-FGF demonstrated angiogenesis in nude mice (Weckbecker et al., 1992, *Angiogenesis: Key principles-Science-Technology-Medicine*, ed R. Steiner). Detmar et al., 1994 *J. Exp. Med*. 180, 1141 reported that VEGF and its receptors were over-expressed in psoriatic skin and psoriatic dermal microvessels, suggesting that VEGF plays a significant role in psoriasis.

4) Rheumatoid arthritis: Immunohistochemistry and in situ hybridization studies on tissues from the joints of patients suffering from rheumatoid arthritis show an increased level of VEGF and its receptors (Fava et al., 1994 *J. Exp. Med*. 180, 341). Additionally, Koch et al., 1994 *J. Immunol*. 152, 4149, found that VEGF-specific antibodies were able to significantly reduce the mitogenic activity of synovial tissues from patients suffering from rheumatoid arthritis. These observations support a direct role for VEGF in rheumatoid arthritis. Other angiogenic factors including those of the present invention may also be involved in arthritis.

5) Endometriosis: Various studies indicate that VEGF is directly implicated in endometriosis. In one study, VEGF concentrations measured by ELISA in peritoneal fluid were found to be significantly higher in women with endometriosis than in women without endometriosis (24.1±15 ng/ml vs 13.3±7.2 ng/ml in normals). In patients with endometriosis, higher concentrations of VEGF were detected in the proliferative phase of the menstrual cycle (33±13 ng/ml) compared to the secretory phase (10.7±5 ng/ml). The cyclic variation was not noted in fluid from normal patients (McLaren et al., 1996, *Human Reprod.* 11, 220–223). In another study, women with moderate to severe endometriosis had significantly higher concentrations of peritoneal fluid VEGF than women without endometriosis. There was a positive correlation between the severity of endometriosis and the concentration of VEGF in peritoneal fluid. In human endometrial biopsies, VEGF expression increased relative to the early proliferative phase approximately 1.6-, 2-, and 3.6-fold in midproliferative, late proliferative, and secretory endometrium (Shifren et al., 1996, *J. Clin. Endocrinol. Metab.* 81, 3112–3118). In a third study, VEGF-positive staining of human ectopic endometrium was shown to be localized to macrophages (double immunofluorescent staining with CD 14 marker). Peritoneal fluid macrophages demonstrated VEGF staining in women with and without endometriosis. However, increased activation of macrophages (acid phosphatatse activity) was demonstrated in fluid from women with endometriosis compared with controls. Peritoneal fluid macrophage conditioned media from patients with endometriosis resulted in significantly increased cell proliferation ([³H] thymidine incorporation) in HUVEC cells compared to controls. The percentage of peritoneal fluid macrophages with VEGFR2 mRNA was higher during the secretory phase, and significantly higher in fluid from women with endometriosis (80±15%) compared with controls (32±20%). Flt-mRNA was detected in peritoneal fluid macrophages from women with and without endometriosis, but there was no difference between the groups or any evidence of cyclic dependence (McLaren et al., 1996, *J. Clin. Invest.* 98, 482–489). In the early proliferative phase of the menstrual cycle, VEGF has been found to be expressed in secretory columnar epithelium (estrogen-responsive) lining both the oviducts and the uterus in female mice. During the secretory phase, VEGF expression was shown to have shifted to the underlying stroma composing the functional endometrium. In addition to examining the endometium, neovascularization of ovarian follicles and the corpus luteum, as well as angiogenesis in embryonic implantation sites have been analyzed. For these processes, VEGF was expressed in spatial and temporal proximity to forming vasculature (Shweiki et al., 1993, *J. Clin. Invest.* 91, 2235–2243).

6) Kidney disease: Autosomal dominant polycystic kidney disease (ADPKD) is the most common life threatening hereditary disease in the USA. It affects about 1:400 to 1:1000 people and approximately 50% of people with ADPKD develop renal failure. ADPKD accounts for about 5–10% of end-stage renal failure in the USA, requiring dialysis and renal transplantation. Angiogenesis is implicated in the progression of ADPKD for growth of cyst cells, as well as increased vascular permeability promoting fluid secretion into cysts. Proliferation of cystic epithelium is a feature of ADPKD because cyst cells in culture produce soluble vascular endothelial growth factor (VEGF). VEGFR1 has been detected in epithelial cells of cystic tubules but not in endothelial cells in the vasculature of cystic kidneys or normal kidneys. VEGFR2 expression is increased in endothelial cells of cyst vessels and in endothelial cells during renal ischemia-reperfusion.

The use of radiation treatments and chemotherapeutics, such as Gemcytabine and cyclophosphamide, are non-limiting examples of chemotherapeutic agents that can be combined with or used in conjunction with the nucleic acid molecules (e.g. siNA molecules) of the instant invention. Those skilled in the art will recognize that other anti-cancer compounds and therapies can similarly be readily combined with the nucleic acid molecules of the instant invention (e.g. siNA molecules) and are hence within the scope of the instant invention. Such compounds and therapies are well known in the art (see for example *Cancer: Principles and Practice of Oncology*, Volumes 1 and 2, eds Devita, V. T., Hellman, S., and Rosenberg, S. A., J. B. Lippincott Company, Philadelphia, USA; incorporated herein by reference) and include, without limitation, folates, antifolates, pyrimidine analogs, fluoropyrimidines, purine analogs, adenosine analogs, topoisomerase I inhibitors, anthrapyrazoles, retinoids, antibiotics, anthacyclins, platinum analogs, alkylating agents, nitrosoureas, plant derived compounds such as vinca alkaloids, epipodophyllotoxins, tyrosine kinase inhibitors, taxols, radiation therapy, surgery, nutritional supplements, gene therapy, radiotherapy, for example 3D-CRT, immunotoxin therapy, for example ricin, and monoclonal antibodies. Specific examples of chemotherapeutic compounds that can be combined with or used in conjuction with the nucleic acid molecules of the invention include, but are not limited to, Paclitaxel; Docetaxel; Methotrexate; Doxorubin; Edatrexate; Vinorelbine; Tomaxifen; Leucovorin; 5-fluoro uridine (5-FU); Ionotecan; Cisplatin; Carboplatin; Amsacrine; Cytarabine; Bleomycin; Mitomycin C; Dactinomycin; Mithramycin; Hexamethylmelamine; Dacarbazine; L-asperginase; Nitrogen mustard; Melphalan, Chlorambucil; Busulfan; Ifosfamide; 4-hydroperoxycyclophosphamide; Thiotepa; Irinotecan (CAMPTOSAR®, CPT-11, Camptothecin-11, Campto) Tamoxifen; Herceptin; IMC C225; ABX-EGF; and combinations thereof. Non-limiting examples of therapies and compounds that can be used in combination with siNA molecules of the invention for ocular based diseases and conditions include submacular surgery, focal laser retinal photocoagulation, limited macular translocation surgery, retina and retinal pigment epithelial transplantation, retinal microchip prosthesis, feeder vessel CNVM laser photocoagulation, interferon alpha treatment, intravitreal steroid therapy, transpupillary thermotherapy, membrane differential filtration therapy, aptamers targeting VEGF (e.g., Macugen™) and/or VEGF receptors, antibodies targeting VEGF (e.g., Lucentis™) and/or VEGF receptors, Visudyne™ (e.g. use in photodynamic therapy, PDT), anti-imflammatory compounds such as Celebrex™ or anecortave acetate (e.g., Retaane™), angiostatic steroids such as glucocorticoids, intravitreal implants such as Posurdex™, FGF2 modulators, antiangiogenic compounds such as squalamine, and/or VEGF traps and other cytokine traps (see for example Economides et al., 2003, *Nature Medicine*, 9, 47–52). The above list of compounds are non-limiting examples of compounds and/or methods that can be combined with or used in conjunction with the nucleic acid molecules (e.g. siNA) of the instant invention. Those skilled in the art will recognize that other drug compounds and therapies can similarly be readily combined with the nucleic acid molecules of the instant invention (e.g., siNA molecules) are hence within the scope of the instant invention.

Example 12

Diagnostic Uses

The siNA molecules of the invention can be used in a variety of diagnostic applications, such as in the identification of molecular targets (e.g., RNA) in a variety of applications, for example, in clinical, industrial, environmental, agricultural and/or research settings. Such diagnostic use of siNA molecules involves utilizing reconstituted RNAi systems, for example, using cellular lysates or partially purified cellular lysates. siNA molecules of this invention can be used as diagnostic tools to examine genetic drift and mutations within diseased cells or to detect the presence of endogenous or exogenous, for example viral, RNA in a cell. The close relationship between siNA activity and the structure of the target RNA allows the detection of mutations in any region of the molecule, which alters the base-pairing and three-dimensional structure of the target RNA. By using multiple siNA molecules described in this invention, one can map nucleotide changes, which are important to RNA structure and function in vitro, as well as in cells and tissues. Cleavage of target RNAs with siNA molecules can be used to inhibit gene expression and define the role of specified gene products in the progression of disease or infection. In this manner, other genetic targets can be defined as important mediators of the disease. These experiments will lead to better treatment of the disease progression by affording the possibility of combination therapies (e.g., multiple siNA molecules targeted to different genes, siNA molecules coupled with known small molecule inhibitors, or intermittent treatment with combinations siNA molecules and/or other chemical or biological molecules). Other in vitro uses of siNA molecules of this invention are well known in the art, and include detection of the presence of mRNAs associated with a disease, infection, or related condition. Such RNA is detected by determining the presence of a cleavage product after treatment with a siNA using standard methodologies, for example, fluorescence resonance emission transfer (FRET).

In a specific example, siNA molecules that cleave only wild-type or mutant forms of the target RNA are used for the assay. The first siNA molecules (i.e., those that cleave only wild-type forms of target RNA) are used to identify wild-type RNA present in the sample and the second siNA molecules (i.e., those that cleave only mutant forms of target RNA) are used to identify mutant RNA in the sample. As reaction controls, synthetic substrates of both wild-type and mutant RNA are cleaved by both siNA molecules to demonstrate the relative siNA efficiencies in the reactions and the absence of cleavage of the "non-targeted" RNA species. The cleavage products from the synthetic substrates also serve to generate size markers for the analysis of wild-type and mutant RNAs in the sample population. Thus, each analysis requires two siNA molecules, two substrates and one unknown sample, which is combined into six reactions. The presence of cleavage products is determined using an RNase protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., disease related or infection related) is adequate to establish risk. If probes of comparable specific activity are used for both transcripts, then a qualitative comparison of RNA levels is adequate and decreases the cost of the initial diagnosis. Higher mutant form to wild-type ratios are correlated with higher risk whether RNA levels are compared qualitatively or quantitatively.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications can be made to the invention disclosed herein without departing from the scope and spirit of the invention. Thus, such additional embodiments are within the scope of the present invention and the following claims. The present invention teaches one skilled in the art to test various combinations and/or substitutions of chemical modifications described herein toward generating nucleic acid constructs with improved activity for mediating RNAi activity. Such improved activity can comprise improved stability, improved bioavailability, and/or improved activation of cellular responses mediating RNAi. Therefore, the specific embodiments described herein are not limiting and one skilled in the art can readily appreciate that specific combinations of the modifications described herein can be tested without undue experimentation toward identifying siNA molecules with improved RNAi activity.

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

TABLE I

VEGF and VEGFr Accession Numbers

NM_005429
*Homo sapiens* vascular endothelial growth factor C
(VEGFC), mRNA
gi|19924300|ref|NM_005429.2|[19924300]
NM_003376
*Homo sapiens* vascular endothelial growth factor
(VEGF), mRNA

TABLE I-continued

VEGF and VEGFr Accession Numbers gi|19923239|ref|NM_003376.2|[19923239]
AF095785
*Homo sapiens* vascular endothelial growth factor (VEGF)
gene, promoter region and
partial cds
gi|4154290|gb|AF095785.1|[4154290]
NM_003377
*Homo sapiens* vascular endothelial growth factor B
(VEGFB), mRNA
gi|20070172|ref|NM_003377.2|[20070172]
AF486837
*Homo sapiens* vascular endothelial growth factor
isoform VEGF165 (VEGF) mRNA,
complete cds
gi|19909064|gb|AF486837.1|[19909064]
AF468110
*Homo sapiens* vascular endothelial growth factor B
isoform (VEGFB) gene, complete
cds, alternatively spliced
gi|18766397|gb|AF468110.1|[18766397]
AF437895
*Homo sapiens* vascular endothelial growth factor (VEGF)
gene, partial cds
gi|16660685|gb|AF437895.1|AF437895[16660685]
AY047581
*Homo sapiens* vascular endothelial growth factor (VEGF)
mRNA, complete cds
gi|15422108|gb|AY047581.1|[15422108]
AF063657
*Homo sapiens* vascular endothelial growth factor
receptor (FLT1) mRNA, complete
cds
gi|3132830|gb|AF063657.1|AF063657[3132830]
AF092127
*Homo sapiens* vascular endothelial growth factor (VEGF)
gene, partial sequence
gi|4139168|gb|AF092127.1|AF092127[4139168]
AF092126
*Homo sapiens* vascular endothelial growth factor (VEGF)
gene, 5' UTR
gi|4139167|gb|AF092126.1|AF092126[4139167]
AF092125
*Homo sapiens* vascular endothelial growth factor (VEGF)
gene, partial cds
gi|4139165|gb|AF092125.1|AF092125[4139165]
E15157
Human VEGF mRNA
gi|5709840|dbj|E15157.1||pat|JP|1998052285|2[5709840]
E15156
Human VEGF mRNA
gi|5709839|dbj|E15156.1||pat|JP|1998052285|1[5709839]
E14233
Human mRNA for vascular endothelial growth factor
(VEGF), complete cds
gi|5708916|dbj|E14233.1||pat|JP|1997286795|1[5708916]
AF024710
*Homo sapiens* vascular endothelial growth factor (VEGF)
mRNA, 3'UTR
gi|2565322|gb|AF024710.1|AF024710[2565322]
AJ010438
*Homo sapiens* mRNA for vascular endothelial growth
factor, splicing variant
VEGF183
gi|3647280|emb|AJ010438.1|HSA010438[3647280]
AF098331
*Homo sapiens* vascular endothelial growth factor (VEGF)
gene, promoter, partial
sequence
gi|4235431|gb|AF098331.1|AF098331[4235431]
AF022375
*Homo sapiens* vascular endothelial growth factor mRNA,
complete cds
gi|13719220|gb|AF022375.1|AF022375[3719220]
AH006909
vascular endothelial growth factor {alternative
splicing} [human, Genomic, 414
nt 5 segments]

gi|1680143|gb|AH006909.1||bbm|191843[1680143]
U01134
Human soluble vascular endothelial cell growth factor
receptor (sflt) mRNA,
complete cds
gi|451321|gb|U01134.1|U01134[451321]
E14000
Human mRNA for FLT
gi|3252767|dbj|E14000.1||pat|JP|1997255700|1[3252767]
E13332
cDNA encoding vascular endodermal cell growth factor
VEGF
gi|3252137|dbj|E13332.1||pat|JP|1997173075|1[3252137]
E13256
Human mRNA for FLT, complete cds
gi|3252061|dbj|E13256.1||pat|JP|1997154588|1[3252061]
AF063658
*Homo sapiens* vascular endothelial growth factor
receptor 2 (KDR) mRNA, complete
cds
gi|3132832|gb|AF063658.1|AF063658[3132832]
AJ000185
*Homo sapiens* mRNA for vascular endothelial growth
factor-D
gi|2879833|emb|AJ000185.1|HSAJ185[2879833]
D89630
*Homo sapiens* mRNA for VEGF-D, complete cds
gi|2780339|dbj|D89630.1|[2780339]
AF035121
*Homo sapiens* KDR/flk-1 protein mRNA, complete cds
gi|2655411|gb|AF035121.1|AF035121[2655411]
AF020393
*Homo sapiens* vascular endothelial growth factor C
gene, partial cds and 5'
upstream region
gi|2582366|gb|AF020393.1|AF020393[2582366]
Y08736
*H. sapiens* vegf gene, 3'UTR
gi|1619596|emb|Y08736.1|HSVEGF3UT[1619596]
X62568
*H. sapiens* vegf gene for vascular endothelial growth
factor
gi|37658|emb|X62568.1|HSVEGF[37658]
X94216
*H. sapiens* mRNA for VEGF-C protein
gi|1177488|emb|X94216.1|HSVEGFC[1177488]
NM_002020
*Homo sapiens* fms-related tyrosine kinase 4 (FLT4),
mRNA
gi|4503752|ref|NM_002020.1|[4503752]
NM_002253
*Homo sapiens* kinase insert domain receptor (a type III
receptor tyrosine kinase)
(KDR), mRNA
gi|11321596|ref|NM_002253.1|[11321596]

TABLE II

VEGFr siNA and Target Sequences

| Pos | Target Sequence | Seq ID | UPos | Upper seq | Seq ID | LPos | Lower seq | Seq ID |
|---|---|---|---|---|---|---|---|---|
| | VEGFR1 gi|4503748|ref|NM_002019.1 | | | | | | | |
| 1 | GCGGACACUCCUCUCGGCU | 1 | 1 | GCGGACACUCCUCUCGGCU | 1 | 23 | AGCCGAGAGGAGUGUCCGC | 428 |
| 19 | UCCUCCCCGGCAGCGGCGG | 2 | 19 | UCCUCCCCGGCAGCGGCGG | 2 | 41 | CCGCCGCUGCCGGGGAGGA | 429 |
| 37 | GCGGCUCGGAGCGGGCUCC | 3 | 37 | GCGGCUCGGAGCGGGCUCC | 3 | 59 | GGAGCCCGCUCCGAGCCGC | 430 |
| 55 | CGGGGCUCGGGUGCAGCGG | 4 | 55 | CGGGGCUCGGGUGCAGCGG | 4 | 77 | CCGCUGCACCCGAGCCCCG | 431 |
| 73 | GCCAGCGGGCCUGGCGGCG | 5 | 73 | GCCAGCGGGCCUGGCGGCG | 5 | 95 | CGCCGCCAGGCCCGCUGGC | 432 |
| 91 | GAGGAUUACCCGGGGAAGU | 6 | 91 | GAGGAUUACCCGGGGAAGU | 6 | 113 | ACUUCCCCGGGUAAUCCUC | 433 |
| 109 | UGGUUGUCUCCUGGCUGGA | 7 | 109 | UGGUUGUCUCCUGGCUGGA | 7 | 131 | UCCAGCCAGGAGACAACCA | 434 |
| 127 | AGCCGCGAGACGGGCGCUC | 8 | 127 | AGCCGCGAGACGGGCGCUC | 8 | 149 | GAGCGCCCGUCUCGCGGCU | 435 |
| 145 | CAGGGCGCGGGGCCGGCGG | 9 | 145 | CAGGGCGCGGGGCCGGCGG | 9 | 167 | CCGCCGGCCCCGCGCCCUG | 436 |
| 163 | GCGGCGAACGAGAGGACGG | 10 | 163 | GCGGCGAACGAGAGGACGG | 10 | 185 | CCGUCCUCUCGUUCGCCGC | 437 |
| 181 | GACUCUGGCGGCCGGGUCG | 11 | 181 | GACUCUGGCGGCCGGGUCG | 11 | 203 | CGACCCGGCCGCCAGAGUC | 438 |
| 199 | GUUGGCCGGGGGAGCGCGG | 12 | 199 | GUUGGCCGGGGGAGCGCGG | 12 | 221 | CCGCGCUCCCCCGGCCAAC | 439 |
| 217 | GGCACCGGGCGAGCAGGCC | 13 | 217 | GGCACCGGGCGAGCAGGCC | 13 | 239 | GGCCUGCUCGCCCGGUGCC | 440 |
| 235 | CGCGUCGCGCUCACCAUGG | 14 | 235 | CGCGUCGCGCUCACCAUGG | 14 | 257 | CCAUGGUGAGCGCGACGCG | 441 |
| 253 | GUCAGCUACUGGGACACCG | 15 | 253 | GUCAGCUACUGGGACACCG | 15 | 275 | CGGUGUCCCAGUAGCUGAC | 442 |
| 271 | GGGGUCCUGCUGUGCGCGC | 16 | 271 | GGGGUCCUGCUGUGCGCGC | 16 | 293 | GCGCGCACAGCAGGACCCC | 443 |
| 289 | CUGCUCAGCUGUCUGCUUC | 17 | 289 | CUGCUCAGCUGUCUGCUUC | 17 | 311 | GAAGCAGACAGCUGAGCAG | 444 |
| 307 | CUCACAGGAUCUAGUUCAG | 18 | 307 | CUCACAGGAUCUAGUUCAG | 18 | 329 | CUGAACUAGAUCCUGUGAG | 445 |
| 325 | GGUUCAAAAUUAAAGAUC | 19 | 325 | GGUUCAAAAUUAAAGAUC | 19 | 347 | GAUCUUUAAUUUUGAACC | 446 |
| 343 | CCUGAACUGAGUUUAAAAG | 20 | 343 | CCUGAACUGAGUUUAAAAG | 20 | 365 | CUUUUAAACUCAGUUCAGG | 447 |
| 361 | GGCACCCAGCACAUCAUGC | 21 | 361 | GGCACCCAGCACAUCAUGC | 21 | 383 | GCAUGAUGUGCUGGGUGCC | 448 |
| 379 | CAAGCAGGCCAGACACUGC | 22 | 379 | CAAGCAGGCCAGACACUGC | 22 | 401 | GCAGUGUCUGGCCUGCUUG | 449 |
| 397 | CAUCUCCAAUGCAGGGGGG | 23 | 397 | CAUCUCCAAUGCAGGGGGG | 23 | 419 | CCCCCCUGCAUUGGAGAUG | 450 |
| 415 | GAAGCAGCCCAUAAAUGGU | 24 | 415 | GAAGCAGCCCAUAAAUGGU | 24 | 437 | ACCAUUUAUGGGCUGCUUC | 451 |
| 433 | UCUUUGCCUGAAAUGGUGA | 25 | 433 | UCUUUGCCUGAAAUGGUGA | 25 | 455 | UCACCAUUUCAGGCAAAGA | 452 |
| 451 | AGUAAGGAAAGCGAAAGGC | 26 | 451 | AGUAAGGAAAGCGAAAGGC | 26 | 473 | GCCUUUCGCUUUCCUUACU | 453 |
| 469 | CUGAGCAUAACUAAAUCUG | 27 | 469 | CUGAGCAUAACUAAAUCUG | 27 | 491 | CAGAUUUAGUUAUGCUCAG | 454 |
| 487 | GCCUGUGGAAGAAAUGGCA | 28 | 487 | GCCUGUGGAAGAAAUGGCA | 28 | 509 | UGCCAUUUCUUCCACAGGC | 455 |
| 505 | AAACAAUUCUGCAGUACUU | 29 | 505 | AAACAAUUCUGCAGUACUU | 29 | 527 | AAGUACUGCAGAAUUGUUU | 456 |
| 523 | UUAACCUUGAACACAGCUC | 30 | 523 | UUAACCUUGAACACAGCUC | 30 | 545 | GAGCUGUGUUCAAGGUUAA | 457 |
| 541 | CAAGCAAACCACACUGGCU | 31 | 541 | CAAGCAAACCACACUGGCU | 31 | 563 | AGCCAGUGUGGUUUGCUUG | 458 |
| 559 | UUCUACAGCUGCAAAUAUC | 32 | 559 | UUCUACAGCUGCAAAUAUC | 32 | 581 | GAUAUUUGCAGCUGUAGAA | 459 |
| 577 | CUAGCUGUACCUACUUCAA | 33 | 577 | CUAGCUGUACCUACUUCAA | 33 | 599 | UUGAAGUAGGUACAGCUAG | 460 |
| 595 | AAGAAGAAGGAAACAGAAU | 34 | 595 | AAGAAGAAGGAAACAGAAU | 34 | 617 | AUUCUGUUUCCUUCUUCUU | 461 |
| 613 | UCUGCAAUCUAUAUAUUUA | 35 | 613 | UCUGCAAUCUAUAUAUUUA | 35 | 635 | UAAAUAUAUAGAUUGCAGA | 462 |
| 631 | AUUAGUGAUACAGGUAGAC | 36 | 631 | AUUAGUGAUACAGGUAGAC | 36 | 653 | GUCUACCUGUAUCACUAAU | 463 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 649 | CCUUUCGUAGAGAUGUACA | 37 | 649 | CCUUUCGUAGAGAUGUACA | 37 | 671 | UGUACAUCUCUACGAAAGG | 464 |
| 667 | AGUGAAAUCCCCGAAAUUA | 38 | 667 | AGUGAAAUCCCCGAAAUUA | 38 | 689 | UAAUUUCGGGGAUUUCACU | 465 |
| 685 | AUACACAUGACUGAAGGAA | 39 | 685 | AUACACAUGACUGAAGGAA | 39 | 707 | UUCCUUCAGUCAUGUGUAU | 466 |
| 703 | AGGGAGCUCGUCAUUCCCU | 40 | 703 | AGGGAGCUCGUCAUUCCCU | 40 | 725 | AGGGAAUGACGAGCUCCCU | 467 |
| 721 | UGCCGGGUUACGUCACCUA | 41 | 721 | UGCCGGGUUACGUCACCUA | 41 | 743 | UAGGUGACGUAACCCGGCA | 468 |
| 739 | AACAUCACUGUUACUUUAA | 42 | 739 | AACAUCACUGUUACUUUAA | 42 | 761 | UUAAAGUAACAGUGAUGUU | 469 |
| 757 | AAAAGUUUCCACUUGACA | 43 | 757 | AAAAGUUUCCACUUGACA | 43 | 779 | UGUCAAGUGGAAACUUUUU | 470 |
| 775 | ACUUUGAUCCCUGAUGGAA | 44 | 775 | ACUUUGAUCCCUGAUGGAA | 44 | 797 | UUCCAUCAGGGAUCAAAGU | 471 |
| 793 | AAACGCAUAAUCUGGGACA | 45 | 793 | AAACGCAUAAUCUGGGACA | 45 | 815 | UGUCCCAGAUUAUGCGUUU | 472 |
| 811 | AGUAGAAAGGGCUUCAUCA | 46 | 811 | AGUAGAAAGGGCUUCAUCA | 46 | 833 | UGAUGAAGCCCUUUCUACU | 473 |
| 829 | AUAUCAAAUGCAACGUACA | 47 | 829 | AUAUCAAAUGCAACGUACA | 47 | 851 | UGUACGUUGCAUUUGAUAU | 474 |
| 847 | AAAGAAAUAGGGCUUCUGA | 48 | 847 | AAAGAAAUAGGGCUUCUGA | 48 | 869 | UCAGAAGCCCUAUUUCUUU | 475 |
| 865 | ACCUGUGAAGCAACAGUCA | 49 | 865 | ACCUGUGAAGCAACAGUCA | 49 | 887 | UGACUGUUGCUUCACAGGU | 476 |
| 883 | AAUGGGCAUUUGUAUAAGA | 50 | 883 | AAUGGGCAUUUGUAUAAGA | 50 | 905 | UCUUAUACAAAUGCCCAUU | 477 |
| 901 | ACAAACUAUCUCACACAUC | 51 | 901 | ACAAACUAUCUCACACAUC | 51 | 923 | GAUGUGUGAGAUAGUUUGU | 478 |
| 919 | CGACAAACCAAUACAAUCA | 52 | 919 | CGACAAACCAAUACAAUCA | 52 | 941 | UGAUUGUAUUGGUUUGUCG | 479 |
| 937 | AUAGAUGUCCAAAUAAGCA | 53 | 937 | AUAGAUGUCCAAAUAAGCA | 53 | 959 | UGCUUAUUUGGACAUCUAU | 480 |
| 955 | ACACCACGCCCAGUCAAAU | 54 | 955 | ACACCACGCCCAGUCAAAU | 54 | 977 | AUUUGACUGGGCGUGGUGU | 481 |
| 973 | UUACUUAGAGGCCAUACUC | 55 | 973 | UUACUUAGAGGCCAUACUC | 55 | 995 | GAGUAUGGCCUCUAAGUAA | 482 |
| 991 | CUUGUCCUCAAUUGUACUG | 56 | 991 | CUUGUCCUCAAUUGUACUG | 56 | 1013 | CAGUACAAUUGAGGACAAG | 483 |
| 1009 | GCUACCACUCCCUUGAACA | 57 | 1009 | GCUACCACUCCCUUGAACA | 57 | 1031 | UGUUCAAGGGAGUGGUAGC | 484 |
| 1027 | ACGAGAGUUCAAAUGACCU | 58 | 1027 | ACGAGAGUUCAAAUGACCU | 58 | 1049 | AGGUCAUUUGAACUCUCGU | 485 |
| 1045 | UGGAGUUACCCUGAUGAAA | 59 | 1045 | UGGAGUUACCCUGAUGAAA | 59 | 1067 | UUUCAUCAGGGUAACUCCA | 486 |
| 1063 | AAAAAUAAGAGAGCUUCCG | 60 | 1063 | AAAAAUAAGAGAGCUUCCG | 60 | 1085 | CGGAAGCUCUCUUAUUUUU | 487 |
| 1081 | GUAAGGCGACGAAUUGACC | 61 | 1081 | GUAAGGCGACGAAUUGACC | 61 | 1103 | GGUCAAUUCGUCGCCUUAC | 488 |
| 1099 | CAAAGCAAUUCCCAUGCCA | 62 | 1099 | CAAAGCAAUUCCCAUGCCA | 62 | 1121 | UGGCAUGGGAAUUGCUUUG | 489 |
| 1117 | AACAUAUUCUACAGUGUUC | 63 | 1117 | AACAUAUUCUACAGUGUUC | 63 | 1139 | GAACACUGUAGAAUAUGUU | 490 |
| 1135 | CUUACUAUUGACAAAAUGC | 64 | 1135 | CUUACUAUUGACAAAAUGC | 64 | 1157 | GCAUUUUGUCAAUAGUAAG | 491 |
| 1153 | CAGAACAAAGACAAAGGAC | 65 | 1153 | CAGAACAAAGACAAAGGAC | 65 | 1175 | GUCCUUUGUCUUUGUUCUG | 492 |
| 1171 | CUUUAUACUUGUCGUGUAA | 66 | 1171 | CUUUAUACUUGUCGUGUAA | 66 | 1193 | UUACACGACAAGUAUAAAG | 493 |
| 1189 | AGGAGUGGACCAUCAUUCA | 67 | 1189 | AGGAGUGGACCAUCAUUCA | 67 | 1211 | UGAAUGAUGGUCCACUCCU | 494 |
| 1207 | AAAUCUGUUAACACCUCAG | 68 | 1207 | AAAUCUGUUAACACCUCAG | 68 | 1229 | CUGAGGUGUUAACAGAUUU | 495 |
| 1225 | GUGCAUAUAUAUGAUAAAG | 69 | 1225 | GUGCAUAUAUAUGAUAAAG | 69 | 1247 | CUUUAUCAUAUAUGCAC | 496 |
| 1243 | GCAUUCAUCACUGUGAAAC | 70 | 1243 | GCAUUCAUCACUGUGAAAC | 70 | 1265 | GUUUCACAGUGAUGAAUGC | 497 |
| 1261 | CAUCGAAAACAGCAGGUGC | 71 | 1261 | CAUCGAAAACAGCAGGUGC | 71 | 1283 | GCACCUGCUGUUUUCGAUG | 498 |
| 1279 | CUUGAAACCGUAGCUGGCA | 72 | 1279 | CUUGAAACCGUAGCUGGCA | 72 | 1301 | UGCCAGCUACGGUUUCAAG | 499 |
| 1297 | AAGCGGUCUUACCGGCUCU | 73 | 1297 | AAGCGGUCUUACCGGCUCU | 73 | 1319 | AGAGCCGGUAAGACCGCUU | 500 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 1315 | UCUAUGAAAGUGAAGGCAU | 74 | 1315 | UCUAUGAAAGUGAAGGCAU | 74 | 1337 | AUGCCUUCACUUUCAUAGA | 501 |
| 1333 | UUUCCCUCGCCGGAAGUUG | 75 | 1333 | UUUCCCUCGCCGGAAGUUG | 75 | 1355 | CAACUUCCGGCGAGGGAAA | 502 |
| 1351 | GUAUGGUUAAAAGAUGGGU | 76 | 1351 | GUAUGGUUAAAAGAUGGGU | 76 | 1373 | ACCCAUCUUUUAACCAUAC | 503 |
| 1369 | UUACCUGCGACUGAGAAAU | 77 | 1369 | UUACCUGCGACUGAGAAAU | 77 | 1391 | AUUUCUCAGUCGCAGGUAA | 504 |
| 1387 | UCUGCUCGCUAUUUGACUC | 78 | 1387 | UCUGCUCGCUAUUUGACUC | 78 | 1409 | GAGUCAAAUAGCGAGCAGA | 505 |
| 1405 | CGUGGCUACUCGUUAAUUA | 79 | 1405 | CGUGGCUACUCGUUAAUUA | 79 | 1427 | UAAUUAACGAGUAGCCACG | 506 |
| 1423 | AUCAAGGACGUAACUGAAG | 80 | 1423 | AUCAAGGACGUAACUGAAG | 80 | 1445 | CUUCAGUUACGUCCUUGAU | 507 |
| 1441 | GAGGAUGCAGGGAAUUAUA | 81 | 1441 | GAGGAUGCAGGGAAUUAUA | 81 | 1463 | UAUAAUUCCCUGCAUCCUC | 508 |
| 1459 | ACAAUCUUGCUGAGCAUAA | 82 | 1459 | ACAAUCUUGCUGAGCAUAA | 82 | 1481 | UUAUGCUCAGCAAGAUUGU | 509 |
| 1477 | AAACAGUCAAAUGUGUUUA | 83 | 1477 | AAACAGUCAAAUGUGUUUA | 83 | 1499 | UAAACACAUUUGACUGUUU | 510 |
| 1495 | AAAAACCUCACUGCCACUC | 84 | 1495 | AAAAACCUCACUGCCACUC | 84 | 1517 | GAGUGGCAGUGAGGUUUUU | 511 |
| 1513 | CUAAUUGUCAAUGUGAAAC | 85 | 1513 | CUAAUUGUCAAUGUGAAAC | 85 | 1535 | GUUUCACAUUGACAAUUAG | 512 |
| 1531 | CCCCAGAUUUACGAAAAGG | 86 | 1531 | CCCCAGAUUUACGAAAAGG | 86 | 1553 | CCUUUUCGUAAAUCUGGGG | 513 |
| 1549 | GCCGUGUCAUCGUUUCCAG | 87 | 1549 | GCCGUGUCAUCGUUUCCAG | 87 | 1571 | CUGGAAACGAUGACACGGC | 514 |
| 1567 | GACCCGGCUCUCUACCCAC | 88 | 1567 | GACCCGGCUCUCUACCCAC | 88 | 1589 | GUGGGUAGAGAGCCGGGUC | 515 |
| 1585 | CUGGGCAGCAGACAAAUCC | 89 | 1585 | CUGGGCAGCAGACAAAUCC | 89 | 1607 | GGAUUUGUCUGCUGCCCAG | 516 |
| 1603 | CUGACUUGUACCGCAUAUG | 90 | 1603 | CUGACUUGUACCGCAUAUG | 90 | 1625 | CAUAUGCGGUACAAGUCAG | 517 |
| 1621 | GGUAUCCCUCAACCUACAA | 91 | 1621 | GGUAUCCCUCAACCUACAA | 91 | 1643 | UUGUAGGUUGAGGGAUACC | 518 |
| 1639 | AUCAAGUGGUUCUGGCACC | 92 | 1639 | AUCAAGUGGUUCUGGCACC | 92 | 1661 | GGUGCCAGAACCACUUGAU | 519 |
| 1657 | CCCUGUAACCAUAAUCAUU | 93 | 1657 | CCCUGUAACCAUAAUCAUU | 93 | 1679 | AAUGAUUAUGGUUACAGGG | 520 |
| 1675 | UCCGAAGCAAGGUGUGACU | 94 | 1675 | UCCGAAGCAAGGUGUGACU | 94 | 1697 | AGUCACACCUUGCUUCGGA | 521 |
| 1693 | UUUUGUUCCAAUAAUGAAG | 95 | 1693 | UUUUGUUCCAAUAAUGAAG | 95 | 1715 | CUUCAUUAUUGGAACAAAA | 522 |
| 1711 | GAGUCCUUUAUCCUGGAUG | 96 | 1711 | GAGUCCUUUAUCCUGGAUG | 96 | 1733 | CAUCCAGGAUAAAGGACUC | 523 |
| 1729 | GCUGACAGCAACAUGGGAA | 97 | 1729 | GCUGACAGCAACAUGGGAA | 97 | 1751 | UUCCCAUGUUGCUGUCAGC | 524 |
| 1747 | AACAGAAUUGAGAGCAUCA | 98 | 1747 | AACAGAAUUGAGAGCAUCA | 98 | 1769 | UGAUGCUCUCAAUUCUGUU | 525 |
| 1765 | ACUCAGCGCAUGGCAAUAA | 99 | 1765 | ACUCAGCGCAUGGCAAUAA | 99 | 1787 | UUAUUGCCAUGCGCUGAGU | 526 |
| 1783 | AUAGAAGGAAAGAAUAAGA | 100 | 1783 | AUAGAAGGAAAGAAUAAGA | 100 | 1805 | UCUUAUUCUUUCCUUCUAU | 527 |
| 1801 | AUGGCUAGCACCUUGGUUG | 101 | 1801 | AUGGCUAGCACCUUGGUUG | 101 | 1823 | CAACCAAGGUGCUAGCCAU | 528 |
| 1819 | GUGGCUGACUCUAGAAUUU | 102 | 1819 | GUGGCUGACUCUAGAAUUU | 102 | 1841 | AAAUUCUAGAGUCAGCCAC | 529 |
| 1837 | UCGGAAUCUACAUUUGCA | 103 | 1837 | UCGGAAUCUACAUUUGCA | 103 | 1859 | UGCAAAUGUAGAUUCCAGA | 530 |
| 1855 | AUAGCUUCCAAUAAAGUUG | 104 | 1855 | AUAGCUUCCAAUAAAGUUG | 104 | 1877 | CAACUUUAUUGGAAGCUAU | 531 |
| 1873 | GGGACUGUGGGAAGAAACA | 105 | 1873 | GGGACUGUGGGAAGAAACA | 105 | 1895 | UGUUUCUUCCCACAGUCCC | 532 |
| 1891 | AUAAGCUUUUAUAUCACAG | 106 | 1891 | AUAAGCUUUUAUAUCACAG | 106 | 1913 | CUGUGAUAUAAAAGCUUAU | 533 |
| 1909 | GAUGUGCCAAAUGGGUUUC | 107 | 1909 | GAUGUGCCAAAUGGGUUUC | 107 | 1931 | GAAACCCAUUUGGCACAUC | 534 |
| 1927 | CAUGUUAACUUGGAAAAAA | 108 | 1927 | CAUGUUAACUUGGAAAAAA | 108 | 1949 | UUUUUUCCAAGUUAACAUG | 535 |
| 1945 | AUGCCGACGGAAGGAGAGG | 109 | 1945 | AUGCCGACGGAAGGAGAGG | 109 | 1967 | CCUCUCCUUCCGUCGGCAU | 536 |
| 1963 | GACCUGAAACUGUCUUGCA | 110 | 1963 | GACCUGAAACUGUCUUGCA | 110 | 1985 | UGCAAGACAGUUUCAGGUC | 537 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 1981 | ACAGUUAACAAGUUCUUAU | 111 | 1981 | ACAGUUAACAAGUUCUUAU | 111 | 2003 | AUAAGAACUUGUUAACUGU | 538 |
| 1999 | UACAGAGACGUUACUUGGA | 112 | 1999 | UACAGAGACGUUACUUGGA | 112 | 2021 | UCCAAGUAACGUCUCUGUA | 539 |
| 2017 | AUUUUACUGCGGACAGUUA | 113 | 2017 | AUUUUACUGCGGACAGUUA | 113 | 2039 | UAACUGUCCGCAGUAAAAU | 540 |
| 2035 | AAUAACAGAACAAUGCACU | 114 | 2035 | AAUAACAGAACAAUGCACU | 114 | 2057 | AGUGCAUUGUUCUGUUAUU | 541 |
| 2053 | UACAGUAUUAGCAAGCAAA | 115 | 2053 | UACAGUAUUAGCAAGCAAA | 115 | 2075 | UUUGCUUGCUAAUACUGUA | 542 |
| 2071 | AAAAUGGCCAUCACUAAGG | 116 | 2071 | AAAAUGGCCAUCACUAAGG | 116 | 2093 | CCUUAGUGAUGGCCAUUUU | 543 |
| 2089 | GAGCACUCCAUCACUCUUA | 117 | 2089 | GAGCACUCCAUCACUCUUA | 117 | 2111 | UAAGAGUGAUGGAGUGCUC | 544 |
| 2107 | AAUCUUACCAUCAUGAAUG | 118 | 2107 | AAUCUUACCAUCAUGAAUG | 118 | 2129 | CAUUCAUGAUGGUAAGAUU | 545 |
| 2125 | GUUUCCUGCAAGAUUCAG | 119 | 2125 | GUUUCCUGCAAGAUUCAG | 119 | 2147 | CUGAAUCUUGCAGGGAAAC | 546 |
| 2143 | GGCACCUAUGCCUGCAGAG | 120 | 2143 | GGCACCUAUGCCUGCAGAG | 120 | 2165 | CUCUGCAGGCAUAGGUGCC | 547 |
| 2161 | GCCAGGAAUGUAUACACAG | 121 | 2161 | GCCAGGAAUGUAUACACAG | 121 | 2183 | CUGUGUAUACAUUCCUGGC | 548 |
| 2179 | GGGGAAGAAAUCCUCCAGA | 122 | 2179 | GGGGAAGAAAUCCUCCAGA | 122 | 2201 | UCUGGAGGAUUUCUUCCCC | 549 |
| 2197 | AAGAAAGAAAUUACAAUCA | 123 | 2197 | AAGAAAGAAAUUACAAUCA | 123 | 2219 | UGAUUGUAAUUUCUUUCUU | 550 |
| 2215 | AGAGAUCAGGAAGCACCAU | 124 | 2215 | AGAGAUCAGGAAGCACCAU | 124 | 2237 | AUGGUGCUUCCUGAUCUCU | 551 |
| 2233 | UACCUCCUGCGAAACCUCA | 125 | 2233 | UACCUCCUGCGAAACCUCA | 125 | 2255 | UGAGGUUUCGCAGGAGGUA | 552 |
| 2251 | AGUGAUCACACAGUGGCCA | 126 | 2251 | AGUGAUCACACAGUGGCCA | 126 | 2273 | UGGCCACUGUGUGAUCACU | 553 |
| 2269 | AUCAGCAGUUCCACCACUU | 127 | 2269 | AUCAGCAGUUCCACCACUU | 127 | 2291 | AAGUGGUGGAACUGCUGAU | 554 |
| 2287 | UUAGACUGUCAUGCUAAUG | 128 | 2287 | UUAGACUGUCAUGCUAAUG | 128 | 2309 | CAUUAGCAUGACAGUCUAA | 555 |
| 2305 | GGUGUCCCCGAGCCUCAGA | 129 | 2305 | GGUGUCCCCGAGCCUCAGA | 129 | 2327 | UCUGAGGCUCGGGGACACC | 556 |
| 2323 | AUCACUUGGUUUAAAAACA | 130 | 2323 | AUCACUUGGUUUAAAAACA | 130 | 2345 | UGUUUUUAAACCAAGUGAU | 557 |
| 2341 | AACCACAAAAUACAACAAG | 131 | 2341 | AACCACAAAAUACAACAAG | 131 | 2363 | CUUGUUGUAUUUUGUGGUU | 558 |
| 2359 | GAGCCUGGAAUUAUUUUAG | 132 | 2359 | GAGCCUGGAAUUAUUUUAG | 132 | 2381 | CUAAAAUAAUUCCAGGCUC | 559 |
| 2377 | GGACCAGGAAGCAGCACGC | 133 | 2377 | GGACCAGGAAGCAGCACGC | 133 | 2399 | GCGUGCUGCUUCCUGGUCC | 560 |
| 2395 | CUGUUUAUUGAAAGAGUCA | 134 | 2395 | CUGUUUAUUGAAAGAGUCA | 134 | 2417 | UGACUCUUUCAAUAAACAG | 561 |
| 2413 | ACAGAAGAGGAUGAAGGUG | 135 | 2413 | ACAGAAGAGGAUGAAGGUG | 135 | 2435 | CACCUUCAUCCUCUUCUGU | 562 |
| 2431 | GUCUAUCACUGCAAAGCCA | 136 | 2431 | GUCUAUCACUGCAAAGCCA | 136 | 2453 | UGGCUUUGCAGUGAUAGAC | 563 |
| 2449 | ACCAACCAGAAGGGCUCUG | 137 | 2449 | ACCAACCAGAAGGGCUCUG | 137 | 2471 | CAGAGCCCUUCUGGUUGGU | 564 |
| 2467 | GUGGAAAGUUCAGCAUACC | 138 | 2467 | GUGGAAAGUUCAGCAUACC | 138 | 2489 | GGUAUGCUGAACUUUCCAC | 565 |
| 2485 | CUCACUGUUCAAGGAACCU | 139 | 2485 | CUCACUGUUCAAGGAACCU | 139 | 2507 | AGGUUCCUUGAACAGUGAG | 566 |
| 2503 | UCGGACAAGUCUAAUCUGG | 140 | 2503 | UCGGACAAGUCUAAUCUGG | 140 | 2525 | CCAGAUUAGACUUGUCCGA | 567 |
| 2521 | GAGCUGAUCACUCUAACAU | 141 | 2521 | GAGCUGAUCACUCUAACAU | 141 | 2543 | AUGUUAGAGUGAUCAGCUC | 568 |
| 2539 | UGCACCUGUGUGGCUGCGA | 142 | 2539 | UGCACCUGUGUGGCUGCGA | 142 | 2561 | UCGCAGCCACACAGGUGCA | 569 |
| 2557 | ACUCUCUUCUGGCUCCUAU | 143 | 2557 | ACUCUCUUCUGGCUCCUAU | 143 | 2579 | AUAGGAGCCAGAAGAGAGU | 570 |
| 2575 | UUAACCCUCCUUAUCCGAA | 144 | 2575 | UUAACCCUCCUUAUCCGAA | 144 | 2597 | UUCGGAUAAGGAGGGUUAA | 571 |
| 2593 | AAAAUGAAAAGGUCUUCUU | 145 | 2593 | AAAAUGAAAAGGUCUUCUU | 145 | 2615 | AAGAAGACCUUUUCAUUUU | 572 |
| 2611 | UCUGAAAUAAAGACUGACU | 146 | 2611 | UCUGAAAUAAAGACUGACU | 146 | 2633 | AGUCAGUCUUUAUUUCAGA | 573 |
| 2629 | UACCUAUCAAUUAUAAUGG | 147 | 2629 | UACCUAUCAAUUAUAAUGG | 147 | 2651 | CCAUUAUAAUUGAUAGGUA | 574 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 2647 | GACCCAGAUGAAGUUCCUU | 148 | 2647 | GACCCAGAUGAAGUUCCUU | 148 | 2669 | AAGGAACUUCAUCUGGGUC | 575 |
| 2665 | UUGGAUGAGCAGUGUGAGC | 149 | 2665 | UUGGAUGAGCAGUGUGAGC | 149 | 2687 | GCUCACACUGCUCAUCCAA | 576 |
| 2683 | CGGCUCCCUUAUGAUGCCA | 150 | 2683 | CGGCUCCCUUAUGAUGCCA | 150 | 2705 | UGGCAUCAUAAGGGAGCCG | 577 |
| 2701 | AGCAAGUGGGAGUUUGCCC | 151 | 2701 | AGCAAGUGGGAGUUUGCCC | 151 | 2723 | GGGCAAACUCCCACUUGCU | 578 |
| 2719 | CGGGAGAGACUUAAACUGG | 152 | 2719 | CGGGAGAGACUUAAACUGG | 152 | 2741 | CCAGUUUAAGUCUCUCCCG | 579 |
| 2737 | GGCAAAUCACUUGGAAGAG | 153 | 2737 | GGCAAAUCACUUGGAAGAG | 153 | 2759 | CUCUUCCAAGUGAUUUGCC | 580 |
| 2755 | GGGGCUUUUGGAAAAGUGG | 154 | 2755 | GGGGCUUUUGGAAAAGUGG | 154 | 2777 | CCACUUUUCCAAAAGCCCC | 581 |
| 2773 | GUUCAAGCAUCAGCAUUUG | 155 | 2773 | GUUCAAGCAUCAGCAUUUG | 155 | 2795 | CAAAUGCUGAUGCUUGAAC | 582 |
| 2791 | GGCAUUAAGAAAUCACCUA | 156 | 2791 | GGCAUUAAGAAAUCACCUA | 156 | 2813 | UAGGUGAUUUCUUAAUGCC | 583 |
| 2809 | ACGUGCCGGACUGUGGCUG | 157 | 2809 | ACGUGCCGGACUGUGGCUG | 157 | 2831 | CAGCCACAGUCCGGCACGU | 584 |
| 2827 | GUGAAAAUGCUGAAAGAGG | 158 | 2827 | GUGAAAAUGCUGAAAGAGG | 158 | 2849 | CCUCUUUCAGCAUUUUCAC | 585 |
| 2845 | GGGGCCACGGCCAGCGAGU | 159 | 2845 | GGGGCCACGGCCAGCGAGU | 159 | 2867 | ACUCGCUGGCCGUGGCCCC | 586 |
| 2863 | UACAAAGCUCUGAUGACUG | 160 | 2863 | UACAAAGCUCUGAUGACUG | 160 | 2885 | CAGUCAUCAGAGCUUUGUA | 587 |
| 2881 | GAGCUAAAAAUCUUGACCC | 161 | 2881 | GAGCUAAAAAUCUUGACCC | 161 | 2903 | GGGUCAAGAUUUUUAGCUC | 588 |
| 2899 | CACAUUGGCCACCAUCUGA | 162 | 2899 | CACAUUGGCCACCAUCUGA | 162 | 2921 | UCAGAUGGUGGCCAAUGUG | 589 |
| 2917 | AACGUGGUUAACCUGCUGG | 163 | 2917 | AACGUGGUUAACCUGCUGG | 163 | 2939 | CCAGCAGGUUAACCACGUU | 590 |
| 2935 | GGAGCCUGCACCAAGCAAG | 164 | 2935 | GGAGCCUGCACCAAGCAAG | 164 | 2957 | CUUGCUUGGUGCAGGCUCC | 591 |
| 2953 | GGAGGGCCUCUGAUGGUGA | 165 | 2953 | GGAGGGCCUCUGAUGGUGA | 165 | 2975 | UCACCAUCAGAGGCCCUCC | 592 |
| 2971 | AUUGUUGAAUACUGCAAAU | 166 | 2971 | AUUGUUGAAUACUGCAAAU | 166 | 2993 | AUUUGCAGUAUUCAACAAU | 593 |
| 2989 | UAUGGAAAUCUCUCCAACU | 167 | 2989 | UAUGGAAAUCUCUCCAACU | 167 | 3011 | AGUUGGAGAGAUUUCCAUA | 594 |
| 3007 | UACCUCAAGAGCAAACGUG | 168 | 3007 | UACCUCAAGAGCAAACGUG | 168 | 3029 | CACGUUUGCUCUUGAGGUA | 595 |
| 3025 | GACUUAUUUUUUCUCAACA | 169 | 3025 | GACUUAUUUUUUCUCAACA | 169 | 3047 | UGUUGAGAAAAAAUAAGUC | 596 |
| 3043 | AAGGAUGCAGCACUACACA | 170 | 3043 | AAGGAUGCAGCACUACACA | 170 | 3065 | UGUGUAGUGCUGCAUCCUU | 597 |
| 3061 | AUGGAGCCUAAGAAAGAAA | 171 | 3061 | AUGGAGCCUAAGAAAGAAA | 171 | 3083 | UUUCUUUCUUAGGCUCCAU | 598 |
| 3079 | AAAAUGGAGCCAGGCCUGG | 172 | 3079 | AAAAUGGAGCCAGGCCUGG | 172 | 3101 | CCAGGCCUGGCUCCAUUUU | 599 |
| 3097 | GAACAAGGCAAGAAACCAA | 173 | 3097 | GAACAAGGCAAGAAACCAA | 173 | 3119 | UUGGUUUCUUGCCUUGUUC | 600 |
| 3115 | AGACUAGAUAGCGUCACCA | 174 | 3115 | AGACUAGAUAGCGUCACCA | 174 | 3137 | UGGUGACGCUAUCUAGUCU | 601 |
| 3133 | AGCAGCGAAAGCUUUGCGA | 175 | 3133 | AGCAGCGAAAGCUUUGCGA | 175 | 3155 | UCGCAAAGCUUUCGCUGCU | 602 |
| 3151 | AGCUCCGGCUUUCAGGAAG | 176 | 3151 | AGCUCCGGCUUUCAGGAAG | 176 | 3173 | CUUCCUGAAAGCCGGAGCU | 603 |
| 3169 | GAUAAAAGUCUGAGUGAUG | 177 | 3169 | GAUAAAAGUCUGAGUGAUG | 177 | 3191 | CAUCACUCAGACUUUUAUC | 604 |
| 3187 | GUUGAGGAAGAGGAGGAUU | 178 | 3187 | GUUGAGGAAGAGGAGGAUU | 178 | 3209 | AAUCCUCCUCUUCCUCAAC | 605 |
| 3205 | UCUGACGGUUUCUACAAGG | 179 | 3205 | UCUGACGGUUUCUACAAGG | 179 | 3227 | CCUUGUAGAAACCGUCAGA | 606 |
| 3223 | GAGCCCAUCACUAUGGAAG | 180 | 3223 | GAGCCCAUCACUAUGGAAG | 180 | 3245 | CUUCCAUAGUGAUGGGCUC | 607 |
| 3241 | GAUCUGAUUUCUUACAGUU | 181 | 3241 | GAUCUGAUUUCUUACAGUU | 181 | 3263 | AACUGUAAGAAAUCAGAUC | 608 |
| 3259 | UUUCAAGUGGCCAGAGGCA | 182 | 3259 | UUUCAAGUGGCCAGAGGCA | 182 | 3281 | UGCCUCUGGCCACUUGAAA | 609 |
| 3277 | AUGGAGUUCCUGUCUUCCA | 183 | 3277 | AUGGAGUUCCUGUCUUCCA | 183 | 3299 | UGGAAGACAGGAACUCCAU | 610 |
| 3295 | AGAAAGUGCAUUCAUCGGG | 184 | 3295 | AGAAAGUGCAUUCAUCGGG | 184 | 3317 | CCCGAUGAAUGCACUUUCU | 611 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 3313 | GACCUGGCAGCGAGAAACA | 185 | 3313 | GACCUGGCAGCGAGAAACA | 185 | 3335 | UGUUUCUCGCUGCCAGGUC | 612 |
| 3331 | AUUCUUUUAUCUGAGAACA | 186 | 3331 | AUUCUUUUAUCUGAGAACA | 186 | 3353 | UGUUCUCAGAUAAAAGAAU | 613 |
| 3349 | AACGUGGUGAAGAUUUGUG | 187 | 3349 | AACGUGGUGAAGAUUUGUG | 187 | 3371 | CACAAAUCUUCACCACGUU | 614 |
| 3367 | GAUUUUGGCCUUGCCCGGG | 188 | 3367 | GAUUUUGGCCUUGCCCGGG | 188 | 3389 | CCCGGGCAAGGCCAAAAUC | 615 |
| 3385 | GAUAUUUAUAAGAACCCCG | 189 | 3385 | GAUAUUUAUAAGAACCCCG | 189 | 3407 | CGGGGUUCUUAUAAAUAUC | 616 |
| 3403 | GAUUAUGUGAGAAAAGGAG | 190 | 3403 | GAUUAUGUGAGAAAAGGAG | 190 | 3425 | CUCCUUUUCUCACAUAAUC | 617 |
| 3421 | GAUACUCGACUUCCUCUGA | 191 | 3421 | GAUACUCGACUUCCUCUGA | 191 | 3443 | UCAGAGGAAGUCGAGUAUC | 618 |
| 3439 | AAAUGGAUGGCUCCCGAAU | 192 | 3439 | AAAUGGAUGGCUCCCGAAU | 192 | 3461 | AUUCGGGAGCCAUCCAUUU | 619 |
| 3457 | UCUAUCUUUGACAAAAUCU | 193 | 3457 | UCUAUCUUUGACAAAAUCU | 193 | 3479 | AGAUUUUGUCAAAGAUAGA | 620 |
| 3475 | UACAGCACCAAGAGCGACG | 194 | 3475 | UACAGCACCAAGAGCGACG | 194 | 3497 | CGUCGCUCUUGGUGCUGUA | 621 |
| 3493 | GUGUGGUCUUACGGAGUAU | 195 | 3493 | GUGUGGUCUUACGGAGUAU | 195 | 3515 | AUACUCCGUAAGACCACAC | 622 |
| 3511 | UUGCUGUGGGAAAUCUUCU | 196 | 3511 | UUGCUGUGGGAAAUCUUCU | 196 | 3533 | AGAAGAUUUCCCACAGCAA | 623 |
| 3529 | UCCUUAGGUGGGUCUCCAU | 197 | 3529 | UCCUUAGGUGGGUCUCCAU | 197 | 3551 | AUGGAGACCCACCUAAGGA | 624 |
| 3547 | UACCCAGGAGUACAAAUGG | 198 | 3547 | UACCCAGGAGUACAAAUGG | 198 | 3569 | CCAUUUGUACUCCUGGGUA | 625 |
| 3565 | GAUGAGGACUUUUGCAGUC | 199 | 3565 | GAUGAGGACUUUUGCAGUC | 199 | 3587 | GACUGCAAAAGUCCUCAUC | 626 |
| 3583 | CGCCUGAGGGAAGGCAUGA | 200 | 3583 | CGCCUGAGGGAAGGCAUGA | 200 | 3605 | UCAUGCCUUCCCUCAGGCG | 627 |
| 3601 | AGGAUGAGAGCUCCUGAGU | 201 | 3601 | AGGAUGAGAGCUCCUGAGU | 201 | 3623 | ACUCAGGAGCUCUCAUCCU | 628 |
| 3619 | UACUCUACUCCUGAAAUCU | 202 | 3619 | UACUCUACUCCUGAAAUCU | 202 | 3641 | AGAUUUCAGGAGUAGAGUA | 629 |
| 3637 | UAUCAGAUCAUGCUGGACU | 203 | 3637 | UAUCAGAUCAUGCUGGACU | 203 | 3659 | AGUCCAGCAUGAUCUGAUA | 630 |
| 3655 | UGCUGGCACAGAGACCCAA | 204 | 3655 | UGCUGGCACAGAGACCCAA | 204 | 3677 | UUGGGUCUCUGUGCCAGCA | 631 |
| 3673 | AAAGAAAGGCCAAGAUUUG | 205 | 3673 | AAAGAAAGGCCAAGAUUUG | 205 | 3695 | CAAAUCUUGGCCUUUCUUU | 632 |
| 3691 | GCAGAACUUGUGGAAAAAC | 206 | 3691 | GCAGAACUUGUGGAAAAAC | 206 | 3713 | GUUUUUCCACAAGUUCUGC | 633 |
| 3709 | CUAGGUGAUUUGCUUCAAG | 207 | 3709 | CUAGGUGAUUUGCUUCAAG | 207 | 3731 | CUUGAAGCAAAUCACCUAG | 634 |
| 3727 | GCAAAUGUACAACAGGAUG | 208 | 3727 | GCAAAUGUACAACAGGAUG | 208 | 3749 | CAUCCUGUUGUACAUUUGC | 635 |
| 3745 | GGUAAAGACUACAUCCCAA | 209 | 3745 | GGUAAAGACUACAUCCCAA | 209 | 3767 | UUGGGAUGUAGUCUUUACC | 636 |
| 3763 | AUCAAUGCCAUACUGACAG | 210 | 3763 | AUCAAUGCCAUACUGACAG | 210 | 3785 | CUGUCAGUAUGGCAUUGAU | 637 |
| 3781 | GGAAAUAGUGGGUUUACAU | 211 | 3781 | GGAAAUAGUGGGUUUACAU | 211 | 3803 | AUGUAAACCCACUAUUUCC | 638 |
| 3799 | UACUCAACUCCUGCCUUCU | 212 | 3799 | UACUCAACUCCUGCCUUCU | 212 | 3821 | AGAAGGCAGGAGUUGAGUA | 639 |
| 3817 | UCUGAGGACUUCUUCAAGG | 213 | 3817 | UCUGAGGACUUCUUCAAGG | 213 | 3839 | CCUUGAAGAAGUCCUCAGA | 640 |
| 3835 | GAAAGUAUUUCAGCUCCGA | 214 | 3835 | GAAAGUAUUUCAGCUCCGA | 214 | 3857 | UCGGAGCUGAAAUACUUUC | 641 |
| 3853 | AAGUUUAAUUCAGGAAGCU | 215 | 3853 | AAGUUUAAUUCAGGAAGCU | 215 | 3875 | AGCUUCCUGAAUUAAACUU | 642 |
| 3871 | UCUGAUGAUGUCAGAUAUG | 216 | 3871 | UCUGAUGAUGUCAGAUAUG | 216 | 3893 | CAUAUCUGACAUCAUCAGA | 643 |
| 3889 | GUAAAUGCUUUCAAGUUCA | 217 | 3889 | GUAAAUGCUUUCAAGUUCA | 217 | 3911 | UGAACUUGAAAGCAUUUAC | 644 |
| 3907 | AUGAGCCUGGAAAGAAUCA | 218 | 3907 | AUGAGCCUGGAAAGAAUCA | 218 | 3929 | UGAUUCUUUCCAGGCUCAU | 645 |
| 3925 | AAAACCUUUGAAGAACUUU | 219 | 3925 | AAAACCUUUGAAGAACUUU | 219 | 3947 | AAAGUUCUUCAAAGGUUUU | 646 |
| 3943 | UUACCGAAUGCCACCUCCA | 220 | 3943 | UUACCGAAUGCCACCUCCA | 220 | 3965 | UGGAGGUGGCAUUCGGUAA | 647 |
| 3961 | AUGUUUGAUGACUACCAGG | 221 | 3961 | AUGUUUGAUGACUACCAGG | 221 | 3983 | CCUGGUAGUCAUCAAACAU | 648 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 3979 | GGCGACAGCAGCACUCUGU | 222 | 3979 | GGCGACAGCAGCACUCUGU | 222 | 4001 | ACAGAGUGCUGCUGUCGCC | 649 |
| 3997 | UUGGCCUCUCCCAUGCUGA | 223 | 3997 | UUGGCCUCUCCCAUGCUGA | 223 | 4019 | UCAGCAUGGGAGAGGCCAA | 650 |
| 4015 | AAGCGCUUCACCUGGACUG | 224 | 4015 | AAGCGCUUCACCUGGACUG | 224 | 4037 | CAGUCCAGGUGAAGCGCUU | 651 |
| 4033 | GACAGCAAACCCAAGGCCU | 225 | 4033 | GACAGCAAACCCAAGGCCU | 225 | 4055 | AGGCCUUGGGUUUGCUGUC | 652 |
| 4051 | UCGCUCAAGAUUGACUUGA | 226 | 4051 | UCGCUCAAGAUUGACUUGA | 226 | 4073 | UCAAGUCAAUCUUGAGCGA | 653 |
| 4069 | AGAGUAACCAGUAAAAGUA | 227 | 4069 | AGAGUAACCAGUAAAAGUA | 227 | 4091 | UACUUUUACUGGUUACUCU | 654 |
| 4087 | AAGGAGUCGGGCUGUCUG | 228 | 4087 | AAGGAGUCGGGCUGUCUG | 228 | 4109 | CAGACAGCCCCGACUCCUU | 655 |
| 4105 | GAUGUCAGCAGGCCCAGUU | 229 | 4105 | GAUGUCAGCAGGCCCAGUU | 229 | 4127 | AACUGGGCCUGCUGACAUC | 656 |
| 4123 | UUCUGCCAUUCCAGCUGUG | 230 | 4123 | UUCUGCCAUUCCAGCUGUG | 230 | 4145 | CACAGCUGGAAUGGCAGAA | 657 |
| 4141 | GGGCACGUCAGCGAAGGCA | 231 | 4141 | GGGCACGUCAGCGAAGGCA | 231 | 4163 | UGCCUUCGCUGACGUGCCC | 658 |
| 4159 | AAGCGCAGGUUCACCUACG | 232 | 4159 | AAGCGCAGGUUCACCUACG | 232 | 4181 | CGUAGGUGAACCUGCGCUU | 659 |
| 4177 | GACCACGCUGAGCUGGAAA | 233 | 4177 | GACCACGCUGAGCUGGAAA | 233 | 4199 | UUUCCAGCUCAGCGUGGUC | 660 |
| 4195 | AGGAAAAUCGCGUGCUGCU | 234 | 4195 | AGGAAAAUCGCGUGCUGCU | 234 | 4217 | AGCAGCACGCGAUUUUCCU | 661 |
| 4213 | UCCCCGCCCCCAGACUACA | 235 | 4213 | UCCCCGCCCCCAGACUACA | 235 | 4235 | UGUAGUCUGGGGGCGGGGA | 662 |
| 4231 | AACUCGGUGGUCCUGUACU | 236 | 4231 | AACUCGGUGGUCCUGUACU | 236 | 4253 | AGUACAGGACCACCGAGUU | 663 |
| 4249 | UCCACCCCACCCAUCUAGA | 237 | 4249 | UCCACCCCACCCAUCUAGA | 237 | 4271 | UCUAGAUGGGUGGGGUGGA | 664 |
| 4267 | AGUUUGACACGAAGCCUUA | 238 | 4267 | AGUUUGACACGAAGCCUUA | 238 | 4289 | UAAGGCUUCGUGUCAAACU | 665 |
| 4285 | AUUUCUAGAAGCACAUGUG | 239 | 4285 | AUUUCUAGAAGCACAUGUG | 239 | 4307 | CACAUGUGCUUCUAGAAAU | 666 |
| 4303 | GUAUUUAUACCCCCAGGAA | 240 | 4303 | GUAUUUAUACCCCCAGGAA | 240 | 4325 | UUCCUGGGGGUAUAAAUAC | 667 |
| 4321 | AACUAGCUUUUGCCAGUAU | 241 | 4321 | AACUAGCUUUUGCCAGUAU | 241 | 4343 | AUACUGGCAAAAGCUAGUU | 668 |
| 4339 | UUAUGCAUAUAUAAGUUUA | 242 | 4339 | UUAUGCAUAUAUAAGUUUA | 242 | 4361 | UAAACUUAUAUAUGCAUAA | 669 |
| 4357 | ACACCUUUAUCUUUCCAUG | 243 | 4357 | ACACCUUUAUCUUUCCAUG | 243 | 4379 | CAUGGAAAGAUAAAGGUGU | 670 |
| 4375 | GGGAGCCAGCUGCUUUUUG | 244 | 4375 | GGGAGCCAGCUGCUUUUUG | 244 | 4397 | CAAAAAGCAGCUGGCUCCC | 671 |
| 4393 | GUGAUUUUUUUAAUAGCGC | 245 | 4393 | GUGAUUUUUUUAAUAGCGC | 245 | 4415 | GCACUAUUAAAAAAAUCAC | 672 |
| 4411 | CUUUUUUUUUUUGACUAAC | 246 | 4411 | CUUUUUUUUUUUGACUAAC | 246 | 4433 | GUUAGUCAAAAAAAAAAAG | 673 |
| 4429 | CAAGAAUGUAACUCCAGAU | 247 | 4429 | CAAGAAUGUAACUCCAGAU | 247 | 4451 | AUCUGGAGUUACAUUCUUG | 674 |
| 4447 | UAGAGAAAUAGUGACAAGU | 248 | 4447 | UAGAGAAAUAGUGACAAGU | 248 | 4469 | ACUUGUCACUAUUUCUCUA | 675 |
| 4465 | UGAAGAACACUACUGCUAA | 249 | 4465 | UGAAGAACACUACUGCUAA | 249 | 4487 | UUAGCAGUAGUGUUCUUCA | 676 |
| 4483 | AAUCCUCAUGUUACUCAGU | 250 | 4483 | AAUCCUCAUGUUACUCAGU | 250 | 4505 | ACUGAGUAACAUGAGGAUU | 677 |
| 4501 | UGUUAGAGAAAUCCUUCCU | 251 | 4501 | UGUUAGAGAAAUCCUUCCU | 251 | 4523 | AGGAAGGAUUUCUCUAACA | 678 |
| 4519 | UAAACCCAAUGACUUCCCU | 252 | 4519 | UAAACCCAAUGACUUCCCU | 252 | 4541 | AGGGAAGUCAUUGGGUUUA | 679 |
| 4537 | UGCUCCAACCCCGCCACC | 253 | 4537 | UGCUCCAACCCCGCCACC | 253 | 4559 | GGUGGCGGGGUUGGAGCA | 680 |
| 4555 | CUCAGGGCACGCAGGACCA | 254 | 4555 | CUCAGGGCACGCAGGACCA | 254 | 4577 | UGGUCCUGCGUGCCCUGAG | 681 |
| 4573 | AGUUUGAUUGAGGAGCUGC | 255 | 4573 | AGUUUGAUUGAGGAGCUGC | 255 | 4595 | GCAGCUCCUCAAUCAAACU | 682 |
| 4591 | CACUGAUCACCCAAUGCAU | 256 | 4591 | CACUGAUCACCCAAUGCAU | 256 | 4613 | AUGCAUUGGGUGAUCAGUG | 683 |
| 4609 | UCACGUACCCCACUGGGCC | 257 | 4609 | UCACGUACCCCACUGGGCC | 257 | 4631 | GGCCCAGUGGGGUACGUGA | 684 |
| 4627 | CAGCCCUGCAGCCCAAAAC | 258 | 4627 | CAGCCCUGCAGCCCAAAAC | 258 | 4649 | GUUUUGGGCUGCAGGGCUG | 685 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 4645 | CCCAGGGCAACAAGCCCGU | 259 | 4645 | CCCAGGGCAACAAGCCCGU | 259 | 4667 | ACGGGCUUGUUGCCCUGGG | 686 |
| 4663 | UUAGCCCCAGGGGAUCACU | 260 | 4663 | UUAGCCCCAGGGGAUCACU | 260 | 4685 | AGUGAUCCCCUGGGGCUAA | 687 |
| 4681 | UGGCUGGCCUGAGCAACAU | 261 | 4681 | UGGCUGGCCUGAGCAACAU | 261 | 4703 | AUGUUGCUCAGGCCAGCCA | 688 |
| 4699 | UCUCGGGAGUCCUCUAGCA | 262 | 4699 | UCUCGGGAGUCCUCUAGCA | 262 | 4721 | UGCUAGAGGACUCCCGAGA | 689 |
| 4717 | AGGCCUAAGACAUGUGAGG | 263 | 4717 | AGGCCUAAGACAUGUGAGG | 263 | 4739 | CCUCACAUGUCUUAGGCCU | 690 |
| 4735 | GAGGAAAAGGAAAAAAAGC | 264 | 4735 | GAGGAAAAGGAAAAAAAGC | 264 | 4757 | GCUUUUUUUCCUUUUCCUC | 691 |
| 4753 | CAAAAAGCAAGGGAGAAAA | 265 | 4753 | CAAAAAGCAAGGGAGAAAA | 265 | 4775 | UUUUCUCCCUUGCUUUUUG | 692 |
| 4771 | AGAGAAACCGGGAGAAGGC | 266 | 4771 | AGAGAAACCGGGAGAAGGC | 266 | 4793 | GCCUUCUCCCGGUUUCUCU | 693 |
| 4789 | CAUGAGAAAGAAUUUGAGA | 267 | 4789 | CAUGAGAAAGAAUUUGAGA | 267 | 4811 | UCUCAAAUUCUUUCUCAUG | 694 |
| 4807 | ACGCACCAUGUGGGCACGG | 268 | 4807 | ACGCACCAUGUGGGCACGG | 268 | 4829 | CCGUGCCCACAUGGUGCGU | 695 |
| 4825 | GAGGGGACGGGGCUCAGC | 269 | 4825 | GAGGGGACGGGGCUCAGC | 269 | 4847 | GCUGAGCCCCGUCCCCUC | 696 |
| 4843 | CAAUGCCAUUUCAGUGGCU | 270 | 4843 | CAAUGCCAUUUCAGUGGCU | 270 | 4865 | AGCCACUGAAAUGGCAUUG | 697 |
| 4861 | UUCCCAGCUCUGACCCUUC | 271 | 4861 | UUCCCAGCUCUGACCCUUC | 271 | 4883 | GAAGGGUCAGAGCUGGGAA | 698 |
| 4879 | CUACAUUUGAGGGCCCAGC | 272 | 4879 | CUACAUUUGAGGGCCCAGC | 272 | 4901 | GCUGGGCCCUCAAAUGUAG | 699 |
| 4897 | CCAGGAGCAGAUGGACAGC | 273 | 4897 | CCAGGAGCAGAUGGACAGC | 273 | 4919 | GCUGUCCAUCUGCUCCUGG | 700 |
| 4915 | CGAUGAGGGGACAUUUUCU | 274 | 4915 | CGAUGAGGGGACAUUUUCU | 274 | 4937 | AGAAAAUGUCCCCUCAUCG | 701 |
| 4933 | UGGAUUCUGGGAGGCAAGA | 275 | 4933 | UGGAUUCUGGGAGGCAAGA | 275 | 4955 | UCUUGCCUCCCAGAAUCCA | 702 |
| 4951 | AAAAGGACAAAUAUCUUUU | 276 | 4951 | AAAAGGACAAAUAUCUUUU | 276 | 4973 | AAAAGAUAUUUGUCCUUUU | 703 |
| 4969 | UUUGGAACUAAAGCAAAUU | 277 | 4969 | UUUGGAACUAAAGCAAAUU | 277 | 4991 | AAUUUGCUUUAGUUCCAAA | 704 |
| 4987 | UUUAGACCUUUACCUAUGG | 278 | 4987 | UUUAGACCUUUACCUAUGG | 278 | 5009 | CCAUAGGUAAAGGUCUAAA | 705 |
| 5005 | GAAGUGGUUCUAUGUCCAU | 279 | 5005 | GAAGUGGUUCUAUGUCCAU | 279 | 5027 | AUGGACAUAGAACCACUUC | 706 |
| 5023 | UUCUCAUUCGUGGCAUGUU | 280 | 5023 | UUCUCAUUCGUGGCAUGUU | 280 | 5045 | AACAUGCCACGAAUGAGAA | 707 |
| 5041 | UUUGAUUUGUAGCACUGAG | 281 | 5041 | UUUGAUUUGUAGCACUGAG | 281 | 5063 | CUCAGUGCUACAAAUCAAA | 708 |
| 5059 | GGGUGGCACUCAACUCUGA | 282 | 5059 | GGGUGGCACUCAACUCUGA | 282 | 5081 | UCAGAGUUGAGUGCCACCC | 709 |
| 5077 | AGCCCAUACUUUUGGCUCC | 283 | 5077 | AGCCCAUACUUUUGGCUCC | 283 | 5099 | GGAGCCAAAAGUAUGGGCU | 710 |
| 5095 | CUCUAGUAAGAUGCACUGA | 284 | 5095 | CUCUAGUAAGAUGCACUGA | 284 | 5117 | UCAGUGCAUCUUACUAGAG | 711 |
| 5113 | AAAACUUAGCCAGAGUUAG | 285 | 5113 | AAAACUUAGCCAGAGUUAG | 285 | 5135 | CUAACUCUGGCUAAGUUUU | 712 |
| 5131 | GGUUGUCUCCAGGCCAUGA | 286 | 5131 | GGUUGUCUCCAGGCCAUGA | 286 | 5153 | UCAUGGCCUGGAGACAACC | 713 |
| 5149 | AUGGCCUUACACUGAAAAU | 287 | 5149 | AUGGCCUUACACUGAAAAU | 287 | 5171 | AUUUUCAGUGUAAGGCCAU | 714 |
| 5167 | UGUCACAUUCUAUUUUGGG | 288 | 5167 | UGUCACAUUCUAUUUUGGG | 288 | 5189 | CCCAAAAUAGAAUGUGACA | 715 |
| 5185 | GUAUUAAUAUAUAGUCCAG | 289 | 5185 | GUAUUAAUAUAUAGUCCAG | 289 | 5207 | CUGGACUAUAUAUUAAUAC | 716 |
| 5203 | GACACUUAACUCAAUUUCU | 290 | 5203 | GACACUUAACUCAAUUUCU | 290 | 5225 | AGAAAUUGAGUUAAGUGUC | 717 |
| 5221 | UUGGUAUUAUUCUGUUUUG | 291 | 5221 | UUGGUAUUAUUCUGUUUUG | 291 | 5243 | CAAAACAGAAUAAUACCAA | 718 |
| 5239 | GCACAGUUAGUUGUGAAAG | 292 | 5239 | GCACAGUUAGUUGUGAAAG | 292 | 5261 | CUUUCACAACUAACUGUGC | 719 |
| 5257 | GAAAGCUGAGAAGAAUGAA | 293 | 5257 | GAAAGCUGAGAAGAAUGAA | 293 | 5279 | UUCAUUCUUCUCAGCUUUC | 720 |
| 5275 | AAAUGCAGUCCUGAGGAGA | 294 | 5275 | AAAUGCAGUCCUGAGGAGA | 294 | 5297 | UCUCCUCAGGACUGCAUUU | 721 |
| 5293 | AGUUUCUCCAUAUCAAAA | 295 | 5293 | AGUUUCUCCAUAUCAAAA | 295 | 5315 | UUUUGAUAUGGAGAAACU | 722 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 5311 | ACGAGGGCUGAUGGAGGAA | 296 | 5311 | ACGAGGGCUGAUGGAGGAA | 296 | 5333 | UUCCUCCAUCAGCCCUCGU | 723 |
| 5329 | AAAAGGUCAAUAAGGUCAA | 297 | 5329 | AAAAGGUCAAUAAGGUCAA | 297 | 5351 | UUGACCUUAUUGACCUUUU | 724 |
| 5347 | AGGGAAGACCCCGUCUCUA | 298 | 5347 | AGGGAAGACCCCGUCUCUA | 298 | 5369 | UAGAGACGGGGUCUUCCCU | 725 |
| 5365 | AUACCAACCAAACCAAUUC | 299 | 5365 | AUACCAACCAAACCAAUUC | 299 | 5387 | GAAUUGGUUUGGUUGGUAU | 726 |
| 5383 | CACCAACACAGUUGGGACC | 300 | 5383 | CACCAACACAGUUGGGACC | 300 | 5405 | GGUCCCAACUGUGUUGGUG | 727 |
| 5401 | CCAAAACACAGGAAGUCAG | 301 | 5401 | CCAAAACACAGGAAGUCAG | 301 | 5423 | CUGACUUCCUGUGUUUUGG | 728 |
| 5419 | GUCACGUUUCCUUUUCAUU | 302 | 5419 | GUCACGUUUCCUUUUCAUU | 302 | 5441 | AAUGAAAAGGAAACGUGAC | 729 |
| 5437 | UUAAUGGGGAUUCCACUAU | 303 | 5437 | UUAAUGGGGAUUCCACUAU | 303 | 5459 | AUAGUGGAAUCCCCAUUAA | 730 |
| 5455 | UCUCACACUAAUCUGAAAG | 304 | 5455 | UCUCACACUAAUCUGAAAG | 304 | 5477 | CUUUCAGAUUAGUGUGAGA | 731 |
| 5473 | GGAUGUGGAAGAGCAUUAG | 305 | 5473 | GGAUGUGGAAGAGCAUUAG | 305 | 5495 | CUAAUGCUCUUCCACAUCC | 732 |
| 5491 | GCUGGCGCAUAUUAAGCAC | 306 | 5491 | GCUGGCGCAUAUUAAGCAC | 306 | 5513 | GUGCUUAAUAUGCGCCAGC | 733 |
| 5509 | CUUUAAGCUCCUUGAGUAA | 307 | 5509 | CUUUAAGCUCCUUGAGUAA | 307 | 5531 | UUACUCAAGGAGCUUAAAG | 734 |
| 5527 | AAAAGGUGGUAUGUAAUUU | 308 | 5527 | AAAAGGUGGUAUGUAAUUU | 308 | 5549 | AAAUUACAUACCACCUUUU | 735 |
| 5545 | UAUGCAAGGUAUUUCUCCA | 309 | 5545 | UAUGCAAGGUAUUUCUCCA | 309 | 5567 | UGGAGAAAUACCUUGCAUA | 736 |
| 5563 | AGUUGGGACUCAGGAUAUU | 310 | 5563 | AGUUGGGACUCAGGAUAUU | 310 | 5585 | AAUAUCCUGAGUCCCAACU | 737 |
| 5581 | UAGUUAAUGAGCCAUCACU | 311 | 5581 | UAGUUAAUGAGCCAUCACU | 311 | 5603 | AGUGAUGGCUCAUUAACUA | 738 |
| 5599 | UAGAAGAAAAGCCCAUUUU | 312 | 5599 | UAGAAGAAAAGCCCAUUUU | 312 | 5621 | AAAAUGGGCUUUUCUUCUA | 739 |
| 5617 | UCAACUGCUUUGAAACUUG | 313 | 5617 | UCAACUGCUUUGAAACUUG | 313 | 5639 | CAAGUUUCAAAGCAGUUGA | 740 |
| 5635 | GCCUGGGGUCUGAGCAUGA | 314 | 5635 | GCCUGGGGUCUGAGCAUGA | 314 | 5657 | UCAUGCUCAGACCCCAGGC | 741 |
| 5653 | AUGGGAAUAGGGAGACAGG | 315 | 5653 | AUGGGAAUAGGGAGACAGG | 315 | 5675 | CCUGUCUCCCUAUUCCCAU | 742 |
| 5671 | GGUAGGAAAGGGCGCCUAC | 316 | 5671 | GGUAGGAAAGGGCGCCUAC | 316 | 5693 | GUAGGCGCCCUUUCCUACC | 743 |
| 5689 | CUCUUCAGGGUCUAAAGAU | 317 | 5689 | CUCUUCAGGGUCUAAAGAU | 317 | 5711 | AUCUUUAGACCCUGAAGAG | 744 |
| 5707 | UCAAGUGGGCCUUGGAUCG | 318 | 5707 | UCAAGUGGGCCUUGGAUCG | 318 | 5729 | CGAUCCAAGGCCCACUUGA | 745 |
| 5725 | GCUAAGCUGGCUCUGUUUG | 319 | 5725 | GCUAAGCUGGCUCUGUUUG | 319 | 5747 | CAAACAGAGCCAGCUUAGC | 746 |
| 5743 | GAUGCUAUUUAUGCAAGUU | 320 | 5743 | GAUGCUAUUUAUGCAAGUU | 320 | 5765 | AACUUGCAUAAAUAGCAUC | 747 |
| 5761 | UAGGGUCUAUGUAUUUAGG | 321 | 5761 | UAGGGUCUAUGUAUUUAGG | 321 | 5783 | CCUAAAUACAUAGACCCUA | 748 |
| 5779 | GAUGCGCCUACUCUUCAGG | 322 | 5779 | GAUGCGCCUACUCUUCAGG | 322 | 5801 | CCUGAAGAGUAGGCGCAUC | 749 |
| 5797 | GGUCUAAAGAUCAAGUGGG | 323 | 5797 | GGUCUAAAGAUCAAGUGGG | 323 | 5819 | CCCACUUGAUCUUUAGACC | 750 |
| 5815 | GCCUUGGAUCGCUAAGCUG | 324 | 5815 | GCCUUGGAUCGCUAAGCUG | 324 | 5837 | CAGCUUAGCGAUCCAAGGC | 751 |
| 5833 | GGCUCUGUUUGAUGCUAUU | 325 | 5833 | GGCUCUGUUUGAUGCUAUU | 325 | 5855 | AAUAGCAUCAAACAGAGCC | 752 |
| 5851 | UUAUGCAAGUUAGGGUCUA | 326 | 5851 | UUAUGCAAGUUAGGGUCUA | 326 | 5873 | UAGACCCUAACUUGCAUAA | 753 |
| 5869 | AUGUAUUUAGGAUGUCGC | 327 | 5869 | AUGUAUUUAGGAUGUCGC | 327 | 5891 | GCAGACAUCCUAAAUACAU | 754 |
| 5887 | CACCUUCUGCAGCCAGUCA | 328 | 5887 | CACCUUCUGCAGCCAGUCA | 328 | 5909 | UGACUGGCUGCAGAAGGUG | 755 |
| 5905 | AGAAGCUGGAGAGGCAACA | 329 | 5905 | AGAAGCUGGAGAGGCAACA | 329 | 5927 | UGUUGCCUCUCCAGCUUCU | 756 |
| 5923 | AGUGGAUUGCUGCUUCUUG | 330 | 5923 | AGUGGAUUGCUGCUUCUUG | 330 | 5945 | CAAGAAGCAGCAAUCCACU | 757 |
| 5941 | GGGGAGAAGAGUAUGCUUC | 331 | 5941 | GGGGAGAAGAGUAUGCUUC | 331 | 5963 | GAAGCAUACUCUUCUCCCC | 758 |
| 5959 | CCUUUUAUCCAUGUAAUUU | 332 | 5959 | CCUUUUAUCCAUGUAAUUU | 332 | 5981 | AAAUUACAUGGAUAAAAGG | 759 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 5977 | UAACUGUAGAACCUGAGCU | 333 | 5977 | UAACUGUAGAACCUGAGCU | 333 | 5999 | AGCUCAGGUUCUACAGUUA | 760 |
| 5995 | UCUAAGUAACCGAAGAAUG | 334 | 5995 | UCUAAGUAACCGAAGAAUG | 334 | 6017 | CAUUCUUCGGUUACUUAGA | 761 |
| 6013 | GUAUGCCUCUGUUCUUAUG | 335 | 6013 | GUAUGCCUCUGUUCUUAUG | 335 | 6035 | CAUAAGAACAGAGGCAUAC | 762 |
| 6031 | GUGCCACAUCCUUGUUUAA | 336 | 6031 | GUGCCACAUCCUUGUUUAA | 336 | 6053 | UUAAACAAGGAUGUGGCAC | 763 |
| 6049 | AAGGCUCUCUGUAUGAAGA | 337 | 6049 | AAGGCUCUCUGUAUGAAGA | 337 | 6071 | UCUUCAUACAGAGAGCCUU | 764 |
| 6067 | AGAUGGGACCGUCAUCAGC | 338 | 6067 | AGAUGGGACCGUCAUCAGC | 338 | 6089 | GCUGAUGACGGUCCCAUCU | 765 |
| 6085 | CACAUUCCCUAGUGAGCCU | 339 | 6085 | CACAUUCCCUAGUGAGCCU | 339 | 6107 | AGGCUCACUAGGGAAUGUG | 766 |
| 6103 | UACUGGCUCCUGGCAGCGG | 340 | 6103 | UACUGGCUCCUGGCAGCGG | 340 | 6125 | CCGCUGCCAGGAGCCAGUA | 767 |
| 6121 | GCUUUUGUGGAAGACUCAC | 341 | 6121 | GCUUUUGUGGAAGACUCAC | 341 | 6143 | GUGAGUCUUCCACAAAAGC | 768 |
| 6139 | CUAGCCAGAAGAGAGGAGU | 342 | 6139 | CUAGCCAGAAGAGAGGAGU | 342 | 6161 | ACUCCUCUCUUCUGGCUAG | 769 |
| 6157 | UGGGACAGUCCUCUCCACC | 343 | 6157 | UGGGACAGUCCUCUCCACC | 343 | 6179 | GGUGGAGAGGACUGUCCCA | 770 |
| 6175 | CAAGAUCUAAAUCCAAACA | 344 | 6175 | CAAGAUCUAAAUCCAAACA | 344 | 6197 | UGUUUGGAUUUAGAUCUUG | 771 |
| 6193 | AAAAGCAGGCUAGAGCCAG | 345 | 6193 | AAAAGCAGGCUAGAGCCAG | 345 | 6215 | CUGGCUCUAGCCUGCUUUU | 772 |
| 6211 | GAAGAGAGGACAAAUCUUU | 346 | 6211 | GAAGAGAGGACAAAUCUUU | 346 | 6233 | AAAGAUUUGUCCUCUCUUC | 773 |
| 6229 | UGUUGUUCCUCUUCUUUAC | 347 | 6229 | UGUUGUUCCUCUUCUUUAC | 347 | 6251 | GUAAAGAAGAGGAACAACA | 774 |
| 6247 | CACAUACGCAAACCACCUG | 348 | 6247 | CACAUACGCAAACCACCUG | 348 | 6269 | CAGGUGGUUUGCGUAUGUG | 775 |
| 6265 | GUGACAGCUGGCAAUUUUA | 349 | 6265 | GUGACAGCUGGCAAUUUUA | 349 | 6287 | UAAAAUUGCCAGCUGUCAC | 776 |
| 6283 | AUAAAUCAGGUAACUGGAA | 350 | 6283 | AUAAAUCAGGUAACUGGAA | 350 | 6305 | UUCCAGUUACCUGAUUUAU | 777 |
| 6301 | AGGAGGUUAAACUCAGAAA | 351 | 6301 | AGGAGGUUAAACUCAGAAA | 351 | 6323 | UUUCUGAGUUUAACCUCCU | 778 |
| 6319 | AAAAGAAGACCUCAGUCAA | 352 | 6319 | AAAAGAAGACCUCAGUCAA | 352 | 6341 | UUGACUGAGGUCUUCUUUU | 779 |
| 6337 | AUUCUCUACUUUUUUUUUU | 353 | 6337 | AUUCUCUACUUUUUUUUUU | 353 | 6359 | AAAAAAAAAAGUAGAGAAU | 780 |
| 6355 | UUUUUUUCCAAAUCAGAUA | 354 | 6355 | UUUUUUUCCAAAUCAGAUA | 354 | 6377 | UAUCUGAUUUGGAAAAAAA | 781 |
| 6373 | AAUAGCCCAGCAAAUAGUG | 355 | 6373 | AAUAGCCCAGCAAAUAGUG | 355 | 6395 | CACUAUUUGCUGGGCUAUU | 782 |
| 6391 | GAUAACAAAUAAAACCUUA | 356 | 6391 | GAUAACAAAUAAAACCUUA | 356 | 6413 | UAAGGUUUUAUUUGUUAUC | 783 |
| 6409 | AGCUGUUCAUGUCUUGAUU | 357 | 6409 | AGCUGUUCAUGUCUUGAUU | 357 | 6431 | AAUCAAGACAUGAACAGCU | 784 |
| 6427 | UUCAAUAAUUAAUUCUAA | 358 | 6427 | UUCAAUAAUUAAUUCUAA | 358 | 6449 | UUAAGAAUUAAUUAUUGAA | 785 |
| 6445 | AUCAUUAAGAGACCAUAAU | 359 | 6445 | AUCAUUAAGAGACCAUAAU | 359 | 6467 | AUUAUGGUCUCUUAAUGAU | 786 |
| 6463 | UAAAUACUCCUUUUCAAGA | 360 | 6463 | UAAAUACUCCUUUUCAAGA | 360 | 6485 | UCUUGAAAAGGAGUAUUUA | 787 |
| 6481 | AGAAAAGCAAAACCAUUAG | 361 | 6481 | AGAAAAGCAAAACCAUUAG | 361 | 6503 | CUAAUGGUUUUGCUUUUCU | 788 |
| 6499 | GAAUUGUUACUCAGCUCCU | 362 | 6499 | GAAUUGUUACUCAGCUCCU | 362 | 6521 | AGGAGCUGAGUAACAAUUC | 789 |
| 6517 | UUCAAACUCAGGUUUGUAG | 363 | 6517 | UUCAAACUCAGGUUUGUAG | 363 | 6539 | CUACAAACCUGAGUUUGAA | 790 |
| 6535 | GCAUACAUGAGUCCAUCCA | 364 | 6535 | GCAUACAUGAGUCCAUCCA | 364 | 6557 | UGGAUGGACUCAUGUAUGC | 791 |
| 6553 | AUCAGUCAAAGAAUGGUUC | 365 | 6553 | AUCAGUCAAAGAAUGGUUC | 365 | 6575 | GAACCAUUCUUUGACUGAU | 792 |
| 6571 | CCAUCUGGAGUCUUAAUGU | 366 | 6571 | CCAUCUGGAGUCUUAAUGU | 366 | 6593 | ACAUUAAGACUCCAGAUGG | 793 |
| 6589 | UAGAAAGAAAAAUGGAGAC | 367 | 6589 | UAGAAAGAAAAAUGGAGAC | 367 | 6611 | GUCUCCAUUUUUCUUUCUA | 794 |
| 6607 | CUUGUAAUAAUGAGCUAGU | 368 | 6607 | CUUGUAAUAAUGAGCUAGU | 368 | 6629 | ACUAGCUCAUUAUUACAAG | 795 |
| 6625 | UUACAAAGUGCUUGUUCAU | 369 | 6625 | UUACAAAGUGCUUGUUCAU | 369 | 6647 | AUGAACAAGCACUUUGUAA | 796 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 6643 | UUAAAAUAGCACUGAAAAU | 370 | 6643 | UUAAAAUAGCACUGAAAAU | 370 | 6665 | AUUUUCAGUGCUAUUUUAA | 797 |
| 6661 | UUGAAACAUGAAUUAACUG | 371 | 6661 | UUGAAACAUGAAUUAACUG | 371 | 6683 | CAGUUAAUUCAUGUUUCAA | 798 |
| 6679 | GAUAAUAUUCCAAUCAUUU | 372 | 6679 | GAUAAUAUUCCAAUCAUUU | 372 | 6701 | AAAUGAUUGGAAUAUUAUC | 799 |
| 6697 | UGCCAUUUAUGACAAAAAU | 373 | 6697 | UGCCAUUUAUGACAAAAAU | 373 | 6719 | AUUUUUGUCAUAAAUGGCA | 800 |
| 6715 | UGGUUGGCACUAACAAAGA | 374 | 6715 | UGGUUGGCACUAACAAAGA | 374 | 6737 | UCUUUGUUAGUGCCAACCA | 801 |
| 6733 | AACGAGCACUUCCUUUCAG | 375 | 6733 | AACGAGCACUUCCUUUCAG | 375 | 6755 | CUGAAAGGAAGUGCUCGUU | 802 |
| 6751 | GAGUUUCUGAGAUAAUGUA | 376 | 6751 | GAGUUUCUGAGAUAAUGUA | 376 | 6773 | UACAUUAUCUCAGAAACUC | 803 |
| 6769 | ACGUGGAACAGUCUGGGUG | 377 | 6769 | ACGUGGAACAGUCUGGGUG | 377 | 6791 | CACCCAGACUGUUCCACGU | 804 |
| 6787 | GGAAUGGGGCUGAAACCAU | 378 | 6787 | GGAAUGGGGCUGAAACCAU | 378 | 6809 | AUGGUUUCAGCCCCAUUCC | 805 |
| 6805 | UGUGCAAGUCUGUGUCUUG | 379 | 6805 | UGUGCAAGUCUGUGUCUUG | 379 | 6827 | CAAGACACAGACUUGCACA | 806 |
| 6823 | GUCAGUCCAAGAAGUGACA | 380 | 6823 | GUCAGUCCAAGAAGUGACA | 380 | 6845 | UGUCACUUCUUGGACUGAC | 807 |
| 6841 | ACCGAGAUGUUAAUUUUAG | 381 | 6841 | ACCGAGAUGUUAAUUUUAG | 381 | 6863 | CUAAAAUUAACAUCUCGGU | 808 |
| 6859 | GGGACCCGUGCCUUGUUUC | 382 | 6859 | GGGACCCGUGCCUUGUUUC | 382 | 6881 | GAAACAAGGCACGGGUCCC | 809 |
| 6877 | CCUAGCCCACAAGAAUGCA | 383 | 6877 | CCUAGCCCACAAGAAUGCA | 383 | 6899 | UGCAUUCUUGUGGGCUAGG | 810 |
| 6895 | AAACAUCAAACAGAUACUC | 384 | 6895 | AAACAUCAAACAGAUACUC | 384 | 6917 | GAGUAUCUGUUUGAUGUUU | 811 |
| 6913 | CGCUAGCCUCAUUUAAAUU | 385 | 6913 | CGCUAGCCUCAUUUAAAUU | 385 | 6935 | AAUUUAAAUGAGGCUAGCG | 812 |
| 6931 | UGAUUAAAGGAGGAGCA | 386 | 6931 | UGAUUAAAGGAGGAGCA | 386 | 6953 | UGCACUCCUCCUUUAAUCA | 813 |
| 6949 | AUCUUUGGCCGACAGUGGU | 387 | 6949 | AUCUUUGGCCGACAGUGGU | 387 | 6971 | ACCACUGUCGGCCAAAGAU | 814 |
| 6967 | UGUAACUGUGUGUGUGUGU | 388 | 6967 | UGUAACUGUGUGUGUGUGU | 388 | 6989 | ACACACACACACAGUUACA | 815 |
| 6985 | UGUGUGUGUGUGUGUGUGU | 389 | 6985 | UGUGUGUGUGUGUGUGUGU | 389 | 7007 | ACACACACACACACACACA | 816 |
| 7003 | UGUGUGUGUGUGGGUGUGG | 390 | 7003 | UGUGUGUGUGUGGGUGUGG | 390 | 7025 | CCACACCCACACACACACA | 817 |
| 7021 | GGUGUAUGUGUGUUUUGUG | 391 | 7021 | GGUGUAUGUGUGUUUUGUG | 391 | 7043 | CACAAAACACACAUACACC | 818 |
| 7039 | GCAUAACUAUUUAAGGAAA | 392 | 7039 | GCAUAACUAUUUAAGGAAA | 392 | 7061 | UUUCCUUAAAUAGUUAUGC | 819 |
| 7057 | ACUGGAAUUUUAAAGUUAC | 393 | 7057 | ACUGGAAUUUUAAAGUUAC | 393 | 7079 | GUAACUUUAAAAUUCCAGU | 820 |
| 7075 | CUUUUAUACAAACCAAGAA | 394 | 7075 | CUUUUAUACAAACCAAGAA | 394 | 7097 | UUCUUGGUUUGUAUAAAAG | 821 |
| 7093 | AUAUAUGCUACAGAUAUAA | 395 | 7093 | AUAUAUGCUACAGAUAUAA | 395 | 7115 | UUAUAUCUGUAGCAUAUAU | 822 |
| 7111 | AGACAGACAUGGUUUGGUC | 396 | 7111 | AGACAGACAUGGUUUGGUC | 396 | 7133 | GACCAAACCAUGUCUGUCU | 823 |
| 7129 | CCUAUAUUUCUAGUCAUGA | 397 | 7129 | CCUAUAUUUCUAGUCAUGA | 397 | 7151 | UCAUGACUAGAAAUAUAGG | 824 |
| 7147 | AUGAAUGUAUUUUGUAUAC | 398 | 7147 | AUGAAUGUAUUUUGUAUAC | 398 | 7169 | GUAUACAAAAUACAUUCAU | 825 |
| 7165 | CCAUCUUCAUAUAAUAUAC | 399 | 7165 | CCAUCUUCAUAUAAUAUAC | 399 | 7187 | GUAUAUUAUAUGAAGAUGG | 826 |
| 7183 | CUUAAAAAUAUUUCUUAAU | 400 | 7183 | CUUAAAAAUAUUUCUUAAU | 400 | 7205 | AUUAAGAAAUAUUUUUAAG | 827 |
| 7201 | UUGGGAUUUGUAAUCGUAC | 401 | 7201 | UUGGGAUUUGUAAUCGUAC | 401 | 7223 | GUACGAUUACAAAUCCCAA | 828 |
| 7219 | CCAACUUAAUUGAUAAACU | 402 | 7219 | CCAACUUAAUUGAUAAACU | 402 | 7241 | AGUUUAUCAAUUAAGUUGG | 829 |
| 7237 | UUGGCAACUGCUUUUAUGU | 403 | 7237 | UUGGCAACUGCUUUUAUGU | 403 | 7259 | ACAUAAAAGCAGUUGCCAA | 830 |
| 7255 | UUCUGUCUCCUUCCAUAAA | 404 | 7255 | UUCUGUCUCCUUCCAUAAA | 404 | 7277 | UUUAUGGAAGGAGACAGAA | 831 |
| 7273 | AUUUUUCAAAAUACUAAUU | 405 | 7273 | AUUUUUCAAAAUACUAAUU | 405 | 7295 | AAUUAGUAUUUUGAAAAAU | 832 |
| 7291 | UCAACAAAGAAAAGCUCU | 406 | 7291 | UCAACAAAGAAAAGCUCU | 406 | 7313 | AGAGCUUUUUCUUUGUUGA | 833 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 7309 | UUUUUUUUCCUAAAAUAAA | 407 | 7309 | UUUUUUUUCCUAAAAUAAA | 407 | 7331 | UUUAUUUUAGGAAAAAAAA | 834 |
| 7327 | ACUCAAAUUUAUCCUUGUU | 408 | 7327 | ACUCAAAUUUAUCCUUGUU | 408 | 7349 | AACAAGGAUAAAUUUGAGU | 835 |
| 7345 | UUAGAGCAGAGAAAAAUUA | 409 | 7345 | UUAGAGCAGAGAAAAAUUA | 409 | 7367 | UAAUUUUUCUCUGCUCUAA | 836 |
| 7363 | AAGAAAAACUUUGAAAUGG | 410 | 7363 | AAGAAAAACUUUGAAAUGG | 410 | 7385 | CCAUUUCAAAGUUUUUCUU | 837 |
| 7381 | GUCUCAAAAAAUUGCUAAA | 411 | 7381 | GUCUCAAAAAAUUGCUAAA | 411 | 7403 | UUUAGCAAUUUUUUGAGAC | 838 |
| 7399 | AUAUUUCAAUGGAAAACU | 412 | 7399 | AUAUUUCAAUGGAAAACU | 412 | 7421 | AGUUUUCCAUUGAAAAUAU | 839 |
| 7417 | UAAAUGUUAGUUUAGCUGA | 413 | 7417 | UAAAUGUUAGUUUAGCUGA | 413 | 7439 | UCAGCUAAACUAACAUUUA | 840 |
| 7435 | AUUGUAUGGGGUUUUCGAA | 414 | 7435 | AUUGUAUGGGGUUUUCGAA | 414 | 7457 | UUCGAAAACCCCAUACAAU | 841 |
| 7453 | ACCUUUCACUUUUUGUUUG | 415 | 7453 | ACCUUUCACUUUUUGUUUG | 415 | 7475 | CAAACAAAAAGUGAAAGGU | 842 |
| 7471 | GUUUUACCUAUUUCACAAC | 416 | 7471 | GUUUUACCUAUUUCACAAC | 416 | 7493 | GUUGUGAAAUAGGUAAAAC | 843 |
| 7489 | CUGUGUAAAUUGCCAAUAA | 417 | 7489 | CUGUGUAAAUUGCCAAUAA | 417 | 7511 | UUAUUGGCAAUUUACACAG | 844 |
| 7507 | AUUCCUGUCCAUGAAAAUG | 418 | 7507 | AUUCCUGUCCAUGAAAAUG | 418 | 7529 | CAUUUUCAUGGACAGGAAU | 845 |
| 7525 | GCAAAUUAUCCAGUGUAGA | 419 | 7525 | GCAAAUUAUCCAGUGUAGA | 419 | 7547 | UCUACACUGGAUAAUUUGC | 846 |
| 7543 | AUAUAUUUGACCAUCACCC | 420 | 7543 | AUAUAUUUGACCAUCACCC | 420 | 7565 | GGGUGAUGGUCAAAUAUAU | 847 |
| 7561 | CUAUGGAUAUUGGCUAGUU | 421 | 7561 | CUAUGGAUAUUGGCUAGUU | 421 | 7583 | AACUAGCCAAUAUCCAUAG | 848 |
| 7579 | UUUGCCUUUAUUAAGCAAA | 422 | 7579 | UUUGCCUUUAUUAAGCAAA | 422 | 7601 | UUUGCUUAAUAAAGGCAAA | 849 |
| 7597 | AUUCAUUUCAGCCUGAAUG | 423 | 7597 | AUUCAUUUCAGCCUGAAUG | 423 | 7619 | CAUUCAGGCUGAAAUGAAU | 850 |
| 7615 | GUCUGCCUAUAUAUUCUCU | 424 | 7615 | GUCUGCCUAUAUAUUCUCU | 424 | 7637 | AGAGAAUAUAUAGGCAGAC | 851 |
| 7633 | UGCUCUUUGUAUUCUCCUU | 425 | 7633 | UGCUCUUUGUAUUCUCCUU | 425 | 7655 | AAGGAGAAUACAAAGAGCA | 852 |
| 7651 | UUGAACCCGUUAAAACAUC | 426 | 7651 | UUGAACCCGUUAAAACAUC | 426 | 7673 | GAUGUUUUAACGGGUUCAA | 853 |
| 7662 | AAAACAUCCUGUGGCACUC | 427 | 7662 | AAAACAUCCUGUGGCACUC | 427 | 7684 | GAGUGCCACAGGAUGUUUU | 854 |

VEGFR2 gi|11321596|ref|NM_002253.1

| Pos | Target Sequence | Seq ID | UPos | Upper seq | Seq ID | LPos | Lower seq | Seq ID |
|---|---|---|---|---|---|---|---|---|
| 1 | ACUGAGUCCCGGGACCCCG | 855 | 1 | ACUGAGUCCCGGGACCCCG | 855 | 23 | CGGGGUCCCGGGACUCAGU | 1179 |
| 19 | GGGAGAGCGGUCAGUGUGU | 856 | 19 | GGGAGAGCGGUCAGUGUGU | 856 | 41 | ACACACUGACCGCUCUCCC | 1180 |
| 37 | UGGUCGCUGCGUUUCCUCU | 857 | 37 | UGGUCGCUGCGUUUCCUCU | 857 | 59 | AGAGGAAACGCAGCGACCA | 1181 |
| 55 | UGCCUGCGCCGGGCAUCAC | 858 | 55 | UGCCUGCGCCGGGCAUCAC | 858 | 77 | GUGAUGCCCGGCGCAGGCA | 1182 |
| 73 | CUUGCGCGCCGCAGAAAGU | 859 | 73 | CUUGCGCGCCGCAGAAAGU | 859 | 95 | ACUUUCUGCGGCGCGCAAG | 1183 |
| 91 | UCCGUCUGGCAGCCUGGAU | 860 | 91 | UCCGUCUGGCAGCCUGGAU | 860 | 113 | AUCCAGGCUGCCAGACGGA | 1184 |
| 109 | UAUCCUCUCCUACCGGCAC | 861 | 109 | UAUCCUCUCCUACCGGCAC | 861 | 131 | GUGCCGGUAGGAGAGGAUA | 1185 |
| 127 | CCCGCAGACGCCCCUGCAG | 862 | 127 | CCCGCAGACGCCCCUGCAG | 862 | 149 | CUGCAGGGGCGUCUGCGGG | 1186 |
| 145 | GCCGCCGGUCGGCGCCCGG | 863 | 145 | GCCGCCGGUCGGCGCCCGG | 863 | 167 | CCGGGCGCCGACCGGCGGC | 1187 |
| 163 | GGCUCCCUAGCCCUGUGCG | 864 | 163 | GGCUCCCUAGCCCUGUGCG | 864 | 185 | CGCACAGGGCUAGGGAGCC | 1188 |
| 181 | GCUCAACUGUCCUGCGCUG | 865 | 181 | GCUCAACUGUCCUGCGCUG | 865 | 203 | CAGCGCAGGACAGUUGAGC | 1189 |
| 199 | GCGGGGUGCCGCGAGUUCC | 866 | 199 | GCGGGGUGCCGCGAGUUCC | 866 | 221 | GGAACUCGCGGCACCCCGC | 1190 |
| 217 | CACCUCCGCGCCUCCUUCU | 867 | 217 | CACCUCCGCGCCUCCUUCU | 867 | 239 | AGAAGGAGGCGCGGAGGUG | 1191 |
| 235 | UCUAGACAGGCGCUGGGAG | 868 | 235 | UCUAGACAGGCGCUGGGAG | 868 | 257 | CUCCCAGCGCCUGUCUAGA | 1192 |
| 253 | GAAAGAACCGGCUCCCGAG | 869 | 253 | GAAAGAACCGGCUCCCGAG | 869 | 275 | CUCGGGAGCCGGUUCUUUC | 1193 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 271 | GUUCUGGGCAUUUCGCCCG | 870 | 271 | GUUCUGGGCAUUUCGCCCG | 870 | 293 | CGGGCGAAAUGCCCAGAAC | 1194 |
| 289 | GGCUCGAGGUGCAGGAUGC | 871 | 289 | GGCUCGAGGUGCAGGAUGC | 871 | 311 | GCAUCCUGCACCUCGAGCC | 1195 |
| 307 | CAGAGCAAGGUGCUGCUGG | 872 | 307 | CAGAGCAAGGUGCUGCUGG | 872 | 329 | CCAGCAGCACCUUGCUCUG | 1196 |
| 325 | GCCGUCGCCCUGUGGCUCU | 873 | 325 | GCCGUCGCCCUGUGGCUCU | 873 | 347 | AGAGCCACAGGGCGACGGC | 1197 |
| 343 | UGCGUGGAGACCCGGGCCG | 874 | 343 | UGCGUGGAGACCCGGGCCG | 874 | 365 | CGGCCCGGGUCUCCACGCA | 1198 |
| 361 | GCCUCUGUGGGUUUGCCUA | 875 | 361 | GCCUCUGUGGGUUUGCCUA | 875 | 383 | UAGGCAAACCCACAGAGGC | 1199 |
| 379 | AGUGUUUCUCUUGAUCUGC | 876 | 379 | AGUGUUUCUCUUGAUCUGC | 876 | 401 | GCAGAUCAAGAGAAACACU | 1200 |
| 397 | CCCAGGCUCAGCAUACAAA | 877 | 397 | CCCAGGCUCAGCAUACAAA | 877 | 419 | UUUGUAUGCUGAGCCUGGG | 1201 |
| 415 | AAAGACAUACUUACAAUUA | 878 | 415 | AAAGACAUACUUACAAUUA | 878 | 437 | UAAUUGUAAGUAUGUCUUU | 1202 |
| 433 | AAGGCUAAUACAACUCUUC | 879 | 433 | AAGGCUAAUACAACUCUUC | 879 | 455 | GAAGAGUUGUAUUAGCCUU | 1203 |
| 451 | CAAAUUACUUGCAGGGGAC | 880 | 451 | CAAAUUACUUGCAGGGGAC | 880 | 473 | GUCCCCUGCAAGUAAUUUG | 1204 |
| 469 | CAGAGGGACUUGGACUGGC | 881 | 469 | CAGAGGGACUUGGACUGGC | 881 | 491 | GCCAGUCCAAGUCCCUCUG | 1205 |
| 487 | CUUUGGCCCAAUAAUCAGA | 882 | 487 | CUUUGGCCCAAUAAUCAGA | 882 | 509 | UCUGAUUAUUGGGCCAAAG | 1206 |
| 505 | AGUGGCAGUGAGCAAAGGG | 883 | 505 | AGUGGCAGUGAGCAAAGGG | 883 | 527 | CCCUUUGCUCACUGCCACU | 1207 |
| 523 | GUGGAGGUGACUGAGUGGA | 884 | 523 | GUGGAGGUGACUGAGUGCA | 884 | 545 | UGCACUCAGUCACCUCCAC | 1208 |
| 541 | AGCGAUGGCCUCUUCUGUA | 885 | 541 | AGCGAUGGCCUCUUCUGUA | 885 | 563 | UACAGAAGAGGCCAUCGCU | 1209 |
| 559 | AAGACACUCACAAUUCCAA | 886 | 559 | AAGACACUCACAAUUCCAA | 886 | 581 | UUGGAAUUGUGAGUGUCUU | 1210 |
| 577 | AAAGUGAUCGGAAAUGACA | 887 | 577 | AAAGUGAUCGGAAAUGACA | 887 | 599 | UGUCAUUUCCGAUCACUUU | 1211 |
| 595 | ACUGGAGCCUACAAGUGCU | 888 | 595 | ACUGGAGCCUACAAGUGCU | 888 | 617 | AGCACUUGUAGGCUCCAGU | 1212 |
| 613 | UUCUACCGGGAAACUGACU | 889 | 613 | UUCUACCGGGAAACUGACU | 889 | 635 | AGUCAGUUUCCCGGUAGAA | 1213 |
| 631 | UUGGCCUCGGUCAUUUAUG | 890 | 631 | UUGGCCUCGGUCAUUUAUG | 890 | 653 | CAUAAAUGACCGAGGCCAA | 1214 |
| 649 | GUCUAUGUUCAAGAUUACA | 891 | 649 | GUCUAUGUUCAAGAUUACA | 891 | 671 | UGUAAUCUUGAACAUAGAC | 1215 |
| 667 | AGAUCUCCAUUUAUUGCUU | 892 | 667 | AGAUCUCCAUUUAUUGCUU | 892 | 689 | AAGCAAUAAAUGGAGAUCU | 1216 |
| 685 | UCUGUUAGUGACCAACAUG | 893 | 685 | UCUGUUAGUGACCAACAUG | 893 | 707 | CAUGUUGGUCACUAACAGA | 1217 |
| 703 | GGAGUCGUGUACAUUACUG | 894 | 703 | GGAGUCGUGUACAUUACUG | 894 | 725 | CAGUAAUGUACACGACUCC | 1218 |
| 721 | GAGAACAAAAACAAAACUG | 895 | 721 | GAGAACAAAAACAAAACUG | 895 | 743 | CAGUUUUGUUUUUGUUCUC | 1219 |
| 739 | GUGGUGAUUCCAUGUCUCG | 896 | 739 | GUGGUGAUUCCAUGUCUCG | 896 | 761 | CGAGACAUGGAAUCACCAC | 1220 |
| 757 | GGGUCCAUUUCAAAUCUCA | 897 | 757 | GGGUCCAUUUCAAAUCUCA | 897 | 779 | UGAGAUUUGAAAUGGACCC | 1221 |
| 775 | AACGUGUCACUUUGUGCAA | 898 | 775 | AACGUGUCACUUUGUGCAA | 898 | 797 | UUGCACAAAGUGACACGUU | 1222 |
| 793 | AGAUACCCAGAAAAGAGAU | 899 | 793 | AGAUACCCAGAAAAGAGAU | 899 | 815 | AUCUCUUUUCUGGGUAUCU | 1223 |
| 811 | UUUGUUCCUGAUGGUAACA | 900 | 811 | UUUGUUCCUGAUGGUAACA | 900 | 833 | UGUUACCAUCAGGAACAAA | 1224 |
| 829 | AGAAUUCCUGGGACAGCA | 901 | 829 | AGAAUUCCUGGGACAGCA | 901 | 851 | UGCUGUCCCAGGAAAUUCU | 1225 |
| 847 | AAGAAGGGCUUUACUAUUC | 902 | 847 | AAGAAGGGCUUUACUAUUC | 902 | 869 | GAAUAGUAAAGCCCUUCUU | 1226 |
| 865 | CCCAGCUACAUGAUCAGCU | 903 | 865 | CCCAGCUACAUGAUCAGCU | 903 | 887 | AGCUGAUCAUGUAGCUGGG | 1227 |
| 883 | UAUGCUGGCAUGGUCUUCU | 904 | 883 | UAUGCUGGCAUGGUCUUCU | 904 | 905 | AGAAGACCAUGCCAGCAUA | 1228 |
| 901 | UGUGAAGCAAAAAUUAAUG | 905 | 901 | UGUGAAGCAAAAAUUAAUG | 905 | 923 | CAUUAAUUUUUGCUUCACA | 1229 |
| 919 | GAUGAAAGUUACCAGUCUA | 906 | 919 | GAUGAAAGUUACCAGUCUA | 906 | 941 | UAGACUGGUAACUUUCAUC | 1230 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 937 | AUUAUGUACAUAGUUGUCG | 907 | 937 | AUUAUGUACAUAGUUGUCG | 907 | 959 | CGACAACUAUGUACAUAAU | 1231 |
| 955 | GUUGUAGGGUAUAGGAUUU | 908 | 955 | GUUGUAGGGUAUAGGAUUU | 908 | 977 | AAAUCCUAUACCCUACAAC | 1232 |
| 973 | UAUGAUGUGGUUCUGAGUC | 909 | 973 | UAUGAUGUGGUUCUGAGUC | 909 | 995 | GACUCAGAACCACAUCAUA | 1233 |
| 991 | CCGUCUCAUGGAAUUGAAC | 910 | 991 | CCGUCUCAUGGAAUUGAAC | 910 | 1013 | GUUCAAUUCCAUGAGACGG | 1234 |
| 1009 | CUAUCUGUUGGAGAAAAGC | 911 | 1009 | CUAUCUGUUGGAGAAAAGC | 911 | 1031 | GCUUUUCUCCAACAGAUAG | 1235 |
| 1027 | CUUGUCUUAAAUUGUACAG | 912 | 1027 | CUUGUCUUAAAUUGUACAG | 912 | 1049 | CUGUACAAUUUAAGACAAG | 1236 |
| 1045 | GCAAGAACUGAACUAAAUG | 913 | 1045 | GCAAGAACUGAACUAAAUG | 913 | 1067 | CAUUUAGUUCAGUUCUUGC | 1237 |
| 1063 | GUGGGGAUUGACUUCAACU | 914 | 1063 | GUGGGGAUUGACUUCAACU | 914 | 1085 | AGUUGAAGUCAAUCCCCAC | 1238 |
| 1081 | UGGGAAUACCCUUCUUCGA | 915 | 1081 | UGGGAAUACCCUUCUUCGA | 915 | 1103 | UCGAAGAAGGGUAUUCCCA | 1239 |
| 1099 | AAGCAUCAGCAUAAGAAAC | 916 | 1099 | AAGCAUCAGCAUAAGAAAC | 916 | 1121 | GUUUCUUAUGCUGAUGCUU | 1240 |
| 1117 | CUUGUAAACCGAGACCUAA | 917 | 1117 | CUUGUAAACCGAGACCUAA | 917 | 1139 | UUAGGUCUCGGUUUACAAG | 1241 |
| 1135 | AAAACCCAGUCUGGGAGUG | 918 | 1135 | AAAACCCAGUCUGGGAGUG | 918 | 1157 | CACUCCCAGACUGGGUUUU | 1242 |
| 1153 | GAGAUGAAGAAAUUUUUGA | 919 | 1153 | GAGAUGAAGAAAUUUUUGA | 919 | 1175 | UCAAAAAUUUCUUCAUCUC | 1243 |
| 1171 | AGCACCUUAACUAUAGAUG | 920 | 1171 | AGCACCUUAACUAUAGAUG | 920 | 1193 | CAUCUAUAGUUAAGGUGCU | 1244 |
| 1189 | GGUGUAACCCGGAGUGACC | 921 | 1189 | GGUGUAACCCGGAGUGACC | 921 | 1211 | GGUCACUCCGGGUUACACC | 1245 |
| 1207 | CAAGGAUUGUACACCUGUG | 922 | 1207 | CAAGGAUUGUACACCUGUG | 922 | 1229 | CACAGGUGUACAAUCCUUG | 1246 |
| 1225 | GCAGCAUCCAGUGGGCUGA | 923 | 1225 | GCAGCAUCCAGUGGGCUGA | 923 | 1247 | UCAGCCCACUGGAUGCUGC | 1247 |
| 1243 | AUGACCAAGAAGAACAGCA | 924 | 1243 | AUGACCAAGAAGAACAGCA | 924 | 1265 | UGCUGUUCUUCUUGGUCAU | 1248 |
| 1261 | ACAUUUGUCAGGGUCCAUG | 925 | 1261 | ACAUUUGUCAGGGUCCAUG | 925 | 1283 | CAUGGACCCUGACAAAUGU | 1249 |
| 1279 | GAAAAACCUUUUGUUGCUU | 926 | 1279 | GAAAAACCUUUUGUUGCUU | 926 | 1301 | AAGCAACAAAAGGUUUUUC | 1250 |
| 1297 | UUUGGAAGUGGCAUGGAAU | 927 | 1297 | UUUGGAAGUGGCAUGGAAU | 927 | 1319 | AUUCCAUGCCACUUCCAAA | 1251 |
| 1315 | UCUCUGGUGGAAGCCACGG | 928 | 1315 | UCUCUGGUGGAAGCCACGG | 928 | 1337 | CCGUGGCUUCCACCAGAGA | 1252 |
| 1333 | GUGGGGAGCGUGUCAGAA | 929 | 1333 | GUGGGGAGCGUGUCAGAA | 929 | 1355 | UUCUGACACGCUCCCCCAC | 1253 |
| 1351 | AUCCCUGCGAAGUACCUUG | 930 | 1351 | AUCCCUGCGAAGUACCUUG | 930 | 1373 | CAAGGUACUUCGCAGGGAU | 1254 |
| 1369 | GGUUACCCACCCCCAGAAA | 931 | 1369 | GGUUACCCACCCCCAGAAA | 931 | 1391 | UUUCUGGGGUGGGUAACC | 1255 |
| 1387 | AUAAAAUGGUAUAAAAAUG | 932 | 1387 | AUAAAAUGGUAUAAAAAUG | 932 | 1409 | CAUUUUUAUACCAUUUUAU | 1256 |
| 1405 | GGAAUACCCCUUGAGUCCA | 933 | 1405 | GGAAUACCCCUUGAGUCCA | 933 | 1427 | UGGACUCAAGGGGUAUUCC | 1257 |
| 1423 | AAUCACACAAUUAAAGCGG | 934 | 1423 | AAUCACACAAUUAAAGCGG | 934 | 1445 | CCGCUUUAAUUGUGUGAUU | 1258 |
| 1441 | GGGCAUGUACUGACGAUUA | 935 | 1441 | GGGCAUGUACUGACGAUUA | 935 | 1463 | UAAUCGUCAGUACAUGCCC | 1259 |
| 1459 | AUGGAAGUGAGUGAAAGAG | 936 | 1459 | AUGGAAGUGAGUGAAAGAG | 936 | 1481 | CUCUUUCACUCACUUCCAU | 1260 |
| 1477 | GACACAGGAAAUUACACUG | 937 | 1477 | GACACAGGAAAUUACACUG | 937 | 1499 | CAGUGUAAUUUCCUGUGUC | 1261 |
| 1495 | GUCAUCCUUACCAAUCCCA | 938 | 1495 | GUCAUCCUUACCAAUCCCA | 938 | 1517 | UGGGAUUGGUAAGGAUGAC | 1262 |
| 1513 | AUUUCAAAGGAGAAGCAGA | 939 | 1513 | AUUUCAAAGGAGAAGCAGA | 939 | 1535 | UCUGCUUCUCCUUUGAAAU | 1263 |
| 1531 | AGCCAUGUGGUCUCUCUGG | 940 | 1531 | AGCCAUGUGGUCUCUCUGG | 940 | 1553 | CCAGAGAGACCACAUGGCU | 1264 |
| 1549 | GUUGUGUAUGUCCCACCCC | 941 | 1549 | GUUGUGUAUGUCCCACCCC | 941 | 1571 | GGGGUGGGACAUACACAAC | 1265 |
| 1567 | CAGAUUGGUGAGAAAUCUC | 942 | 1567 | CAGAUUGGUGAGAAAUCUC | 942 | 1589 | GAGAUUUCUCACCAAUCUG | 1266 |
| 1585 | CUAAUCUCUCCUGUGGAUU | 943 | 1585 | CUAAUCUCUCCUGUGGAUU | 943 | 1607 | AAUCCACAGGAGAGAUUAG | 1267 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 1603 | UCCUACCAGUACGGCACCA | 944 | 1603 | UCCUACCAGUACGGCACCA | 944 | 1625 | UGGUGCCGUACUGGUAGGA | 1268 |
| 1621 | ACUCAAACGCUGACAUGUA | 945 | 1621 | ACUCAAACGCUGACAUGUA | 945 | 1643 | UACAUGUCAGCGUUUGAGU | 1269 |
| 1639 | ACGGUCUAUGCCAUUCCUC | 946 | 1639 | ACGGUCUAUGCCAUUCCUC | 946 | 1661 | GAGGAAUGGCAUAGACCGU | 1270 |
| 1657 | CCCCCGCAUCACAUCCACU | 947 | 1657 | CCCCCGCAUCACAUCCACU | 947 | 1679 | AGUGGAUGUGAUGCGGGGG | 1271 |
| 1675 | UGGUAUUGGCAGUUGGAGG | 948 | 1675 | UGGUAUUGGCAGUUGGAGG | 948 | 1697 | CCUCCAACUGCCAAUACCA | 1272 |
| 1693 | GAAGAGUGCGCCAACGAGC | 949 | 1693 | GAAGAGUGCGCCAACGAGC | 949 | 1715 | GCUCGUUGGCGCACUCUUC | 1273 |
| 1711 | CCCAGCCAAGCUGUCUCAG | 950 | 1711 | CCCAGCCAAGCUGUCUCAG | 950 | 1733 | CUGAGACAGCUUGGCUGGG | 1274 |
| 1729 | GUGACAAACCCAUACCCUU | 951 | 1729 | GUGACAAACCCAUACCCUU | 951 | 1751 | AAGGGUAUGGGUUUGUCAC | 1275 |
| 1747 | UGUGAAGAAUGGAGAAGUG | 952 | 1747 | UGUGAAGAAUGGAGAAGUG | 952 | 1769 | CACUUCUCCAUUCUUCACA | 1276 |
| 1765 | GUGGAGGACUUCCAGGGAG | 953 | 1765 | GUGGAGGACUUCCAGGGAG | 953 | 1787 | CUCCCUGGAAGUCCUCCAC | 1277 |
| 1783 | GGAAAUAAAAUUGAAGUUA | 954 | 1783 | GGAAAUAAAAUUGAAGUUA | 954 | 1805 | UAACUUCAAUUUUAUUUCC | 1278 |
| 1801 | AAUAAAAAUCAAUUUGCUC | 955 | 1801 | AAUAAAAAUCAAUUUGCUC | 955 | 1823 | GAGCAAAUUGAUUUUUAUU | 1279 |
| 1819 | CUAAUUGAAGGAAAAAACA | 956 | 1819 | CUAAUUGAAGGAAAAAACA | 956 | 1841 | UGUUUUUUCCUUCAAUUAG | 1280 |
| 1837 | AAAACUGUAAGUACCCUUG | 957 | 1837 | AAAACUGUAAGUACCCUUG | 957 | 1859 | CAAGGGUACUUACAGUUUU | 1281 |
| 1855 | GUUAUCCAAGCGGCAAAUG | 958 | 1855 | GUUAUCCAAGCGGCAAAUG | 958 | 1877 | CAUUUGCCGCUUGGAUAAC | 1282 |
| 1873 | GUGUCAGCUUUGUACAAAU | 959 | 1873 | GUGUCAGCUUUGUACAAAU | 959 | 1895 | AUUUGUACAAAGCUGACAC | 1283 |
| 1891 | UGUGAAGCGGUCAACAAAG | 960 | 1891 | UGUGAAGCGGUCAACAAAG | 960 | 1913 | CUUUGUUGACCGCUUCACA | 1284 |
| 1909 | GUCGGGAGAGGAGAGAGGG | 961 | 1909 | GUCGGGAGAGGAGAGAGGG | 961 | 1931 | CCCUCUCUCCUCUCCCGAC | 1285 |
| 1927 | GUGAUCUCCUUCCACGUGA | 962 | 1927 | GUGAUCUCCUUCCACGUGA | 962 | 1949 | UCACGUGGAAGGAGAUCAC | 1286 |
| 1945 | ACCAGGGGUCCUGAAAUUA | 963 | 1945 | ACCAGGGGUCCUGAAAUUA | 963 | 1967 | UAAUUUCAGGACCCCUGGU | 1287 |
| 1963 | ACUUUGCAACCUGACAUGC | 964 | 1963 | ACUUUGCAACCUGACAUGC | 964 | 1985 | GCAUGUCAGGUUGCAAAGU | 1288 |
| 1981 | CAGCCCACUGAGCAGGAGA | 965 | 1981 | CAGCCCACUGAGCAGGAGA | 965 | 2003 | UCUCCUGCUCAGUGGGCUG | 1289 |
| 1999 | AGCGUGUCUUUGUGGUGCA | 966 | 1999 | AGCGUGUCUUUGUGGUGCA | 966 | 2021 | UGCACCACAAAGACACGCU | 1290 |
| 2017 | ACUGCAGACAGAUCUACGU | 967 | 2017 | ACUGCAGACAGAUCUACGU | 967 | 2039 | ACGUAGAUCUGUCUGCAGU | 1291 |
| 2035 | UUUGAGAACCUCACAUGGU | 968 | 2035 | UUUGAGAACCUCACAUGGU | 968 | 2057 | ACCAUGUGAGGUUCUCAAA | 1292 |
| 2053 | UACAAGCUUGGCCCACAGC | 969 | 2053 | UACAAGCUUGGCCCACAGC | 969 | 2075 | GCUGUGGGCCAAGCUUGUA | 1293 |
| 2071 | CCUCUGCCAAUCCAUGUGG | 970 | 2071 | CCUCUGCCAAUCCAUGUGG | 970 | 2093 | CCACAUGGAUUGGCAGAGG | 1294 |
| 2089 | GGAGAGUUGCCCACACCUG | 971 | 2089 | GGAGAGUUGCCCACACCUG | 971 | 2111 | CAGGUGUGGGCAACUCUCC | 1295 |
| 2107 | GUUUGCAAGAACUUGGAUA | 972 | 2107 | GUUUGCAAGAACUUGGAUA | 972 | 2129 | UAUCCAAGUUCUUGCAAAC | 1296 |
| 2125 | ACUCUUUGGAAAUUGAAUG | 973 | 2125 | ACUCUUUGGAAAUUGAAUG | 973 | 2147 | CAUUCAAUUUCCAAAGAGU | 1297 |
| 2143 | GCCACCAUGUUCUCUAAUA | 974 | 2143 | GCCACCAUGUUCUCUAAUA | 974 | 2165 | UAUUAGAGAACAUGGUGGC | 1298 |
| 2161 | AGCACAAAGACAUUUUGA | 975 | 2161 | AGCACAAAGACAUUUUGA | 975 | 2183 | UCAAAAUGCAUUUGUGCU | 1299 |
| 2179 | AUCAUGGAGCUUAAGAAUG | 976 | 2179 | AUCAUGGAGCUUAAGAAUG | 976 | 2201 | CAUUCUUAAGCUCCAUGAU | 1300 |
| 2197 | GCAUCCUUGCAGGACCAAG | 977 | 2197 | GCAUCCUUGCAGGACCAAG | 977 | 2219 | CUUGGUCCUGCAAGGAUGC | 1301 |
| 2215 | GGAGACUAUGUCUGCCUUG | 978 | 2215 | GGAGACUAUGUCUGCCUUG | 978 | 2237 | CAAGGCAGACAUAGUCUCC | 1302 |
| 2233 | GCUCAAGACAGGAAGACCA | 979 | 2233 | GCUCAAGACAGGAAGACCA | 979 | 2255 | UGGUCUUCCUGUCUUGAGC | 1303 |
| 2251 | AAGAAAAGACAUUGCGUGG | 980 | 2251 | AAGAAAAGACAUUGCGUGG | 980 | 2273 | CCACGCAAUGUCUUUUCUU | 1304 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 2269 | GUCAGGCAGCUCACAGUCC | 981 | 2269 | GUCAGGCAGCUCACAGUCC | 981 | 2291 | GGACUGUGAGCUGCCUGAC | 1305 |
| 2287 | CUAGAGCGUGUGGCACCCA | 982 | 2287 | CUAGAGCGUGUGGCACCCA | 982 | 2309 | UGGGUGCCACACGCUCUAG | 1306 |
| 2305 | ACGAUCACAGGAAACCUGG | 983 | 2305 | ACGAUCACAGGAAACCUGG | 983 | 2327 | CCAGGUUUCCUGUGAUCGU | 1307 |
| 2323 | GAGAAUCAGACGACAAGUA | 984 | 2323 | GAGAAUCAGACGACAAGUA | 984 | 2345 | UACUUGUCGUCUGAUUCUC | 1308 |
| 2341 | AUUGGGGAAAGCAUCGAAG | 985 | 2341 | AUUGGGGAAAGCAUCGAAG | 985 | 2363 | CUUCGAUGCUUUCCCCAAU | 1309 |
| 2359 | GUCUCAUGCACGGCAUCUG | 986 | 2359 | GUCUCAUGCACGGCAUCUG | 986 | 2381 | CAGAUGCCGUGCAUGAGAC | 1310 |
| 2377 | GGGAAUCCCCUCCACAGA | 987 | 2377 | GGGAAUCCCCUCCACAGA | 987 | 2399 | UCUGUGGAGGGGAUUCCC | 1311 |
| 2395 | AUCAUGUGGUUUAAAGAUA | 988 | 2395 | AUCAUGUGGUUUAAAGAUA | 988 | 2417 | UAUCUUUAAACCACAUGAU | 1312 |
| 2413 | AAUGAGACCCUUGUAGAAG | 989 | 2413 | AAUGAGACCCUUGUAGAAG | 989 | 2435 | CUUCUACAAGGGUCUCAUU | 1313 |
| 2431 | GACUCAGGCAUUGUAUUGA | 990 | 2431 | GACUCAGGCAUUGUAUUGA | 990 | 2453 | UCAAUACAAUGCCUGAGUC | 1314 |
| 2449 | AAGGAUGGGAACCGGAACC | 991 | 2449 | AAGGAUGGGAACCGGAACC | 991 | 2471 | GGUUCCGGUUCCCAUCCUU | 1315 |
| 2467 | CUCACUAUCCGCAGAGUGA | 992 | 2467 | CUCACUAUCCGCAGAGUGA | 992 | 2489 | UCACUCUGCGGAUAGUGAG | 1316 |
| 2485 | AGGAAGGAGGACGAAGGCC | 993 | 2485 | AGGAAGGAGGACGAAGGCC | 993 | 2507 | GGCCUUCGUCCUCCUUCCU | 1317 |
| 2503 | CUCUACACCUGCCAGGCAU | 994 | 2503 | CUCUACACCUGCCAGGCAU | 994 | 2525 | AUGCCUGGCAGGUGUAGAG | 1318 |
| 2521 | UGCAGUGUUCUUGGCUGUG | 995 | 2521 | UGCAGUGUUCUUGGCUGUG | 995 | 2543 | CACAGCCAAGAACACUGCA | 1319 |
| 2539 | GCAAAAGUGGAGGCAUUUU | 996 | 2539 | GCAAAAGUGGAGGCAUUUU | 996 | 2561 | AAAAUGCCUCCACUUUUGC | 1320 |
| 2557 | UUCAUAAUAGAAGGUGCCC | 997 | 2557 | UUCAUAAUAGAAGGUGCCC | 997 | 2579 | GGGCACCUUCUAUUAUGAA | 1321 |
| 2575 | CAGGAAAAGACGAACUUGG | 998 | 2575 | CAGGAAAAGACGAACUUGG | 998 | 2597 | CCAAGUUCGUCUUUUCCUG | 1322 |
| 2593 | GAAAUCAUUAUUCUAGUAG | 999 | 2593 | GAAAUCAUUAUUCUAGUAG | 999 | 2615 | CUACUAGAAUAAUGAUUUC | 1323 |
| 2611 | GGCACGGCGGUGAUUGCCA | 1000 | 2611 | GGCACGGCGGUGAUUGCCA | 1000 | 2633 | UGGCAAUCACCGCCGUGCC | 1324 |
| 2629 | AUGUUCUUCUGGCUACUUC | 1001 | 2629 | AUGUUCUUCUGGCUACUUC | 1001 | 2651 | GAAGUAGCCAGAAGAACAU | 1325 |
| 2647 | CUUGUCAUCAUCCUACGGA | 1002 | 2647 | CUUGUCAUCAUCCUACGGA | 1002 | 2669 | UCCGUAGGAUGAUGACAAG | 1326 |
| 2665 | ACCGUUAAGCGGGCCAAUG | 1003 | 2665 | ACCGUUAAGCGGGCCAAUG | 1003 | 2687 | CAUUGGCCCGCUUAACGGU | 1327 |
| 2683 | GGAGGGAACUGAAGACAG | 1004 | 2683 | GGAGGGAACUGAAGACAG | 1004 | 2705 | CUGUCUUCAGUUCCCCUCC | 1328 |
| 2701 | GGCUACUUGUCCAUCGUCA | 1005 | 2701 | GGCUACUUGUCCAUCGUCA | 1005 | 2723 | UGACGAUGGACAAGUAGCC | 1329 |
| 2719 | AUGGAUCCAGAUGAACUCC | 1006 | 2719 | AUGGAUCCAGAUGAACUCC | 1006 | 2741 | GGAGUUCAUCUGGAUCCAU | 1330 |
| 2737 | CCAUUGGAUGAACAUUGUG | 1007 | 2737 | CCAUUGGAUGAACAUUGUG | 1007 | 2759 | CACAAUGUUCAUCCAAUGG | 1331 |
| 2755 | GAACGACUGCCUUAUGAUG | 1008 | 2755 | GAACGACUGCCUUAUGAUG | 1008 | 2777 | CAUCAUAAGGCAGUCGUUC | 1332 |
| 2773 | GCCAGCAAAUGGGAAUUCC | 1009 | 2773 | GCCAGCAAAUGGGAAUUCC | 1009 | 2795 | GGAAUUCCCAUUUGCUGGC | 1333 |
| 2791 | CCCAGAGACCGGCUGAAGC | 1010 | 2791 | CCCAGAGACCGGCUGAAGC | 1010 | 2813 | GCUUCAGCCGGUCUCUGGG | 1334 |
| 2809 | CUAGGUAAGCCUCUUGGCC | 1011 | 2809 | CUAGGUAAGCCUCUUGGCC | 1011 | 2831 | GGCCAAGAGGCUUACCUAG | 1335 |
| 2827 | CGUGGUGCCUUUGGCCAAG | 1012 | 2827 | CGUGGUGCCUUUGGCCAAG | 1012 | 2849 | CUUGGCCAAAGGCACCACG | 1336 |
| 2845 | GUGAUUGAAGCAGAUGCCU | 1013 | 2845 | GUGAUUGAAGCAGAUGCCU | 1013 | 2867 | AGGCAUCUGCUUCAAUCAC | 1337 |
| 2863 | UUUGGAAUUGACAAGCAG | 1014 | 2863 | UUUGGAAUUGACAAGCAG | 1014 | 2885 | CUGUCUGUCAAUUCCAAA | 1338 |
| 2881 | GCAACUUGCAGGACAGUAG | 1015 | 2881 | GCAACUUGCAGGACAGUAG | 1015 | 2903 | CUACUGUCCUGCAAGUUGC | 1339 |
| 2899 | GCAGUCAAAUGUUGAAAG | 1016 | 2899 | GCAGUCAAAUGUUGAAAG | 1016 | 2921 | CUUUCAACAUUUGACUGC | 1340 |
| 2917 | GAAGGAGCAACACACAGUG | 1017 | 2917 | GAAGGAGCAACACACAGUG | 1017 | 2939 | CACUGUGUGUUGCUCCUUC | 1341 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 2935 | GAGCAUCGAGCUCUCAUGU | 1018 | 2935 | GAGCAUCGAGCUCUCAUGU | 1018 | 2957 | ACAUGAGAGCUCGAUGCUC | 1342 |
| 2953 | UCUGAACUCAAGAUCCUCA | 1019 | 2953 | UCUGAACUCAAGAUCCUCA | 1019 | 2975 | UGAGGAUCUUGAGUUCAGA | 1343 |
| 2971 | AUUCAUAUUGGUCACCAUC | 1020 | 2971 | AUUCAUAUUGGUCACCAUC | 1020 | 2993 | GAUGGUGACCAAUAUGAAU | 1344 |
| 2989 | CUCAAUGUGGUCAACCUUC | 1021 | 2989 | CUCAAUGUGGUCAACCUUC | 1021 | 3011 | GAAGGUUGACCACAUUGAG | 1345 |
| 3007 | CUAGGUGCCUGUACCAAGC | 1022 | 3007 | CUAGGUGCCUGUACCAAGC | 1022 | 3029 | GCUUGGUACAGGCACCUAG | 1346 |
| 3025 | CCAGGAGGGCCACUCAUGG | 1023 | 3025 | CCAGGAGGGCCACUCAUGG | 1023 | 3047 | CCAUGAGUGGCCCUCCUGG | 1347 |
| 3043 | GUGAUUGUGGAAUUCUGCA | 1024 | 3043 | GUGAUUGUGGAAUUCUGCA | 1024 | 3065 | UGCAGAAUUCCACAAUCAC | 1348 |
| 3061 | AAAUUUGGAAACCUGUCCA | 1025 | 3061 | AAAUUUGGAAACCUGUCCA | 1025 | 3083 | UGGACAGGUUUCCAAAUUU | 1349 |
| 3079 | ACUUACCUGAGGAGCAAGA | 1026 | 3079 | ACUUACCUGAGGAGCAAGA | 1026 | 3101 | UCUUGCUCCUCAGGUAAGU | 1350 |
| 3097 | AGAAAUGAAUUUGUCCCCU | 1027 | 3097 | AGAAAUGAAUUUGUCCCCU | 1027 | 3119 | AGGGGACAAAUUCAUUUCU | 1351 |
| 3115 | UACAAGACCAAAGGGGCAC | 1028 | 3115 | UACAAGACCAAAGGGGCAC | 1028 | 3137 | GUGCCCCUUUGGUCUUGUA | 1352 |
| 3133 | CGAUUCCGUCAAGGGAAAG | 1029 | 3133 | CGAUUCCGUCAAGGGAAAG | 1029 | 3155 | CUUUCCCUUGACGGAAUCG | 1353 |
| 3151 | GACUACGUUGGAGCAAUCC | 1030 | 3151 | GACUACGUUGGAGCAAUCC | 1030 | 3173 | GGAUUGCUCCAACGUAGUC | 1354 |
| 3169 | CCUGUGGAUCUGAAACGGC | 1031 | 3169 | CCUGUGGAUCUGAAACGGC | 1031 | 3191 | GCCGUUUCAGAUCCACAGG | 1355 |
| 3187 | CGCUUGGACAGCAUCACCA | 1032 | 3187 | CGCUUGGACAGCAUCACCA | 1032 | 3209 | UGGUGAUGCUGUCCAAGCG | 1356 |
| 3205 | AGUAGCCAGAGCUCAGCCA | 1033 | 3205 | AGUAGCCAGAGCUCAGCCA | 1033 | 3227 | UGGCUGAGCUCUGGCUACU | 1357 |
| 3223 | AGCUCUGGAUUUGUGGAGG | 1034 | 3223 | AGCUCUGGAUUUGUGGAGG | 1034 | 3245 | CCUCCACAAAUCCAGAGCU | 1358 |
| 3241 | GAGAAGUCCCUCAGUGAUG | 1035 | 3241 | GAGAAGUCCCUCAGUGAUG | 1035 | 3263 | CAUCACUGAGGGACUUCUC | 1359 |
| 3259 | GUAGAAGAAGAGGAAGCUC | 1036 | 3259 | GUAGAAGAAGAGGAAGCUC | 1036 | 3281 | GAGCUUCCUCUUCUUCUAC | 1360 |
| 3277 | CCUGAAGAUCUGUAUAAGG | 1037 | 3277 | CCUGAAGAUCUGUAUAAGG | 1037 | 3299 | CCUUAUACAGAUCUUCAGG | 1361 |
| 3295 | GACUUCCUGACCUUGGAGC | 1038 | 3295 | GACUUCCUGACCUUGGAGC | 1038 | 3317 | GCUCCAAGGUCAGGAAGUC | 1362 |
| 3313 | CAUCUCAUCUGUUACAGCU | 1039 | 3313 | CAUCUCAUCUGUUACAGCU | 1039 | 3335 | AGCUGUAACAGAUGAGAUG | 1363 |
| 3331 | UUCCAAGUGGCUAAGGGCA | 1040 | 3331 | UUCCAAGUGGCUAAGGGCA | 1040 | 3353 | UGCCCUUAGCCACUUGGAA | 1364 |
| 3349 | AUGGAGUUCUUGGCAUCGC | 1041 | 3349 | AUGGAGUUCUUGGCAUCGC | 1041 | 3371 | GCGAUGCCAAGAACUCCAU | 1365 |
| 3367 | CGAAAGUGUAUCCACAGGG | 1042 | 3367 | CGAAAGUGUAUCCACAGGG | 1042 | 3389 | CCCUGUGGAUACACUUUCG | 1366 |
| 3385 | GACCUGGCGGCACGAAAUA | 1043 | 3385 | GACCUGGCGGCACGAAAUA | 1043 | 3407 | UAUUUCGUGCCGCCAGGUC | 1367 |
| 3403 | AUCCUCUUAUCGGAGAAGA | 1044 | 3403 | AUCCUCUUAUCGGAGAAGA | 1044 | 3425 | UCUUCUCCGAUAAGAGGAU | 1368 |
| 3421 | AACGUGGUUAAAAUCUGUG | 1045 | 3421 | AACGUGGUUAAAAUCUGUG | 1045 | 3443 | CACAGAUUUUAACCACGUU | 1369 |
| 3439 | GACUUUGGCUUGGCCCGGG | 1046 | 3439 | GACUUUGGCUUGGCCCGGG | 1046 | 3461 | CCCGGGCCAAGCCAAAGUC | 1370 |
| 3457 | GAUAUUUAUAAAGAUCCAG | 1047 | 3457 | GAUAUUUAUAAAGAUCCAG | 1047 | 3479 | CUGGAUCUUUAUAAAUAUC | 1371 |
| 3475 | GAUUAUGUCAGAAAAGGAG | 1048 | 3475 | GAUUAUGUCAGAAAAGGAG | 1048 | 3497 | CUCCUUUUCUGACAUAAUC | 1372 |
| 3493 | GAUGCUCGCCUCCCUUUGA | 1049 | 3493 | GAUGCUCGCCUCCCUUUGA | 1049 | 3515 | UCAAAGGGAGGCGAGCAUC | 1373 |
| 3511 | AAAUGGAUGGCCCCAGAAA | 1050 | 3511 | AAAUGGAUGGCCCCAGAAA | 1050 | 3533 | UUUCUGGGGCCAUCCAUUU | 1374 |
| 3529 | ACAAUUUUUGACAGAGUGU | 1051 | 3529 | ACAAUUUUUGACAGAGUGU | 1051 | 3551 | ACACUCUGUCAAAAAUUGU | 1375 |
| 3547 | UACACAAUCCAGAGUGACG | 1052 | 3547 | UACACAAUCCAGAGUGACG | 1052 | 3569 | CGUCACUCUGGAUUGUGUA | 1376 |
| 3565 | GUCUGGUCUUUUGGUGUUU | 1053 | 3565 | GUCUGGUCUUUUGGUGUUU | 1053 | 3587 | AAACACCAAAAGACCAGAC | 1377 |
| 3583 | UUGCUGUGGGAAAUAUUUU | 1054 | 3583 | UUGCUGUGGGAAAUAUUUU | 1054 | 3605 | AAAAUAUUUCCCACAGCAA | 1378 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 3601 | UCCUUAGGUGCUUCUCCAU | 1055 | 3601 | UCCUUAGGUGCUUCUCCAU | 1055 | 3623 | AUGGAGAAGCACCUAAGGA | 1379 |
| 3619 | UAUCCUGGGGUAAAGAUUG | 1056 | 3619 | UAUCCUGGGGUAAAGAUUG | 1056 | 3641 | CAAUCUUUACCCCAGGAUA | 1380 |
| 3637 | GAUGAAGAAUUUUGUAGGC | 1057 | 3637 | GAUGAAGAAUUUUGUAGGC | 1057 | 3659 | GCCUACAAAAUUCUUCAUC | 1381 |
| 3655 | CGAUUGAAAGAAGGAACUA | 1058 | 3655 | CGAUUGAAAGAAGGAACUA | 1058 | 3677 | UAGUUCCUUCUUUCAAUCG | 1382 |
| 3673 | AGAAUGAGGGCCCCUGAUU | 1059 | 3673 | AGAAUGAGGGCCCCUGAUU | 1059 | 3695 | AAUCAGGGGCCCUCAUUCU | 1383 |
| 3691 | UAUACUACACCAGAAAUGU | 1060 | 3691 | UAUACUACACCAGAAAUGU | 1060 | 3713 | ACAUUUCUGGUGUAGUAUA | 1384 |
| 3709 | UACCAGACCAUGCUGGACU | 1061 | 3709 | UACCAGACCAUGCUGGACU | 1061 | 3731 | AGUCCAGCAUGGUCUGGUA | 1385 |
| 3727 | UGCUGGCACGGGGAGCCCA | 1062 | 3727 | UGCUGGCACGGGGAGCCCA | 1062 | 3749 | UGGGCUCCCCGUGCCAGCA | 1386 |
| 3745 | AGUCAGAGACCCACGUUUU | 1063 | 3745 | AGUCAGAGACCCACGUUUU | 1063 | 3767 | AAAACGUGGGUCUCUGACU | 1387 |
| 3763 | UCAGAGUUGGUGGAACAUU | 1064 | 3763 | UCAGAGUUGGUGGAACAUU | 1064 | 3785 | AAUGUUCCACCAACUCUGA | 1388 |
| 3781 | UUGGGAAAUCUCUUGCAAG | 1065 | 3781 | UUGGGAAAUCUCUUGCAAG | 1065 | 3803 | CUUGCAAGAGAUUUCCCAA | 1389 |
| 3799 | GCUAAUGCUCAGCAGGAUG | 1066 | 3799 | GCUAAUGCUCAGCAGGAUG | 1066 | 3821 | CAUCCUGCUGAGCAUUAGC | 1390 |
| 3817 | GGCAAAGACUACAUUGUUC | 1067 | 3817 | GGCAAAGACUACAUUGUUC | 1067 | 3839 | GAACAAUGUAGUCUUUGCC | 1391 |
| 3835 | CUUCCGAUAUCAGAGACUU | 1068 | 3835 | CUUCCGAUAUCAGAGACUU | 1068 | 3857 | AAGUCUCUGAUAUCGGAAG | 1392 |
| 3853 | UUGAGCAUGGAAGAGGAUU | 1069 | 3853 | UUGAGCAUGGAAGAGGAUU | 1069 | 3875 | AAUCCUCUUCCAUGCUCAA | 1393 |
| 3871 | UCUGGACUCUCUCUGCCUA | 1070 | 3871 | UCUGGACUCUCUCUGCCUA | 1070 | 3893 | UAGGCAGAGAGAGUCCAGA | 1394 |
| 3889 | ACCUCACCUGUUUCCUGUA | 1071 | 3889 | ACCUCACCUGUUUCCUGUA | 1071 | 3911 | UACAGGAAACAGGUGAGGU | 1395 |
| 3907 | AUGGAGGAGGAGGAAGUAU | 1072 | 3907 | AUGGAGGAGGAGGAAGUAU | 1072 | 3929 | AUACUUCCUCCUCCUCCAU | 1396 |
| 3925 | UGUGACCCCAAAUUCCAUU | 1073 | 3925 | UGUGACCCCAAAUUCCAUU | 1073 | 3947 | AAUGGAAUUUGGGGUCACA | 1397 |
| 3943 | UAUGACAACACAGCAGGAA | 1074 | 3943 | UAUGACAACACAGCAGGAA | 1074 | 3965 | UUCCUGCUGUGUUGUCAUA | 1398 |
| 3961 | AUCAGUCAGUAUCUGCAGA | 1075 | 3961 | AUCAGUCAGUAUCUGCAGA | 1075 | 3983 | UCUGCAGAUACUGACUGAU | 1399 |
| 3979 | AACAGUAAGCGAAAGAGCC | 1076 | 3979 | AACAGUAAGCGAAAGAGCC | 1076 | 4001 | GGCUCUUUCGCUUACUGUU | 1400 |
| 3997 | CGGCCUGUGAGUGUAAAAA | 1077 | 3997 | CGGCCUGUGAGUGUAAAAA | 1077 | 4019 | UUUUUACACUCACAGGCCG | 1401 |
| 4015 | ACAUUUGAAGAUAUCCCGU | 1078 | 4015 | ACAUUUGAAGAUAUCCCGU | 1078 | 4037 | ACGGGAUAUCUUCAAAUGU | 1402 |
| 4033 | UUAGAAGAACCAGAAGUAA | 1079 | 4033 | UUAGAAGAACCAGAAGUAA | 1079 | 4055 | UUACUUCUGGUUCUUCUAA | 1403 |
| 4051 | AAAGUAAUCCCAGAUGACA | 1080 | 4051 | AAAGUAAUCCCAGAUGACA | 1080 | 4073 | UGUCAUCUGGGAUUACUUU | 1404 |
| 4069 | AACCAGACGGACAGUGGUA | 1081 | 4069 | AACCAGACGGACAGUGGUA | 1081 | 4091 | UACCACUGUCCGUCUGGUU | 1405 |
| 4087 | AUGGUUCUUGCCUCAGAAG | 1082 | 4087 | AUGGUUCUUGCCUCAGAAG | 1082 | 4109 | CUUCUGAGGCAAGAACCAU | 1406 |
| 4105 | GAGCUGAAAACUUUGGAAG | 1083 | 4105 | GAGCUGAAAACUUUGGAAG | 1083 | 4127 | CUUCCAAAGUUUUCAGCUC | 1407 |
| 4123 | GACAGAACCAAAUUAUCUC | 1084 | 4123 | GACAGAACCAAAUUAUCUC | 1084 | 4145 | GAGAUAAUUUGGUUCUGUC | 1408 |
| 4141 | CCAUCUUUUGGUGGAAUGG | 1085 | 4141 | CCAUCUUUUGGUGGAAUGG | 1085 | 4163 | CCAUUCCACCAAAAGAUGG | 1409 |
| 4159 | GUGCCCAGCAAAAGCAGGG | 1086 | 4159 | GUGCCCAGCAAAAGCAGGG | 1086 | 4181 | CCCUGCUUUUGCUGGGCAC | 1410 |
| 4177 | GAGUCUGUGGCAUCUGAAG | 1087 | 4177 | GAGUCUGUGGCAUCUGAAG | 1087 | 4199 | CUUCAGAUGCCACAGACUC | 1411 |
| 4195 | GGCUCAAACCAGACAAGCG | 1088 | 4195 | GGCUCAAACCAGACAAGCG | 1088 | 4217 | CGCUUGUCUGGUUUGAGCC | 1412 |
| 4213 | GGCUACCAGUCCGGAUAUC | 1089 | 4213 | GGCUACCAGUCCGGAUAUC | 1089 | 4235 | GAUAUCCGGACUGGUAGCC | 1413 |
| 4231 | CACUCCGAUGACACAGACA | 1090 | 4231 | CACUCCGAUGACACAGACA | 1090 | 4253 | UGUCUGUGUCAUCGGAGUG | 1414 |
| 4249 | ACCACCGUGUACUCCAGUG | 1091 | 4249 | ACCACCGUGUACUCCAGUG | 1091 | 4271 | CACUGGAGUACACGGUGGU | 1415 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 4267 | GAGGAAGCAGAACUUUUAA | 1092 | 4267 | GAGGAAGCAGAACUUUUAA | 1092 | 4289 | UUAAAAGUUCUGCUUCCUC | 1416 |
| 4285 | AAGCUGAUAGAGAUUGGAG | 1093 | 4285 | AAGCUGAUAGAGAUUGGAG | 1093 | 4307 | CUCCAAUCUCUAUCAGCUU | 1417 |
| 4303 | GUGCAAACCGGUAGCACAG | 1094 | 4303 | GUGCAAACCGGUAGCACAG | 1094 | 4325 | CUGUGCUACCGGUUUGCAC | 1418 |
| 4321 | GCCCAGAUUCUCCAGCCUG | 1095 | 4321 | GCCCAGAUUCUCCAGCCUG | 1095 | 4343 | CAGGCUGGAGAAUCUGGGC | 1419 |
| 4339 | GACUCGGGGACCACACUGA | 1096 | 4339 | GACUCGGGGACCACACUGA | 1096 | 4361 | UCAGUGUGGUCCCCGAGUC | 1420 |
| 4357 | AGCUCUCCUCCUGUUUAAA | 1097 | 4357 | AGCUCUCCUCCUGUUUAAA | 1097 | 4379 | UUUAAACAGGAGGAGAGCU | 1421 |
| 4375 | AAGGAAGCAUCCACACCCC | 1098 | 4375 | AAGGAAGCAUCCACACCCC | 1098 | 4397 | GGGGUGUGGAUGCUUCCUU | 1422 |
| 4393 | CAACUCCCGGACAUCACAU | 1099 | 4393 | CAACUCCCGGACAUCACAU | 1099 | 4415 | AUGUGAUGUCCGGGAGUUG | 1423 |
| 4411 | UGAGAGGUCUGCUCAGAUU | 1100 | 4411 | UGAGAGGUCUGCUCAGAUU | 1100 | 4433 | AAUCUGAGCAGACCUCUCA | 1424 |
| 4429 | UUUGAAGUGUUGUUCUUUC | 1101 | 4429 | UUUGAAGUGUUGUUCUUUC | 1101 | 4451 | GAAAGAACAACACUUCAAA | 1425 |
| 4447 | CCACCAGCAGGAAGUAGCC | 1102 | 4447 | CCACCAGCAGGAAGUAGCC | 1102 | 4469 | GGCUACUUCCUGCUGGUGG | 1426 |
| 4465 | CGCAUUUGAUUUUCAUUUC | 1103 | 4465 | CGCAUUUGAUUUUCAUUUC | 1103 | 4487 | GAAAUGAAAAUCAAAUGCG | 1427 |
| 4483 | CGACAACAGAAAAAGGACC | 1104 | 4483 | CGACAACAGAAAAAGGACC | 1104 | 4505 | GGUCCUUUUUCUGUUGUCG | 1428 |
| 4501 | CUCGGACUGCAGGGAGCCA | 1105 | 4501 | CUCGGACUGCAGGGAGCCA | 1105 | 4523 | UGGCUCCCUGCAGUCCGAG | 1429 |
| 4519 | AGUCUUCUAGGCAUAUCCU | 1106 | 4519 | AGUCUUCUAGGCAUAUCCU | 1106 | 4541 | AGGAUAUGCCUAGAAGACU | 1430 |
| 4537 | UGGAAGAGGCUUGUGACCC | 1107 | 4537 | UGGAAGAGGCUUGUGACCC | 1107 | 4559 | GGGUCACAAGCCUCUUCCA | 1431 |
| 4555 | CAAGAAUGUGUCUGUGUCU | 1108 | 4555 | CAAGAAUGUGUCUGUGUCU | 1108 | 4577 | AGACACAGACACAUUCUUG | 1432 |
| 4573 | UUCUCCCAGUGUUGACCUG | 1109 | 4573 | UUCUCCCAGUGUUGACCUG | 1109 | 4595 | CAGGUCAACACUGGGAGAA | 1433 |
| 4591 | GAUCCUCUUUUUUCAUUCA | 1110 | 4591 | GAUCCUCUUUUUUCAUUCA | 1110 | 4613 | UGAAUGAAAAAAGAGGAUC | 1434 |
| 4609 | AUUUAAAAAGCAUUAUCAU | 1111 | 4609 | AUUUAAAAAGCAUUAUCAU | 1111 | 4631 | AUGAUAAUGCUUUUUAAAU | 1435 |
| 4627 | UGCCCCUGCUGCGGGUCUC | 1112 | 4627 | UGCCCCUGCUGCGGGUCUC | 1112 | 4649 | GAGACCCGCAGCAGGGGCA | 1436 |
| 4645 | CACCAUGGGUUUAGAACAA | 1113 | 4645 | CACCAUGGGUUUAGAACAA | 1113 | 4667 | UUGUUCUAAACCCAUGGUG | 1437 |
| 4663 | AAGAGCUUCAAGCAAUGGC | 1114 | 4663 | AAGAGCUUCAAGCAAUGGC | 1114 | 4685 | GCCAUUGCUUGAAGCUCUU | 1438 |
| 4681 | CCCCAUCCUCAAAGAAGUA | 1115 | 4681 | CCCCAUCCUCAAAGAAGUA | 1115 | 4703 | UACUUCUUUGAGGAUGGGG | 1439 |
| 4699 | AGCAGUACCUGGGGAGCUG | 1116 | 4699 | AGCAGUACCUGGGGAGCUG | 1116 | 4721 | CAGCUCCCCAGGUACUGCU | 1440 |
| 4717 | GACACUUCUGUAAAACUAG | 1117 | 4717 | GACACUUCUGUAAAACUAG | 1117 | 4739 | CUAGUUUUACAGAAGUGUC | 1441 |
| 4735 | GAAGAUAAACCAGGCAACG | 1118 | 4735 | GAAGAUAAACCAGGCAACG | 1118 | 4757 | CGUUGCCUGGUUUAUCUUC | 1442 |
| 4753 | GUAAGUGUUCGAGGUGUUG | 1119 | 4753 | GUAAGUGUUCGAGGUGUUG | 1119 | 4775 | CAACACCUCGAACACUUAC | 1443 |
| 4771 | GAAGAUGGGAAGGAUUUGC | 1120 | 4771 | GAAGAUGGGAAGGAUUUGC | 1120 | 4793 | GCAAAUCCUUCCCAUCUUC | 1444 |
| 4789 | CAGGGCUGAGUCUAUCCAA | 1121 | 4789 | CAGGGCUGAGUCUAUCCAA | 1121 | 4811 | UUGGAUAGACUCAGCCCUG | 1445 |
| 4807 | AGAGGCUUUGUUUAGGACG | 1122 | 4807 | AGAGGCUUUGUUUAGGACG | 1122 | 4829 | CGUCCUAAACAAAGCCUCU | 1446 |
| 4825 | GUGGGUCCCAAGCCAAGCC | 1123 | 4825 | GUGGGUCCCAAGCCAAGCC | 1123 | 4847 | GGCUUGGCUUGGGACCCAC | 1447 |
| 4843 | CUUAAGUGUGGAAUUCGGA | 1124 | 4843 | CUUAAGUGUGGAAUUCGGA | 1124 | 4865 | UCCGAAUUCCACACUUAAG | 1448 |
| 4861 | AUUGAUAGAAAGGAAGACU | 1125 | 4861 | AUUGAUAGAAAGGAAGACU | 1125 | 4883 | AGUCUUCCUUUCUAUCAAU | 1449 |
| 4879 | UAACGUUACCUUGCUUUGG | 1126 | 4879 | UAACGUUACCUUGCUUUGG | 1126 | 4901 | CCAAAGCAAGGUAACGUUA | 1450 |
| 4897 | GAGAGUACGGAGCCUGCA | 1127 | 4897 | GAGAGUACGGAGCCUGCA | 1127 | 4919 | UGCAGGCUCCAGUACUCUC | 1451 |
| 4915 | AAAUGCAUUGUGUUUGCUC | 1128 | 4915 | AAAUGCAUUGUGUUUGCUC | 1128 | 4937 | GAGCAAACACAAUGCAUUU | 1452 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 4933 | CUGGUGGAGGUGGGCAUGG | 1129 | 4933 | CUGGUGGAGGUGGGCAUGG | 1129 | 4955 | CCAUGCCCACCUCCACCAG | 1453 |
| 4951 | GGGUCUGUUCUGAAAUGUA | 1130 | 4951 | GGGUCUGUUCUGAAAUGUA | 1130 | 4973 | UACAUUUCAGAACAGACCC | 1454 |
| 4969 | AAAGGGUUCAGACGGGGUU | 1131 | 4969 | AAAGGGUUCAGACGGGGUU | 1131 | 4991 | AACCCCGUCUGAACCCUUU | 1455 |
| 4987 | UUCUGGUUUUAGAAGGUUG | 1132 | 4987 | UUCUGGUUUUAGAAGGUUG | 1132 | 5009 | CAACCUUCUAAAACCAGAA | 1456 |
| 5005 | GCGUGUUCUUCGAGUUGGG | 1133 | 5005 | GCGUGUUCUUCGAGUUGGG | 1133 | 5027 | CCCAACUCGAAGAACACGC | 1457 |
| 5023 | GCUAAAGUAGAGUUCGUUG | 1134 | 5023 | GCUAAAGUAGAGUUCGUUG | 1134 | 5045 | CAACGAACUCUACUUUAGC | 1458 |
| 5041 | GUGCUGUUUCUGACUCCUA | 1135 | 5041 | GUGCUGUUUCUGACUCCUA | 1135 | 5063 | UAGGAGUCAGAAACAGCAC | 1459 |
| 5059 | AAUGAGAGUUCCUUCCAGA | 1136 | 5059 | AAUGAGAGUUCCUUCCAGA | 1136 | 5081 | UCUGGAAGGAACUCUCAUU | 1460 |
| 5077 | ACCGUUAGCUGUCUCCUUG | 1137 | 5077 | ACCGUUAGCUGUCUCCUUG | 1137 | 5099 | CAAGGAGACAGCUAACGGU | 1461 |
| 5095 | GCCAAGCCCCAGGAAGAAA | 1138 | 5095 | GCCAAGCCCCAGGAAGAAA | 1138 | 5117 | UUUCUUCCUGGGGCUUGGC | 1462 |
| 5113 | AAUGAUGCAGCUCUGGCUC | 1139 | 5113 | AAUGAUGCAGCUCUGGCUC | 1139 | 5135 | GAGCCAGAGCUGCAUCAUU | 1463 |
| 5131 | CCUUGUCUCCCAGGCUGAU | 1140 | 5131 | CCUUGUCUCCCAGGCUGAU | 1140 | 5153 | AUCAGCCUGGGAGACAAGG | 1464 |
| 5149 | UCCUUUAUUCGAAUACCA | 1141 | 5149 | UCCUUUAUUCGAAUACCA | 1141 | 5171 | UGGUAUUCUGAAUAAAGGA | 1465 |
| 5167 | ACAAAGAAAGGACAUUCAG | 1142 | 5167 | ACAAAGAAAGGACAUUCAG | 1142 | 5189 | CUGAAUGUCCUUUCUUUGU | 1466 |
| 5185 | GCUCAAGGCUCCCUGCCGU | 1143 | 5185 | GCUCAAGGCUCCCUGCCGU | 1143 | 5207 | ACGGCAGGGAGCCUUGAGC | 1467 |
| 5203 | UGUUGAAGAGUUCUGACUG | 1144 | 5203 | UGUUGAAGAGUUCUGACUG | 1144 | 5225 | CAGUCAGAACUCUUCAACA | 1468 |
| 5221 | GCACAAACCAGCUUCUGGU | 1145 | 5221 | GCACAAACCAGCUUCUGGU | 1145 | 5243 | ACCAGAAGCUGGUUUGUGC | 1469 |
| 5239 | UUUCUUCUGGAAUGAAUAC | 1146 | 5239 | UUUCUUCUGGAAUGAAUAC | 1146 | 5261 | GUAUUCAUUCCAGAAGAAA | 1470 |
| 5257 | CCCUCAUAUCUGUCCUGAU | 1147 | 5257 | CCCUCAUAUCUGUCCUGAU | 1147 | 5279 | AUCAGGACAGAUAUGAGGG | 1471 |
| 5275 | UGUGAUAUGUCUGAGACUG | 1148 | 5275 | UGUGAUAUGUCUGAGACUG | 1148 | 5297 | CAGUCUCAGACAUAUCACA | 1472 |
| 5293 | GAAUGCGGGAGGUUCAAUG | 1149 | 5293 | GAAUGCGGGAGGUUCAAUG | 1149 | 5315 | CAUUGAACCUCCCGCAUUC | 1473 |
| 5311 | GUGAAGCUGUGUGUGGUGU | 1150 | 5311 | GUGAAGCUGUGUGUGGUGU | 1150 | 5333 | ACACCACACACAGCUUCAC | 1474 |
| 5329 | UCAAAGUUUCAGGAAGGAU | 1151 | 5329 | UCAAAGUUUCAGGAAGGAU | 1151 | 5351 | AUCCUUCCUGAAACUUUGA | 1475 |
| 5347 | UUUUACCCUUUUGUUCUUC | 1152 | 5347 | UUUUACCCUUUUGUUCUUC | 1152 | 5369 | GAAGAACAAAAGGGUAAAA | 1476 |
| 5365 | CCCCCUGUCCCCAACCCAC | 1153 | 5365 | CCCCCUGUCCCCAACCCAC | 1153 | 5387 | GUGGGUUGGGGACAGGGGG | 1477 |
| 5383 | CUCUCACCCCGCAACCCAU | 1154 | 5383 | CUCUCACCCCGCAACCCAU | 1154 | 5405 | AUGGGUUGCGGGGUGAGAG | 1478 |
| 5401 | UCAGUAUUUUAGUUAUUUG | 1155 | 5401 | UCAGUAUUUUAGUUAUUUG | 1155 | 5423 | CAAAUAACUAAAAUACUGA | 1479 |
| 5419 | GGCCUCUACUCCAGUAAAC | 1156 | 5419 | GGCCUCUACUCCAGUAAAC | 1156 | 5441 | GUUUACUGGAGUAGAGGCC | 1480 |
| 5437 | CCUGAUUGGGUUUGUUCAC | 1157 | 5437 | CCUGAUUGGGUUUGUUCAC | 1157 | 5459 | GUGAACAAACCCAAUCAGG | 1481 |
| 5455 | CUCUCUGAAUGAUUAUUAG | 1158 | 5455 | CUCUCUGAAUGAUUAUUAG | 1158 | 5477 | CUAAUAAUCAUUCAGAGAG | 1482 |
| 5473 | GCCAGACUUCAAAAUUAUU | 1159 | 5473 | GCCAGACUUCAAAAUUAUU | 1159 | 5495 | AAUAAUUUUGAAGUCUGGC | 1483 |
| 5491 | UUUAUAGCCCAAAUUAUAA | 1160 | 5491 | UUUAUAGCCCAAAUUAUAA | 1160 | 5513 | UUAUAAUUUGGGCUAUAAA | 1484 |
| 5509 | ACAUCUAUUGUAUUAUUUA | 1161 | 5509 | ACAUCUAUUGUAUUAUUUA | 1161 | 5531 | UAAAUAAUACAAUAGAUGU | 1485 |
| 5527 | AGACUUUUAACAUAUAGAG | 1162 | 5527 | AGACUUUUAACAUAUAGAG | 1162 | 5549 | CUCUAUAUGUUAAAAGUCU | 1486 |
| 5545 | GCUAUUUCUACUGAUUUUU | 1163 | 5545 | GCUAUUUCUACUGAUUUUU | 1163 | 5567 | AAAAAUCAGUAGAAAUAGC | 1487 |
| 5563 | UGCCCUUGUUCUGUCCUUU | 1164 | 5563 | UGCCCUUGUUCUGUCCUUU | 1164 | 5585 | AAAGGACAGAACAAGGGCA | 1488 |
| 5581 | UUUUUCAAAAAAGAAAAUG | 1165 | 5581 | UUUUUCAAAAAAGAAAAUG | 1165 | 5603 | CAUUUUCUUUUUUGAAAAA | 1489 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 5599 | GUGUUUUUUGUUUGGUACC | 1166 | 5599 | GUGUUUUUUGUUUGGUACC | 1166 | 5621 | GGUACCAAACAAAAAACAC | 1490 |
| 5617 | CAUAGUGUGAAAUGCUGGG | 1167 | 5617 | CAUAGUGUGAAAUGCUGGG | 1167 | 5639 | CCCAGCAUUUCACACUAUG | 1491 |
| 5635 | GAACAAUGACUAUAAGACA | 1168 | 5635 | GAACAAUGACUAUAAGACA | 1168 | 5657 | UGUCUUAUAGUCAUUGUUC | 1492 |
| 5653 | AUGCUAUGGCACAUAUAUU | 1169 | 5653 | AUGCUAUGGCACAUAUAUU | 1169 | 5675 | AAUAUAUGUGCCAUAGCAU | 1493 |
| 5671 | UUAUAGUCUGUUUAUGUAG | 1170 | 5671 | UUAUAGUCUGUUUAUGUAG | 1170 | 5693 | CUACAUAAACAGACUAUAA | 1494 |
| 5689 | GAAACAAAUGUAAUAUAUU | 1171 | 5689 | GAAACAAAUGUAAUAUAUU | 1171 | 5711 | AAUAUAUUACAUUUGUUUC | 1495 |
| 5707 | UAAAGCCUUAUAUAUAAUG | 1172 | 5707 | UAAAGCCUUAUAUAUAAUG | 1172 | 5729 | CAUUAUAUAUAAGGCUUUA | 1496 |
| 5725 | GAACUUUGUACUAUUCACA | 1173 | 5725 | GAACUUUGUACUAUUCACA | 1173 | 5747 | UGUGAAUAGUACAAAGUUC | 1497 |
| 5743 | AUUUUGUACAGUAUUAUG | 1174 | 5743 | AUUUUGUACAGUAUUAUG | 1174 | 5765 | CAUAAUACUGAUACAAAAU | 1498 |
| 5761 | GUAGCAUAACAAAGGUCAU | 1175 | 5761 | GUAGCAUAACAAAGGUCAU | 1175 | 5783 | AUGACCUUUGUUAUGCUAC | 1499 |
| 5779 | UAAUGCUUUCAGCAAUUGA | 1176 | 5779 | UAAUGCUUUCAGCAAUUGA | 1176 | 5801 | UCAAUUGCUGAAAGCAUUA | 1500 |
| 5797 | AUGUCAUUUUAUUAAAGAA | 1177 | 5797 | AUGUCAUUUUAUUAAAGAA | 1177 | 5819 | UUCUUUAAUAAAAUGACAU | 1501 |
| 5812 | AGAACAUUGAAAAACUUGA | 1178 | 5812 | AGAACAUUGAAAAACUUGA | 1178 | 5834 | UCAAGUUUUUCAAUGUUCU | 1502 |

VEGFR3 gi|4503752|ref|NM_002020.1

| Pos | Target Sequence | Seq ID | UPos | Upper seq | Seq ID | LPos | Lower seq | Seq ID |
|---|---|---|---|---|---|---|---|---|
| 1 | ACCCACGCGCAGCGGCCGG | 1503 | 1 | ACCCACGCGCAGCGGCCGG | 1503 | 23 | CCGGCCGCUGCGCGUGGGU | 1750 |
| 19 | GAGAUGCAGCGGGGCGCCG | 1504 | 19 | GAGAUGCAGCGGGGCGCCG | 1504 | 41 | CGGCGCCCCGCUGCAUCUC | 1751 |
| 37 | GCGCUGUGCCUGCGACUGU | 1505 | 37 | GCGCUGUGCCUGCGACUGU | 1505 | 59 | ACAGUCGCAGGCACAGCGC | 1752 |
| 55 | UGGCUCUGCCUGGGACUCC | 1506 | 55 | UGGCUCUGCCUGGGACUCC | 1506 | 77 | GGAGUCCCAGGCAGAGCCA | 1753 |
| 73 | CUGGACGGCCUGGUGAGUG | 1507 | 73 | CUGGACGGCCUGGUGAGUG | 1507 | 95 | CACUCACCAGGCCGUCCAG | 1754 |
| 91 | GACUACUCCAUGACCCCCC | 1508 | 91 | GACUACUCCAUGACCCCCC | 1508 | 113 | GGGGGGUCAUGGAGUAGUC | 1755 |
| 109 | CCGACCUUGAACAUCACGG | 1509 | 109 | CCGACCUUGAACAUCACGG | 1509 | 131 | CCGUGAUGUUCAAGGUCGG | 1756 |
| 127 | GAGGAGUCACACGUCAUCG | 1510 | 127 | GAGGAGUCACACGUCAUCG | 1510 | 149 | CGAUGACGUGUGACUCCUC | 1757 |
| 145 | GACACCGGUGACAGCCUGU | 1511 | 145 | GACACCGGUGACAGCCUGU | 1511 | 167 | ACAGGCUGUCACCGGUGUC | 1758 |
| 163 | UCCAUCUCCUGCAGGGGAC | 1512 | 163 | UCCAUCUCCUGCAGGGGAC | 1512 | 185 | GUCCCCUGCAGGAGAUGGA | 1759 |
| 181 | CAGCACCCCCUCGAGUGGG | 1513 | 181 | CAGCACCCCCUCGAGUGGG | 1513 | 203 | CCCACUCGAGGGGGUGCUG | 1760 |
| 199 | GCUUGGCCAGGAGCUCAGG | 1514 | 199 | GCUUGGCCAGGAGCUCAGG | 1514 | 221 | CCUGAGCUCCUGGCCAAGC | 1761 |
| 217 | GAGGCGCCAGCCACCGGAG | 1515 | 217 | GAGGCGCCAGCCACCGGAG | 1515 | 239 | CUCCGGUGGCUGGCGCCUC | 1762 |
| 235 | GACAAGGACAGCGAGGACA | 1516 | 235 | GACAAGGACAGCGAGGACA | 1516 | 257 | UGUCCUCGCUGUCCUUGUC | 1763 |
| 253 | ACGGGGUGGUGCGAGACU | 1517 | 253 | ACGGGGUGGUGCGAGACU | 1517 | 275 | AGUCUCGCACCACCCCCGU | 1764 |
| 271 | UGCGAGGGCACAGACGCCA | 1518 | 271 | UGCGAGGGCACAGACGCCA | 1518 | 293 | UGGCGUCUGUGCCCUCGCA | 1765 |
| 289 | AGGCCCUACUGCAAGGUGU | 1519 | 289 | AGGCCCUACUGCAAGGUGU | 1519 | 311 | ACACCUUGCAGUAGGGCCU | 1766 |
| 307 | UUGCUGCUGCACGAGGUAC | 1520 | 307 | UUGCUGCUGCACGAGGUAC | 1520 | 329 | GUACCUCGUGCAGCAGCAA | 1767 |
| 325 | CAUGCCAACGACACAGGCA | 1521 | 325 | CAUGCCAACGACACAGGCA | 1521 | 347 | UGCCUGUGUCGUUGGCAUG | 1768 |
| 343 | AGCUACGUCUGCUACUACA | 1522 | 343 | AGCUACGUCUGCUACUACA | 1522 | 365 | UGUAGUAGCAGACGUAGCU | 1769 |
| 361 | AAGUACAUCAAGGCACGCA | 1523 | 361 | AAGUACAUCAAGGCACGCA | 1523 | 383 | UGCGUGCCUUGAUGUACUU | 1770 |
| 379 | AUCGAGGGCACCACGGCCG | 1524 | 379 | AUCGAGGGCACCACGGCCG | 1524 | 401 | CGGCCGUGGUGCCCUCGAU | 1771 |
| 397 | GCCAGCUCCUACGUGUUCG | 1525 | 397 | GCCAGCUCCUACGUGUUCG | 1525 | 419 | CGAACACGUAGGAGCUGGC | 1772 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 415 | GUGAGAGACUUUGAGCAGC | 1526 | 415 | GUGAGAGACUUUGAGCAGC | 1526 | 437 | GCUGCUCAAAGUCUCUCAC | 1773 |
| 433 | CCAUUCAUCAACAAGCCUG | 1527 | 433 | CCAUUCAUCAACAAGCCUG | 1527 | 455 | CAGGCUUGUUGAUGAAUGG | 1774 |
| 451 | GACACGCUCUUGGUCAACA | 1528 | 451 | GACACGCUCUUGGUCAACA | 1528 | 473 | UGUUGACCAAGAGCGUGUC | 1775 |
| 469 | AGGAAGGACGCCAUGUGGG | 1529 | 469 | AGGAAGGACGCCAUGUGGG | 1529 | 491 | CCCACAUGGCGUCCUUCCU | 1776 |
| 487 | GUGCCCUGUCUGGUGUCCA | 1530 | 487 | GUGCCCUGUCUGGUGUCCA | 1530 | 509 | UGGACACCAGACAGGGCAC | 1777 |
| 505 | AUCCCCGGCCUCAAUGUCA | 1531 | 505 | AUCCCCGGCCUCAAUGUCA | 1531 | 527 | UGACAUUGAGGCCGGGGAU | 1778 |
| 523 | ACGCUGCGCUCGCAAAGCU | 1532 | 523 | ACGCUGCGCUCGCAAAGCU | 1532 | 545 | AGCUUUGCGAGCGCAGCGU | 1779 |
| 541 | UCGGUGCUGUGGCCAGACG | 1533 | 541 | UCGGUGCUGUGGCCAGACG | 1533 | 563 | CGUCUGGCCACAGCACCGA | 1780 |
| 559 | GGGCAGGAGGUGGUGUGGG | 1534 | 559 | GGGCAGGAGGUGGUGUGGG | 1534 | 581 | CCCACACCACCUCCUGCCC | 1781 |
| 577 | GAUGACCGGCGGGGCAUGC | 1535 | 577 | GAUGACCGGCGGGGCAUGC | 1535 | 599 | GCAUGCCCCGCCGGUCAUC | 1782 |
| 595 | CUCGUGUCCACGCCACUGC | 1536 | 595 | CUCGUGUCCACGCCACUGC | 1536 | 617 | GCAGUGGCGUGGACACGAG | 1783 |
| 613 | CUGCACGAUGCCCUGUACC | 1537 | 613 | CUGCACGAUGCCCUGUACC | 1537 | 635 | GGUACAGGGCAUCGUGCAG | 1784 |
| 631 | CUGCAGUGCGAGACCACCU | 1538 | 631 | CUGCAGUGCGAGACCACCU | 1538 | 653 | AGGUGGUCUCGCACUGCAG | 1785 |
| 649 | UGGGGAGACCAGGACUUCC | 1539 | 649 | UGGGGAGACCAGGACUUCC | 1539 | 671 | GGAAGUCCUGGUCUCCCCA | 1786 |
| 667 | CUUUCCAACCCCUUCCUGG | 1540 | 667 | CUUUCCAACCCCUUCCUGG | 1540 | 689 | CCAGGAAGGGGUUGGAAAG | 1787 |
| 685 | GUGCACAUCACAGGCAACG | 1541 | 685 | GUGCACAUCACAGGCAACG | 1541 | 707 | CGUUGCCUGUGAUGUGCAC | 1788 |
| 703 | GAGCUCUAUGACAUCCAGC | 1542 | 703 | GAGCUCUAUGACAUCCAGC | 1542 | 725 | GCUGGAUGUCAUAGAGCUC | 1789 |
| 721 | CUGUUGCCCAGGAAGUCGC | 1543 | 721 | CUGUUGCCCAGGAAGUCGC | 1543 | 743 | GCGACUUCCUGGGCAACAG | 1790 |
| 739 | CUGGAGCUGCUGGUAGGGG | 1544 | 739 | CUGGAGCUGCUGGUAGGGG | 1544 | 761 | CCCCUACCAGCAGCUCCAG | 1791 |
| 757 | GAGAAGCUGGUCCUCAACU | 1545 | 757 | GAGAAGCUGGUCCUCAACU | 1545 | 779 | AGUUGAGGACCAGCUUCUC | 1792 |
| 775 | UGCACCGUGUGGGCUGAGU | 1546 | 775 | UGCACCGUGUGGGCUGAGU | 1546 | 797 | ACUCAGCCCACACGGUGCA | 1793 |
| 793 | UUUAACUCAGGUGUCACCU | 1547 | 793 | UUUAACUCAGGUGUCACCU | 1547 | 815 | AGGUGACACCUGAGUUAAA | 1794 |
| 811 | UUUGACUGGGACUACCCAG | 1548 | 811 | UUUGACUGGGACUACCCAG | 1548 | 833 | CUGGGUAGUCCCAGUCAAA | 1795 |
| 829 | GGGAAGCAGGCAGAGCGGG | 1549 | 829 | GGGAAGCAGGCAGAGCGGG | 1549 | 851 | CCCGCUCUGCCUGCUUCCC | 1796 |
| 847 | GGUAAGUGGGUGCCCGAGC | 1550 | 847 | GGUAAGUGGGUGCCCGAGC | 1550 | 869 | GCUCGGGCACCCACUUACC | 1797 |
| 865 | CGACGCUCCCAACAGACCC | 1551 | 865 | CGACGCUCCCAACAGACCC | 1551 | 887 | GGGUCUGUUGGGAGCGUCG | 1798 |
| 883 | CACACAGAACUCUCCAGCA | 1552 | 883 | CACACAGAACUCUCCAGCA | 1552 | 905 | UGCUGGAGAGUUCUGUGUG | 1799 |
| 901 | AUCCUGACCAUCCACAACG | 1553 | 901 | AUCCUGACCAUCCACAACG | 1553 | 923 | CGUUGUGGAUGGUCAGGAU | 1800 |
| 919 | GUCAGCCAGCACGACCUGG | 1554 | 919 | GUCAGCCAGCACGACCUGG | 1554 | 941 | CCAGGUCGUGCUGGCUGAC | 1801 |
| 937 | GGCUCGUAUGUGUGCAAGG | 1555 | 937 | GGCUGGUAUGUGUGCAAGG | 1555 | 959 | CCUUGCACACAUACGAGCC | 1802 |
| 955 | GCCAACAACGGCAUCCAGC | 1556 | 955 | GCCAACAACGGCAUCCAGC | 1556 | 977 | GCUGGAUGCCGUUGUUGGC | 1803 |
| 973 | CGAUUUCGGAGAGCACCG | 1557 | 973 | CGAUUUCGGAGAGCACCG | 1557 | 995 | CGGUGCUCUCCCGAAAUCG | 1804 |
| 991 | GAGGUCAUUGUGCAUGAAA | 1558 | 991 | GAGGUCAUUGUGCAUGAAA | 1558 | 1013 | UUUCAUGCACAAUGACCUC | 1805 |
| 1009 | AAUCCCUUCAUCAGCGUCG | 1559 | 1009 | AAUCCCUUCAUCAGCGUCG | 1559 | 1031 | CGACGCUGAUGAAGGGAUU | 1806 |
| 1027 | GAGUGGCUCAAAGGACCCA | 1560 | 1027 | GAGUGGCUCAAAGGACCCA | 1560 | 1049 | UGGGUCCUUUGAGCCACUC | 1807 |
| 1045 | AUCCUGGAGGCCACGGCAG | 1561 | 1045 | AUCCUGGAGGCCACGGCAG | 1561 | 1067 | CUGCCGUGGCCUCCAGGAU | 1808 |
| 1063 | GGAGACGAGCUGGUGAAGC | 1562 | 1063 | GGAGACGAGCUGGUGAAGC | 1562 | 1085 | GCUUCACCAGCUCGUCUCC | 1809 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 1081 | CUGCCCGUGAAGCUGGCAG | 1563 | 1081 | CUGCCCGUGAAGCUGGCAG | 1563 | 1103 | CUGCCAGCUUCACGGGCAG | 1810 |
| 1099 | GCGUACCCCCGCCCGAGU | 1564 | 1099 | GCGUACCCCCGCCCGAGU | 1564 | 1121 | ACUCGGGCGGGGGUACGC | 1811 |
| 1117 | UUCCAGUGGUACAAGGAUG | 1565 | 1117 | UUCCAGUGGUACAAGGAUG | 1565 | 1139 | CAUCCUUGUACCACUGGAA | 1812 |
| 1135 | GGAAAGGCACUGUCCGGGC | 1566 | 1135 | GGAAAGGCACUGUCCGGGC | 1566 | 1157 | GCCCGGACAGUGCCUUUCC | 1813 |
| 1153 | CGCCACAGUCCACAUGCCC | 1567 | 1153 | CGCCACAGUCCACAUGCCC | 1567 | 1175 | GGGCAUGUGGACUGUGGCG | 1814 |
| 1171 | CUGGUGCUCAAGGAGGUGA | 1568 | 1171 | CUGGUGCUCAAGGAGGUGA | 1568 | 1193 | UCACCUCCUUGAGCACCAG | 1815 |
| 1189 | ACAGAGGCCAGCACAGGCA | 1569 | 1189 | ACAGAGGCCAGCACAGGCA | 1569 | 1211 | UGCCUGUGCUGGCCUCUGU | 1816 |
| 1207 | ACCUACACCCUCGCCCUGU | 1570 | 1207 | ACCUACACCCUCGCCCUGU | 1570 | 1229 | ACAGGGCGAGGGUGUAGGU | 1817 |
| 1225 | UGGAACUCCGCUGCUGGCC | 1571 | 1225 | UGGAACUCCGCUGCUGGCC | 1571 | 1247 | GGCCAGCAGCGGAGUUCCA | 1818 |
| 1243 | CUGAGGCGCAACAUCAGCC | 1572 | 1243 | CUGAGGCGCAACAUCAGCC | 1572 | 1265 | GGCUGAUGUUGCGCCUCAG | 1819 |
| 1261 | CUGGAGCUGGUGGUGAAUG | 1573 | 1261 | CUGGAGCUGGUGGUGAAUG | 1573 | 1283 | CAUUCACCACCAGCUCCAG | 1820 |
| 1279 | GUGCCCCCCAGAUACAUG | 1574 | 1279 | GUGCCCCCCAGAUACAUG | 1574 | 1301 | CAUGUAUCUGGGGGGGCAC | 1821 |
| 1297 | GAGAAGGAGGCCUCCUCCC | 1575 | 1297 | GAGAAGGAGGCCUCCUCCC | 1575 | 1319 | GGGAGGAGGCCUCCUUCUC | 1822 |
| 1315 | CCCAGCAUCUACUCGCGUC | 1576 | 1315 | CCCAGCAUCUACUCGCGUC | 1576 | 1337 | GACGCGAGUAGAUGCUGGG | 1823 |
| 1333 | CACAGCCGCCAGGCCCUCA | 1577 | 1333 | CACAGCCGCCAGGCCCUCA | 1577 | 1355 | UGAGGGCCUGGCGGCUGUG | 1824 |
| 1351 | ACCUGCACGGCCUACGGGG | 1578 | 1351 | ACCUGCACGGCCUACGGGG | 1578 | 1373 | CCCCGUAGGCCGUGCAGGU | 1825 |
| 1369 | GUGCCCCUGCCUCUCAGCA | 1579 | 1369 | GUGCCCCUGCCUCUCAGCA | 1579 | 1391 | UGCUGAGAGGCAGGGGCAC | 1826 |
| 1387 | AUCCAGUGGCACUGGCGGC | 1580 | 1387 | AUCCAGUGGCACUGGCGGC | 1580 | 1409 | GCCGCCAGUGCCACUGGAU | 1827 |
| 1405 | CCCUGGACACCCUGCAAGA | 1581 | 1405 | CCCUGGACACCCUGCAAGA | 1581 | 1427 | UCUUGCAGGGUGUCCAGGG | 1828 |
| 1423 | AUGUUUGCCCAGCGUAGUC | 1582 | 1423 | AUGUUUGCCCAGCGUAGUC | 1582 | 1445 | GACUACGCUGGGCAAACAU | 1829 |
| 1441 | CUCCGGCGGCGGCAGCAGC | 1583 | 1441 | CUCCGGCGGCGGCAGCAGC | 1583 | 1463 | GCUGCUGCCGCCGCCGGAG | 1830 |
| 1459 | CAAGACCUCAUGCCACAGU | 1584 | 1459 | CAAGACCUCAUGCCACAGU | 1584 | 1481 | ACUGUGGCAUGAGGUCUUG | 1831 |
| 1477 | UGCCGUGACUGGAGGGCGG | 1585 | 1477 | UGCCGUGACUGGAGGGCGG | 1585 | 1499 | CCGCCCUCCAGUCACGGCA | 1832 |
| 1495 | GUGACCACGCAGGAUGCCG | 1586 | 1495 | GUGACCACGCAGGAUGCCG | 1586 | 1517 | CGGCAUCCUGCGUGGUCAC | 1833 |
| 1513 | GUGAACCCCAUCGAGAGCC | 1587 | 1513 | GUGAACCCCAUCGAGAGCC | 1587 | 1535 | GGCUCUCGAUGGGGUUCAC | 1834 |
| 1531 | CUGGACACCUGGACCGAGU | 1588 | 1531 | CUGGACACCUGGACCGAGU | 1588 | 1553 | ACUCGGUCCAGGUGUCCAG | 1835 |
| 1549 | UUUGUGGAGGGAAAGAAUA | 1589 | 1549 | UUUGUGGAGGGAAAGAAUA | 1589 | 1571 | UAUUCUUUCCCUCCACAAA | 1836 |
| 1567 | AAGACUGUGAGCAAGCUGG | 1590 | 1567 | AAGACUGUGAGCAAGCUGG | 1590 | 1589 | CCAGCUUGCUCACAGUCUU | 1837 |
| 1585 | GUGAUCCAGAAUGCCAACG | 1591 | 1585 | GUGAUCCAGAAUGCCAACG | 1591 | 1607 | CGUUGGCAUUCUGGAUCAC | 1838 |
| 1603 | GUGUCUGCCAUGUACAAGU | 1592 | 1603 | GUGUCUGCCAUGUACAAGU | 1592 | 1625 | ACUUGUACAUGGCAGACAC | 1839 |
| 1621 | UGUGGGUCUCCAACAAGG | 1593 | 1621 | UGUGGGUCUCCAACAAGG | 1593 | 1643 | CCUUGUUGGAGACCACACA | 1840 |
| 1639 | GUGGGCCAGGAUGAGCGGC | 1594 | 1639 | GUGGGCCAGGAUGAGCGGC | 1594 | 1661 | GCCGCUCAUCCUGGCCCAC | 1841 |
| 1657 | CUCAUCUACUUCUAUGUGA | 1595 | 1657 | CUCAUCUACUUCUAUGUGA | 1595 | 1679 | UCACAUAGAAGUAGAUGAG | 1842 |
| 1675 | ACCACCAUCCCCGACGGCU | 1596 | 1675 | ACCACCAUCCCCGACGGCU | 1596 | 1697 | AGCCGUCGGGGAUGGUGGU | 1843 |
| 1693 | UUCACCAUCGAAUCCAAGC | 1597 | 1693 | UUCACCAUCGAAUCCAAGC | 1597 | 1715 | GCUUGGAUUCGAUGGUGAA | 1844 |
| 1711 | CCAUCCGAGGAGCUACUAG | 1598 | 1711 | CCAUCCGAGGAGCUACUAG | 1598 | 1733 | CUAGUAGCUCCUCGGAUGG | 1845 |
| 1729 | GAGGGCCAGCCGGUGCUCC | 1599 | 1729 | GAGGGCCAGCCGGUGCUCC | 1599 | 1751 | GGAGCACCGGCUGGCCCUC | 1846 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 1747 | CUGAGCUGCCAAGCCGACA | 1600 | 1747 | CUGAGCUGCCAAGCCGACA | 1600 | 1769 | UGUCGGCUUGGCAGCUCAG | 1847 |
| 1765 | AGCUACAAGUACGAGCAUC | 1601 | 1765 | AGCUACAAGUACGAGCAUC | 1601 | 1787 | GAUGCUCGUACUUGUAGCU | 1848 |
| 1783 | CUGCGCUGGUACCGCCUCA | 1602 | 1783 | CUGCGCUGGUACCGCCUCA | 1602 | 1805 | UGAGGCGGUACCAGCGCAG | 1849 |
| 1801 | AACCUGUCCACGCUGCACG | 1603 | 1801 | AACCUGUCCACGCUGCACG | 1603 | 1823 | CGUGCAGCGUGGACAGGUU | 1850 |
| 1819 | GAUGCGCACGGGAACCCGC | 1604 | 1819 | GAUGCGCACGGGAACCCGC | 1604 | 1841 | GCGGGUUCCCGUGCGCAUC | 1851 |
| 1837 | CUUCUGCUCGACUGCAAGA | 1605 | 1837 | CUUCUGCUCGACUGCAAGA | 1605 | 1859 | UCUUGCAGUCGAGCAGAAG | 1852 |
| 1855 | AACGUGCAUCUGUUCGCCA | 1606 | 1855 | AACGUGCAUCUGUUCGCCA | 1606 | 1877 | UGGCGAACAGAUGCACGUU | 1853 |
| 1873 | ACCCCUCUGGCCGCCAGCC | 1607 | 1873 | ACCCCUCUGGCCGCCAGCC | 1607 | 1895 | GGCUGGCGGCCAGAGGGGU | 1854 |
| 1891 | CUGGAGGAGGUGGCACCUG | 1608 | 1891 | CUGGAGGAGGUGGCACCUG | 1608 | 1913 | CAGGUGCCACCUCCUCCAG | 1855 |
| 1909 | GGGGCGCGCCACGCCACGC | 1609 | 1909 | GGGGCGCGCCACGCCACGC | 1609 | 1931 | GCGUGGCGUGGCGCGCCCC | 1856 |
| 1927 | CUCAGCCUGAGUAUCCCCC | 1610 | 1927 | CUCAGCCUGAGUAUCCCCC | 1610 | 1949 | GGGGGAUACUCAGGCUGAG | 1857 |
| 1945 | CGCGUCGCGCCCGAGCACG | 1611 | 1945 | CGCGUCGCGCCCGAGCACG | 1611 | 1967 | CGUGCUCGGGCGCGACGCG | 1858 |
| 1963 | GAGGGCCACUAUGUGUGCG | 1612 | 1963 | GAGGGCCACUAUGUGUGCG | 1612 | 1985 | CGCACACAUAGUGGCCCUC | 1859 |
| 1981 | GAAGUGCAAGACCGGCGCA | 1613 | 1981 | GAAGUGCAAGACCGGCGCA | 1613 | 2003 | UGCGCCGGUCUUGCACUUC | 1860 |
| 1999 | AGCCAUGACAAGCACUGCC | 1614 | 1999 | AGCCAUGACAAGCACUGCC | 1614 | 2021 | GGCAGUGCUUGUCAUGGCU | 1861 |
| 2017 | CACAAGAAGUACCUGUCGG | 1615 | 2017 | CACAAGAAGUACCUGUCGG | 1615 | 2039 | CCGACAGGUACUUCUUGUG | 1862 |
| 2035 | GUGCAGGCCCUGGAAGCCC | 1616 | 2035 | GUGCAGGCCCUGGAAGCCC | 1616 | 2057 | GGGCUUCCAGGGCCUGCAC | 1863 |
| 2053 | CCUCGGCUCACGCAGAACU | 1617 | 2053 | CCUCGGCUCACGCAGAACU | 1617 | 2075 | AGUUCUGCGUGAGCCGAGG | 1864 |
| 2071 | UUGACCGACCUCCUGGUGA | 1618 | 2071 | UUGACCGACCUCCUGGUGA | 1618 | 2093 | UCACCAGGAGGUCGGUCAA | 1865 |
| 2089 | AACGUGAGCGACUCGCUGG | 1619 | 2089 | AACGUGAGCGACUCGCUGG | 1619 | 2111 | CCAGCGAGUCGCUCACGUU | 1866 |
| 2107 | GAGAUGCAGUGCUUGGUGG | 1620 | 2107 | GAGAUGCAGUGCUUGGUGG | 1620 | 2129 | CCACCAAGCACUGCAUCUC | 1867 |
| 2125 | GCCGGAGCGCACGCGCCCA | 1621 | 2125 | GCCGGAGCGCACGCGCCCA | 1621 | 2147 | UGGGCGCGUGCGCUCCGGC | 1868 |
| 2143 | AGCAUCGUGUGGUACAAAG | 1622 | 2143 | AGCAUCGUGUGGUACAAAG | 1622 | 2165 | CUUUGUACCACACGAUGCU | 1869 |
| 2161 | GACGAGAGGCUGCUGGAGG | 1623 | 2161 | GACGAGAGGCUGCUGGAGG | 1623 | 2183 | CCUCCAGCAGCCUCUCGUC | 1870 |
| 2179 | GAAAAGUCUGGAGUCGACU | 1624 | 2179 | GAAAAGUCUGGAGUCGACU | 1624 | 2201 | AGUCGACUCCAGACUUUUC | 1871 |
| 2197 | UUGGCGGACUCCAACCAGA | 1625 | 2197 | UUGGCGGACUCCAACCAGA | 1625 | 2219 | UCUGGUUGGAGUCCGCCAA | 1872 |
| 2215 | AAGCUGAGCAUCCAGCGCG | 1626 | 2215 | AAGCUGAGCAUCCAGCGCG | 1626 | 2237 | CGCGCUGGAUGCUCAGCUU | 1873 |
| 2233 | GUGCGCGAGGAGGAUGCGG | 1627 | 2233 | GUGCGCGAGGAGGAUGCGG | 1627 | 2255 | CCGCAUCCUCCUCGCGCAC | 1874 |
| 2251 | GGACCGUAUCUGUGCAGCG | 1628 | 2251 | GGACCGUAUCUGUGCAGCG | 1628 | 2273 | CGCUGCACAGAUACGGUCC | 1875 |
| 2269 | GUGUGCAGACCCAAGGGCU | 1629 | 2269 | GUGUGCAGACCCAAGGGCU | 1629 | 2291 | AGCCCUUGGGUCUGCACAC | 1876 |
| 2287 | UGCGUCAACUCCUCCGCCA | 1630 | 2287 | UGCGUCAACUCCUCCGCCA | 1630 | 2309 | UGGCGGAGGAGUUGACGCA | 1877 |
| 2305 | AGCGUGGCCGUGGAAGGCU | 1631 | 2305 | AGCGUGGCCGUGGAAGGCU | 1631 | 2327 | AGCCUUCCACGGCCACGCU | 1878 |
| 2323 | UCCGAGGAUAAGGGCAGCA | 1632 | 2323 | UCCGAGGAUAAGGGCAGCA | 1632 | 2345 | UGCUGCCCUUAUCCUCGGA | 1879 |
| 2341 | AUGGAGAUCGUGAUCCUUG | 1633 | 2341 | AUGGAGAUCGUGAUCCUUG | 1633 | 2363 | CAAGGAUCACGAUCUCCAU | 1880 |
| 2359 | GUCGGUACCGGCGUCAUCG | 1634 | 2359 | GUCGGUACCGGCGUCAUCG | 1634 | 2381 | CGAUGACGCCGGUACCGAC | 1881 |
| 2377 | GCUGUCUUCUUCUGGGUCC | 1635 | 2377 | GCUGUCUUCUUCUGGGUCC | 1635 | 2399 | GGACCCAGAAGAAGACAGC | 1882 |
| 2395 | CUCCUCCUCCUCAUCUUCU | 1636 | 2395 | CUCCUCCUCCUCAUCUUCU | 1636 | 2417 | AGAAGAUGAGGAGGAGGAG | 1883 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 2413 | UGUAACAUGAGGAGGCCGG | 1637 | 2413 | UGUAACAUGAGGAGGCCGG | 1637 | 2435 | CCGGCCUCCUCAUGUUACA | 1884 |
| 2431 | GCCCACGCAGACAUCAAGA | 1638 | 2431 | GCCCACGCAGACAUCAAGA | 1638 | 2453 | UCUUGAUGUCUGCGUGGGC | 1885 |
| 2449 | ACGGGCUACCUGUCCAUCA | 1639 | 2449 | ACGGGCUACCUGUCCAUCA | 1639 | 2471 | UGAUGGACAGGUAGCCCGU | 1886 |
| 2467 | AUCAUGGACCCCGGGGAGG | 1640 | 2467 | AUCAUGGACCCCGGGGAGG | 1640 | 2489 | CCUCCCCGGGGUCCAUGAU | 1887 |
| 2485 | GUGCCUCUGGAGGAGCAAU | 1641 | 2485 | GUGCCUCUGGAGGAGCAAU | 1641 | 2507 | AUUGCUCCUCCAGAGGCAC | 1888 |
| 2503 | UGCGAAUACCUGUCCUACG | 1642 | 2503 | UGCGAAUACCUGUCCUACG | 1642 | 2525 | CGUAGGACAGGUAUUCGCA | 1889 |
| 2521 | GAUGCCAGCCAGUGGGAAU | 1643 | 2521 | GAUGCCAGCCAGUGGGAAU | 1643 | 2543 | AUUCCCACUGGCUGGCAUC | 1890 |
| 2539 | UUCCCCGAGAGCGGCUGC | 1644 | 2539 | UUCCCCGAGAGCGGCUGC | 1644 | 2561 | GCAGCCGCUCUCGGGGAA | 1891 |
| 2557 | CACCUGGGGAGAGUGCUCG | 1645 | 2557 | CACCUGGGGAGAGUGCUCG | 1645 | 2579 | CGAGCACUCUCCCCAGGUG | 1892 |
| 2575 | GGCUACGGCGCCUUCGGGA | 1646 | 2575 | GGCUACGGCGCCUUCGGGA | 1646 | 2597 | UCCCGAAGGCGCCGUAGCC | 1893 |
| 2593 | AAGGUGGUGGAAGCCUCCG | 1647 | 2593 | AAGGUGGUGGAAGCCUCCG | 1647 | 2615 | CGGAGGCUUCCACCACCUU | 1894 |
| 2611 | GCUUUCGGCAUCCACAAGG | 1648 | 2611 | GCUUUCGGCAUCCACAAGG | 1648 | 2633 | CCUUGUGGAUGCCGAAAGC | 1895 |
| 2629 | GGCAGCAGCUGUGACACCG | 1649 | 2629 | GGCAGCAGCUGUGACACCG | 1649 | 2651 | CGGUGUCACAGCUGCUGCC | 1896 |
| 2647 | GUGGCCGUGAAAAUGCUGA | 1650 | 2647 | GUGGCCGUGAAAAUGCUGA | 1650 | 2669 | UCAGCAUUUUCACGGCCAC | 1897 |
| 2665 | AAAGAGGGCGCCACGGCCA | 1651 | 2665 | AAAGAGGGCGCCACGGCCA | 1651 | 2687 | UGGCCGUGGCGCCCUCUUU | 1898 |
| 2683 | AGCGAGCAGCGCGCGCUGA | 1652 | 2683 | AGCGAGCAGCGCGCGCUGA | 1652 | 2705 | UCAGCGCGCGCUGCUCGCU | 1899 |
| 2701 | AUGUCGGAGCUCAAGAUCC | 1653 | 2701 | AUGUCGGAGCUCAAGAUCC | 1653 | 2723 | GGAUCUUGAGCUCCGACAU | 1900 |
| 2719 | CUCAUUCACAUCGGCAACC | 1654 | 2719 | CUCAUUCACAUCGGCAACC | 1654 | 2741 | GGUUGCCGAUGUGAAUGAG | 1901 |
| 2737 | CACCUCAACGUGGUCAACC | 1655 | 2737 | CACCUCAACGUGGUCAACC | 1655 | 2759 | GGUUGACCACGUUGAGGUG | 1902 |
| 2755 | CUCCUCGGGGCGUGCACCA | 1656 | 2755 | CUCCUCGGGGCGUGCACCA | 1656 | 2777 | UGGUGCACGCCCCGAGGAG | 1903 |
| 2773 | AAGCCGCAGGGCCCCCUCA | 1657 | 2773 | AAGCCGCAGGGCCCCCUCA | 1657 | 2795 | UGAGGGGGCCCUGCGGCUU | 1904 |
| 2791 | AUGGUGAUCGUGGAGUUCU | 1658 | 2791 | AUGGUGAUCGUGGAGUUCU | 1658 | 2813 | AGAACUCCACGAUCACCAU | 1905 |
| 2809 | UGCAAGUACGGCAACCUCU | 1659 | 2809 | UGCAAGUACGGCAACCUCU | 1659 | 2831 | AGAGGUUGCCGUACUUGCA | 1906 |
| 2827 | UCCAACUUCCUGCGCGCCA | 1660 | 2827 | UCCAACUUCCUGCGCGCCA | 1660 | 2849 | UGGCGCGCAGGAAGUUGGA | 1907 |
| 2845 | AAGCGGGACGCCUUCAGCC | 1661 | 2845 | AAGCGGGACGCCUUCAGCC | 1661 | 2867 | GGCUGAAGGCGUCCCGCUU | 1908 |
| 2863 | CCCUGCGCGGAGAAGUCUC | 1662 | 2863 | CCCUGCGCGGAGAAGUCUC | 1662 | 2885 | GAGACUUCUCCGCGCAGGG | 1909 |
| 2881 | CCCGAGCAGCGCGGACGCU | 1663 | 2881 | CCCGAGCAGCGCGGACGCU | 1663 | 2903 | AGCGUCCGCGCUGCUCGGG | 1910 |
| 2899 | UUCCGCGCCAUGGUGGAGC | 1664 | 2899 | UUCCGCGCCAUGGUGGAGC | 1664 | 2921 | GCUCCACCAUGGCGCGGAA | 1911 |
| 2917 | CUCGCCAGGCUGGAUCGGA | 1665 | 2917 | CUCGCCAGGCUGGAUCGGA | 1665 | 2939 | UCCGAUCCAGCCUGGCGAG | 1912 |
| 2935 | AGGCGGCCGGGGAGCAGCG | 1666 | 2935 | AGGCGGCCGGGGAGCAGCG | 1666 | 2957 | CGCUGCUCCCCGGCCGCCU | 1913 |
| 2953 | GACAGGGUCCUCUUCGCGC | 1667 | 2953 | GACAGGGUCCUCUUCGCGC | 1667 | 2975 | GCGCGAAGAGGACCCUGUC | 1914 |
| 2971 | CGGUUCUCGAAGACCGAGG | 1668 | 2971 | CGGUUCUCGAAGACCGAGG | 1668 | 2993 | CCUCGGUCUUCGAGAACCG | 1915 |
| 2989 | GGCGGAGCGAGGCGGGCUU | 1669 | 2989 | GGCGGAGCGAGGCGGGCUU | 1669 | 3011 | AAGCCCGCCUCGCUCCGCC | 1916 |
| 3007 | UCUCCAGACCAAGAAGCUG | 1670 | 3007 | UCUCCAGACCAAGAAGCUG | 1670 | 3029 | CAGCUUCUUGGUCUGGAGA | 1917 |
| 3025 | GAGGACCUGUGGCUGAGCC | 1671 | 3025 | GAGGACCUGUGGCUGAGCC | 1671 | 3047 | GGCUCAGCCACAGGUCCUC | 1918 |
| 3043 | CCGCUGACCAUGGAAGAUC | 1672 | 3043 | CCGCUGACCAUGGAAGAUC | 1672 | 3065 | GAUCUUCCAUGGUCAGCGG | 1919 |
| 3061 | CUUGUCUGCUACAGCUUCC | 1673 | 3061 | CUUGUCUGCUACAGCUUCC | 1673 | 3083 | GGAAGCUGUAGCAGACAAG | 1920 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 3079 | CAGGUGGCCAGAGGGAUGG | 1674 | 3079 | CAGGUGGCCAGAGGGAUGG | 1674 | 3101 | CCAUCCCUCUGGCCACCUG | 1921 |
| 3097 | GAGUUCCUGGCUUCCCGAA | 1675 | 3097 | GAGUUCCUGGCUUCCCGAA | 1675 | 3119 | UUCGGGAAGCCAGGAACUC | 1922 |
| 3115 | AAGUGCAUCCACAGAGACC | 1676 | 3115 | AAGUGCAUCCACAGAGACC | 1676 | 3137 | GGUCUCUGUGGAUGCACUU | 1923 |
| 3133 | CUGGCUGCUCGGAACAUUC | 1677 | 3133 | CUGGCUGCUCGGAACAUUC | 1677 | 3155 | GAAUGUUCCGAGCAGCCAG | 1924 |
| 3151 | CUGCUGUCGGAAAGCGACG | 1678 | 3151 | CUGCUGUCGGAAAGCGACG | 1678 | 3173 | CGUCGCUUUCCGACAGCAG | 1925 |
| 3169 | GUGGUGAAGAUCUGUGACU | 1679 | 3169 | GUGGUGAAGAUCUGUGACU | 1679 | 3191 | AGUCACAGAUCUUCACCAC | 1926 |
| 3187 | UUUGGCCUUGCCCGGGACA | 1680 | 3187 | UUUGGCCUUGCCCGGGACA | 1680 | 3209 | UGUCCCGGGCAAGGCCAAA | 1927 |
| 3205 | AUCUACAAAGACCCCGACU | 1681 | 3205 | AUCUACAAAGACCCCGACU | 1681 | 3227 | AGUCGGGGUCUUUGUAGAU | 1928 |
| 3223 | UACGUCCGCAAGGGCAGUG | 1682 | 3223 | UACGUCCGCAAGGGCAGUG | 1682 | 3245 | CACUGCCCUUGCGGACGUA | 1929 |
| 3241 | GCCCGGCUGCCCCUGAAGU | 1683 | 3241 | GCCCGGCUGCCCCUGAAGU | 1683 | 3263 | ACUUCAGGGGCAGCCGGGC | 1930 |
| 3259 | UGGAUGGCCCCUGAAAGCA | 1684 | 3259 | UGGAUGGCCCCUGAAAGCA | 1684 | 3281 | UGCUUUCAGGGGCCAUCCA | 1931 |
| 3277 | AUCUUCGACAAGGUGUACA | 1685 | 3277 | AUCUUCGACAAGGUGUACA | 1685 | 3299 | UGUACACCUUGUCGAAGAU | 1932 |
| 3295 | ACCACGCAGAGUGACGUGU | 1686 | 3295 | ACCACGCAGAGUGACGUGU | 1686 | 3317 | ACACGUCACUCUGCGUGGU | 1933 |
| 3313 | UGGUCCUUUGGGGUGCUUC | 1687 | 3313 | UGGUCCUUUGGGGUGCUUC | 1687 | 3335 | GAAGCACCCCAAAGGACCA | 1934 |
| 3331 | CUCUGGGAGAUCUUCUCUC | 1688 | 3331 | CUCUGGGAGAUCUUCUCUC | 1688 | 3353 | GAGAGAAGAUCUCCCAGAG | 1935 |
| 3349 | CUGGGGGCCUCCCCGUACC | 1689 | 3349 | CUGGGGGCCUCCCCGUACC | 1689 | 3371 | GGUACGGGGAGGCCCCCAG | 1936 |
| 3367 | CCUGGGGUGCAGAUCAAUG | 1690 | 3367 | CCUGGGGUGCAGAUCAAUG | 1690 | 3389 | CAUUGAUCUGCACCCCAGG | 1937 |
| 3385 | GAGGAGUUCUGCCAGCGCG | 1691 | 3385 | GAGGAGUUCUGCCAGCGCG | 1691 | 3407 | CGCGCUGGCAGAACUCCUC | 1938 |
| 3403 | GUGAGAGACGGCACAAGGA | 1692 | 3403 | GUGAGAGACGGCACAAGGA | 1692 | 3425 | UCCUUGUGCCGUCUCUCAC | 1939 |
| 3421 | AUGAGGGCCCCGGAGCUGG | 1693 | 3421 | AUGAGGGCCCCGGAGCUGG | 1693 | 3443 | CCAGCUCCGGGGCCCUCAU | 1940 |
| 3439 | GCCACUCCCGCCAUACGCC | 1694 | 3439 | GCCACUCCCGCCAUACGCC | 1694 | 3461 | GGCGUAUGGCGGGAGUGGC | 1941 |
| 3457 | CACAUCAUGCUGAACUGCU | 1695 | 3457 | CACAUCAUGCUGAACUGCU | 1695 | 3479 | AGCAGUUCAGCAUGAUGUG | 1942 |
| 3475 | UGGUCCGGAGACCCCAAGG | 1696 | 3475 | UGGUCCGGAGACCCCAAGG | 1696 | 3497 | CCUUGGGGUCUCCGGACCA | 1943 |
| 3493 | GCGAGACCUGCAUUCUCGG | 1697 | 3493 | GCGAGACCUGCAUUCUCGG | 1697 | 3515 | CCGAGAAUGCAGGUCUCGC | 1944 |
| 3511 | GACCUGGUGGAGAUCCUGG | 1698 | 3511 | GACCUGGUGGAGAUCCUGG | 1698 | 3533 | CCAGGAUCUCCACCAGGUC | 1945 |
| 3529 | GGGGACCUGCUCCAGGGCA | 1699 | 3529 | GGGGACCUGCUCCAGGGCA | 1699 | 3551 | UGCCCUGGAGCAGGUCCCC | 1946 |
| 3547 | AGGGGCCUGCAAGAGGAAG | 1700 | 3547 | AGGGGCCUGCAAGAGGAAG | 1700 | 3569 | CUUCCUCUUGCAGGCCCCU | 1947 |
| 3565 | GAGGAGGUCUGCAUGGCCC | 1701 | 3565 | GAGGAGGUCUGCAUGGCCC | 1701 | 3587 | GGGCCAUGCAGACCUCCUC | 1948 |
| 3583 | CCGCGCAGCUCUCAGAGCU | 1702 | 3583 | CCGCGCAGCUCUCAGAGCU | 1702 | 3605 | AGCUCUGAGAGCUGCGCGG | 1949 |
| 3601 | UCAGAAGAGGGCAGCUUCU | 1703 | 3601 | UCAGAAGAGGGCAGCUUCU | 1703 | 3623 | AGAAGCUGCCCUCUUCUGA | 1950 |
| 3619 | UCGCAGGUGUCCACCAUGG | 1704 | 3619 | UCGCAGGUGUCCACCAUGG | 1704 | 3641 | CCAUGGUGGACACCUGCGA | 1951 |
| 3637 | GCCCUACACAUCGCCCAGG | 1705 | 3637 | GCCCUACACAUCGCCCAGG | 1705 | 3659 | CCUGGGCGAUGUGUAGGGC | 1952 |
| 3655 | GCUGACGCUGAGGACAGCC | 1706 | 3655 | GCUGACGCUGAGGACAGCC | 1706 | 3677 | GGCUGUCCUCAGCGUCAGC | 1953 |
| 3673 | CCGCCAAGCCUGCAGCGCC | 1707 | 3673 | CCGCCAAGCCUGCAGCGCC | 1707 | 3695 | GGCGCUGCAGGCUUGGCGG | 1954 |
| 3691 | CACAGCCUGGCCGCCAGGU | 1708 | 3691 | CACAGCCUGGCCGCCAGGU | 1708 | 3713 | ACCUGGCGGCCAGGCUGUG | 1955 |
| 3709 | UAUUACAACUGGGGUGUCCU | 1709 | 3709 | UAUUACAACUGGGGUGUCCU | 1709 | 3731 | AGGACACCCAGUUGUAAUA | 1956 |
| 3727 | UUUCCCGGGUGCCUGGCCA | 1710 | 3727 | UUUCCCGGGUGCCUGGCCA | 1710 | 3749 | UGGCCAGGCACCCGGGAAA | 1957 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 3745 | AGAGGGCUGAGACCCGUG | 1711 | 3745 | AGAGGGCUGAGACCCGUG | 1711 | 3767 | CACGGGUCUCAGCCCCUCU | 1958 |
| 3763 | GGUUCCUCCAGGAUGAAGA | 1712 | 3763 | GGUUCCUCCAGGAUGAAGA | 1712 | 3785 | UCUUCAUCCUGGAGGAACC | 1959 |
| 3781 | ACAUUUGAGGAAUUCCCA | 1713 | 3781 | ACAUUUGAGGAAUUCCCA | 1713 | 3803 | UGGGGAAUUCCUCAAAUGU | 1960 |
| 3799 | AUGACCCCAACGACCUACA | 1714 | 3799 | AUGACCCCAACGACCUACA | 1714 | 3821 | UGUAGGUCGUUGGGGUCAU | 1961 |
| 3817 | AAAGGCUCUGUGGACAACC | 1715 | 3817 | AAAGGCUCUGUGGACAACC | 1715 | 3839 | GGUUGUCCACAGAGCCUUU | 1962 |
| 3835 | CAGACAGACAGUGGGAUGG | 1716 | 3835 | CAGACAGACAGUGGGAUGG | 1716 | 3857 | CCAUCCCACUGUCUGUCUG | 1963 |
| 3853 | GUGCUGGCCUCGGAGGAGU | 1717 | 3853 | GUGCUGGCCUCGGAGGAGU | 1717 | 3875 | ACUCCUCCGAGGCCAGCAC | 1964 |
| 3871 | UUUGAGCAGAUAGAGAGCA | 1718 | 3871 | UUUGAGCAGAUAGAGAGCA | 1718 | 3893 | UGCUCUCUAUCUGCUCAAA | 1965 |
| 3889 | AGGCAUAGACAAGAAAGCG | 1719 | 3889 | AGGCAUAGACAAGAAAGCG | 1719 | 3911 | CGCUUUCUUGUCUAUGCCU | 1966 |
| 3907 | GGCUUCAGGUAGCUGAAGC | 1720 | 3907 | GGCUUCAGGUAGCUGAAGC | 1720 | 3929 | GCUUCAGCUACCUGAAGCC | 1967 |
| 3925 | CAGAGAGAGAGAAGGCAGC | 1721 | 3925 | CAGAGAGAGAGAAGGCAGC | 1721 | 3947 | GCUGCCUUCUCUCUCUCUG | 1968 |
| 3943 | CAUACGUCAGCAUUUUCUU | 1722 | 3943 | CAUACGUCAGCAUUUUCUU | 1722 | 3965 | AAGAAAAUGCUGACGUAUG | 1969 |
| 3961 | UCUCUGCACUUAUAAGAAA | 1723 | 3961 | UCUCUGCACUUAUAAGAAA | 1723 | 3983 | UUUCUUAUAAGUGCAGAGA | 1970 |
| 3979 | AGAUCAAAGACUUUAAGAC | 1724 | 3979 | AGAUCAAAGACUUUAAGAC | 1724 | 4001 | GUCUUAAAGUCUUUGAUCU | 1971 |
| 3997 | CUUUCGCUAUUUCUUCUAC | 1725 | 3997 | CUUUCGCUAUUUCUUCUAC | 1725 | 4019 | GUAGAAGAAAUAGCGAAAG | 1972 |
| 4015 | CUGCUAUCUACUACAAACU | 1726 | 4015 | CUGCUAUCUACUACAAACU | 1726 | 4037 | AGUUUGUAGUAGAUAGCAG | 1973 |
| 4033 | UUCAAAGAGGAACCAGGAG | 1727 | 4033 | UUCAAAGAGGAACCAGGAG | 1727 | 4055 | CUCCUGGUUCCUCUUUGAA | 1974 |
| 4051 | GGACAAGAGGAGCAUGAAA | 1728 | 4051 | GGACAAGAGGAGCAUGAAA | 1728 | 4073 | UUUCAUGCUCCUCUUGUCC | 1975 |
| 4069 | AGUGGACAAGGAGUGUGAC | 1729 | 4069 | AGUGGACAAGGAGUGUGAC | 1729 | 4091 | GUCACACUCCUUGUCCACU | 1976 |
| 4087 | CCACUGAAGCACCACAGGG | 1730 | 4087 | CCACUGAAGCACCACAGGG | 1730 | 4109 | CCCUGUGGUGCUUCAGUGG | 1977 |
| 4105 | GAGGGGUUAGGCCUCCGGA | 1731 | 4105 | GAGGGGUUAGGCCUCCGGA | 1731 | 4127 | UCCGGAGGCCUAACCCCUC | 1978 |
| 4123 | AUGACUGCGGGCAGGCCUG | 1732 | 4123 | AUGACUGCGGGCAGGCCUG | 1732 | 4145 | CAGGCCUGCCCGCAGUCAU | 1979 |
| 4141 | GGAUAAUAUCCAGCCUCCC | 1733 | 4141 | GGAUAAUAUCCAGCCUCCC | 1733 | 4163 | GGGAGGCUGGAUAUUAUCC | 1980 |
| 4159 | CACAAGAAGCUGGUGGAGC | 1734 | 4159 | CACAAGAAGCUGGUGGAGC | 1734 | 4181 | GCUCCACCAGCUUCUUGUG | 1981 |
| 4177 | CAGAGUGUUCCCUGACUCC | 1735 | 4177 | CAGAGUGUUCCCUGACUCC | 1735 | 4199 | GGAGUCAGGGAACACUCUG | 1982 |
| 4195 | CUCCAAGGAAAGGGAGACG | 1736 | 4195 | CUCCAAGGAAAGGGAGACG | 1736 | 4217 | CGUCUCCCUUUCCUUGGAG | 1983 |
| 4213 | GCCCUUUCAUGGUCUGCUG | 1737 | 4213 | GCCCUUUCAUGGUCUGCUG | 1737 | 4235 | CAGCAGACCAUGAAAGGGC | 1984 |
| 4231 | GAGUAACAGGUGCCUUCCC | 1738 | 4231 | GAGUAACAGGUGCCUUCCC | 1738 | 4253 | GGGAAGGCACCUGUUACUC | 1985 |
| 4249 | CAGACACUGGCGUUACUGC | 1739 | 4249 | CAGACACUGGCGUUACUGC | 1739 | 4271 | GCAGUAACGCCAGUGUCUG | 1986 |
| 4267 | CUUGACCAAAGAGCCCUCA | 1740 | 4267 | CUUGACCAAAGAGCCCUCA | 1740 | 4289 | UGAGGGCUCUUUGGUCAAG | 1987 |
| 4285 | AAGCGGCCCUUAUGCCAGC | 1741 | 4285 | AAGCGGCCCUUAUGCCAGC | 1741 | 4307 | GCUGGCAUAAGGGCCGCUU | 1988 |
| 4303 | CGUGACAGAGGGCUCACCU | 1742 | 4303 | CGUGACAGAGGGCUCACCU | 1742 | 4325 | AGGUGAGCCCUCUGUCACG | 1989 |
| 4321 | UCUUGCCUUCUAGGUCACU | 1743 | 4321 | UCUUGCCUUCUAGGUCACU | 1743 | 4343 | AGUGACCUAGAAGGCAAGA | 1990 |
| 4339 | UUCCACAAUGUCCCUUCA | 1744 | 4339 | UUCCACAAUGUCCCUUCA | 1744 | 4361 | UGAAGGGACAUUGUGAGAA | 1991 |
| 4357 | AGCACCUGACCCUGUGCCC | 1745 | 4357 | AGCACCUGACCCUGUGCCC | 1745 | 4379 | GGGCACAGGGUCAGGUGCU | 1992 |
| 4375 | CGCCGAUUAUUCCUUGGUA | 1746 | 4375 | CGCCGAUUAUUCCUUGGUA | 1746 | 4397 | UACCAAGGAAUAAUCGCGG | 1993 |
| 4393 | AAUAUGAGUAAUACAUCAA | 1747 | 4393 | AAUAUGAGUAAUACAUCAA | 1747 | 4415 | UUGAUGUAUUACUCAUAUU | 1994 |

TABLE II-continued

VEGFr siNA and Target Sequences

| Pos | Target Sequence | Seq ID | UPos | Upper seq | Seq ID | LPos | Lower seq | Seq ID |
|---|---|---|---|---|---|---|---|---|
| 4411 | AAGAGUAGUAUUAAAAGCU | 1748 | 4411 | AAGAGUAGUAUUAAAAGCU | 1748 | 4433 | AGCUUUUAAUACUACUCUU | 1995 |
| 4429 | UAAUUAAUCAUGUUUAUAA | 1749 | 4429 | UAAUUAAUCAUGUUUAUAA | 1749 | 4451 | UUAUAAACAUGAUUAAUUA | 1996 |

The 3'-ends of the Upper sequence and the Lower sequence of the siNA construct can include an overhang sequence, for example about 1, 2, 3, or 4 nucleotides in length, preferably 2 nucleotides in length, wherein the overhanging sequence of the lower sequence is optionally complementary to a portion of the target sequence. The overhang can comprise the general structure NN or NsN, where N stands for any nucleotide (e.g., thymidine) and s stands for phosphorothioate or other internucleotide linkage as described herein (e.g. internucleotide linkage having Formula I). The upper sequence is also referred to as the sense strand, whereas the lower sequence is also referred to as the antisense strand. The upper and lower sequences in the Table can further comprise a chemical modification having Formulae I–VII or any combination thereof (see for example chemical modifications as shown in Table V herein).

TABLE III

VEGFr Synthetic Modified siNA constructs

| Target | Seq ID | COMPOUND# | Aliases | Sequence | Seq ID |
|---|---|---|---|---|---|
| | | | VEGFR1 | | |
| GCUGUCUGCUUCUCACAGGAUCU | 1997 | | FLT1:298U21 siNA sense | UGUCUGCUUCUCACAGGAUTT | 2020 |
| GAAGGAGAGGACCUGAAACUGUC | 1998 | | FLT1:1956U21 siNA sense | AGGAGAGGACCUGAAACUGTT | 2021 |
| AAGGAGAGGACCUGAAACUGUCU | 1999 | | FLT1:1957U21 siNA sense | GGAGAGGACCUGAAACUGUTT | 2022 |
| GCAUUUGGCAUUAAGAAAUCACC | 2000 | | FLT1:2787U21 siNA sense | AUUUGGCAUUAAGAAAUCATT | 2023 |
| GCUGUCUGCUUCUCACAGGAUCU | 1997 | | FLT1:316L21 siNA (298C) antisense | AUCCUGUGAGAAGCAGACATT | 2024 |
| GAAGGAGAGGACCUGAAACUGUC | 1998 | | FLT1:1974L21 siNA (1956C) antisense | CAGUUUCAGGUCCUCUCCUTT | 2025 |
| AAGGAGAGGACCUGAAACUGUCU | 1999 | | FLT1:1975L21 siNA (1957C) antisense | ACAGUUUCAGGUCCUCUCCTT | 2026 |
| GCAUUUGGCAUUAAGAAAUCACC | 2000 | | FLT1:2805L21 siNA (2787C) antisense | UGAUUUCUUAAUGCCAAAUTT | 2027 |
| GCUGUCUGCUUCUCACAGGAUCU | 1997 | | FLT1:298U21 siNA stab04 sense | B uGucuGcuucucAcAGGAuTT B | 2028 |
| GAAGGAGAGGACCUGAAACUGUC | 1998 | | FLT1:1956U21 siNA stab04 sense | B AGGAGAGGAccuGAAAcuGTT B | 2029 |
| AAGGAGAGGACCUGAAACUGUCU | 1999 | | FLT1:1957U21 siNA stab04 sense | B GGAGAGGAccuGAAAcuGuTT B | 2030 |
| GCAUUUGGCAUUAAGAAAUCACC | 2000 | | FLT1:2787U21 siNA stab04 sense | B AuuuGGcAuuAAGAAAucATT B | 2031 |
| GCUGUCUGCUUCUCACAGGAUCU | 1997 | | FLT1:316L21 siNA (298C) stab05 antisense | AuccuGuGAGAAGcAGAcATsT | 2032 |
| GAAGGAGAGGACCUGAAACUGUC | 1998 | | FLT1:1974L21 siNA (1956C) stab05 antisense | cAGuuucAGGuccucuccuTsT | 2033 |
| AAGGAGAGGACCUGAAACUGUCU | 1999 | | FLT1:1975L21 siNA (1957C) stab05 antisense | AcAGuuucAGGuccucuccTsT | 2034 |
| GCAUUUGGCAUUAAGAAAUCACC | 2000 | | FLT1:2805L21 siNA (2787C) stab05 antisense | uGAuuucuuAAuGccAAAuTsT | 2035 |
| GCUGUCUGCUUCUCACAGGAUCU | 1997 | | FLT1:298U21 siNA stab07 sense | B uGucuGcuucucAcAGGAuTT B | 2036 |
| GAAGGAGAGGACCUGAAACUGUC | 1998 | | FLT1:1956U21 siNA stab07 sense | B AGGAGAGGAccuGAAAcuGTT B | 2037 |
| AAGGAGAGGACCUGAAACUGUCU | 1999 | | FLT1:1957U21 siNA stab07 sense | B GGAGAGGACcuGAAAcuGuTT B | 2038 |
| GCAUUUGGCAUUAAGAAAUCACC | 2000 | | FLT1:2787U21 siNA stab07 sense | B AuuuGGcAuuAAGAAAucATT B | 2039 |
| GCUGUCUGCUUCUCACAGGAUCU | 1997 | | FLT1:316L21 siNA (298C) stab11 antisense | AuccuGuGAGAAGcAGAcATsT | 2040 |
| GAAGGAGAGGACCUGAAACUGUC | 1998 | | FLT1:1974L21 siNA (1956C) stab11 antisense | cAGuuucAGGuccucuccuTsT | 2041 |
| AAGGAGAGGACCUGAAACUGUCU | 1999 | | FLT1:1975L21 siNA (1957C) stab11 antisense | AcAGuuucAGGuccucuccTsT | 2042 |
| GCAUUUGGCAUUAAGAAAUCACC | 2000 | | FLT1:2805L21 siNA (2787C) stab11 antisense | uGAuuucuuAAuGccAAAuTsT | 2043 |
| AACUGAGUUUAAAAGGCACCCAG | 2009 | 31209 | FLT1:367L21 siNA (349C) stab05 inv antisense | GAcucAAAuuuccGuGGGTsT | 2176 |
| AAGCAAGGAGGGCCUCUGAUGGU | 2012 | 31210 | FLT1:2967L21 siNA (2949C) stab05 inv antisense | cGuuccucccGGAGAcuAcTsT | 2177 |
| AGCCUGGAAAGAAUCAAAACCUU | 2011 | 31211 | FLT1:3930L21 siNA (3912C) stab05 inv antisense | GGAccuuucuuAGuuuuGGTsT | 2178 |
| AACUGAGUUUAAAAGGCACCCAG | 2009 | 31212 | FLT1:349U21 siNA stab07 inv sense | B cccAcGGAAAAuuuGAGucTT B | 2179 |
| AAGCAAGGAGGGCCUCUGAUGGU | 2012 | 31213 | FLT1:2949U21 siNA stab07 inv sense | B GuAGucuccGGGAGGAcGTT B | 2180 |
| AGCCUGGAAAGAAUCAAAACCUU | 2011 | 31214 | FLT1:3912U21 siNA stab07 inv sense | B ccAAAAcuAAGAAAGGuccTT B | 2181 |
| AACUGAGUUUAAAAGGCACCCAG | 2009 | 31215 | FLT1:367L21 siNA (349C) stab08 inv antisense | GAcucAAAuuuccGuGGGTsT | 2182 |
| AAGCAAGGAGGGCCUCUGAUGGU | 2012 | 31216 | FLT1:2967L21 siNA (2949C) stab08 inv antisense | cGuuccucccGGAGAcuAcTsT | 2183 |
| AGCCUGGAAAGAAUCAAAACCUU | 2011 | 31217 | FLT1:3930L21 siNA (3912C) stab08 inv antisense | GGAccuuucuuAGuuuuGGTsT | 2184 |

TABLE III-continued

| | | | | | |
|---|---|---|---|---|---|
| AACUGAGUUUAAAAGGCACCCAG | 2009 | 31270 | FLT1:349U21 siNA stab09 sense | B CUGAGUUUAAAAGGCACCCUU B | 2185 |
| AAGCAAGGAGGGCCUCUGAUGGU | 2012 | 31271 | FLT1:2949U21 siNA stab09 sense | B GCAAGGAGGGCCUCUGAUGUU B | 2186 |
| AGCCUGGAAAGAAUCAAAACCUU | 2011 | 31272 | FLT1:3912U21 siNA stab09 sense | B CCUGGAAAGAAUCAAAACCUU B | 2187 |
| AACUGAGUUUAAAAGGCACCCAG | 2009 | 31273 | FLT1:367L21 siNA (349C) stab10 antisense | GGGUGCCUUUUAAACUCAGTsT | 2188 |
| AAGCAAGGAGGGCCUCUGAUGGU | 2012 | 31274 | FLT1:2967L21 siNA (2949C) stab10 antisense | CAUCAGAGGCCCUCCUUGCTsT | 2189 |
| AGCCUGGAAAGAAUCAAAACCUU | 2011 | 31275 | FLT1:3930L21 siNA (3912C) stab10 antisense | GGUUUUGAUUCUUUCCAGGTsT | 2190 |
| AACUGAGUUUAAAAGGCACCCAG | 2009 | 31276 | FLT1:349U21 siNA stab09 inv sense | B CCCACGGAAAAUUUGAGUCUU B | 2191 |
| AAGCAAGGAGGGCCUCUGAUGGU | 2012 | 31277 | FLT1:2949U21 siNA stab09 inv sense | B GUAGUCUCCGGGAGGAACGUU B | 2192 |
| AGCCUGGAAAGAAUCAAAACCUU | 2011 | 31278 | FLT1:3912U21 siNA stab09 inv sense | B CCAAAACUAAGAAAGGUCCUU B | 2193 |
| AACUGAGUUUAAAAGGCACCCAG | 2009 | 31279 | FLT1:367L21 siNA (349C) stab10 inv antisense | GACUCAAAUUUUCCGUGGGTsT | 2194 |
| AAGCAAGGAGGGCCUCUGAUGGU | 2012 | 31280 | FLT1:2967L21 siNA (2949C) stab10 inv antisense | CGUUCCUCCCGGAGACUACTsT | 2195 |
| AGCCUGGAAAGAAUCAAAACCUU | 2011 | 31281 | FLT1:3930L21 siNA (3912C) stab10 inv antisense | GGACCUUUCUUAGUUUUGGTsT | 2196 |
| AACAACCACAAAAUACAACAAGA | 2010 | 31424 | FLT1:2358L21 siNA (2340C) stab11 3'-BrdU antisense | uuGuuGuAuuuuGuGGuuGXsX | 2197 |
| AAGCAAGGAGGGCCUCUGAUGGU | 2012 | 31425 | FLT1:2967L21 siNA (2949C) stab11 3'-BrdU antisense | cAucAGAGGcccuccuuGcXsX | 2198 |
| AACAACCACAAAAUACAACAAGA | 2010 | 31442 | FLT1:2358L21 siNA (2340C) stab11 3'-BrdU antisense | uuGuuGuAuuuuGuGGuuGXsT | 2199 |
| AAGCAAGGAGGGCCUCUGAUGGU | 2012 | 31443 | FLT1:2967L21 siNA (2949C) stab11 3'-BrdU antisense | cAucAGAGGcccuccuuGcXsT | 2200 |
| AACAACCACAAAAUACAACAAGA | 2010 | 31449 | FLT1:2340U21 siNA stab09 sense | B CAACCACAAAAUACAACAAUU B | 2201 |
| AACAACCACAAAAUACAACAAGA | 2010 | 31450 | FLT1:2340U21 siNA inv stab09 sense | B AACAACAUAAAACACCAACUU B | 2202 |
| AACAACCACAAAAUACAACAAGA | 2010 | 31451 | FLT1:2358L21 siNA (2340C) stab10 antisense | UUGUUGUAUUUUGUGGUUGTsT | 2203 |
| AACAACCACAAAAUACAACAAGA | 2010 | 31452 | FLT1:2358L21 siNA (2340C) inv stab10 antisense | GUUGGUGUUUUAUGUUGUUTsT | 2204 |
| AACAACCACAAAAUACAACAAGA | 2010 | 31509 | FLT1:2358L21 siNA (2340C) stab11 antisense | uuGuuGuAuuuuGuGGuuGTsT | 2217 |
| AACUGAGUUUAAAAGGCACCCAG | 2009 | 31794 | 2x cholesterol + R31194 FLT1:349U21 siNA stab07 sense | (H)2ZTa B cuGAGuuuAAAAGGcAcccTT B | 2218 |
| AACUGAGUUUAAAAGGCACCCAG | 2009 | 31795 | 2x cholesterol + R31212 FLT1:349U21 siNA stab07 inv sense | (H)2ZTa B cccAcGGAAAAuuuGAGucTT B | 2219 |
| AACUGAGUUUAAAAGGCACCCAG | 2009 | 31796 | 2x cholesterol + R31270 FLT1:349U21 siNA stab09 sense | (H)2ZTA B CUGAGUUUAAAAGGCACCCUU B | 2220 |
| AACUGAGUUUAAAAGGCACCCAG | 2009 | 31797 | 2x cholesterol + R31276 FLT1:349U21 siNA stab09 inv sense | (H)2ZTa B CCCACGGAAAAUUUGAGUCUU B | 2221 |
| AACUGAGUUUAAAAGGCACCCAG | 2009 | 31798 | 2x C18 phospholipid + R31194 FLT1:349U21 siNA stab07 sense | (L)2 ZTa B cuGAGuuuAAAAGGcAcccTT B | 2222 |
| AACUGAGUUUAAAAGGCACCCAG | 2009 | 31799 | 2x C18 phospholipid + R31212 FLT1:349U21 siNA stab07 inv sense | (L)2 ZTa B cccAcGGAAAAuuuGAGucTT B | 2223 |
| AACUGAGUUUAAAAGGCACCCAG | 2009 | 31800 | 2x C18 phospholipid + R31270 FLT1:349U21 siNA stab09 sense | (L)2 ZTA B CUGAGUUUAAAAGGCACCCUU B | 2224 |
| AACUGAGUUUAAAAGGCACCCAG | 2009 | 31801 | 2x C18 phospholipid + R31276 FLT1:349U21 siNA stab09 inv sense | (L)2 ZTA B CCCACGGAAAAUUUGAGUCUU B | 2225 |
| CAUGCUGGACUGCUGGCAC | 2244 | 32235 | FLT1:3645U21 siNA sense | CAUGCUGGACUGCUGGCACTT | 2275 |
| AUGCUGGACUGCUGGCACA | 2245 | 32236 | FLT1:3646U21 siNA sense | AUGCUGGACUGCUGGCACATT | 2276 |
| UGCUGGACUGCUGGCACAG | 2246 | 32237 | FLT1:3647U21 siNA sense | UGCUGGACUGCUGGCACAGTT | 2277 |
| CAUGCUGGACUGCUGGCAC | 2244 | 32250 | FLT1:3663L21 siNA (3645C) antisense | GUGCCAGCAGUCCAGCAUGTT | 2278 |
| AUGCUGGACUGCUGGCACA | 2245 | 32251 | FLT1:3664L21 siNA (3646C) antisense | UGUGCCAGCAGUCCAGCAUTT | 2279 |
| UGCUGGACUGCUGGCACAG | 2246 | 32252 | FLT1:3665L21 siNA (3647C) antisense | CUGUGCCAGCAGUCCAGCATT | 2280 |
| AACUGAGUUUAAAAGGCACCCAG | 2009 | 32278 | FLT1:349U21 siNA stab16 sense | B CUGAGUUUAAAAGGCACCCUU B | 2281 |
| AACUGAGUUUAAAAGGCACCCAG | 2009 | 32279 | FLT1:349U21 siNA stab18 sense | B cuGAGuuuAAAAGGcAcccTT B | 2282 |
| AACUGAGUUUAAAAGGCACCCAG | 2009 | 32280 | FLT1:349U21 siNA inv stab16 sense | B CCCACGGAAAAUUUGAGUCUU B | 2283 |
| AACUGAGUUUAAAAGGCACCCAG | 2009 | 32281 | FLT1:349U21 siNA inv stab18 sense | B cccAcGGAAAAuuuGAGucTT B | 2284 |
| CUGAACUGAGUUUAAAAGGCACC | 2247 | 32282 | FLT1:346U21 siNA stab09 sense | B GAACUGAGUUUAAAAGGCAUU B | 2285 |
| UGAACUGAGUUUAAAAGGCACCC | 2248 | 32283 | FLT1:347U21 siNA stab09 sense | B AACUGAGUUUAAAAGGCACUU B | 2286 |
| GAACUGAGUUUAAAAGGCACCCA | 2249 | 32284 | FLT1:348U21 siNA stab09 sense | B ACUGAGUUUAAAAGGCACCUU B | 2287 |
| ACUGAGUUUAAAAGGCACCCAGC | 2250 | 32285 | FLT1:350U21 siNA stab09 sense | B UGAGUUUAAAAGGCACCCAUU B | 2288 |
| CUGAGUUUAAAAGGCACCCAGCA | 2251 | 32286 | FLT1:351U21 siNA stab09 sense | B GAGUUUAAAAGGCACCCAGUU B | 2289 |
| UGAGUUUAAAAGGCACCCAGCAC | 2252 | 32287 | FLT1:352U21 siNA stab09 sense | B AGUUUAAAAGGCACCCAGCUU B | 2290 |
| GAGUUUAAAAGGCACCCAGCACA | 2253 | 32288 | FLT1:353U21 siNA stab09 sense | B GUUUAAAAGGCACCCAGCAUU B | 2291 |
| CUGAACUGAGUUUAAAAGGCACC | 2247 | 32289 | FLT1:364L21 siNA (346C) stab10 antisense | UGCCUUUUAAACUCAGUUCTsT | 2292 |
| UGAACUGAGUUUAAAAGGCACCC | 2248 | 32290 | FLT1:365L21 siNA (347C) stab10 antisense | GUGCCUUUUAAACUCAGUUTsT | 2293 |
| GAACUGAGUUUAAAAGGCACCCA | 2249 | 32291 | FLT1:366L21 siNA (348C) stab10 antisense | GGUGCCUUUUAAACUCAGUTsT | 2294 |
| ACUGAGUUUAAAAGGCACCCAGC | 2250 | 32292 | FLT1:368L21 siNA (350C) stab10 antisense | UGGGUGCCUUUUAAACUCATsT | 2295 |
| CUGAGUUUAAAAGGCACCCAGCA | 2251 | 32293 | FLT1:369L21 siNA (351C) stab10 antisense | CUGGGUGCCUUUUAAACUCTsT | 2296 |
| UGAGUUUAAAAGGCACCCAGCAC | 2252 | 32294 | FLT1:370L21 siNA (352C) stab10 antisense | GCUGGGUGCCUUUUAAACUTsT | 2297 |

TABLE III-continued

| | | | | |
|---|---|---|---|---|
| GAGUUUAAAAGGCACCCAGCACA | 2253 | 32295 | FLT1:371L21 siNA (353C) stab10 antisense | UGCUGGGUGCCUUUUAAACTsT | 2298 |
| CUGAACUGAGUUUAAAAGGCACC | 2247 | 32296 | FLT1:346U21 siNA inv stab09 sense | B ACGGAAAAUUUGAGUCAAGTT B | 2299 |
| UGAACUGAGUUUAAAAGGCACCC | 2248 | 32297 | FLT1:347U21 siNA inv stab09 sense | B CACGGAAAAUUUGAGUCAATT B | 2300 |
| GAACUGAGUUUAAAAGGCACCCA | 2249 | 32298 | FLT1:348U21 siNA inv stab09 sense | B CCACGGAAAAUUUGAGUCATT B | 2301 |
| ACUGAGUUUAAAAGGCACCCAGC | 2250 | 32299 | FLT1:350U21 siNA inv stab09 sense | B ACCCACGGAAAAUUUGAGUTT B | 2302 |
| CUGAGUUUAAAAGGCACCCAGCA | 2251 | 32300 | FLT1:351U21 siNA inv stab09 sense | B GACCCACGGAAAAUUUGAGTT B | 2303 |
| UGAGUUUAAAAGGCACCCAGCAC | 2252 | 32301 | FLT1:352U21 siNA inv stab09 sense | B CGACCCACGGAAAAUUUGATT B | 2304 |
| GAGUUUAAAAGGCACCCAGCACA | 2253 | 32302 | FLT1:353U21 siNA inv stab09 sense | B ACGACCCACGGAAAAUUUGTT B | 2305 |
| CUGAACUGAGUUUAAAAGGCACC | 2247 | 32303 | FLT1:364L21 siNA (346C) inv stab10 antisense | CUUGACUCAAAUUUUCCGUTsT | 2306 |
| UGAACUGAGUUUAAAAGGCACCC | 2248 | 32304 | FLT1:365L21 siNA (347C) inv stab10 antisense | UUGACUCAAAUUUUCCGUGTsT | 2307 |
| GAACUGAGUUUAAAAGGCACCCA | 2249 | 32305 | FLT1:366L21 siNA (348C) inv stab10 antisense | UGACUCAAAUUUUCCGUGGTsT | 2308 |
| ACUGAGUUUAAAAGGCACCCAGC | 2250 | 32306 | FLT1:368L21 siNA (350C) inv stab10 antisense | ACUCAAAUUUUCCGUGGGUTsT | 2309 |
| CUGAGUUUAAAAGGCACCCAGCA | 2251 | 32307 | FLT1:369L21 siNA (351C) inv stab10 antisense | CUCAAAUUUUCCGUGGGUCTsT | 2310 |
| UGAGUUUAAAAGGCACCCAGCAC | 2252 | 32308 | FLT1:370L21 siNA (352C) inv stab10 antisense | UCAAAUUUUCCGUGGGUCGTsT | 2311 |
| GAGUUUAAAAGGCACCCAGCACA | 2253 | 32309 | FLT1:371L21 siNA (353C) inv stab10 antisense | CAAAUUUUCCGUGGGUCGUTsT | 2312 |
| AACUGAGUUUAAAAGGCACCCAG | 2009 | 32338 | FLT1:367L21 siNA (349C) stab10 3'-BrdU antisense | GGGUGCCUUUUAAACUCAGXsT | 2313 |
| AACUGAGUUUAAAAGGCACCCAG | 2009 | 32718 | FLT1:367L21 siNA (349C) v1 5'p antisense | pGGGUGCCUUUUAAACUC GAGUUUAAAAG B | 2314 |
| AACUGAGUUUAAAAGGCACCCAG | 2009 | 32719 | FLT1:367L21 siNA (349C) v2 5'p antisense | pGGGUGCCUUUUAAACUCAG GAGUUUAAAAGB | 2315 |
| AAGCAAGGAGGGCCUCUGAUGGU | 2012 | 32720 | FLT1:2967L21 siNA (2949C) v1 5'p antisense | pCAUCAGAGGCCCUCCUUGC AAGGAGGGCCUCU B | 2316 |
| AAGCAAGGAGGGCCUCUGAUGGU | 2012 | 32721 | FLT1:2967L21 siNA (2949C) v2 5'p antisense | pCAUCAGAGGCCCUCCUU AAGGAGGGCCUCUG B | 2317 |
| AAGCAAGGAGGGCCUCUGAUGGU | 2012 | 32722 | FLT1:2967L21 siNA (2949C) v3 5'p antisense | pCAUCAGAGGCCCUCCU AGGAGGGCCUCUG B | 2318 |
| CUGAACUGAGUUUAAAAGGCACC | 2247 | 32748 | FLT1:346U21 siNA stab07 sense | B GAAcuGAGuuuAAAAGGcATT B | 2319 |
| UGAACUGAGUUUAAAAGGCACCC | 2248 | 32749 | FLT1:347U21 siNA stab07 sense | B AAcuGAGuuuAAAAGGcAcTT B | 2320 |
| GAACUGAGUUUAAAAGGCACCCA | 2249 | 32750 | FLT1:348U21 siNA stab07 sense | B AcuGAGuuuAAAAGGcAccTT B | 2321 |
| ACUGAGUUUAAAAGGCACCCAGC | 2250 | 32751 | FLT1:350U21 siNA stab07 sense | B uGAGuuuAAAAGGcAcccATT B | 2322 |
| CUGAGUUUAAAAGGCACCCAGCA | 2251 | 32752 | FLT1:351U21 siNA stab07 sense | B GAGuuuAAAAGGcAcccAGTT B | 2323 |
| UGAGUUUAAAAGGCACCCAGCAC | 2252 | 32753 | FLT1:352U21 siNA stab07 sense | B AGuuuAAAAGGcAcccAGcTT B | 2324 |
| GAGUUUAAAAGGCACCCAGCACA | 2253 | 32754 | FLT1:353U21 siNA stab07 sense | B GuuuAAAAGGcAcccAGcATT B | 2325 |
| CUGAACUGAGUUUAAAAGGCACC | 2247 | 32755 | FLT1:364L21 siNA (346C) stab08 antisense | uGccuuuuAAAcucAGuucTsT | 2326 |
| UGAACUGAGUUUAAAAGGCACCC | 2248 | 32756 | FLT1:365L21 siNA (347C) stab08 antisense | GuGccuuuuAAAcucAGuuTsT | 2327 |
| GAACUGAGUUUAAAAGGCACCCA | 2249 | 32757 | FLT1:366L21 siNA (348C) stab08 antisense | GGuGccuuuuAAAcucAGuTsT | 2328 |
| ACUGAGUUUAAAAGGCACCCAGC | 2250 | 32758 | FLT1:368L21 siNA (350C) stab08 antisense | uGGGuGccuuuuAAAcucATsT | 2329 |
| CUGAGUUUAAAAGGCACCCAGCA | 2251 | 32759 | FLT1:369L21 siNA (351C) stab08 antisense | cuGGGuGccuuuuAAAcucTsT | 2330 |
| UGAGUUUAAAAGGCACCCAGCAC | 2252 | 32760 | FLT1:370L21 siNA (352C) stab08 antisense | GcuGGGuGccuuuuAAAcuTsT | 2331 |
| GAGUUUAAAAGGCACCCAGCACA | 2253 | 32761 | FLT1:371L21 siNA (353C) stab08 antisense | uGcuGGGuGccuuuuAAAcTsT | 2332 |
| CUGAACUGAGUUUAAAAGGCACC | 2247 | 32772 | FLT1:346U21 siNA inv stab07 sense | B AcGGAAAAuuuGAGucAAGTT B | 2333 |
| UGAACUGAGUUUAAAAGGCACCC | 2248 | 32773 | FLT1:347U21 siNA inv stab07 sense | B cAcGGAAAAuuuGAGucAATT B | 2334 |
| GAACUGAGUUUAAAAGGCACCCA | 2249 | 32774 | FLT1:348U21 siNA inv stab07 sense | B ccAcGGAAAAuuuGAGucATT B | 2335 |
| ACUGAGUUUAAAAGGCACCCAGC | 2250 | 32775 | FLT1:350U21 siNA inv stab07 sense | B AcccAcGGAAAAuuuGAGuTT B | 2336 |
| CUGAGUUUAAAAGGCACCCAGCA | 2251 | 32776 | FLT1:351U21 siNA inv stab07 sense | B GAcccAcGGAAAAuuuGAGTT B | 2337 |
| UGAGUUUAAAAGGCACCCAGCAC | 2252 | 32777 | FLT1:352U21 siNA inv stab07 sense | B cGAcccAcGGAAAAuuuGATT B | 2338 |
| GAGUUUAAAAGGCACCCAGCACA | 2253 | 32778 | FLT1:353U21 siNA inv stab07 sense | B AcGAcccAcGGAAAAuuuGTT B | 2339 |
| CUGAACUGAGUUUAAAAGGCACC | 2247 | 32779 | FLT1:364L21 siNA (346C) inv stab08 antisense | cuuGAcucAAAuuuuccGuTsT | 2340 |
| UGAACUGAGUUUAAAAGGCACCC | 2248 | 32780 | FLT1:365L21 siNA (3470) inv stab08 antisense | uuGAcucAAAuuuuccGuGTsT | 2341 |
| GAACUGAGUUUAAAAGGCACCCA | 2249 | 32781 | FLT1:366L21 siNA (348C) inv stab08 antisense | uGAcucAAAuuuuccGuGGTsT | 2342 |
| ACUGAGUUUAAAAGGCACCCAGC | 2250 | 32782 | FLT1:368L21 siNA (3500) inv stab08 antisense | AcucAAAuuuuccGuGGGuTsT | 2343 |
| CUGAGUUUAAAAGGCACCCAGCA | 2251 | 32783 | FLT1:369L21 siNA (3510) inv stab08 antisense | cucAAAuuuuccGuGGGucTsT | 2344 |
| UGAGUUUAAAAGGCACCCAGCAC | 2252 | 32784 | FLT1:370L21 siNA (352C) inv stab08 antisense | ucAAAuuuuccGuGGGucGTsT | 2345 |
| GAGUUUAAAAGGCACCCAGCACA | 2253 | 32785 | FLT1:371L21 siNA (353C) inv stab08 antisense | cAAAuuuuccGuGGGucGuTsT | 2346 |
| AGTTTAAAAGGCACCCAGCACATC | 2254 | 32805 | FLT1:373L21 siNA (354C) v1 5'p antisense | pGUGCUGGGUGCCUUUUAAA AGGCACCCAGC B | 2347 |

TABLE III-continued

| | | | | |
|---|---|---|---|---|
| AGTTTAAAAGGCACCCAGCACATC | 2254 | 32806 FLT1:373L21 siNA (354C) v2 5'p antisense | pGUGCUGGGUGCCUUUAAA GGCACCCAGC B | 2348 |
| AGTTTAAAAGGCACCCAGCACATC | 2254 | 32807 FLT1:373L21 siNA (354C) v3 5'p antisense | pGUGCUGGGUGCCUUAAGGCACC CAGC B | 2349 |
| GCATATATATGATAAAGCATTCA | 2255 | 32808 FLT1:1247L21 siNA (1229C) v1 5'p antisense | pAAUGCUUUAUCAUAUAUAU GAUAAAGC B | 2350 |
| GCATATATATGATAAAGCATTCA | 2255 | 32809 FLT1:1247L21 siNA (1229C) v2 5'p antisense | pAAUGCUUUAUCAUAUAU GAUAAAGC B | 2351 |
| GCATATATATGATAAAGCATTCA | 2255 | 32810 FLT1:1247L21 siNA (1229C) v3 5'p antisense | pAAUGCUUUAUCAUAU GAUAAAGC B | 2352 |
| GCATATATATGATAAAGCATTCA | 2255 | 32811 FLT1:1247L21 siNA (1229C) v4 5'p antisense | pAAUGCUUUAUCAUAU GAUAAAGCA B | 2353 |
| GCATATATATGATAAAGCATTCA | 2255 | 32812 FLT1:1247L21 siNA (1229C) v5 5'p antisense | pAAUGCUUUAUCAUAUAU GAUAAAGCAUU B | 2354 |
| GCATATATATGATAAAGCATTCA | 2255 | 32813 FLT1:1247L21 siNA (1229C) v6 5'p antisense | pAAUGCUUUAUCAUAU GAUAAAGCAUU B | 2355 |
| AACUGAGUUUAAAAGGCACCCAG | 2009 | 33056 FLT1:367L21 siNA (349C) v3 5'p antisense | pGGGUGCCUUUUAAACUCAG GAGUUUAAAAGG B | 2356 |
| AACUGAGUUUAAAAGGCACCCAG | 2009 | 33057 FLT1:367L21 siNA (349C) v4 5'p antisense | pGGGUGCCUUUUAAACUC GAGUUUAAAAGGCA B | 2357 |
| AACUGAGUUUAAAAGGCACCCAG | 2009 | 33058 FLT1:367L21 siNA (349C) v5 5'p antisense | pGGGUGCCUUUUAAACU AGUUUAAAAGG B | 2358 |
| AACUGAGUUUAAAAGGCACCCAG | 2009 | 33059 FLT1:367L21 siNA (349C) v6 5'p antisense | pGGGUGCCUUUUAAACU AGUUUAAAAGGC B | 2359 |
| AACUGAGUUUAAAAGGCACCCAG | 2009 | 33060 FLT1:367L21 siNA (349C) v7 5'p antisense | pGGGUGCCUUUUAAACU AGUUUAAAAGGCA B | 2360 |
| AACUGAGUUUAAAAGGCACCCAG | 2009 | 33061 FLT1:367L21 siNA (349C) v8 5'p antisense | pGGGUGCCUUUUAAACU AGUUUAAAAGGCAC B | 2361 |
| AACUGAGUUUAAAAGGCACCCAG | 2009 | 33062 FLT1:367L21 siNA (349C) v9 5'p antisense | pGGGUGCCUUUUAAAC GUUUAAAAGGC B | 2362 |
| AACUGAGUUUAAAAGGCACCCAG | 2009 | 33063 FLT1:367L21 siNA (349C) v10 5'p antisense | pGGGUGCCUUUUAAAC GUUUAAAAGGCA B | 2363 |
| AACUGAGUUUAAAAGGCACCCAG | 2009 | 33064 FLT1:367L21 siNA (349C) v11 5'p antisense | pGGGUGCCUUUUAAAC GUUUAAAAGGCAC B | 2364 |
| AACUGAGUUUAAAAGGCACCCAG | 2009 | 33121 FLT1:349U21 siNA stab22 | CUGAGUUUAAAAGGCACCCTTB | 2444 |
| AACUGAGUUUAAAAGGCACCCAG | 2009 | 33321 FLT1:367L21 siNA (349C) stab08 + 5'P | pGGGuGccuuuuAAAcucAGTsT | 2445 |
| AACUGAGUUUAAAAGGCACCCAG | 2009 | 33338 FLT1:367L21 siNA (349C) stab08 + 5' aminoL | L GGGuGccuuuuAAAcucAGTsT | 2447 |
| AACUGAGUUUAAAAGGCACCCAG | 2009 | 33553 FLT1:367L21 siNA (349C) stab08 + 5' aminoL | L GGGuGccuuuuAAAcucAGTsT | 2447 |
| AACUGAGUUUAAAAGGCACCCAG | 2009 | 33571 FLT1:367L21 siNA (349C) stab10 + 5'I | GGUGCCUUUUAAACUCAGTT | 2448 |
| CAUGCUGGACUGCUGGCAC | 2244 | 33725 FLT1:3645U21 siNA stab07 | B cAuGcuGGAcuGcuGGcAcTT B | 2449 |
| AUGCUGGACUGCUGGCACA | 2245 | 33726 FLT1:3646U21 siNA stab07 | B AuGcuGGAcuGcuGGcAcATT B | 2450 |
| CAUGCUGGACUGCUGGCAC | 2244 | 33731 FLT1:3663L21 siNA (3645C) stab08 | GuGccAGcAGuccAGcAuGTsT | 2451 |
| AUGCUGGACUGCUGGCACA | 2245 | 33732 FLT1:3664L21 siNA (3646C) stab08 | uGuGccAGcAGuccAGcAuTsT | 2452 |
| CAUGCUGGACUGCUGGCAC | 2244 | 33737 FLT1:3645U21 siNA stab09 | B CAUGCUGGACUGCUGGCACTT B | 2453 |
| AUGCUGGACUGCUGGCACA | 2245 | 33738 FLT1:3646U21 siNA stab09 | B AUGCUGGACUGCUGGCACATT B | 2454 |
| CAUGCUGGACUGCUGGCAC | 2244 | 33743 FLT1:3663L21 siNA (3645C) stab10 | GUGCCAGCAGUCCAGCAUGTsT | 2455 |
| AUGCUGGACUGCUGGCACA | 2245 | 33744 FLT1:3664L21 siNA (3646C) stab10 | UGUGCCAGCAGUCCAGCAUTsT | 2456 |
| CAUGGUGGACUGCUGGCAC | 2244 | 33749 FLT1:3645U21 siNA inv stab07 | B cAcGGucGucAGGucGuAcTT B | 2457 |
| AUGCUGGACUGCUGGCACA | 2245 | 33750 FLT1:3646U21 siNA inv stab07 | B AcAcGGucGucAGGucGuATT B | 2458 |
| CAUGCUGGACUGCUGGCAC | 2244 | 33755 FLT1:3663L21 siNA (3645C) inv stab08 | GuAcGAccuGAcGAccGuGTsT | 2459 |
| AUGCUGGACUGCUGGCACA | 2245 | 33756 FLT1:3664L21 siNA (3646C) inv stab08 | uAcGAccuGAcGAccGuGuTsT | 2460 |
| CAUGCUGGACUGCUGGCAC | 2244 | 33761 FLT1:3645U21 siNA inv stab09 | B CACGGUCGUCAGGUCGUACTT B | 2461 |
| AUGCUGGACUGCUGGCACA | 2245 | 33762 FLT1:3646U21 siNA inv stab09 | B ACACGGUCGUCAGGUCGUATT B | 2462 |
| CAUGCUGGACUGCUGGCAC | 2244 | 33767 FLT1:3663L21 siNA (3645C) inv stab10 | GUACGACCUGACGACCGUGTsT | 2463 |
| AUGCUGGACUGCUGGCACA | 2245 | 33768 FLT1:3664L21 siNA (3646C) inv stab10 | UACGACCUGACGACCGUGUTsT | 2464 |
| AGUUUAAAAGGCACCCAGCACAU | 2438 | 34092 FLT1:373L18 siNA (354C) v4 5'p | pUGCUGGGUGCCUUUUAAA AGGCACCCAGC B | 2465 |
| AGUUUAAAAGGCACCCAGCACAU | 2438 | 34093 FLT1:373L17 siNA (354C) v5 5'p | pGCUGGGUGCCUUUUAAA AGGCACCCAGC B | 2466 |
| AGUUUAAAAGGCACCCAGCACAU | 2438 | 34094 FLT1:373L17 siNA (354C) v6 5'p | pGCUGGGUGCCUUUUAAA AGGCACCCAGCT B | 2467 |
| AGUUUAAAAGGCACCCAGCACAU | 2438 | 34095 FLT1:373L17 siNA (354C) v7 5'p | pGCUGGGUGCCUUUUAAA AGGCACCCAG B | 2468 |
| AGUUUAAAAGGCACCCAGCACAU | 2438 | 34096 FLT1:373L16 siNA (354C) v8 5'p | pCUGGGUGCCUUUUAAA AGGCACCCAG B | 2469 |
| AGUUUAAAAGGCACCCAGCACAU | 2438 | 34097 FLT1:373L16 siNA (354C) v9 5'p | pCUGGGUGCCUUUUAAA AGGCACCCA B | 2470 |
| AGUUUAAAAGGCACCCAGCACAU | 2438 | 34098 FLT1:373L15 siNA (354C) v10 5'p | pUGGGUGCCUUUUAAA AGGCACCCA B | 2471 |
| AGUUUAAAAGGCACCCAGCACAU | 2438 | 34099 FLT1:373L15 siNA (354C) v11 5'p | pUGGGUGCCUUUUAAA AGGCACCCAT B | 2472 |
| AGUUUAAAAGGCACCCAGCACAU | 2438 | 34100 FLT1:373L15 siNA (354C) v12 5'p | pUGGGUGCCUUUUAAA AGGCACCCATT B | 2473 |
| GCAUAUAUAUGAUAAAGCAUUCA | 2439 | 34101 FLT1:1247L21 siNA (1229C) v14 5'p | pUGCUUUAUCAUAUAUAU GAUAAAGCA B | 2474 |

TABLE III-continued

| | | | | | |
|---|---|---|---|---|---|
| GCAUAUAUAUGAUAAAGCAUUCA | 2439 | 34102 | FLT1:1247L21 siNA (1229C) v15 5'p | pUGCUUUAUCAUAUAUAU GAUAAAGC B | 2475 |
| GCAUAUAUAUGAUAAAGCAUUCA | 2439 | 34103 | FLT1:1247L21 siNA (1229C) v16 5'p | pGCUUUAUCAUAUAUAU GAUAAAGC B | 2476 |
| GCAUAUAUAUGAUAAAGCAUUCA | 2439 | 34104 | FLT1:1247L17 siNA (1229C) v5 | AAUGCUUUAUCAUAUAU GAUAAAGCAUU B | 2477 |
| GCAUAUAUAUGAUAAAGCAUUCA | 2439 | 34105 | FLT1:1247L17 siNA (1229C) v7 5'p | pAAUGCUUUAUCAUAUAU GAUAAAGCAUUU B | 2478 |
| GCAUAUAUAUGAUAAAGCAUUCA | 2439 | 34106 | FLT1:1247L17 siNA (1229C) v8 5'p | pAAUGCUUUAUCAUAUAU GAUAAAGCAUUTT B | 2479 |
| GCAUAUAUAUGAUAAAGCAUUCA | 2439 | 34107 | FLT1:1247L17 siNA (1229C) v9 5'p | pAAUGCUUUAUCAUAUAU GAUAAAGCAU B | 2480 |
| GCAUAUAUAUGAUAAAGCAUUCA | 2439 | 34108 | FLT1:1247L16 siNA (1229C) v10 5'p | pAUGCUUUAUCAUAUAU GAUAAAGCAU B | 2481 |
| GCAUAUAUAUGAUAAAGCAUUCA | 2439 | 34109 | FLT1:1247L16 siNA (1229C) v11 5'p | pAUGCUUUAUCAUAUAU GAUAAAGCAUT B | 2482 |
| GCAUAUAUAUGAUAAAGCAUUCA | 2439 | 34110 | FLT1:1247LI6siNA (1229C) v12 5'p | pAUGCUUUAUCAUAUAU GAUAAAGCAUTT B | 2483 |
| GCAUAUAUAUGAUAAAGCAUUCA | 2439 | 34111 | FLT1:1247L16 siNA (1229C) v13 5'p | pAUGCUUUAUCAUAUAU GAUAAAGCA B | 2484 |
| GCAUAUAUAUGAUAAAGCAUUCA | 2439 | 34112 | FLT1:1247L17 siNA (1229C) v14 5'p | pAAUGCUUUAUCAUAUAU CUAUAAGCAUU B | 2485 |
| GCAUAUAUAUGAUAAAGCAUUCA | 2439 | 34113 | FLT1:1247L17 siNA (1229C) vIS 5'p | pAAUGCUUUUAGUUAUAU GAUAAAGCAUU B | 2486 |
| GCAUAUAUAUGAUAAAGCAUUCA | 2439 | 34114 | FLT1:1247L17 siNA (1229C) v16 5'p | pAAUCCUUAAUCUUAUUU GAUPAAGCAUU B | 2487 |
| GCAUAUAUAUGAUAAAGCAUUCA | 2439 | 34115 | FLT1:1247L17 siNA (1229C) v17 5'p | pAAuGcuuuAucAuAuAu GAuAAAGcAuu B | 2488 |
| GCAUAUAUAUGAUAAAGCAUUCA | 2439 | 34116 | FLT1:1247L17 siNA (1229C) v18 5'p | pAAuGcuuuAucAuAuAu GAuAAAGcAuu B | 2489 |
| AACUGAGUUUAAAAGGCACCCAG | 2009 | 34487 | FLT1:349U21 siNA stab09 w/block PS | B CsUsGAGUUUsAsAsAsGGCACCs CsTsT B | 2490 |
| AACUGAGUUUAAAAGGCACCCAG | 2009 | 34488 | FLT1:367L21 siNA (349C) stab10 w/block PS | GGGsUsGsCsCsUUUUAAsAsCsUsC sAGTsT | 2491 |
| AACUGAGUUUAAAAGGCACCCAG | 2009 | 34489 | FLT1:349U21 siNA stab09 inv w/block PS | B CsCsCACGGAsAsAsAsUsUUGAGUs CsTsT B | 2492 |
| AACUGAGUUUAAAAGGCACCCAG | 2009 | 34490 | FLT1:367L21 siNA (349C) stab10 inv w/block PS | GACUsCsAsAsAUUUUCsCsGsUsG sGGTsT | 2493 |
| | | | VEGFR2 | | |
| UGACCUUGGAGCAUCUCAUCUGU | 2001 | | KDR:3304U21 siNA stab04 sense | B AccuuGGAGcAucucAucuTT B | 2052 |
| UCACCUGUUUCCUGUAUGGAGGA | 2003 | | KDR:3894U21 siNA stab04 sense | B AccuGuuuccuGuAuGGAGTT B | 2054 |
| UGACCUUGGAGCAUCUCAUCUGU | 2001 | | KDR:3322L21 siNA (3304C) stab05 antisense | AGAuGAGAuGcuccAAGGuTsT | 2056 |
| UCACCUGUUUCCUGUAUGGAGGA | 2003 | | KDR:3912L21 siNA (3894C) stab05 antisense | cuccAuAcAGGAAAcAGGuTsT | 2058 |
| UGACCUUGGAGCAUCUCAUCUGU | 2001 | | KDR:3304U21 siNA stab07 sense | B AccuuGGAGcAucucAucuTT B | 2060 |
| UCACCUGUUUCCUGUAUGGAGGA | 2003 | 32766 | KDR:3894U21 siNA stab07 sense | B AccuGuuuccuGuAuGGAGTT B | 2062 |
| UGACCUUGGAGCAUCUCAUCUGU | 2001 | | KDR:3322L21 siNA (3304C) stab11 antisense | AGAuGAGAuGcuccAAGGuTsT | 2064 |
| UUUGAGCAUGGAAGAGGAUUCUG | 2002 | | KDR:3872L21 siNA (3854C) stab11 antisense | GAAuccucuuccAuGcucATsT | 2065 |
| UCACCUGUUUCCUGUAUGGAGGA | 2003 | | KDR:3912L21 siNA (3894C) stab11 antisense | cuccAuAcAGGAAAcAGGuTsT | 2066 |
| GACAACACAGCAGGAAUCAGUCA | 2004 | | KDR:3966L21 siNA (3948C) stab11 antisense | AcuGAuuccuGcuGuGuuGTsT | 2067 |
| UGUCCACUUACCUGAGGAGCAAG | 2017 | 30785 | KDR:3076U21 siNA stab04 sense | B uccAcuuAccuGAGGAGcATT B | 2205 |
| UUUGAGCAUGGAAGAGGAUUCUG | 2002 | 30786 | KDR:3854U21 siNA stab04 sense | B uGAGcAuGGAAGAGGAuucTT B | 2053 |
| AUGGUUCUUGCCUCAGAAGAGCU | 2018 | 30787 | KDR:4089U21 siNA stab04 sense | B GGuucuGccucAGAAGAGTT B | 2206 |
| UCUGAAGGCUCAAACCAGACAAG | 2019 | 30788 | KDR:4191U21 siNA stab04 sense | B uGAAGGcucAAAccAGAcATT B | 2207 |
| UGUCCACUUACCUGAGGAGCAAG | 2017 | 30789 | KDR:3094L21 siNA (3076C) stab05 antisense | uGcuccucAGGuAAGuGGATsT | 2208 |
| UUUGAGCAUGGAAGAGGAUUCUG | 2002 | 30790 | KCR:3872L21 siNA (3854C) stab05 antisense | GAAuccucuuccAuGcucATsT | 2057 |
| AUGGUUCUUGCCUCAGAAGAGCU | 2018 | 30791 | KDR:4107L21 siNA (4089C) stab05 antisense | cucuucuGAGGcAAGAAccTsT | 2209 |
| UCUGAAGGCUCAAACCAGACAAG | 2019 | 30792 | KDR:4209L21 siNA (4191C) stab05 antisense | uGucuGGuuuGAGccuucATsT | 2210 |
| UGUCCACUUACCUGAGGAGCAAG | 2017 | 31426 | KDR:3076U21 siNA sense | UCCACUUACCUGAGGAGCAU | 2211 |
| UUUGAGCAUGGAAGAGGAUUCUG | 2002 | 31435 | KDR:3854U21 siNA sense | UGAGCAUGGAAGAGGAUUCUU | 2045 |
| AUGGUUCUUGCCUCAGAAGAGCU | 2018 | 31428 | KDR:4089U21 siNA sense | GGUUCUUGCCUCAGAAGAGUU | 2212 |
| UCUGAAGGCUCAAACCAGACAAG | 2019 | 31429 | KDR:4191U21 siNA sense | UGAAGGCUCAAACCAGACAUU | 2213 |
| UGUCCACUUACCUGAGGAGCAAG | 2017 | 31430 | KDR:3094L21 siNA (3076C) antisense | UGCUCCUCAGGUAAGUGGAUU | 2214 |
| UUUGAGCAUGGAAGAGGAUUCUG | 2002 | 31439 | KDR:3872L21 siNA (3854C) antisense | GAAUCCUCUUCCAUGCUCAUU | 2049 |

TABLE III-continued

| | | | | |
|---|---|---|---|---|
| AUGGUUCUUGCCUCAGAAGAGCU | 2018 | 31432 KDR:4107L21 siNA (4089C) antisense | CUCUUCUGAGGCAAGAACCUU | 2215 |
| UCUGAAGGCUCAAACCAGACAAG | 2019 | 31433 KDR:4209L21 siNA (4191C) antisense | UGUCUGGUUUGAGCCUUCAUU | 2216 |
| UGACCUUGGAGCAUCUCAUCUGU | 2001 | 31434 KDR:3304U21 siNA sense | ACCUUGGAGCAUCUCAUCUUU | 2044 |
| UCACCUGUUUCCUGUAUGGAGGA | 2003 | 31436 KDR:3894U21 siNA sense | ACCUGUUUCCUGUAUGGAGUU | 2046 |
| GACAACACAGCAGGAAUCAGUCA | 2004 | 31437 KDR:3948U21 siNA sense | CAACACAGCAGGAAUCAGUUU | 2047 |
| UGACCUUGGAGCAUCUCAUCUGU | 2001 | 31438 KDR:3322L21 siNA (3304C) antisense | AGAUGAGAUGCUCCAAGGUU | 2048 |
| UCACCUGUUUCCUGUAUGGAGGA | 2003 | 31440 KDR:3912L21 siNA (3894C) antisense | CUCCAUACAGGAAACAGGUU | 2050 |
| GACAACACAGCAGGAAUCAGUCA | 2004 | 31441 KDR:3966L21 siNA (3948C) antisense | ACUGAUUCCUGCUGUGUUGUU | 2051 |
| GACAACACAGCAGGAAUCAGUCA | 2004 | 31856 KDR:3948U21 siNA stab04 sense | B cAAcAcAgCAGGAAucAGuTT B | 2055 |
| GACAACACAGCAGGAAUCAGUCA | 2004 | 31857 KDR:3966L21 siNA (3948C) stab05 antisense | AcuGAuuccuGcuGuGuuGTsT | 2059 |
| UUUGAGCAUGGAAGAGGAUUCUG | 2002 | 31858 KDR:3854U21 siNA stab07 sense | B uGAGcAuGGAAGAGGAuucTT B | 2061 |
| GACAACACAGCAGGAAUCAGUCA | 2004 | 31859 KDR:3948U21 siNA stab07 sense | B cAAcAcAGcAGGAAucAGuTT B | 2063 |
| UUUGAGCAUGGAAGAGGAUUCUG | 2002 | 31860 KDR:3872L21 siNA (38540) stab08 antisense | GAAuccucuuccAuGcucATsT | 2226 |
| GACAACACAGCAGGAAUCAGUCA | 2004 | 31861 KDR:3966L21 siNA (39480) stab08 antisense | AcuGAuuccuGcuGuGuuGTsT | 2227 |
| UUUGAGCAUGGAAGAGGAUUCUG | 2002 | 31862 KDR:3854U21 siNA stab09 sense | B UGAGCAUGGAAGAGGAUUCTT B | 2228 |
| GACAACACAGCAGGAAUCAGUCA | 2004 | 31863 KDR:3948U21 siNA stab09 sense | B CAACACAGCAGGAAUCAGUUU B | 2229 |
| UUUGAGCAUGGAAGAGGAUUCUG | 2002 | 31864 KDR:3872L21 siNA (3854C) stab10 antisense | GAAUCCUCUUC0AUGCUCATsT | 2230 |
| GACAACACAG0AGGAAUCAGUCA | 2004 | 31865 KDR:3966L21 siNA (39480) stab10 antisense | ACUGAUUCCUGCUGUGUUGTsT | 2231 |
| UUUGAGCAUGGAAGAGGAUUCUG | 2002 | 31878 KDR:3854U21 siNA inv stab04 sense | B cuuAGGAGAAGGuAcGAGuTT B | 2232 |
| GACAACACAGCAGGAAUCAGUCA | 2004 | 31879 KDR:3948U21 siNA inv stab04 sense | B uGAcuAAGGAcGAcAcAAcTT B | 2233 |
| UUUGAGCAUGGAAGAGGAUUCUG | 2002 | 31880 KDR:3872L21 siNA (3854C) inv stab05 antisense | AcucGuAccuucucccuAAGTsT | 2234 |
| GACAACACAGCAGGAAUCAGUCA | 2004 | 31881 KDR:3966L21 siNA (3948C) inv stab05 antisense | GuuGuGucGuccuuAGucATsT | 2235 |
| UUUGAGCAUGGAAGAGGAUUCUG | 2002 | 31882 KDR:3854U21 siNA inv stab07 sense | B cuuAGGAGAAGGuAcGAGuTT B | 2236 |
| GACAACACAGCAGGAAUCAGUCA | 2004 | 31883 KDR:3948U21 siNA inv stab07 sense | B uGAcuAAGGAcGAcAcAAcTT B | 2237 |
| UUUGAGCAUGGAAGAGGAUUCUG | 2002 | 31884 KDR:3872L21 siNA (3854C) inv stab08 antisense | AcucGuAccuucuccuAAGTsT | 2238 |
| GACAACACAGCAGGAAUCAGUCA | 2004 | 31885 KDR:3966L21 siNA (3948C) inv stab08 antisense | GuuGuGucGuccuuAGucATsT | 2239 |
| UUUGAGCAUGGAAGAGGAUUCUG | 2002 | 31886 KDR:3854U21 siNA inv stab09 sense | B CUUAGGAGAAGGUACGAGUUU B | 2240 |
| GACAA0A0AGCAGGAAUCAGUCA | 2004 | 31887 KDR:3948U21 siNA inv stab09 sense | B UGACUAAGGA0GACACAACUU B | 2241 |
| UUUGAGCAUGGAAGAGGAUUCUG | 2002 | 31888 KDR:3872L21 siNA (3854C) inv stab10 antisense | ACUCGUACCUUCUCCUAAGTsT | 2242 |
| GACAACACAGCAGGAAUCAGUCA | 2004 | 31889 KDR:3966L21 siNA (3948C) inv stab10 antisense | GUUGUGUCGUCCUUAGUCATsT | 2243 |
| CCUUAUGAUGCCAGCAAAU | 2256 | 32238 KDR:2764U21 siNA sense | CCUUAUGAUGCCAGCAAAUUU | 2365 |
| CUUAUGAUGCCAGCAAAUG | 2257 | 32239 KDR:2765U21 siNA sense | CUUAUGAUGCCAGCAAAUGUU | 2366 |
| UUAUGAUGCCAGCAAAUGG | 2258 | 32240 KDR:2766U21 siNA sense | UUAUGAUGCCAGCAAAUGGUU | 2367 |
| UAUGAUGCCAGCAAAUGGG | 2259 | 32241 KDR:2767U21 siNA sense | UAUGAUGCCAGCAAAUGGGUU | 2368 |
| AUGAUGCCAGCAAAUGGGA | 2260 | 32242 KDR:2768U21 siNA sense | AUGAUGCCAGCAAAUGGGAUU | 2369 |
| CAGACCAUGCUGGACUGCU | 2261 | 32243 KDR:3712U21 siNA sense | CAGACCAUGCUGGACUGCUUU | 2370 |
| AGACCAUGCUGGACUGCuG | 2262 | 32244 KDR:3713U21 siNA sense | AGACCAUGGUGGACUGCUGUU | 2371 |
| GACCAUGCUGGACUGCUGG | 2263 | 32245 KDR:3714U21 siNA sense | GACCAUGCUGGACUGCUGGUU | 2372 |
| ACCAUGCUGGACUGCuGGC | 2264 | 32246 KDR:3715U21 siNA sense | ACCAUGCUGGACUGCUGGCUU | 2373 |
| CCAUGCUGGACUGCUGGCA | 2265 | 32247 KDR:3716U21 siNA sense | CCAUGCUGGACUGCUGGCAUU | 2374 |
| CAGGAUGGCAAAGACUACA | 2266 | 32248 KDR:3811U21 siNA sense | CAGGAUGGCAAAGACUACAUU | 2375 |
| AGGAUGGCAAAGACUACAU | 2267 | 32249 KDR:3812U21 siNA sense | AGGAUGGCAAAGACUACAUUU | 2376 |
| CCUUAUGAUGCCAGCAAAU | 2256 | 32253 KDR:2782L21 siNA (2764C) antisense | AUUUGCUGGCAUCAUAAGGUU | 2377 |
| CUUAUGAUGCCAGCAAAUG | 2257 | 32254 KDR:2783L21 siNA (2765C) antisense | CAUUUGCUGGCAUCAUAAGUU | 2378 |
| UUAUGAUGCCAGCAAAUGG | 2258 | 32255 KDR:2784L21 siNA (2766C) antisense | CCAUUUGCUGGCAUCAUAAUU | 2379 |
| UAUGAUGCCAGCAAAUGGG | 2259 | 32256 KDR:2785L21 siNA (2767C) antisense | CCCAUUUGCUGGCAUCAUAUU | 2380 |
| AUGAUGCCAGCAAAUGGGA | 2260 | 32257 KDR:2786L21 siNA (2768C) antisense | UCCCAUUUGCUGGCAUCAUUU | 2381 |
| CAGACCAUGCUGGACUGCU | 2261 | 32258 KDR:3730L21 siNA (3712C) antisense | AGCAGUCCAGCAUGGUCUGUU | 2382 |
| AGACCAUGCUGGACUGCUG | 2262 | 32259 KDR:3731L21 siNA (3713C) antisense | CAGCAGUCCAGCAUGGUCUUU | 2383 |
| GACCAUGCUGGACUGCUGG | 2263 | 32260 KDR:3732L21 siNA (3714C) antisense | CCAGCAGUCCAGCAUGGUCUU | 2384 |
| ACCAUGCUGGACUGCUGGC | 2264 | 32261 KDR:3733L21 siNA (3715C) antisense | GCCAGCAGUCCAGCAUGGUUU | 2385 |
| CCAUGCUGGACUGCUGGCA | 2265 | 32262 KDR:3734L21 siNA (3716C) antisense | UGCCAGCAGUCCAGCAUGGUU | 2386 |
| CAGGAUGGCAAAGACUACA | 2266 | 32263 KDR:3829L21 siNA (3811C) antisense | UGUAGUCUUUGCCAUCCUGUU | 2387 |
| AGGAUGGCAAAGACUACAU | 2267 | 32264 KDR:3830L21 siNA (3812C) antisense | AUGUAGUCUUUGCCAUCCUUU | 2388 |
| UGACCUUGGAGCAUCUCAUCUGU | 2001 | 32310 KDR:3304U21 siNA stab09 sense | B ACCUUGGAGCAUCUCAUCUUU B | 2389 |
| UCACCUGUUUCCUGUAUGGAGGA | 2003 | 32311 KDR:3894U21 siNA stab09 sense | B ACCUGUUUCCUGUAUGGAGUU B | 2390 |
| UGACCUUGGAGCAUCUCAUCUGU | 2001 | 32312 KDR:3322L21 siNA (33040) stab10 antisense | AGAUGAGAUGCUCCAAGGUsT | 2391 |
| UCACCUGUUUCCUGUAUGGAGGA | 2003 | 32313 KDR:3912L21 siNA (38940) stab10 antisense | CUCCAUACAGGAAACAGGUsT | 2392 |
| UGACCUUGGAGCAUCUCAUCUGU | 2001 | 32314 KDR:3304U21 siNA inv stab09 sense | B UCUACUCUACGAGGUUCCAUU B | 2393 |
| UCACCUGUUUCCUGUAUGGAGGA | 2003 | 32315 KDR:3894U21 siNA inv stab09 sense | B GAGGUAUGUCCUUUGUCCAUU B | 2394 |
| UGACCUUGGAGCAUCUCAUCUGU | 2001 | 32316 KDR:3322L21 siNA (3304C) inv stab10 antisense | UGGAACCUCGUAGAGUAGATsT | 2395 |
| UCACCUGUUUCCUGUAUGGAGGA | 2003 | 32317 KDR:3912L21 siNA (38940) inv stab10 antisense | UGGACAAAGGACAUACCUCTsT | 2396 |

TABLE III-continued

| | | | | |
|---|---|---|---|---|
| AACAGAAUUUCCUGGGACAGCAA | 2268 | 32762 KDR:828U21 siNA stab07 sense | B cAGAAuuccuGGGAcAGcTT B | 2397 |
| UGGAGCAUCUCAUCUGUUACAGC | 2269 | 32763 KDR:3310U21 siNA stab07 sense | B GAGcAucucAucuGuuAcATT B | 2398 |
| CACGUUUUCAGAGUUGGUGAAC | 2270 | 32764 KDR:3758U21 siNA stab07 sense | B cGuuuucAGAGuuGGuGGATT B | 2399 |
| CUCACCUGUUUCCUGUAUGGAG | 2271 | 32765 KDR:3893U21 siNA stab07 sense | B cAccuGuuuccuGuAuGGATT B | 2400 |
| AACAGAAUUUCCUGGGACAGCAA | 2268 | 32767 KDR:846L21 siNA (828C) stab08 antisense | GcuGucccAGGAAAuucuGTsT | 2401 |
| UGGAGCAUCUCAUCUGUUACAGC | 2269 | 32768 KDR:3328L21 siNA (3310C) stab08 antisense | uGuAAcAGAuGAGAuGcucTsT | 2402 |
| CACGUUUUCAGAGUUGGUGAAC | 2270 | 32769 KDR:3776L21 siNA (3758C) stab08 antisense | uccAccAAcucuGAAAAcGTsT | 2403 |
| CUCACCUGUUUCCUGUAUGGAGG | 2271 | 32770 KDR:391 1L21 siNA (3893C) stab08 antisense | uccAuAcAGGAAAcAGGuGTsT | 2404 |
| UCACCUGUUUCCUGUAUGGAGGA | 2003 | 32771 KDR:3912L21 siNA (3894C) stab08 antisense | cuccAuAcAGGAAAcAGGuTsT | 2405 |
| AACAGAAUUUCCUGGGACAGCAA | 2268 | 32786 KDR:828U21 siNA inv stab07 sense | B cGAcAGGGuccuuuAAGAcTT B | 2406 |
| UGGAGCAUCUCAUCUGUUACAGC | 2269 | 32787 KDR:3310U21 siNA inv stab07 sense | B AcAuGucuAcucuAcGAGTT B | 2407 |
| CACGUUUUCAGAGUUGGUGAAC | 2270 | 32788 KDR:3758U21 siNA inv stab07 sense | B AGGuGGuuGAGAcuuuuGcTT B | 2408 |
| CUCACCUGUUUCCUGUAUGGAGG | 2271 | 32789 KDR:3893U21 siNA inv stab07 sense | B AGGuAuGuccuuuGuccAcTT B | 2409 |
| UCACCUGUUUCCUGUAUGGAGGA | 2003 | 32790 KDR:3894U21 siNA inv stab07 sense | B GAGGuAuGuccuuuGuccATT B | 2410 |
| AACAGAAUUUCCUGGGACAGCAA | 2268 | 32791 KDR:846L21 siNA (828C) inv stab08 antisense | GucuuAAAGGAcccuGucGTsT | 2411 |
| UGGAGCAUCUCAUCUGUUACAGC | 2269 | 32792 KDR:3328L21 siNA (3310C) inv stab08 antisense | cucGuAGAGuAGAcAAuGTsT | 2412 |
| CACGUUUUCAGAGUUGGUGAAC | 2270 | 32793 KDR:3776L21 siNA (3758C) inv stab08 antisense | GcAAAAGucucAAccAccuTsT | 2413 |
| CUCACCUGUUUCCUGUAUGGAGG | 2271 | 32794 KDR:3911L21 siNA(3893C) inv stab08 antisense | GuGGAcAAAGGAcAuAccuTsT | 2414 |
| UCACCUGUUUCCUGUAUGGAGGA | 2003 | 32795 KDR:3912L21 siNA (3894C) inv stab08 antisense | uGGAcAAAGGAcAuAccucTsT | 2415 |
| AACAGAAUUUCCUGGGACAGCAA | 2268 | 32958 KDR:828U21 siNA stab09 sense | B CAGAAUUUCCUGGGACAGCTT B | 2416 |
| UGGAGCAUCUCAUCUGUUACAGC | 2269 | 32959 KDR:3310U21 siNA stab09 sense | B GAGCAUCUCAUCUGUUACATT B | 2417 |
| CACGUUUUCAGAGUUGGUGAAC | 2270 | 32960 KDR:3758U21 siNA stab09 sense | B CGUUUUCAGAGUUGGUGGATT B | 2418 |
| CUCACCUGUUUCCUGUAUGGAGG | 2271 | 32961 KDR:3893U21 siNA stab09 sense | B CACCUGUUUCCUGUAUGGATT B | 2419 |
| AACAGAAUUUCCUGGGACAGCAA | 2268 | 32963 KDR:846L21 siNA (828c) stab10 antisense | GCUGUCCCAGGAAAUUCUGTsT | 2420 |
| UGGAGCAUCUCAUCUGUUACAGC | 2269 | 32964 KDR:3328L21 siNA (3310C) stab10 antisense | UGUAACAGAUGAGAUGCUCTsT | 2421 |
| CACGUUUUCAGAGUUGGUGAAC | 2270 | 32965 KDR:3776L21 siNA (3758C) stab10 antisense | UCCACCAACUCUGAAAACGTsT | 2422 |
| CUCACCUGUUUCCUGUAUGGAGG | 2271 | 32966 KDR:3911L21 siNA (3893C) stab10 antisense | UCCAUACAGGAAACAGGUGTsT | 2423 |
| AACAGAAUUUCCUGGGACAGCAA | 2268 | 32988 KDR:828U21 siNA inv stab09 sense | B CGACAGGGUCCUUUAAGACTT B | 2424 |
| UGGAGCAUCUCAUCUGUUACAGC | 2269 | 32989 KDR:3310U21 siNA inv stab09 sense | B ACAUUGUCUACUCUACGAGTT B | 2425 |
| CACGUUUUCAGAGUUGGUGAAC | 2270 | 32990 KDR:3758U21 siNA inv stab09 sense | B AGGUGGUUGAGACUUUUGCTT B | 2426 |
| CUCACCUGUUUCCUGUAUGGAGG | 2271 | 32991 KDR:3893U21 siNA inv stab09 sense | B AGGUAUGUCCUUUGUCCACTT B | 2427 |
| AACAGAAUUUCCUGGGACAGCAA | 2268 | 32993 KDR:846L21 siNA (828C) inv stab10 antisense | GUCUUAAAGGACCCUGUCGTsT | 2428 |
| UGGAGCAUCUCAUCUGUUACAGC | 2269 | 32994 KDR:3328L21 siNA (3310C) inv stab10 antisense | CUCGUAGAGUAGACCAUGTsT | 2429 |
| CACGUUUUCAGAGUUGGUGAAC | 2270 | 32995 KDR:3776L21 siNA (3758C) inv stab10 antisense | GCAAAAGUCUCAACCACCUTsT | 2430 |
| CUCACCUGUUUCCUGUAUGGAGG | 2271 | 32996 KDR:391 1121 siNA (3893C) inv stab10 antisense | GUGGACAAAGGACAUACCUTsT | 2431 |
| UAUGAUGCCAGCAAAUGGG | 2259 | 33727 KDR:2767U21 siNA stab07 | B uAuGAuGccAGcAAAuGGGTT B | 2494 |
| AUGAUGCCAGCAAAUGGGA | 2260 | 33728 KDR:2768U21 siNA stab07 | B AuGAuGccAGcAAAuGGGATT B | 2495 |
| ACCAUGCUGGACUGGUGGC | 2264 | 33729 KDR:3715U21 siNA stab07 | B AccAuGcuGGAcuGcuGGcTT B | 2496 |
| CCAUGCUGGACUGCUGGCA | 2265 | 33730 KDR:3716U21 siNA stab07 | B ccAuGcuGGAcuGcuGGcATT B | 2497 |
| UAUGAUGCCAGCAAAUGGG | 2259 | 33733 KDR:2785L21 siNA (2767C) stab08 | cccAuuuGcuGGcAucAuATsT | 2498 |
| AUGAUGCCAGCAAAUGGGA | 2260 | 33734 KDR:2786L21 siNA (2768C) stab08 | ucccAuuuGpcuGGcAucAuTsT | 2499 |
| ACCAUGCUGGACUGCUGGC | 2264 | 33735 KDR:3733L21 siNA (3715C) stab08 | GccAGcAGuccAGcAuGGuTsT | 2500 |
| CCAUGCUGGACUGCUGGCA | 2265 | 33736 KDR:3734L21 siNA (3716C) stab08 | uGccAGcAGuccAGcAuGGTsT | 2501 |
| UAUGAUGCCAGCAAAUGGG | 2259 | 33739 KDR:2767U21 siNA stab09 | B UAUGAUGCCAGCAAAUGGGTT B | 2502 |
| AUGAUGCCAGCAAAUGGGA | 2260 | 33740 KDR:2768U21 siNA stab09 | B AUGAUGCCAGCAAAUGGGATT B | 2503 |
| ACCAUGCUGGACUGCUGGC | 2264 | 33741 KDR:3715U21 siNA stab09 | B ACCAUGCUGGACUGCUGGCTT B | 2504 |
| CCAUGCUGGACUGCUGGCA | 2265 | 33742 KDR:3716U21 siNA stab09 | B CCAUGCUGGACUGCUGGCATT B | 2505 |
| UAUGAUGCCAGCAAAUGGG | 2259 | 33745 KDR:2785L21 siNA (2767C) stab10 | CCCAUUUGCUGGCAUCAUATsT | 2506 |
| AUGAUGCCAGCAAAUGGGA | 2260 | 33746 KDR:2786L21 siNA (2768C) stab10 | UCCCAUUUGCUGGCAUCAUTsT | 2507 |
| ACCAUGCUGGACUGCUGGC | 2264 | 33747 KDR:3733L21 siNA (3715C) stab10 | GCCAGCAGUCCAGCAUGGUTsT | 2508 |
| CCAUGCUGGACUGCUGGCA | 2265 | 33748 KDR:3734L21 siNA (3716C) stab10 | UGCCAGCAGUCCAGCAUGGTsT | 2509 |
| UAUGAUGCCAGCAAAUGGG | 2259 | 33751 KDR:2767U21 siNA inv stab07 | B GGGuAAAcGAccGuAGuAuTT B | 2510 |
| AUGAUGCCAGCAAAUGGGA | 2260 | 33752 KDR:2768U21 siNA inv stab07 | B AGGGuAAAcGAccGuAGuATT B | 2511 |
| ACCAUGCUGGACUGCUGGC | 2264 | 33753 KDR:3715U21 siNA inv stab07 | B cGGucGucAGGucGuAccATT B | 2512 |
| CCAUGCUGGACUGCUGGCA | 2265 | 33754 KDR:3716U21 siNA inv stab07 | B AcGGucGucAGGucGuAccTT B | 2513 |
| UAUGAUGCCAGCAAAUGGG | 2259 | 33757 KDR:2785L21 siNA (2767C) inv stab08 | AuAcuAcGGucGuuuAcccTsT | 2514 |
| AUGAUGCCAGCAAAUGGGA | 2260 | 33758 KDR:2786L21 siNA (2768C) inv stab08 | uAcuAcGGucGuuuAcccuTsT | 2515 |
| ACCAUGCUGGACUGCUGGC | 2264 | 33759 KDR:3733L21 siNA (3715C) inv stab08 | uGGuAcGAccuGAcGAccGTsT | 2516 |

TABLE III-continued

| | | | | |
|---|---|---|---|---|
| CCAUGCUGGACUGCUGGCA | 2265 | 33760 KDR:3734L21 siNA (3716C) inv stab08 | GGuAcGAccuGAcGAccGuTsT | 2517 |
| UAUGAUGCCAGCAAAUGGG | 2259 | 33763 KDR:2767U21 siNA inv stab09 | B GGGUAAACGACCGUAGUAUTT B | 2518 |
| AUGAUGCCAGCAAAUGGGA | 2260 | 33764 KDR:2768U21 siNA inv stab09 | B AGGGUAAACGACCGUAGUATT B | 2519 |
| ACCAUGCUGGACUGCUGGC | 2264 | 33765 KDR:3715U21 siNA inv stab09 | B CGGUCGUCAGGUCGUACCATT B | 2520 |
| CCAUGCUGGACUGCUGGCA | 2265 | 33766 KDR:3716U21 siNA inv stab09 | B ACGGUCGUCAGGUCGUACCTT B | 2521 |
| UAUGAUGCCAGCAAAUGGG | 2259 | 33769 KDR:2785L21 siNA (2767C) inv stab10 | AUACUACGGUCGUUUACCCTsT | 2522 |
| AUGAUGCCAGCAAAUGGGA | 2260 | 33770 KDR:2786L21 siNA (2768C) inv stab10 | UACUACGGUCGUUUACCCUTsT | 2523 |
| ACCAUGCUGGACUGCUGGC | 2264 | 33771 KDR:3733L21 siNA (3715C) inv stab10 | UGGUACGACCUGACGACCGTsT | 2524 |
| CCAUGCUGGACUGCUGGCA | 2265 | 33772 KDR:3734L21 siNA (3716C) inv stab10 | GGUACGACCUGACGACCGUTsT | 2525 |
| | | VEGFR3 | | |
| AGCACUGCCACAAGAAGUACCUG | 2005 | 31904 FLT4:2011U21 siNA sense | CACUGCCACAAGAAGUACCTT | 2068 |
| CUGAAGCAGAGAGAGAAGGCA | 2006 | FLT4:3921U21 siNA sense | GAAGCAGAGAGAGAAGGTT | 2069 |
| AAAGAGGAACCAGGAGGACAAGA | 2007 | FLT4:4038U21 siNA sense | AGAGGAACCAGGAGGACAATT | 2070 |
| GACAAGAGGAGCAUGAAAGUGGA | 2008 | FLT4:4054U21 siNA sense | CAAGAGGAGCAUGAAAGUGTT | 2071 |
| AGCACUGCCACAAGAAGUACCUG | 2005 | 31908 FLT4:2029L21 siNA (2011C) antisense | GGUACUUCUUGUGGCAGUGTT | 2072 |
| CUGAAGCAGAGAGAGAAGGCA | 2006 | FLT4:3939L21 siNA (3921C) antisense | CCUUCUCUCUCUCUGCUUCTT | 2073 |
| AAAGAGGAACCAGGAGGACAAGA | 2007 | FLT4:4056L21 siNA (4038C) antisense | UUGUCCUCCUGGUUCCUCUTT | 2074 |
| GACAAGAGGAGCAUGAAAGUGGA | 2008 | FLT4:4072L21 siNA (4054C) antisense | CACUUUCAUGCUCCUCUUGTT | 2075 |
| AGCACUGCCACAAGAAGUACCUG | 2005 | FLT4:2011U21 siNA stab04 sense | B cAcuGccAcAAGAAGuAccTT B | 2076 |
| CUGAAGCAGAGAGAGAAGGCA | 2006 | FLT4:3921U21 siNA stab04 sense | B GAAGcAGAGAGAGAAGGTT B | 2077 |
| AAAGAGGAACCAGGAGGACAAGA | 2007 | FLT4:4038U21 siNA stab04 sense | B AGAGGAAccAGGAGGAcAATT B | 2078 |
| GACAAGAGGAGCAUGAAAGUGGA | 2008 | FLT4:4054U21 siNA stab04 sense | B cAAGAGGAGcAuGAAAGuGTT B | 2079 |
| AGCACUGCCACAAGAAGUACCUG | 2005 | FLT4:2029L21 siNA (2011C) stab05 antisense | GGuAcuucuuGuGGcAGuGTsT | 2080 |
| CUGAAGCAGAGAGAGAAGGCA | 2006 | FLT4:3939L21 siNA (3921C) stab05 antisense | ccuucucucucucuGcuucTsT | 2081 |
| AAAGAGGAACCAGGAGGACAAGA | 2007 | FLT4:4056L21 siNA (4038C) stab05 antisense | uuGuccuccuGGuuccucuTsT | 2082 |
| GACAAGAGGAGCAUGAAAGUGGA | 2008 | FLT4:4072L21 siNA (4054C) stabCS antisense | cAcuuucAuGcuccucuuGTsT | 2083 |
| AGCACUGCCACAAGAAGUACCUG | 2005 | FLT4:2011U21 siNA stab07 sense | B cAcuGccAcAAGAAGuAccTT B | 2084 |
| CUGAAGCAGAGAGAGAAGGCA | 2006 | FLT4:3921U21 siNA stab07 sense | B GAAGcAGAGAGAGAAGGTT B | 2085 |
| AAAGAGGAACCAGGAGGACAAGA | 2007 | FLT4:4038U21 siNA stab07 sense | B AGAGGAAccAGGAGGAcAATT B | 2086 |
| GACAAGAGGAGCAUGAAAGUGGA | 2008 | FLT4:4054U21 siNA stab07 sense | B cAAGAGGAGcAuGAAAGuGTT B | 2087 |
| AGCACUGCCACAAGAAGUACCUG | 2005 | FLT4:2029L21 siNA (2011C) stab11 antisense | GGuAcuucuuGuGGcAGuGTsT | 2088 |
| CUGAAGCAGAGAGAGAAGGCA | 2006 | FLT4:3939L21 siNA (3921C) stab11 antisense | ccuucucucucucuGcuucTsT | 2089 |
| AAAGAGGAACCAGGAGGACAAGA | 2007 | FLT4:4056L21 siNA (4038C) stab11 antisense | uuGuccuccuGGuuccucuTsT | 2090 |
| GACAAGAGGAGCAUGAAAGUGGA | 2008 | FLT4:4072L21 siNA (4054C) stab11 antisense | cAcuuucAuGcuccucuuGTsT | 2091 |
| ACUUCUAUGUGACCACCAUCCCC | 2272 | 31902 FLT4:1666U21 siNA sense | UUCUAUGUGACCACCAUCCTT | 2432 |
| CAAGCACUGCCACAAGAAGUACC | 2273 | 31903 FLT4:2009U21 siNA sense | AGCACUGCCACAAGAAGUATT | 2433 |
| AGUACGGCAACCUCUCCAACUUC | 2274 | 31905 FLT4:2815U21 siNA sense | UACGGCAACCUCUCCAACUTT | 2434 |
| ACUUCUAUGUGACCACCAUCCCC | 2272 | 31906 FLT4:1684L21 siNA (1666C) antisense | GGAUGGUGGUCACAUAGAATT | 2435 |
| CAAGCACUGCCACAAGAAGUACC | 2273 | 31907 FLT4:2027L21 siNA (2009C) antisense | UACUUCUUGUGGCAGUGCTT | 2436 |
| AGUACGGCAACCUCUCCAACUUC | 2274 | 31909 FLT4:2833L21 siNA (2815C) antisense | AGUUGGAGAGGUUGCCGUATT | 2437 |
| CUGCCAUGUACAAGUGUGUGGUC | 2440 | 34383 FLT4:1609U21 siNA stab09 | B GCCAUGUACAAGUGUGUGGTT B | 2526 |
| ACUUCUAUGUGACCACCAUCCCC | 2272 | 34384 FLT4:1666U21 siNA stab09 | B UUCUAUGUGACCACCAUCCTT B | 2527 |
| CAAGCACUGCCACAAGAAGUACC | 2273 | 34385 FLT4:2009U21 siNA stab09 | B AGCACUGCCACAAGAAGUATT B | 2528 |
| AGCACUGCCACAAGAAGUACCUG | 2005 | 34386 FLT4:2011U21 siNA stab09 | B CACUGCCACAAGAAGUACCTT B | 2529 |
| ACUGCCACAAGAAGUACCUGUCG | 2441 | 34387 FLT4:2014U21 siNA stab09 | B UGCCACAAGAAGUACCUGTT B | 2530 |
| AGUACGGCAACCUCUCCAACUUC | 2274 | 34388 FLT4:2815U21 siNA stab09 | B UACGGCAACCUCUCCAACUTT B | 2531 |
| UGGUGAAGAUCUGUGACUUUGGC | 2442 | 34389 FLT4:3172U21 siNA stab09 | B GUGAAGAUCUGUGACUUUGTT B | 2532 |
| GAAGAUCUGUGACUUUGGCCUUG | 2443 | 34390 FLT4:3176U21 siNA stab09 | B AGAUCUGUGACUUUGGCCTT B | 2533 |
| CUGCCAUGUACAAGUGUGUGGUC | 2440 | 34391 FLT4:1627L21 siNA (1609C) stab10 | CCACACACUUGUACAUGGCTsT | 2534 |

TABLE III-continued

| | | | | |
|---|---|---|---|---|
| ACUUCUAUGUGACCACCAUCCCC | 2272 | 34392 FLT4:1684L21 siNA (1666C) stab10 | GGAUGGUGGUCACAUAGAATsT | 2535 |
| CAAGCACUGCCACAAGAAGUACC | 2273 | 34393 FLT4:2027L21 siNA (2009C) stab10 | UACUUCUUGUGGCAGUGCUTsT | 2536 |
| AGCACUGCCACAAGAAGUACCUG | 2005 | 34394 FLT4:2029L21 siNA (2011C) stab10 | GGUACUUCUUGUGGCAGUGTsT | 2537 |
| ACUGCCACAAGAAGUACCUGUCG | 2441 | 34395 FLT4:2032L21 siNA (2014C) stab10 | ACAGGUACUUCUUGUGGCATsT | 2538 |
| AGUACGGCAACCUCUCCAACUUC | 2274 | 34396 FLT4:2833L21 siNA (2815C) stab10 | AGUGGAGAGGUUGCCGUATsT | 2539 |
| UGGUGAAGAUCUGUGACUUUGGC | 2442 | 34397 FLT4:3190L21 siNA (3172C) stab10 | CAAAGUCACAGAUCUUCACTsT | 2540 |
| GAAGAUCUGUGACUUUGGCCUUG | 2443 | 34398 FLT4:3194L21 siNA (3176C) stab10 | AGGCCAAAGUCACAGAUCUTsT | 2541 |
| CUGCCAUGUACAAGUGUGUGGUC | 2440 | 34399 FLT4:1627L21 siNA (1609C) stab08 | ccAcAcAcuuGuAcAuGGcTsT | 2542 |
| ACUUCUAUGUGACCACCAUCCCC | 2272 | 34400 FLT4:1684L21 siNA (1666C) stab08 | GGAuGGuGGucAcAuAGAATsT | 2543 |
| CAAGCACUGCCACAAGAAGUACC | 2273 | 34401 FLT4:2027L21 siNA (2009C) stab08 | uAcuucuuGuGGcAGuGcuTsT | 2544 |
| AGCACUGCCACAAGAAGUACCUG | 2005 | 34402 FLT4:2029L21 siNA (2011C) stab08 | GGuAcuucuuGuGGcAGuGTsT | 2545 |
| ACUGCCACAAGAAGUACCUGUCG | 2441 | 34403 FLT4:2032L21 siNA (2014C) stab08 | AcAGGuAcuucuuGuGGcATsT | 2546 |
| AGUACGGCAACCUCUCCAACUUC | 2274 | 34404 FLT4:2833L21 siNA (2815C) stab08 | AGuuGGAGAGGuuGccGuATsT | 2547 |
| UGGUGAAGAUCUGUGACUUUGGC | 2442 | 34405 FLT4:3190L21 siNA (3172C) stab08 | cAAAGucAcAGAucuucAcTsT | 2548 |
| GAAGAUCUGUGACUUUGGCCUUG | 2443 | 34406 FLT4:3194L21 siNA (3176C) stab08 | AGGccAAAGucAcAGAucuTsT | 2549 |
| | | VEGFR1 and VEGFR2 homologous sequences | | |
| CAUGCUGGACUGCUGGCAC | 2244 | 32235 FLT1:3645U21 siNA | CAUGCUGGACUGCUGGCACTT | 2275 |
| AUGCUGGACUGCUGGCACA | 2245 | 32236 FLT1:3646U21 siNA | AUGCUGGACUGCUGGCACATT | 2276 |
| UGCUGGACUGCUGGCACAG | 2246 | 32237 FLT1:3647U21 siNA | UGCUGGACUGCUGGCACAGTT | 2277 |
| CAUGCUGGACUGCUGGCAC | 2244 | 32250 FLT1:3663L21 siNA (3645C) | GUGCCAGCAGUCCAGCAUGTT | 2278 |
| AUGCUGGACUGCUGGCACA | 2245 | 32251 FLT1:3664L21 siNA (3646C) | UGUGCCAGCAGUCCAGCAUTT | 2279 |
| UGCUGGACUGCUGGCACAG | 2246 | 32252 FLT1:3665L21 siNA (3647C) | CUGUGCCAGCAGUCCAGCATT | 2280 |
| CCUUAUGAUGCCAGCAAAU | 2256 | 32238 KDR:2764U21 siNA | CCUUAUGAUGCCAGCAAAUTT | 2365 |
| CUUAUGAUGCCAGCAAAUG | 2257 | 32239 KDR:2765U21 siNA | CUUAUGAUGCCAGCAAAUGTT | 2366 |
| UUAUGAUGCCAGCAAAUGG | 2258 | 32240 KDR:2766U21 siNA | UUAUGAUGCCAGCAAAUGGTT | 2367 |
| UAUGAUGCCAGCAAAUGGG | 2259 | 32241 KDR:2767U21 siNA | UAUGAUGCCAGCAAAUGGGTT | 2368 |
| AUGAUGCCAGCAAAUGGGA | 2260 | 32242 KDR:2768U21 siNA | AUGAUGCCAGCAAAUGGGATT | 2369 |
| CAGACCAUGCUGGACUGCU | 2261 | 32243 KDR:3712U21 siNA | CAGACCAUGCUGGACUGCUTT | 2370 |
| AGACCAUGCUGGACUGCUG | 2262 | 32244 KDR:3713U21 siNA | AGACCAUGCUGGACUGCUGTT | 2371 |
| GACCAUGCUGGACUGCUGG | 2263 | 32245 KDR:3714U21 siNA | GACCAUGCUGGACUGCUGGTT | 2372 |
| ACCAUGCUGGACUGCUGGC | 2264 | 32246 KDR:3715U21 siNA | ACCAUGCUGGACUGCUGGCTT | 2373 |
| CCAUGCUGGACUGCUGGCA | 2265 | 32247 KDR:3716U21 siNA | CCAUGCUGGACUGCUGGCATT | 2374 |
| CAGGAUGGCAAAGACUACA | 2266 | 32248 KDR:3811U21 siNA | CAGGAUGG0AAAGACUACAFU | 2375 |
| AGGAUGGCAAAGACUACAU | 2267 | 32249 KDR:3812U21 siNA | AGGAUGGCAAAGACUACAUTT | 2376 |
| CCUUAUGAUGCCAGCAAAU | 2256 | 32253 KDR:2782L21 siNA (2764C) | AUUUGCUGGCAUCAUAAGGTT | 2377 |
| CUUAUGAUGCCAGCAAAUG | 2257 | 32254 KDR:2783L21 siNA (2765C) | CAUUUGCUGGCAUCAUAAGTT | 2378 |
| UUAUGAUGCCAGCAAAUGG | 2258 | 32255 KDR:2784L21 siNA (2766C) | CCAUUUGCUGGCAUCAUAATT | 2379 |
| UAUGAUGCCAGCAAAUGGG | 2259 | 32256 KDR:2785L21 siNA (2767C) | CCCAUUUGCUGGCAUCAUATT | 2380 |
| AUGAUGCCAGCAAAUGGGA | 2260 | 32257 KDR:2786L21 siNA (2768C) | UCCCAUUUGCUGGCAUCAUTT | 2381 |
| CAGACCAUGCUGGACUGCU | 2261 | 32258 KDR:3730L21 siNA (3712C) | AGCAGUCCAGCAUGGUCUGTT | 2382 |
| AGACCAUGCUGGACUGCUG | 2262 | 32259 KDR:3731l21 siNA (3713C) | CAGCAGUCCAGCAUGGUCUTT | 2383 |
| GACCAUGCUGGACUGCUGG | 2263 | 32260 KDR:3732L21 siNA (3714C) | CCAGCAGUCCAGCAUGGUCTT | 2384 |
| ACCAUGCUGGACUGCUGGC | 2264 | 32261 KDR:3733L21 siNA (3715C) | GCCAGCAGUCCAGCAUGGUTT | 2385 |
| CCAUGCUGGACUGCUGGCA | 2265 | 32262 KDR:3734L21 siNA (3716C) | UGCCAGCAGUCCAGCAUGGTT | 2386 |
| CAGGAUGGCAAAGACUACA | 2266 | 32263 KDR:3829L21 siNA (3811C) | UGUAGUCUUUGCCAUCCUGTT | 2387 |
| AGGAUGGCAAAGACUACAU | 2267 | 32264 KDR:3830L21 siNA (3812C) | AUGUAGUCUUUGCCAUCCUTT | 2388 |
| CAUGCUGGACUGCUGGCAC | 2244 | 33725 FLT1:3645U21 siNA stab07 | B cAuGcuGGAcuGcuGGcAcTT B | 2449 |
| AUGCUGGACUGCUGGCACA | 2245 | 33726 FLT1:3646U21 siNA stab07 | B AuGcuGGAcuGcuGGcAcATT B | 2450 |
| CAUGCUGGACUGCUGGCAC | 2244 | 33731 FLT1:3663L21 siNA (3645C) stab08 | GuGccAGcAGuccAGcAuGTsT | 2451 |
| AUGCUGGACUGCUGGCACA | 2245 | 33732 FLT1:3664L21 siNA (3646C) stab08 | uGuGccAGcAGuccAGcAuTsT | 2452 |
| CAUGCUGGACUGCUGGCAC | 2244 | 33737 FLT1:3645U21 siNA stab09 | B CAUGCUGGACUGCUGGCACTT B | 2453 |
| AUGCUGGACUGCUGGCACA | 2245 | 33738 FLT1:3646U21 siNA stab09 | B AUGCUGGACUGCUGGCACATT B | 2454 |
| CAUGCUGGACUGGUGGCAC | 2244 | 33743 FLT1:3663L21 siNA (3645C) stab10 | GUGCCAGCAGUCCAGCAUGTsT | 2455 |
| AUGCUGGACUGCUGGCACA | 2245 | 33744 FLT1:3664L21 siNA (3646C) stab10 | UGUGCCAGCAGUCCAGCAUTsT | 2456 |
| CAUGGUGGACUGGUGGCAC | 2244 | 33749 FLT1:3645U21 siNA inv stab07 | B cAcGGucGucAGGucGuAcTT B | 2457 |
| AUGGUGGACUGCUGGCACA | 2245 | 33750 FLT1:3646U21 siNA inv stab07 | B AcAcGGucGucAGGucGuATT B | 2458 |
| CAUGCUGGACUGCUGGCAC | 2244 | 33755 FLT1:3663L21 siNA (36450) inv stab08 | GuAcAccuGAcGAccGuGTsT | 2459 |
| AUGCUGGACUGCUGGCACA | 2245 | 33756 FLT1:3664L21 siNA (3646C) inv stab08 | uAcGAccuGAcGAccGuGTsT | 2460 |

TABLE III-continued

| | | | | |
|---|---|---|---|---|
| CAUGCUGGACUGCUGGCAC | 2244 | 33761 FLT1:3645U21 siNA inv stab09 | B CACGGUCGUCAGGUCGUACTT B | 2461 |
| AUGCUGGACUGCUGGCACA | 2245 | 33762 FLT1:3646U21 siNA inv stab09 | B ACACGGUCGUCAGGUCGUATT B | 2462 |
| CAUGCUGGACUGCUGGCAC | 2244 | 33767 FLT1:3663L21 siNA (3645C) inv stab10 | GUACGACCUGACGACCGUGTsT | 2463 |
| AUGCUGGACUGCUGGCACA | 2245 | 33768 FLT1:3664L21 siNA (36460) inv stab10 | UACGACCUGACGACCGUGUTsT | 2464 |
| UAUGAUGCCAGCAAAUGGG | 2259 | 33727 KDR:2767U21 siNA stab07 | B u*A*u*GA*u*G*cc*AG*c*AAA*u*GGG*TT B | 2494 |
| AUGAUGCCAGCAAAUGGGA | 2260 | 33728 KDR:2768U21 siNA stab07 | B *A*u*GA*u*G*cc*AG*c*AAA*u*GGG*ATT B | 2495 |
| ACCAUGCUGGACUGCUGGC | 2264 | 33729 KDR:3715U21 siNA stab07 | B *A*cc*A*u*G*c*u*GG*A*c*u*G*c*u*GG*cTT B | 2496 |
| CCAUGCUGGACUGCUGGCA | 2265 | 33730 KDR:3716U21 siNA stab07 | B cc*A*u*G*c*u*GG*A*c*u*G*c*u*GG*c*ATT B | 2497 |
| UAUGAUGCCAGCAAAUGGG | 2259 | 33733 KDR:2785L21 siNA (2767C) stab08 | ccc*A*uuu*G*c*u*GG*c*A*uc*A*u*A*TsT | 2498 |
| AUGAUGCCAGCAAAUGGGA | 2260 | 33734 KDR:2786L21 siNA (2768C) stab08 | uccc*A*uuu*G*c*u*GG*c*A*uc*A*u*TsT | 2499 |
| ACCAUGCUGGACUGCUGGC | 2264 | 33735 KDR:3733L21 siNA (3715C) stab08 | *G*cc*AG*c*AG*ucc*AG*c*A*u*GG*TsT | 2500 |
| CCAUGCUGGACUGCUGGCA | 2265 | 33736 KDR:3734L21 siNA (3716C) stab08 | u*G*cc*AG*c*AG*ucc*AG*c*A*u*GG*TsT | 2501 |
| UAUGAUGCCAGCAAAUGGG | 2259 | 33739 KDR:2767U21 siNA stab09 | B UAUGAUGCCAGCAAAUGGGTT B | 2502 |
| AUGAUGCCAGCAAAUGGGA | 2260 | 33740 KDR:2768U21 siNA stab09 | B AUGAUGCCAGCAAAUGGGATT B | 2503 |
| ACCAUGCUGGACUGCUGGC | 2264 | 33741 KDR:3715U21 siNA stab09 | B ACCAUGCUGGACUGCUGGCTT B | 2504 |
| CCAUGCUGGACUGCUGGCA | 2265 | 33742 KDR:3716U21 siNA stab09 | B CCAUGCUGGACUGCUGGCATT B | 2505 |
| UAUGAUGCCAGCAAAUGGG | 2259 | 33745 KDR:2785L21 siNA (2767C) stab10 | CCCAUUUGCUGGCAUCAUATsT | 2506 |
| AUGAUGCCAGCAAAUGGGA | 2260 | 33746 KDR:2786L21 siNA (2768C) stab10 | UCCCAUUUGCUGGCAUCAUTsT | 2507 |
| ACCAUGCUGGACUGCUGGC | 2264 | 33747 KDR:3733L21 siNA (3715C) stab10 | GCCAGCAGUCCAGCAUGGUTsT | 2508 |
| CCAUGCUGGACUGCUGGCA | 2265 | 33748 KDR:3734L21 siNA (3716C) stab10 | UGCCAGCAGUCCAGCAUGGTsT | 2509 |
| UAUGAUGCCAGCAAAUGGG | 2259 | 33751 KDR:2767U21 smNA inv stab07 | B *GGG*u*AAA*c*GA*cc*G*u*AG*u*A*TT B | 2510 |
| AUGAUGCCAGCAAAUGGGA | 2260 | 33752 KDR:2768U21 siNA inv stab07 | B *AGGG*u*AAA*c*GA*cc*G*u*AG*u*ATT B | 2511 |
| ACCAUGCUGGACUGCUGGC | 2264 | 33753 KDR:3715U21 siNA inv stab07 | B c*GG*uc*G*uc*AGG*uc*G*u*A*cc*ATT B | 2512 |
| CCAUGCUGGACUGCUGGCA | 2265 | 33754 KDR:3716U21 siNA inv stab07 | B *A*c*GG*uc*G*uc*AGG*uc*G*u*A*cc*TT B | 2513 |
| UAUGAUGCCAGCAAAUGGG | 2259 | 33757 KDR:2785L21 siNA (2767C) inv stab08 | *A*u*A*cu*A*c*GG*uc*G*uuu*A*ccc*TsT | 2514 |
| AUGAUGCCAGCAAAUGGGA | 2260 | 33758 KDR:2786L21 siNA (2768C) inv stab08 | u*A*cu*A*c*GG*uc*G*uuu*A*ccu*TsT | 2515 |
| ACCAUGCUGGACUGCUGGC | 2264 | 33759 KDR:3733L21 siNA (3715C) inv stab08 | u*GG*u*A*c*GA*ccu*GA*c*GA*cc*GTsT | 2516 |
| CCAUGCUGGACUGCUGGCA | 2265 | 33760 KDR:3734L21 siNA (3716C) inv stab08 | *GG*u*A*c*GA*ccu*GA*c*GA*cc*G*u*TsT | 2517 |
| UAUGAUGCCAGCAAAUGGG | 2259 | 33763 KDR:2767U21 siNA inv stab09 | B GGGUAAACGACCGUAGUAUTT B | 2518 |
| AUGAUGCCAGCAAAUGGGA | 2260 | 33764 KDR:2768U21 siNA inv stab09 | B AGGGUAAACGACCGUAGUATT B | 2519 |
| ACCAUGCUGGACUGCUGGC | 2264 | 33765 KDR:3715U21 siNA inv stab09 | B CGGUCGUCAGGUCGUACCATT B | 2520 |
| CCAUGCUGGACUGCUGGCA | 2265 | 33766 KDR:3716U21 siNA inv stab09 | B ACGGUCGUCAGGUCGUACCTT B | 2521 |
| UAUGAUGCCAGCAAAUGGG | 2259 | 33769 KDR:2785L21 siNA (2767C) inv stab10 | AUACUACGGUCGUUUACCCTsT | 2522 |
| AUGAUGCCAGCAAAUGGGA | 2260 | 33770 KDR:2786L21 siNA (2768C) inv stab10 | UACUACGGUCGUUUACCCUTsT | 2523 |
| ACCAUGGUGGACUGGUGGC | 2264 | 33771 KDR:3733L21 siNA (3715C) inv stab10 | UGGUACGACCUGACGACCGTsT | 2524 |
| CCAUGCUGGACUGCUGGCA | 2265 | 33772 KDR:3734L21 siNA (3716C) inv stab10 | GGUACGACCUGACGACCGUTsT | 2525 |

Uppercase = ribonucleotide
u,c = 2'-deoxy-2'-fluoro U,C
T = thymidine
B = inverted deoxy abasic
s = phosphorothioate linkage
*A* = deoxy Adenosine
*G* = deoxy Guanosine
A = 2'-O-methyl Adenosine
G = 2'-O-methyl Guanosine
X = nitroindole universal base
Z = nitropyrole universal base
Y = 3',3'-inverted thymidine
M = glyceryl
N = 3'-C-methyl uridine
P = L-thymidine
Z = sbL: symmetrical bifunctional linker
H = chol2: capped Cholesterol
TEG
L = C18 phospholipid
Q = L-uridine
R = 5-bromo-deoxy-uridine Sequence alignments between select Human (h), Rat (r), and Mouse (m) VEGFR1 (FLT1) and VEGFR2 (KDR) 23mer target sequences

| Gene | Pos | Sequence | SEQ ID |
|---|---|---|---|
| hFLT1 | 3645 | AUCAUGCUGGACUGCUGGCACAG | 2572 |
| hKDR | 3717 | AcCAUGCUGGACUGCUGGCACgG | 2573 |
| mFLT1 | 3422 | AUCAUGUUGGAUUGCUGGCACAa | 2574 |
| mKDR | 3615 | AcCAUGCUGGACUGCUGGCAUga | 2575 |
| rFLT1 | 3632 | AUCAUGCUGGAUUGCUGGCACAa | 2576 |
| rKDR | 3650 | AcCAUGCUGGAUUGCUGGCAUga | 2577 |
| hFLT1 | 3646 | UCAUGCUGGACUGCUGGCACAGA | 2578 |
| hKDR | 3718 | cCAUGCUGGACUGCUGGCACgGg | 2579 |
| mFLT1 | 3423 | UCAUGUUGGAUUGCUGGCACAaA | 2580 |
| mKDR | 3616 | cCAUGCUGGACUGCUGGCAUgag | 2581 |
| rFLT1 | 3633 | UCAUGCUGGAUUGCUGGCACAaA | 2582 |
| rKDR | 3651 | cCAUGCUGGAUUGCUGGCAUgag | 2583 |
| hFLT1 | 3647 | CAUGCUGGACUGCUGGCACAGAG | 2584 |
| hKDR | 3719 | CAUGCUGGACUGCUGGCACgGgG | 2585 |
| mFLT1 | 3424 | CAUGUUGGAUUGCUGGCACAaAG | 2586 |
| mKDR | 3617 | CAUGCUGGACUGCUGGCAUgagG | 2587 |
| rFLT1 | 3634 | CAUGCUGGAUUGCUGGCACAaAG | 2588 |
| rKDR | 3652 | CAUGCUGGAUUGCUGGCAUgagG | 2589 |
| hKDR | 2764 | UGCCUUAUGAUGCCAGCAAAUGG | 2590 |
| hFLT1 | 2689 | UcCCUUAUGAUGCCAGCAAgUGG | 2591 |
| mFLT1 | 2469 | UGCCcUAUGAUGCCAGCAAgUGG | 2592 |
| mKDR | 2662 | UGCCUUAUGAUGCCAGCAAgUGG | 2593 |
| rFLT1 | 2676 | UGCCcUAUGAUGCCAGCAAgUGG | 2594 |
| rKDR | 2697 | UGCCUUAUGAUGCCAGCAAgUGG | 2595 |
| hKDR | 2765 | GCCUUAUGAUGCCAGCAAAUGGG | 2596 |
| hFLT1 | 2690 | cCCUUAUGAUGCCAGCAAgUGGG | 2597 |
| mFLT1 | 2470 | GCCcUAUGAUGCCAGCAAgUGGG | 2598 |
| mKDR | 2663 | GCCUUAUGAUGCCAGCAAgUGGG | 2599 |
| rFLT1 | 2677 | GCCcUAUGAUGCCAGCAAgUGGG | 2600 |
| rKDR | 2698 | GCCUUAUGAUGCCAGCAAgUGGG | 2601 |
| hKDR | 2766 | CCUUAUGAUGCCAGCAAAUGGA | 2602 |
| hFLT1 | 2691 | CCUUAUGAUGCCAGCAAgUGGGA | 2603 |
| mFLT1 | 2471 | CCcUAUGAUGCCAGCAAgUGGGA | 2604 |
| mKDR | 2664 | CCUUAUGAUGCCAGCAAgUGGGA | 2605 |
| rFLT1 | 2678 | CCcUAUGAUGCCAGCAAgUGGGA | 2606 |
| rKDR | 2699 | CCUUAUGAUGCCAGCAAgUGGGA | 2607 |
| hKDR | 2767 | CUUAUGAUGCCAGCAAAUGGGAA | 2608 |
| hFLT1 | 2692 | CUUAUGAUGGCAGCAAgUGGGAg | 2609 |
| mFLT1 | 2472 | CcUAUGAUGCCAGCAAgUGGGAg | 2610 |
| mKDR | 2665 | CUUAUGAUGCCAGCAAgUGGGAA | 2611 |
| rFLT1 | 2679 | CcUAUGAUGCCAGCAAgUGGGAg | 2612 |
| rKDR | 2700 | CUUAUGAUGCCAGCAAgUGGGAg | 2613 |
| hKDR | 2768 | UUAUGAUGCCAGCAAAUGGGAAU | 2614 |
| hFLT1 | 2693 | UUAUGAUGCCAGCAAgUGGGAgU | 2615 |
| mFLT1 | 2473 | cUAUGAUGCCAGCAAgUGGGAgU | 2616 |
| mKDR | 2666 | UUAUGAUGCCAGCAAgUGGGAAU | 2617 |
| rFLT1 | 2680 | cUAUGAUGCCAGCAAgUGGGAgU | 2618 |
| rKDR | 2701 | UUAUGAUGCCAGCAAgUGGGAgU | 2619 |
| hKDR | 3712 | ACCAGACCAUGCUGGACUGCUGG | 2620 |
| hFLT1 | 3640 | AUCAGAUCAUGCUGGACUGCUGG | 2621 |
| mFLT1 | 3417 | ACCAaUCAUGUUGGAUUGCUGG | 2622 |
| mKDR | 3610 | ACCAGACCAUGCUGGACUGCUGG | 2623 |
| rFLT1 | 3627 | ACCAaUCAUGCUGGAUUGCUGG | 2624 |
| rKDR | 3645 | ACCAaACCAUGCUGGAUUGCUGG | 2625 |
| hKDR | 3713 | CCAGACCAUGCUGGACUGCUGGC | 2626 |
| hFLT1 | 3641 | UCAGAUCAUGCUGGACUGCUGGC | 2627 |
| mFLT1 | 3418 | CCAaUCAUGUUGGAUUGCUGGC | 2628 |
| mKDR | 3611 | CCAGACCAUGCUGGACUGCUGGC | 2629 |
| rFLT1 | 3628 | CCAaUCAUGCUGGAUUGCUGGC | 2630 |
| rKDR | 3646 | CCAaACCAUGCUGGAUUGCUGGC | 2631 |
| hKDR | 3714 | CAGACCAUGCUGGACUGCUGGCA | 2632 |
| hFLT1 | 3642 | CAGAUCAUGCUGGACUGCUGGCA | 2633 |
| mFLT1 | 3419 | CAaUCAUGUUGGAUUGCUGGCA | 2634 |
| mKDR | 3612 | CAGACCAUGCUGGACUGCUGGCA | 2635 |
| rFLT1 | 3629 | CAaUCAUGCUGGAUUGCUGGCA | 2636 |
| rKDR | 3647 | CAaACCAUGCUGGAUUGCUGGCA | 2637 |
| hKDR | 3715 | AGACCAUGCUGGACUGCUGGCAC | 2638 |
| hFLT1 | 3643 | AGAUCAUGCUGGACUGCUGGCAC | 2639 |
| mFLT1 | 3420 | AaUCAUGUUGGAUUGCUGGCAC | 2640 |
| mKDR | 3613 | AGACCAUGCUGGACUGCUGGCAU | 2641 |
| rFLT1 | 3630 | AaUCAUGCUGGAUUGCUGGCAC | 2642 |
| rKDR | 3648 | AaACCAUGCUGGAUUGCUGGCAU | 2643 |
| hKDR | 3716 | GACCAUGCUGGACUGCUGGCACG | 2644 |

| Sequence alignments between select Human (h), Rat (r), and Mouse (m) VEGFR1 (FLT1) and VEGFR2 (KDR) 23mer target sequences ||||
|---|---|---|---|
| Gene | Pos | Sequence | SEQ ID |
| hFLT1 | 3644 | GAUCAUGGUGGACUGGUGGOACa | 2645 |
| mFLT1 | 3421 | aAUCAUGUUGGAUUGCUGGCACa | 2646 |
| mKDR | 3614 | GACCAUGCUGGACUGCUGGCAUG | 2647 |
| rFLT1 | 3631 | aAUCAUGCUGGAUUGCUGGCACa | 2648 |
| rKDR | 3649 | aACCAUGCUGGAUUGCUGGCAUG | 2649 |
| hKDR | 3811 | AGCAGGAUGGCAAAGACUACAUU | 2650 |
| hFLT1 | 3739 | AaCAGGAUGGUAAAGACUACAUc | 2651 |
| mFLT1 | 3516 | AaCAGGAUGGgAAAGAUUACAUc | 2652 |
| mKDR | 3709 | AGCAGGAUGGCAAAGACUAUAUU | 2653 |
| rFLT1 | 3726 | AaCAGGAUGGUAAAGACUACAUc | 2654 |
| rKDR | 3744 | AGCAGGAUGGCAAAGACUAUAUU | 2655 |
| hKDR | 3812 | GCAGGAUGGCAAAGACUACAUuG | 2656 |
| hFLT1 | 3740 | aCAGGAUGGUAAAGACUACAUcc | 2657 |
| mFLT1 | 3517 | aCAGGAUGGgAAAGAUUACAUcc | 2658 |
| mKDR | 3710 | GCAGGAUGGCAAAGACUAUAUUG | 2659 |
| rFLT1 | 3727 | aCAGGAUGGUAAAGACUACAUcc | 2660 |
| rKDR | 3745 | GCAGGAUGGCAAAGACUAUAUUG | 2661 |

Lower case nucleotides represent mismatches

| Sequence alignments between select Human (h), Rat (r), and Mouse (m) VEGFr1 (FLT1) and VEGFr2 (KDR) 19mer target sequences ||||
|---|---|---|---|
| Gene | Pos | Seq | SEQ ID |
| hFLT1 | 3645 | CAUGCUGGACUGCUGGCAC | 2662 |
| hKDR | 3717 | CAUGCUGGACUGCUGGCAC | 2663 |
| mFLT1 | 3422 | CAUGuUGGAuUGCUGGCAC | 2664 |
| mKDR | 3615 | CAUGCUGGACUGCUGGCAu | 2665 |
| rFLT1 | 3632 | CAUGCUGGAuUGCUGGCAC | 2666 |
| rKDR | 3650 | CAUGCUGGAuUGCUGGCAu | 2667 |
| hFLT1 | 3646 | AUGCUGGACUGCUGGCACA | 2668 |
| hKDR | 3718 | AUGCUGGACUGCUGGCACg | 2669 |
| mFLT1 | 3423 | AUGuUGGAuUGCUGGCACa | 2670 |
| mKDR | 3616 | AUGCUGGACUGCUGGCAug | 2671 |
| rFLT1 | 3633 | AUGCUGGAuUGCUGGCACA | 2672 |
| rKDR | 3651 | AUGCUGGAuUGCUGGCAug | 2673 |
| hFLT1 | 3647 | UGCUGGACUGCUGGCACAG | 2674 |
| hKDR | 3719 | UGCUGGACUGCUGGCACgG | 2675 |
| mFLT1 | 3424 | UGuUGGAuUGCUGGCACAa | 2676 |
| mKDR | 3617 | UGCUGGACUGCUGGCAuga | 2677 |
| rFLT1 | 3634 | UGCUGGAuUGCUGGCACAa | 2678 |
| rKDR | 3652 | UGCUGGAuUGCUGGCAuga | 2679 |
| hKDR | 2764 | CCUUAUGAUGCCAGCAAAU | 2680 |
| hFLT1 | 2689 | CCUUAUGAUGCCAGCAAgU | 2681 |
| mFLT1 | 2469 | CCcUAUGAUGCCAGCAAgU | 2682 |
| mKDR | 2662 | CCUUAUGAUGCCAGCAAgU | 2683 |
| rFLT1 | 2676 | CCcUAUGAUGCCAGCAAgU | 2684 |
| rKDR | 2697 | CCUUAUGAUGCCAGCAAgU | 2685 |
| hKDR | 2765 | CUUAUGAUGCCAGCAAAUG | 2686 |
| hFLT1 | 2690 | CUUAUGAUGCCAGCAAgUG | 2687 |
| mFLT1 | 2470 | CcUAUGAUGCCAGCAAgUG | 2688 |
| mKDR | 2663 | CUUAUGAUGCCAGCAAgUG | 2689 |
| rFLT1 | 2677 | CcUAUGAUGCCAGCAAgUG | 2690 |
| rKDR | 2698 | CUUAUGAUGCCAGCAAgUG | 2691 |
| hKDR | 2766 | UUAUGAUGCCAGCAAAUGG | 2692 |
| hFLT1 | 2691 | UUAUGAUGCCAGCAAgUGG | 2693 |
| mFLT1 | 2471 | cUAUGAUGCCAGCAAgUGG | 2694 |
| mKDR | 2664 | UUAUGAUGCCAGCAAgUGG | 2695 |
| rFLT1 | 2678 | cUAUGAUGCCAGCAAgUGG | 2696 |
| rKDR | 2699 | UUAUGAUGCCAGCAAgUGG | 2697 |
| hKDR | 2767 | UAUGAUGCCAGCAAAUGGG | 2698 |
| hFLT1 | 2692 | UAUGAUGCCAGCAAgUGGG | 2699 |
| mFLT1 | 2472 | UAUGAUGCCAGCAAgUGGG | 2700 |
| mKDR | 2665 | UAUGAUGCCAGCAAgUGGG | 2701 |
| rFLT1 | 2679 | UAUGAUGCCAGCAAgUGGG | 2702 |
| rKDR | 2700 | UAUGAUGCCAGCAAgUGGG | 2703 |
| hKDR | 2768 | AUGAUGCCAGCAAAUGGGA | 2704 |
| hFLT1 | 2693 | AUGAUGCCAGCAAgUGGGA | 2705 |
| mFLT1 | 2473 | AUGAUGCCAGCAAgUGGGA | 2706 |
| mKDR | 2666 | AUGAUGCCAGCAAgUGGGA | 2707 |
| rFLT1 | 2680 | AUGAUGCCAGCAAgUGGGA | 2708 |
| rKDR | 2701 | AUGAUGCCAGCAAgUGGGA | 2709 |
| hKDR | 3712 | CAGACCAUGCUGGACUGCU | 2710 |
| hFLT1 | 3640 | CAGAuCAUGCUGGACUGCU | 2711 |
| mFLT1 | 3417 | CAaAuCAUGuUGGAuUGCU | 2712 |
| mKDR | 3610 | CAGACCAUGCUGGACUGCU | 2713 |
| rFLT1 | 3627 | CAaAuCAUGCUGGAuUGCU | 2714 |
| rKDR | 3645 | CAaACCAUGCUGGAuUGCU | 2715 |
| hKDR | 3713 | AGACCAUGCUGGACUGCUG | 2716 |
| hFLT1 | 3641 | AGAuCAUGCUGGACUGCUG | 2717 |
| mFLT1 | 3418 | AaAuCAUGuUGGAuUGCUG | 2718 |
| mKDR | 3611 | AGACCAUGCUGGACUGCUG | 2719 |
| rFLT1 | 3628 | AaAuCAUGCUGGAuUGCUG | 2720 |
| rKDR | 3646 | AaACCAUGCUGGAuUGCUG | 2721 |
| hKDR | 3714 | GACCAUGCUGGACUGCUGG | 2722 |
| hFLT1 | 3642 | GAuCAUGCUGGACUGCUGG | 2723 |
| mFLT1 | 3419 | aAuCAUGuUGGAuUGCUGG | 2724 |
| mKDR | 3612 | GACCAUGCUGGACUGCUGG | 2725 |
| rFLT1 | 3629 | aAuCAUGCUGGAuUGCUGG | 2726 |
| rKDR | 3647 | aACCAUGCUGGAuUGCUGG | 2727 |
| hKDR | 3715 | ACCAUGCUGGACUGCUGGC | 2728 |
| hFLT1 | 3643 | AuCAUGCUGGACUGCUGGC | 2729 |
| mFLT1 | 3420 | AuCAUGuUGGAuUGCUGGC | 2730 |
| mKDR | 3613 | ACCAUGCUGGACUGCUGGC | 2731 |
| rFLT1 | 3630 | AuCAUGCUGGAuUGCUGGC | 2732 |
| rKDR | 3648 | ACCAUGCUGGAuUGCUGGC | 2733 |
| hKDR | 3716 | CCAUGCUGGACUGCUGGCA | 2734 |
| hFLT1 | 3644 | uCAUGCUGGACUGCUGGCA | 2735 |
| mFLT1 | 3421 | uCAUGuUGGAuUGCUGGCA | 2736 |
| mKDR | 3614 | CCAUGCUGGACUGCUGGCA | 2737 |
| rFLT1 | 3631 | uCAUGCUGGAuUGCUGGCA | 2738 |
| rKDR | 3649 | CCAUGCUGGAuUGCUGGCA | 2739 |
| hKDR | 3811 | CAGGAUGGCAAAGACUACA | 2740 |
| hFLT1 | 3739 | CAGGAUGGuAAAGACUACA | 2741 |
| mFLT1 | 3516 | CAGGAUGGgAAAGAuUACA | 2742 |
| mKDR | 3709 | CAGGAUGGCAAAGACUAuA | 2743 |
| rFLT1 | 3726 | CAGGAUGGuAAAGACUACA | 2744 |
| rKDR | 3744 | CAGGAUGGCAAAGACUAuA | 2745 |
| hKDR | 3812 | AGGAUGGCAAAGACUACAU | 2746 |
| hFLT1 | 3740 | AGGAUGGuAAAGACUACAU | 2747 |

Sequence alignments between select Human (h), Rat (r), and Mouse (m) VEGFr1 (FLT1) and VEGFr2 (KDR) 19mer target sequences

| Gene | Pos | Seq | SEQ ID |
|---|---|---|---|
| mFLT1 | 3517 | AGGAUGGgAAAGAuUACAU | 2748 |
| mKDR | 3710 | AGGAUGGCAAAGACUAuAU | 2749 |
| rFLT1 | 3727 | AGGAUGGuAAAGACUACAU | 2750 |
| rKDR | 3745 | AGGAUGGCAAAGACUAuAU | 2751 |

Lower case nucleotides represent mismatches, such mismatches can be used a non-canonical base-pairs in selecting siNA molecules that target VEGFR1 and VEGFR2.

TABLE IV

Non-limiting examples of Stabilization Chemistries for chemically modified siNA constructs

| Chemistry | pyrimidine | Purine | cap | p = S | Strand |
|---|---|---|---|---|---|
| "Stab 00" | Ribo | Ribo | TT at 3'-ends | | S/AS |
| "Stab 1" | Ribo | Ribo | — | 5 at 5'-end 1 at 3'-end | S/AS |
| "Stab 2" | Ribo | Ribo | — | All linkages | Usually AS |
| "Stab 3" | 2'-fluoro | Ribo | — | 4 at 5'-end 4 at 3'-end | Usually S |
| "Stab 4" | 2'-fluoro | Ribo | 5' and 3'-ends | — | Usually S |
| "Stab 5" | 2'-fluoro | Ribo | — | 1 at 3'-end | Usually AS |
| "Stab 6" | 2'-O-Methyl | Ribo | 5' and 3'-ends | — | Usually S |
| "Stab 7" | 2'-fluoro | 2'-deoxy | 5' and 3'-ends | — | Usually S |
| "Stab 8" | 2'-fluoro | 2'-O-Methyl | — | 1 at 3'-end | Usually AS |
| "Stab 9" | Ribo | Ribo | 5' and 3'-ends | — | Usually S |
| "Stab 10" | Ribo | Ribo | — | 1 at 3'-end | Usually AS |
| "Stab 11" | 2'-fluoro | 2'-deoxy | — | 1 at 3'-end | Usually AS |
| "Stab 12" | 2'-fluoro | LNA | 5' and 3'-ends | | Usually S |
| "Stab 13" | 2'-fluoro | LNA | | 1 at 3'-end | Usually AS |
| "Stab 14" | 2'-fluoro | 2'-deoxy | | 2 at 5'-end 1 at 3'-end | Usually AS |
| "Stab 15" | 2'-deoxy | 2'-deoxy | | 2 at 5'-end 1 at 3'-end | Usually AS |
| "Stab 16 | Ribo | 2'-O-Methyl | 5' and 3'-ends | | Usually S |
| "Stab 17" | 2'-O-Methyl | 2'-O-Methyl | 5' and 3'-ends | | Usually S |
| "Stab 18" | 2'-fluoro | 2'-O-Methyl | 5' and 3'-ends | 1 at 3'-end | Usually S |
| "Stab 19" | 2'-fluoro | 2'-O-Methyl | 3'-end | | Usually AS |
| "Stab 20" | 2'-fluoro | 2'-deoxy | 3'-end | | Usually AS |
| "Stab 21" | 2'-fluoro | Ribo | 3'-end | | Usually AS |
| "Stab 22" | Ribo | Ribo | 3'-end- | | Usually AS |
| "Stab 23" | 2'-fluoro* | 2'-deoxy* | 5' and 3'-ends | | Usually S |
| "Stab 24" | 2'-fluoro* | 2'-O-Methyl* | — | 1 at 3'-end | Usually AS |

Figure 10:
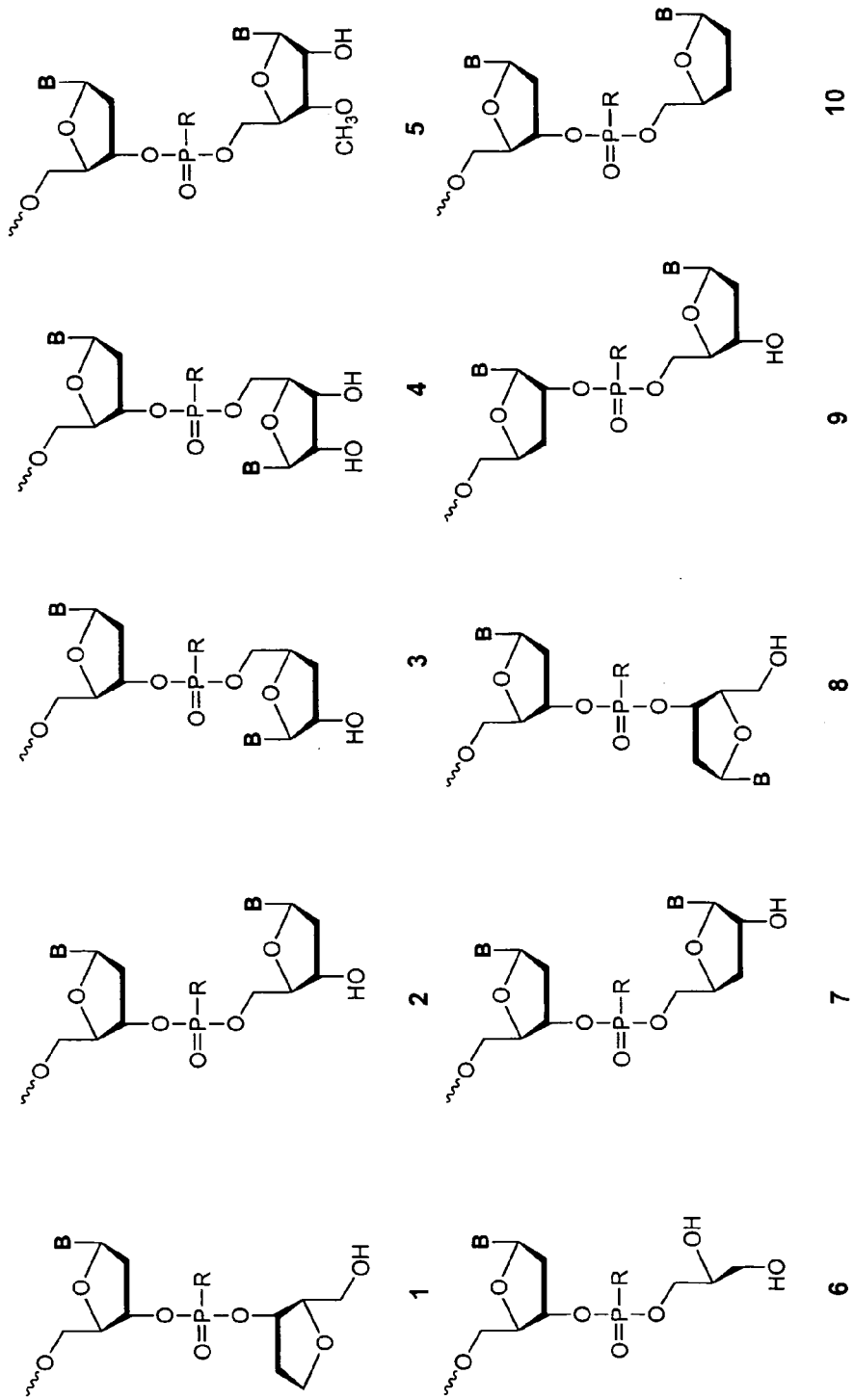
FIG. 10 shows non-limiting examples of different stabilization chemistries (1–10) that can be used, for example, to stabilize the 3'-end of siNA sequences of the invention, including (1) [3-3']-inverted deoxyribose; (2) deoxyribonucleotide; (3) [5'-3']-3'-deoxyribonucleotide; (4) [5'-3']-ribonucleotide; (5) [5'-3']-3'-O-methyl ribonucleotide; (6) 3'-glyceryl; (7) [3'-5']-3'-deoxyribonucleotide; (8) [3'-3']-deoxyribonucleotide; (9) [5'-2']-deoxyribonucleotide; and (10) [5-3']-dideoxyribonucleotide. In addition to modified and unmodified backbone chemistries indicated in the figure, these chemistries can be combined with different backbone modifications as described herein, for example, backbone modifications having Formula I. In addition, the 2'-deoxy nucleotide shown 5' to the terminal modifications shown can be another modified or unmodified nucleotide or non-nucleotide described herein, for example modifications having any of Formulae I–VII or any combination thereof.

CAP = any terminal cap, see for example FIG. 10.
All Stab 1–24 chemistries can comprise 3'-terminal thymidine (TT) residues
All Stab 1–24 chemistries typically comprise about 21 nucleotides, but can vary as described herein.
S = sense strand
AS = antisense strand
*Stab 23 has single ribonucleotide adjacent to 3'-CAP
*Stab 24 has single ribonucleotide at 5'-terminus

TABLE V

| Reagent | Equivalents | Amount | Wait Time* DNA | Wait Time* 2'-O-methyl | Wait Time* RNA |
|---|---|---|---|---|---|
| A. 2.5 μmol Synthesis Cycle ABI 394 Instrument | | | | | |
| Phosphoramidites | 6.5 | 163 μL | 45 sec | 2.5 min | 7.5 min |
| S-Ethyl Tetrazole | 23.8 | 238 μL | 45 sec | 2.5 min | 7.5 min |
| Acetic Anhydride | 100 | 233 μL | 5 sec | 5 sec | 5 sec |
| N-Methyl Imidazole | 186 | 233 μL | 5 sec | 5 sec | 5 sec |
| TCA | 176 | 2.3 mL | 21 sec | 21 sec | 21 sec |
| Iodine | 11.2 | 1.7 mL | 45 sec | 45 sec | 45 sec |
| Beaucage | 12.9 | 645 μL | 100 sec | 300 sec | 300 sec |
| Acetonitrile | NA | 6.67 mL | NA | NA | NA |
| B. 0.2 μmol Synthesis Cycle ABI 394 Instrument | | | | | |
| Phosphoramidites | 15 | 31 μL | 45 sec | 233 sec | 465 sec |
| S-Ethyl Tetrazole | 38.7 | 31 μL | 45 sec | 233 min | 465 sec |
| Acetic Anhydride | 655 | 124 μL | 5 sec | 5 sec | 5 sec |
| N-Methyl | 1245 | 124 μL | 5 sec | 5 sec | 5 sec |

TABLE V-continued

| | | | | | |
|---|---|---|---|---|---|
| Imidazole | | | | | |
| TCA | 700 | 732 µL | 10 sec | 10 sec | 10 sec |
| Iodine | 20.6 | 244 µL | 15 sec | 15 sec | 15 sec |
| Beaucage | 7.7 | 232 µL | 100 sec | 300 sec | 300 sec |
| Acetonitrile | NA | 2.64 mL | NA | NA | NA |

C. 0.2 µmol Synthesis Cycle 96 well Instrument

| Reagent | Equivalents: DNA/ 2'-O-methyl/Ribo | Amount: DNA/2'-O-methyl/Ribo | Wait Time* DNA | Wait Time* 2'-O-methyl | Wait Time* Ribo |
|---|---|---|---|---|---|
| Phosphoramidites | 22/33/66 | 40/60/120 µL | 60 sec | 180 sec | 360 sec |
| S-Ethyl Tetrazole | 70/105/210 | 40/60/120 µL | 60 sec | 180 min | 360 sec |
| Acetic Anhydride | 265/265/265 | 50/50/50 µL | 10 sec | 10 sec | 10 sec |
| N-Methyl Imidazole | 502/502/502 | 50/50/50 µL | 10 sec | 10 sec | 10 sec |
| TCA | 238/475/475 | 250/500/500 µL | 15 sec | 15 sec | 15 sec |
| Iodine | 6.8/6.8/6.8 | 80/80/80 µL | 30 sec | 30 sec | 30 sec |
| Beaucage | 34/51/51 | 80/120/120 µL | 100 sec | 200 sec | 200 sec |
| Acetonitrile | NA | 1150/1150/1150 µL | NA | NA | NA |

Wait time does not include contact time during delivery.
Tandem synthesis utilizes double coupling of linker molecule

TABLE VI

| Group | Cell type/Location of tumor | Inoculum | Number of Animals | Treatment | Endpoints | Growth Period |
|---|---|---|---|---|---|---|
| 1 | 4T1-luciferase cells/animal in right flank | $1.0 \times 10^6$ | 10 | NA | Tumors collected and flash frozen for analysis of luciferase expression | 15 d |
| 2 | 4T1-luciferase cells/animal in right flank | $1.0 \times 10^6$ | 10 | Saline, Daily IV injection, 100 µL | Tumor volume, tumors flash frozen for IHC, expression of VEGFR-1 and R2 and endoglin | 21 d |
| 3 | 4T1-luciferase cells/animal in right flank | $1.0 \times 10^6$ | 10 | 349-9/10 ACTIVE, 30 mg/kg/d, daily IV | Tumor volume, tumors flash frozen for IHC, expression of VEGFR-1 and R2 and endoglin | 21 d |
| 4 | 4T1-luciferase cells/animal in right flank | $1.0 \times 10^6$ | 10 | 349-9/10 INVERTED, 30 mg/kg/d, daily IV | Tumor volume, tumors flash frozen for IHC, expression of VEGFR-1 and R2 and endoglin | 21 d |

TABLE VII

| Group | Solution on Filter | Stock VEGF concentration | Number of Animals | Injectate (1.2 µL) | Dose | Conc. injectate |
|---|---|---|---|---|---|---|
| 1 | R&D Systems hVEGF | 3.53 µg/µL | 5 | water | 1.0 µg | 0.833 µg/µL Each strand |
| 2 | R&D Systems hVEGF | 3.53 µg/µL | 5 | siRNA 3645-9/10-Active | 1.0 µg | 0.833 µg/µL Each strand |
| 3 | R&D Systems hVEGF | 3.53 µg/µL | 5 | siRNA 3646-9/10-Active | 10 µg | 0.833 µg/µL Each strand |
| 4 | R&D Systems hVEGF | 3.53 µg/µL | 5 | siRNA 3715-9/10-Active | 1.0 µg | 0.833 µg/µL Each strand |
| 5 | R&D Systems hVEGF | 3.53 µg/µL | 5 | siRNA 3716-9/10-Active | 1.0 µg | 0.833 µg/µL Each strand |
| 6 | R&D Systems hVEGF | 3.53 µg/µL | 5 | siRNA 3645-9/10-Inverted | 1.0 µg | 0.833 µg/µL Each strand |
| 7 | R&D Systems hVEGF | 3.53 µg/µL | 5 | siRNA 3645-9/10-Active | 1.0 µg | 0.833 µg/µL Each strand |
| 8 | R&D Systems hVEGF | 3.53 µg/µL | 5 | siRNA 3646-9/10-Active | 1.0 µg | 0.833 µg/µL Each strand |
| 9 | R&D Systems hVEGF | 3.53 µg/µL | 5 | siRNA 3715-9/10-Active | 1.0 µg. | 0.833 µg/µL Each strand |
| 10 | R&D Systems hVEGF | 3.53 µg/µL | 5 | siRNA 3716-9/10-Active | 1.0 µg. | 0.833 µg/µL Each strand |
| 11 | R&D Systems hVEGF | 3.53 µg/µL | 5 | siRNA 3645-9/10-Inverted | 1.0 µg. | 0.833 µg/µL Each strand |
| 12 | R&D Systems hVEGF | 3.53 µg/µL | 5 | SiRNA 349-9/10 Active | 1.0 µg. | 0.833 µg/µL Each strand |

What we claim is:

1. A chemically synthesized double stranded short interfering nucleic acid (siNA) molecule that directs cleavage of a vascular endothelial growth factor receptor 1 (VEGER1) RNA via RNA interference (RNAi) wherein:
   a. each strand of said siNA molecule is about 21 nucleotides in length;
   b. one strand of said siNA molecule comprises a nucleotide sequence having sufficient complementarity to said VEGFR1 RNA for the siNA molecule to direct cleavage of the VEGFR1 RNA via RNA interference; and
   c. said siNA comprises SEQ ID NO: 2185 and SEQ ID NO: 2188.

2. A composition comprising the siNA of claim 1 and a pharmaceutically acceptable carrier or diluent.

* * * * *